(12) United States Patent
Halvorsen et al.

(10) Patent No.: US 10,851,073 B2
(45) Date of Patent: Dec. 1, 2020

(54) PROTEIN TYROSINE PHOSPHATASE INHIBITORS AND METHODS OF USE THEREOF

(71) Applicants: Calico Life Sciences LLC, South San Francisco, CA (US); AbbVie Inc., North Chicago, IL (US)

(72) Inventors: Geoff T. Halvorsen, Lake Bluff, IL (US); Jennifer M. Frost, Gurnee, IL (US); Philip R. Kym, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/892,786

(22) Filed: Jun. 4, 2020

(65) Prior Publication Data

US 2020/0299246 A1 Sep. 24, 2020

Related U.S. Application Data

(63) Continuation of application No. PCT/US2020/022717, filed on Mar. 13, 2020.

(60) Provisional application No. 62/818,447, filed on Mar. 14, 2019.

(51) Int. Cl.
C07D 285/10 (2006.01)
(52) U.S. Cl.
CPC .................................. *C07D 285/10* (2013.01)
(58) Field of Classification Search
CPC .................................................. C07D 285/10
See application file for complete search history.

(56) References Cited

U.S. PATENT DOCUMENTS

| | | |
|---|---|---|
| 8,252,820 B2 | 8/2012 | Barnes et al. |
| 9,217,012 B2 | 12/2015 | Zhang et al. |
| 9,828,399 B2 | 11/2017 | Tremblay et al. |
| 10,005,804 B2 | 6/2018 | Tremblay et al. |
| 10,072,043 B2 | 9/2018 | Zhang et al. |
| 10,150,787 B2 | 12/2018 | Tremblay et al. |
| 2010/0160228 A1 | 6/2010 | Ivaska et al. |
| 2010/0168101 A1 | 7/2010 | Bombrun et al. |
| 2013/0202577 A1 | 8/2013 | Tiganis et al. |
| 2017/0224731 A1 | 8/2017 | Tiganis et al. |
| 2018/0325925 A1 | 11/2018 | Suk et al. |

FOREIGN PATENT DOCUMENTS

| | | |
|---|---|---|
| WO | WO-2007/067612 A1 | 6/2007 |
| WO | WO-2008/142198 A2 | 11/2008 |
| WO | WO-2010/008852 A2 | 1/2010 |
| WO | WO-2010/118241 A2 | 10/2010 |
| WO | WO-2011/057331 A1 | 5/2011 |
| WO | WO-2011/094806 A1 | 8/2011 |
| WO | WO-2015/127548 A1 | 9/2015 |
| WO | WO-2015/188228 A1 | 12/2015 |
| WO | WO-2017/078499 A2 | 5/2017 |
| WO | WO-2018/148378 A1 | 8/2018 |
| WO | WO-2018/227248 A1 | 12/2018 |
| WO | WO-2019/036815 A1 | 2/2019 |
| WO | WO2019246513 | * 12/2019 |

OTHER PUBLICATIONS

Asante-Appiah et al. "Conformation-assisted Inhibition of Protein-tyrosine Phosphatase-1B Elicits Inhibitor Selectivity over T-cell Protein-tyrosine Phosphatase" The Journal of Biological Chemistry vol. 281, No. 12, Mar. 24, 2006, pp. 8010-8015.

Barluenga et al. "Novel PTP1B inhibitors identified by DNA display of fragment pairs" Bioorg. Med. Chem. Lett. 26 (2016) pp. 1080-1085.

Bourdeau et al. "10 Structure and function of the T-cell protein tyrosine phosphatase" Topics in Current Genetics, vol. 5, 2004, pp. 185-200.

Bourdeau et al. "Inhibition of T Cell Protein Tyrosine Phosphatase Enhances Interleukin-18- Dependent Hematopoietic Stem Cell Expansion" Stem Cells 2013;31: pp. 293-304.

Chen et al. "Investigation of selective binding of inhibitors to PTP1B and TCPTP by accelerated molecular dynamics simulations" Journal of Biomolecular Structure and Dynamics, 2018, pp. 1-11.

Chen et al. "Virtual Screening of Novel and Selective Inhibitors of Protein Tyrosine Phosphatase 1B over T-Cell Protein Tyrosine Phosphatase Using a Bidentate Inhibition Strategy" J. Chem. Inf. Model. 2018, 58, pp. 837-847.

Chen et al. "Wedelolactone, a Naturally Occurring Coumestan, Enhances Interferon-γ Signaling through Inhibiting STAT1 Protein Dephosphorylation" The Journal of Biological Chemistry vol. 288, No. 20, pp. 14417-14427, May 17, 2013.

Deng et al. "Identification of 2-substituted ethenesulfonic acid ester derivatives as novel, potent and selective inhibitors of protein tyrosine phosphatase 1B" Pharmazie 70: pp. 777-783 (2015).

Fang et al. "Studies of the Mechanism of Selectivity of Protein Tyrosine Phosphatase 1B (PTP1B) Bidentate Inhibitors Using Molecular Dynamics Simulations and Free Energy Calculations" J. Chem. Inf. Model. 2008, 48, pp. 2030-2041.

Haftchenary et al. "Identification of a potent salicylic acid-based inhibitor of tyrosine phosphatase PTP1B" Med. Chem. Commun., 2013, pp. 987-992.

He et al. "Small molecule tools for function al interrogation of protein tyrosine phosphatases" FEBS Journal 280 (2013) pp. 731-750, 2012.

Iversen et al. "Steric Hindrance as a Basis for Structure-Based Design of Selective Inhibitors of Protein-Tyrosine Phosphatases" American Chemical Society, Biochemistry 2001, 40, pp. 14812-14820.

(Continued)

*Primary Examiner* — Karen Cheng
(74) *Attorney, Agent, or Firm* — Goodwin Procter LLP

(57) ABSTRACT

Provided herein are compounds, compositions, and methods useful for inhibiting protein tyrosine phosphatase, e.g., protein tyrosine phosphatase non-receptor type 2 (PTPN2) and/or protein tyrosine phosphatase non-receptor type 1 (PTPN1), and for treating related diseases, disorders and conditions favorably responsive to PTPN1 or PTPN2 inhibitor treatment, e.g., a cancer or a metabolic disease.

3 Claims, No Drawings

Specification includes a Sequence Listing.

(56) References Cited

OTHER PUBLICATIONS

Iverson et al. "Structure Determination of T Cell Protein-tyrosine Phosphatase" The Journal of Biological Chemistry, vol. 277, No. 22, Issue of May 31, pp. 19982-19990, 2002.
Khavrienko et al. "α,α-Difluoro-β-ketophosphonates on a tetraazamacrocyclic platform: Synthesis and inhibitory activity against protein tyrosine phosphatases" 2014, 9; pp. 109-115.
Kim et al. "Inhibition of PTPN2 by PTP inhibitor V" Bull. Korean Chem. Soc. 2013, vol. 34, No. 12, pp. 3874-3876.
Le et al. "Inhibition of protein tyrosine phosphatase non-receptor type 2 by PTP inhibitor XIX: Its role as a multiphosphatase inhibitor" BMB Rep. 2017; 50(6): pp. 329-334.
Liu et al. "Design, synthesis, and biological evaluation of 2-substituted ethenesulfonic acid ester derivatives as selective PTP1B inhibitors" Pharmazie 70 (2015), pp. 446-451.
Liu et al. "Function-Oriented Synthesis of Marine Phidianidine Derivatives as Potential PTP1B Inhibitors with Specific Selectivity" marine drugs, 2018, 16, 97, pp. 1-14.
Loh et al. "Elevated Hypothalamic TCPTP in Obesity Contributes to Cellular Leptin Resistance" Cell Metabolism 14, Nov. 2, 2011, 2011 Elsevier Inc., pp. 684-699.
Ma et al. "The Discovery of a Novel and Selective Inhibitor of PTP1B Over TCPTP: 3D QSAR Pharmacophore Modeling, Virtual Screening, Synthesis, and Biological Evaluation" Chem Biol Drug Des 2014; 83: pp. 697-709.
Mattila et al. "Inhibition of receptor tyrosine kinase signalling by small molecule agonist of T-cell protein tyrosine phosphatase" BMC Cancer 2010, 10:7, pp. 1-12.
Parker et al. "Development of High Throughout Screening Assays Using Fluorescence Polarization: Nuclear Receptor-Ligand-Binding and Kinase*/Phosphatase Assays" Journal of Biomolecular Screening, vol. 5, No. 2, 2000, pp. 77-88.
Penafuerte et al. "Downregulation of PTP1B and TC-PTP phosphatases potentiate dendritic cell-based immunotherapy through IL-12/IFN$_\gamma$ signaling" Oncoimmunology 2017, vol. 6, No. 6, e1321185 (14 pages).
Qin et al. "Identification of flavonolignans from *Silybum marianum* seeds as allosteric protein tyrosine phosphatase 1B inhibitors" Journal of Enzyme Inhibition and Medicinal Chemistry, 2018, vol. 33, No. 1, pp. 1283-1291.
Qing et al. "PTPs Inhibition by Zinc(II) Complexes with Multibenzimidazole Derivatives" Chinese Journal of Inorganic Chemistry, vol. 32, No. 6, pp. 1001-1008.
Reddy et al. "Developing Selective Inhibitors of PTP1B Over TCPTP" Journal of Global Trends in Pharmaceutical Sciences, vol. 3, Issue 1, Jan.-Mar. 2012, pp. 558-563.
Reddy et al. "Diphenylether Derivative as Selective Inhibitor of Protein Tyrosine Phosphatase 1B (PTP1B) Over T-cell Protein Tyrosine Phosphatase (TCPTP) Identified through Virtual Screening" Mini-Reviews in Medicinal Chemistry, 2013, 13, pp. 1-5.
Reddy et al. "Small Molecule Inhibitors of PTP1B and TCPTP" Int.J.Pharm.Phytopharmacol.Res. 2012, 1(5): pp. 287-291.
Scrivens et al. "Cdc25A-inhibitory properties and antineoplastic activity of bisperoxovanadium analogues" American Association for Cancer Research, Molecular Cancer Therapeutics, 2003, pp. 1053-1059.
Seo et al. "Ethyl-3,4-dephostatin Inhibits PTPN2 and Induces ERK Activation" Bull. Korean Chem. Soc. 2011, vol. 32, No. 7; pp. 2476-2478.
Wakuda et al. "Manzamenones Inhibit T-Cell Protein Tyrosine Phosphatase" Mar. Drugs 2006, 4, pp. 9-14.
Xie et al. "A Two Stage Click-Based Library of Protein Tyrosine Phosphatase Inhibitors" Bioorg Med Chem. Jan. 1, 2007; 15(1): pp. 458-473.
Yanhong et al. "Synthesis, Crystal Structure and Protein Tyrosine Photopastase Inhibitiion of a Copper (II) Complex with N-(2-Pyridylmethyl)-L-serine" Chemical Journal of Chinese Universities, 2016, pp. 2138-2143.
Zhang et al. "A Combinatorial Strategy for the Acquisition of Potent and Specific Protein Tyrosine Phosphatase Inhibitors" Rational Drug Design: Methods and Protocols, Methods in Molecular Biology, vol. 928, 2012, pp. 53-65.
Zhang et al. "Acquisition of a Potent and Selective TC-PTP Inhibitor via a Stepwise Fluorophore-Tagged Combinatorial Synthesis and Screening Strategy" J. Am. Chem. Soc. 2009, 131, pp. 13072-13079.
Zhang et al. "Protein tyrosine phosphatases in hypothalamic insulin and leptin signaling" Trends in Pharmacological Sciences, 36(10), 2005, pp. 661-674.
Zhang et al. "The development of protein tyrosine phosphatase1B inhibitors defined by binding sites in crystalline complexes" Future Med. Chem. (2018) 10(19), pp. 2345-2367.
International Search Report and Written Opinion of the International Searching Authority for International Application No. PCT/US2020/022717 dated May 27, 2020 (18 pages).

\* cited by examiner

SEQUENCE LISTING

```
<160> NUMBER OF SEQ ID NOS: 3

<210> SEQ ID NO 1
<211> LENGTH: 404
<212> TYPE: PRT
<213> ORGANISM: artificial sequence
<220> FEATURE:
<223> OTHER INFORMATION: synthetic peptide

<400> SEQUENCE: 1

Met Ala Met Pro Thr Thr Ile Glu Arg Glu Phe Glu Glu Leu Asp Thr
1               5                   10                  15

Gln Arg Arg Trp Gln Pro Leu Tyr Leu Glu Ile Arg Asn Glu Ser His
            20                  25                  30

Asp Tyr Pro His Arg Val Ala Lys Phe Pro Glu Asn Arg Asn Arg Asn
        35                  40                  45

Arg Tyr Arg Asp Val Ser Pro Tyr Asp His Ser Arg Val Lys Leu Gln
    50                  55                  60

Asn Ala Glu Asn Asp Tyr Ile Asn Ala Ser Leu Val Asp Ile Glu Glu
65                  70                  75                  80

Ala Gln Arg Ser Tyr Ile Leu Thr Gln Gly Pro Leu Pro Asn Thr Cys
                85                  90                  95

Cys His Phe Trp Leu Met Val Trp Gln Gln Lys Thr Lys Ala Val Val
            100                 105                 110

Met Leu Asn Arg Ile Val Glu Lys Glu Ser Val Lys Cys Ala Gln Tyr
        115                 120                 125

Trp Pro Thr Asp Asp Gln Glu Met Leu Phe Lys Glu Thr Gly Phe Ser
    130                 135                 140

Val Lys Leu Leu Ser Glu Asp Val Lys Ser Tyr Tyr Thr Val His Leu
```

```
                145                 150                 155                 160
Leu Gln Leu Glu Asn Ile Asn Ser Gly Glu Thr Arg Thr Ile Ser His
                    165                 170                 175

Phe His Tyr Thr Thr Trp Pro Asp Phe Gly Val Pro Glu Ser Pro Ala
                180                 185                 190

Ser Phe Leu Asn Phe Leu Phe Lys Val Arg Glu Ser Gly Ser Leu Asn
                195                 200                 205

Pro Asp His Gly Pro Ala Val Ile His Cys Ser Ala Gly Ile Gly Arg
            210                 215                 220

Ser Gly Thr Phe Ser Leu Val Asp Thr Cys Leu Val Leu Met Glu Lys
225                 230                 235                 240

Gly Asp Asp Ile Asn Ile Lys Gln Val Leu Leu Asn Met Arg Lys Tyr
                245                 250                 255

Arg Met Gly Leu Ile Gln Thr Pro Asp Gln Leu Arg Phe Ser Tyr Met
                260                 265                 270

Ala Ile Ile Glu Gly Ala Lys Cys Ile Lys Gly Asp Ser Ser Ile Gln
            275                 280                 285

Lys Arg Trp Lys Glu Leu Ser Lys Glu Asp Leu Ser Pro Ala Phe Asp
290                 295                 300

His Ser Pro Asn Lys Ile Met Thr Glu Lys Tyr Asn Gly Asn Arg Ile
305                 310                 315                 320

Gly Leu Glu Glu Glu Lys Leu Thr Gly Asp Arg Cys Thr Gly Leu Ser
                325                 330                 335

Ser Lys Met Gln Asp Thr Met Glu Glu Asn Ser Glu Ser Ala Leu Arg
                340                 345                 350

Lys Arg Ile Arg Glu Asp Arg Lys Ala Thr Thr Ala Gln Lys Val Gln
                355                 360                 365

Gln Met Lys Gln Arg Leu Asn Glu Asn Glu Arg Lys Arg Lys Arg Pro
            370                 375                 380

Arg Leu Thr Asp Thr Glu Asn Leu Tyr Phe Gln Ser His His His His
385                 390                 395                 400

His His His His

<210> SEQ ID NO 2
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: X
<222> LOCATION: (1)..(1)
<223> OTHER INFORMATION: (Oregon Green)-(NH-CH2-CH2-O-CH2-CH2-O-CH2-CO)-
      L-threonine
<220> FEATURE:
<221> NAME/KEY: X
<222> LOCATION: (5)..(5)
<223> OTHER INFORMATION: O-phospho-L-tyrosine
<220> FEATURE:
<221> NAME/KEY: X
<222> LOCATION: (13)..(13)
<223> OTHER INFORMATION: L-lysine-NH2

<400> SEQUENCE: 2

Xaa Arg Asp Ile Xaa Glu Thr Asp Tyr Tyr Arg Lys Xaa
1               5                   10

<210> SEQ ID NO 3
<211> LENGTH: 339
<212> TYPE: PRT
```

<213> ORGANISM: Artificial
<220> FEATURE:
<223> OTHER INFORMATION: synthetic peptide

<400> SEQUENCE: 3

```
Met Ala His His His His His His Ser Ser Gly Leu Val Pro Arg Gly
1               5                   10                  15

Ser His Met Glu Met Glu Lys Glu Phe Glu Gln Ile Asp Lys Ser Gly
            20                  25                  30

Ser Trp Ala Ala Ile Tyr Gln Asp Ile Arg His Glu Ala Ser Asp Phe
        35                  40                  45

Pro Cys Arg Val Ala Lys Leu Pro Lys Asn Lys Asn Arg Asn Arg Tyr
    50                  55                  60

Arg Asp Val Ser Pro Phe Asp His Ser Arg Ile Lys Leu His Gln Glu
65                  70                  75                  80

Asp Asn Asp Tyr Ile Asn Ala Ser Leu Ile Lys Met Glu Glu Ala Gln
                85                  90                  95

Arg Ser Tyr Ile Leu Thr Gln Gly Pro Leu Pro Asn Thr Cys Gly His
            100                 105                 110

Phe Trp Glu Met Val Trp Glu Gln Lys Ser Arg Gly Val Val Met Leu
        115                 120                 125

Asn Arg Val Met Glu Lys Gly Ser Leu Lys Cys Ala Gln Tyr Trp Pro
130                 135                 140

Gln Lys Glu Glu Lys Glu Met Ile Phe Glu Asp Thr Asn Leu Lys Leu
145                 150                 155                 160

Thr Leu Ile Ser Glu Asp Ile Lys Ser Tyr Tyr Thr Val Arg Gln Leu
                165                 170                 175

Glu Leu Glu Asn Leu Thr Thr Gln Glu Thr Arg Glu Ile Leu His Phe
            180                 185                 190

His Tyr Thr Thr Trp Pro Asp Phe Gly Val Pro Glu Ser Pro Ala Ser
        195                 200                 205

Phe Leu Asn Phe Leu Phe Lys Val Arg Glu Ser Gly Ser Leu Ser Pro
    210                 215                 220

Glu His Gly Pro Val Val His Cys Ser Ala Gly Ile Gly Arg Ser
225                 230                 235                 240

Gly Thr Phe Cys Leu Ala Asp Thr Cys Leu Leu Leu Met Asp Lys Arg
                245                 250                 255

Lys Asp Pro Ser Ser Val Asp Ile Lys Lys Val Leu Leu Glu Met Arg
            260                 265                 270

Lys Phe Arg Met Gly Leu Ile Gln Thr Ala Asp Gln Leu Arg Phe Ser
        275                 280                 285

Tyr Leu Ala Val Ile Glu Gly Ala Lys Phe Ile Met Gly Asp Ser Ser
    290                 295                 300

Val Gln Asp Gln Trp Lys Glu Leu Ser His Glu Asp Leu Glu Pro Pro
305                 310                 315                 320

Pro Glu His Ile Pro Pro Pro Arg Pro Lys Arg Ile Leu Glu
                325                 330                 335

Pro His Asn
```

PROTEIN TYROSINE PHOSPHATASE INHIBITORS AND METHODS OF USE THEREOF

CROSS REFERENCE TO RELATED APPLICATIONS

This application is a continuation of PCT/US2020/022717, filed on Mar. 13, 2020, which claims the benefit of, and priority to, U.S. Provisional Application No. 62/818,447, filed on Mar. 14, 2019, the content of each of which is hereby incorporated by reference in its entirety.

BACKGROUND

Cancer immunotherapy regimens targeting immune evasion mechanisms including checkpoint blockade (e.g. PD-1/PD-L1 and A CTLA-4 blocking antibodies) have been shown to be effective in treating in a variety of cancers, dramatically improving outcomes in some population's refractory to conventional therapies. However, incomplete clinical responses and the development of intrinsic or acquired resistance will continue to limit the patient populations who could benefit from checkpoint blockade.

Protein tyrosine phosphatase non-receptor type 2 (PTPN2), also known as T cell protein tyrosine phosphatase (TC-PTP), is an intracellular member of the class 1 subfamily of phospho-tyrosine specific phosphatases that control multiple cellular regulatory processes by removing phosphate groups from tyrosine substrates. PTPN2 is ubiquitously expressed, but expression is highest in hematopoietic and placental cells (Mosinger, B. Jr. et al., *Proc Natl Acad Sci USA* 89:499-503; 1992). In humans, PTPN2 expression is controlled post-transcriptionally by the existence of two splice variants: a 45 kDa form that contains a nuclear localization signal at the C-terminus upstream of the splice junction, and a 48 kDa canonical form which has a C-terminal ER retention motif (Tillmann U. et al., *Mol Cell Biol* 14:3030-3040; 1994). The 45 kDa isoform can passively transfuse into the cytosol under certain cellular stress conditions. Both isoforms share an N-terminal phospho-tyrosine phosphatase catalytic domain. PTPN2 negatively regulates signaling of non-receptor tyrosine kinases (e.g. JAK1, JAK3), receptor tyrosine kinases (e.g. INSR, EGFR, CSF1R, PDGFR), transcription factors (e.g. STAT1, STAT3, STAT5a/b), and Src family kinases (e.g. Fyn, Lck). As a critical negative regulator of the JAK-STAT pathway, PTPN2 functions to directly regulate signaling through cytokine receptors, including IFNγ. The PTPN2 catalytic domain shares 74% sequence homology with PTPN1 (also called PTP1B), and shares similar enzymatic kinetics (Romsicki Y. et al., *Arch Biochem Biophys* 414:40-50; 2003).

Data from a loss of function in vivo genetic screen using CRISPR/Cas9 genome editing in a mouse B16F10 transplantable tumor model show that deletion of Ptpn2 gene in tumor cells improved response to the immunotherapy regimen of a GM-CSF secreting vaccine (GVAX) plus PD-1 checkpoint blockade (Manguso R. T. et al., *Nature* 547:413-418; 2017). Loss of Ptpn2 sensitized tumors to immunotherapy by enhancing IFNγ-mediated effects on antigen presentation and growth suppression. The same screen also revealed that genes known to be involved in immune evasion, including PD-L1 and CD47, were also depleted under immunotherapy selective pressure, while genes involved in the IFNγ signaling pathway, including IFNGR, JAK1, and STAT1, were enriched. These observations point to a putative role for therapeutic strategies that enhance IFNγ sensing and signaling in enhancing the efficacy of cancer immunotherapy regimens.

Protein tyrosine phosphatase non-receptor type 1 (PTPN1), also known as protein tyrosine phosphatase-1B (PTP1B), has been shown to play a key role in insulin and leptin signaling and is a primary mechanism for down-regulating both the insulin and leptin receptor signaling pathways (Kenner K. A. et al., *J Biol Chem* 271: 19810-19816, 1996). Animals deficient in PTPN1 have improved glucose regulation and lipid profiles and are resistant to weight gain when treated with a high fat diet (Elchebly M. et al., *Science* 283: 1544-1548, 1999). Thus, PTPN1 inhibitors are expected to be useful for the treatment of type 2 diabetes, obesity, and metabolic syndrome.

SUMMARY

The present disclosure is directed, at least in part, to compounds, compositions, and methods for the inhibition of protein tyrosine phosphatase, e.g., protein tyrosine phosphatase non-receptor type 2 (PTPN2) and/or protein tyrosine phosphatase non-receptor type 1 ((PTPN1), also known as protein tyrosine phosphatase-1B (PTP1B)). In some embodiments, disclosed herein is an inhibitor of protein tyrosine phosphatase, e.g., PTPN2 and/or PTPN1, comprising a compound disclosed herein. In other embodiments, disclosed herein are methods of treating a disease or disorder, e.g., cancer, type-2 diabetes, obesity, a metabolic disease, or any other disease, disorder or ailment favorably responsive to PTPN2 or PTPN1 inhibitor treatment, comprising administering an effective amount of a compound disclosed herein.

For example, disclosed herein is a compound represented by Formula (I):

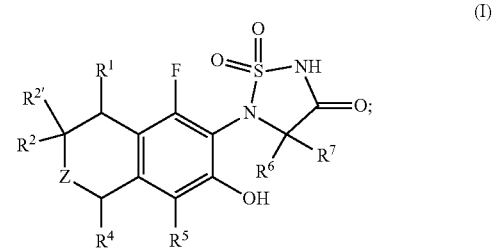

or a pharmaceutically acceptable salt thereof, wherein:
Z is selected from the group consisting of $C(H)(R^3)$, a bond and $N(R^8)$;
$R^1$ is selected from the group consisting of hydrogen, halogen, $C_{1-6}$alkyl, $C_{3-6}$cycloalkyl and —O—$C_{1-6}$alkyl;
   wherein $C_{1-6}$alkyl, $C_{3-6}$cycloalkyl and —O—$C_{1-6}$alkyl may optionally be substituted on one or more available carbons by one, two, three or more substituents each independently selected from $R^g$;
$R^2$ is selected from the group consisting of hydrogen, —$C_{1-6}$alkyl, —$C_{2-6}$alkenyl, —O—$C_{1-6}$alkyl, —$NH_2$, —$N(R^a)$—$C_{1-8}$alkyl, —$N(R^a)$—$C_{3-6}$cycloalkyl, —$N(R^a)$—$C_{1-6}$alkylene-$C_{3-6}$cycloalkyl, —$N(R^a)$—$C_{1-6}$alkylene-$Si(R^c)_3$, —$C_{1-6}$alkylene-$N(R^a)$—$C_{1-6}$alkyl, —$C_{1-6}$alkylene-$N(R^a)$—$C_{1-6}$alkylene-$C_{3-6}$cycloalkyl, —$C_{1-6}$alkylene-$N(R^a)(R^b)$, —$N(R^a)$—(C=N(R^b))—$C_{1-6}$alkyl, —$S(O)_w$—$C_{1-6}$alkyl, —$C(O)$—$N(R^a)$—$C_{1-6}$alkyl, —$N(R^a)$—$C(O)$—$C_{1-6}$alkyl, —O—C (O)—N(R$^a$)—C$_{1-6}$alkyl, —O—C(O)—N(R$^a$)-phenyl, —N(R$^a$)—C(O)—O—C$_{1-6}$alkyl, C$_{3-6}$cycloalkyl, —C$_{1-6}$alkylene-C$_{3-6}$cycloalkyl, —O—C$_{1-6}$alkylene-C$_{3-6}$cycloalkyl, 5-6 membered heteroaryl, 4-6 membered heterocyclyl, —N(R$^a$)-4-6 membered heterocyclyl, —C$_{1-6}$alkylene-4-6 membered heterocyclyl, —O—C$_{1-6}$alkylene-4-6 membered heterocyclyl, —N(R$^a$)—C$_{1-6}$alkylene-4-6 membered heterocyclyl, —N(R$^a$)—C$_{1-6}$alkylene-5-6 membered heteroaryl and —N(R$^a$)—C$_{1-6}$alkylene-phenyl;

wherein —C$_{1-6}$alkyl, —C$_{2-6}$alkenyl, —O—C$_{1-6}$alkyl, —N(R$^a$)—C$_{1-8}$alkyl, —N(R$^a$)—C$_{3-6}$cycloalkyl, —N(R$^a$)—C$_{1-6}$alkylene-C$_{3-6}$cycloalkyl, —N(R$^a$)—C$_{1-6}$alkylene-Si(R$^c$)$_3$, —C$_{1-6}$alkylene-N(R$^a$)—C$_{1-6}$alkyl, —C$_{1-6}$alkylene-N(R$^a$)—C$_{1-6}$alkylene-C$_{3-6}$cycloalkyl, —N(R$^a$)—(C═N(R$^b$))—C$_{1-6}$alkyl, —S(O)$_w$—C$_{1-6}$alkyl, —C(O)—N(R$^a$)—C$_{1-6}$alkyl, —N(R$^a$)—C(O)—C$_{1-6}$alkyl, —O—C(O)—N(R$^a$)—C$_{1-6}$alkyl, —O—C(O)—N(R$^a$)-phenyl, —N(R$^a$)—C(O)—O—C$_{1-6}$alkyl, C$_{3-6}$cycloalkyl, —C$_{1-6}$alkylene-C$_{3-6}$cycloalkyl, —O—C$_{1-6}$alkylene-C$_{3-6}$cycloalkyl, 5-6 membered heteroaryl, 4-6 membered heterocyclyl, —N(R$^a$)-4-6 membered heterocyclyl, —C$_{1-6}$alkylene-4-6 membered heterocyclyl, —O—C$_{1-6}$alkylene-4-6 membered heterocyclyl, —N(R$^a$)—C$_{1-6}$alkylene-4-6 membered heterocyclyl, —N(R$^a$)—C$_{1-6}$alkylene-5-6 membered heteroaryl and —N(R$^a$)—C$_{1-6}$alkylene-phenyl may optionally be substituted on one or more available carbons by one, two, three or more substituents each independently selected from R$^g$;

wherein if 5-6 membered heteroaryl, 4-6 membered heterocyclyl, —N(R$^a$)-4-6 membered heterocyclyl, —C$_{1-6}$alkylene-4-6 membered heterocyclyl, —O—C$_{1-6}$alkylene-4-6 membered heterocyclyl, —N(R$^a$)—C$_{1-6}$alkylene-4-6 membered heterocyclyl or —N(R$^a$)—C$_{1-6}$alkylene-5-6 membered heteroaryl contains a substitutable ring nitrogen atom, that ring nitrogen atom may optionally be substituted by R$^h$; and wherein if Z is C(H)(R$^3$), then R$^2$ is not —CH$_2$—CH$_3$;

R$^{2'}$ is selected from the group consisting of hydrogen, —NR$^a$R$^b$ and —N(R$^a$)—N(R$^b$)—C(O)-phenyl;

R$^3$ is selected from the group consisting of hydrogen, —C$_{1-6}$alkyl, —O—C$_{1-6}$alkyl, —O—C$_{1-6}$alkylene-C$_{3-6}$cycloalkyl, —N(R$^a$)—C$_{1-6}$alkyl, —N(R$^a$)—C$_{1-6}$alkylene-C$_{3-6}$cycloalkyl, —S(O)$_w$—C$_{1-6}$alkyl, —C(O)—N(R$^a$)—C$_{1-6}$alkyl, —N(R$^a$)—C(O)—C$_{1-6}$alkyl and —C$_{1-6}$alkylene-4-6 membered heterocyclyl;

wherein —C$_{1-6}$alkyl, —O—C$_{1-6}$alkyl, —O—C$_{1-6}$alkylene-C$_{3-6}$cycloalkyl, —N(R$^a$)—C$_{1-6}$alkyl, —N(R$^a$)—C$_{1-6}$alkylene-C$_{3-6}$cycloalkyl, —S(O)$_w$—C$_{1-6}$alkyl, —C(O)—N(R$^a$)—C$_{1-6}$alkyl, —N(R$^a$)—C(O)—C$_{1-6}$alkyl and —C$_{1-6}$alkylene-4-6 membered heterocyclyl may optionally be substituted on one or more available carbons by one, two, three or more substituents each independently selected from R$^g$; and wherein if —C$_{1-6}$alkylene-4-6 membered heterocyclyl contains a substitutable ring nitrogen atom, that ring nitrogen atom may optionally be substituted by R$^h$;

R$^4$ is selected from the group consisting of hydrogen, halogen, C$_{1-6}$alkyl, C$_{3-6}$cycloalkyl and —C$_{1-6}$alkylene-4-6 membered heterocyclyl;

wherein C$_{1-6}$alkyl, C$_{3-6}$cycloalkyl and —C$_{1-6}$alkylene-4-6 membered heterocyclyl may optionally be substituted on one or more available carbons by one, two, three or more substituents each independently selected from R$^g$; and wherein if —C$_{1-6}$alkylene-4-6 membered heterocyclyl contains a substitutable ring nitrogen atom, that ring nitrogen atom may optionally be substituted by R$^h$;

R$^5$ is selected from the group consisting of hydrogen, deuterium, halogen, C$_{1-6}$alkyl, C$_{3-6}$cycloalkyl and —C$_{1-6}$alkylene-4-6 membered heterocyclyl;

wherein C$_{1-6}$alkyl, C$_{3-6}$cycloalkyl and —C$_{1-6}$alkylene-4-6 membered heterocyclyl may optionally be substituted on one or more available carbons by one, two, three or more substituents each independently selected from R$^g$; and wherein if —C$_{1-6}$alkylene-4-6 membered heterocyclyl contains a substitutable ring nitrogen atom, that ring nitrogen atom may optionally be substituted by R$^h$;

R$^6$ is selected from the group consisting of hydrogen and deuterium;

R$^7$ is selected from the group consisting of hydrogen and deuterium;

R$^8$ is selected from the group consisting of hydrogen and C$_{1-6}$alkyl,

R$^g$ is independently selected for each occurrence from the group consisting of hydrogen, halogen, hydroxyl, cyano, nitro, oxo, R$^a$R$^b$N—, R$^a$R$^b$N—C(O)—, R$^a$R$^b$N—SO$_w$—, R$^a$R$^b$N—C(O)—N(R$^a$)—, C$_{1-6}$alkyl, C$_{2-6}$alkenyl, C$_{2-6}$alkynyl, C$_{3-6}$cycloalkyl, C$_{3-6}$cycloalkyl-C$_{1-6}$alkylene-, C$_{1-6}$alkoxy, C$_{3-6}$alkenyloxy, C$_{3-6}$alkynyloxy, C$_{3-6}$cycloalkoxy, C$_{1-6}$alkyl-C(O)—, C$_{1-6}$alkyl-O—C(O)—, C$_{1-6}$alkyl-C(O)—O—, C$_{1-6}$alkyl-S(O)$_w$—, C$_{1-6}$alkyl-N(R$^a$)—, C$_{1-6}$alkyl-N(R$^a$)—C(O)—, C$_{1-6}$alkyl-C(O)—N(R$^a$), C$_{1-6}$alkyl-N(R$^a$)—C(O)—N(R$^a$)—, C$_{1-6}$alkyl-N(R$^a$)—SO$_w$—, C$_{3-6}$cycloalkyl-N(R$^a$)—SO$_w$—, C$_{1-6}$alkyl-SO$_w$—N(R$^a$)—, C$_{3-6}$cycloalkyl-SO$_w$—N(R$^a$)—, C$_{1-6}$alkoxy-C(O)—N(R$^a$)—, C$_{1-6}$alkyl-C(O)—N(R$^a$)—C$_{1-6}$alkyl-, C$_{1-6}$alkyl-N(R$^a$)—C(O)—C$_{1-6}$alkyl- and C$_{1-6}$alkoxy-C$_{1-6}$alkyl-; wherein C$_{1-6}$alkyl, C$_{2-6}$alkenyl, C$_{2-6}$alkynyl, C$_{3-6}$cycloalkyl, —C$_{1-6}$alkylene-C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-C(O)—, C$_{1-6}$alkyl-O—C(O)—, C$_{1-6}$alkyl-C(O)—O—, C$_{1-6}$alkyl-S(O)$_w$—, C$_{1-6}$alkyl-N(R$^a$)—, C$_{1-6}$alkyl-N(R$^a$)—C(O)—, C$_{1-6}$alkyl-C(O)—N(R$^a$), C$_{1-6}$alkyl-N(R$^a$)—C(O)—N(R$^a$)—, C$_{1-6}$alkyl-N(R$^a$)—SO$_w$—, C$_{3-6}$cycloalkyl-N(R$^a$)—SO$_w$—, C$_{1-6}$alkyl-SO$_w$—N(R$^a$)—, C$_{3-6}$cycloalkyl-SO$_w$—N(R$^a$)—, C$_{1-6}$alkoxy-C(O)—N(R$^a$)—, C$_{1-6}$alkyl-C(O)—N(R$^a$)—C$_{1-6}$alkyl-, C$_{1-6}$alkyl-N(R$^a$)—C(O)—C$_{1-6}$alkyl- and C$_{1-6}$alkoxy-C$_{1-6}$alkyl- may optionally be substituted by one, two three or more substituents each independently selected from R$^P$;

R$^h$ is independently selected for each occurrence from the group consisting of C$_{1-6}$alkyl, C$_{3-6}$alkenyl, C$_{3-6}$alkynyl, C$_{3-6}$cycloalkyl, —C$_{1-6}$alkylene-C$_{3-6}$cycloalkyl, C$_{1-6}$alkyl-S(O)$_2$—, C$_{3-6}$cycloalkyl-S(O)$_2$—, C$_{1-6}$alkyl-C(O)—, C$_{1-6}$alkoxy-C(O)—, R$^a$R$^b$N—C(O)— and R$^a$R$^b$N—SO$_2$—; wherein C$_{1-6}$alkyl, C$_{3-6}$alkenyl, C$_{3-6}$alkynyl, C$_{3-6}$cycloalkyl, C$_{1-6}$alkyl-S(O)$_2$—, C$_{3-6}$cycloalkyl-S(O)$_2$—, C$_{1-6}$alkyl-C(O)—, C$_{1-6}$alkoxy-C(O)—, R$^a$R$^b$N—C(O)— and R$^a$R$^b$N—SO$_2$— may optionally be substituted by one, two three or more substituents each independently selected from R$^P$;

R$^P$ is independently selected for each occurrence from the group consisting of halogen, hydroxyl, cyano, $C_{1-6}$alkoxy, $C_{3-6}$cycloalkyl, $R^aR^bN-$, $R^aR^bN$-carbonyl-, $R^aR^bN-SO_2-$, and $R^aR^b$N-carbonyl-N($R^a$)—;

$R^a$ and $R^b$ are independently selected, for each occurrence, from the group consisting of hydrogen and $C_{1-6}$alkyl; wherein $C_{1-6}$alkyl may optionally be substituted by one or more substituents each independently selected from the group consisting of halogen, cyano, oxo and hydroxyl;

or $R^a$ and $R^b$ together with the nitrogen to which they are attached form a 4-6 membered heterocyclyl, wherein 4-6 membered heterocyclyl may optionally be substituted by one or more substituents each independently selected from the group consisting of halogen, cyano, oxo and hydroxyl;

$R^c$ is independently selected, for each occurrence, from the group consisting of hydroxyl, $C_{1-4}$alkyl and phenyl; and w is 0, 1 or 2.

Also disclosed herein is a compound represented by Formula (II):

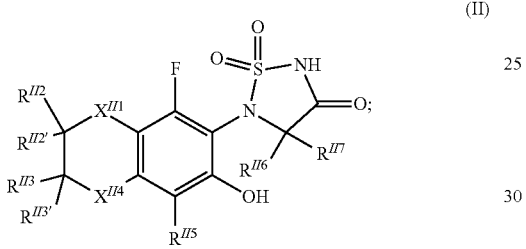

(II)

or a pharmaceutically acceptable salt thereof, wherein:

$X^{II1}$ is selected from the group consisting of O and $C(R^{II1})(R^{II1'})$;

$X^{II4}$ is selected from the group consisting of O and $C(R^{II4})(R^{II4'})$;

wherein at least one of $X^{II1}$ and $X^{II4}$ is O;

$R^{II1}$ and $R^{II1'}$ are each independently selected from the group consisting of hydrogen, halogen, $C_{1-6}$alkyl, $C_{2-6}$alkenyl, $C_{2-6}$alkynyl and $C_{3-6}$cycloalkyl;

wherein $C_{1-6}$alkyl, $C_{2-6}$alkenyl, $C_{2-6}$alkynyl and $C_{3-6}$cycloalkyl may optionally be substituted on one or more available carbons by one, two, three or more substituents each independently selected from $R^{IIg}$;

$R^{II2}$ is selected from the group consisting of hydrogen, $C_{1-6}$alkyl, $C_{2-6}$alkenyl, $C_{2-6}$alkynyl, —O—$C_{1-6}$alkyl, —N($R^{IIa}$)—$C_{1-6}$alkyl, —N($R^{IIa}$)—$C_{1-6}$alkylene-$C_{3-6}$cycloalkyl, —S(O)$_2$—$C_{1-6}$alkyl, —C(O)—N($R^{IIa}$)—$C_{1-6}$alkyl, —N($R^{IIa}$)—C(O)—$C_{1-6}$alkyl, —O—C(O)—N($R^{IIa}$)—$C_{1-6}$alkyl, —N($R^{IIa}$)—C(O)—O—$C_{1-6}$alkyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl, —$C_{1-6}$alkylene-4-6 membered heterocyclyl, —O—$C_{1-6}$alkylene-$C_{3-6}$cycloalkyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, —N($R^{IIa}$)—$C_{1-6}$alkylene-5-6 membered heteroaryl and —N($R^{IIa}$)—$C_{1-6}$alkylene-phenyl;

wherein $C_{1-6}$alkyl, $C_{2-6}$alkenyl, $C_{2-6}$alkynyl, —O—$C_{1-6}$alkyl, —N($R^{IIa}$)—$C_{1-6}$alkyl, —N($R^{IIa}$)—$C_{1-6}$alkylene-$C_{3-6}$cycloalkyl, —S(O)$_2$—$C_{1-6}$alkyl, —C(O)—N($R^{IIa}$)—$C_{1-6}$alkyl, —N($R^{IIa}$)—C(O)—$C_{1-6}$alkyl, —O—C(O)—N($R^{IIa}$)—$C_{1-6}$alkyl, —N($R^{IIa}$)—C(O)—O—$C_{1-6}$alkyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl, —$C_{1-6}$alkylene-4-6 membered heterocyclyl, —O—$C_{1-6}$alkylene-$C_{3-6}$cycloalkyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, —N($R^{IIa}$)—$C_{1-6}$alkylene-5-6 membered heteroaryl and —N($R^{IIa}$)—$C_{1-6}$alkylene-phenyl may optionally be substituted on one or more available carbons by one, two, three or more substituents each independently selected from $R^{IIg}$;

wherein if 5-6 membered heteroaryl, 4-6 membered heterocyclyl, —$C_{1-6}$alkylene-5-6 membered heteroaryl, —$C_{1-6}$alkylene-4-6 membered heterocyclyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, or —N($R^{IIa}$)—$C_{1-6}$alkylene-5-6 membered heteroaryl contains a substitutable ring nitrogen atom, that ring nitrogen atom may optionally be substituted by $R^{IIh}$; and wherein if $R^{II2}$ is —O—$C_{1-6}$alkyl, —N($R^{IIa}$)—$C_{1-6}$alkyl, —N($R^{IIa}$)—$C_{1-6}$alkylene-$C_{3-6}$cycloalkyl, —S(O)$_2$—$C_{1-6}$alkyl, —N($R^{IIa}$)—C(O)—$C_{1-6}$alkyl, —O—C(O)—N($R^{IIa}$)—$C_{1-6}$alkyl, —N($R^{IIa}$)—C(O)—O—$C_{1-6}$alkyl, —O—$C_{1-6}$alkylene-$C_{3-6}$cycloalkyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, —N($R^{IIa}$)—$C_{1-6}$alkylene-5-6 membered heteroaryl or —N($R^{IIa}$)—$C_{1-6}$alkylene-phenyl; then $X^1$ is $C(R^{II1})(R^{II1'})$ and $X^{II4}$ is O;

$R^{II2'}$ is selected from the group consisting of hydrogen, $C_{1-6}$alkyl, $C_{2-6}$alkenyl, $C_{2-6}$alkynyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl and —$C_{1-6}$alkylene-4-6 membered heterocyclyl;

wherein $C_{1-6}$alkyl, $C_{2-6}$alkenyl, $C_{2-6}$alkynyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl and —$C_{1-6}$alkylene-4-6 membered heterocyclyl may optionally be substituted on one or more available carbons by one, two, three or more substituents each independently selected from $R^{IIg}$; and wherein if 5-6 membered heteroaryl, 4-6 membered heterocyclyl, —$C_{1-6}$alkylene-5-6 membered heteroaryl or —$C_{1-6}$alkylene-4-6 membered heterocyclyl contains a substitutable ring nitrogen atom, that ring nitrogen atom may optionally be substituted by $R^{IIh}$;

$R^{II3}$ and $R^{II3'}$ are each independently selected from the group consisting of hydrogen, $C_{1-6}$alkyl, $C_{2-6}$alkenyl, $C_{2-6}$alkynyl and $C_{3-6}$cycloalkyl;

wherein $C_{1-6}$alkyl, $C_{2-6}$alkenyl, $C_{2-6}$alkynyl and $C_{3-6}$cycloalkyl may optionally be substituted on one or more available carbons by one, two, three or more substituents each independently selected from $R^{IIg}$;

$R^{II4}$ and $R^{II4'}$ are each independently selected from the group consisting of hydrogen, halogen, $C_{1-6}$alkyl, $C_{2-6}$alkenyl, $C_{2-6}$alkynyl and $C_{3-6}$cycloalkyl;

wherein $C_{1-6}$alkyl, $C_{2-6}$alkenyl, $C_{2-6}$alkynyl and $C_{3-6}$cycloalkyl may optionally be substituted on one or more available carbons by one, two, three or more substituents each independently selected from $R^{IIg}$;

$R^{II5}$ is selected from the group consisting of hydrogen, deuterium, halogen, $C_{1-6}$alkyl and $C_{3-6}$cycloalkyl;
wherein $C_{1-6}$alkyl and $C_{3-6}$cycloalkyl may optionally be substituted on one or more available carbons by one, two, three or more substituents each independently selected from $R^{IIg}$;

$R^{II6}$ is selected from the group consisting of hydrogen and deuterium;

$R^{II7}$ is selected from the group consisting of hydrogen and deuterium;

$R^{IIg}$ is independently selected for each occurrence from the group consisting of hydrogen, halogen, hydroxyl, cyano, nitro, oxo, $R^{IIa}R^{IIb}N$—, $R^{IIa}R^{IIb}N$—C(O)—, $R^{IIa}R^{IIb}N$—$SO_w$—, $R^{IIa}R^{IIb}N$—C(O)—N($R^{IIa}$)—, $C_{1-6}$alkyl, $C_{2-6}$alkenyl, $C_{2-6}$alkynyl, $C_{3-6}$cycloalkyl, $C_{3-6}$cycloalkyl-$C_{1-6}$alkylene-, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^{IIa}$)—, $C_{1-6}$alkyl-N($R^{IIa}$)—C(O)—, $C_{1-6}$alkyl-C(O)—N($R^{IIa}$), $C_{1-6}$alkyl-N($R^{IIa}$)—C(O)—N($R^{IIa}$)—, $C_{1-6}$alkyl-N($R^{IIa}$)—$SO_w$—, $C_{3-6}$cycloalkyl-N($R^{IIa}$)—$SO_w$—, $C_{1-6}$alkyl-$SO_w$—N($R^{IIa}$)—, $C_{3-6}$cycloalkyl-$SO_w$—N($R^{IIa}$)—, $C_{1-6}$alkoxy-C(O)—N($R^{IIa}$)—, $C_{1-6}$alkyl-C(O)—N($R^{IIa}$)—$C_{1-6}$alkyl-, $C_{1-6}$alkyl-N($R^{IIa}$)—C(O)—$C_{1-6}$alkyl- and $C_{1-6}$alkoxy-$C_{1-6}$alkyl-; wherein $C_{1-6}$alkyl, $C_{2-6}$alkenyl, $C_{2-6}$alkynyl, $C_{3-6}$cycloalkyl, —$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^{IIa}$)—, $C_{1-6}$alkyl-N($R^{IIa}$)—C(O)—, $C_{1-6}$alkyl-C(O)—N($R^{IIa}$), $C_{1-6}$alkyl-N($R^{IIa}$)—C(O)—N($R^{IIa}$)—, $C_{1-6}$alkyl-N($R^{IIa}$)—$SO_w$—, $C_{3-6}$cycloalkyl-N($R^{IIa}$)—$SO_w$—, $C_{1-6}$alkyl-$SO_w$—N($R^{IIa}$)—, $C_{3-6}$cycloalkyl-$SO_w$—N($R^{IIa}$)—, $C_{1-6}$alkoxy-C(O)—N($R^{IIa}$)—, $C_{1-6}$alkyl-C(O)—N($R^{IIa}$)—$C_{1-6}$alkyl-, $C_{1-6}$alkyl-N($R^{IIa}$)—C(O)—$C_{1-6}$alkyl- and $C_{1-6}$alkoxy-$C_{1-6}$alkyl- may optionally be substituted by one, two three or more substituents each independently selected from $R^{IIp}$;

$R^{IIh}$ is independently selected for each occurrence from the group consisting of $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^{IIa}R^{IIb}N$—C(O)— and $R^{IIa}R^{IIb}N$—$SO_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^{IIa}R^{IIb}N$—C(O)— and $R^{IIa}R^{IIb}N$—$SO_2$— may optionally be substituted by one, two three or more substituents each independently selected from $R^{IIp}$;

$R^{IIp}$ is independently selected for each occurrence from the group consisting of halogen, hydroxyl, cyano, $C_{1-6}$alkoxy, $C_{3-6}$cycloalkyl, $R^{IIa}R^{IIb}N$—, $R^{IIa}R^{IIb}N$-carbonyl-, $R^{IIa}R^{IIb}N$—$SO_2$—, and $R^{IIa}R^{IIb}N$-carbonyl-N($R^{IIa}$)—;

$R^{IIa}$ and $R^{IIb}$ are independently selected, for each occurrence, from the group consisting of hydrogen and $C_{1-3}$alkyl; wherein $C_{1-3}$alkyl may optionally be substituted by one or more substituents each independently selected from the group consisting of halogen, cyano, oxo and hydroxyl;

or $R^{IIa}$ and $R^{IIb}$ together with the nitrogen to which they are attached form a 4-6 membered heterocyclyl, wherein 4-6 membered heterocyclyl may optionally be substituted by one or more substituents each independently selected from the group consisting of halogen, cyano, oxo and hydroxyl; and w is 0, 1 or 2.

Further disclosed herein is a compound represented by Formula (III):

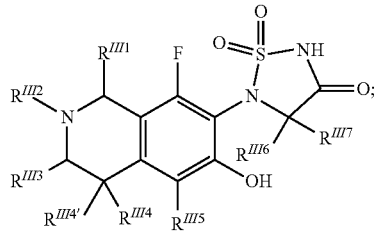

(III)

or a pharmaceutically acceptable salt thereof, wherein:

$R^{III1}$ is selected from the group consisting of hydrogen, $C_{1-6}$alkyl, $C_{2-6}$alkenyl and $C_{2-6}$alkynyl;

$R^{III2}$ is selected from the group consisting of hydrogen, $C_{1-6}$alkyl, $C_{2-6}$alkenyl, $C_{2-6}$alkynyl, $C_{3-6}$cycloalkyl, phenyl, 4-7 membered heterocyclyl, 5-6 membered heteroaryl, —$C_{1-6}$alkylene-$C_{3-8}$cycloalkyl, —$C_{1-6}$alkylene-phenyl, —$C_{1-6}$alkylene-4-7 membered heterocyclyl, —$C_{1-6}$alkylene-5-6 membered heteroaryl, —C(O)—$C_{1-6}$alkyl, —C(O)—O—$C_{1-6}$alkyl, —C(O)—$C_{1-6}$alkylene-$C_{3-8}$cycloalkyl, —C(O)—N($R^{IIIa}$)—$C_{1-6}$alkyl, —C(O)—N($R^{IIIa}$)—$C_{1-6}$alkylene-$C_{3-6}$cycloalkyl, —C(O)—N($R^{IIIa}$)—$C_{1-6}$alkylene-phenyl, —C(O)—N($R^{IIIa}$)—$C_{1-6}$alkylene-4-7 membered heterocyclyl, —C(O)—N($R^{IIIa}$)—$C_{1-6}$alkylene-5-6 membered heteroaryl, —C=N($R^{IIIa}$)—$C_{1-6}$alkyl and —S(O)$_2$—$C_{1-6}$alkyl;

wherein $C_{1-6}$alkyl, $C_{2-6}$alkenyl, $C_{2-6}$alkynyl, $C_{3-6}$cycloalkyl, phenyl, 4-7 membered heterocyclyl, 5-6 membered heteroaryl, —$C_{1-6}$alkylene-$C_{3-8}$cycloalkyl, —$C_{1-6}$alkylene-phenyl, —$C_{1-6}$alkylene-4-7 membered heterocyclyl, —$C_{1-6}$alkylene-5-6 membered heteroaryl, —C(O)—$C_{1-6}$alkyl, —C(O)—O—$C_{1-6}$alkyl, —C(O)—$C_{1-6}$alkylene-$C_{3-8}$cycloalkyl, —C(O)—N($R^{IIIa}$)—$C_{1-6}$alkyl, —C(O)—N($R^{IIIa}$)—$C_{1-6}$alkylene-$C_{3-6}$cycloalkyl, —C(O)—N($R^{IIIa}$)—$C_{1-6}$alkylene-phenyl, —C(O)—N($R^{IIIa}$)—$C_{1-6}$alkylene-4-7 membered heterocyclyl, —C(O)—N($R^{IIIa}$)—$C_{1-6}$alkylene-5-6 membered heteroaryl, —C=N($R^{IIIa}$)—$C_{1-6}$alkyl and —S(O)$_2$—$C_{1-6}$alkyl may optionally be substituted on one or more available carbons by one, two, three or more substituents each independently selected from $R^{IIg}$; and wherein if 4-7 membered heterocyclyl, 5-6 membered heteroaryl, —$C_{1-6}$alkylene-4-7 membered heterocyclyl, —$C_{1-6}$alkylene-5-6 membered heterocyclyl, —C(O)—N($R^{IIIa}$)—$C_{1-6}$alkylene-4-7 membered heterocyclyl or —C(O)—N($R^{IIIa}$)—$C_{1-6}$alkylene-5-6 membered heteroaryl contains a substitutable ring nitrogen atom, that ring nitrogen atom may optionally be substituted by $R^{IIIh}$;

$R^{III3}$ is selected from the group consisting of hydrogen, $C_{1-6}$alkyl, $C_{2-6}$alkenyl and $C_{2-6}$alkynyl;

$R^{III4}$ is selected from the group consisting of hydrogen, halogen, $C_{1-6}$alkyl, $C_{2-6}$alkenyl and $C_{2-6}$alkynyl;

$R^{III4'}$ is selected from the group consisting of hydrogen, halogen, $C_{1-6}$alkyl, $C_{2-6}$alkenyl and $C_{2-6}$alkynyl;

$R^{IIIS}$ is selected from the group consisting of hydrogen, halogen and $C_{1-6}$alkyl;

$R^{III6}$ is selected from the group consisting of hydrogen and deuterium;

$R^{III7}$ is selected from the group consisting of hydrogen and deuterium;

$R^{IIIg}$ is independently selected for each occurrence from the group consisting of hydrogen, halogen, hydroxyl, cyano, nitro, oxo, $R^{IIa}R^{IIb}N$—, $R^{IIIa}R^{IIIb}N$—C(O)—, $R^{IIIa\,IIIb}N$—$SO_w$—, $R^{IIa}R^{IIIb}N$—C(O)—N($R^{IIIa}$)—, $C_{1-6}$alkyl, $C_{2-6}$alkenyl, $C_{2-6}$alkynyl, $C_{3-6}$cycloalkyl, $C_{3-6}$cycloalkyl-$C_{1-6}$alkylene-, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^{IIa}$)—, $C_{1-6}$alkyl-N($R^{IIIa}$)—C(O)—, $C_{1-6}$alkyl-C(O)—N($R^{IIIa}$), $C_{1-6}$alkyl-N($R^{IIIa}$)—C(O)—N($R^{IIIa}$)—, $C_{1-6}$alkyl-N($R^{IIIa}$)—$SO_w$—, $C_{3-6}$cycloalkyl-N($R^{IIIa}$)—$SO_w$—, $C_{1-6}$alkyl-$SO_w$—N($R^{IIIa}$)—, $C_{3-6}$cycloalkyl-$SO_w$—N($R^{IIIa}$)—, $C_{1-6}$alkoxy-C(O)—N($R^{IIIa}$)—, $C_{1-6}$alkyl-C(O)—N($R^{IIIa}$)—$C_{1-6}$alkyl-, $C_{1-6}$alkyl-N($R^{IIIa}$)C(O)—$C_{1-6}$alkyl-, $C_{1-6}$alkoxy-$C_{1-6}$alkyl- and 5-6 membered heteroaryl; wherein $C_{1-6}$alkyl, $C_{2-6}$alkenyl, $C_{2-6}$alkynyl, $C_{3-6}$cycloalkyl, —$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^{IIIa}$)—, $C_{1-6}$alkyl-N($R^{IIIa}$)—C(O)—, $C_{1-6}$alkyl-C(O)—N($R^{IIa}$), $C_{1-6}$alkyl-N($R^{IIa}$)—C(O)—N($R^{IIIa}$)—, $C_{1-6}$alkyl-N($R^{IIIa}$)—$SO_w$—, $C_{3-6}$cycloalkyl-N($R^{IIIa}$)—$SO_w$—, $C_{1-6}$alkyl-$SO_w$—N($R^{IIIa}$)—, $C_{3-6}$cycloalkyl-$SO_w$—N($R^{IIIa}$)—, $C_{1-6}$alkoxy-C(O)—N($R^{IIIa}$)—, $C_{1-6}$alkyl-C(O)—N($R^{IIa}$)—$C_{1-6}$alkyl-, $C_{1-6}$alkyl-N($R^{IIIa}$)—C(O)—$C_{1-6}$alkyl-, $C_{1-6}$alkoxy-$C_{1-6}$alkyl- and 5-6 membered heteroaryl may optionally be substituted by one, two three or more substituents each independently selected from $R^{IIIp}$;

$R^{IIIh}$ is independently selected for each occurrence from the group consisting of $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^{IIIa}R^{IIIb}N$—C(O)—, $R^{IIIa}R^{IIIb}N$—$SO_2$— and —$C_{1-6}$alkylene-5-6 membered heteroaryl; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^{IIIa}R^{IIIb}N$—C(O)—, $R^{IIIa}R^{IIIb}N$—$SO_2$— and —$C_{1-6}$alkylene-5-6 membered heteroaryl may optionally be substituted by one, two three or more substituents each independently selected from $R^{IIIp}$;

$R^{IIIp}$ is independently selected for each occurrence from the group consisting of halogen, hydroxyl, cyano, $C_{1-6}$alkoxy, $C_{3-6}$cycloalkyl, $R^{IIIa}R^{IIIb}N$—, $R^{IIIa}R^{IIIb}N$-carbonyl-, $R^{IIIa}R^{IIIb}N$—$SO_2$—, and $R^{IIIa}R^{IIIb}N$-carbonyl-N($R^{IIIa}$)—;

$R^{IIIa}$ and $R^{IIIb}$ are independently selected, for each occurrence, from the group consisting of hydrogen and $C_{1-3}$alkyl; wherein $C_{1-3}$alkyl may optionally be substituted by one or more substituents each independently selected from the group consisting of halogen, cyano, oxo and hydroxyl;

or $R^{IIIa}$ and $R^{IIIb}$ together with the nitrogen to which they are attached form a 4-6 membered heterocyclyl; wherein 4-6 membered heterocyclyl may optionally be substituted by one or more substituents each independently selected from the group consisting of halogen, cyano, oxo and hydroxyl; and w is 0, 1 or 2.

Further disclosed herein is a compound selected from the group consisting of:

5-[1-fluoro-3-hydroxy-7-(3-methylbutoxy)-5,6,7,8-tetrahydronaphthalen-2-yl]-1$\lambda^6$,2,5-thiadiazolidine-1,1,3-trione;

5-{7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione;

5-{1-fluoro-3-hydroxy-7-[(3-methylbutyl)amino]-5,6,7,8-tetrahydronaphthalen-2-yl}-1$\lambda^6$,2,5-thiadiazolidine-1,1,3-trione;

5-{7-[(cyclopropylmethyl)amino]-1-fluoro-3-hydroxy-5,6,7,8-tetrahydronaphthalen-2-yl}-1$\lambda^6$,2,5-thiadiazolidine-1,1,3-trione;

5-[(7R)-1-fluoro-3-hydroxy-7-methoxy-5,6,7,8-tetrahydronaphthalen-2-yl]-1$\lambda^6$,2,5-thiadiazolidine-1,1,3-trione;

5-[7-(2-cyclopropylethyl)-1-fluoro-3-hydroxy-5,6,7,8-tetrahydronaphthalen-2-yl]-1$\lambda^6$,2,5-thiadiazolidine-1,1,3-trione;

5-[1-fluoro-3-hydroxy-7-(2-methoxyethoxy)-5,6,7,8-tetrahydronaphthalen-2-yl]-1$\lambda^6$,2,5-thiadiazolidine-1,1,3-trione;

5-[7-(cyclopropylmethoxy)-1-fluoro-3-hydroxy-5,6,7,8-tetrahydronaphthalen-2-yl]-1$\lambda^6$,2,5-thiadiazolidine-1,1,3-trione;

5-(1-fluoro-3-hydroxy-5,6,7,8-tetrahydronaphthalen-2-yl)-1$\lambda^6$,2,5-thiadiazolidine-1,1,3-trione;

5-[(7S)-1-fluoro-3-hydroxy-7-methoxy-5,6,7,8-tetrahydronaphthalen-2-yl]-1$\lambda^6$,2,5-thiadiazolidine-1,1,3-trione;

5-(1-fluoro-3-hydroxy-7-methoxy-5,6,7,8-tetrahydronaphthalen-2-yl)-1$\lambda^6$,2,5-thiadiazolidine-1,1,3-trione;

5-(5-fluoro-7-hydroxy-3,4-dihydro-2H-1-benzopyran-6-yl)-1$\lambda^6$,2,5-thiadiazolidine-1,1,3-trione;

5-(5-fluoro-7-hydroxy-2,2-dimethyl-3,4-dihydro-2H-1-benzopyran-6-yl)-1$\lambda^6$,2,5-thiadiazolidine-1,1,3-trione;

5-(8-fluoro-6-hydroxy-2,2-dimethyl-3,4-dihydro-2H-1-benzopyran-7-yl)-1$\lambda^6$,2,5-thiadiazolidine-1,1,3-trione;

5-(1,4-difluoro-3-hydroxy-7-methoxy-5,6,7,8-tetrahydronaphthalen-2-yl)-1$\lambda^6$,2,5-thiadiazolidine-1,1,3-trione;

5-(7-{[2-(azetidin-1-yl)ethyl]amino}-1-fluoro-3-hydroxy-5,6,7,8-tetrahydronaphthalen-2-yl)-1$\lambda^6$,2,5-thiadiazolidine-1,1,3-trione;

5-{1-fluoro-3-hydroxy-7-[(3,3,3-trifluoropropyl)amino]-5,6,7,8-tetrahydronaphthalen-yl}-1$\lambda^6$,2,5-thiadiazolidine-1,1,3-trione;

5-{(7S)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione;

5-{(7R)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione;

5-{7-[(3,3-difluorocyclobutyl)methoxy]-1-fluoro-3-hydroxy-5,6,7,8-tetrahydronaphthalen-2-yl}-1$\lambda^6$,2,5-thiadiazolidine-1,1,3-trione;

5-{1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione;

5-{1-fluoro-3-hydroxy-7-[(4-methoxy-3,3-dimethylbutyl)amino]-5,6,7,8-tetrahydronaphthalen-2-yl}-1$\lambda^6$,2,5-thiadiazolidine-1,1,3-trione;

5-{1-fluoro-3-hydroxy-7-[(3-methoxy-3-methylbutyl)amino]-5,6,7,8-tetrahydronaphthalen-2-yl}-1$\lambda^6$,2,5-thiadiazolidine-1,1,3-trione;

5-{1-fluoro-3-hydroxy-7-[(4,4,4-trifluoro-3,3-dimethylbutyl)amino]-5,6,7,8-tetrahydronaphthalen-2-yl}-1$\lambda^6$,2,5-thiadiazolidine-1,1,3-trione;

5-[1-fluoro-3-hydroxy-7-({2-[1-(trifluoromethyl)cyclopropyl]ethyl}amino)-5,6,7,8-tetrahydronaphthalen-2-yl]-1$\lambda^6$,2,5-thiadiazolidine-1,1,3-trione;

5-{7-[(2,2-difluoro-2-phenylethyl)amino]-1-fluoro-3-hydroxy-5,6,7,8-tetrahydronaphthalen-2-yl}-1$\lambda^6$,2,5-thiadiazolidine-1,1,3-trione;

5-{7-[(3-cyclopropyl-2,2-difluoropropyl)amino]-1-fluoro-3-hydroxy-5,6,7,8-tetrahydronaphthalen-2-yl}-1$\lambda^6$,2,5-thiadiazolidine-1,1,3-trione;

5-{1-fluoro-3-hydroxy-7-[(3-hydroxy-3-methylbutyl)amino]-5,6,7,8-tetrahydronaphthalen-2-yl}-1$\lambda^6$,2,5-thiadiazolidine-1,1,3-trione;

5-{1-fluoro-3-hydroxy-7-[methyl(3-methylbutyl)amino]-5,6,7,8-tetrahydronaphthalen-2-yl}-1$\lambda^6$,2,5-thiadiazolidine-1,1,3-trione;

5-{1-fluoro-3-hydroxy-7-[(4-methylpentyl)amino]-5,6,7,8-tetrahydronaphthalen-2-yl}-1$\lambda^6$,2,5-thiadiazolidine-1,1,3-trione;

5-(1-fluoro-3-hydroxy-7-{[4,4,4-trifluoro-3-hydroxy-3-(trifluoromethyl)butyl]amino}-5,6,7,8-tetrahydronaphthalen-2-yl)-1$\lambda^6$,2,5-thiadiazolidine-1,1,3-trione;

5-(1-fluoro-3-hydroxy-7-{[4,4,4-trifluoro-3-(trifluoromethyl)butyl]amino}-5,6,7,8-tetrahydronaphthalen-2-yl)-1$\lambda^6$,2,5-thiadiazolidine-1,1,3-trione;

5-{7-[(2,2-difluoropropyl)amino]-1-fluoro-3-hydroxy-5,6,7,8-tetrahydronaphthalen-2-yl}-1$\lambda^6$,2,5-thiadiazolidine-1,1,3-trione;

5-{(7R)-7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione;

5-{(7S)-7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione;

5-(1-fluoro-3-hydroxy-7-{[2-(pyridin-2-yl)ethyl]amino}-5,6,7,8-tetrahydronaphthalen-2-yl)-1$\lambda^6$,2,5-thiadiazolidine-1,1,3-trione;

5-{(7RS)-1-fluoro-3-hydroxy-7-[(3RS)-pyrrolidin-3-yl]-5,6,7,8-tetrahydronaphthalen-2-yl}-1$\lambda^6$,2,5-thiadiazolidine-1,1,3-trione;

5-{(7RS)-7-[(3RS)-1-(cyclopropanesulfonyl)pyrrolidin-3-yl]-1-fluoro-3-hydroxy-5,6,7,8-tetrahydronaphthalen-2-yl}-1$\lambda^6$,2,5-thiadiazolidine-1,1,3-trione;

5-{(7RS)-1-fluoro-3-hydroxy-7-[(3SR)-pyrrolidin-3-yl]-5,6,7,8-tetrahydronaphthalen-2-yl}-1$\lambda^6$,2,5-thiadiazolidine-1,1,3-trione;

5-{(7RS)-7-[(3SR)-1-(cyclopropanesulfonyl)pyrrolidin-3-yl]-1-fluoro-3-hydroxy-5,6,7,8-tetrahydronaphthalen-2-yl}-1$\lambda^6$,2,5-thiadiazolidine-1,1,3-trione;

5-{7-[1-(cyclopropylmethyl)pyrrolidin-3-yl]-1-fluoro-3-hydroxy-5,6,7,8-tetrahydronaphthalen-2-yl}-1$\lambda^6$,2,5-thiadiazolidine-1,1,3-trione;

5-(1-fluoro-3-hydroxy-7-{[2-(1H-pyrazol-1-yl)ethyl]amino}-5,6,7,8-tetrahydronaphthalen-2-yl)-1$\lambda^6$,2,5-thiadiazolidine-1,1,3-trione;

5-[1-fluoro-3-hydroxy-7-(4,4,4-trifluorobutoxy)-5,6,7,8-tetrahydronaphthalen-2-yl]-1$\lambda^6$,2,5-thiadiazolidine-1,1,3-trione;

5-(8-fluoro-6-hydroxy-1,2,3,4-tetrahydroisoquinolin-7-yl)-1$\lambda^6$,2,5-thiadiazolidine-1,1,3-trione;

5-[8-fluoro-6-hydroxy-2-(4-methylpentanoyl)-1,2,3,4-tetrahydroisoquinolin-7-yl]-1$\lambda^6$,2,5-thiadiazolidine-1,1,3-trione;

5-[8-fluoro-6-hydroxy-2-(4-methylpentyl)-1,2,3,4-tetrahydroisoquinolin-7-yl]-1$\lambda^6$,2,5-thiadiazolidine-1,1,3-trione;

5-{(7R)-1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione;

5-{(7S)-1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione;

5-[(7R)-1-fluoro-3-hydroxy-7-({2-[1-(trifluoromethyl)cyclopropyl]ethyl}amino)-5,6,7,8-tetrahydronaphthalen-2-yl]-1$\lambda^6$,2,5-thiadiazolidine-1,1,3-trione;

8-fluoro-6-hydroxy-7-(1,1,4-trioxo-1$\lambda^6$,2,5-thiadiazolidin-2-yl)-1,2,3,4-tetrahydronaphthalen-2-yl phenylcarbamate;

4-{[8-fluoro-6-hydroxy-7-(1,1,4-trioxo-1$\lambda^6$,2,5-thiadiazolidin-2-yl)-1,2,3,4-tetrahydronaphthalen-2-yl]amino}-2,2-dimethylbutanenitrile;

5-{1-fluoro-3-hydroxy-7-[(4,4,4-trifluoro-3-hydroxybutyl)amino]-5,6,7,8-tetrahydronaphthalen-2-yl}-1$\lambda^6$,2,5-thiadiazolidine-1,1,3-trione;

5-{1-fluoro-3-hydroxy-7-[(4,4,4-trifluoro-3-methoxybutyl)amino]-5,6,7,8-tetrahydronaphthalen-2-yl}-1$\lambda^6$,2,5-thiadiazolidine-1,1,3-trione;

5-[8-fluoro-6-hydroxy-2-(5,5,5-trifluoropentyl)-1,2,3,4-tetrahydroisoquinolin-7-yl]-1$\lambda^6$,2,5-thiadiazolidine-1,1,3-trione;

5-(1-fluoro-3-hydroxy-7-{(3-methylbutyl)[(pyridin-2-yl)methyl]amino}-5,6,7,8-tetrahydronaphthalen-2-yl)-1$\lambda^6$,2,5-thiadiazolidine-1,1,3-trione;

5-(1-fluoro-3-hydroxy-7-{[(pyridin-2-yl)methyl]amino}-5,6,7,8-tetrahydronaphthalen-2-yl)-1$\lambda^6$,2,5-thiadiazolidine-1,1,3-trione;

5-{1-fluoro-3-hydroxy-7-[(4,4,4-trifluoro-2-hydroxybutyl)amino]-5,6,7,8-tetrahydronaphthalen-2-yl}-1$\lambda^6$,2,5-thiadiazolidine-1,1,3-trione;

5-(7-{[2-(difluoromethoxy)ethyl]amino}-1-fluoro-3-hydroxy-5,6,7,8-tetrahydronaphthalen-2-yl)-1$\lambda^6$,2,5-thiadiazolidine-1,1,3-trione;

5-(8-fluoro-6-hydroxy-2-pentanimidoyl-1,2,3,4-tetrahydroisoquinolin-7-yl)-1$\lambda^6$,2,5-thiadiazolidine-1,1,3-trione;

5-[2-(3-cyclopropylpropyl)-8-fluoro-6-hydroxy-1,2,3,4-tetrahydroisoquinolin-7-yl]-1$\lambda^6$,2,5-thiadiazolidine-1,1,3-trione;

5-[2-(2-azaspiro[3.3]heptan-6-yl)-8-fluoro-6-hydroxy-1,2,3,4-tetrahydroisoquinolin-7-yl]-1$\lambda^6$,2,5-thiadiazolidine-1,1,3-trione;

5-[8-fluoro-6-hydroxy-2-(6,6,6-trifluorohexyl)-1,2,3,4-tetrahydroisoquinolin-7-yl]-1$\lambda^6$,2,5-thiadiazolidine-1,1,3-trione;

5-{2-[(3,3-difluorocyclobutyl)methyl]-8-fluoro-6-hydroxy-1,2,3,4-tetrahydroisoquinolin-7-yl}-1$\lambda^6$,2,5-thiadiazolidine-1,1,3-trione;

5-[2-(azetidin-3-yl)-8-fluoro-6-hydroxy-1,2,3,4-tetrahydroisoquinolin-7-yl]-1$\lambda^6$,2,5-thiadiazolidine-1,1,3-trione;

5-(8-fluoro-6-hydroxy-2-{2-[(propan-2-yl)amino]ethyl})-1,2,3,4-tetrahydroisoquinolin-7-yl)-1$\lambda^6$,2,5-thiadiazolidine-1,1,3-trione;

5-{2-[(azetidin-3-yl)methyl]-8-fluoro-6-hydroxy-1,2,3,4-tetrahydroisoquinolin-7-yl}-1$\lambda^6$,2,5-thiadiazolidine-1,1,3-trione;

5-{2-[(azetidin-3-yl)methyl]-8-fluoro-6-hydroxy-1,2,3,4-tetrahydroisoquinolin-7-yl}-1$\lambda^6$,2,5-thiadiazolidine-1,1,3-trione;

5-(1-fluoro-3-hydroxy-7-{(3-methylbutyl)[2-(pyridin-2-yl)ethyl]amino}-5,6,7,8-tetrahydronaphthalen-2-yl)-1$\lambda^6$,2,5-thiadiazolidine-1,1,3-trione;

5-{8-fluoro-6-hydroxy-2-[(spiro[2.3]hexan-5-yl)methyl]-1,2,3,4-tetrahydroisoquinolin-7-yl}-1$\lambda^6$,2,5-thiadiazolidine-1,1,3-trione;

5-(1-fluoro-3-hydroxy-7-{[2-(trifluoromethoxy)ethyl]amino}-5,6,7,8-tetrahydronaphthalen-2-yl)-1λ⁶,2,5-thiadiazolidine-1,1,3-trione;

5-[8-fluoro-6-hydroxy-2-(3-hydroxy-3-methylbutyl)-1,2,3,4-tetrahydroisoquinolin-7-yl]-1λ⁶,2,5-thiadiazolidine-1,1,3-trione;

3-hydroxybutyl 8-fluoro-6-hydroxy-7-(1,1,4-trioxo-1λ⁶,2,5-thiadiazolidin-2-yl)-3,4-dihydroisoquinoline-2(1H)-carboxylate;

5-{1-fluoro-3-hydroxy-7-[3-(propan-2-yl)pyrrolidin-1-yl]-5,6,7,8-tetrahydronaphthalen-2-yl}-1λ⁶,2,5-thiadiazolidine-1,1,3-trione;

5-{7-[(2-cyclohexylethyl)amino]-1-fluoro-3-hydroxy-5,6,7,8-tetrahydronaphthalen-2-yl}-1λ⁶,2,5-thiadiazolidine-1,1,3-trione;

5-{7-[(3,3-dimethylbutyl)amino]-1-fluoro-3-hydroxy-5,6,7,8-tetrahydronaphthalen-2-yl}-1λ⁶,2,5-thiadiazolidine-1,1,3-trione;

5-[7-(butylamino)-1-fluoro-3-hydroxy-5,6,7,8-tetrahydronaphthalen-2-yl]-1λ⁶,2,5-thiadiazolidine-1,1,3-trione;

5-{(7S)-1-fluoro-3-hydroxy-7-[(4,4,4-trifluoro-3,3-dimethylbutyl)amino]-5,6,7,8-tetrahydronaphthalen-2-yl}-1λ⁶,2,5-thiadiazolidine-1,1,3-trione;

5-{(7R)-1-fluoro-3-hydroxy-7-[(4,4,4-trifluoro-3,3-dimethylbutyl)amino]-5,6,7,8-tetrahydronaphthalen-2-yl}-1λ⁶,2,5-thiadiazolidine-1,1,3-trione;

5-{7-[(2-cyclopentylethyl)amino]-1-fluoro-3-hydroxy-5,6,7,8-tetrahydronaphthalen-2-yl}-1λ⁶,2,5-thiadiazolidine-1,1,3-trione;

5-[2-(2-cyclohexylethyl)-8-fluoro-6-hydroxy-1,2,3,4-tetrahydroisoquinolin-7-yl]-1λ⁶,2,5-thiadiazolidine-1,1,3-trione;

5-{1-fluoro-3-hydroxy-7-[(2-hydroxyethyl)amino]-5,6,7,8-tetrahydronaphthalen-2-yl}-1λ⁶,2,5-thiadiazolidine-1,1,3-trione;

5-{1-fluoro-3-hydroxy-7-[2-(propan-2-yl)morpholin-4-yl]-5,6,7,8-tetrahydronaphthalen-2-yl}-1λ⁶,2,5-thiadiazolidine-1,1,3-trione;

5-{1-fluoro-3-hydroxy-7-[(2R)-2-(propan-2-yl)morpholin-4-yl]-5,6,7,8-tetrahydronaphthalen-2-yl}-1λ⁶,2,5-thiadiazolidine-1,1,3-trione;

5-{8-fluoro-6-hydroxy-2-[(pyrrolidin-2-yl)methyl]-1,2,3,4-tetrahydroisoquinolin-7-yl}-1λ⁶,2,5-thiadiazolidine-1,1,3-trione;

5-{8-fluoro-6-hydroxy-2-[(pyridin-2-yl)methyl]-1,2,3,4-tetrahydroisoquinolin-7-yl}-1λ⁶,2,5-thiadiazolidine-1,1,3-trione;

5-{7-[(2-cyclobutylethyl)amino]-1-fluoro-3-hydroxy-5,6,7,8-tetrahydronaphthalen-2-yl}-1λ⁶,2,5-thiadiazolidine-1,1,3-trione;

5-{1-fluoro-3-hydroxy-7-({2-[(propan-2-yl)oxy]ethyl}amino)-5,6,7,8-tetrahydronaphthalen-2-yl}-1λ⁶,2,5-thiadiazolidine-1,1,3-trione;

5-{1-fluoro-3-hydroxy-7-[(2-hydroxy-3-methylbutyl)amino]-5,6,7,8-tetrahydronaphthalen-2-yl}-1λ⁶,2,5-thiadiazolidine-1,1,3-trione;

5-{7-[(2-cyclopropyl-2-hydroxyethyl)amino]-1-fluoro-3-hydroxy-5,6,7,8-tetrahydronaphthalen-2-yl}-1λ⁶,2,5-thiadiazolidine-1,1,3-trione;

5-(1-fluoro-3-hydroxy-7-{[3-(trimethylsilyl)propyl]amino}-5,6,7,8-tetrahydronaphthalen-2-yl)-1λ⁶,2,5-thiadiazolidine-1,1,3-trione;

5-[1-fluoro-3-hydroxy-7-({3-[hydroxy(dimethyl)silyl]propyl}amino)-5,6,7,8-tetrahydronaphthalen-2-yl]-1λ⁶,2,5-thiadiazolidine-1,1,3-trione;

5-[8-fluoro-6-hydroxy-2-(pyridin-2-yl)-1,2,3,4-tetrahydroisoquinolin-7-yl]-1λ⁶,2,5-thiadiazolidine-1,1,3-trione;

5-{2-[2-(3,3-difluorocyclobutyl)ethyl]-8-fluoro-6-hydroxy-1,2,3,4-tetrahydroisoquinolin-7-yl}-1λ⁶,2,5-thiadiazolidine-1,1,3-trione;

5-{8-fluoro-6-hydroxy-2-[2-(pyrrolidin-1-yl)ethyl]-1,2,3,4-tetrahydroisoquinolin-7-yl}-1λ⁶,2,5-thiadiazolidine-1,1,3-trione;

5-{2-[2-(3,5-dimethyl-1H-pyrazol-4-yl)ethyl]-8-fluoro-6-hydroxy-1,2,3,4-tetrahydroisoquinolin-7-yl}-1λ⁶,2,5-thiadiazolidine-1,1,3-trione;

N-[8-fluoro-6-hydroxy-7-(1,1,4-trioxo-1λ⁶,2,5-thiadiazolidin-2-yl)-1,2,3,4-tetrahydronaphthalen-2-yl]-3-methylbutanimidamide;

5-{8-fluoro-6-hydroxy-2-[3-(oxan-4-yl)propyl]-1,2,3,4-tetrahydroisoquinolin-7-yl}-1λ⁶,2,5-thiadiazolidine-1,1,3-trione;

5-[1-fluoro-3-hydroxy-7-(3-hydroxy-3-methylbutoxy)-5,6,7,8-tetrahydronaphthalen-2-yl]-1λ⁶,2,5-thiadiazolidine-1,1,3-trione;

5-[(7R)-7-amino-1-fluoro-3-hydroxy-5,6,7,8-tetrahydronaphthalen-2-yl]-1λ⁶,2,5-thiadiazolidine-1,1,3-trione;

5-{(7R)-7-[(4,4-difluorobutyl)amino]-1-fluoro-3-hydroxy-5,6,7,8-tetrahydronaphthalen-2-yl}-1λ⁶,2,5-thiadiazolidine-1,1,3-trione;

5-{(7R)-7-[(2-cyclopentylethyl)amino]-1-fluoro-3-hydroxy-5,6,7,8-tetrahydronaphthalen-2-yl}-1λ⁶,2,5-thiadiazolidine-1,1,3-trione;

5-{(7R)-7-[(2-cyclobutylethyl)amino]-1-fluoro-3-hydroxy-5,6,7,8-tetrahydronaphthalen-2-yl}-1λ⁶,2,5-thiadiazolidine-1,1,3-trione;

5-[(7R)-7-{[2-(3,3-difluorocyclobutyl)ethyl]amino}-1-fluoro-3-hydroxy-5,6,7,8-tetrahydronaphthalen-2-yl]-1λ⁶,2,5-thiadiazolidine-1,1,3-trione;

5-{(7R)-1-fluoro-3-hydroxy-7-[(3-methylpentyl)amino]-5,6,7,8-tetrahydronaphthalen-2-yl}-1λ⁶,2,5-thiadiazolidine-1,1,3-trione;

5-{(7R)-7-[(3-ethylpentyl)amino]-1-fluoro-3-hydroxy-5,6,7,8-tetrahydronaphthalen-2-yl}-1λ⁶,2,5-thiadiazolidine-1,1,3-trione;

8-fluoro-6-hydroxy-N-(3-methylbutyl)-7-(1,1,4-trioxo-1λ⁶,2,5-thiadiazolidin-2-yl)-3,4-dihydroisoquinoline-2(1H)-carboxamide;

8-fluoro-6-hydroxy-N-(2-methylpropyl)-7-(1,1,4-trioxo-1λ⁶,2,5-thiadiazolidin-2-yl)-3,4-dihydroisoquinoline-2(1H)-carboxamide;

5-{8-fluoro-6-hydroxy-2-[3-(pyridin-3-yl)propyl]-1,2,3,4-tetrahydroisoquinolin-7-yl}-1λ⁶,2,5-thiadiazolidine-1,1,3-trione;

5-{2-[(3,5-dimethyl-1,2-oxazol-4-yl)methyl]-8-fluoro-6-hydroxy-1,2,3,4-tetrahydroisoquinolin-7-yl}-1λ⁶,2,5-thiadiazolidine-1,1,3-trione;

5-{8-fluoro-6-hydroxy-2-[2-(1,3,5-trimethyl-1H-pyrazol-4-yl)ethyl]-1,2,3,4-tetrahydroisoquinolin-7-yl}-1λ⁶,2,5-thiadiazolidine-1,1,3-trione;

5-{8-fluoro-6-hydroxy-2-[2-(pyrimidin-5-yl)ethyl]-1,2,3,4-tetrahydroisoquinolin-7-yl}-1λ⁶,2,5-thiadiazolidine-1,1,3-trione;

5-{2-[2-(3,5-dimethyl-1,2-oxazol-4-yl)ethyl]-8-fluoro-6-hydroxy-1,2,3,4-tetrahydroisoquinolin-7-yl}-1λ⁶,2,5-thiadiazolidine-1,1,3-trione;

5-{2-[(3,5-dimethyl-1H-pyrazol-4-yl)methyl]-8-fluoro-6-hydroxy-1,2,3,4-tetrahydroisoquinolin-7-yl}-1λ⁶,2,5-thiadiazolidine-1,1,3-trione;

5-{8-fluoro-6-hydroxy-2-[(1,3,5-trimethyl-1H-pyrazol-4-yl)methyl]-1,2,3,4-tetrahydroisoquinolin-7-yl}-1λ⁶,2,5-thiadiazolidine-1,1,3-trione;

5-{8-fluoro-6-hydroxy-2-[2-(oxan-4-yl)ethyl]-1,2,3,4-tetrahydroisoquinolin-7-yl}-1$\lambda^6$,2,5-thiadiazolidine-1,1,3-trione;
5-[2-(2-cyclohexyl-2-hydroxyethyl)-8-fluoro-6-hydroxy-1,2,3,4-tetrahydroisoquinolin-7-yl]-1$\lambda^6$,2,5-thiadiazolidine-1,1,3-trione;
5-[8-fluoro-6-hydroxy-2-(2-methoxyethyl)-1,2,3,4-tetrahydroisoquinolin-7-yl]-1$\lambda^6$,2,5-thiadiazolidine-1,1,3-trione;
5-[8-fluoro-6-hydroxy-2-(3-methoxypropyl)-1,2,3,4-tetrahydroisoquinolin-7-yl]-1$\lambda^6$,2,5-thiadiazolidine-1,1,3-trione;
5-[2-(3-aminopropyl)-8-fluoro-6-hydroxy-1,2,3,4-tetrahydroisoquinolin-7-yl]-1$\lambda^6$,2,5-thiadiazolidine-1,1,3-trione;
5-{8-fluoro-6-hydroxy-2-[3-(piperidin-4-yl)propyl]-1,2,3,4-tetrahydroisoquinolin-7-yl}-1$\lambda^6$,2,5-thiadiazolidine-1,1,3-trione;
5-[8-fluoro-6-hydroxy-2-(3-methylbutyl)-1,2,3,4-tetrahydroisoquinolin-7-yl]-1$\lambda^6$,2,5-thiadiazolidine-1,1,3-trione;
tert-butyl 8-fluoro-6-hydroxy-7-(1,1,4-trioxo-1$\lambda^6$,2,5-thiadiazolidin-2-yl)-3,4-dihydroisoquinoline-2(1H)-carboxylate;
5-{8-fluoro-6-hydroxy-2-[(7-oxabicyclo[2.2.1]heptan-2-yl)methyl]-1,2,3,4-tetrahydroisoquinolin-7-yl}-1$\lambda^6$,2,5-thiadiazolidine-1,1,3-trione;
5-{7-[(3,3-difluoropropyl)amino]-1-fluoro-3-hydroxy-5,6,7,8-tetrahydronaphthalen-2-yl}-1$\lambda^6$,2,5-thiadiazolidine-1,1,3-trione;
5-(8-fluoro-6-hydroxy-2-{1-[(1,3,5-trimethyl-1H-pyrazol-4-yl)methyl]azetidin-3-yl}-1,2,3,4-tetrahydroisoquinolin-7-yl)-1$\lambda^6$,2,5-thiadiazolidine-1,1,3-trione;
5-{8-fluoro-6-hydroxy-2-[2-(7-oxabicyclo[2.2.1]heptan-2-yl)ethyl]-1,2,3,4-tetrahydroisoquinolin-7-yl}-1$\lambda^6$,2,5-thiadiazolidine-1,1,3-trione;
5-(2-{2-[1-(2,2-difluoroethyl)-3,5-dimethyl-1H-pyrazol-4-yl]ethyl}-4,4,8-trifluoro-6-hydroxy-1,2,3,4-tetrahydroisoquinolin-7-yl)-1$\lambda^6$,2,5-thiadiazolidine-1,1,3-trione;
5-(4-{[8-fluoro-6-hydroxy-7-(1,1,4-trioxo-1$\lambda^6$,2,5-thiadiazolidin-2-yl)-3,4-dihydroisoquinolin-2(1H)-yl]methyl}-3,5-dimethyl-1H-pyrazol-1-yl)-2,2-dimethylpentanenitrile;
5-{8-fluoro-6-hydroxy-2-[(piperidin-4-yl)methyl]-1,2,3,4-tetrahydroisoquinolin-7-yl}-1$\lambda^6$,2,5-thiadiazolidine-1,1,3-trione;
5-{8-fluoro-6-hydroxy-2-[3-(morpholin-4-yl)propyl]-1,2,3,4-tetrahydroisoquinolin-7-yl}-1$\lambda^6$,2,5-thiadiazolidine-1,1,3-trione;
5-{8-fluoro-6-hydroxy-2-[2-(piperidin-4-yl)ethyl]-1,2,3,4-tetrahydroisoquinolin-7-yl}-1$\lambda^6$,2,5-thiadiazolidine-1,1,3-trione;
5-(8-fluoro-6-hydroxy-2-{2-[(1s,3r)-3-(trifluoromethoxy)cyclobutyl]ethyl}-1,2,3,4-tetrahydroisoquinolin-7-yl)-1$\lambda^6$,2,5-thiadiazolidine-1,1,3-trione;
5-{8-fluoro-6-hydroxy-2-[3-(4-methylpiperazin-1-yl)propyl]-1,2,3,4-tetrahydroisoquinolin-7-yl}-1$\lambda^6$,2,5-thiadiazolidine-1,1,3-trione;
5-(8-fluoro-6-hydroxy-2-{2-[(propan-2-yl)oxy]ethyl}-1,2,3,4-tetrahydroisoquinolin-7-yl)-1$\lambda^6$,2,5-thiadiazolidine-1,1,3-trione;
5-[1-fluoro-3-hydroxy-7-({2-[(1s,3r)-3-(trifluoromethoxy)cyclobutyl]ethyl}amino)-5,6,7,8-tetrahydronaphthalen-2-yl]-1$\lambda^6$,2,5-thiadiazolidine-1,1,3-trione;
5-(1-fluoro-3-hydroxy-7-{[(1s,3s)-3-(trifluoromethoxy)cyclobutyl]amino}-5,6,7,8-tetrahydronaphthalen-2-yl)-1$\lambda^6$,2,5-thiadiazolidine-1,1,3-trione;
5-(8-fluoro-6-hydroxy-2-{1-[(1,3,5-trimethyl-1H-pyrazol-4-yl)methyl]piperidin-4-yl}-1,2,3,4-tetrahydroisoquinolin-7-yl)-1$\lambda^6$,2,5-thiadiazolidine-1,1,3-trione;
5-(8-fluoro-6-hydroxy-2-{2-[(1,3,5-trimethyl-1H-pyrazol-4-yl)methyl]-2-azaspiro[3.3]heptan-6-yl}-1,2,3,4-tetrahydroisoquinolin-7-yl)-1$\lambda^6$,2,5-thiadiazolidine-1,1,3-trione;
5-(2-{2-[1-(difluoromethyl)-3,5-dimethyl-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione;
5-{2-[2-(bicyclo[2.2.1]heptan-1-yl)ethyl]-8-fluoro-6-hydroxy-1,2,3,4-tetrahydroisoquinolin-7-yl}-1$\lambda^6$,2,5-thiadiazolidine-1,1,3-trione;
5-[7-amino-1-fluoro-3-hydroxy-7-(prop-2-en-1-yl)-5,6,7,8-tetrahydronaphthalen-2-yl]-1$\lambda^6$,2,5-thiadiazolidine-1,1,3-trione;
N-[8-fluoro-6-hydroxy-2-propyl-7-(1,1,4-trioxo-1$\lambda^6$,2,5-thiadiazolidin-2-yl)-1,2,3,4-tetrahydronaphthalen-2-yl]benzohydrazide;
5-[8-fluoro-6-hydroxy-2-(3-hydroxybutyl)-1,2,3,4-tetrahydroisoquinolin-7-yl]-1$\lambda^6$,2,5-thiadiazolidine-1,1,3-trione;
5-(8-fluoro-6-hydroxy-2-{2-[1-(trifluoromethyl)cyclopropyl]ethyl})-1,2,3,4-tetrahydroisoquinolin-7-yl)-1$\lambda^6$,2,5-thiadiazolidine-1,1,3-trione;
5-[8-fluoro-6-hydroxy-2-(3-hydroxypropyl)-1,2,3,4-tetrahydroisoquinolin-7-yl]-1$\lambda^6$,2,5-thiadiazolidine-1,1,3-trione;
5-{2-[(2S)-2-aminopropyl]-8-fluoro-6-hydroxy-1,2,3,4-tetrahydroisoquinolin-7-yl}-1$\lambda^6$,2,5-thiadiazolidine-1,1,3-trione;
5-{2-[(2R)-2-aminopropyl]-8-fluoro-6-hydroxy-1,2,3,4-tetrahydroisoquinolin-7-yl}-1$\lambda^6$,2,5-thiadiazolidine-1,1,3-trione;
5-{8-fluoro-6-hydroxy-2-[2-(piperazin-1-yl)ethyl]-1,2,3,4-tetrahydroisoquinolin-7-yl}-1$\lambda^6$,2,5-thiadiazolidine-1,1,3-trione;
5-(8-fluoro-6-hydroxy-2-{[rac-(1R,2R)-2-(pyridin-4-yl)cyclopropyl]methyl})-1,2,3,4-tetrahydroisoquinolin-7-yl)-1$\lambda^6$,2,5-thiadiazolidine-1,1,3-trione;
5-[2-(2-cyclopentyl-2-methoxyethyl)-8-fluoro-6-hydroxy-1,2,3,4-tetrahydroisoquinolin-7-yl]-1$\lambda^6$,2,5-thiadiazolidine-1,1,3-trione;
5-{2-[(2R)-2-amino-4-cyclohexylbutanoyl]-8-fluoro-6-hydroxy-1,2,3,4-tetrahydroisoquinolin-7-yl}-1$\lambda^6$,2,5-thiadiazolidine-1,1,3-trione;
5-(8-fluoro-6-hydroxy-2-{3-[(propan-2-yl)oxy]propyl}-1,2,3,4-tetrahydroisoquinolin-7-yl)-1$\lambda^6$,2,5-thiadiazolidine-1,1,3-trione;
5-{8-fluoro-6-hydroxy-2-[2-(1-methyl-1H-pyrazol-4-yl)ethyl]-1,2,3,4-tetrahydroisoquinolin-7-yl}-1$\lambda^6$,2,5-thiadiazolidine-1,1,3-trione;
5-(2-{2-[1-(2,2-difluoroethyl)-3,5-dimethyl-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione;
5-[7-amino-1-fluoro-3-hydroxy-7-(4-methylpentyl)-5,6,7,8-tetrahydronaphthalen-2-yl]-1$\lambda^6$,2,5-thiadiazolidine-1,1,3-trione;
5-(7-amino-1-fluoro-3-hydroxy-7-propyl-5,6,7,8-tetrahydronaphthalen-2-yl)-1$\lambda^6$,2,5-thiadiazolidine-1,1,3-trione;
5-{2-[2-(1,3-dimethyl-1H-pyrazol-4-yl)ethyl]-8-fluoro-6-hydroxy-1,2,3,4-tetrahydroisoquinolin-7-yl}-1$\lambda^6$,2,5-thiadiazolidine-1,1,3-trione;
5-{2-[2-(1,5-dimethyl-1H-pyrazol-4-yl)ethyl]-8-fluoro-6-hydroxy-1,2,3,4-tetrahydroisoquinolin-7-yl}-1$\lambda^6$,2,5-thiadiazolidine-1,1,3-trione;
N-(cyclopropylmethyl)-8-fluoro-6-hydroxy-7-(1,1,4-trioxo-1$\lambda^6$,2,5-thiadiazolidin-2-yl)-3,4-dihydroisoquinoline-2(1H)-carboxamide;

5-{(7S)-7-[(3,3-difluoropropyl)amino]-1-fluoro-3-hydroxy-5,6,7,8-tetrahydronaphthalen-2-yl}-1$\lambda^6$,2,5-thiadiazolidine-1,1,3-trione;

5-{(7R)-7-[(3,3-difluoropropyl)amino]-1-fluoro-3-hydroxy-5,6,7,8-tetrahydronaphthalen-2-yl}-1$\lambda^6$,2,5-thiadiazolidine-1,1,3-trione;

8-fluoro-6-hydroxy-N-[(oxan-4-yl)methyl]-7-(1,1,4-trioxo-1$\lambda^6$,2,5-thiadiazolidin-2-yl)-3,4-dihydroisoquinoline-2(1H)-carboxamide;

N-[(3,3-difluorocyclobutyl)methyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

8-fluoro-6-hydroxy-N-[(oxolan-2-yl)methyl]-7-(1,1,4-trioxo-1$\lambda^6$,2,5-thiadiazolidin-2-yl)-3,4-dihydroisoquinoline-2(1H)-carboxamide;

N-(2-cyclopropylethyl)-8-fluoro-6-hydroxy-7-(1,1,4-trioxo-1$\lambda^6$,2,5-thiadiazolidin-2-yl)-3,4-dihydroisoquinoline-2(1H)-carboxamide;

N-[(1,3-dimethyl-1H-pyrazol-5-yl)methyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

5-{2-[2-(1-tert-butyl-3,5-dimethyl-1H-pyrazol-4-yl)ethyl]-8-fluoro-6-hydroxy-1,2,3,4-tetrahydroisoquinolin-7-yl}-1$\lambda^6$,2,5-thiadiazolidine-1,1,3-trione;

5-[2-(aminomethyl)-4-fluoro-6-hydroxy-2,3-dihydro-1H-inden-5-yl]-1$\lambda^6$,2,5-thiadiazolidine-1,1,3-trione:

5-(4-fluoro-6-hydroxy-2-{[(3-methylbutyl)amino]methyl}-2,3-dihydro-1H-inden-5-yl)-1$\lambda^6$,2,5-thiadiazolidine-1,1,3-trione;

5-(2-{[bis(3-methylbutyl)amino]methyl}-4-fluoro-6-hydroxy-2,3-dihydro-1H-inden-5-yl)-1$\lambda^6$,2,5-thiadiazolidine-1,1,3-trione 8-fluoro-6-hydroxy-N-[(oxolan-3-yl)methyl]-7-(1,1,4-trioxo-1$\lambda^6$,2,5-thiadiazolidin-2-yl)-3,4-dihydroisoquinoline-2(1H)-carboxamide;

N-[(1,5-dimethyl-1H-pyrazol-4-yl)methyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

8-fluoro-6-hydroxy-N-[(1-methyl-1H-pyrazol-5-yl)methyl]-7-(1,1,4-trioxo-1$\lambda^6$,2,5-thiadiazolidin-2-yl)-3,4-dihydroisoquinoline-2(1H)-carboxamide;

5-(2-{2-[3,5-dimethyl-1-(propan-2-yl)-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione;

5-(2-{[(3-cyclopropylpropyl)amino]methyl}-4-fluoro-6-hydroxy-2,3-dihydro-1H-inden-5-yl)-1$\lambda^6$,2,5-thiadiazolidine-1,1,3-trione;

5-(4-fluoro-6-hydroxy-2-{[(2-methylpropyl)amino]methyl}-2,3-dihydro-1H-inden-5-yl)-1$\lambda^6$,2,5-thiadiazolidine-1,1,3-trione;

5-{2-[2-(1-ethyl-3,5-dimethyl-1H-pyrazol-4-yl)ethyl]-8-fluoro-6-hydroxy-1,2,3,4-tetrahydroisoquinolin-7-yl}-1$\lambda^6$,2,5-thiadiazolidine-1,1,3-trione;

N-(2,2-dimethylpropyl)-8-fluoro-6-hydroxy-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(3-methoxypropyl)-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(3-methoxy-2,2-dimethylpropyl)-7-(1,1,4-trioxo-1$\lambda^6$,2,5-thiadiazolidin-2-yl)-3,4-dihydroisoquinoline-2(1H)-carboxamide;

N-[2-(dimethylamino)ethyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

8-fluoro-6-hydroxy-N-[2-(1-methylcyclopropyl)ethyl]-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(2-methoxyethyl)-7-(1,1,4-trioxo-1$\lambda^6$,2,5-thiadiazolidin-2-yl)-3,4-dihydroisoquinoline-2(1H)-carboxamide;

8-fluoro-6-hydroxy-N-[(oxetan-3-yl)methyl]-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(2-phenylethyl)-7-(1,1,4-trioxo-1$\lambda^6$,2,5-thiadiazolidin-2-yl)-3,4-dihydroisoquinoline-2(1H)-carboxamide;

N-[3-(dimethylamino)propyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

5-[2-(3-cyclohexylpropyl)-8-fluoro-6-hydroxy-1,2,3,4-tetrahydroisoquinolin-7-yl]-1$\lambda^6$,2,5-thiadiazolidine-1,1,3-trione;

5-(7-{[(3,5-dimethyl-1,2-oxazol-4-yl)methyl]amino}-1-fluoro-3-hydroxy-5,6,7,8-tetrahydronaphthalen-2-yl)-1$\lambda^6$,2,5-thiadiazolidine-1,1,3-trione;

5-{2-[3-(2,2-dimethylcyclopropyl)propyl]-8-fluoro-6-hydroxy-1,2,3,4-tetrahydroisoquinolin-7-yl}-1$\lambda^6$,2,5-thiadiazolidine-1,1,3-trione;

5-[(3S)-5-fluoro-7-hydroxy-3-methyl-1,2,3,4-tetrahydroisoquinolin-6-yl]-1$\lambda^6$,2,5-thiadiazolidine-1,1,3-trione;

5-(7-{[2-(3,5-dimethyl-1,2-oxazol-4-yl)ethyl]amino}-1-fluoro-3-hydroxy-5,6,7,8-tetrahydronaphthalen-2-yl)-1$\lambda^6$,2,5-thiadiazolidine-1,1,3-trione;

5-[(2R)-4-fluoro-6-hydroxy-2-{[(3-methylbutyl)amino]methyl}-2,3-dihydro-1H-inden-5-yl]-1$\lambda^6$,2,5-thiadiazolidine-1,1,3-trione;

5-[(2S)-4-fluoro-6-hydroxy-2-{[(3-methylbutyl)amino]methyl}-2,3-dihydro-1H-inden-5-yl]-1$\lambda^6$,2,5-thiadiazolidine-1,1,3-trione;

5-[8-fluoro-6-hydroxy-2-(4-methoxybutyl)-1,2,3,4-tetrahydroisoquinolin-7-yl]-1$\lambda^6$,2,5-thiadiazolidine-1,1,3-trione;

5-(8-fluoro-6-hydroxy-2-{3-[3-(trifluoromethyl)phenyl]propyl})-1,2,3,4-tetrahydroisoquinolin-7-yl)-1$\lambda^6$,2,5-thiadiazolidine-1,1,3-trione;

5-(8-fluoro-6-hydroxy-2-{2-methyl-3-[4-(propan-2-yl)phenyl]propyl})-1,2,3,4-tetrahydroisoquinolin-7-yl)-1$\lambda^6$,2,5-thiadiazolidine-1,1,3-trione;

5-{2-[4-(5,5-dimethyl-1,3-dioxan-2-yl)butyl]-8-fluoro-6-hydroxy-1,2,3,4-tetrahydroisoquinolin-7-yl}-1$\lambda^6$,2,5-thiadiazolidine-1,1,3-trione;

5-{8-fluoro-6-hydroxy-2-[2-(2,6,6-trimethylcyclohex-1-en-1-yl)ethyl]-1,2,3,4-tetrahydroisoquinolin-7-yl}-1$\lambda^6$,2,5-thiadiazolidine-1,1,3-trione;

5-(8-fluoro-6-hydroxy-2-pentyl-1,2,3,4-tetrahydroisoquinolin-7-yl)-1$\lambda^6$,2,5-thiadiazolidine-1,1,3-trione;

5-{8-fluoro-2-[3-(4-fluorophenyl)propyl]-6-hydroxy-1,2,3,4-tetrahydroisoquinolin-7-yl}-1$\lambda^6$,2,5-thiadiazolidine-1,1,3-trione;

tert-butyl [(1r,4r)-4-{2-[8-fluoro-6-hydroxy-7-(1,1,4-trioxo-1$\lambda^6$,2,5-thiadiazolidin-2-yl)-3,4-dihydroisoquinolin-2(1H)-yl]ethyl}cyclohexyl]carbamate;

5-{2-[3-(4-tert-butylphenyl)propyl]-8-fluoro-6-hydroxy-1,2,3,4-tetrahydroisoquinolin-7-yl}-1$\lambda^6$,2,5-thiadiazolidine-1,1,3-trione;

5-[8-fluoro-6-hydroxy-2-(3,5,5-trimethylhexyl)-1,2,3,4-tetrahydroisoquinolin-7-yl]-1$\lambda^6$,2,5-thiadiazolidine-1,1,3-trione;

5-{8-fluoro-2-[3-(2-fluorophenyl)propyl]-6-hydroxy-1,2,3,4-tetrahydroisoquinolin-7-yl}-1$\lambda^6$,2,5-thiadiazolidine-1,1,3-trione;

3-hydroxybutyl 4,4,8-trifluoro-6-hydroxy-7-(1,1,4-trioxo-1λ⁶,2,5-thiadiazolidin-2-yl)-3,4-dihydroisoquinoline-2(1H)-carboxylate;
5-(2-{[(2-cyclobutylethyl)amino]methyl}-4-fluoro-6-hydroxy-2,3-dihydro-1H-inden-5-yl)-1λ⁶,2,5-thiadiazolidine-1,1,3-trione;
5-{2-[2-(3,5-dimethyl-1,2-oxazol-4-yl)ethyl]-4,4,8-trifluoro-6-hydroxy-1,2,3,4-tetrahydroisoquinolin-7-yl}-1λ⁶,2,5-thiadiazolidine-1,1,3-trione;
5-[(7R)-1-fluoro-3-hydroxy-7-{[(3R)-3-hydroxybutyl]amino}-5,6,7,8-tetrahydronaphthalen-2-yl]-1λ⁶,2,5-thiadiazolidine-1,1,3-trione;
5-{(7R)-1-fluoro-3-hydroxy-7-[(4-hydroxy-3,3-dimethylbutyl)amino]-5,6,7,8-tetrahydronaphthalen-2-yl}-1λ⁶,2,5-thiadiazolidine-1,1,3-trione;
5-[1-fluoro-3-hydroxy-6-(3-hydroxy-3-methylbutoxy)-5,6,7,8-tetrahydronaphthalen-2-yl]-1λ⁶,2,5-thiadiazolidine-1,1,3-trione;
5-[6-(cyclopropylmethoxy)-1-fluoro-3-hydroxy-5,6,7,8-tetrahydronaphthalen-2-yl]-1λ⁶,2,5-thiadiazolidine-1,1,3-trione;
5-{6-[(4,4-difluorobutyl)amino]-1-fluoro-3-hydroxy-5,6,7,8-tetrahydronaphthalen-2-yl}-1λ⁶,2,5-thiadiazolidine-1,1,3-trione;
5-[6-(4,4-difluorobutoxy)-1-fluoro-3-hydroxy-5,6,7,8-tetrahydronaphthalen-2-yl]-1λ⁶,2,5-thiadiazolidine-1,1,3-trione;
5-{1-fluoro-3-hydroxy-6-[(3-methylbutyl)amino]-5,6,7,8-tetrahydronaphthalen-2-yl}-1λ⁶,2,5-thiadiazolidine-1,1,3-trione;
5-[1-fluoro-3-hydroxy-6-(3-methylbutoxy)-5,6,7,8-tetrahydronaphthalen-2-yl]-1λ⁶,2,5-thiadiazolidine-1,1,3-trione;
5-{1-fluoro-3-hydroxy-6-[(3-hydroxy-3-methylbutyl)amino]-5,6,7,8-tetrahydronaphthalen-2-yl}-1λ⁶,2,5-thiadiazolidine-1,1,3-trione;
tert-butyl (2-{[5-fluoro-7-hydroxy-6-(1,1,4-trioxo-1λ⁶,2,5-thiadiazolidin-2-yl)-1,2,3,4-tetrahydronaphthalen-2-yl]oxy}ethyl)carbamate;
5-(1-fluoro-3-hydroxy-6-methoxy-5,6,7,8-tetrahydronaphthalen-2-yl)-1λ⁶,2,5-thiadiazolidine-1,1,3-trione;
5-{6-[(cyclopropylmethyl)amino]-1-fluoro-3-hydroxy-5,6,7,8-tetrahydronaphthalen-2-yl}-1λ⁶,2,5-thiadiazolidine-1,1,3-trione;
5-[6-(2-aminoethoxy)-1-fluoro-3-hydroxy-5,6,7,8-tetrahydronaphthalen-2-yl]-1λ⁶,2,5-thiadiazolidine-1,1,3-trione;
5-{2-[2-(3,5-dimethyl-1H-pyrazol-4-yl)ethyl]-4,4,8-trifluoro-6-hydroxy-1,2,3,4-tetrahydroisoquinolin-7-yl}-1λ⁶,2,5-thiadiazolidine-1,1,3-trione;
N-(cyclohexylmethyl)-8-fluoro-6-hydroxy-7-(1,1,4-trioxo-1λ⁶,2,5-thiadiazolidin-2-yl)-3,4-dihydroisoquinoline-2(1H)-carboxamide;
N-[8-fluoro-6-hydroxy-7-(1,1,4-trioxo-1λ⁶,2,5-thiadiazolidin-2-yl)-1,2,3,4-tetrahydronaphthalen-2-yl]acetamide;
5-[1-fluoro-3-hydroxy-7-(4-methylpentyl)-5,6,7,8-tetrahydronaphthalen-2-yl]-1λ⁶,2,5-thiadiazolidine-1,1,3-trione;
5-(8-fluoro-6-hydroxy-2-{[(2S)-5-oxopyrrolidin-2-yl]methyl}-1,2,3,4-tetrahydroisoquinolin-7-yl)-1λ⁶,2,5-thiadiazolidine-1,1,3-trione;
5-[(3S)-5-fluoro-7-hydroxy-3-(4-methylpentyl)-1,2,3,4-tetrahydroisoquinolin-6-yl]-1λ⁶,2,5-thiadiazolidine-1,1,3-trione;
and a pharmaceutically acceptable salt thereof.

In some embodiments, a compound disclosed herein is formulated as a pharmaceutically acceptable composition comprising a disclosed compound and a pharmaceutically acceptable carrier.

Also disclosed herein is a method of treating cancer in a patient in need thereof, comprising administering to the patient an effective amount of a compound disclosed herein in combination with an additional therapeutic agent. In some embodiments, the additional therapeutic agent is an immunotherapeutic agent. For example, in some embodiments, the immunotherapeutic agent is selected from the group consisting of an anti-PD-1 antibody, an anti-PD-L1 antibody and an anti-CTLA-4 antibody.

For example, disclosed herein is a method of treating cancer in a patient in need thereof, comprising administering to the patient an effective amount of a compound disclosed herein.

Further provided herein is a method of treating type-2 diabetes in a patient in need thereof, comprising administering to the patient an effective amount of a compound disclosed herein.

Disclosed herein, for example, is a method of treating and/or controlling obesity in a patient in need thereof, comprising administering to the patient an effective amount of a compound disclosed herein.

For example, disclosed herein is a method of inhibiting further weight gain in an overweight or obese patient in need thereof, comprising administering to the patient an effective amount of a compound disclosed herein.

Further disclosed herein is a method of treating a metabolic disease in a patient in need thereof, comprising administering to the patient an effective amount of a compound disclosed herein.

In some embodiments, the method comprises the treatment of cancer. In some embodiments, the cancer comprises pancreatic cancer, breast cancer, multiple myeloma, melanoma, or a cancer of the secretory cells. In some embodiments, the method comprises the treatment of a metabolic disease. In some embodiments, the metabolic disease comprises non-alcoholic steatohepatitis (NASH), non-alcoholic fatty liver disease (NAFLD), liver fibrosis, obesity, type-2 diabetes, heart disease, atherosclerosis, arthritis, cystinosis, phenylketonuria, proliferative retinopathy, metabolic syndrome or Kearns-Sayre disease.

Also disclosed herein is a composition for use in treating cancer in a patient in need thereof, wherein the composition comprises a compound disclosed herein, in combination with an additional therapeutic agent. In some embodiments, the additional therapeutic agent is an immunotherapeutic agent. For example, in some embodiments, the immunotherapeutic agent is selected from the group consisting of an anti-PD-1 antibody, an anti-PD-L1 antibody and an anti-CTLA-4 antibody.

For example, disclosed herein is a composition for use in treating cancer in a patient in need thereof, wherein the composition comprises a compound disclosed herein.

Further provided herein is a composition for use in treating type-2 diabetes in a patient in need thereof, wherein the composition comprises a compound disclosed herein.

Disclosed herein, for example, is a composition for use in treating and/or controlling obesity in a patient in need thereof, wherein the composition comprises a compound disclosed herein.

For example, disclosed herein is a composition for use in inhibiting further weight gain in an overweight or obese patient in need thereof, wherein the composition comprises a compound disclosed herein.

Further disclosed herein is a composition for use in treating a metabolic disease in a patient in need thereof, wherein the composition comprises a compound disclosed herein.

In some embodiments, the cancer comprises pancreatic cancer, breast cancer, multiple myeloma, melanoma, or a cancer of the secretory cells. In some embodiments, the metabolic disease comprises non-alcoholic steatohepatitis (NASH), non-alcoholic fatty liver disease (NAFLD), liver fibrosis, obesity, type-2 diabetes, heart disease, atherosclerosis, arthritis, cystinosis, phenylketonuria, proliferative retinopathy, metabolic syndrome or Kearns-Sayre disease.

BRIEF DESCRIPTION OF THE SEQUENCE LISTING

Incorporated herein by reference in its entirety is a Sequence Listing entitled, "CLS-016WOC1 SEQ ID List_ST25.txt", comprising SEQ ID NO: 1 through SEQ ID NO: 3, which includes the amino acid sequences disclosed herein. The Sequence Listing has been submitted herewith in ASCII text format via EFS. The Sequence Listing was first created on Feb. 19, 2020 and is 7254 bytes in size.

DETAILED DESCRIPTION

The present disclosure is directed, at least in part, to compounds, compositions, and methods for the inhibition of protein tyrosine phosphatase, e.g., protein tyrosine phosphatase non-receptor type 2 (PTPN2) and/or protein tyrosine phosphatase non-receptor type 1 ((PTPN1), also known as protein tyrosine phosphatase-1B (PTP1B)).

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

"Isotopically enriched variant" as used herein refers to a disclosed compound having one or more isotopic substitutions, wherein one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, hydrogen (H) may be in any isotopic form, including $^{1}$H, $^{2}$H (D or deuterium), and $^{3}$H (T or tritium); carbon (C) may be in any isotopic form, including $^{12}$C, $^{13}$C, and $^{14}$C; oxygen (O) may be in any isotopic form, including $^{16}$O and $^{18}$O; and the like. For example, an isotopically enriched variant as disclosed herein may have one or more hydrogen atoms replaced with deuterium.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present disclosure.

"Alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-6}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present disclosure. The term "alkenylene," by itself or as part of another substituent, means, unless otherwise stated, a divalent radical derived from an alkene. An alkylene group may be described as, e.g., a $C_1$-$C_6$-membered alkylene, wherein the term "membered" refers to the non-hydrogen atoms within the moiety.

"Alkenyl" refers to a radical of a straight-chain or branched hydrocarbon group having from 2 to 20 carbon atoms, one or more carbon-carbon double bonds, and no triple bonds ("$C_2$-$C_{20}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, e.g., unsubstituted (an "unsubstituted alkenyl") or substituted (a "substituted alkenyl") with one or more substituents, e.g., from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include, but are not limited to, phenyl, naphthyl, indenyl, and tetrahydronaphthyl. Each instance of an aryl group may be independently optionally substituted, e.g., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

In certain embodiments, an aryl group is substituted with one or more of groups selected from halo, $C_1$-$C_8$ alkyl, halo-$C_1$-$C_8$ alkyl, haloxy-$C_1$-$C_8$ alkyl, cyano, hydroxy, alkoxy $C_1$-$C_8$ alkyl, and amino.

Examples of representative substituted aryls include the following

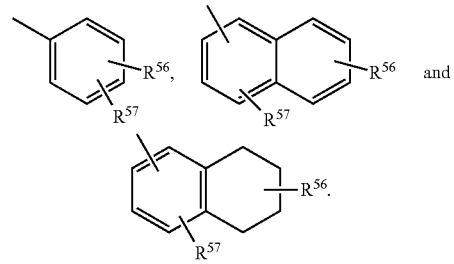

wherein one of $R^{56}$ and $R^{57}$ may be hydrogen and at least one of $R^{56}$ and $R^{57}$ is each independently selected from $C_1$-$C_8$ alkyl, halo-$C_1$-$C_8$ alkyl, 4-10 membered heterocyclyl, alkanoyl, alkoxy-$C_1$-$C_8$ alkyl, heteroaryloxy, alkylamino, arylamino, heteroarylamino, $NR^{58}COR^{59}$, $NR^{58}SOR^{59}NR^{58}SO_2R^{59}$, C(O)Oalkyl, C(O)Oaryl, $CONR^{58}R^{59}$, $CONR^{58}OR^{59}$, $NR^{58}R^{59}$, $SO_2NR^{58}R^{59}$, S-alkyl, S(O)-alkyl, $S(O)_2$-alkyl, S-aryl, S(O)-aryl, $S(O_2)$-aryl; or $R^{56}$ and $R^{57}$ may be joined to form a cyclic ring (saturated or unsaturated) from 5 to 8 atoms, optionally containing one or more heteroatoms selected from the group N, O, or S.

Other representative aryl groups having a fused heterocyclyl group include the following:

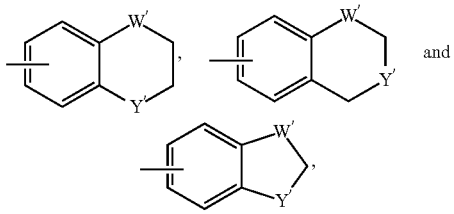

wherein each W' is selected from C(R$^{66}$)$_2$, NR$^{66}$, O, and S; and each Y' is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

Additionally, terms such as "haloalkyl" are meant to include monohaloalkyl and polyhaloalkyl. For example, the term "halo-C$_1$-C$_6$ alkyl" includes, but is not limited to, fluoromethyl, difluoromethyl, trifluoromethyl, 2,2,2-trifluoroethyl, 4-chlorobutyl, 3-bromopropyl, and the like.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —S(O)$_2$—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, and —O—CH$_2$—CH$_3$. Up to two or three heteroatoms may be consecutive, such as, for example, —CH$_2$—NH—OCH$_3$ and —CH$_2$—O—Si(CH$_3$)$_3$.

Where "heteroalkyl" is recited, followed by recitations of specific heteroalkyl groups, such as —CH$_2$O—CH$_3$, —NR$^B$R$^C$, or the like, it will be understood that the terms heteroalkyl and —CH$_2$O—CH$_3$ or —NR$^B$R$^C$ are not redundant or mutually exclusive. Rather, the specific heteroalkyl groups are recited to add clarity. Thus, the term "heteroalkyl" should not be interpreted herein as excluding specific heteroalkyl groups, such as —CH$_2$O—CH$_3$, —NR$^B$R$^C$, or the like.

Similarly, the term "heteroalkylene," by itself or as part of another substituent, means, unless otherwise stated, a divalent radical derived from heteroalkyl, as exemplified, but not limited by, —CH$_2$O— and —CH$_2$CH$_2$O—. A heteroalkylene group may be described as, e.g., a 2-7-membered heteroalkylene, wherein the term "membered" refers to the non-hydrogen atoms within the moiety. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

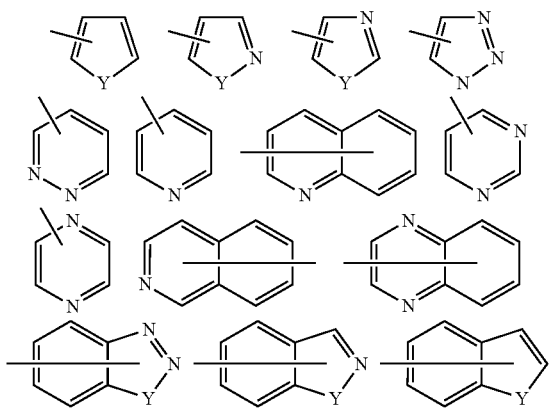

wherein each Y is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_8$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, e.g., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

In some embodiments, "cycloalkyl" is a monocyclic, saturated cycloalkyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_5$) and cyclohexyl ($C_5$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_8$ cycloalkyl groups include the aforementioned $C_3$-$C_6$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is substituted $C_3$-$C_{10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

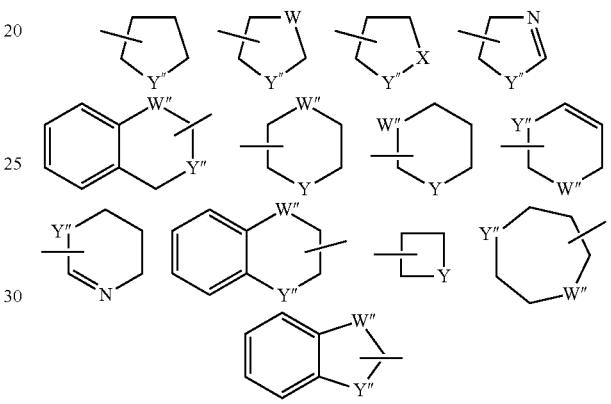

wherein each W" is selected from $CR^{67}$, $C(R^{67})_2$, $NR^{67}$, O, and S; and each Y" is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Amino" refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. In some embodiments, amino refers to $NH_2$.

"Cyano" refers to the radical —CN.

"Hydroxy" or "hydroxyl" refers to the radical —OH.

In some embodiments one or more of the nitrogen atoms of a disclosed compound if present are oxidized to the corresponding N-oxide.

Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66: 1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in a first buffer, e.g., in 1 mM-50 mM histidine, 0.1%-2% sucrose, 2%-7% mannitol at a pH range of 4.5 to 5.5, that is combined with a second buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)-for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

"Treating" or "treatment" includes preventing or delaying the onset of the symptoms, complications, or biochemical indicia of a disease, alleviating or ameliorating the symptoms or arresting or inhibiting further development of the disease, condition, or disorder. "Treating" or "treatment" includes any effect, e.g., lessening, reducing, modulating, or eliminating, that results in the improvement of the condition, disease, disorder and the like. For example certain methods herein treat cancer by decreasing or reducing or preventing the occurrence, growth, metastasis, or progression of cancer or decreasing a symptom of cancer. The term "treating" and conjugations thereof, include prevention of an injury, pathology, condition, or disease (e.g. preventing the development of one or more symptoms of a disease, disorder, or condition described herein).

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A "reduction" of a symptom or symptoms (and grammatical equivalents of this phrase) means decreasing of the severity or frequency of the symptom(s), or elimination of the symptom(s).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme, e.g., a protein tyrosine phosphatase, e.g., protein tyrosine phosphatase non-receptor type 2 (PTPN2) or protein tyrosine phosphatase non-receptor type 1 (PTPN1).

As defined herein, the term "inhibition", "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a protein tyrosine phosphatase, e.g., protein tyrosine phosphatase non-receptor type 2 (PTPN2) or protein tyrosine phosphatase non-receptor type 1 (PTPN1). Thus, inhibition may include, at least in part, partially or totally decreasing stimulation, decreasing or reducing activation, or inactivating, desensitizing, or down-regulating signal transduction or enzymatic activity or the amount of a protein tyrosine phosphatase, e.g., protein tyrosine phosphatase non-receptor type 2 (PTPN2) or protein tyrosine phosphatase non-receptor type 1 (PTPN1).

"Patient" or "subject" in need thereof refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease", "disorder" or "condition" refers to a state of being or health status of a patient or subject capable of being treated with a compound, pharmaceutical composition, or method provided herein. In some embodiments, the compounds and methods described herein comprise reduction or elimination of one or more symptoms of the disease, disorder, or condition, e.g., through administration of a compound disclosed herein, a pharmaceutically acceptable salt thereof, or a pharmaceutical composition comprising a compound disclosed herein, or a pharmaceutically acceptable salt thereof, and a pharmaceutically acceptable carrier.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's solution, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a compound or composition described herein is administered at the same time, just prior to, or just after the administration of one or more additional therapies (e.g., anti-cancer agent, chemotherapeutic, or immunotherapeutic agent). The compounds or compositions described herein can be administered alone or can be coadministered to the patient. Coadministration is meant to include simultaneous or sequential administration of the compound or composition individually or in combination (more than one compound or agent). Thus, the preparations can also be combined, when desired, with other active substances (e.g. to reduce metabolic degradation).

The term "PTPN2" as used herein refers to protein tyrosine phosphatase non-receptor type 2. The term "PTPN1" refers to protein tyrosine phosphatase non-receptor type 1 (PTPN1), also known as protein tyrosine phosphatase-1B (PTP1B), Compounds Disclosed herein, for example, is a compound represented by Formula (I):

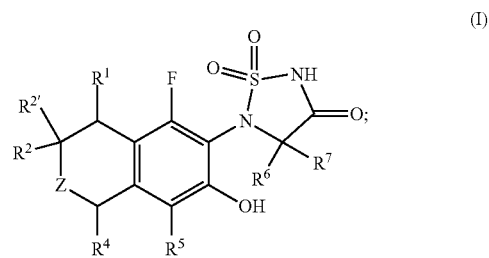

or a pharmaceutically acceptable salt thereof, wherein:
Z is selected from the group consisting of $C(H)(R^3)$, a bond and $N(R^8)$;
$R^1$ is selected from the group consisting of hydrogen, halogen, $C_{1-6}$alkyl, $C_{3-6}$cycloalkyl and —O—$C_{1-6}$alkyl;
wherein $C_{1-6}$alkyl, $C_{3-6}$cycloalkyl and —O—$C_{1-6}$alkyl may optionally be substituted on one or more available carbons by one, two, three or more substituents each independently selected from $R^g$;
$R^2$ is selected from the group consisting of hydrogen, —$C_{1-6}$alkyl, —$C_{2-6}$alkenyl, —O—$C_{1-6}$alkyl, —$NH_2$, —$N(R^a)$—$C_{1-5}$alkyl, —$N(R^a)$—$C_{3-6}$cycloalkyl, —$N(R^a)$—$C_{1-6}$alkylene-$C_{3-6}$cycloalkyl, —$N(R^a)$—$C_{1-6}$alkylene-$Si(R^c)_3$, —$C_{1-6}$alkylene-$N(R^a)$—$C_{1-6}$alkyl, —$C_{1-6}$alkylene-$N(R^a)$—$C_{1-6}$alkylene-$C_{3-6}$cycloalkyl, —$C_{1-6}$alkylene-$N(R^a)(R^b)$, —$N(R^a)$—(C=N($R^b$))—$C_{1-6}$alkyl, —$S(O)_w$—$C_{1-6}$alkyl, —C(O)—N($R^a$)—$C_{1-6}$alkyl, —$N(R^a)$—C(O)—$C_{1-6}$alkyl, —O—C(O)—N($R^a$)—$C_{1-6}$alkyl, —O—C(O)—N($R^a$)-phenyl, —$N(R^a)$—C(O)—O—$C_{1-6}$alkyl, $C_{3-6}$cycloalkyl, —$C_{1-6}$alkylene-$C_{3-6}$cycloalkyl, —O—$C_{1-6}$alkylene-$C_{3-6}$cycloalkyl, 5-6 membered heteroaryl, 4-6 membered heterocyclyl, —$N(R^a)$-4-6 membered heterocyclyl, —$C_{1-6}$alkylene-4-6 membered heterocyclyl, —O—$C_{1-6}$alkylene-4-6 membered heterocyclyl, —$N(R^a)$—$C_{1-6}$alkylene-4-6 membered heterocyclyl, —$N(R^a)$—$C_{1-6}$alkylene-5-6 membered heteroaryl and —$N(R^a)$—$C_{1-6}$alkylene-phenyl;
wherein —$C_{1-6}$alkyl, —$C_{2-6}$alkenyl, —O—$C_{1-6}$alkyl, —$N(R^a)$—$C_{1-8}$alkyl, —$N(R^a)$—$C_{3-6}$cycloalkyl, —N($R^a$)—$C_{1-6}$alkylene-$C_{3-6}$cycloalkyl, —N($R^a$)—$C_{1-6}$alkylene-Si($R^c$)$_3$, —$C_{1-6}$alkylene-N($R^a$)—$C_{1-6}$alkyl, —$C_{1-6}$alkylene-N($R^a$)—$C_{1-6}$alkylene-$C_{3-6}$cycloalkyl, —N($R^a$)—(C═N($R^b$))—$C_{1-6}$alkyl, —S(O)$_w$—$C_{1-6}$alkyl, —C(O)—N($R^a$)—$C_{1-6}$alkyl, —N($R^a$)—C(O)—$C_{1-6}$alkyl, —O—C(O)—N($R^a$)—$C_{1-6}$alkyl, —O—C(O)—N($R^a$)-phenyl, —N($R^a$)—C(O)—O—$C_{1-6}$alkyl, $C_{3-6}$cycloalkyl, —$C_{1-6}$alkylene-$C_{3-6}$cycloalkyl, —O—$C_{1-6}$alkylene-$C_{3-6}$cycloalkyl, 5-6 membered heteroaryl, 4-6 membered heterocyclyl, —N($R^a$)-4-6 membered heterocyclyl, —$C_{1-6}$alkylene-4-6 membered heterocyclyl, —O—$C_{1-6}$alkylene-4-6 membered heterocyclyl, —N($R^a$)—$C_{1-6}$alkylene-4-6 membered heterocyclyl, —N($R^a$)—$C_{1-6}$alkylene-5-6 membered heteroaryl and —N($R^a$)—$C_{1-6}$alkylene-phenyl may optionally be substituted on one or more available carbons by one, two, three or more substituents each independently selected from $R^g$;
wherein if 5-6 membered heteroaryl, 4-6 membered heterocyclyl, —N($R^a$)-4-6 membered heterocyclyl, —$C_{1-6}$alkylene-4-6 membered heterocyclyl, —O—$C_{1-6}$alkylene-4-6 membered heterocyclyl, —N($R^a$)—$C_{1-6}$alkylene-4-6 membered heterocyclyl or —N($R^a$)—$C_{1-6}$alkylene-5-6 membered heteroaryl contains a substitutable ring nitrogen atom, that ring nitrogen atom may optionally be substituted by $R^h$; and
wherein if Z is C(H)($R^3$), then $R^2$ is not —$CH_2$—$CH_3$;
$R^{2'}$ is selected from the group consisting of hydrogen, —$NR^aR^b$ and —N($R^a$)—N($R^b$)—C(O)-phenyl;
$R^3$ is selected from the group consisting of hydrogen, —$C_{1-6}$alkyl, —O—$C_{1-6}$alkyl, —O—$C_{1-6}$alkylene-$C_{3-6}$cycloalkyl, —N($R^a$)—$C_{1-6}$alkyl, —N($R^a$)—$C_{1-6}$alkylene-$C_{3-6}$cycloalkyl, —S(O)$_w$—$C_{1-6}$alkyl, —C(O)—N($R^a$)—$C_{1-6}$alkyl, —N($R^a$)—C(O)—$C_{1-6}$alkyl and —$C_{1-6}$alkylene-4-6 membered heterocyclyl;
wherein —$C_{1-6}$alkyl, —O—$C_{1-6}$alkyl, —O—$C_{1-6}$alkylene-$C_{3-6}$cycloalkyl, —N($R^a$)—$C_{1-6}$alkyl, —N($R^a$)—$C_{1-6}$alkylene-$C_{3-6}$cycloalkyl, —S(O)$_w$—$C_{1-6}$alkyl, —C(O)—N($R^a$)—$C_{1-6}$alkyl, —N($R^a$)—C(O)—$C_{1-6}$alkyl and —$C_{1-6}$alkylene-4-6 membered heterocyclyl may be substituted on one or more available carbons by one, two, three or more substituents each independently selected from $R^g$; and
wherein if —$C_{1-6}$alkylene-4-6 membered heterocyclyl contains a substitutable ring nitrogen atom, that ring nitrogen atom may optionally be substituted by $R^h$;
$R^4$ is selected from the group consisting of hydrogen, halogen, $C_{1-6}$alkyl, $C_{3-6}$cycloalkyl and —$C_{1-6}$alkylene-4-6 membered heterocyclyl;
wherein $C_{1-6}$alkyl, $C_{3-6}$cycloalkyl and —$C_{1-6}$alkylene-4-6 membered heterocyclyl may optionally be substituted on one or more available carbons by one, two, three or more substituents each independently selected from $R^g$; and
wherein if —$C_{1-6}$alkylene-4-6 membered heterocyclyl contains a substitutable ring nitrogen atom, that ring nitrogen atom may optionally be substituted by $R^h$;
$R^5$ is selected from the group consisting of hydrogen, deuterium, halogen, $C_{1-6}$alkyl, $C_{3-6}$cycloalkyl and —$C_{1-6}$alkylene-4-6 membered heterocyclyl;
wherein $C_{1-6}$alkyl, $C_{3-6}$cycloalkyl and —$C_{1-6}$alkylene-4-6 membered heterocyclyl may optionally be substituted on one or more available carbons by one, two, three or more substituents each independently selected from $R^g$; and
wherein if —$C_{1-6}$alkylene-4-6 membered heterocyclyl contains a substitutable ring nitrogen atom, that ring nitrogen atom may optionally be substituted by $R^h$;
$R^6$ is selected from the group consisting of hydrogen and deuterium;
$R^7$ is selected from the group consisting of hydrogen and deuterium;
$R^8$ is selected from the group consisting of hydrogen and $C_{1-6}$alkyl,
$R^g$ is independently selected for each occurrence from the group consisting of hydrogen, halogen, hydroxyl, cyano, nitro, oxo, $R^aR^bN$—, $R^aR^bN$—C(O)—, $R^aR^bN$—SO$_w$—, $R^aR^bN$—C(O)—N($R^a$)—, $C_{1-6}$alkyl, $C_{2-6}$alkenyl, $C_{2-6}$alkynyl, $C_{3-6}$cycloalkyl, $C_{3-6}$cycloalkyl-$C_{1-6}$alkylene-, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^a$)—, $C_{1-6}$alkyl-N($R^a$)—C(O)—, $C_{1-6}$alkyl-C(O)—N($R^a$), $C_{1-6}$alkyl-N($R^a$)—C(O)—N($R^a$)—, $C_{1-6}$alkyl-N($R^a$)—SO$_w$—, $C_{1-6}$alkyl-SO$_w$—N($R^a$)—, $C_{3-6}$cycloalkyl-N($R^a$)—SO$_w$—, $C_{1-6}$alkyl-SO$_w$—N($R^a$)—, $C_{3-6}$cycloalkyl-SO$_w$—N($R^a$)—, $C_{1-6}$alkoxy-C(O)—N($R^a$)—, $C_{1-6}$alkyl-C(O)—N($R^a$)—$C_{1-6}$alkyl-, $C_{1-6}$alkyl-N($R^a$)—C(O)—$C_{1-6}$alkyl- and $C_{1-6}$alkoxy-$C_{1-6}$alkyl-; wherein $C_{1-6}$alkyl, $C_{2-6}$alkenyl, $C_{2-6}$alkynyl, $C_{3-6}$cycloalkyl, —$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^a$)—, $C_{1-6}$alkyl-N($R^a$)—C(O)—, $C_{1-6}$alkyl-C(O)—N($R^a$), $C_{1-6}$alkyl-N($R^a$)—C(O)—N($R^a$)—, $C_{1-6}$alkyl-N($R^a$)—SO$_w$—, $C_{3-6}$cycloalkyl-N($R^a$)—SO$_w$—, $C_{1-6}$alkyl-SO$_w$—N($R^a$)—, $C_{3-6}$cycloalkyl-SO$_w$—N($R^a$)—, $C_{1-6}$alkoxy-C(O)—N($R^a$)—, $C_{1-6}$alkyl-C(O)—N($R^a$)—$C_{1-6}$alkyl-, $C_{1-6}$alkyl-N($R^a$)—C(O)—$C_{1-6}$alkyl- and $C_{1-6}$alkoxy-$C_{1-6}$alkyl- may optionally be substituted by one, two three or more substituents each independently selected from $R^P$;
$R^h$ is independently selected for each occurrence from the group consisting of $C_{1-6}$alkyl, $C_{3-6}$alkenyl, $C_{3-6}$alkynyl, $C_{3-6}$cycloalkyl, —$C_{1-6}$alkylene-$C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^aR^bN$—C(O)— and $R^aR^bN$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^aR^bN$—C(O)— and $R^aR^bN$—SO$_2$— may optionally be substituted by one, two three or more substituents each independently selected from $R^P$;
$R^P$ is independently selected for each occurrence from the group consisting of halogen, hydroxyl, cyano, $C_{1-6}$alkoxy, $C_{3-6}$cycloalkyl, $R^aR^bN$—, $R^aR^bN$-carbonyl-, $R^aR^bN$—SO$_2$—, and $R^aR^bN$-carbonyl-N($R^a$)—;
$R^a$ and $R^b$ are independently selected, for each occurrence, from the group consisting of hydrogen and $C_{1-6}$alkyl; wherein $C_{1-6}$alkyl may optionally be substituted by one or more substituents each independently selected from the group consisting of halogen, cyano, oxo and hydroxyl;
or $R^a$ and $R^b$ together with the nitrogen to which they are attached form a 4-6 membered heterocyclyl, wherein 4-6 membered heterocyclyl may optionally be substituted by one or more substituents each independently selected from the group consisting of halogen, cyano, oxo and hydroxyl;

$R^c$ is independently selected, for each occurrence, from the group consisting of hydroxyl, $C_{1-4}$alkyl and phenyl; and w is 0, 1 or 2.

For example, a compound disclosed herein may be represented by Formula (Ia):

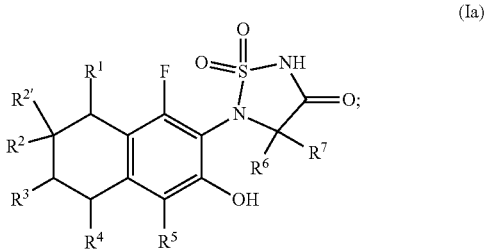

(Ia)

or a pharmaceutically acceptable salt thereof, wherein:

$R^1$ is selected from the group consisting of hydrogen, halogen, $C_{1-6}$alkyl, $C_{3-6}$cycloalkyl and —O—$C_{1-6}$alkyl;
  wherein $C_{1-6}$alkyl, $C_{3-6}$cycloalkyl and —O—$C_{1-6}$alkyl may optionally be substituted on one or more available carbons by one, two, three or more substituents each independently selected from $R^g$;

$R^2$ is selected from the group consisting of hydrogen, —$C_{1-6}$alkyl, —$C_{2-6}$alkenyl, —O—$C_{1-6}$alkyl, —NH$_2$, —N($R^a$)—$C_{1-8}$alkyl, —N($R^a$)—$C_{3-6}$cycloalkyl, —N($R^a$)—$C_{1-6}$alkylene-$C_{3-6}$cycloalkyl, —N($R^a$)—$C_{1-6}$alkylene-Si($R^c$)$_3$, —N($R^a$)—(C=N($R^b$))—$C_{1-6}$alkyl, —S(O)$_w$—$C_{1-6}$alkyl, —C(O)—N($R^a$)—$C_{1-6}$alkyl, —N($R^a$)—C(O)—$C_{1-6}$alkyl, —O—C(O)—N($R^a$)—$C_{1-6}$alkyl, —O—C(O)—N($R^a$)-phenyl, —N($R^a$)—C(O)—O—$C_{1-6}$alkyl, $C_{3-6}$cycloalkyl, —$C_{1-6}$alkylene-$C_{3-6}$cycloalkyl, —O—$C_{1-6}$alkylene-$C_{3-6}$cycloalkyl, 5-6 membered heteroaryl, 4-6 membered heterocyclyl, —N($R^a$)-4-6 membered heterocyclyl, —$C_{1-6}$alkylene-4-6 membered heterocyclyl, —O—$C_{1-6}$alkylene-4-6 membered heterocyclyl, —N($R^a$)—$C_{1-6}$alkylene-4-6 membered heterocyclyl, —N($R^a$)—$C_{1-6}$alkylene-5-6 membered heteroaryl and —N($R^a$)—$C_{1-6}$alkylene-phenyl;
  wherein —$C_{1-6}$alkyl, —$C_{2-6}$alkenyl, —O—$C_{1-6}$alkyl, —N($R^a$)—$C_{1-5}$alkyl, —N($R^a$)—$C_{3-6}$cycloalkyl, —N($R^a$)—$C_{1-6}$alkylene-$C_{3-6}$cycloalkyl, —N($R^a$)—$C_{1-6}$alkylene-Si($R^c$)$_3$, —N($R^a$)—(C=N($R^b$))—$C_{1-6}$alkyl, —S(O)$_w$—$C_{1-6}$alkyl, —C(O)—N($R^a$)—$C_{1-6}$alkyl, —N($R^a$)—C(O)—$C_{1-6}$alkyl, —O—C(O)—N($R^a$)—$C_{1-6}$alkyl, —O—C(O)—N($R^a$)-phenyl, —N($R^a$)—C(O)—O—$C_{1-6}$alkyl, $C_{3-6}$cycloalkyl, —$C_{1-6}$alkylene-$C_{3-6}$cycloalkyl, —O—$C_{1-6}$alkylene-$C_{3-6}$cycloalkyl, 5-6 membered heteroaryl, 4-6 membered heterocyclyl, —N($R^a$)-4-6 membered heterocyclyl, —$C_{1-6}$alkylene-4-6 membered heterocyclyl, —O—$C_{1-6}$alkylene-4-6 membered heterocyclyl, —N($R^a$)—$C_{1-6}$alkylene-4-6 membered heterocyclyl, —N($R^a$)—$C_{1-6}$alkylene-5-6 membered heteroaryl and —N($R^a$)—$C_{1-6}$alkylene-phenyl may optionally be substituted on one or more available carbons by one, two, three or more substituents each independently selected from $R^g$; and
  wherein if 5-6 membered heteroaryl, 4-6 membered heterocyclyl, —N($R^a$)-4-6 membered heterocyclyl, —$C_{1-6}$alkylene-4-6 membered heterocyclyl, —O—$C_{1-6}$alkylene-4-6 membered heterocyclyl, —N($R^a$)—$C_{1-6}$alkylene-4-6 membered heterocyclyl or —N($R^a$)—$C_{1-6}$alkylene-5-6 membered heteroaryl contains a substitutable ring nitrogen atom, that ring nitrogen atom may optionally be substituted by $R^h$;

$R^{2'}$ is selected from the group consisting of hydrogen, —NR$^a$R$^b$ and —N($R^a$)—N($R^b$)—C(O)-phenyl;

$R^3$ is selected from the group consisting of hydrogen, —$C_{1-6}$alkyl, —O—$C_{1-6}$alkyl, —O—$C_{1-6}$alkylene-$C_{3-6}$cycloalkyl, —N($R^a$)—$C_{1-6}$alkyl, —N($R^a$)—$C_{1-6}$alkylene-$C_{3-6}$cycloalkyl, —S(O)$_w$—$C_{1-6}$alkyl, —C(O)—N($R^a$)—$C_{1-6}$alkyl, —N($R^a$)—C(O)—$C_{1-6}$alkyl and —$C_{1-6}$alkylene-4-6 membered heterocyclyl;
  wherein —$C_{1-6}$alkyl, —O—$C_{1-6}$alkyl, —O—$C_{1-6}$alkylene-$C_{3-6}$cycloalkyl, —N($R^a$)—$C_{1-6}$alkyl, —N($R^a$)—$C_{1-6}$alkylene-$C_{3-6}$cycloalkyl, —S(O)$_w$—$C_{1-6}$alkyl, —C(O)—N($R^a$)—$C_{1-6}$alkyl, —N($R^a$)—C(O)—$C_{1-6}$alkyl and —$C_{1-6}$alkylene-4-6 membered heterocyclyl may optionally be substituted on one or more available carbons by one, two, three or more substituents each independently selected from $R^g$; and
  wherein if —$C_{1-6}$alkylene-4-6 membered heterocyclyl contains a substitutable ring nitrogen atom, that ring nitrogen atom may optionally be substituted by $R^h$;

$R^4$ is selected from the group consisting of hydrogen, halogen, $C_{1-6}$alkyl, $C_{3-6}$cycloalkyl and —$C_{1-6}$alkylene-4-6 membered heterocyclyl;
  wherein $C_{1-6}$alkyl, $C_{3-6}$cycloalkyl and —$C_{1-6}$alkylene-4-6 membered heterocyclyl may optionally be substituted on one or more available carbons by one, two, three or more substituents each independently selected from $R^g$; and
  wherein if —$C_{1-6}$alkylene-4-6 membered heterocyclyl contains a substitutable ring nitrogen atom, that ring nitrogen atom may optionally be substituted by $R^h$;

$R^5$ is selected from the group consisting of hydrogen, deuterium, halogen, $C_{1-6}$alkyl, $C_{3-6}$cycloalkyl and —$C_{1-6}$alkylene-4-6 membered heterocyclyl;
  wherein $C_{1-6}$alkyl, $C_{3-6}$cycloalkyl and —$C_{1-6}$alkylene-4-6 membered heterocyclyl may optionally be substituted on one or more available carbons by one, two, three or more substituents each independently selected from $R^g$; and
  wherein if —$C_{1-6}$alkylene-4-6 membered heterocyclyl contains a substitutable ring nitrogen atom, that ring nitrogen atom may optionally be substituted by $R^h$;

$R^6$ is selected from the group consisting of hydrogen and deuterium;

$R^7$ is selected from the group consisting of hydrogen and deuterium;

$R^g$ is independently selected for each occurrence from the group consisting of hydrogen, halogen, hydroxyl, cyano, nitro, oxo, $R^aR^bN$—, $R^aR^bN$—C(O)—, $R^aR^bN$—SO$_w$—, $R^aR^bN$—C(O)—N($R^a$)—, $C_{1-6}$alkyl, $C_{2-6}$alkenyl, $C_{2-6}$alkynyl, $C_{3-6}$cycloalkyl, $C_{3-6}$cycloalkyl-$C_{1-6}$alkylene-, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^a$)—, $C_{1-6}$alkyl-N($R^a$)—C(O)—, $C_{1-6}$alkyl-C(O)—N($R^a$), $C_{1-6}$alkyl-N($R^a$)—C(O)—N($R^a$)—, $C_{1-6}$alkyl-N($R^a$)—SO$_w$—, $C_{3-6}$cycloalkyl-N($R^a$)—SO$_w$—, $C_{1-6}$alkyl-SO$_w$—N($R^a$)—, $C_{3-6}$cycloalkyl-SO$_w$—N($R^a$)—, $C_{1-6}$alkoxy-C (O)—N(R$^a$)—, C$_{1-6}$alkyl-C(O)—N(R$^a$)—C$_{1-6}$alkyl-, C$_{1-6}$alkyl-N(R$^a$)—C(O)—C$_{1-6}$alkyl- and C$_{1-6}$alkoxy-C$_{1-6}$alkyl-; wherein C$_{1-6}$alkyl, C$_{2-6}$alkenyl, C$_{2-6}$alkynyl, C$_{3-6}$cycloalkyl, —C$_{1-6}$alkylene-C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-C(O)—, C$_{1-6}$alkyl-O—C(O)—, C$_{1-6}$alkyl-C(O)—O—, C$_{1-6}$alkyl-S(O)$_w$—, C$_{1-6}$alkyl-N(R$^a$)—, C$_{1-6}$alkyl-N(R$^a$)—C(O)—, C$_{1-6}$alkyl-C(O)—N(R$^a$), C$_{1-6}$alkyl-N(R$^a$)—C(O)—N(R$^a$)—, C$_{1-6}$alkyl-N(R$^a$)—SO—, C$_{3-6}$cycloalkyl-N(R$^a$)—SO$_w$—, C$_{1-6}$alkyl-SO$_w$—N(R$^a$)—, C$_{3-6}$cycloalkyl-SO$_w$—N(R$^a$)—, C$_{1-6}$alkoxy-C(O)—N(R$^a$)—, C$_{1-6}$alkyl-C(O)—N(R$^a$)—C$_{1-6}$alkyl-, C$_{1-6}$alkyl-N(R$^a$)—C(O)—C$_{1-6}$alkyl- and C$_{1-6}$alkoxy-C$_{1-6}$alkyl- may optionally be substituted by one, two three or more substituents each independently selected from R$^P$;

R$^h$ is independently selected for each occurrence from the group consisting of C$_{1-6}$alkyl, C$_{3-6}$alkenyl, C$_{3-6}$alkynyl, C$_{3-6}$cycloalkyl, —C$_{1-6}$alkylene-C$_{3-6}$cycloalkyl, C$_{1-6}$alkyl-S(O)$_2$—, C$_{3-6}$cycloalkyl-S(O)$_2$—, C$_{1-6}$alkyl-C(O)—, C$_{1-6}$alkoxy-C(O)—, R$^a$R$^b$N—C(O)— and R$^a$R$^b$N—SO$_2$—; wherein C$_{1-6}$alkyl, C$_{3-6}$alkenyl, C$_{3-6}$alkynyl, C$_{3-6}$cycloalkyl, C$_{1-6}$alkyl-S(O)$_2$—, C$_{3-6}$cycloalkyl-S(O)$_2$—, C$_{1-6}$alkyl-C(O)—, C$_{1-6}$alkoxy-C(O)—, R$^a$R$^b$N—C(O)— and R$^a$R$^b$N—SO$_2$— may optionally be substituted by one, two three or more substituents each independently selected from R$^P$;

R$^P$ is independently selected for each occurrence from the group consisting of halogen, hydroxyl, cyano, C$_{1-6}$alkoxy, C$_{3-6}$cycloalkyl, R$^a$R$^b$N—, R$^a$R$^b$N-carbonyl-, R$^a$R$^b$N—SO$_2$—, and R$^a$R$^b$N-carbonyl-N(R$^a$)—;

R$^a$ and R$^b$ are independently selected, for each occurrence, from the group consisting of hydrogen and C$_{1-6}$alkyl; wherein C$_{1-6}$alkyl may optionally be substituted by one or more substituents each independently selected from the group consisting of halogen, cyano, oxo and hydroxyl;

or R$^a$ and R$^b$ together with the nitrogen to which they are attached form a 4-6 membered heterocyclyl, wherein 4-6 membered heterocyclyl may optionally be substituted by one or more substituents each independently selected from the group consisting of halogen, cyano, oxo and hydroxyl;

R$^c$ is independently selected, for each occurrence, from the group consisting of hydroxyl, C$_{1-4}$alkyl and phenyl; and w is 0, 1 or 2.

In some embodiments, R$^1$ is selected from the group consisting of hydrogen and fluorine. In some embodiments, R$^1$ is hydrogen.

In certain embodiments, R$^2$ is —O—C$_{1-6}$alkyl; wherein R$^2$ may optionally be substituted by one, two, three or more substituents each independently selected from R$^g$. In some embodiments, R$^2$ may optionally be substituted by one, two, three or more substituents each independently selected for each occurrence from the group consisting of fluorine, hydroxyl, C$_{1-6}$alkoxy and R$^a$R$^b$N—. For example, R$^2$ may be selected from the group consisting of: —OCH$_3$,

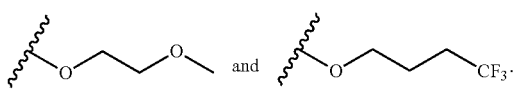

In other embodiments, R$^2$ is —N(R$^a$)—C$_{1-8}$alkyl, wherein R$^2$ may optionally be substituted by one, two, three or more substituents each independently selected from R$^g$. In some embodiments, R$^2$ may optionally be substituted by one, two, three or more substituents each independently selected from the group consisting of fluorine, hydroxyl, cyano and C$_{1-6}$alkoxy, wherein C$_{1-6}$alkoxy may optionally be substituted by one, two or three fluorines. In some embodiments, R$^a$ is hydrogen. In some embodiments, R$^2$ is —N(R$^a$)—C$_5$alkyl. For example, R$^2$ may be selected from the group consisting of

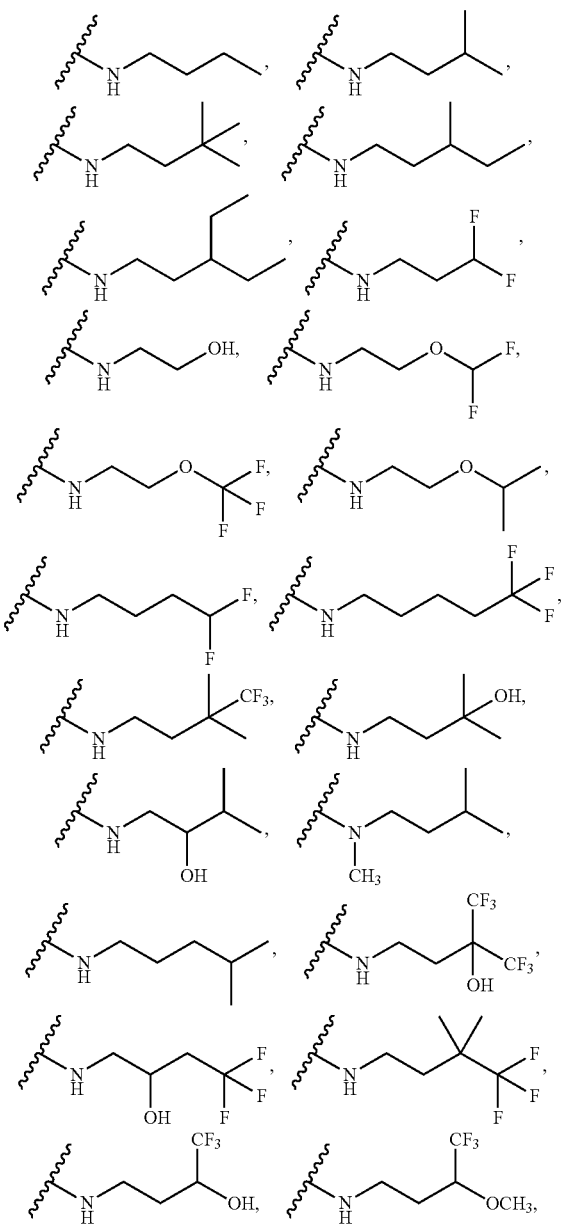

-continued

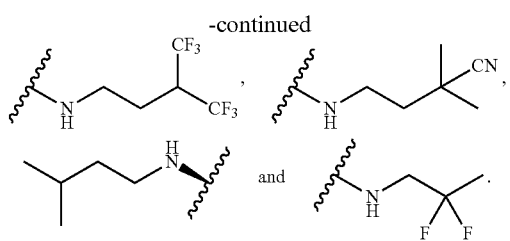

In some embodiments, $R^2$ is selected from the group consisting of —$NH_2$, —$N(R^a)$—$C_{1-8}$alkyl, —$N(R^a)$—$C_{3-6}$cycloalkyl, —$N(R^a)$—$C_{1-6}$alkylene-$C_{3-6}$cycloalkyl, —$N(R^a)$—$C_{1-6}$alkylene-Si$(R^c)_3$, —$N(R^a)$-4-6 membered heterocyclyl, —$N(R^a)$—$C_{1-6}$alkylene-4-6 membered heterocyclyl, —$N(R^a)$—$C_{1-6}$alkylene-5-6 membered heteroaryl and —$N(R^a)$—$C_{1-6}$alkylene-phenyl and the moiety is attached to the tetralin bicycle to form the R-enantiomer;

wherein —$N(R^a)$—$C_{1-5}$alkyl, —$N(R^a)$—$C_{3-6}$cycloalkyl, —$N(R^a)$—$C_{1-6}$alkylene-$C_{3-6}$cycloalkyl, —$N(R^a)$—$C_{1-6}$alkylene-Si$(R^c)_3$, —$N(R^a)$-4-6 membered heterocyclyl, —$N(R^a)$—$C_{1-6}$alkylene-4-6 membered heterocyclyl, —$N(R^a)$—$C_{1-6}$alkylene-5-6 membered heteroaryl and —$N(R^a)$—$C_{1-6}$alkylene-phenyl may optionally be substituted on one or more available carbons by one, two, three or more substituents each independently selected from $R^g$; and wherein if —$N(R^a)$-4-6 membered heterocyclyl, —$N(R^a)$—$C_{1-6}$alkylene-4-6 membered heterocyclyl or —$N(R^a)$—$C_{1-6}$alkylene-5-6 membered heteroaryl contains a substitutable ring nitrogen atom, that ring nitrogen atom may optionally be substituted by $R^h$.

For example, $R^2$ may be selected from the group consisting of

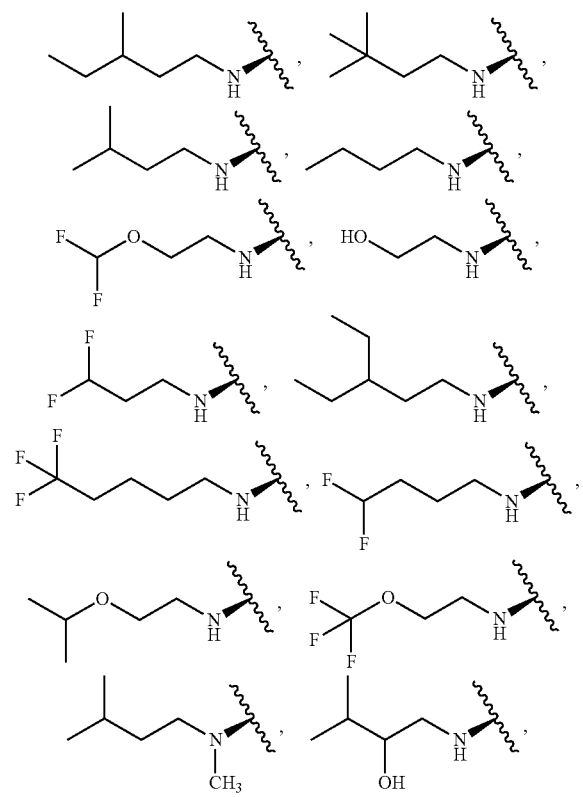

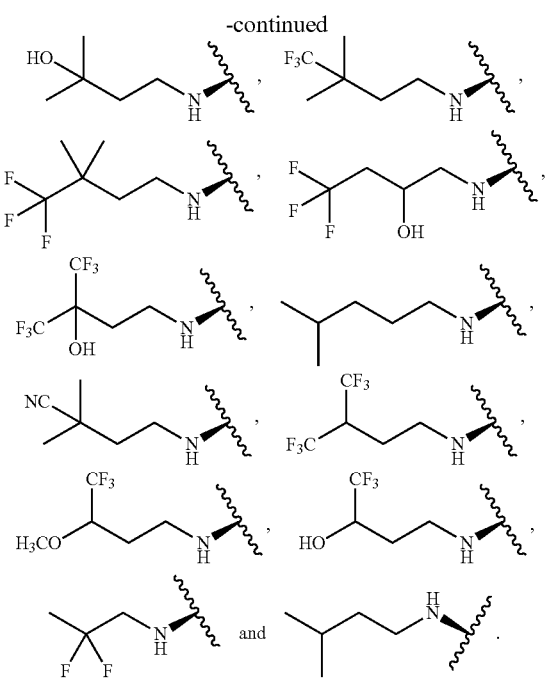

In some embodiments, $R^2$ is

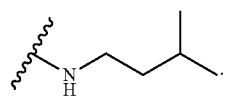 [SMILES: *NCCC(C)C]

In other embodiments, $R^2$ is

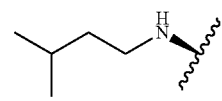

In some embodiments, $R^2$ is —$C_{1-6}$alkylene-$C_{3-6}$cycloalkyl. For example, $R^2$ may be represented by

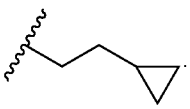 [SMILES: *CCC1CC1]

In other embodiments, $R^2$ is —O—$C_{1-6}$alkylene-$C_{3-6}$cycloalkyl, wherein $R^2$ may optionally be substituted by one, two, three or more substituents each independently selected from $R^g$. In some embodiments, $R^2$ may optionally be substituted by one, two or three fluorine atoms. For example, $R^2$ may be selected from the group consisting of

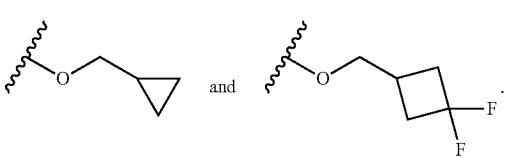 [SMILES: *OCC1CC1 ; *OCC1CC(F)(F)C1]

In further embodiments, R² is —N(Rᵃ)—C₁₋₆alkylene-C₃₋₆cycloalkyl, wherein R² may optionally be substituted by one, two, three or more substituents each independently selected from R⁹. For example, R² may be selected from the group consisting of

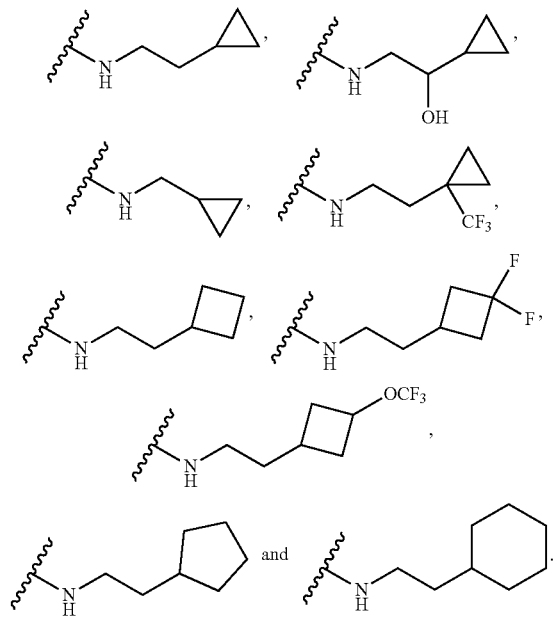

For example, R² may be selected from the group consisting of

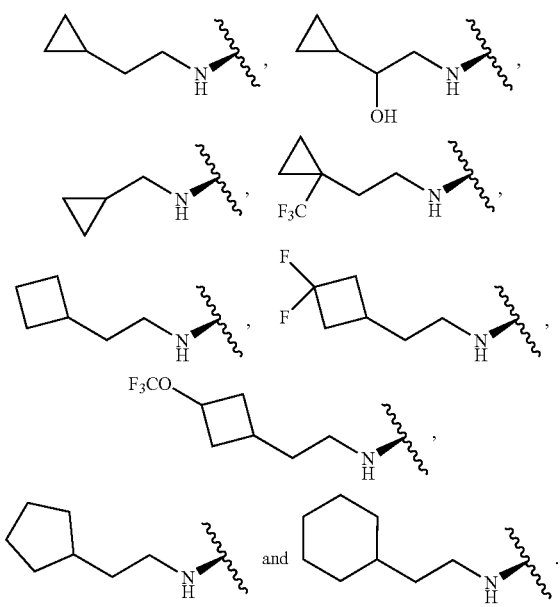

In yet further embodiments, R² is —N(Rᵃ)—C₁₋₆alkylene-4-6 membered heterocyclyl. For example, R² may be represented by

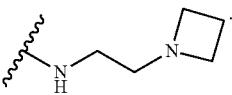 [SMILES: *NCCN1CCC1]

For example, R² may be represented by

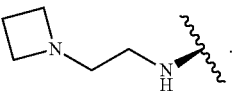

In certain embodiments, R² is —N(Rᵃ)—C₁₋₆alkylene-phenyl, wherein R² may optionally be substituted by one, two, three or more substituents each independently selected from R⁸. In some embodiments, R² may optionally be substituted by one, two or three fluorine atoms. For example, R² may be represented by

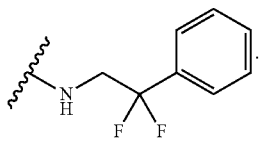 [SMILES: *NCC(F)(F)c1ccccc1]

For example, R² may be represented by

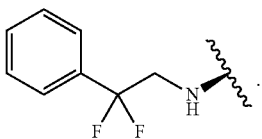

In some embodiments, R² is —N(Rᵃ)—C₁₋₆alkylene-5-6 membered heteroaryl, wherein R² may optionally be substituted by one, two, three or more substituents each independently selected from R⁸. For example, R² may be selected from the group consisting of

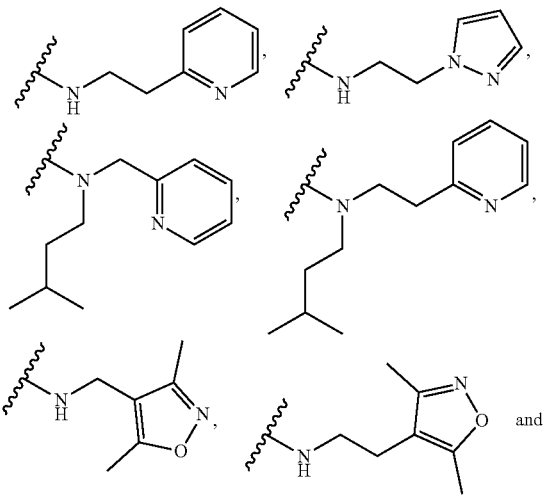

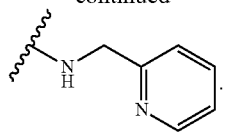

For example, R² may be selected from the group consisting of

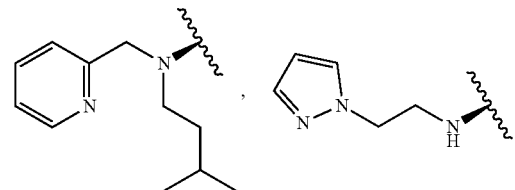

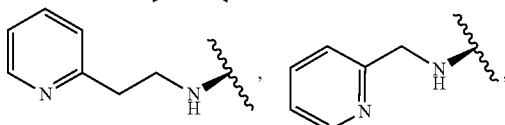

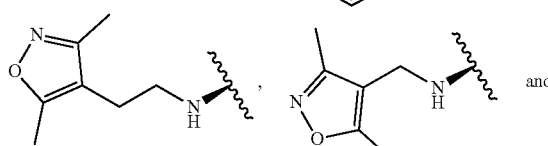

In other embodiments, R² is 4-6 membered heterocyclyl, wherein 4-6 membered heterocyclyl may optionally be substituted by one, two, three or more substituents each independently selected from R^g, and wherein if 4-6 membered heterocyclyl contains a substitutable ring nitrogen atom, that ring nitrogen atom may optionally be substituted by R^h For example, R² may be pyrrolidinyl, wherein pyrrolidinyl may optionally be substituted by R^h In some embodiments, R^h is selected from the group consisting of $C_{1-6}$alkyl, —$C_{1-6}$alkylene-$C_{3-6}$cycloalkyl and $C_{3-6}$cycloalkyl-S(O)₂—. For example, R² may be selected from the group consisting of

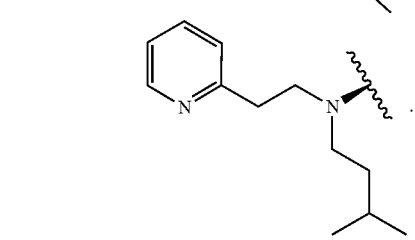

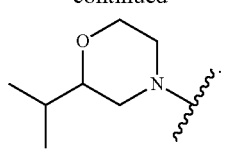

In further embodiments, R² is —O—C(O)—N(R^a)-phenyl. For example, R² may be represented by

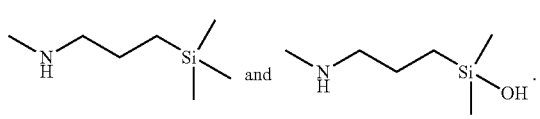

In some embodiments, R² is —N(R^a)—$C_{1-6}$alkylene-Si(R^c)₃. For example, R² may be selected from the group consisting of

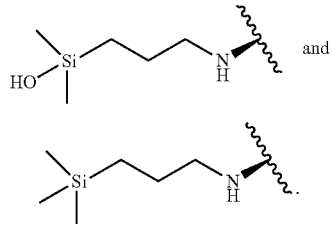

For example, R² may be selected from the group consisting of

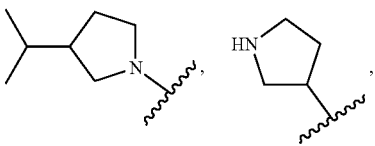

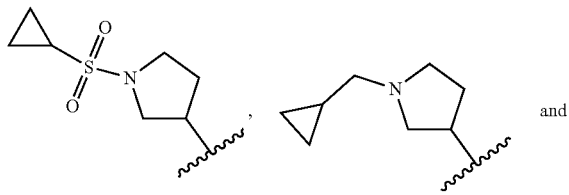

In some embodiments, R² is —N(R^a)—(C=N(R^b))—$C_{1-6}$alkyl. For example, R² may represented by

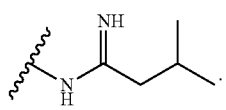

In some embodiments, R² is —N(R^a)—$C_{3-6}$cycloalkyl, wherein R² may optionally be substituted by one, two, three or more substituents each independently selected from R^g. For example, R² may be represented by

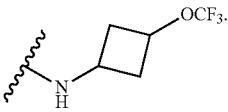

For example, $R^2$ may be represented as

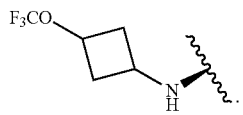

In some embodiments, $R^{2'}$ is hydrogen. In other embodiments, $R^{2'}$ is selected from the group consisting of hydrogen and $-NH_2$.

In some embodiments, $R^3$ is hydrogen. In other embodiments, $R^3$ is selected from the group consisting of $-O-C_{1-6}$alkyl and $-O-C_{1-6}$alkylene-$C_{3-6}$cycloalkyl, wherein $R^3$ may optionally be substituted by one, two, three or more substituents each independently selected from $R^g$. For example, $R^3$ may be selected from the group consisting of $-OCH_3$,

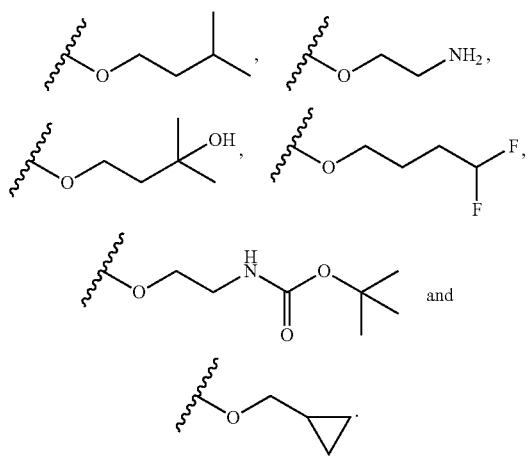

In some embodiments, $R^3$ is selected from the group consisting of $-N(R^a)-C_{1-6}$alkyl and $-N(R^a)-C_{1-6}$alkylene-$C_{3-6}$cycloalkyl, wherein $R^3$ may optionally be substituted by one, two, three or more substituents each independently selected from $R^g$. For example, $R^3$ may be selected from the group consisting of,

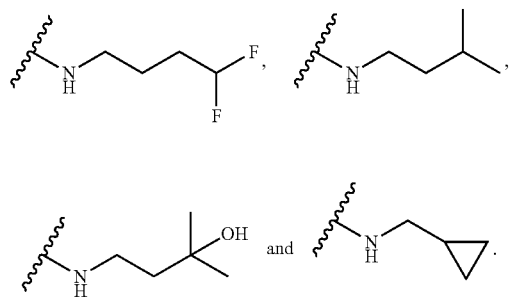

Further disclosed herein is a compound is represented by Formula I(c):

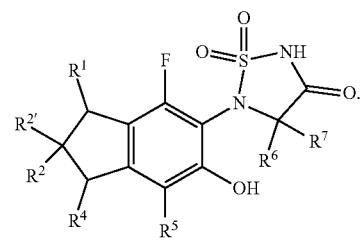

In some embodiments, $R^2$ is selected from the group consisting of $-C_{1-6}$alkylene-$N(R^a)-C_{1-6}$alkyl, $-C_{1-6}$alkylene-$N(R^a)(R^b)$ and $-C_{1-6}$alkylene-$N(R^a)-C_{1-6}$alkylene-$C_{3-6}$cycloalkyl, wherein $R^2$ may optionally be substituted by one, two, three or more substituents each independently selected from $R^g$. For example, $R^2$ may be selected from the group consisting of

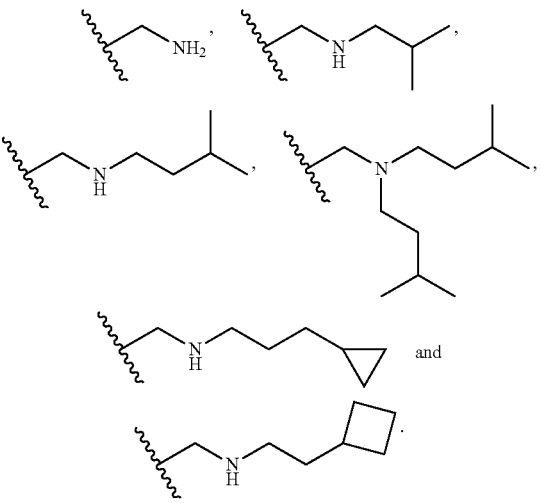

Further disclosed herein is a compound is represented by Formula I(d):

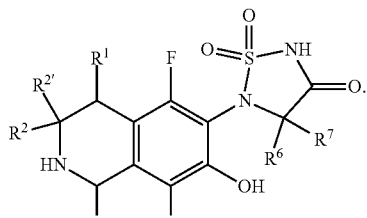

In some embodiments, $R^2$ is $C_{1-6}$alkyl.

In other embodiments, $R^4$ is hydrogen. In further embodiments, $R^5$ is selected from the group consisting of hydrogen and fluorine. In certain embodiments, $R^6$ is hydrogen. In yet further embodiments, $R^7$ is hydrogen.

Also disclosed herein is a compound represented by Formula (II):

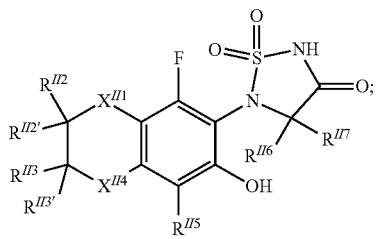

(II)

or a pharmaceutically acceptable salt thereof, wherein:

$X^{II1}$ is selected from the group consisting of O and $C(R^{II1})(R^{II1'})$;

$X^{II4}$ is selected from the group consisting of O and $C(R^{II4})(R^{II4'})$;

wherein at least one of $X^{II1}$ and $X^{II4}$ is O;

$R^{II1}$ and $R^{II1'}$ are each independently selected from the group consisting of hydrogen, halogen, $C_{1-6}$alkyl, $C_{2-6}$alkenyl, $C_{2-6}$alkynyl and $C_{3-6}$cycloalkyl;

wherein $C_{1-6}$alkyl, $C_{2-6}$alkenyl, $C_{2-6}$alkynyl and $C_{3-6}$cycloalkyl may optionally be substituted on one or more available carbons by one, two, three or more substituents each independently selected from $R^{IIg}$;

$R^{II2}$ is selected from the group consisting of hydrogen, $C_{1-6}$alkyl, $C_{2-6}$alkenyl, $C_{2-6}$alkynyl, —O—$C_{1-6}$alkyl, —N($R^{IIa}$)—$C_{1-6}$alkyl, —N($R^{IIa}$)—$C_{1-6}$alkylene-$C_{3-6}$cycloalkyl, —S(O)$_2$—$C_{1-6}$alkyl, —C(O)—N($R^{IIa}$)—$C_{1-6}$alkyl, —N($R^{IIa}$)—C(O)—$C_{1-6}$alkyl, —O—C(O)—N($R^{IIa}$)—$C_{1-6}$alkyl, —N($R^{IIa}$)—C(O)—O—$C_{1-6}$alkyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl, —$C_{1-6}$alkylene-4-6 membered heterocyclyl, —O—$C_{1-6}$alkylene-$C_{3-6}$cycloalkyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, —N($R^{IIa}$)—$C_{1-6}$alkylene-5-6 membered heteroaryl and —N($R^{IIa}$)—$C_{1-6}$alkylene-phenyl;

wherein $C_{1-6}$alkyl, $C_{2-6}$alkenyl, $C_{2-6}$alkynyl, —O—$C_{1-6}$alkyl, —N($R^{IIa}$)—$C_{1-6}$alkyl, —N($R^{IIa}$)—$C_{1-6}$alkylene-$C_{3-6}$cycloalkyl, —S(O)$_2$—$C_{1-6}$alkyl, —C(O)—N($R^{IIa}$)—$C_{1-6}$alkyl, —N($R^{IIa}$)—C(O)—$C_{1-6}$alkyl, —O—C(O)—N($R^{IIa}$)—$C_{1-6}$alkyl, —N($R^{IIa}$)—C(O)—O—$C_{1-6}$alkyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl, —$C_{1-6}$alkylene-4-6 membered heterocyclyl, —O—$C_{1-6}$alkylene-$C_{3-6}$cycloalkyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, —N($R^{IIa}$)—$C_{1-6}$alkylene-5-6 membered heteroaryl and —N($R^{IIa}$)—$C_{1-6}$alkylene-phenyl may optionally be substituted on one or more available carbons by one, two, three or more substituents each independently selected from $R^{IIg}$;

wherein if 5-6 membered heteroaryl, 4-6 membered heterocyclyl, —$C_{1-6}$alkylene-5-6 membered heteroaryl, —$C_{1-6}$alkylene-4-6 membered heterocyclyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, or —N($R^{IIa}$)—$C_{1-6}$alkylene-5-6 membered heteroaryl contains a substitutable ring nitrogen atom, that ring nitrogen atom may optionally be substituted by $R^{IIh}$; and wherein if $R^{II2}$ is —O—$C_{1-6}$alkyl, —N($R^{IIa}$)—$C_{1-6}$alkyl, —N($R^{IIa}$)—$C_{1-6}$alkylene-$C_{3-6}$cycloalkyl, —S(O)$_2$—$C_{1-6}$alkyl, —N($R^{IIa}$)—C(O)—$C_{1-6}$alkyl, —O—C(O)—N($R^{IIa}$)—$C_{1-6}$alkyl, —N($R^{IIa}$)—C(O)—O—$C_{1-6}$alkyl, —O—$C_{1-6}$alkylene-$C_{3-6}$cycloalkyl, —N($R^{IIa}$)-4-6 membered heterocyclyl, —O—$C_{1-6}$alkylene-4-6 membered heterocyclyl, —N($R^{IIa}$)—$C_{1-6}$alkylene-4-6 membered heterocyclyl, —N($R^{IIa}$)—$C_{1-6}$alkylene-5-6 membered heteroaryl or —N($R^{IIa}$)—$C_{1-6}$alkylene-phenyl; then $X^{II1}$ is $C(R^{II1})(R^{II1'})$ and $X^{II4}$ is O;

$R^{II2'}$ is selected from the group consisting of hydrogen, $C_{1-6}$alkyl, $C_{2-6}$alkenyl, $C_{2-6}$alkynyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl and —$C_{1-6}$alkylene-4-6 membered heterocyclyl;

wherein $C_{1-6}$alkyl, $C_{2-6}$alkenyl, $C_{2-6}$alkynyl, $C_{3-6}$cycloalkyl, phenyl, 5-6 membered heteroaryl, 4-6 membered heterocyclyl, —$C_{1-6}$alkylene-$C_{3-6}$cycloalkyl, —$C_{1-6}$alkylene-phenyl, —$C_{1-6}$alkylene-5-6 membered heteroaryl and —$C_{1-6}$alkylene-4-6 membered heterocyclyl may optionally be substituted on one or more available carbons by one, two, three or more substituents each independently selected from $R^g$; and wherein if 5-6 membered heteroaryl, 4-6 membered heterocyclyl, —$C_{1-6}$alkylene-5-6 membered heteroaryl or —$C_{1-6}$alkylene-4-6 membered heterocyclyl contains a substitutable ring nitrogen atom, that ring nitrogen atom may optionally be substituted by $R^{IIh}$;

$R^{II3}$ and $R^{II3'}$ are each independently selected from the group consisting of hydrogen, $C_{1-6}$alkyl, $C_{2-6}$alkenyl, $C_{2-6}$alkynyl and $C_{3-6}$cycloalkyl;

wherein $C_{1-6}$alkyl, $C_{2-6}$alkenyl, $C_{2-6}$alkynyl and $C_{3-6}$cycloalkyl may optionally be substituted on one or more available carbons by one, two, three or more substituents each independently selected from $R^{IIg}$;

$R^{II4}$ and $R^{II4'}$ are each independently selected from the group consisting of hydrogen, halogen, $C_{1-6}$alkyl, $C_{2-6}$alkenyl, $C_{2-6}$alkynyl and $C_{3-6}$cycloalkyl;

wherein $C_{1-6}$alkyl, $C_{2-6}$alkenyl, $C_{2-6}$alkynyl and $C_{3-6}$cycloalkyl may optionally be substituted on one or more available carbons by one, two, three or more substituents each independently selected from $R^{IIg}$;

$R^{II5}$ is selected from the group consisting of hydrogen, deuterium, halogen, $C_{1-6}$alkyl and $C_{3-6}$cycloalkyl;

wherein $C_{1-6}$alkyl and $C_{3-6}$cycloalkyl may optionally be substituted on one or more available carbons by one, two, three or more substituents each independently selected from $R^{IIg}$;

$R^{II6}$ is selected from the group consisting of hydrogen and deuterium;

$R^{II7}$ is selected from the group consisting of hydrogen and deuterium;

$R^{IIg}$ is independently selected for each occurrence from the group consisting of hydrogen, halogen, hydroxyl, cyano, nitro, oxo, $R^{IIa}R^{IIb}N$—, $R^{IIa}R^{IIb}N$—C(O)—, $R^{IIa}R^{IIb}N$—SO$_w$—, $R^{IIa}R^{IIb}N$—C(O)—N($R^{IIa}$)—, $C_{1-6}$alkyl, $C_{2-6}$alkenyl, $C_{2-6}$alkynyl, $C_{3-6}$cycloalkyl, $C_{3-6}$cycloalkyl-$C_{1-6}$alkylene-, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^{IIa}$)—, $C_{1-6}$alkyl-N($R^{IIa}$)—C(O)—, $C_{1-6}$alkyl-C(O)—N($R^{IIa}$), $C_{1-6}$alkyl-N($R^{IIa}$)—C(O)—N($R^{IIa}$)—, $C_{1-6}$alkyl-N($R^{IIa}$)—SO$_w$—, $C_{3-6}$cycloalkyl-N($R^{IIa}$)—SO$_w$—, $C_{1-6}$alkyl-SO$_w$—N($R^{IIa}$)—, $C_{3-6}$cycloalkyl-SO$_w$—N($R^{IIa}$)—, $C_{1-6}$alkoxy-C(O)—N($R^{IIa}$)—, $C_{1-6}$alkyl-C(O)—N($R^{IIa}$)—$C_{1-6}$alkyl-, $C_{1-6}$alkyl-N($R^{IIa}$)—C(O)—$C_{1-6}$alkyl- and $C_{1-6}$alkoxy-$C_{1-6}$alkyl-; wherein $C_{1-6}$alkyl, $C_{2-6}$alkenyl, $C_{2-6}$alkynyl, $C_{3-6}$cycloalkyl, —$C_{1-6}$alkylene-$C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-C(O)—, $C_{1-6}$alkyl-O—C(O)—, $C_{1-6}$alkyl-C(O)—O—, $C_{1-6}$alkyl-S(O)$_w$—, $C_{1-6}$alkyl-N($R^{IIa}$)—, $C_{1-6}$alkyl-N($R^{IIa}$)—C(O)—, $C_{1-6}$alkyl-C(O)—N($R^{IIa}$), $C_{1-6}$alkyl-N($R^{IIa}$)—C(O)—N($R^{IIa}$)—, $C_{1-6}$alkyl-N($R^{IIa}$)—SO$_w$—, $C_{3-6}$cycloalkyl-N($R^{IIa}$)—SO$_w$—, $C_{1-6}$alkyl-SO$_w$—N($R^{IIa}$)—, $C_{3-6}$cycloalkyl-SO$_w$—N($R^{IIa}$)—, $C_{1-6}$alkoxy-C(O)—N($R^{IIa}$)—, $C_{1-6}$alkyl-C(O)—N($R^{IIa}$)—$C_{1-6}$alkyl-, $C_{1-6}$alkyl-N($R^{IIa}$)—C(O)—$C_{1-6}$alkyl- and $C_{1-6}$alkoxy-$C_{1-6}$alkyl- may optionally be substituted by one, two three or more substituents each independently selected from $R^{IIP}$;

$R^{IIh}$ is independently selected for each occurrence from the group consisting of $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^{IIa}R^{IIb}$N—C(O)— and $R^{IIa}R^{IIb}$N—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{3-6}$cycloalkyl-S(O)$_2$—, $C_{1-6}$alkyl-C(O)—, $C_{1-6}$alkoxy-C(O)—, $R^{IIa}R^{IIb}$N—C(O)— and $R^{IIa}R^{IIb}$N—SO$_2$— may optionally be substituted by one, two three or more substituents each independently selected from $R^{IIP}$;

$R^{IIP}$ is independently selected for each occurrence from the group consisting of halogen, hydroxyl, cyano, $C_{1-6}$alkoxy, $C_{3-6}$cycloalkyl, $R^{IIa}R^{IIb}$N—, $R^{IIa}R^{IIb}$N-carbonyl-, $R^{IIa}R^{IIb}$N—SO$_2$—, and $R^{IIa}R^{IIb}$N-carbonyl-N($R^{IIa}$)—;

$R^{IIa}$ and $R^{IIb}$ are independently selected, for each occurrence, from the group consisting of hydrogen and $C_{1-3}$alkyl; wherein $C_{1-3}$alkyl may optionally be substituted by one or more substituents each independently selected from the group consisting of halogen, cyano, oxo and hydroxyl;

or $R^{IIa}$ and $R^{IIb}$ together with the nitrogen to which they are attached form a 4-6 membered heterocyclyl, wherein 4-6 membered heterocyclyl may optionally be substituted by one or more substituents each independently selected from the group consisting of halogen, cyano, oxo and hydroxyl; and w is 0, 1 or 2.

In some embodiments, $R^{II5}$, $R^{II6}$ and $R^{II7}$ are each hydrogen. In other embodiments, either $R^{II1}$ and $R^{II1'}$, or $R^{II4}$ and $R^{II4'}$ are each hydrogen.

In certain embodiments, a compound disclosed herein is represented by

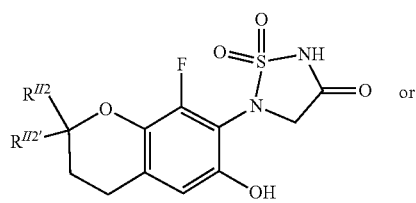

or

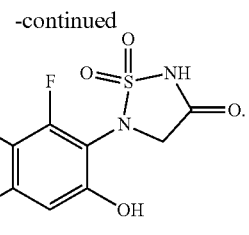

For example, $R^{II2}$ and $R^{II2'}$ may each be independently selected from the group consisting of hydrogen and —CH$_3$. For example, $R^{II3}$ and $R^{II3'}$ may each be independently selected from the group consisting of hydrogen and —CH$_3$.

Also disclosed herein is a compound represented by Formula (III):

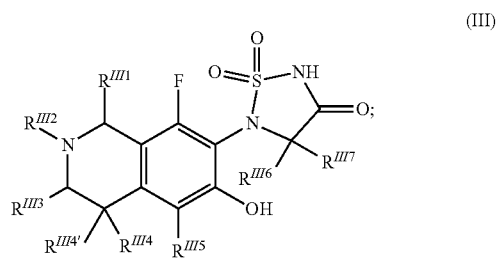

or a pharmaceutically acceptable salt thereof, wherein:

$R^{III1}$ is selected from the group consisting of hydrogen, $C_{1-6}$alkyl, $C_{2-6}$alkenyl and $C_{2-6}$alkynyl;

$R^{III2}$ is selected from the group consisting of hydrogen, $C_{1-6}$alkyl, $C_{2-6}$alkenyl, $C_{2-6}$alkynyl, $C_{3-6}$cycloalkyl, phenyl, 4-7 membered heterocyclyl, 5-6 membered heteroaryl, —$C_{1-6}$alkylene-$C_{3-8}$cycloalkyl, —$C_{1-6}$alkylene-phenyl, —$C_{1-6}$alkylene-4-7 membered heterocyclyl, —$C_{1-6}$alkylene-5-6 membered heteroaryl, —C(O)—$C_{1-6}$alkyl, —C(O)—O—$C_{1-6}$alkyl, —C(O)—$C_{1-6}$alkylene-$C_{3-8}$cycloalkyl, —C(O)—N($R^{IIIa}$)—$C_{1-6}$alkyl, —C(O)—N($R^{IIIa}$)—$C_{1-6}$alkylene-$C_{3-6}$cycloalkyl, —C(O)—N($R^{IIIa}$)—$C_{1-6}$alkylene-phenyl, —C(O)—N($R^{IIIa}$)—$C_{1-6}$alkylene-4-7 membered heterocyclyl, —C(O)—N($R^{IIIa}$)—$C_{1-6}$alkylene-5-6 membered heteroaryl, —C=N($R^{IIIa}$)—$C_{1-6}$alkyl and —S(O)$_2$—$C_{1-6}$alkyl;

wherein $C_{1-6}$alkyl, $C_{2-6}$alkenyl, $C_{2-6}$alkynyl, $C_{3-6}$cycloalkyl, phenyl, 4-7 membered heterocyclyl, 5-6 membered heteroaryl, —$C_{1-6}$alkylene-$C_{3-8}$cycloalkyl, —$C_{1-6}$alkylene-phenyl, —$C_{1-6}$alkylene-4-7 membered heterocyclyl, —$C_{1-6}$alkylene-5-6 membered heteroaryl, —C(O)—$C_{1-6}$alkyl, —C(O)—O—$C_{1-6}$alkyl, —C(O)—$C_{1-6}$alkylene-$C_{3-8}$cycloalkyl, —C(O)—N($R^{IIIa}$)—$C_{1-6}$alkyl, —C(O)—N($R^{IIIa}$)—$C_{1-6}$alkylene-$C_{3-6}$cycloalkyl, —C(O)—N($R^{IIIa}$)—$C_{1-6}$alkylene-phenyl, —C(O)—N($R^{IIIa}$)—$C_{1-6}$alkylene-4-7 membered heterocyclyl, —C(O)—N($R^{IIIa}$)—$C_{1-6}$alkylene-5-6 membered heteroaryl, —C=N($R^{IIIa}$)—$C_{1-6}$alkyl and —S(O)$_2$—$C_{1-6}$alkyl may optionally be substituted on one or more available carbons by one, two, three or more substituents each independently selected from $R^{IIIg}$; and wherein if 4-7 membered heterocyclyl, 5-6 membered heteroaryl, —$C_{1-6}$alkylene-4-7 membered heterocyclyl, —$C_{1-6}$alkylene-5-6 membered heteroaryl, —C(O)—N(R$^{IIIa}$)—C$_{1-6}$alkylene-4-7 membered heterocyclyl or —C(O)—N(R$^{IIIa}$)—C$_{1-6}$alkylene-5-6 membered heteroaryl contains a substitutable ring nitrogen atom, that ring nitrogen atom may optionally be substituted by R$^{IIIh}$;

R$^{III3}$ is selected from the group consisting of hydrogen, C$_{1-6}$alkyl, C$_{2-6}$alkenyl and C$_{2-6}$alkynyl;

R$^{III4}$ is selected from the group consisting of hydrogen, halogen, C$_{1-6}$alkyl, C$_{2-6}$alkenyl and C$_{2-6}$alkynyl;

R$^{III4'}$ is selected from the group consisting of hydrogen, halogen, C$_{1-6}$alkyl, C$_{2-6}$alkenyl and C$_{2-6}$alkynyl;

R$^{III5}$ is selected from the group consisting of hydrogen, halogen and C$_{1-6}$alkyl;

R$^{III6}$ is selected from the group consisting of hydrogen and deuterium;

R$^{III7}$ is selected from the group consisting of hydrogen and deuterium;

R$^{IIIg}$ is independently selected for each occurrence from the group consisting of hydrogen, halogen, hydroxyl, cyano, nitro, oxo, R$^{IIIa}$R$^{IIIb}$N—, R$^{IIIa}$R$^{IIIb}$N—C(O)—, R$^{IIIa}$$^{IIIb}$N—SO$_w$—, R$^{IIIa}$R$^{IIIb}$N—C(O)—N(R$^{IIIa}$)—, C$_{1-6}$alkyl, C$_{2-6}$alkenyl, C$_{2-6}$alkynyl, C$_{3-6}$cycloalkyl, C$_{3-6}$cycloalkyl-C$_{1-6}$alkylene-, C$_{1-6}$alkoxy, C$_{3-6}$alkenyloxy, C$_{3-6}$alkynyloxy, C$_{3-6}$cycloalkoxy, C$_{1-6}$alkyl-C(O)—, C$_{1-6}$alkyl-O—C(O)—, C$_{1-6}$alkyl-C(O)—O—, C$_{1-6}$alkyl-S(O)$_w$—, C$_{1-6}$alkyl-N(R$^{IIIa}$)—, C$_{1-6}$alkyl-N(R$^{IIIa}$)—C(O)—, C$_{1-6}$alkyl-C(O)—N(R$^{IIIa}$), C$_{1-6}$alkyl-N(R$^{IIIa}$)—C(O)—N(R$^{IIIa}$)—, C$_{1-6}$alkyl-N(R$^{IIIa}$)—SO$_w$—, C$_{3-6}$cycloalkyl-N(R$^{IIIa}$)—SO$_w$—, C$_{1-6}$alkyl-SO$_w$—N(R$^{IIIa}$)—, C$_{3-6}$cycloalkyl-SO$_w$—N(R$^{IIIa}$)—, C$_{1-6}$alkoxy-C(O)—N(R$^{IIIa}$)—, C$_{1-6}$alkyl-C(O)—N(R$^{IIIa}$)—C$_{1-6}$alkyl-, C$_{1-6}$alkyl-N(R$^{IIIa}$)C(O)—C$_{1-6}$alkyl-, C$_{1-6}$alkoxy-C$_{1-6}$alkyl- and 5-6 membered heteroaryl; wherein C$_{1-6}$alkyl, C$_{2-6}$alkenyl, C$_{2-6}$alkynyl, C$_{3-6}$cycloalkyl, —C$_{1-6}$alkylene-C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-C(O)—, C$_{1-6}$alkyl-O—C(O)—, C$_{1-6}$alkyl-C(O)—O—, C$_{1-6}$alkyl-S(O)$_w$—, C$_{1-6}$alkyl-N(R$^{IIIa}$)—, C$_{1-6}$alkyl-N(R$^{IIIa}$)—C(O)—, C$_{1-6}$alkyl-C(O)—N(R$^{IIIa}$), C$_{1-6}$alkyl-N(R$^{IIIa}$)—C(O)—N(R$^{IIIa}$)—, C$_{1-6}$alkyl-N(R$^{IIIa}$)—SO$_w$—, C$_{3-6}$cycloalkyl-N(R$^{IIIa}$)—SO$_w$—, C$_{1-6}$alkyl-SO$_w$—N(R$^{IIIa}$)—, C$_{3-6}$cycloalkyl-SO$_w$—N(R$^{IIIa}$)—, C$_{1-6}$alkoxy-C(O)—N(R$^{IIIa}$)—, C$_{1-6}$alkyl-C(O)—N(R$^{IIIa}$)—C$_{1-6}$alkyl-, C$_{1-6}$alkyl-N(R$^{IIIa}$)—C(O)—C$_{1-6}$alkyl-, C$_{1-6}$alkoxy-C$_{1-6}$alkyl- and 5-6 membered heteroaryl may optionally be substituted by one, two three or more substituents each independently selected from R$^{IIIp}$;

R$^{IIIh}$ is independently selected for each occurrence from the group consisting of C$_{1-6}$alkyl, C$_{3-6}$alkenyl, C$_{3-6}$alkynyl, C$_{3-6}$cycloalkyl, C$_{1-6}$alkyl-S(O)$_2$—, C$_{3-6}$cycloalkyl-S(O)$_2$—, C$_{1-6}$alkyl-C(O)—, C$_{1-6}$alkoxy-C(O)—, R$^{IIIa}$R$^{IIIb}$N—C(O)—, R$^{IIIa}$R$^{IIIb}$N—SO$_2$— and —C$_{1-6}$alkylene-5-6 membered heteroaryl; wherein C$_{1-6}$alkyl, C$_{3-6}$alkenyl, C$_{3-6}$alkynyl, C$_{3-6}$cycloalkyl, C$_{1-6}$alkyl-S(O)$_2$—, C$_{3-6}$cycloalkyl-S(O)$_2$—, C$_{1-6}$alkyl-C(O)—, C$_{1-6}$alkoxy-C(O)—, R$^{IIIa}$R$^{IIIb}$N—C(O)—, R$^{IIIa}$R$^{IIIb}$N—SO$_2$— and —C$_{1-6}$alkylene-5-6 membered heteroaryl may optionally be substituted by one, two three or more substituents each independently selected from R$^{IIIp}$;

R$^{IIIp}$ is independently selected for each occurrence from the group consisting of halogen, hydroxyl, cyano, C$_{1-6}$alkoxy, C$_{3-6}$cycloalkyl, R$^{IIIa}$R$^{IIIb}$N—, R$^{IIIa}$R$^{IIIb}$N-carbonyl-, R$^{IIIa}$R$^{IIIb}$N—SO$_2$—, and R$^{IIIa}$R$^{IIIb}$N-carbonyl-N(R$^{IIIa}$)—;

R$^{IIIa}$ and R$^{IIIb}$ are independently selected, for each occurrence, from the group consisting of hydrogen and C$_{1-3}$alkyl; wherein C$_{1-3}$alkyl may optionally be substituted by one or more substituents each independently selected from the group consisting of halogen, cyano, oxo and hydroxyl;

or R$^{IIIa}$ and R$^{IIIb}$ together with the nitrogen to which they are attached form a 4-6 membered heterocyclyl, wherein 4-6 membered heterocyclyl may optionally be substituted by one or more substituents each independently selected from the group consisting of halogen, cyano, oxo and hydroxyl; and w is 0, 1 or 2.

In some embodiments, R$^{III5}$ is selected from the group consisting of hydrogen and fluorine. In other embodiments, R$^{III6}$ and R$^{III7}$ are each hydrogen. In further embodiments, R$^{III4}$ and R$^{III4'}$ are each independently selected from the group consisting of hydrogen and fluorine. In yet further embodiments, R$^{III1}$, R$^{III3}$, R$^{III4}$ and R$^{III4'}$ are each hydrogen.

For example, disclosed herein is a compound is represented by:

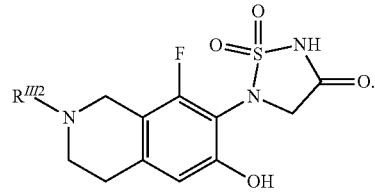

In some embodiments, R$^{III2}$ is selected from the group consisting of hydrogen, C$_{1-6}$alkyl and —C(O)—C$_{1-6}$alkyl, wherein R$^{III2}$ may optionally be substituted by one, two, three or more substituents each independently selected from R$^{IIIg}$. For example R$^{III2}$ may selected from the group consisting of hydrogen,

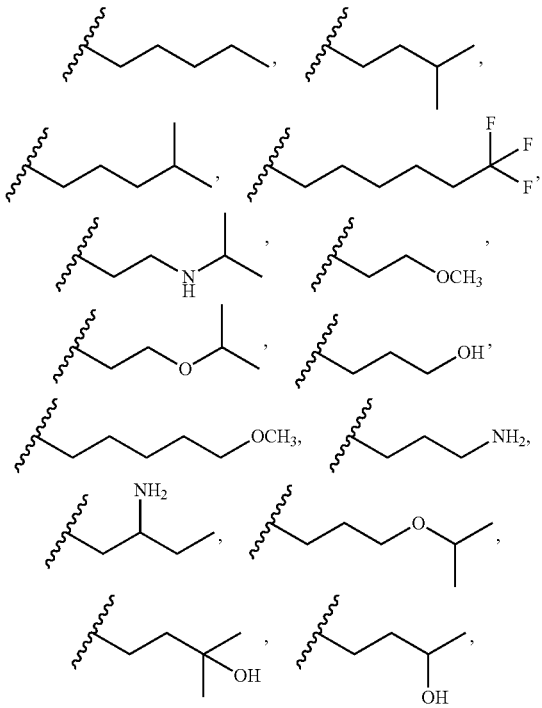

-continued

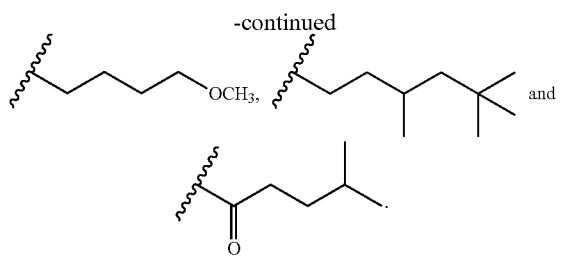

In other embodiments, $R^{III2}$ is 4-7 membered heterocyclyl, wherein 4-7 membered heterocyclyl may optionally be substituted on one or more available carbons by one, two, three or more substituents each independently selected from $R^{IIg}$; and wherein if 4-7 membered heterocyclyl contains a substitutable ring nitrogen atom, that ring nitrogen atom may optionally be substituted by $R^{IIIh}$. For example, $R^{III2}$ may be selected from the group consisting of

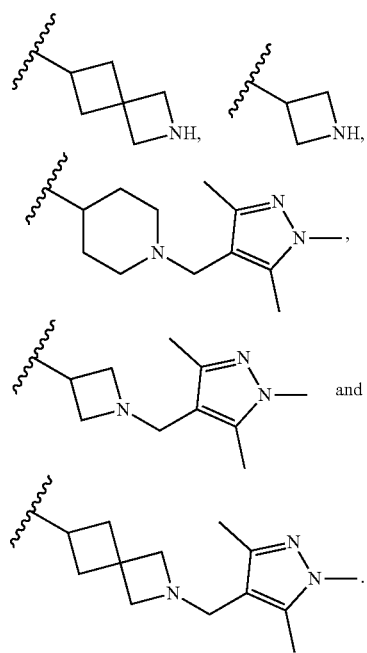

In certain embodiments, $R^{III2}$ is 5-6 membered heteroaryl, wherein 5-6 membered heteroaryl may optionally be substituted on one or more available carbons by one, two, three or more substituents each independently selected from $R^{IIIg}$; and wherein if 4-7 membered heterocyclyl contains a substitutable ring nitrogen atom, that ring nitrogen atom may optionally be substituted by $R^{IIIh}$. For example, $R^{III2}$ may be represented by

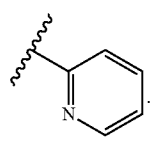

In some embodiments, $R^{III2}$ is —$C_{1-6}$alkylene-5-6 membered heteroaryl, wherein —$C_{1-6}$alkylene-5-6 membered heteroaryl may optionally be substituted on one or more available carbons by one, two, three or more substituents each independently selected from $R^{IIIg}$; and wherein if 4-7 membered heteroaryl contains a substitutable ring nitrogen atom, that ring nitrogen atom may optionally be substituted by $R^{IIIh}$. For example, $R^{III2}$ may be selected from the group consisting of

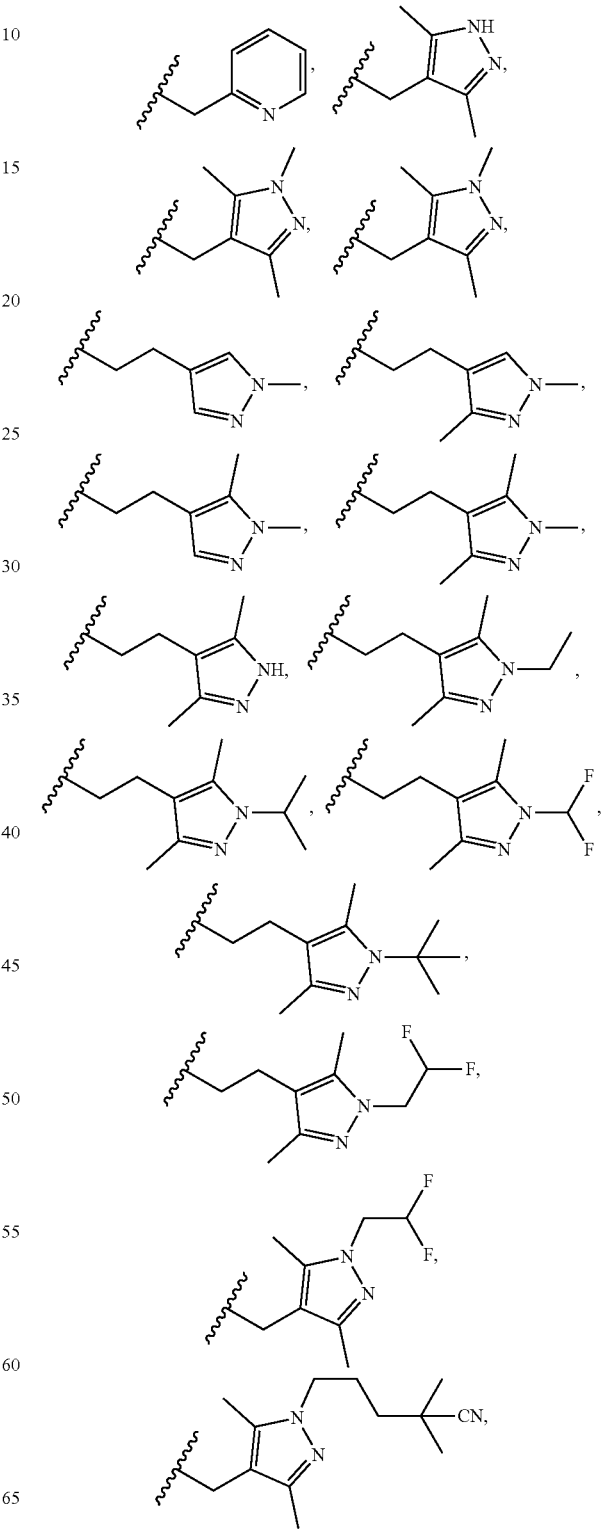

-continued

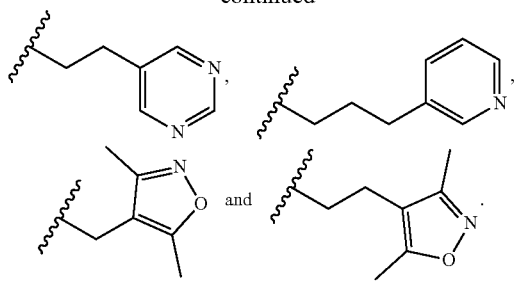

In other embodiments, $R^{III2}$ is —$C_{1-6}$alkylene-phenyl, wherein $R^{III2}$ may optionally be substituted by one, two, three or more substituents each independently selected from $R^{IIIg}$. For example, $R^{III2}$ may be selected from the group consisting of

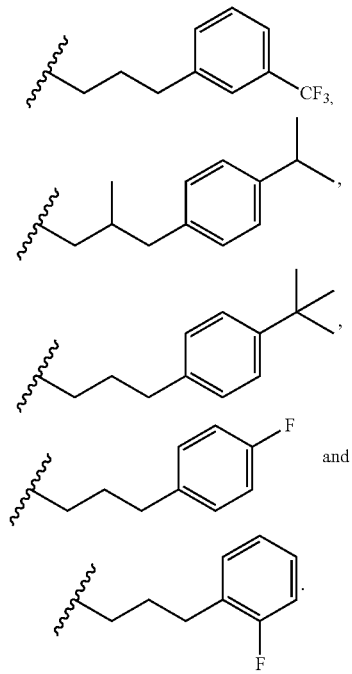

In further embodiments, $R^{III2}$ is —$C_{1-6}$alkylene-4-7 membered heterocyclyl, wherein —$C_{1-6}$alkylene-4-7 membered heterocyclyl may optionally be substituted on one or more available carbons by one, two, three or more substituents each independently selected from $R^{IIIg}$; and wherein if —$C_{1-6}$alkylene-4-7 membered heterocyclyl contains a substitutable ring nitrogen atom, that ring nitrogen atom may optionally be substituted by $R^{IIIh}$. For example, $R^{III2}$ may be selected from the group consisting of

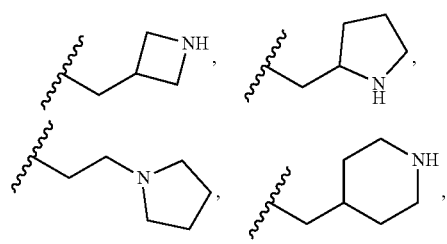

-continued

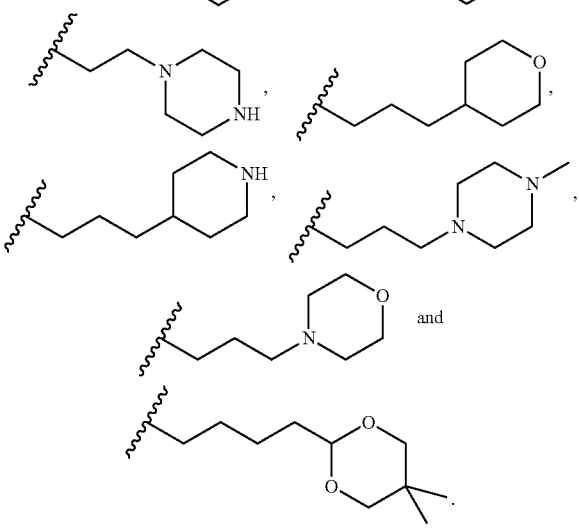

In some embodiments, $R^{III2}$ is —C(O)—O—$C_{1-6}$alkyl, wherein $R^{III2}$ may optionally be substituted by one, two, three or more substituents each independently selected from $R^{IIIg}$. For example, $R^{III2}$ is selected from the group consisting of

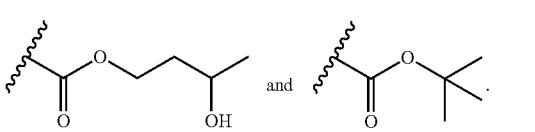

In other embodiments, $R^{III2}$ is —C(O)—N($R^{IIIa}$)—$C_{1-6}$alkyl, wherein $R^{III2}$ may optionally be substituted by one, two, three or more substituents each independently selected from $R^{IIIg}$. For example, $R^{III2}$ may be selected from the group consisting of

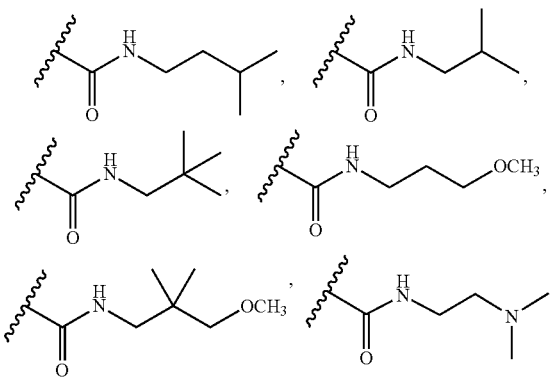

-continued

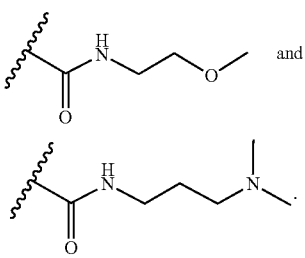 and

In further embodiments, $R^{III2}$ is —$C_{1-6}$alkylene-$C_{3-8}$cycloalkyl, wherein $R^{III2}$ may optionally be substituted by one, two, three or more substituents each independently selected from $R^{IIIg}$. For example, $R^{III2}$ may be selected from the group consisting of

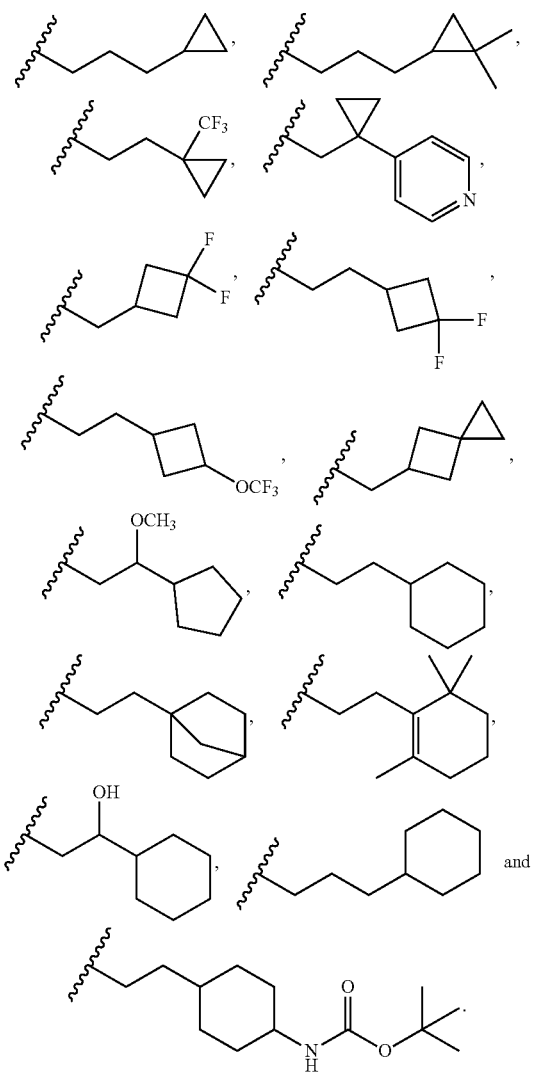

In some embodiments, $R^{III2}$ is —C(O)—$C_{1-6}$alkylene-$C_{3-8}$cycloalkyl, wherein $R^{III2}$ may optionally be substituted by one, two, three or more substituents each independently selected from $R^{IIIg}$. For example, $R^{III2}$ may be represented by

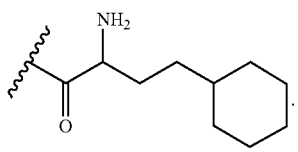 [SMILES: *C(=O)C(N)CCC1CCCCC1]

In some embodiments, $R^{III2}$ is —C=N($R^{IIIa}$)—$C_{1-6}$alkyl. For example, $R^{III2}$ may be represented by

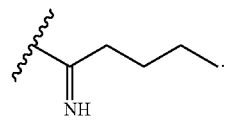 [SMILES: *C(=N)CCCC]

In other embodiments, $R^{III2}$ is selected from the group consisting of —C(O)—N($R^{IIIa}$)—$C_{1-6}$alkylene-$C_{3-6}$cycloalkyl, —C(O)—N($R^{IIIa}$)—$C_{1-6}$alkylene-phenyl, —C(O)—N($R^{IIIa}$)—$C_{1-6}$alkylene-4-7 membered heterocyclyl and —C(O)—N($R^{IIIa}$)—$C_{1-6}$alkylene-5-6 membered heteroaryl, wherein —C(O)—N($R^{IIIa}$)—$C_{1-6}$alkylene-$C_{3-6}$cycloalkyl, —C(O)—N($R^{IIIa}$)—$C_{1-6}$alkylene-phenyl, —C(O)—N($R^{IIIa}$)—$C_{1-6}$alkylene-4-7 membered heterocyclyl or —C(O)—N($R^{IIIa}$)—$C_{1-6}$alkylene-5-6 membered heteroaryl may optionally be substituted on one or more available carbons by one, two, three or more substituents each independently selected from $R^{IIIg}$; and wherein if —C(O)—N($R^{IIIa}$)—$C_{1-6}$alkylene-4-7 membered heterocyclyl or —C(O)—N($R^{IIIa}$)—$C_{1-6}$alkylene-5-6 membered heteroaryl contains a substitutable ring nitrogen atom, that ring nitrogen atom may optionally be substituted by $R^{IIIh}$. For example, $R^{III2}$ may be selected from the group consisting of

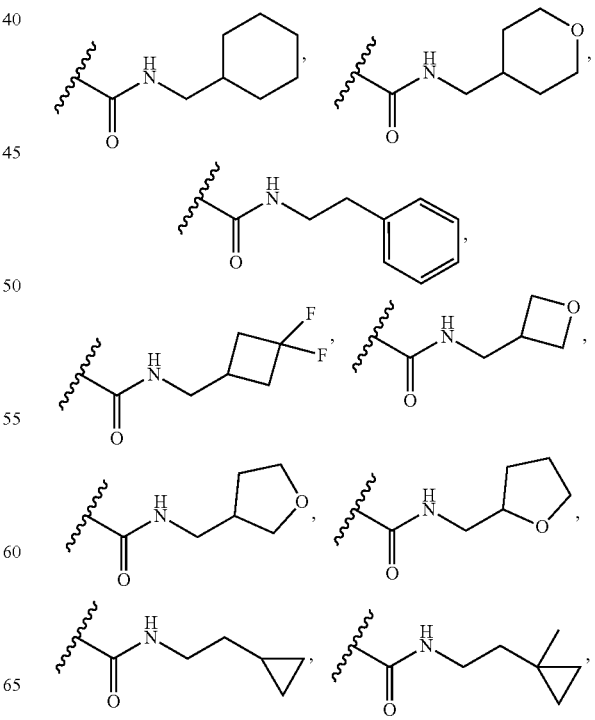

-continued

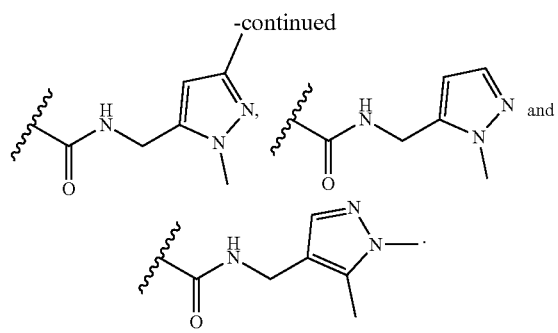

and

Further disclosed herein is a compound selected from the group consisting of:
5-[1-fluoro-3-hydroxy-7-(3-methylbutoxy)-5,6,7,8-tetrahydronaphthalen-2-yl]-1$\lambda^6$,2,5-thiadiazolidine-1,1,3-trione;
5-{7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione;
5-{1-fluoro-3-hydroxy-7-[(3-methylbutyl)amino]-5,6,7,8-tetrahydronaphthalen-2-yl}-1$\lambda^6$,2,5-thiadiazolidine-1,1,3-trione;
5-{7-[(cyclopropylmethyl)amino]-1-fluoro-3-hydroxy-5,6,7,8-tetrahydronaphthalen-2-yl}-1$\lambda^6$,2,5-thiadiazolidine-1,1,3-trione;
5-[(7R)-1-fluoro-3-hydroxy-7-methoxy-5,6,7,8-tetrahydronaphthalen-2-yl]-1$\lambda^6$,2,5-thiadiazolidine-1,1,3-trione;
5-[7-(2-cyclopropylethyl)-1-fluoro-3-hydroxy-5,6,7,8-tetrahydronaphthalen-2-yl]-1$\lambda^6$,2,5-thiadiazolidine-1,1,3-trione;
5-[1-fluoro-3-hydroxy-7-(2-methoxyethoxy)-5,6,7,8-tetrahydronaphthalen-2-yl]-1$\lambda^6$,2,5-thiadiazolidine-1,1,3-trione;
5-[7-(cyclopropylmethoxy)-1-fluoro-3-hydroxy-5,6,7,8-tetrahydronaphthalen-2-yl]-1$\lambda^6$,2,5-thiadiazolidine-1,1,3-trione;
5-(1-fluoro-3-hydroxy-5,6,7,8-tetrahydronaphthalen-2-yl)-1$\lambda^6$,2,5-thiadiazolidine-1,1,3-trione;
5-[(7S)-1-fluoro-3-hydroxy-7-methoxy-5,6,7,8-tetrahydronaphthalen-2-yl]-1$\lambda^6$,2,5-thiadiazolidine-1,1,3-trione;
5-(1-fluoro-3-hydroxy-7-methoxy-5, 6,7,8-tetrahydronaphthalen-2-yl)-1$\lambda^6$,2,5-thiadiazolidine-1,1,3-trione;
5-(5-fluoro-7-hydroxy-3,4-dihydro-2H-1-benzopyran-6-yl)-1$\lambda^6$,2,5-thiadiazolidine-1,1,3-trione;
5-(5-fluoro-7-hydroxy-2,2-dimethyl-3,4-dihydro-2H-1-benzopyran-6-yl)-1$\lambda^6$,2,5-thiadiazolidine-1,1,3-trione;
5-(8-fluoro-6-hydroxy-2,2-dimethyl-3,4-dihydro-2H-1-benzopyran-7-yl)-1$\lambda^6$,2,5-thiadiazolidine-1,1,3-trione;
5-(1,4-difluoro-3-hydroxy-7-methoxy-5,6,7,8-tetrahydronaphthalen-2-yl)-1$\lambda^6$,2,5-thiadiazolidine-1,1,3-trione;
5-(7-{[2-(azetidin-1-yl)ethyl]amino}-1-fluoro-3-hydroxy-5,6,7,8-tetrahydronaphthalen-2-yl)-1$\lambda^6$,2,5-thiadiazolidine-1,1,3-trione;
5-{1-fluoro-3-hydroxy-7-[(3,3,3-trifluoropropyl)amino]-5,6,7,8-tetrahydronaphthalen-2-yl}-1$\lambda^6$,2,5-thiadiazolidine-1,1,3-trione;
5-{(7S)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione;
5-{(7R)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione;
5-{7-[(3,3-difluorocyclobutyl)methoxy]-1-fluoro-3-hydroxy-5,6,7,8-tetrahydronaphthalen-2-yl}-1$\lambda^6$,2,5-thiadiazolidine-1,1,3-trione;
5-{1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione;
5-{1-fluoro-3-hydroxy-7-[(4-methoxy-3,3-dimethylbutyl)amino]-5,6,7,8-tetrahydronaphthalen-2-yl}-1$\lambda^6$,2,5-thiadiazolidine-1,1,3-trione;
5-{1-fluoro-3-hydroxy-7-[(3-methoxy-3-methylbutyl)amino]-5,6,7,8-tetrahydronaphthalen-2-yl}-1$\lambda^6$,2,5-thiadiazolidine-1,1,3-trione;
5-{1-fluoro-3-hydroxy-7-[(4,4,4-trifluoro-3,3-dimethylbutyl)amino]-5,6,7,8-tetrahydronaphthalen-2-yl}-1$\lambda^6$,2,5-thiadiazolidine-1,1,3-trione;
5-[1-fluoro-3-hydroxy-7-({2-[1-(trifluoromethyl)cyclopropyl]ethyl}amino)-5,6,7,8-tetrahydronaphthalen-2-yl]-1$\lambda^6$,2,5-thiadiazolidine-1,1,3-trione;
5-{7-[(2,2-difluoro-2-phenylethyl)amino]-1-fluoro-3-hydroxy-5,6,7,8-tetrahydronaphthalen-2-yl}-1$\lambda^6$,2,5-thiadiazolidine-1,1,3-trione;
5-{7-[(3-cyclopropyl-2,2-difluoropropyl)amino]-1-fluoro-3-hydroxy-5,6,7,8-tetrahydronaphthalen-2-yl}-1$\lambda^6$,2,5-thiadiazolidine-1,1,3-trione;
5-{1-fluoro-3-hydroxy-7-[(3-hydroxy-3-methylbutyl)amino]-5,6,7,8-tetrahydronaphthalen-2-yl}-1$\lambda^6$,2,5-thiadiazolidine-1,1,3-trione;
5-{1-fluoro-3-hydroxy-7-[methyl(3-methylbutyl)amino]-5,6,7,8-tetrahydronaphthalen-2-yl}-1$\lambda^6$,2,5-thiadiazolidine-1,1,3-trione;
5-{1-fluoro-3-hydroxy-7-[(4-methylpentyl)amino]-5,6,7,8-tetrahydronaphthalen-2-yl}-1$\lambda^6$,2,5-thiadiazolidine-1,1,3-trione;
5-(1-fluoro-3-hydroxy-7-{[4,4,4-trifluoro-3-hydroxy-3-(trifluoromethyl)butyl]amino}-5,6,7,8-tetrahydronaphthalen-2-yl)-1$\lambda^6$,2,5-thiadiazolidine-1,1,3-trione;
5-(1-fluoro-3-hydroxy-7-{[4,4,4-trifluoro-3-(trifluoromethyl)butyl]amino}-5,6,7,8-tetrahydronaphthalen-2-yl)-1$\lambda^6$,2,5-thiadiazolidine-1,1,3-trione;
5-{7-[(2,2-difluoropropyl)amino]-1-fluoro-3-hydroxy-5,6,7,8-tetrahydronaphthalen-2-yl}-1$\lambda^6$,2,5-thiadiazolidine-1,1,3-trione;
5-{(7R)-7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione;
5-{(7S)-7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione;
5-(1-fluoro-3-hydroxy-7-{[2-(pyridin-2-yl)ethyl]amino}-5,6,7,8-tetrahydronaphthalen-2-yl)-1$\lambda^6$,2,5-thiadiazolidine-1,1,3-trione;
5-{(7RS)-1-fluoro-3-hydroxy-7-[(3RS)-pyrrolidin-3-yl]-5,6,7,8-tetrahydronaphthalen-2-yl}-1$\lambda^6$,2,5-thiadiazolidine-1,1,3-trione;
5-{(7RS)-7-[(3RS)-1-(cyclopropanesulfonyl)pyrrolidin-3-yl]-1-fluoro-3-hydroxy-5,6,7,8-tetrahydronaphthalen-2-yl}-1$\lambda^6$,2,5-thiadiazolidine-1,1,3-trione;
5-{(7RS)-1-fluoro-3-hydroxy-7-[(3SR)-pyrrolidin-3-yl]-5,6,7,8-tetrahydronaphthalen-2-yl}-1$\lambda^6$,2,5-thiadiazolidine-1,1,3-trione;
5-{(7RS)-7-[(3SR)-1-(cyclopropanesulfonyl)pyrrolidin-3-yl]-1-fluoro-3-hydroxy-5,6,7,8-tetrahydronaphthalen-2-yl}-1$\lambda^6$,2,5-thiadiazolidine-1,1,3-trione;
5-{7-[1-(cyclopropylmethyl)pyrrolidin-3-yl]-1-fluoro-3-hydroxy-5,6,7,8-tetrahydronaphthalen-2-yl}-1$\lambda^6$,2,5-thiadiazolidine-1,1,3-trione;
5-(1-fluoro-3-hydroxy-7-{[2-(1H-pyrazol-1-yl)ethyl]amino}-5,6,7,8-tetrahydronaphthalen-2-yl)-1$\lambda^6$,2,5-thiadiazolidine-1,1,3-trione;

5-[1-fluoro-3-hydroxy-7-(4,4,4-trifluorobutoxy)-5,6,7,8-tetrahydronaphthalen-2-yl]-1$\lambda^6$,2,5-thiadiazolidine-1,1,3-trione;

5-(8-fluoro-6-hydroxy-1,2,3,4-tetrahydroisoquinolin-7-yl)-1$\lambda^6$,2,5-thiadiazolidine-1,1,3-trione;

5-[8-fluoro-6-hydroxy-2-(4-methylpentanoyl)-1,2,3,4-tetrahydroisoquinolin-7-yl]-1$\lambda^6$,2,5-thiadiazolidine-1,1,3-trione;

5-[8-fluoro-6-hydroxy-2-(4-methylpentyl)-1,2,3,4-tetrahydroisoquinolin-7-yl]-1$\lambda^6$,2,5-thiadiazolidine-1,1,3-trione;

5-{(7R)-1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione;

5-{(7S)-1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione;

5-[(7R)-1-fluoro-3-hydroxy-7-({2-[1-(trifluoromethyl)cyclopropyl]ethyl}amino)-5,6,7,8-tetrahydronaphthalen-2-yl]-1$\lambda^6$,2,5-thiadiazolidine-1,1,3-trione;

8-fluoro-6-hydroxy-7-(1,1,4-trioxo-1$\lambda^6$,2,5-thiadiazolidin-2-yl)-1,2,3,4-tetrahydronaphthalen-2-yl phenylcarbamate;

4-{[8-fluoro-6-hydroxy-7-(1,1,4-trioxo-1$\lambda^6$,2,5-thiadiazolidin-2-yl)-1,2,3,4-tetrahydronaphthalen-2-yl]amino}-2,2-dimethylbutanenitrile;

5-{1-fluoro-3-hydroxy-7-[(4,4,4-trifluoro-3-hydroxybutyl)amino]-5,6,7,8-tetrahydronaphthalen-2-yl}-1$\lambda^6$,2,5-thiadiazolidine-1,1,3-trione;

5-{1-fluoro-3-hydroxy-7-[(4,4,4-trifluoro-3-methoxybutyl)amino]-5,6,7,8-tetrahydronaphthalen-2-yl}-1$\lambda^6$,2,5-thiadiazolidine-1,1,3-trione;

5-[8-fluoro-6-hydroxy-2-(5,5,5-trifluoropentyl)-1,2,3,4-tetrahydroisoquinolin-7-yl]-1$\lambda^6$,2,5-thiadiazolidine-1,1,3-trione;

5-(1-fluoro-3-hydroxy-7-{(3-methylbutyl)[(pyridin-2-yl)methyl]amino}-5,6,7,8-tetrahydronaphthalen-2-yl)-1$\lambda^6$,2,5-thiadiazolidine-1,1,3-trione;

5-(1-fluoro-3-hydroxy-7-{[(pyridin-2-yl)methyl]amino}-5,6,7,8-tetrahydronaphthalen-2-yl)-1$\lambda^6$,2,5-thiadiazolidine-1,1,3-trione;

5-{1-fluoro-3-hydroxy-7-[(4,4,4-trifluoro-2-hydroxybutyl)amino]-5,6,7,8-tetrahydronaphthalen-2-yl}-1$\lambda^6$,2,5-thiadiazolidine-1,1,3-trione;

5-(7-{[2-(difluoromethoxy)ethyl]amino}-1-fluoro-3-hydroxy-5,6,7,8-tetrahydronaphthalen-2-yl)-1$\lambda^6$,2,5-thiadiazolidine-1,1,3-trione;

5-(8-fluoro-6-hydroxy-2-pentanimidoyl-1,2,3,4-tetrahydroisoquinolin-7-yl)-1$\lambda^6$,2,5-thiadiazolidine-1,1,3-trione;

5-[2-(3-cyclopropylpropyl)-8-fluoro-6-hydroxy-1,2,3,4-tetrahydroisoquinolin-7-yl]-1$\lambda^6$,2,5-thiadiazolidine-1,1,3-trione;

5-[2-(2-azaspiro[3.3]heptan-6-yl)-8-fluoro-6-hydroxy-1,2,3,4-tetrahydroisoquinolin-7-yl]-1$\lambda^6$,2,5-thiadiazolidine-1,1,3-trione;

5-[8-fluoro-6-hydroxy-2-(6,6,6-trifluorohexyl)-1,2,3,4-tetrahydroisoquinolin-7-yl]-1$\lambda^6$,2,5-thiadiazolidine-1,1,3-trione;

5-{2-[(3,3-difluorocyclobutyl)methyl]-8-fluoro-6-hydroxy-1,2,3,4-tetrahydroisoquinolin-7-yl}-1$\lambda^6$,2,5-thiadiazolidine-1,1,3-trione;

5-[2-(azetidin-3-yl)-8-fluoro-6-hydroxy-1,2,3,4-tetrahydroisoquinolin-7-yl]-1$\lambda^6$,2,5-thiadiazolidine-1,1,3-trione;

5-(8-fluoro-6-hydroxy-2-{2-[(propan-2-yl)amino]ethyl})-1,2,3,4-tetrahydroisoquinolin-7-yl)-1$\lambda^6$,2,5-thiadiazolidine-1,1,3-trione;

5-{2-[(azetidin-3-yl)methyl]-8-fluoro-6-hydroxy-1,2,3,4-tetrahydroisoquinolin-7-yl}-1$\lambda^6$,2,5-thiadiazolidine-1,1,3-trione;

5-{2-[(azetidin-3-yl)methyl]-8-fluoro-6-hydroxy-1,2,3,4-tetrahydroisoquinolin-7-yl}-1$\lambda^6$,2,5-thiadiazolidine-1,1,3-trione;

5-(1-fluoro-3-hydroxy-7-{(3-methylbutyl)[2-(pyridin-2-yl)ethyl]amino}-5,6,7,8-tetrahydronaphthalen-2-yl)-1$\lambda^6$,2,5-thiadiazolidine-1,1,3-trione;

5-{8-fluoro-6-hydroxy-2-[(spiro[2.3]hexan-5-yl)methyl]-1,2,3,4-tetrahydroisoquinolin-7-yl}-1$\lambda^6$,2,5-thiadiazolidine-1,1,3-trione;

5-(1-fluoro-3-hydroxy-7-{[2-(trifluoromethoxy)ethyl]amino}-5,6,7,8-tetrahydronaphthalen-2-yl)-1$\lambda^6$,2,5-thiadiazolidine-1,1,3-trione;

5-[8-fluoro-6-hydroxy-2-(3-hydroxy-3-methylbutyl)-1,2,3,4-tetrahydroisoquinolin-7-yl]-1$\lambda^6$,2,5-thiadiazolidine-1,1,3-trione;

3-hydroxybutyl 8-fluoro-6-hydroxy-7-(1,1,4-trioxo-1$\lambda^6$,2,5-thiadiazolidin-2-yl)-3,4-dihydroisoquinoline-2(1H)-carboxylate;

5-{1-fluoro-3-hydroxy-7-[3-(propan-2-yl)pyrrolidin-1-yl]-5,6,7,8-tetrahydronaphthalen-2-yl}-1$\lambda^6$,2,5-thiadiazolidine-1,1,3-trione;

5-{7-[(2-cyclohexylethyl)amino]-1-fluoro-3-hydroxy-5,6,7,8-tetrahydronaphthalen-2-yl}-1$\lambda^6$,2,5-thiadiazolidine-1,1,3-trione;

5-{7-[(3,3-dimethylbutyl)amino]-1-fluoro-3-hydroxy-5,6,7,8-tetrahydronaphthalen-2-yl}-1$\lambda^6$,2,5-thiadiazolidine-1,1,3-trione;

5-[7-(butylamino)-1-fluoro-3-hydroxy-5,6,7,8-tetrahydronaphthalen-2-yl]-1$\lambda^6$,2,5-thiadiazolidine-1,1,3-trione;

5-{(7S)-1-fluoro-3-hydroxy-7-[(4,4,4-trifluoro-3,3-dimethylbutyl)amino]-5,6,7,8-tetrahydronaphthalen-2-yl}-1$\lambda^6$,2,5-thiadiazolidine-1,1,3-trione;

5-{(7R)-1-fluoro-3-hydroxy-7-[(4,4,4-trifluoro-3,3-dimethylbutyl)amino]-5,6,7,8-tetrahydronaphthalen-2-yl}-1$\lambda^6$,2,5-thiadiazolidine-1,1,3-trione;

5-{7-[(2-cyclopentylethyl)amino]-1-fluoro-3-hydroxy-5,6,7,8-tetrahydronaphthalen-2-yl}-1$\lambda^6$,2,5-thiadiazolidine-1,1,3-trione;

5-[2-(2-cyclohexylethyl)-8-fluoro-6-hydroxy-1,2,3,4-tetrahydroisoquinolin-7-yl]-1$\lambda^6$,2,5-thiadiazolidine-1,1,3-trione;

5-{1-fluoro-3-hydroxy-7-[(2-hydroxyethyl)amino]-5,6,7,8-tetrahydronaphthalen-2-yl}-1$\lambda^6$,2,5-thiadiazolidine-1,1,3-trione;

5-{1-fluoro-3-hydroxy-7-[2-(propan-2-yl)morpholin-4-yl]-5,6,7,8-tetrahydronaphthalen-2-yl}-1$\lambda^6$,2,5-thiadiazolidine-1,1,3-trione;

5-{1-fluoro-3-hydroxy-7-[(2R)-2-(propan-2-yl)morpholin-4-yl]-5,6,7,8-tetrahydronaphthalen-2-yl}-1$\lambda^6$,2,5-thiadiazolidine-1,1,3-trione;

5-{8-fluoro-6-hydroxy-2-[(pyrrolidin-2-yl)methyl]-1,2,3,4-tetrahydroisoquinolin-7-yl}-1$\lambda^6$,2,5-thiadiazolidine-1,1,3-trione;

5-{8-fluoro-6-hydroxy-2-[(pyridin-2-yl)methyl]-1,2,3,4-tetrahydroisoquinolin-7-yl}-1$\lambda^6$,2,5-thiadiazolidine-1,1,3-trione;

5-{7-[(2-cyclobutylethyl)amino]-1-fluoro-3-hydroxy-5,6,7,8-tetrahydronaphthalen-2-yl}-1$\lambda^6$,2,5-thiadiazolidine-1,1,3-trione;

5-[1-fluoro-3-hydroxy-7-({2-[(propan-2-yl)oxy]ethyl}amino)-5,6,7,8-tetrahydronaphthalen-2-yl]-1$\lambda^6$,2,5-thiadiazolidine-1,1,3-trione;

5-{1-fluoro-3-hydroxy-7-[(2-hydroxy-3-methylbutyl)amino]-5,6,7,8-tetrahydronaphthalen-2-yl}-1λ⁶,2,5-thiadiazolidine-1,1,3-trione;
5-{7-[(2-cyclopropyl-2-hydroxyethyl)amino]-1-fluoro-3-hydroxy-5,6,7,8-tetrahydronaphthalen-2-yl}-1λ⁶,2,5-thiadiazolidine-1,1,3-trione;
5-(1-fluoro-3-hydroxy-7-{[3-(trimethylsilyl)propyl]amino}-5,6,7,8-tetrahydronaphthalen-2-yl)-1λ⁶,2,5-thiadiazolidine-1,1,3-trione;
5-[1-fluoro-3-hydroxy-7-({3-[hydroxy(dimethyl)silyl]propyl}amino)-5,6,7,8-tetrahydronaphthalen-2-yl]-1λ⁶,2,5-thiadiazolidine-1,1,3-trione;
5-[8-fluoro-6-hydroxy-2-(pyridin-2-yl)-1,2,3,4-tetrahydroisoquinolin-7-yl]-1λ⁶,2,5-thiadiazolidine-1,1,3-trione;
5-{2-[2-(3,3-difluorocyclobutyl)ethyl]-8-fluoro-6-hydroxy-1,2,3,4-tetrahydroisoquinolin-7-yl}-1λ⁶,2,5-thiadiazolidine-1,1,3-trione;
5-{8-fluoro-6-hydroxy-2-[2-(pyrrolidin-1-yl)ethyl]-1,2,3,4-tetrahydroisoquinolin-7-yl}-1λ⁶,2,5-thiadiazolidine-1,1,3-trione;
5-{2-[2-(3,5-dimethyl-1H-pyrazol-4-yl)ethyl]-8-fluoro-6-hydroxy-1,2,3,4-tetrahydroisoquinolin-7-yl}-1λ⁶,2,5-thiadiazolidine-1,1,3-trione;
N-[8-fluoro-6-hydroxy-7-(1,1,4-trioxo-1λ⁶,2,5-thiadiazolidin-2-yl)-1,2,3,4-tetrahydronaphthalen-2-yl]-3-methylbutanimidamide;
5-{8-fluoro-6-hydroxy-2-[3-(oxan-4-yl)propyl]-1,2,3,4-tetrahydroisoquinolin-7-yl}-1λ⁶,2,5-thiadiazolidine-1,1,3-trione;
5-[1-fluoro-3-hydroxy-7-(3-hydroxy-3-methylbutoxy)-5,6,7,8-tetrahydronaphthalen-2-yl]-1λ⁶,2,5-thiadiazolidine-1,1,3-trione;
5-[(7R)-7-amino-1-fluoro-3-hydroxy-5,6,7,8-tetrahydronaphthalen-2-yl]-1λ⁶,2,5-thiadiazolidine-1,1,3-trione;
5-{(7R)-7-[(4,4-difluorobutyl)amino]-1-fluoro-3-hydroxy-5,6,7,8-tetrahydronaphthalen-2-yl}-1λ⁶,2,5-thiadiazolidine-1,1,3-trione;
5-{(7R)-7-[(2-cyclopentylethyl)amino]-1-fluoro-3-hydroxy-5,6,7,8-tetrahydronaphthalen-2-yl}-1λ⁶,2,5-thiadiazolidine-1,1,3-trione;
5-{(7R)-7-[(2-cyclobutylethyl)amino]-1-fluoro-3-hydroxy-5,6,7,8-tetrahydronaphthalen-2-yl}-1λ⁶,2,5-thiadiazolidine-1,1,3-trione;
5-[(7R)-7-{[2-(3,3-difluorocyclobutyl)ethyl]amino}-1-fluoro-3-hydroxy-5,6,7,8-tetrahydronaphthalen-2-yl]-1λ⁶,2,5-thiadiazolidine-1,1,3-trione;
5-{(7R)-1-fluoro-3-hydroxy-7-[(3-methylpentyl)amino]-5,6,7,8-tetrahydronaphthalen-2-yl}-1λ⁶,2,5-thiadiazolidine-1,1,3-trione;
5-{(7R)-7-[(3-ethylpentyl)amino]-1-fluoro-3-hydroxy-5,6,7,8-tetrahydronaphthalen-2-yl}-1λ⁶,2,5-thiadiazolidine-1,1,3-trione;
8-fluoro-6-hydroxy-N-(3-methylbutyl)-7-(1,1,4-trioxo-1λ⁶,2,5-thiadiazolidin-2-yl)-3,4-dihydroisoquinoline-2(1H)-carboxamide;
8-fluoro-6-hydroxy-N-(2-methylpropyl)-7-(1,1,4-trioxo-1λ⁶,2,5-thiadiazolidin-2-yl)-3,4-dihydroisoquinoline-2(1H)-carboxamide;
5-{8-fluoro-6-hydroxy-2-[3-(pyridin-3-yl)propyl]-1,2,3,4-tetrahydroisoquinolin-7-yl}-1λ⁶,2,5-thiadiazolidine-1,1,3-trione;
5-{2-[(3,5-dimethyl-1,2-oxazol-4-yl)methyl]-8-fluoro-6-hydroxy-1,2,3,4-tetrahydroisoquinolin-7-yl}-1λ⁶,2,5-thiadiazolidine-1,1,3-trione;
5-{8-fluoro-6-hydroxy-2-[2-(1,3,5-trimethyl-1H-pyrazol-4-yl)ethyl]-1,2,3,4-tetrahydroisoquinolin-7-yl}-1λ⁶,2,5-thiadiazolidine-1,1,3-trione;
5-{8-fluoro-6-hydroxy-2-[2-(pyrimidin-5-yl)ethyl]-1,2,3,4-tetrahydroisoquinolin-7-yl}-1λ⁶,2,5-thiadiazolidine-1,1,3-trione;
5-{2-[2-(3,5-dimethyl-1,2-oxazol-4-yl)ethyl]-8-fluoro-6-hydroxy-1,2,3,4-tetrahydroisoquinolin-7-yl}-1λ⁶,2,5-thiadiazolidine-1,1,3-trione;
5-{2-[(3,5-dimethyl-1H-pyrazol-4-yl)methyl]-8-fluoro-6-hydroxy-1,2,3,4-tetrahydroisoquinolin-7-yl}-1λ⁶,2,5-thiadiazolidine-1,1,3-trione;
5-{8-fluoro-6-hydroxy-2-[(1,3,5-trimethyl-1H-pyrazol-4-yl)methyl]-1,2,3,4-tetrahydroisoquinolin-7-yl}-1λ⁶,2,5-thiadiazolidine-1,1,3-trione;
5-{8-fluoro-6-hydroxy-2-[2-(oxan-4-yl)ethyl]-1,2,3,4-tetrahydroisoquinolin-7-yl}-1λ⁶,2,5-thiadiazolidine-1,1,3-trione;
5-[2-(2-cyclohexyl-2-hydroxyethyl)-8-fluoro-6-hydroxy-1,2,3,4-tetrahydroisoquinolin-7-yl]-1λ⁶,2,5-thiadiazolidine-1,1,3-trione;
5-[8-fluoro-6-hydroxy-2-(2-methoxyethyl)-1,2,3,4-tetrahydroisoquinolin-7-yl]-1λ⁶,2,5-thiadiazolidine-1,1,3-trione;
5-[8-fluoro-6-hydroxy-2-(3-methoxypropyl)-1,2,3,4-tetrahydroisoquinolin-7-yl]-1λ⁶,2,5-thiadiazolidine-1,1,3-trione;
5-[2-(3-aminopropyl)-8-fluoro-6-hydroxy-1,2,3,4-tetrahydroisoquinolin-7-yl]-1λ⁶,2,5-thiadiazolidine-1,1,3-trione;
5-{8-fluoro-6-hydroxy-2-[3-(piperidin-4-yl)propyl]-1,2,3,4-tetrahydroisoquinolin-7-yl}-1λ⁶,2,5-thiadiazolidine-1,1,3-trione;
5-[8-fluoro-6-hydroxy-2-(3-methylbutyl)-1,2,3,4-tetrahydroisoquinolin-7-yl]-1λ⁶,2,5-thiadiazolidine-1,1,3-trione;
tert-butyl 8-fluoro-6-hydroxy-7-(1,1,4-trioxo-1λ⁶,2,5-thiadiazolidin-2-yl)-3,4-dihydroisoquinoline-2(1H)-carboxylate;
5-{8-fluoro-6-hydroxy-2-[(7-oxabicyclo[2.2.1]heptan-2-yl)methyl]-1,2,3,4-tetrahydroisoquinolin-7-yl}-1λ⁶,2,5-thiadiazolidine-1,1,3-trione;
5-{7-[(3,3-difluoropropyl)amino]-1-fluoro-3-hydroxy-5,6,7,8-tetrahydronaphthalen-2-yl}-1λ⁶,2,5-thiadiazolidine-1,1,3-trione;
5-(8-fluoro-6-hydroxy-2-{1-[(1,3,5-trimethyl-1H-pyrazol-4-yl)methyl]azetidin-3-yl}-1,2,3,4-tetrahydroisoquinolin-7-yl)-1λ⁶,2,5-thiadiazolidine-1,1,3-trione;
5-{8-fluoro-6-hydroxy-2-[2-(7-oxabicyclo[2.2.1]heptan-2-yl)ethyl]-1,2,3,4-tetrahydroisoquinolin-7-yl}-1λ⁶,2,5-thiadiazolidine-1,1,3-trione;
5-(2-{2-[1-(2,2-difluoroethyl)-3,5-dimethyl-1H-pyrazol-4-yl]ethyl}-4,4,8-trifluoro-6-hydroxy-1,2,3,4-tetrahydroisoquinolin-7-yl)-1λ⁶,2,5-thiadiazolidine-1,1,3-trione;
5-(4-{[8-fluoro-6-hydroxy-7-(1,1,4-trioxo-1λ⁶,2,5-thiadiazolidin-2-yl)-3,4-dihydroisoquinolin-2(1H)-yl]methyl}-3,5-dimethyl-1H-pyrazol-1-yl)-2,2-dimethylpentanenitrile;
5-{8-fluoro-6-hydroxy-2-[(piperidin-4-yl)methyl]-1,2,3,4-tetrahydroisoquinolin-7-yl}-1λ⁶,2,5-thiadiazolidine-1,1,3-trione;
5-{8-fluoro-6-hydroxy-2-[3-(morpholin-4-yl)propyl]-1,2,3,4-tetrahydroisoquinolin-7-yl}-1λ⁶,2,5-thiadiazolidine-1,1,3-trione;
5-{8-fluoro-6-hydroxy-2-[2-(piperidin-4-yl)ethyl]-1,2,3,4-tetrahydroisoquinolin-7-yl}-1λ⁶,2,5-thiadiazolidine-1,1,3-trione;
5-(8-fluoro-6-hydroxy-2-{2-[(1s,3r)-3-(trifluoromethoxy)cyclobutyl]ethyl}-1,2,3,4-tetrahydroisoquinolin-7-yl)-1λ⁶,2,5-thiadiazolidine-1,1,3-trione;
5-{8-fluoro-6-hydroxy-2-[3-(4-methylpiperazin-1-yl)propyl]-1,2,3,4-tetrahydroisoquinolin-7-yl}-1λ⁶,2,5-thiadiazolidine-1,1,3-trione;

5-(8-fluoro-6-hydroxy-2-{2-[(propan-2-yl)oxy]ethyl}-1,2,3,4-tetrahydroisoquinolin-7-yl)-1λ$^6$,2,5-thiadiazolidine-1,1,3-trione;

5-[1-fluoro-3-hydroxy-7-({2-[(1s,3r)-3-(trifluoromethoxy)cyclobutyl]ethyl}amino)-5,6,7,8-tetrahydronaphthalen-2-yl]-1λ$^6$,2,5-thiadiazolidine-1,1,3-trione;

5-(1-fluoro-3-hydroxy-7-{[(1s,3s)-3-(trifluoromethoxy)cyclobutyl]amino}-5,6,7,8-tetrahydronaphthalen-2-yl)-1λ$^6$,2,5-thiadiazolidine-1,1,3-trione;

5-(8-fluoro-6-hydroxy-2-{1-[(1,3,5-trimethyl-1H-pyrazol-4-yl)methyl]piperidin-4-yl}-1,2,3,4-tetrahydroisoquinolin-7-yl)-1λ$^6$,2,5-thiadiazolidine-1,1,3-trione;

5-(8-fluoro-6-hydroxy-2-{2-[(1,3,5-trimethyl-1H-pyrazol-4-yl)methyl]-2-azaspiro[3.3]heptan-6-yl}-1,2,3,4-tetrahydroisoquinolin-7-yl)-1λ$^6$,2,5-thiadiazolidine-1,1,3-trione;

5-(2-{2-[1-(difluoromethyl)-3,5-dimethyl-1H-pyrazol-4-yl]ethyl}-8-fluoro-6-hydroxy-1,2,3,4-tetrahydroisoquinolin-7-yl)-1λ$^6$,2,5-thiadiazolidine-1,1,3-trione;

5-{2-[2-(bicyclo[2.2.1]heptan-1-yl)ethyl]-8-fluoro-6-hydroxy-1,2,3,4-tetrahydroisoquinolin-7-yl}-1λ$^6$,2,5-thiadiazolidine-1,1,3-trione;

5-[7-amino-1-fluoro-3-hydroxy-7-(prop-2-en-1-yl)-5,6,7,8-tetrahydronaphthalen-2-yl]-1λ$^6$,2,5-thiadiazolidine-1,1,3-trione;

N-[8-fluoro-6-hydroxy-2-propyl-7-(1,1,4-trioxo-1λ$^6$,2,5-thiadiazolidin-2-yl)-1,2,3,4-tetrahydronaphthalen-2-yl]benzohydrazide;

5-[8-fluoro-6-hydroxy-2-(3-hydroxybutyl)-1,2,3,4-tetrahydroisoquinolin-7-yl]-1λ$^6$,2,5-thiadiazolidine-1,1,3-trione;

5-(8-fluoro-6-hydroxy-2-{2-[1-(trifluoromethyl)cyclopropyl]ethyl}-1,2,3,4-tetrahydroisoquinolin-7-yl)-1λ$^6$,2,5-thiadiazolidine-1,1,3-trione;

5-[8-fluoro-6-hydroxy-2-(3-hydroxypropyl)-1,2,3,4-tetrahydroisoquinolin-7-yl]-1λ$^6$,2,5-thiadiazolidine-1,1,3-trione;

5-{2-[(2S)-2-aminopropyl]-8-fluoro-6-hydroxy-1,2,3,4-tetrahydroisoquinolin-7-yl}-1λ$^6$,2,5-thiadiazolidine-1,1,3-trione;

5-{2-[(2R)-2-aminopropyl]-8-fluoro-6-hydroxy-1,2,3,4-tetrahydroisoquinolin-7-yl}-1λ$^6$,2,5-thiadiazolidine-1,1,3-trione;

5-{8-fluoro-6-hydroxy-2-[2-(piperazin-1-yl)ethyl]-1,2,3,4-tetrahydroisoquinolin-7-yl}-1λ$^6$,2,5-thiadiazolidine-1,1,3-trione;

5-(8-fluoro-6-hydroxy-2-{[rac-(1R,2R)-2-(pyridin-4-yl)cyclopropyl]methyl})-1,2,3,4-tetrahydroisoquinolin-7-yl)-1λ$^6$,2,5-thiadiazolidine-1,1,3-trione;

5-[2-(2-cyclopentyl-2-methoxyethyl)-8-fluoro-6-hydroxy-1,2,3,4-tetrahydroisoquinolin-7-yl]-1λ$^6$,2,5-thiadiazolidine-1,1,3-trione;

5-{2-[(2R)-2-amino-4-cyclohexylbutanoyl]-8-fluoro-6-hydroxy-1,2,3,4-tetrahydroisoquinolin-7-yl}-1λ$^6$,2,5-thiadiazolidine-1,1,3-trione;

5-(8-fluoro-6-hydroxy-2-{3-[(propan-2-yl)oxy]propyl}-1,2,3,4-tetrahydroisoquinolin-7-yl)-1λ$^6$,2,5-thiadiazolidine-1,1,3-trione;

5-{8-fluoro-6-hydroxy-2-[2-(1-methyl-1H-pyrazol-4-yl)ethyl]-1,2,3,4-tetrahydroisoquinolin-7-yl}-1λ$^6$,2,5-thiadiazolidine-1,1,3-trione;

5-(2-{2-[1-(2,2-difluoroethyl)-3,5-dimethyl-1H-pyrazol-4-yl]ethyl}-8-fluoro-6-hydroxy-1,2,3,4-tetrahydroisoquinolin-7-yl)-1λ$^6$,2,5-thiadiazolidine-1,1,3-trione;

5-[7-amino-1-fluoro-3-hydroxy-7-(4-methylpentyl)-5,6,7,8-tetrahydronaphthalen-2-yl]-1λ$^6$,2,5-thiadiazolidine-1,1,3-trione;

5-(7-amino-1-fluoro-3-hydroxy-7-propyl-5,6,7,8-tetrahydronaphthalen-2-yl)-1λ$^6$,2,5-thiadiazolidine-1,1,3-trione;

5-{2-[2-(1,3-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione;

5-{2-[2-(1,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione;

N-(cyclopropylmethyl)-8-fluoro-6-hydroxy-7-(1,1,4-trioxo-1λ$^6$,2,5-thiadiazolidin-2-yl)-3,4-dihydroisoquinoline-2(1H)-carboxamide;

5-{(7S)-7-[(3,3-difluoropropyl)amino]-1-fluoro-3-hydroxy-5,6,7,8-tetrahydronaphthalen-2-yl}-1λ$^6$,2,5-thiadiazolidine-1,1,3-trione;

5-{(7R)-7-[(3,3-difluoropropyl)amino]-1-fluoro-3-hydroxy-5,6,7,8-tetrahydronaphthalen-2-yl}-1λ$^6$,2,5-thiadiazolidine-1,1,3-trione;

8-fluoro-6-hydroxy-N-[(oxan-4-yl)methyl]-7-(1,1,4-trioxo-1λ$^6$,2,5-thiadiazolidin-2-yl)-3,4-dihydroisoquinoline-2(1H)-carboxamide;

N-[(3,3-difluorocyclobutyl)methyl]-8-fluoro-6-hydroxy-7-(1,1,4-trioxo-1λ$^6$,2,5-thiadiazolidin-2-yl)-3,4-dihydroisoquinoline-2(1H)-carboxamide;

8-fluoro-6-hydroxy-N-[(oxolan-2-yl)methyl]-7-(1,1,4-trioxo-1λ$^6$,2,5-thiadiazolidin-2-yl)-3,4-dihydroisoquinoline-2(1H)-carboxamide;

N-(2-cyclopropylethyl)-8-fluoro-6-hydroxy-7-(1,1,4-trioxo-1λ$^6$,2,5-thiadiazolidin-2-yl)-3,4-dihydroisoquinoline-2(1H)-carboxamide;

N-[(1,3-dimethyl-1H-pyrazol-5-yl)methyl]-8-fluoro-6-hydroxy-7-(1,1,4-trioxo-1λ$^6$,2,5-thiadiazolidin-2-yl)-3,4-dihydroisoquinoline-2(1H)-carboxamide;

5-{2-[2-(1-tert-butyl-3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione;

5-[2-(aminomethyl)-4-fluoro-6-hydroxy-2,3-dihydro-1H-inden-5-yl]-1λ$^6$,2,5-thiadiazolidine-1,1,3-trione:

5-(4-fluoro-6-hydroxy-2-{[(3-methylbutyl)amino]methyl}-2,3-dihydro-1H-inden-5-yl)-1λ$^6$,2,5-thiadiazolidine-1,1,3-trione;

5-(2-{[bis(3-methylbutyl)amino]methyl}-4-fluoro-6-hydroxy-2,3-dihydro-1H-inden-5-yl)-1λ$^6$,2,5-thiadiazolidine-1,1,3-trione 8-fluoro-6-hydroxy-N-[(oxolan-3-yl)methyl]-7-(1,1,4-trioxo-1λ$^6$,2,5-thiadiazolidin-2-yl)-3,4-dihydroisoquinoline-2(1H)-carboxamide;

N-[(1,5-dimethyl-1H-pyrazol-4-yl)methyl]-8-fluoro-6-hydroxy-7-(1,1,4-trioxo-1λ$^6$,2,5-thiadiazolidin-2-yl)-3,4-dihydroisoquinoline-2(1H)-carboxamide;

8-fluoro-6-hydroxy-N-[(1-methyl-1H-pyrazol-5-yl)methyl]-7-(1,1,4-trioxo-1λ$^6$,2,5-thiadiazolidin-2-yl)-3,4-dihydroisoquinoline-2(1H)-carboxamide;

5-(2-{2-[3,5-dimethyl-1-(propan-2-yl)-1H-pyrazol-4-yl]ethyl}-8-fluoro-6-hydroxy-1,2,3,4-tetrahydroisoquinolin-7-yl)-1λ$^6$,2,5-thiadiazolidine-1,1,3-trione;

5-(2-{[(3-cyclopropylpropyl)amino]methyl}-4-fluoro-6-hydroxy-2,3-dihydro-1H-inden-5-yl)-1λ$^6$,2,5-thiadiazolidine-1,1,3-trione;

5-(4-fluoro-6-hydroxy-2-{[(2-methylpropyl)amino]methyl}-2,3-dihydro-1H-inden-5-yl)-1λ$^6$,2,5-thiadiazolidine-1,1,3-trione;

5-{2-[2-(1-ethyl-3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione;

N-(2,2-dimethylpropyl)-8-fluoro-6-hydroxy-7-(1,1,4-trioxo-1λ$^6$,2,5-thiadiazolidin-2-yl)-3,4-dihydroisoquinoline-2(1H)-carboxamide;

8-fluoro-6-hydroxy-N-(3-methoxypropyl)-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(3-methoxy-2,2-dimethylpropyl)-7-(1,1,4-trioxo-1$\lambda^6$,2,5-thiadiazolidin-2-yl)-3,4-dihydroisoquinoline-2(1H)-carboxamide;

N-[2-(dimethylamino)ethyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

8-fluoro-6-hydroxy-N-[2-(1-methylcyclopropyl)ethyl]-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(2-methoxyethyl)-7-(1,1,4-trioxo-1$\lambda^6$,2,5-thiadiazolidin-2-yl)-3,4-dihydroisoquinoline-2(1H)-carboxamide;

8-fluoro-6-hydroxy-N-[(oxetan-3-yl)methyl]-7-(1,1,4-trioxo-1$\lambda^6$,2,5-thiadiazolidin-2-yl)-3,4-dihydroisoquinoline-2(1H)-carboxamide;

8-fluoro-6-hydroxy-N-(2-phenylethyl)-7-(1,1,4-trioxo-1$\lambda^6$,2,5-thiadiazolidin-2-yl)-3,4-dihydroisoquinoline-2(1H)-carboxamide;

N-[3-(dimethylamino)propyl]-8-fluoro-6-hydroxy-7-(1,1,4-trioxo-1$\lambda^6$,2,5-thiadiazolidin-2-yl)-3,4-dihydroisoquinoline-2(1H)-carboxamide;

5-[2-(3-cyclohexylpropyl)-8-fluoro-6-hydroxy-1,2,3,4-tetrahydroisoquinolin-7-yl]-1$\lambda^6$,2,5-thiadiazolidine-1,1,3-trione;

5-(7-{[(3,5-dimethyl-1,2-oxazol-4-yl)methyl]amino}-1-fluoro-3-hydroxy-5,6,7,8-tetrahydronaphthalen-2-yl)-1$\lambda^6$,2,5-thiadiazolidine-1,1,3-trione;

5-{2-[3-(2,2-dimethylcyclopropyl)propyl]-8-fluoro-6-hydroxy-1,2,3,4-tetrahydroisoquinolin-7-yl}-1$\lambda^6$,2,5-thiadiazolidine-1,1,3-trione;

5-[(3S)-5-fluoro-7-hydroxy-3-methyl-1,2,3,4-tetrahydroisoquinolin-6-yl]-1$\lambda^6$,2,5-thiadiazolidine-1,1,3-trione;

5-(7-{[2-(3,5-dimethyl-1,2-oxazol-4-yl)ethyl]amino}-1-fluoro-3-hydroxy-5,6,7,8-tetrahydronaphthalen-2-yl)-1$\lambda^6$,2,5-thiadiazolidine-1,1,3-trione;

5-[(2R)-4-fluoro-6-hydroxy-2-{[(3-methylbutyl)amino]methyl}-2,3-dihydro-1H-inden-5-yl]-1$\lambda^6$,2,5-thiadiazolidine-1,1,3-trione;

5-[(2S)-4-fluoro-6-hydroxy-2-{[(3-methylbutyl)amino]methyl}-2,3-dihydro-1H-inden-5-yl]-1$\lambda^6$,2,5-thiadiazolidine-1,1,3-trione;

5-[8-fluoro-6-hydroxy-2-(4-methoxybutyl)-1,2,3,4-tetrahydroisoquinolin-7-yl]-1$\lambda^6$,2,5-thiadiazolidine-1,1,3-trione;

5-(8-fluoro-6-hydroxy-2-{3-[3-(trifluoromethyl)phenyl]propyl}-1,2,3,4-tetrahydroisoquinolin-7-yl)-1$\lambda^6$,2,5-thiadiazolidine-1,1,3-trione;

5-(8-fluoro-6-hydroxy-2-{2-methyl-3-[4-(propan-2-yl)phenyl]propyl}-1,2,3,4-tetrahydroisoquinolin-7-yl)-1$\lambda^6$,2,5-thiadiazolidine-1,1,3-trione;

5-{2-[4-(5,5-dimethyl-1,3-dioxan-2-yl)butyl]-8-fluoro-6-hydroxy-1,2,3,4-tetrahydroisoquinolin-7-yl}-1$\lambda^6$,2,5-thiadiazolidine-1,1,3-trione;

5-{8-fluoro-6-hydroxy-2-[2-(2,6,6-trimethylcyclohex-1-en-1-yl)ethyl]-1,2,3,4-tetrahydroisoquinolin-7-yl}-1$\lambda^6$,2,5-thiadiazolidine-1,1,3-trione;

5-(8-fluoro-6-hydroxy-2-pentyl-1,2,3,4-tetrahydroisoquinolin-7-yl)-1$\lambda^6$,2,5-thiadiazolidine-1,1,3-trione;

5-{8-fluoro-2-[3-(4-fluorophenyl)propyl]-6-hydroxy-1,2,3,4-tetrahydroisoquinolin-7-yl}-1$\lambda^6$,2,5-thiadiazolidine-1,1,3-trione;

tert-butyl [(1r,4r)-4-{2-[8-fluoro-6-hydroxy-7-(1,1,4-trioxo-1$\lambda^6$,2,5-thiadiazolidin-2-yl)-3,4-dihydroisoquinolin-2(1H)-yl]ethyl}cyclohexyl]carbamate;

5-{2-[3-(4-tert-butylphenyl)propyl]-8-fluoro-6-hydroxy-1,2,3,4-tetrahydroisoquinolin-7-yl}-1$\lambda^6$,2,5-thiadiazolidine-1,1,3-trione;

5-[8-fluoro-6-hydroxy-2-(3,5,5-trimethylhexyl)-1,2,3,4-tetrahydroisoquinolin-7-yl]-1$\lambda^6$,2,5-thiadiazolidine-1,1,3-trione;

5-{8-fluoro-2-[3-(2-fluorophenyl)propyl]-6-hydroxy-1,2,3,4-tetrahydroisoquinolin-7-yl}-1$\lambda^6$,2,5-thiadiazolidine-1,1,3-trione;

3-hydroxybutyl 4,4,8-trifluoro-6-hydroxy-7-(1,1,4-trioxo-1$\lambda^6$,2,5-thiadiazolidin-2-yl)-3,4-dihydroisoquinoline-2(1H)-carboxylate;

5-(2-{[(2-cyclobutylethyl)amino]methyl}-4-fluoro-6-hydroxy-2,3-dihydro-1H-inden-5-yl)-1$\lambda^6$,2,5-thiadiazolidine-1,1,3-trione;

5-{2-[2-(3,5-dimethyl-1,2-oxazol-4-yl)ethyl]-4,4,8-trifluoro-6-hydroxy-1,2,3,4-tetrahydroisoquinolin-7-yl}-1$\lambda^6$,2,5-thiadiazolidine-1,1,3-trione;

5-[(7R)-1-fluoro-3-hydroxy-7-{[(3R)-3-hydroxybutyl]amino}-5,6,7,8-tetrahydronaphthalen-2-yl]-1$\lambda^6$,2,5-thiadiazolidine-1,1,3-trione;

5-{(7R)-1-fluoro-3-hydroxy-7-[(4-hydroxy-3,3-dimethylbutyl)amino]-5,6,7,8-tetrahydronaphthalen-2-yl}-1$\lambda^6$,2,5-thiadiazolidine-1,1,3-trione;

5-[1-fluoro-3-hydroxy-6-(3-hydroxy-3-methylbutoxy)-5,6,7,8-tetrahydronaphthalen-2-yl]-1$\lambda^6$,2,5-thiadiazolidine-1,1,3-trione;

5-[6-(cyclopropylmethoxy)-1-fluoro-3-hydroxy-5,6,7,8-tetrahydronaphthalen-2-yl]-1$\lambda^6$,2,5-thiadiazolidine-1,1,3-trione;

5-{6-[(4,4-difluorobutyl)amino]-1-fluoro-3-hydroxy-5,6,7,8-tetrahydronaphthalen-2-yl}-1$\lambda^6$,2,5-thiadiazolidine-1,1,3-trione;

5-[6-(4,4-difluorobutoxy)-1-fluoro-3-hydroxy-5,6,7,8-tetrahydronaphthalen-2-yl]-1$\lambda^6$,2,5-thiadiazolidine-1,1,3-trione;

5-{1-fluoro-3-hydroxy-6-[(3-methylbutyl)amino]-5,6,7,8-tetrahydronaphthalen-2-yl}-1$\lambda^6$,2,5-thiadiazolidine-1,1,3-trione;

5-[1-fluoro-3-hydroxy-6-(3-methylbutoxy)-5,6,7,8-tetrahydronaphthalen-2-yl]-1$\lambda^6$,2,5-thiadiazolidine-1,1,3-trione;

5-{1-fluoro-3-hydroxy-6-[(3-hydroxy-3-methylbutyl)amino]-5,6,7,8-tetrahydronaphthalen-2-yl}-1$\lambda^6$,2,5-thiadiazolidine-1,1,3-trione;

tert-butyl (2-{[5-fluoro-7-hydroxy-6-(1,1,4-trioxo-1$\lambda^6$,2,5-thiadiazolidin-2-yl)-1,2,3,4-tetrahydronaphthalen-2-yl]oxy}ethyl)carbamate;

5-(1-fluoro-3-hydroxy-6-methoxy-5,6,7,8-tetrahydronaphthalen-2-yl)-1$\lambda^6$,2,5-thiadiazolidine-1,1,3-trione;

5-{6-[(cyclopropylmethyl)amino]-1-fluoro-3-hydroxy-5,6,7,8-tetrahydronaphthalen-2-yl}-1$\lambda^6$,2,5-thiadiazolidine-1,1,3-trione;

5-[6-(2-aminoethoxy)-1-fluoro-3-hydroxy-5,6,7,8-tetrahydronaphthalen-2-yl]-1$\lambda^6$,2,5-thiadiazolidine-1,1,3-trione;

5-{2-[2-(3,5-dimethyl-1H-pyrazol-4-yl)ethyl]-4,4,8-trifluoro-6-hydroxy-1,2,3,4-tetrahydroisoquinolin-7-yl}-1$\lambda^6$,2,5-thiadiazolidine-1,1,3-trione;

N-(cyclohexylmethyl)-8-fluoro-6-hydroxy-7-(1,1,4-trioxo-1$\lambda^6$,2,5-thiadiazolidin-2-yl)-3,4-dihydroisoquinoline-2(1H)-carboxamide;

N-[8-fluoro-6-hydroxy-7-(1,1,4-trioxo-1$\lambda^6$,2,5-thiadiazolidin-2-yl)-1,2,3,4-tetrahydronaphthalen-2-yl]acetamide;

5-[1-fluoro-3-hydroxy-7-(4-methylpentyl)-5,6,7,8-tetrahydronaphthalen-2-yl]-1$\lambda^6$,2,5-thiadiazolidine-1,1,3-trione;

5-(8-fluoro-6-hydroxy-2-{[(2S)-5-oxopyrrolidin-2-yl]methyl}-1,2,3,4-tetrahydroisoquinolin-7-yl)-1$\lambda^6$,2,5-thiadiazolidine-1,1,3-trione;

5-[(3S)-5-fluoro-7-hydroxy-3-(4-methylpentyl)-1,2,3,4-tetrahydroisoquinolin-6-yl]-1λ⁶,2,5-thiadiazolidine-1,1,3-trione;
and a pharmaceutically acceptable salt thereof.

In some embodiments, the compound is 5-{(7R)-1-fluoro-3-hydroxy-7-[(3-methylbutyl)amino]-5,6,7,8-tetrahydronaphthalen-2-yl}-1λ⁶,2,5-thiadiazolidine-1,1,3-trione or a pharmaceutically acceptable salt thereof.

In some embodiments, the compound is 5-{(7R)-1-fluoro-3-hydroxy-7-[(3-methylbutyl)amino]-5,6,7,8-tetrahydronaphthalen-2-yl}-1λ⁶,2,5-thiadiazolidine-1,1,3-trione.

In some embodiments, the compound is a pharmaceutically acceptable salt of 5-{(7R)-1-fluoro-3-hydroxy-7-[(3-methylbutyl)amino]-5,6,7,8-tetrahydronaphthalen-2-yl}-1λ⁶,2,5-thiadiazolidine-1,1,3-trione.

In some embodiments, the compound is

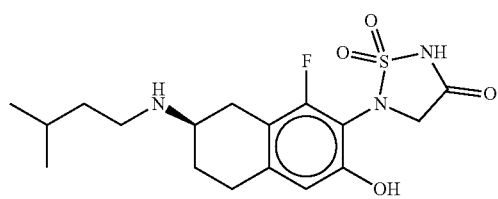

or a pharmaceutically acceptable salt thereof.

In some embodiments, the compound is

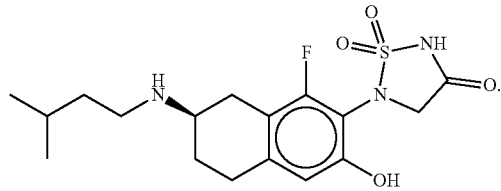

In some embodiments, a compound disclosed herein is formulated as a pharmaceutically acceptable composition comprising a disclosed compound and a pharmaceutically acceptable carrier.

In some embodiments, a compound disclosed herein is selected from a compound set forth in Table 1.

TABLE 1

Exemplary compounds of the disclosure.

| Compound Number | Structure |
|---|---|
| 100 | 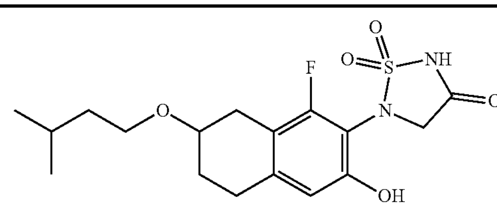 |
| 101 | 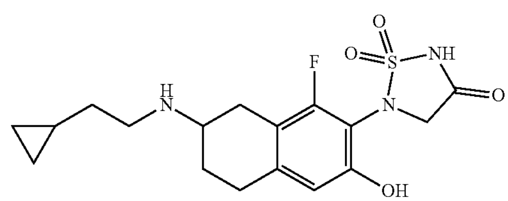 [SMILES: O=C1CN(c2c(O)cc3c(c2F)CC(NCCC2CC2)CC3)S(=O)(=O)N1] |
| 102 | 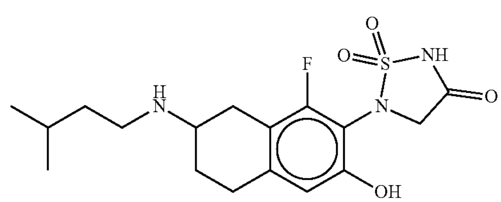 |
| 103 | 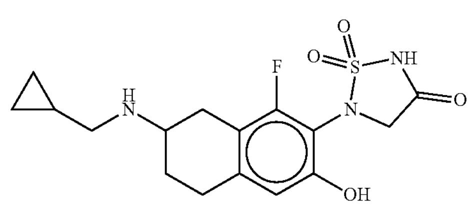 |

TABLE 1-continued

Exemplary compounds of the disclosure.

| Compound Number | Structure |
|---|---|
| 104 | 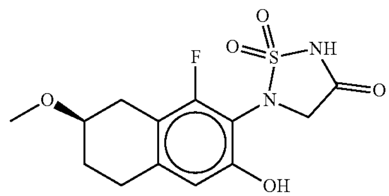 |
| 105 | 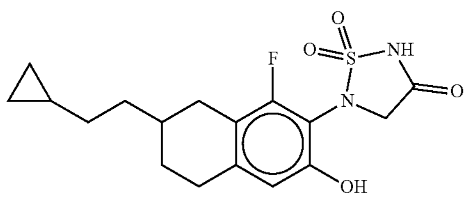 |
| 106 | 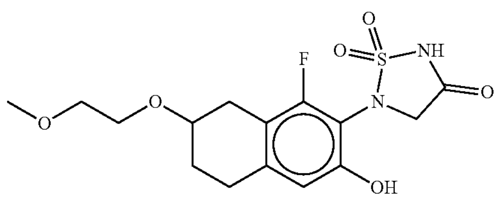 |
| 107 | 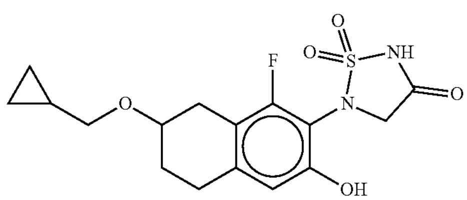 |
| 108 | 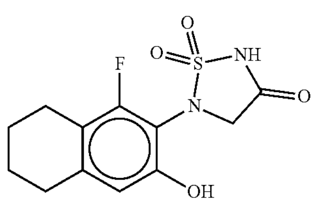 |
| 109 | 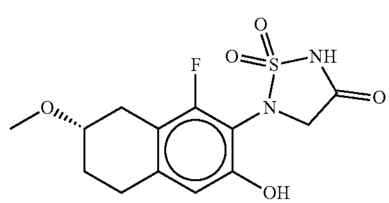 |
| 110 | 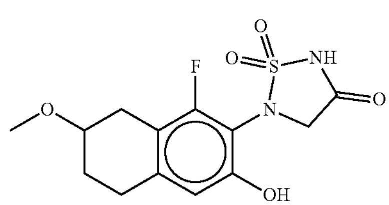 |

TABLE 1-continued

Exemplary compounds of the disclosure.

| Compound Number | Structure |
|---|---|
| 111 | 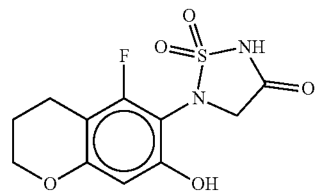 |
| 112 | 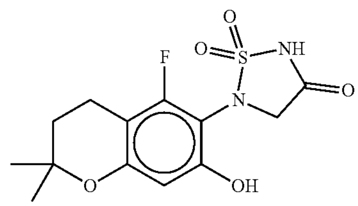 |
| 113 | 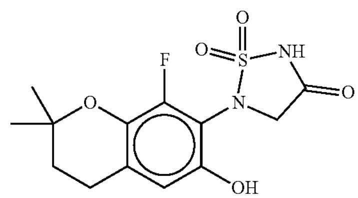 |
| 114 | 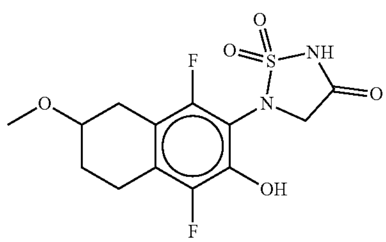 |
| 115 | 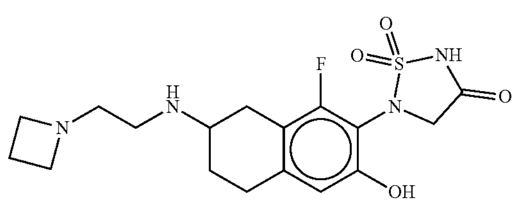 |
| 116 | 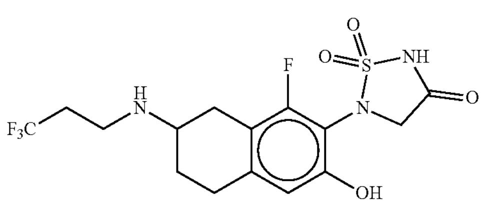 |
| 117 | 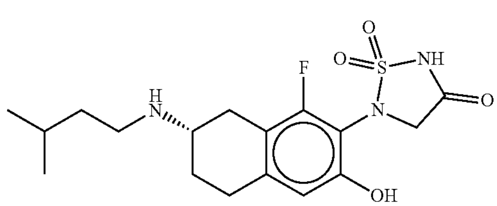 |

TABLE 1-continued
Exemplary compounds of the disclosure.
| Compound Number | Structure |
|---|---|
| 118 | 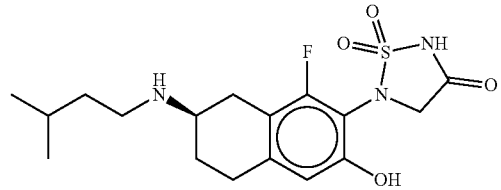 |
| 119 | 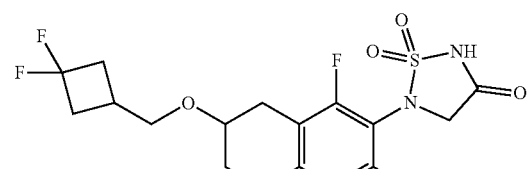 |
| 120 | 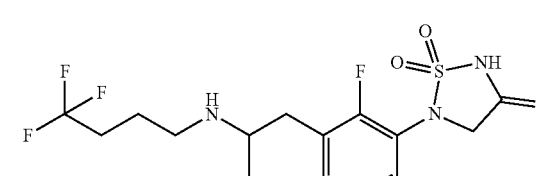 |
| 121 | 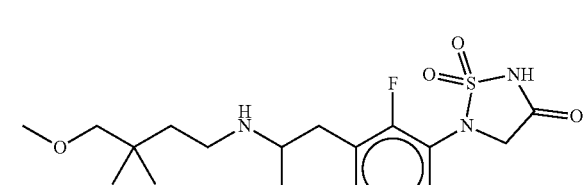 |
| 122 | 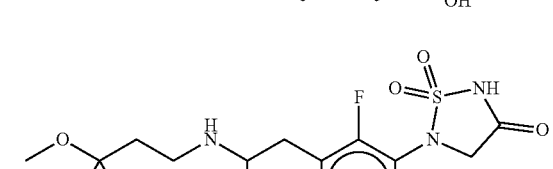 |
| 123 | 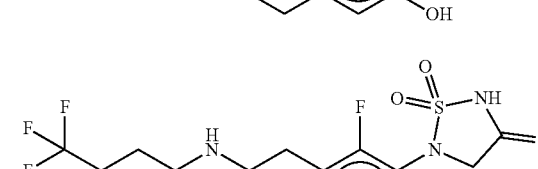 |
| 124 | 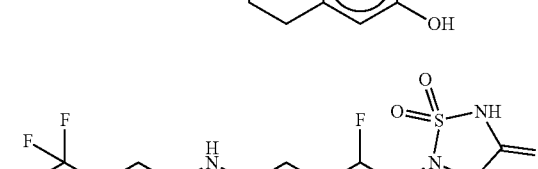 |

TABLE 1-continued

Exemplary compounds of the disclosure.

| Compound Number | Structure |
|---|---|
| 125 | 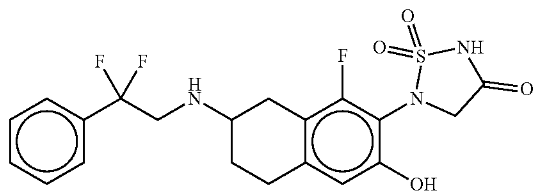 |
| 126 | 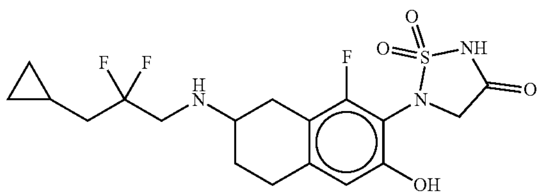 |
| 127 | 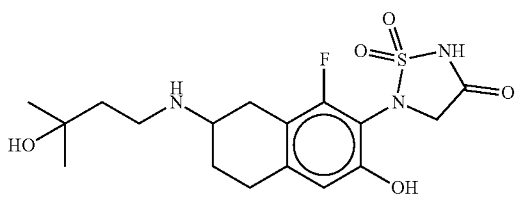 |
| 128 | 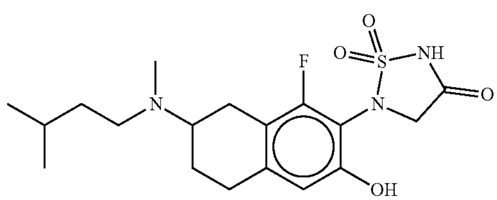 |
| 129 | 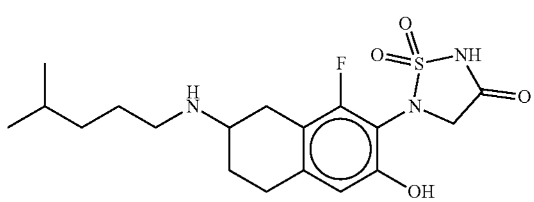 |
| 130 | 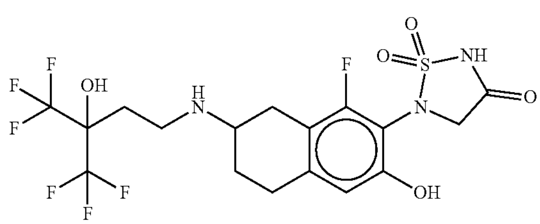 |
| 131 | 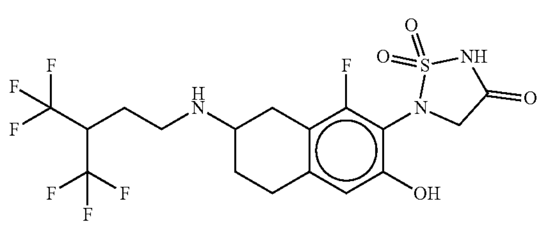 |

TABLE 1-continued

Exemplary compounds of the disclosure.

| Compound Number | Structure |
|---|---|
| 132 | 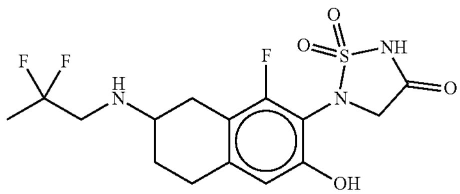 |
| 133 | 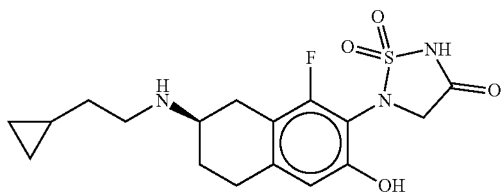 |
| 134 | 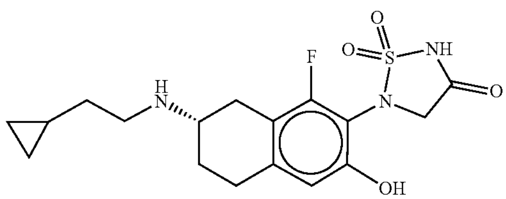 |
| 135 | 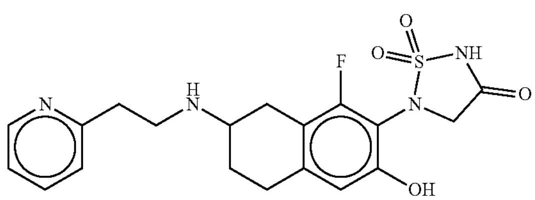 |
| 136 | 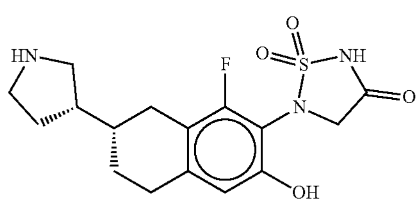 |
| 137 | 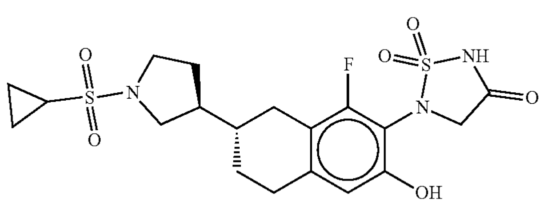 |
| 138 | 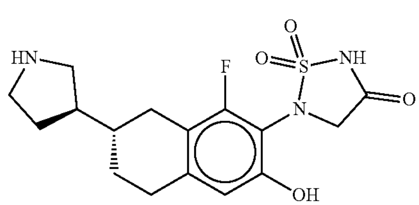 |

TABLE 1-continued

Exemplary compounds of the disclosure.

| Compound Number | Structure |
|---|---|
| 139 | 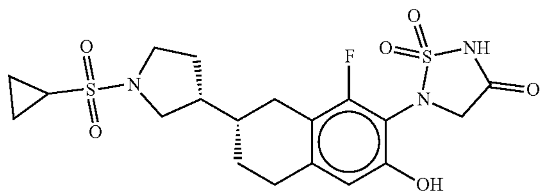 |
| 140 | 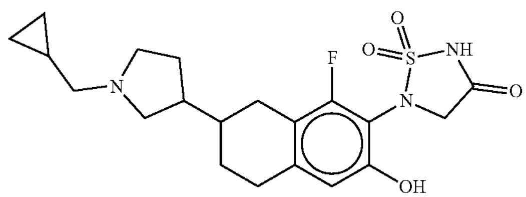 |
| 141 | 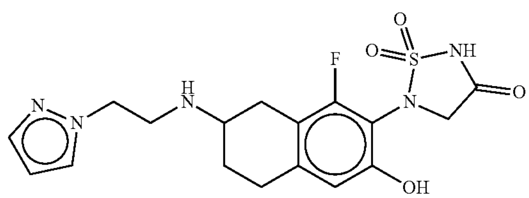 |
| 142 | 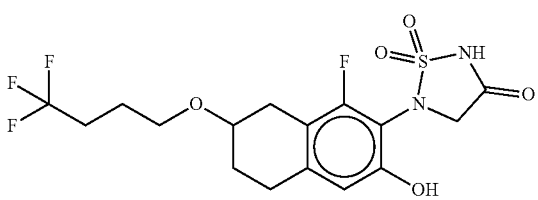 |
| 143 | 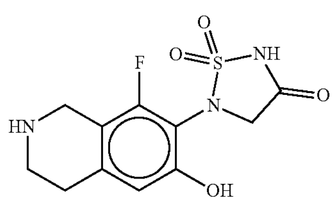 |
| 144 | 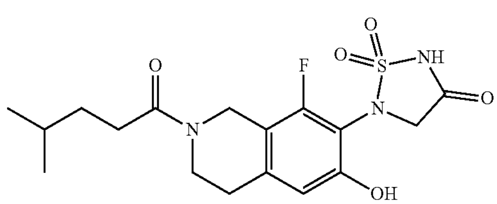 [SMILES: CC(C)CCC(=O)N1CCc2cc(O)c(N3CC(=O)NS3(=O)=O)c(F)c2C1] |
| 145 | 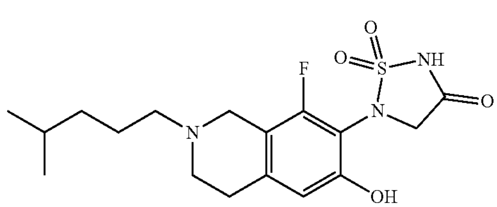 [SMILES: CC(C)CCCN1CCc2cc(O)c(N3CC(=O)NS3(=O)=O)c(F)c2C1] |

TABLE 1-continued

Exemplary compounds of the disclosure.

| Compound Number | Structure |
|---|---|
| 146 | 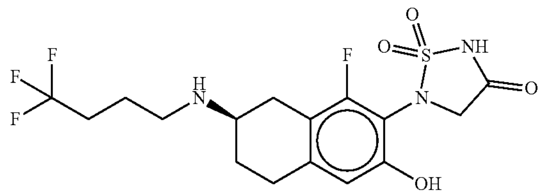 |
| 147 | 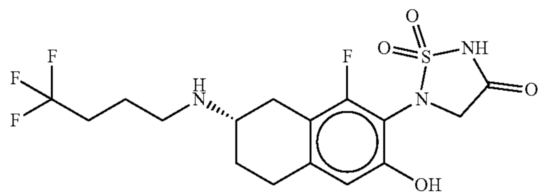 |
| 148 | 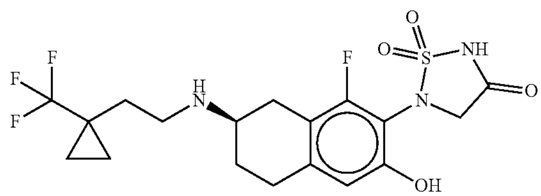 |
| 149 | 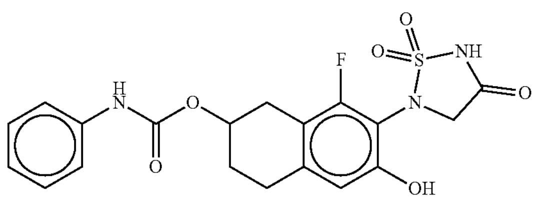 |
| 150 | 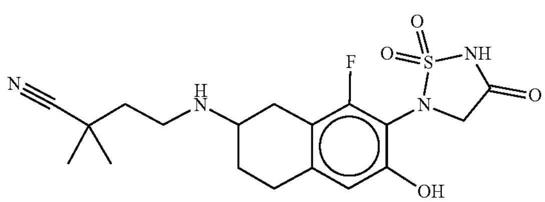 |
| 151 | 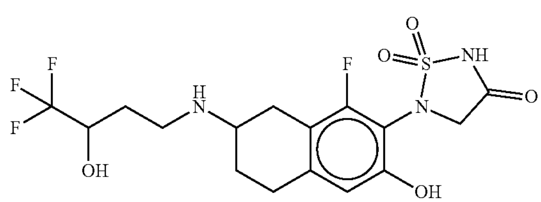 |
| 152 | 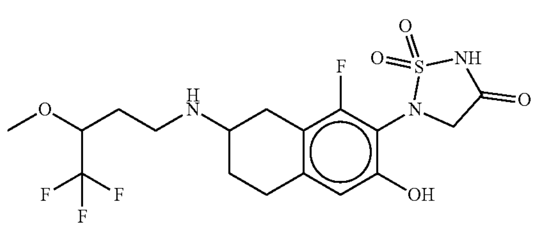 |

TABLE 1-continued

Exemplary compounds of the disclosure.

| Compound Number | Structure |
|---|---|
| 153 | 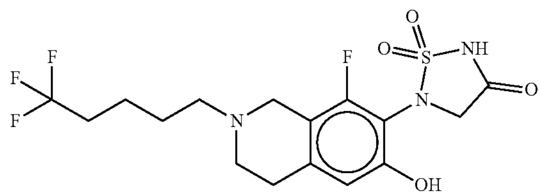 |
| 154 | 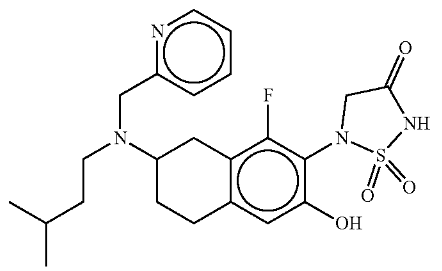 |
| 155 | 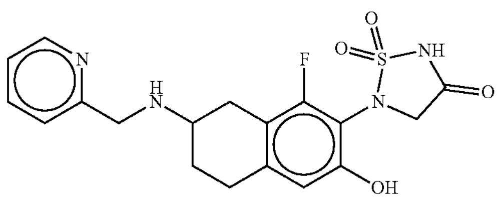 |
| 156 | 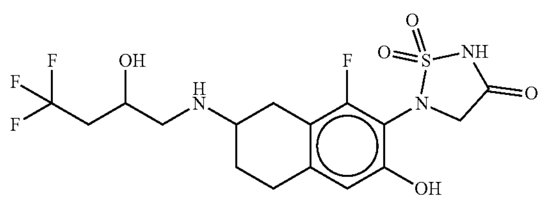 |
| 157 | 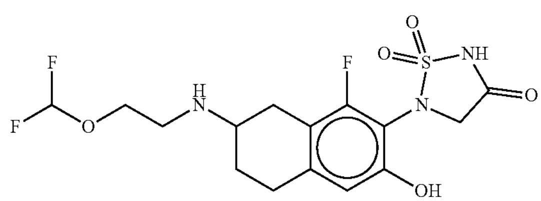 |
| 158 | 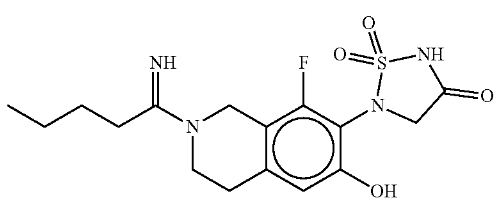 |
| 159 | 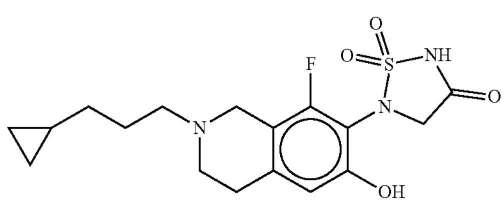 |

TABLE 1-continued

Exemplary compounds of the disclosure.

| Compound Number | Structure |
|---|---|
| 160 | 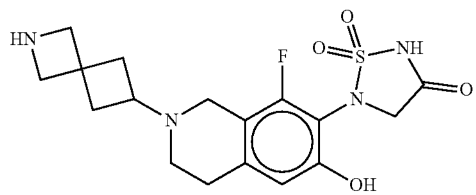 |
| 161 | 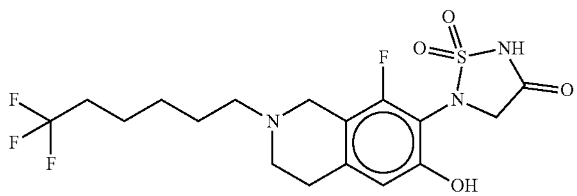 |
| 162 | 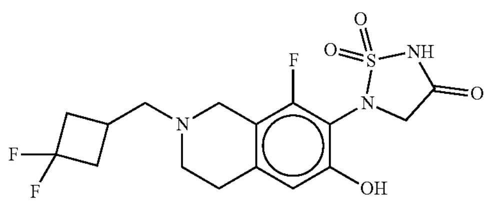 |
| 163 | 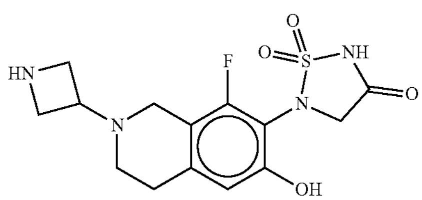 |
| 164 | 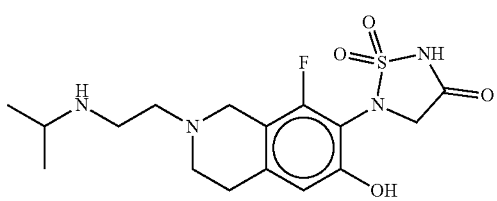 |
| 165 | 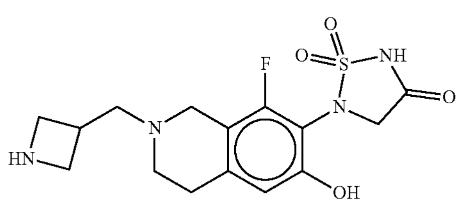 |
| 166 | 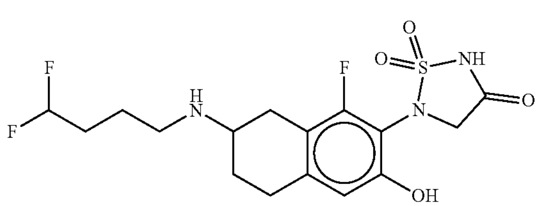 |

TABLE 1-continued

Exemplary compounds of the disclosure.

| Compound Number | Structure |
| --- | --- |
| 167 | 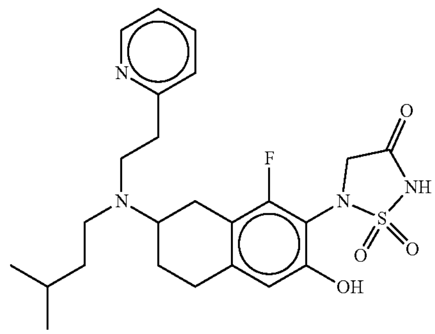 |
| 168 | 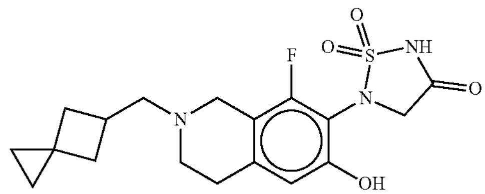 |
| 169 | 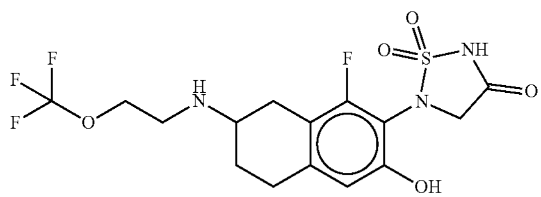 |
| 170 | 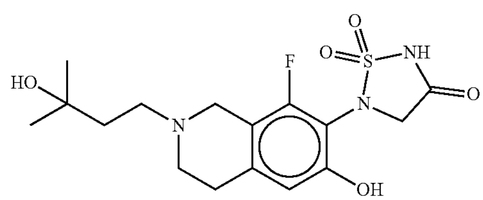 |
| 171 | 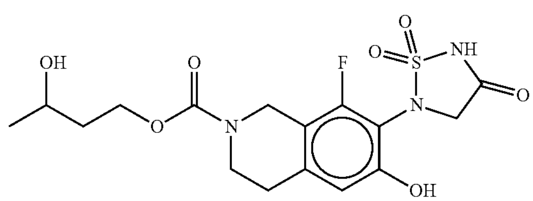 |
| 172 | 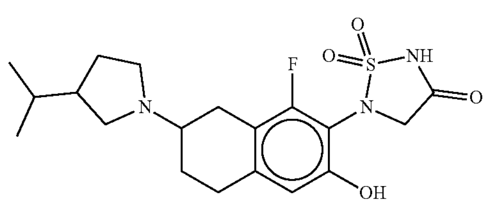 |
| 173 | 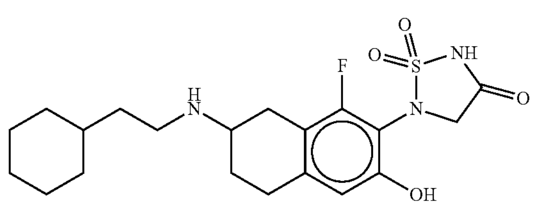 |

TABLE 1-continued

Exemplary compounds of the disclosure.

| Compound Number | Structure |
|---|---|
| 174 | 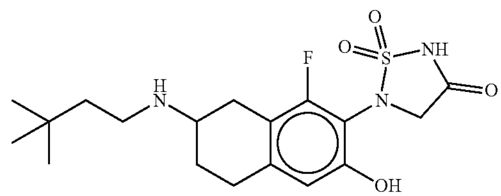 |
| 175 | 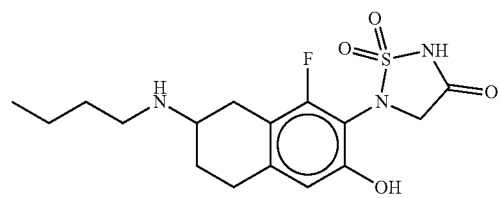 |
| 176 | 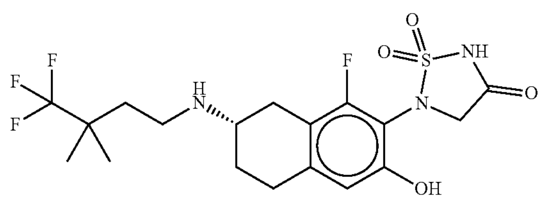 |
| 177 | 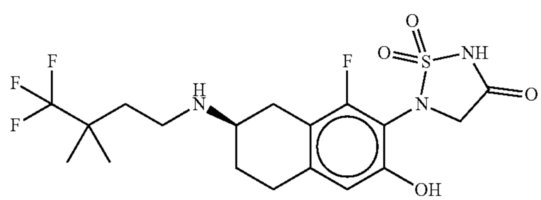 |
| 178 | 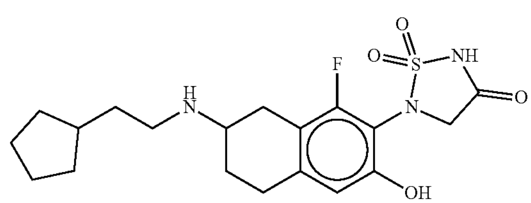 |
| 179 | 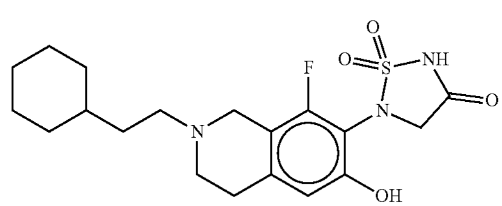 |
| 180 | 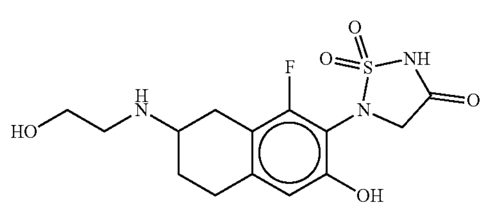 |

TABLE 1-continued

Exemplary compounds of the disclosure.

| Compound Number | Structure |
|---|---|
| 181 | 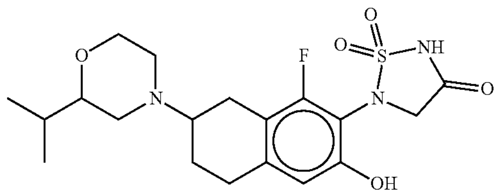 |
| 182 | 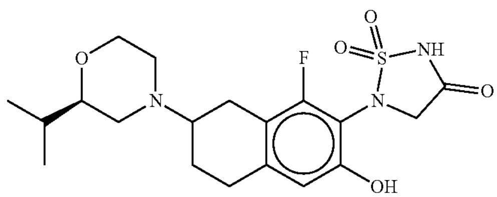 |
| 183 | 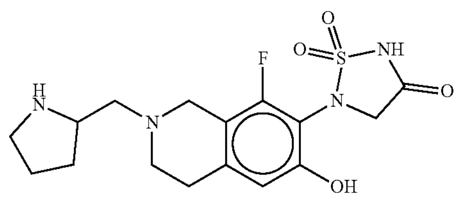 |
| 184 | 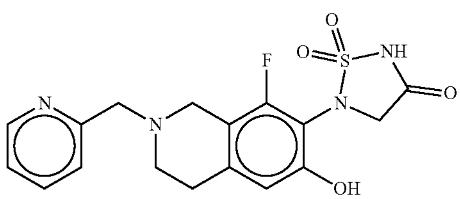 |
| 185 | 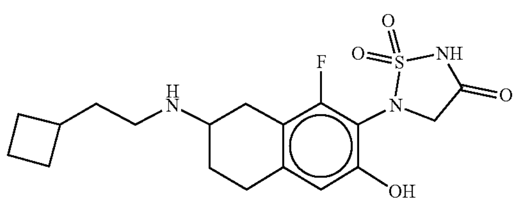 |
| 186 | 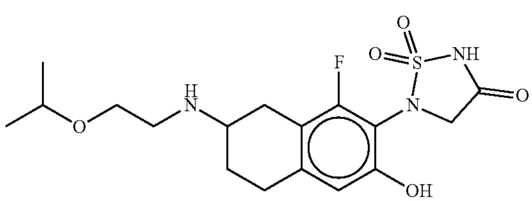 |
| 187 | 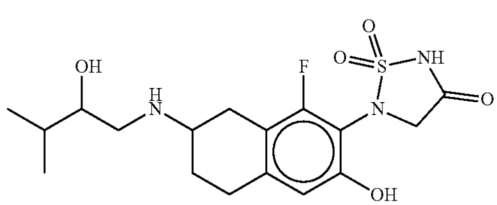 |

TABLE 1-continued

Exemplary compounds of the disclosure.

| Compound Number | Structure |
|---|---|
| 188 | 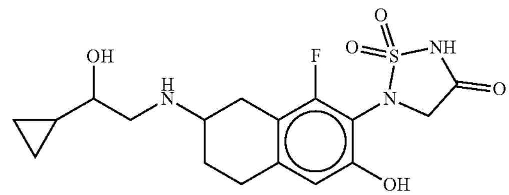 |
| 189 | 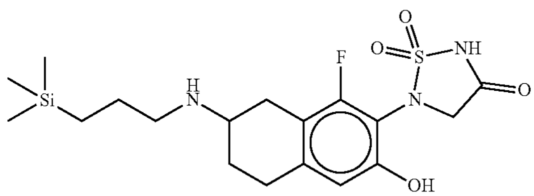 |
| 190 | 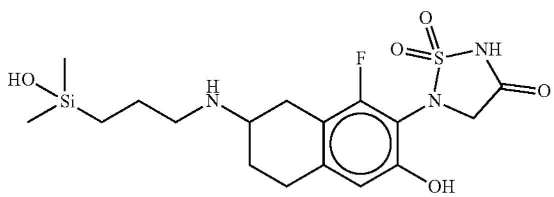 |
| 191 | 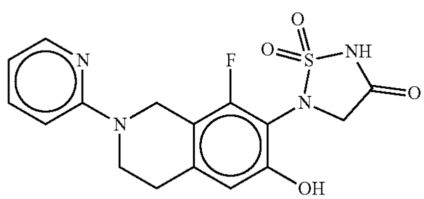 |
| 192 | 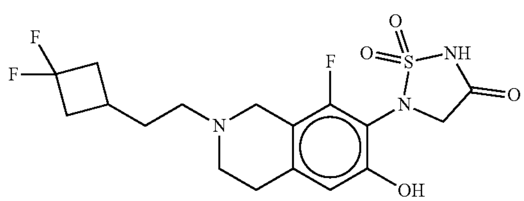 |
| 193 | 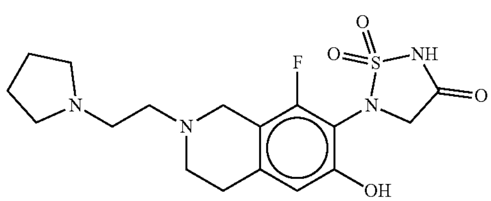 |
| 194 | 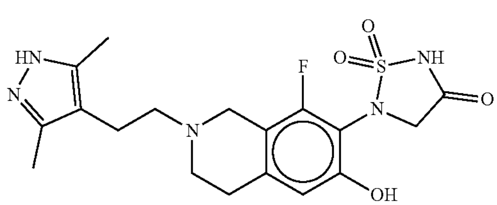 |

TABLE 1-continued

Exemplary compounds of the disclosure.

| Compound Number | Structure |
|---|---|
| 195 | 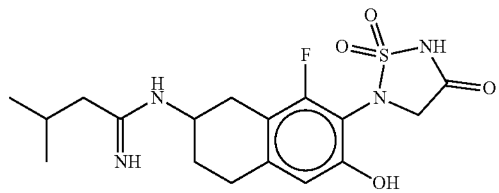 |
| 196 | 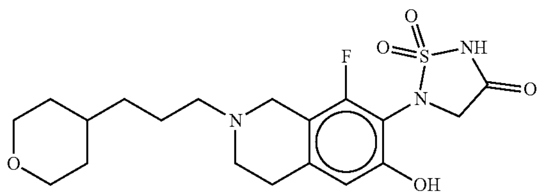 |
| 197 | 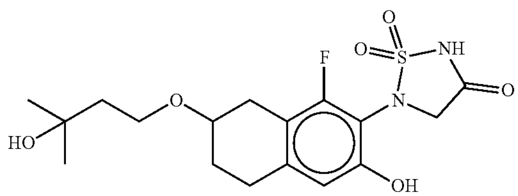 |
| 198 | 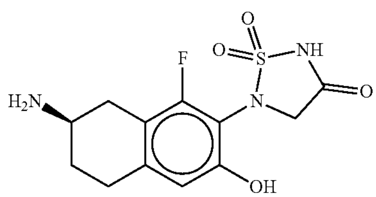 |
| 199 | 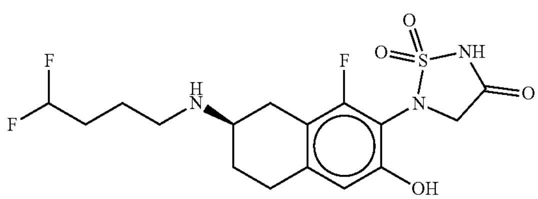 |
| 200 | 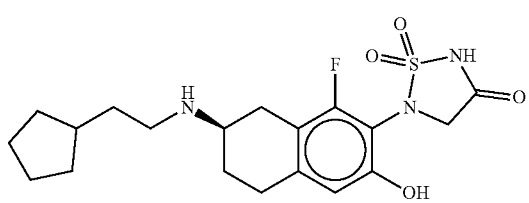 |
| 201 | 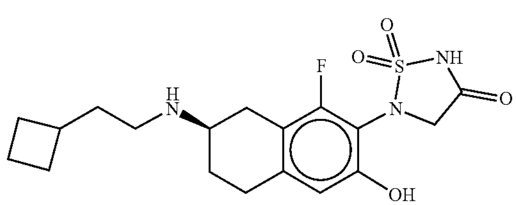 |

TABLE 1-continued

Exemplary compounds of the disclosure.

| Compound Number | Structure |
|---|---|
| 202 | 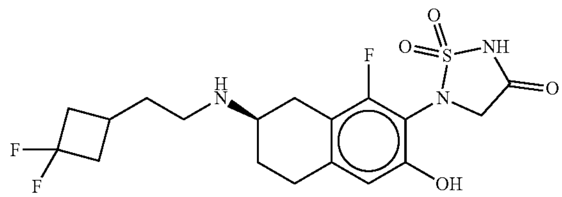 |
| 203 | 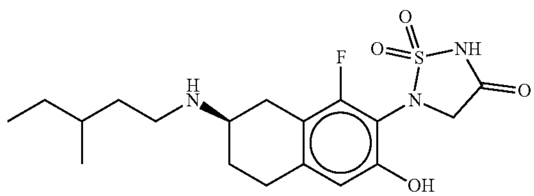 |
| 204 | 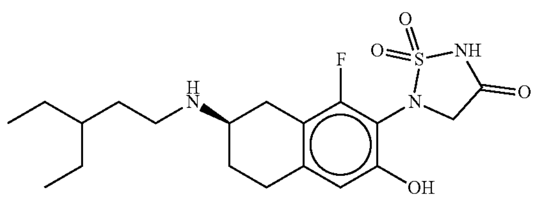 |
| 205 | 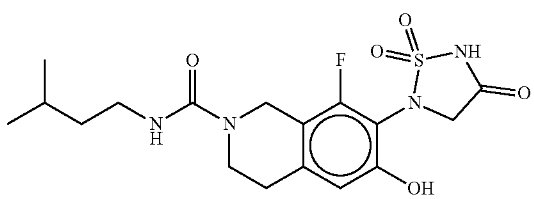 |
| 206 | 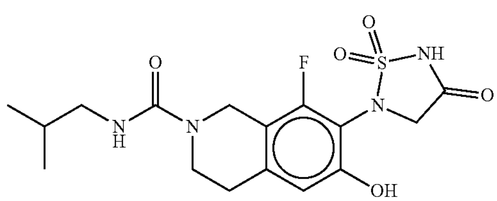 |
| 207 | 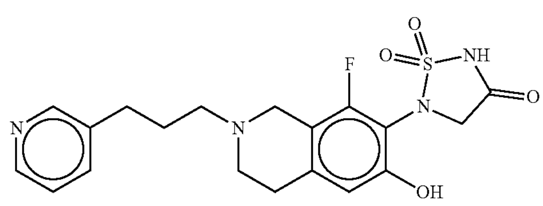 |
| 208 | 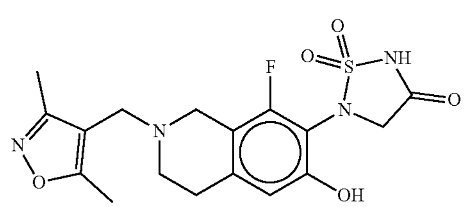 |

TABLE 1-continued

Exemplary compounds of the disclosure.

| Compound Number | Structure |
|---|---|
| 209 | 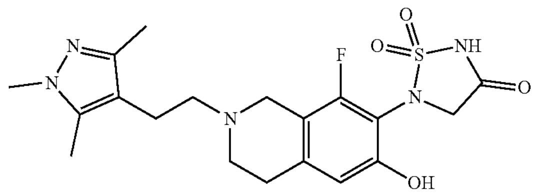 [SMILES: Cc1nn(C)c(C)c1CCN1CCc2cc(O)c(N3CC(=O)NS3(=O)=O)c(F)c2C1] |
| 210 | 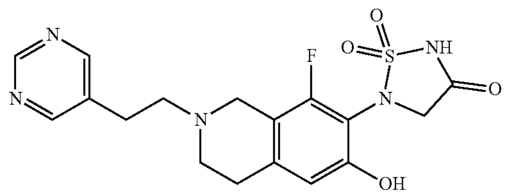 [SMILES: O=C1CN(c2c(O)cc3c(c2F)CN(CCc2cncnc2)CC3)S(=O)(=O)N1] |
| 211 | 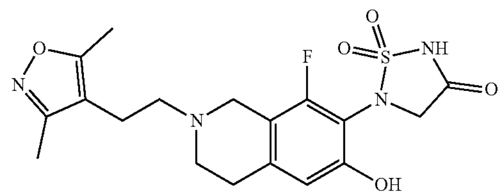 [SMILES: Cc1noc(C)c1CCN1CCc2cc(O)c(N3CC(=O)NS3(=O)=O)c(F)c2C1] |
| 212 | 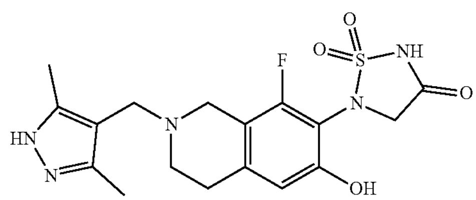 |
| 213 | 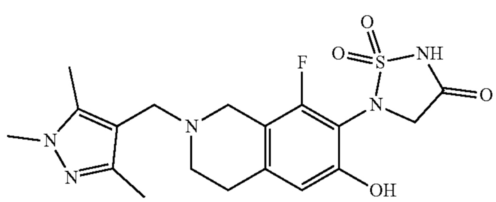 |
| 214 | 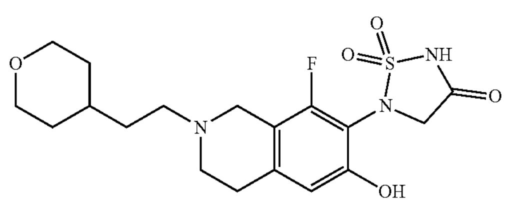 [SMILES: O=C1CN(c2c(O)cc3c(c2F)CN(CCC2CCOCC2)CC3)S(=O)(=O)N1] |
| 215 | 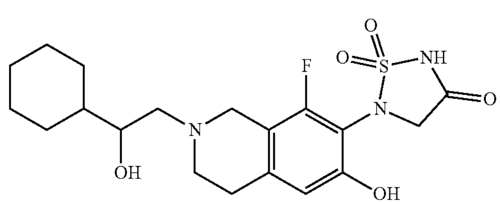 [SMILES: O=C1CN(c2c(O)cc3c(c2F)CN(CC(O)C2CCCCC2)CC3)S(=O)(=O)N1] |

TABLE 1-continued

Exemplary compounds of the disclosure.

| Compound Number | Structure |
|---|---|
| 216 | 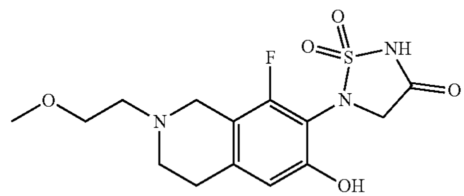 [SMILES: COCCN1CCc2cc(O)c(N3CC(=O)NS3(=O)=O)c(F)c2C1] |
| 217 | 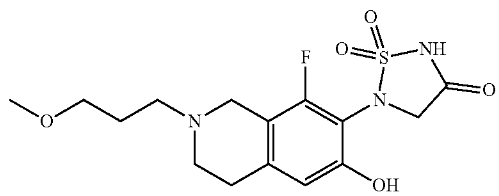 [SMILES: COCCCN1CCc2cc(O)c(N3CC(=O)NS3(=O)=O)c(F)c2C1] |
| 218 | 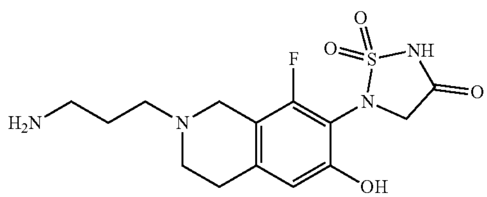 [SMILES: NCCCN1CCc2cc(O)c(N3CC(=O)NS3(=O)=O)c(F)c2C1] |
| 219 | 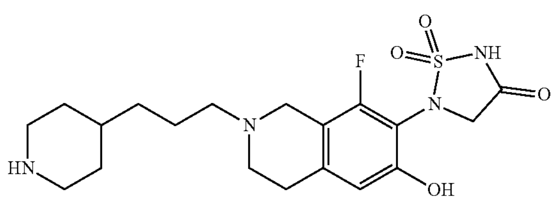 [SMILES: O=C1CN(c2c(O)cc3c(c2F)CN(CCCC2CCNCC2)CC3)S(=O)(=O)N1] |
| 220 | 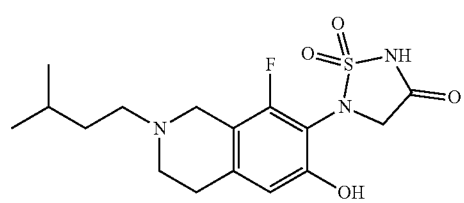 [SMILES: CC(C)CCN1CCc2cc(O)c(N3CC(=O)NS3(=O)=O)c(F)c2C1] |
| 221 | 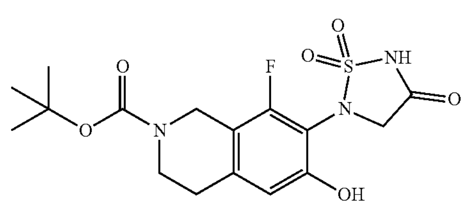 [SMILES: CC(C)(C)OC(=O)N1CCc2cc(O)c(N3CC(=O)NS3(=O)=O)c(F)c2C1] |
| 222 | 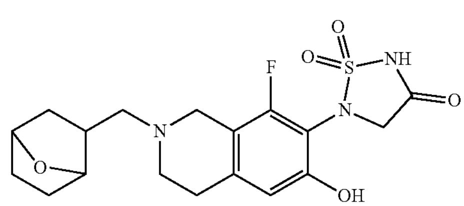 [SMILES: O=C1CN(c2c(O)cc3c(c2F)CN(CC2CC4CCC2O4)CC3)S(=O)(=O)N1] |

TABLE 1-continued

Exemplary compounds of the disclosure.

| Compound Number | Structure |
|---|---|
| 223 | 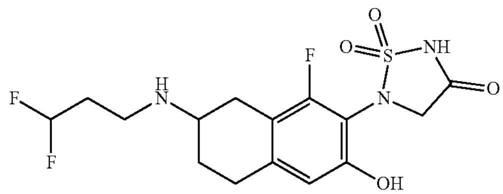 [SMILES: O=C1CN(c2c(O)cc3c(c2F)CC(NCCC(F)F)CC3)S(=O)(=O)N1] |
| 224 | 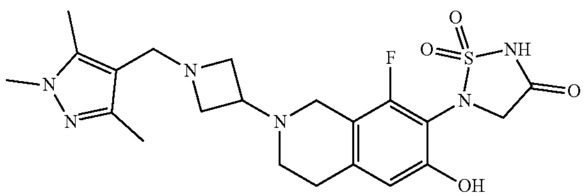 [SMILES: Cc1nn(C)c(C)c1CN1CC(N2CCc3cc(O)c(N4CC(=O)NS4(=O)=O)c(F)c3C2)C1] |
| 225 | 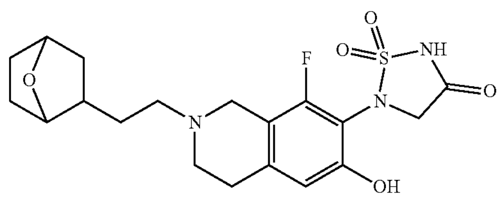 [SMILES: O=C1CN(c2c(O)cc3c(c2F)CN(CCC2CC4CCC2O4)CC3)S(=O)(=O)N1] |
| 226 | 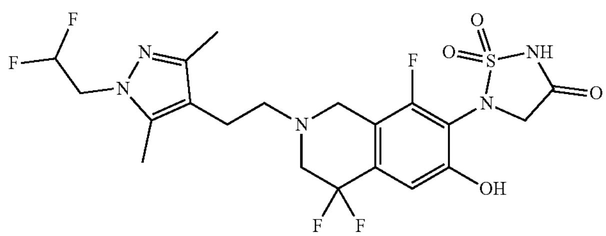 [SMILES: Cc1nn(CC(F)F)c(C)c1CCN1Cc2c(cc(O)c(N3CC(=O)NS3(=O)=O)c2F)C(F)(F)C1] |
| 227 | 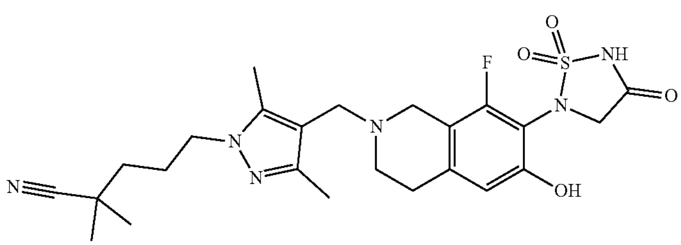 [SMILES: Cc1nn(CCCC(C)(C)C#N)c(C)c1CN1CCc2cc(O)c(N3CC(=O)NS3(=O)=O)c(F)c2C1] |
| 228 | 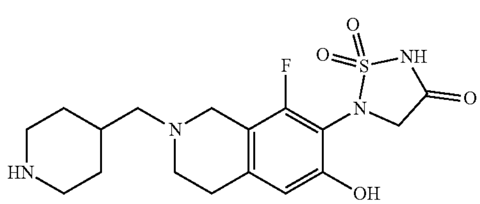 [SMILES: O=C1CN(c2c(O)cc3c(c2F)CN(CC2CCNCC2)CC3)S(=O)(=O)N1] |
| 229 | 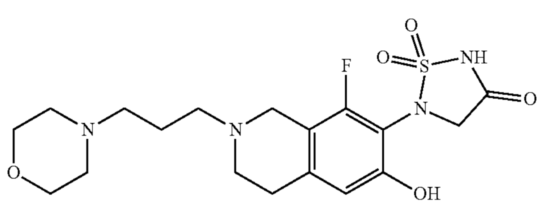 [SMILES: O=C1CN(c2c(O)cc3c(c2F)CN(CCCN2CCOCC2)CC3)S(=O)(=O)N1] |

TABLE 1-continued

Exemplary compounds of the disclosure.

| Compound Number | Structure |
|---|---|
| 230 | 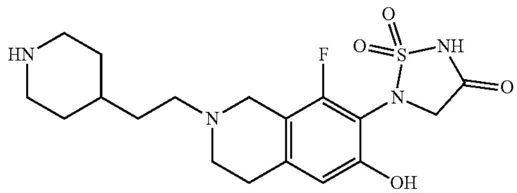 |
| 231 | 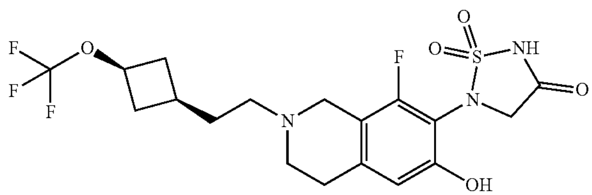 [SMILES: O=C1CN(c2c(O)cc3c(c2F)CN(CC[C@H]2C[C@@H](OC(F)(F)F)C2)CC3)S(=O)(=O)N1] |
| 232 | 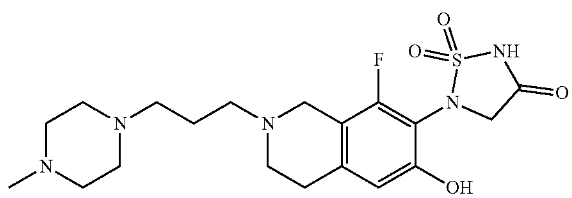 [SMILES: CN1CCN(CCCN2CCc3cc(O)c(N4CC(=O)NS4(=O)=O)c(F)c3C2)CC1] |
| 233 | 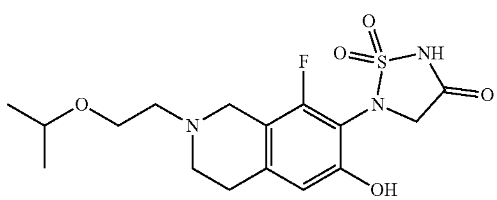 [SMILES: CC(C)OCCN1CCc2cc(O)c(N3CC(=O)NS3(=O)=O)c(F)c2C1] |
| 234 | 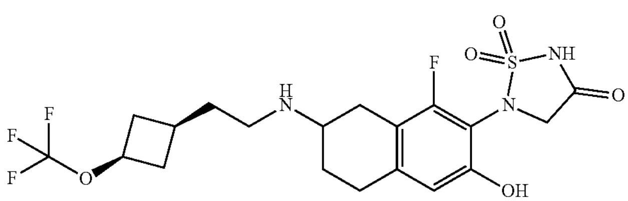 [SMILES: O=C1CN(c2c(O)cc3c(c2F)CC(NCC[C@H]2C[C@@H](OC(F)(F)F)C2)CC3)S(=O)(=O)N1] |
| 235 | 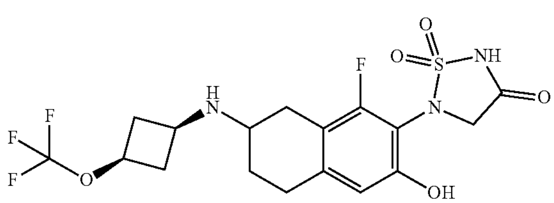 [SMILES: O=C1CN(c2c(O)cc3c(c2F)CC(N[C@H]2C[C@@H](OC(F)(F)F)C2)CC3)S(=O)(=O)N1] |
| 236 | 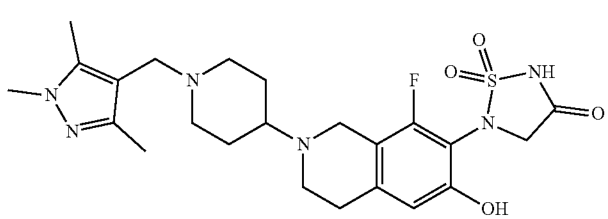 [SMILES: Cc1nn(C)c(C)c1CN1CCC(N2CCc3cc(O)c(N4CC(=O)NS4(=O)=O)c(F)c3C2)CC1] |

TABLE 1-continued

Exemplary compounds of the disclosure.

| Compound Number | Structure |
|---|---|
| 237 | 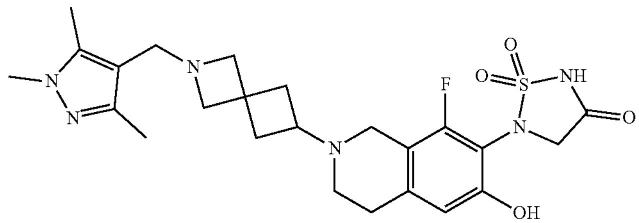 [SMILES: Cc1nn(C)c(C)c1CN1CC2(CC(N3CCc4cc(O)c(N5CC(=O)NS5(=O)=O)c(F)c4C3)C2)C1] |
| 238 | 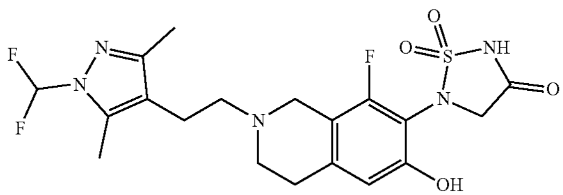 [SMILES: Cc1nn(C(F)F)c(C)c1CCN1CCc2cc(O)c(N3CC(=O)NS3(=O)=O)c(F)c2C1] |
| 239 | 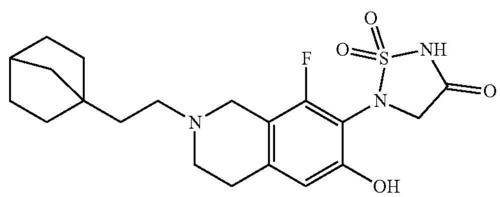 [SMILES: O=C1CN(c2c(O)cc3c(c2F)CN(CCC24CCC(CC2)C4)CC3)S(=O)(=O)N1] |
| 240 | 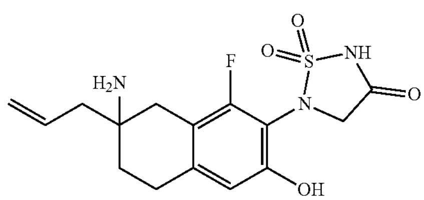 [SMILES: C=CCC1(N)CCc2cc(O)c(N3CC(=O)NS3(=O)=O)c(F)c2C1] |
| 241 | 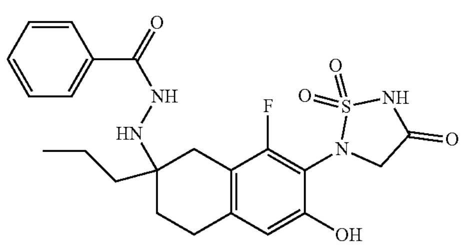 [SMILES: CCCC1(NNC(=O)c2ccccc2)CCc2cc(O)c(N3CC(=O)NS3(=O)=O)c(F)c2C1] |
| 242 | 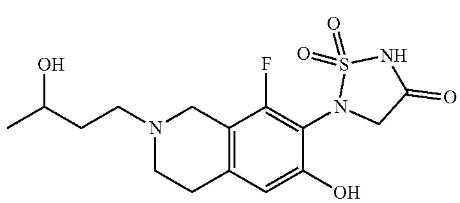 [SMILES: CC(O)CCN1CCc2cc(O)c(N3CC(=O)NS3(=O)=O)c(F)c2C1] |
| 243 | 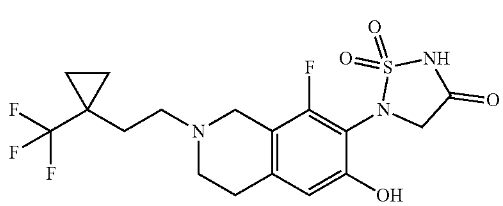 [SMILES: O=C1CN(c2c(O)cc3c(c2F)CN(CCC2(C(F)(F)F)CC2)CC3)S(=O)(=O)N1] |

TABLE 1-continued

Exemplary compounds of the disclosure.

| Compound Number | Structure |
|---|---|
| 244 | 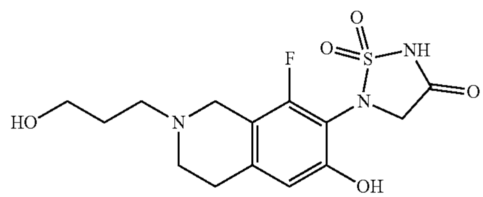 [SMILES: O=C1CN(c2c(O)cc3c(c2F)CN(CCCO)CC3)S(=O)(=O)N1] |
| 245 | 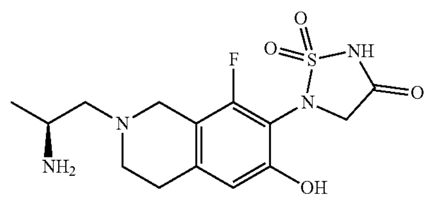 [SMILES: C[C@H](N)CN1CCc2cc(O)c(N3CC(=O)NS3(=O)=O)c(F)c2C1] |
| 246 | 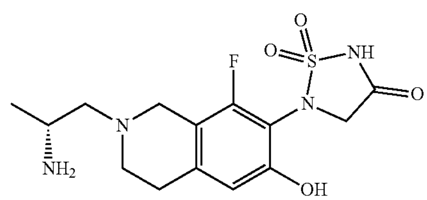 [SMILES: C[C@@H](N)CN1CCc2cc(O)c(N3CC(=O)NS3(=O)=O)c(F)c2C1] |
| 247 | 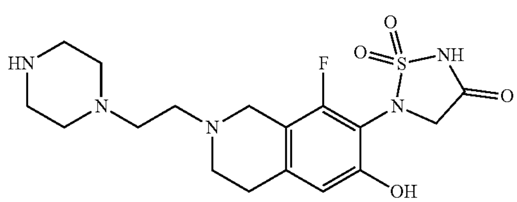 [SMILES: O=C1CN(c2c(O)cc3c(c2F)CN(CCN2CCNCC2)CC3)S(=O)(=O)N1] |
| 248 | 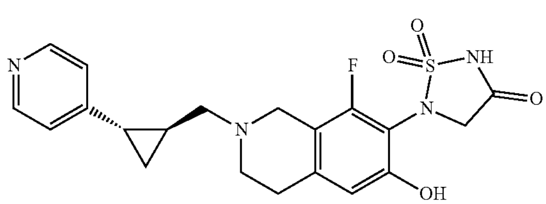 [SMILES: O=C1CN(c2c(O)cc3c(c2F)CN(C[C@H]2C[C@@H]2c2ccncc2)CC3)S(=O)(=O)N1] |
| 249 | 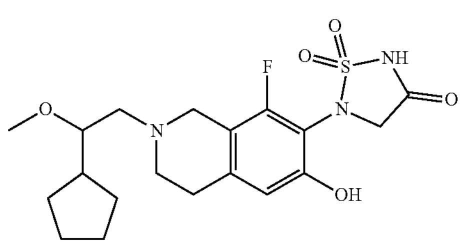 [SMILES: COC(CN1CCc2cc(O)c(N3CC(=O)NS3(=O)=O)c(F)c2C1)C1CCCC1] |
| 250 | 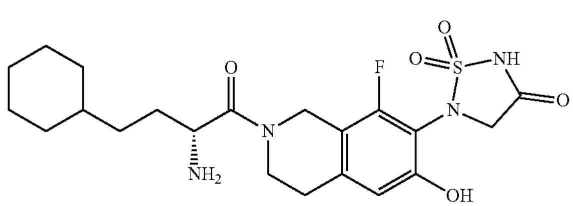 [SMILES: N[C@H](CCC1CCCCC1)C(=O)N1CCc2cc(O)c(N3CC(=O)NS3(=O)=O)c(F)c2C1] |

TABLE 1-continued
Exemplary compounds of the disclosure.
| Compound Number | Structure |
|---|---|
| 251 | 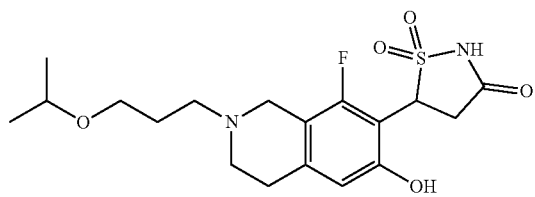 [SMILES: CC(C)OCCCN1CCc2cc(O)c(C3CC(=O)NS3(=O)=O)c(F)c2C1] |
| 252 | 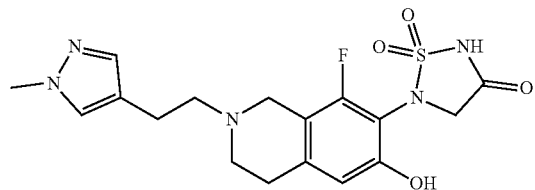 [SMILES: Cn1cc(CCN2CCc3cc(O)c(N4CC(=O)NS4(=O)=O)c(F)c3C2)cn1] |
| 253 | 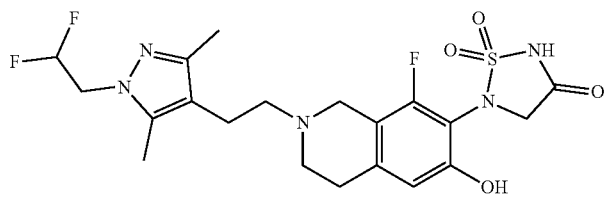 [SMILES: Cc1nn(CC(F)F)c(C)c1CCN1CCc2cc(O)c(N3CC(=O)NS3(=O)=O)c(F)c2C1] |
| 254 | 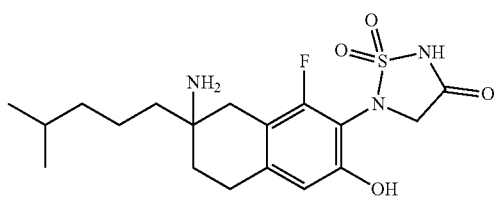 [SMILES: CC(C)CCCC1(N)CCc2cc(O)c(N3CC(=O)NS3(=O)=O)c(F)c2C1] |
| 255 | 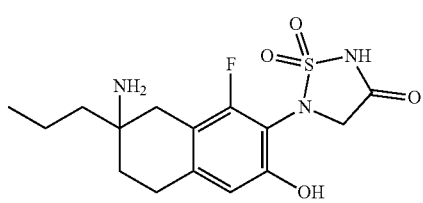 [SMILES: CCCC1(N)CCc2cc(O)c(N3CC(=O)NS3(=O)=O)c(F)c2C1] |
| 256 | 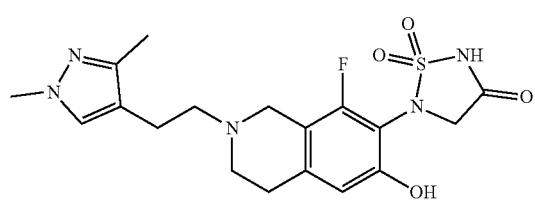 [SMILES: Cc1nn(C)cc1CCN1CCc2cc(O)c(N3CC(=O)NS3(=O)=O)c(F)c2C1] |
| 257 | 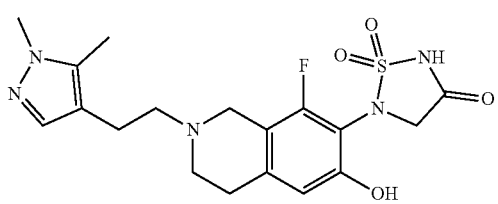 [SMILES: Cc1c(CCN2CCc3cc(O)c(N4CC(=O)NS4(=O)=O)c(F)c3C2)cnn1C] |

TABLE 1-continued
Exemplary compounds of the disclosure.
| Compound Number | Structure |
|---|---|
| 258 | 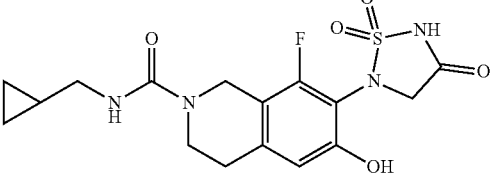 |
| 259 | 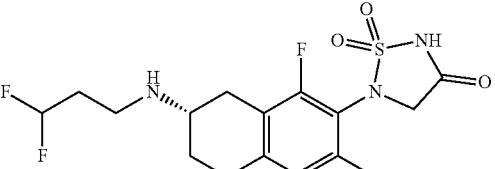 |
| 260 | 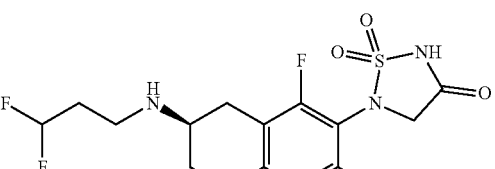 |
| 261 | 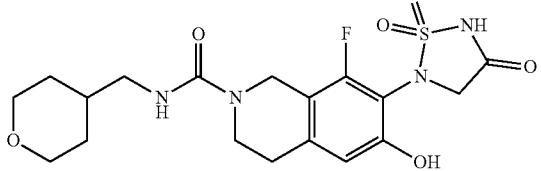 |
| 262 | 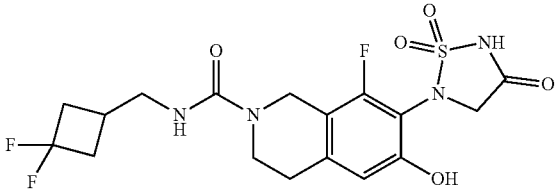 [SMILES: O=C1CN(c2c(O)cc3c(c2F)CN(C(=O)NCC2CC(F)(F)C2)CC3)S(=O)(=O)N1] |
| 263 | 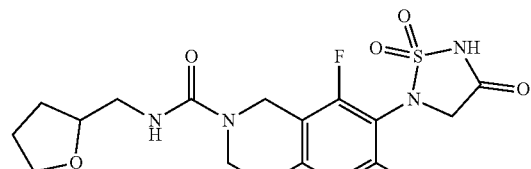 |
| 264 | 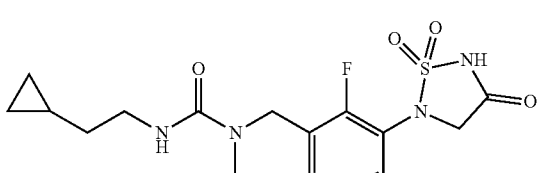 |

TABLE 1-continued

Exemplary compounds of the disclosure.

| Compound Number | Structure |
| --- | --- |
| 265 | 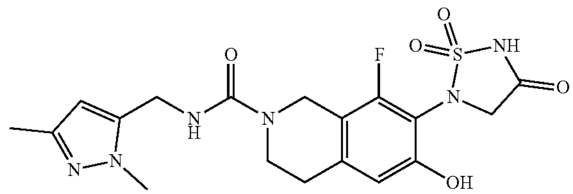 [SMILES: Cc1cc(CNC(=O)N2CCc3cc(O)c(N4CC(=O)NS4(=O)=O)c(F)c3C2)n(C)n1] |
| 266 | 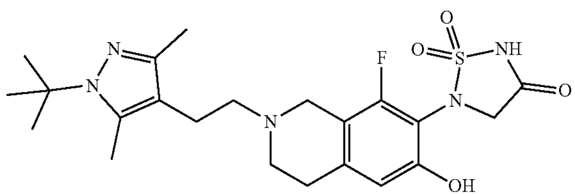 [SMILES: Cc1nn(C(C)(C)C)c(C)c1CCN1CCc2cc(O)c(N3CC(=O)NS3(=O)=O)c(F)c2C1] |
| 267 | 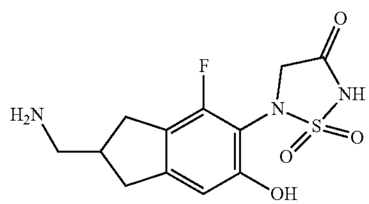 [SMILES: NCC1Cc2cc(O)c(N3CC(=O)NS3(=O)=O)c(F)c2C1] |
| 268 | 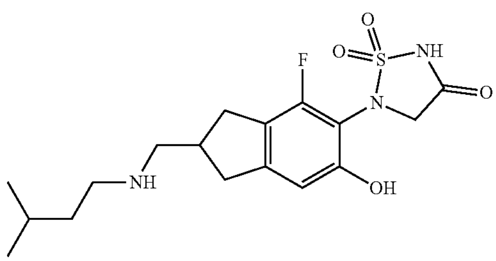 |
| 269 | 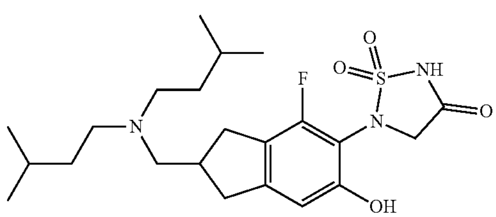 [SMILES: CC(C)CCN(CCC(C)C)CC1Cc2cc(O)c(N3CC(=O)NS3(=O)=O)c(F)c2C1] |
| 270 | 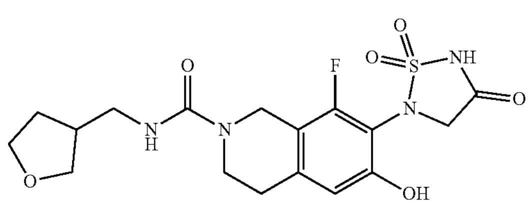 [SMILES: O=C1CN(c2c(O)cc3c(c2F)CN(C(=O)NCC2CCOC2)CC3)S(=O)(=O)N1] |
| 271 | 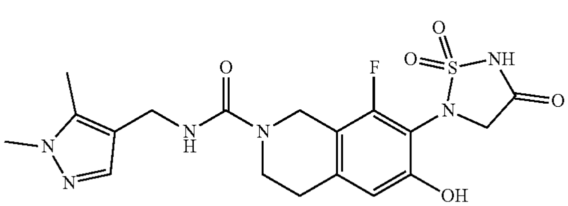 [SMILES: Cc1c(CNC(=O)N2CCc3cc(O)c(N4CC(=O)NS4(=O)=O)c(F)c3C2)cnn1C] |

TABLE 1-continued

Exemplary compounds of the disclosure.

| Compound Number | Structure |
|---|---|
| 272 | 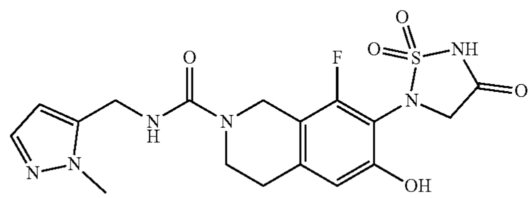 [SMILES: Cn1nccc1CNC(=O)N1CCc2cc(O)c(N3CC(=O)NS3(=O)=O)c(F)c2C1] |
| 273 | 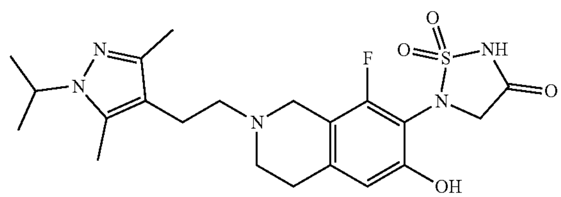 [SMILES: Cc1nn(C(C)C)c(C)c1CCN1CCc2cc(O)c(N3CC(=O)NS3(=O)=O)c(F)c2C1] |
| 274 | 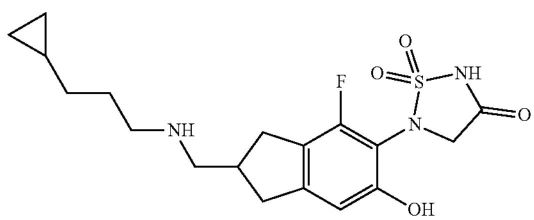 [SMILES: O=C1CN(c2c(O)cc3c(c2F)CC(CNCCCC2CC2)C3)S(=O)(=O)N1] |
| 275 | 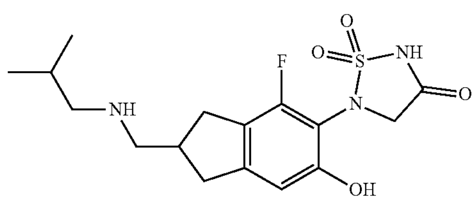 [SMILES: CC(C)CNCC1Cc2cc(O)c(N3CC(=O)NS3(=O)=O)c(F)c2C1] |
| 276 | 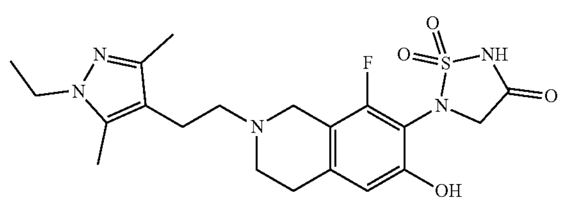 [SMILES: CCn1nc(C)c(CCN2CCc3cc(O)c(N4CC(=O)NS4(=O)=O)c(F)c3C2)c1C] |
| 277 | 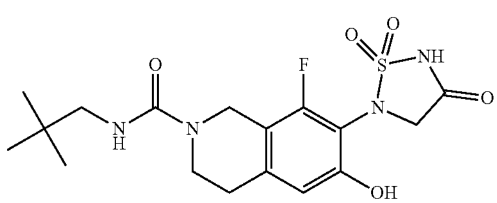 [SMILES: CC(C)(C)CNC(=O)N1CCc2cc(O)c(N3CC(=O)NS3(=O)=O)c(F)c2C1] |
| 278 | 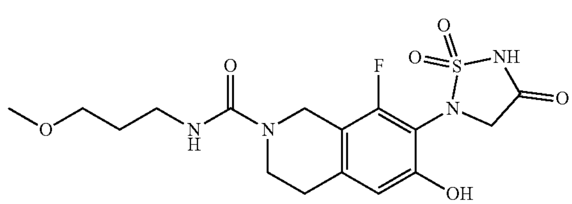 [SMILES: COCCCNC(=O)N1CCc2cc(O)c(N3CC(=O)NS3(=O)=O)c(F)c2C1] |

TABLE 1-continued

Exemplary compounds of the disclosure.

| Compound Number | Structure |
|---|---|
| 279 | 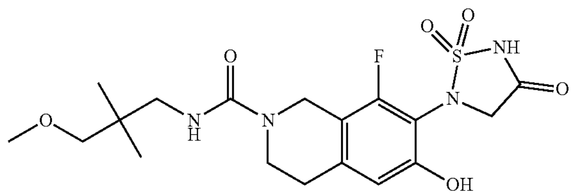 [SMILES: COCC(C)(C)CNC(=O)N1CCc2cc(O)c(N3CC(=O)NS3(=O)=O)c(F)c2C1] |
| 280 | 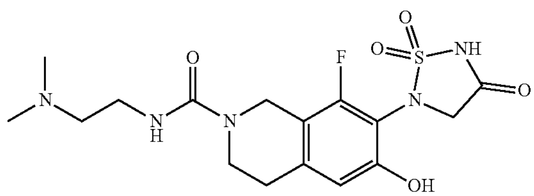 [SMILES: CN(C)CCNC(=O)N1CCc2cc(O)c(N3CC(=O)NS3(=O)=O)c(F)c2C1] |
| 281 | 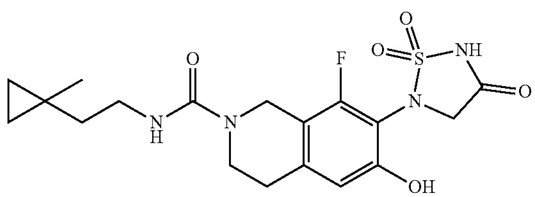 [SMILES: CC1(CCNC(=O)N2CCc3cc(O)c(N4CC(=O)NS4(=O)=O)c(F)c3C2)CC1] |
| 282 | 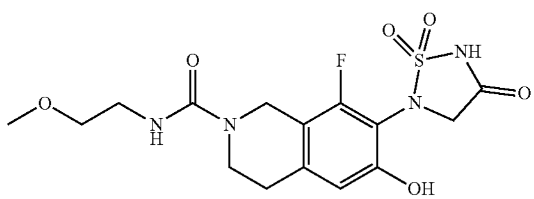 [SMILES: COCCNC(=O)N1CCc2cc(O)c(N3CC(=O)NS3(=O)=O)c(F)c2C1] |
| 283 | 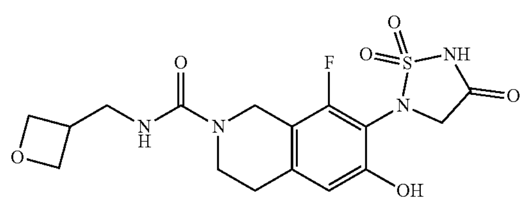 [SMILES: O=C1CN(c2c(O)cc3c(c2F)CN(C(=O)NCC2COC2)CC3)S(=O)(=O)N1] |
| 284 | 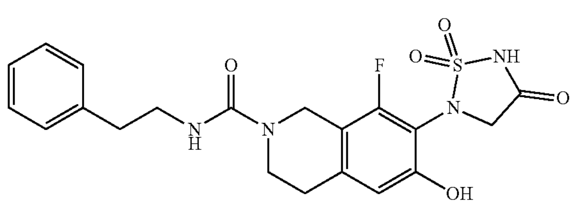 [SMILES: O=C1CN(c2c(O)cc3c(c2F)CN(C(=O)NCCc2ccccc2)CC3)S(=O)(=O)N1] |
| 285 | 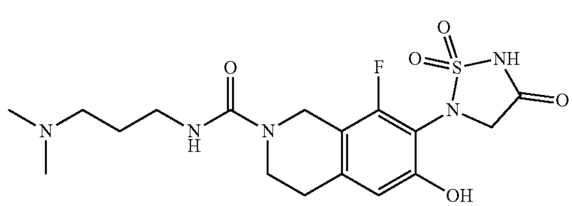 [SMILES: CN(C)CCCNC(=O)N1CCc2cc(O)c(N3CC(=O)NS3(=O)=O)c(F)c2C1] |

TABLE 1-continued

Exemplary compounds of the disclosure.

| Compound Number | Structure |
|---|---|
| 286 | 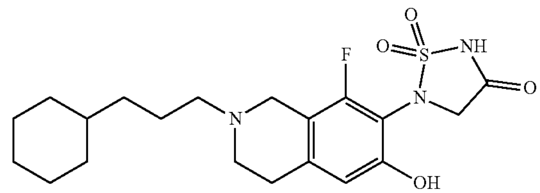 [SMILES: O=C1CN(c2c(O)cc3c(c2F)CN(CCCC2CCCCC2)CC3)S(=O)(=O)N1] |
| 287 | 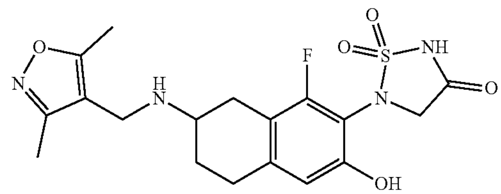 [SMILES: Cc1noc(C)c1CNC1CCc2cc(O)c(N3CC(=O)NS3(=O)=O)c(F)c2C1] |
| 288 | 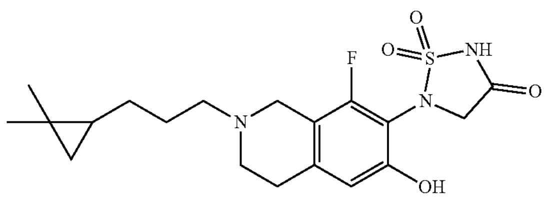 [SMILES: CC1(C)CC1CCCN1CCc2cc(O)c(N3CC(=O)NS3(=O)=O)c(F)c2C1] |
| 289 | 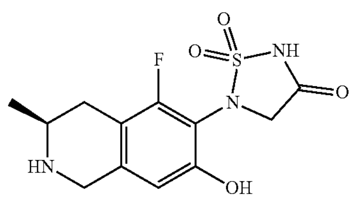 [SMILES: C[C@H]1Cc2c(cc(O)c(N3CC(=O)NS3(=O)=O)c2F)CN1] |
| 290 | 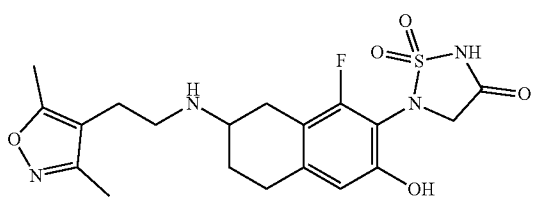 [SMILES: Cc1noc(C)c1CCNC1CCc2cc(O)c(N3CC(=O)NS3(=O)=O)c(F)c2C1] |
| 291 | 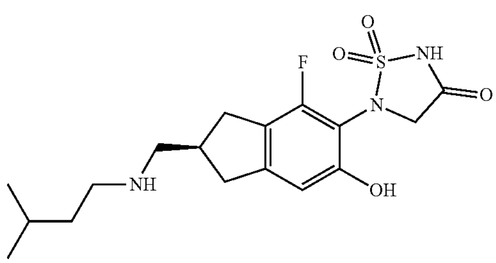 [SMILES: CC(C)CCNC[C@@H]1Cc2cc(O)c(N3CC(=O)NS3(=O)=O)c(F)c2C1] |
| 292 | 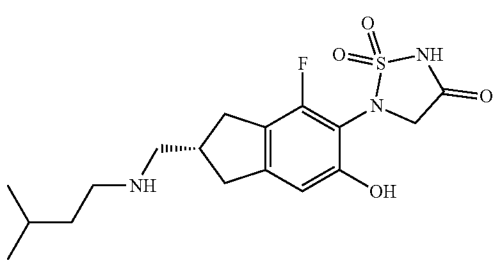 [SMILES: CC(C)CCNC[C@H]1Cc2cc(O)c(N3CC(=O)NS3(=O)=O)c(F)c2C1] |

TABLE 1-continued

Exemplary compounds of the disclosure.

| Compound Number | Structure |
|---|---|
| 293 | 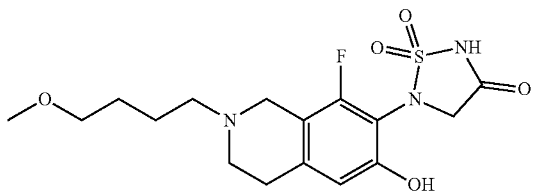 [SMILES: COCCCCN1CCc2cc(O)c(N3CC(=O)NS3(=O)=O)c(F)c2C1] |
| 294 | 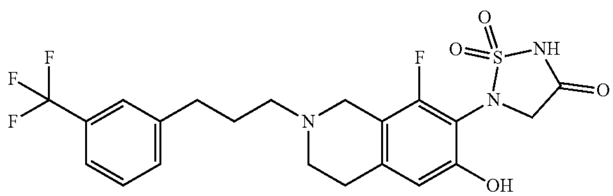 [SMILES: O=C1CN(c2c(O)cc3c(c2F)CN(CCCc2cccc(C(F)(F)F)c2)CC3)S(=O)(=O)N1] |
| 295 | 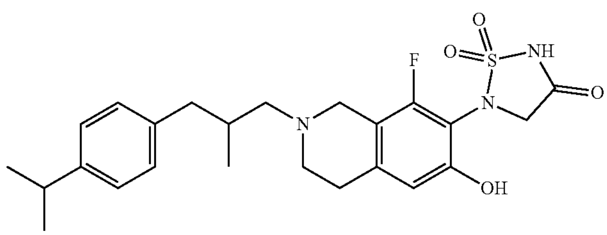 [SMILES: CC(Cc1ccc(C(C)C)cc1)CN1CCc2cc(O)c(N3CC(=O)NS3(=O)=O)c(F)c2C1] |
| 296 | 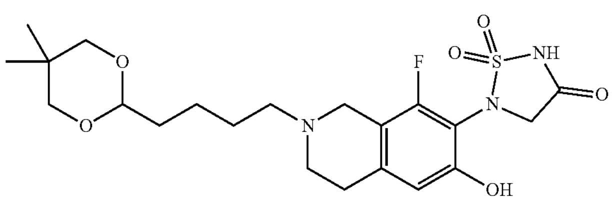 [SMILES: CC1(C)COC(CCCCN2CCc3cc(O)c(N4CC(=O)NS4(=O)=O)c(F)c3C2)OC1] |
| 297 | 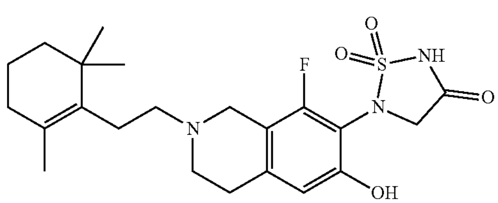 [SMILES: CC1=C(CCN2CCc3cc(O)c(N4CC(=O)NS4(=O)=O)c(F)c3C2)C(C)(C)CCC1] |
| 298 | 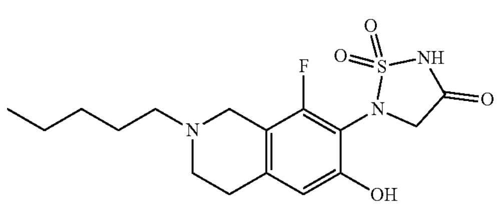 [SMILES: CCCCCN1CCc2cc(O)c(N3CC(=O)NS3(=O)=O)c(F)c2C1] |
| 299 | 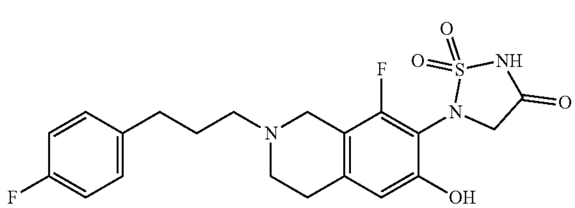 [SMILES: O=C1CN(c2c(O)cc3c(c2F)CN(CCCc2ccc(F)cc2)CC3)S(=O)(=O)N1] |

TABLE 1-continued
Exemplary compounds of the disclosure.
| Compound Number | Structure |
|---|---|
| 300 | 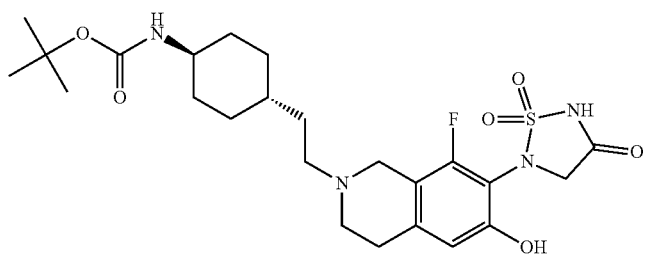 [SMILES: CC(C)(C)OC(=O)N[C@H]1CC[C@H](CCN2CCc3cc(O)c(N4CC(=O)NS4(=O)=O)c(F)c3C2)CC1] |
| 301 | 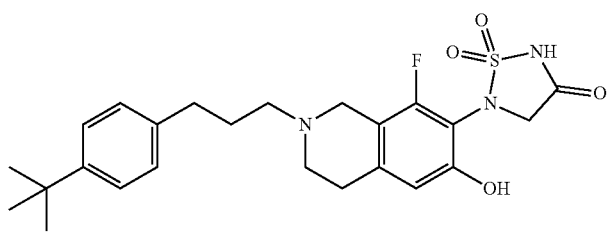 [SMILES: CC(C)(C)c1ccc(CCCN2CCc3cc(O)c(N4CC(=O)NS4(=O)=O)c(F)c3C2)cc1] |
| 302 | 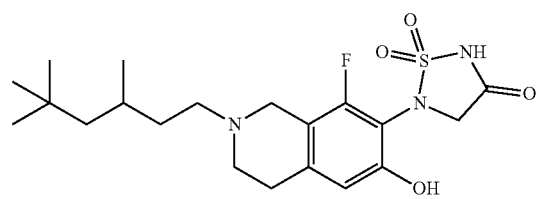 [SMILES: CC(CCN1CCc2cc(O)c(N3CC(=O)NS3(=O)=O)c(F)c2C1)CC(C)(C)C] |
| 303 | 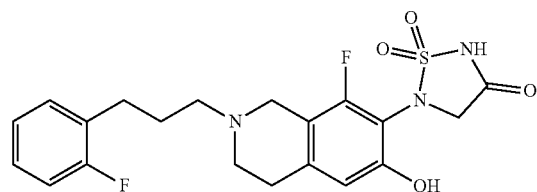 [SMILES: O=C1CN(c2c(O)cc3c(c2F)CN(CCCc2ccccc2F)CC3)S(=O)(=O)N1] |
| 304 | 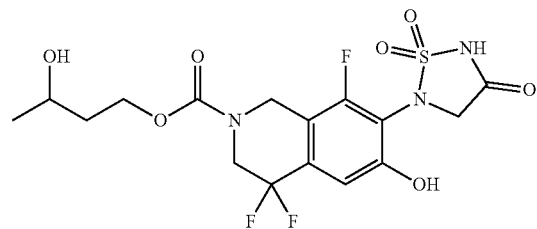 [SMILES: CC(O)CCOC(=O)N1Cc2c(cc(O)c(N3CC(=O)NS3(=O)=O)c2F)C(F)(F)C1] |
| 305 | 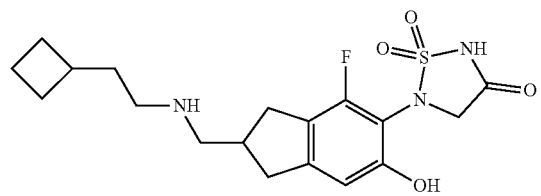 [SMILES: O=C1CN(c2c(O)cc3c(c2F)CC(CNCCC2CCC2)C3)S(=O)(=O)N1] |

TABLE 1-continued

Exemplary compounds of the disclosure.

| Compound Number | Structure |
|---|---|
| 306 | 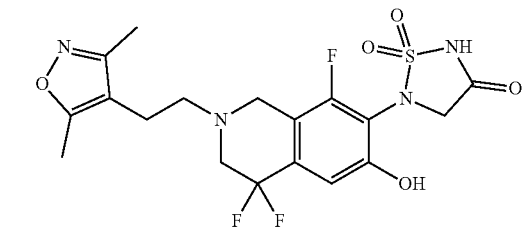 [SMILES: Cc1noc(C)c1CCN1Cc2c(cc(O)c(N3CC(=O)NS3(=O)=O)c2F)C(F)(F)C1] |
| 307 | 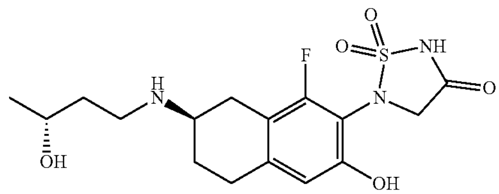 [SMILES: C[C@@H](O)CCN[C@@H]1CCc2cc(O)c(N3CC(=O)NS3(=O)=O)c(F)c2C1] |
| 308 | 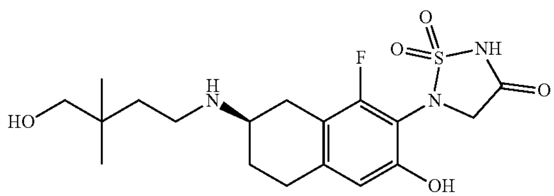 [SMILES: CC(C)(CO)CCN[C@@H]1CCc2cc(O)c(N3CC(=O)NS3(=O)=O)c(F)c2C1] |
| 309 | 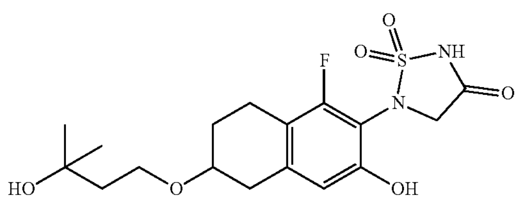 [SMILES: CC(C)(O)CCOC1CCc2c(cc(O)c(N3CC(=O)NS3(=O)=O)c2F)C1] |
| 310 | 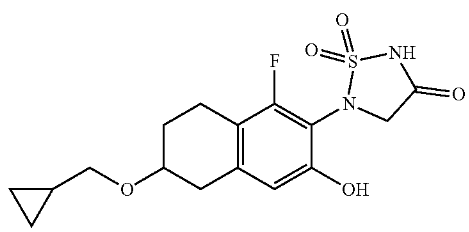 [SMILES: O=C1CN(c2c(O)cc3c(c2F)CCC(OCC2CC2)C3)S(=O)(=O)N1] |
| 311 | 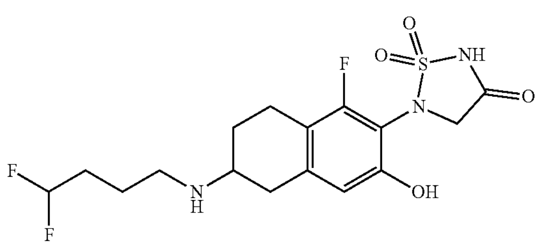 [SMILES: O=C1CN(c2c(O)cc3c(c2F)CCC(NCCCC(F)F)C3)S(=O)(=O)N1] |
| 312 | 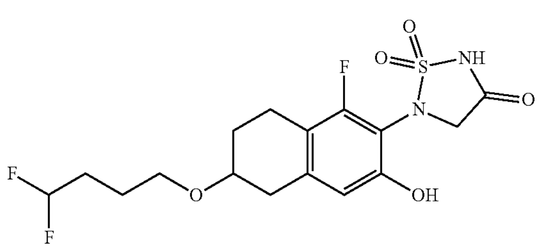 [SMILES: O=C1CN(c2c(O)cc3c(c2F)CCC(OCCCC(F)F)C3)S(=O)(=O)N1] |

TABLE 1-continued
Exemplary compounds of the disclosure.
| Compound Number | Structure |
|---|---|
| 313 | 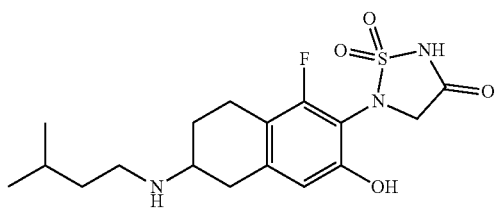 [SMILES: CC(C)CCNC1CCc2c(cc(O)c(N3CC(=O)NS3(=O)=O)c2F)C1] |
| 314 | 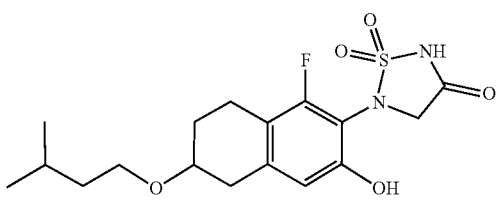 [SMILES: CC(C)CCOC1CCc2c(cc(O)c(N3CC(=O)NS3(=O)=O)c2F)C1] |
| 315 | 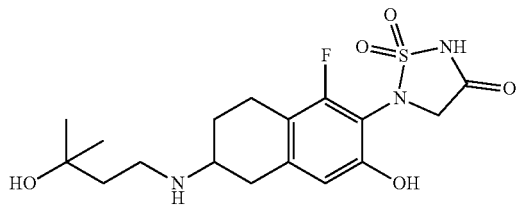 [SMILES: CC(C)(O)CCNC1CCc2c(cc(O)c(N3CC(=O)NS3(=O)=O)c2F)C1] |
| 316 | 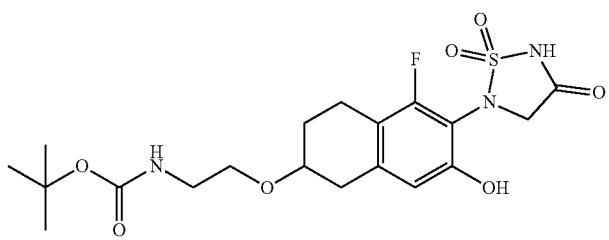 [SMILES: CC(C)(C)OC(=O)NCCOC1CCc2c(cc(O)c(N3CC(=O)NS3(=O)=O)c2F)C1] |
| 317 | 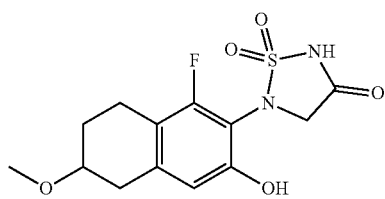 [SMILES: COC1CCc2c(cc(O)c(N3CC(=O)NS3(=O)=O)c2F)C1] |
| 318 | 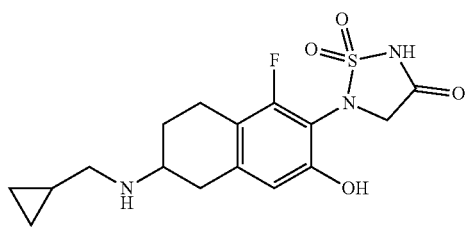 [SMILES: O=C1CN(c2c(O)cc3c(c2F)CCC(NCC2CC2)C3)S(=O)(=O)N1] |
| 319 | 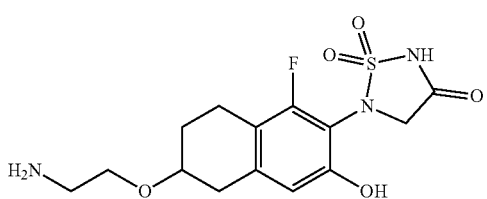 [SMILES: NCCOC1CCc2c(cc(O)c(N3CC(=O)NS3(=O)=O)c2F)C1] |

US 10,851,073 B2
137                                                                     138
TABLE 1-continued
Exemplary compounds of the disclosure.
| Compound Number | Structure |
|---|---|
| 320 | 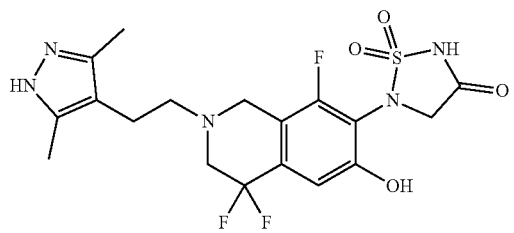 [SMILES: Cc1n[nH]c(C)c1CCN1Cc2c(cc(O)c(N3CC(=O)NS3(=O)=O)c2F)C(F)(F)C1] |
| 321 | 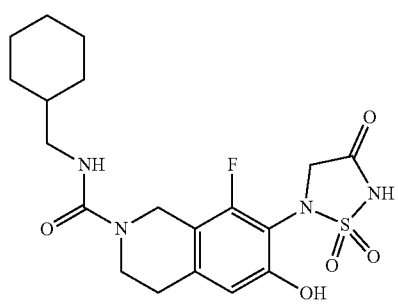 [SMILES: O=C1CN(c2c(O)cc3c(c2F)CN(C(=O)NCC2CCCCC2)CC3)S(=O)(=O)N1] |
| 322 | 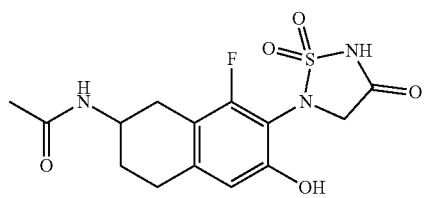 [SMILES: CC(=O)NC1CCc2cc(O)c(N3CC(=O)NS3(=O)=O)c(F)c2C1] |
| 323 | 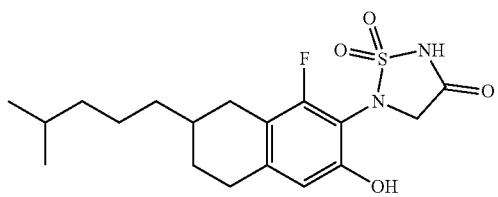 [SMILES: CC(C)CCCC1CCc2cc(O)c(N3CC(=O)NS3(=O)=O)c(F)c2C1] |
| 324 | 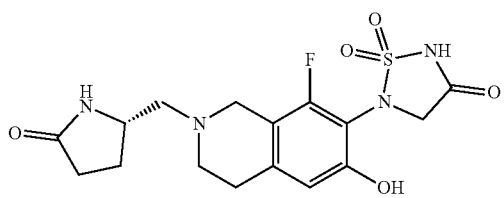 [SMILES: O=C1CC[C@@H](CN2CCc3cc(O)c(N4CC(=O)NS4(=O)=O)c(F)c3C2)N1] |
| 325 | 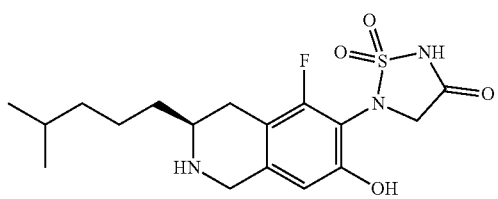 [SMILES: CC(C)CCC[C@H]1Cc2c(cc(O)c(N3CC(=O)NS3(=O)=O)c2F)CN1] |

Methods of Making Exemplary Compounds

The compounds of the present disclosure may be better understood in connection with the following synthetic schemes and methods which illustrate a means by which the compounds can be prepared. The compounds of the present disclosure can be prepared by a variety of synthetic procedures. Representative synthetic procedures are shown in, but not limited to, Schemes 1-19. The variables $R^1$, $R^{II1}$, $R^{II1'}$, $R^{III1}$, $R^2$, $R^3$, $R^{II3}$, $R^{II3'}$, $R^{III3}$, $R^4$, $R^5$, $R^{II5}$, $R^{III5}$, $R^6$, $R^{II6}$, $R^{III6}$, $R^7$, $R^{II7}$, $R^{III7}$, and $R^a$ are defined as detailed herein, e.g., in the Summary.

Scheme 1: Representative scheme for synthesis of exemplary compounds of the disclosure.

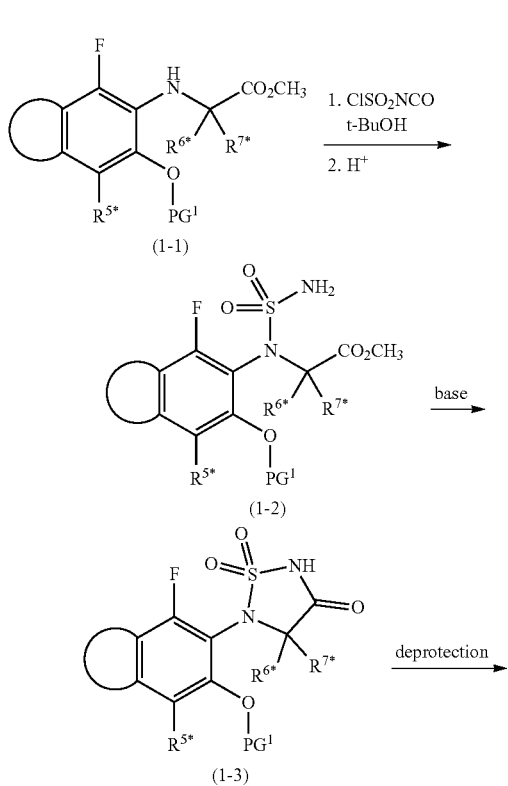

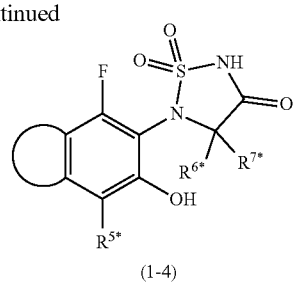

As shown in Scheme 1, compounds of formula (1-4) can be prepared from compounds of formula (1-1), wherein $R^{5*}$ is $R^5$, $R^{II5}$, or $R^{III5}$, $R^{6*}$ is $R^6$, $R^{II6}$, or $R^{III6}$, and $R^{7*}$ is $R^7$, $R^{II7}$, or $R^{III7}$. Compounds of formula (1-1), prepared as described in the Examples and Schemes below, wherein $PG^1$ is a protecting group such as benzyl, can be reacted in a first step with a preformed mixture of chlorosulfonyl isocyanate and tert-butanol in a solvent such as but not limited to cooled (−10-10° C.) dichloromethane in the presence of a tertiary amine base such as triethylamine or diisopropylethylamine. The intermediate can then be treated under acidic conditions such as trifluoroacetic acid in dichloromethane or hydrochloric acid in dioxane to give compounds of formula (1-2). Compounds of formula (1-2) can be reacted with an alkoxide base such as sodium methoxide in a solvent such as tetrahydrofuran at or near ambient temperature to give compounds of formula (1-3). The protecting group, $PG^1$, of compounds of formula (1-3) can be removed to give compounds of formula (1-4). When $PG^1$ is a benzyl group, the deprotection can be accomplished by catalytic hydrogenation. Compounds of formula (1-4) are representative of compounds of formula (I), formula (II), and formula (III).

Scheme 2: Representative scheme for synthesis of exemplary compounds of the disclosure.

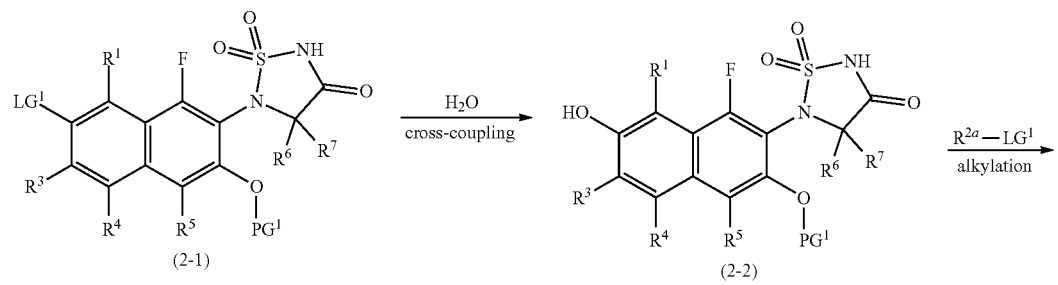

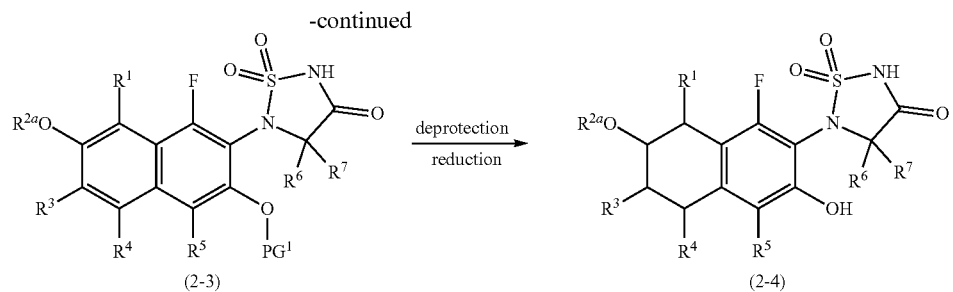

(2-3)  (2-4)

-continued deprotection / reduction deprotection ↓  ↓ reduction

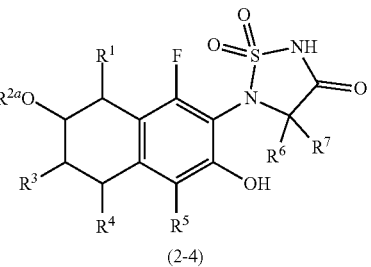

(2-5)

As shown in Scheme 2, compounds of formula (2-4) can be prepared from compounds of formula (2-1), wherein $LG^1$ is a leaving group such as chlorine, bromine, iodine or a sulfonate and $PG^1$ is a protecting group such as but not limited to benzyl. Compounds of formula (2-1) can be cross-coupled with water under palladium-catalyzed cross-coupling conditions including a catalyst or precatalyst, a base such as cesium carbonate, and a heated solvent mixture such as N,N-dimethylformamide and water to give compounds of formula (2-2). Compounds of formula (2-2) can be alkylated with compounds of formula $R^{2a}$-$LG^1$, wherein $R^{2a}$ is an optionally substituted $C_{1-6}$alkyl, $C_{3-6}$cycloalkyl $C_{1-6}$alkylene, or (3-6-membered heterocyclyl)$C_{1-6}$alkylene and $LG^1$ is a leaving group such as chlorine, bromine, iodine or a sulfonate in the presence of a base such as cesium carbonate and a solvent such as N,N-dimethylformamide to give compounds of formula (2-3). Compounds of formula (2-3) can be transformed to compounds of formula (2-4) using catalytic hydrogenation (130-150 psi) over 30-50 hours in a solvent such as 2,2,2-trifluoroethanol to remove both the protecting group, $PG^1$, and reduce the aromatic ring. Alternatively, compounds of formula (2-3) can be deprotected using methodologies known to one of skill in the art to give compounds of formula (2-5). When $PG^1$ is benzyl, treatment of compounds of formula (2-3) with boron trichloride in the presence of pentamethylbenzene in cold dichloromethane gives compounds of formula (2-5). Compounds of formula (2-5) can then be converted under catalytic hydrogenation conditions in acetic acid to compounds of formula (2-4). Compounds of formula (2-4) are representative of compounds of formula (I).

Scheme 3: Representative scheme for synthesis of exemplary compounds of the disclosure.

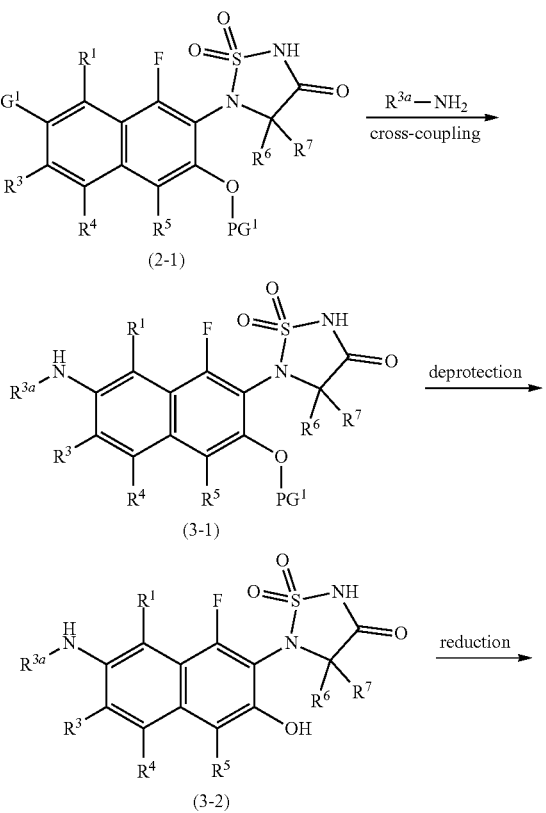

(2-1)

$R^{3a}$—$NH_2$
cross-coupling →

(3-1)

deprotection →

(3-2)

reduction →

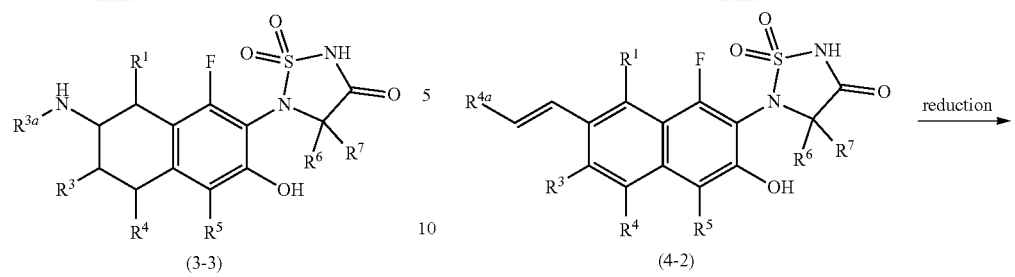

(3-3)

(4-2)

As shown in Scheme 3, compounds of formula (3-3) can be prepared from compounds of formula (2-1), wherein $LG^1$ is a leaving group such as chlorine, bromine, iodine or a sulfonate and $PG^1$ is a protecting group such as but not limited to benzyl. Compounds of formula (2-1) can be cross-coupled with amines of formula $R^{3a}$—$NH_2$, wherein $R^{3a}$ is an optionally substituted $C_{1-6}$alkyl, optionally substituted $C_{1-6}$cycloalkyl$C_{1-6}$alkylene, optionally substituted 4-6-membered heterocyclyl, optionally substituted (4-6-membered heterocyclyl)$C_{1-6}$alkylene, optionally substituted (5-6-membered heteroaryl)$C_{1-6}$alkylene or optionally substituted phenyl-$C_{1-6}$alkylene under palladium-catalyzed cross-coupling conditions including a catalyst or precatalyst, a ligand a base such as cesium carbonate, and a heated solvent such as tert-amyl alcohol to give compounds of formula (3-1). Compounds of formula (3-1) can be deprotected as described in Scheme 2 to give compounds of formula (3-2). Compounds of formula (3-2) can be reduced to compounds of formula (3-3) using catalytic hydrogenation conditions in acetic acid or a mixture of methanol and acetic acid. Compounds of formula (3-3) are representative of compounds of formula (I).

Scheme 4: Representative scheme for synthesis of exemplary compounds of the disclosure.

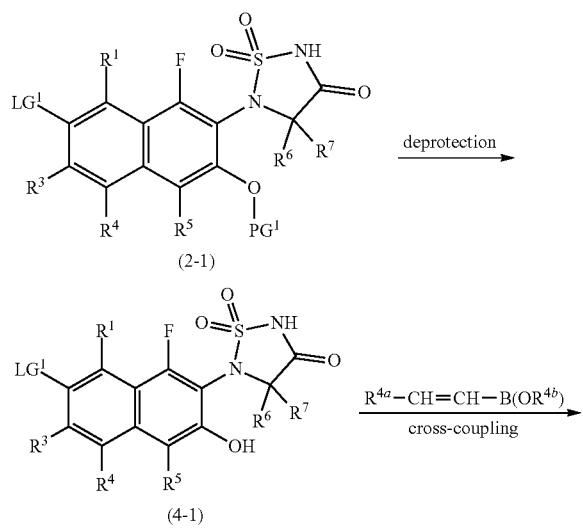

(4-3)

As shown in Scheme 4, compounds of formula (4-3) can be prepared from compounds of formula (2-1), wherein $LG^1$ is a leaving group such as chlorine, bromine, iodine or a sulfonate and $PG^1$ is a protecting group such as but not limited to benzyl. Compounds of formula (2-1) can be deprotected using methodologies known to one of skill in the art to give compounds of formula (4-1). When $PG^1$ is benzyl, treatment of compounds of formula (2-1) with boron trichloride in the presence of pentamethylbenzene in cold dichloromethane gives compounds of formula (4-1). Compounds of formula (4-1) can be cross-coupled with $R^{4a}$—CH=CH—$B(OR^{4b})_2$, wherein —$B(OR^{4b})_2$ represents a boronic acid or boronate and $R^{4a}$ is an optionally substituted $C_{3-6}$cycloalkyl and optionally substituted 4-6-membered heterocyclyl, for example under Suzuki reaction conditions to give compounds of formula (4-2). Reduction of compounds of formula (4-2) under catalytic hydrogenation conditions in a solvent such as but not limited to 2,2,2-trifluoroethanol gives compounds of formula (4-3). Compounds of formula (4-3) are representative of compounds of formula (I).

Scheme 5: Representative scheme for synthesis of exemplary compounds of the disclosure.

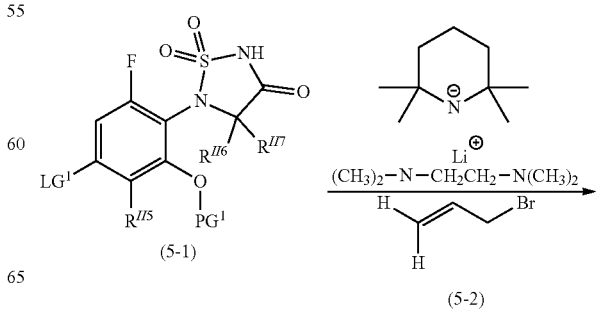

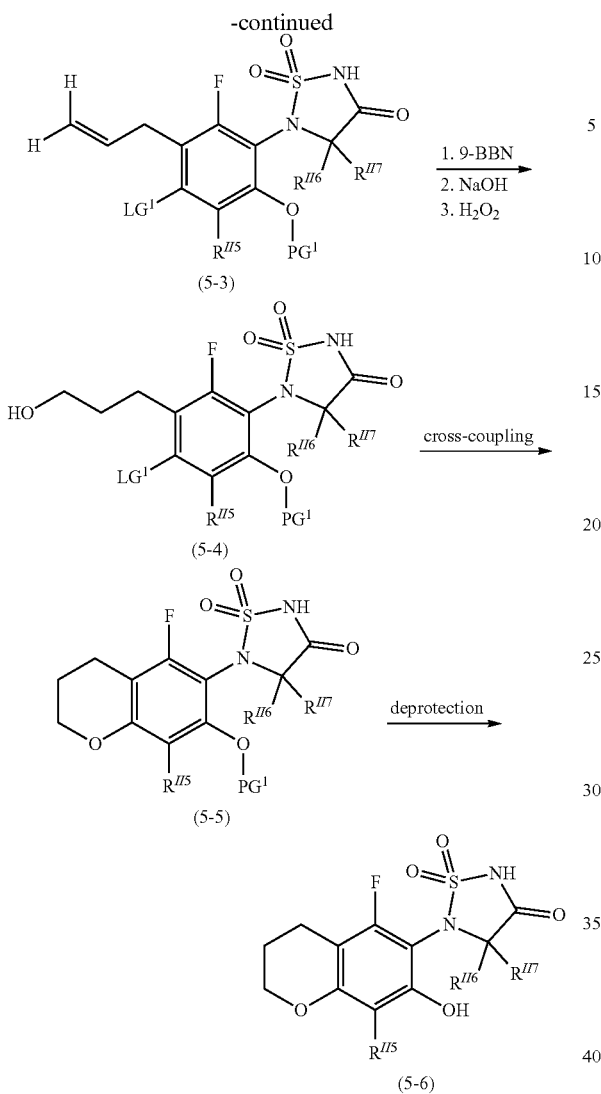

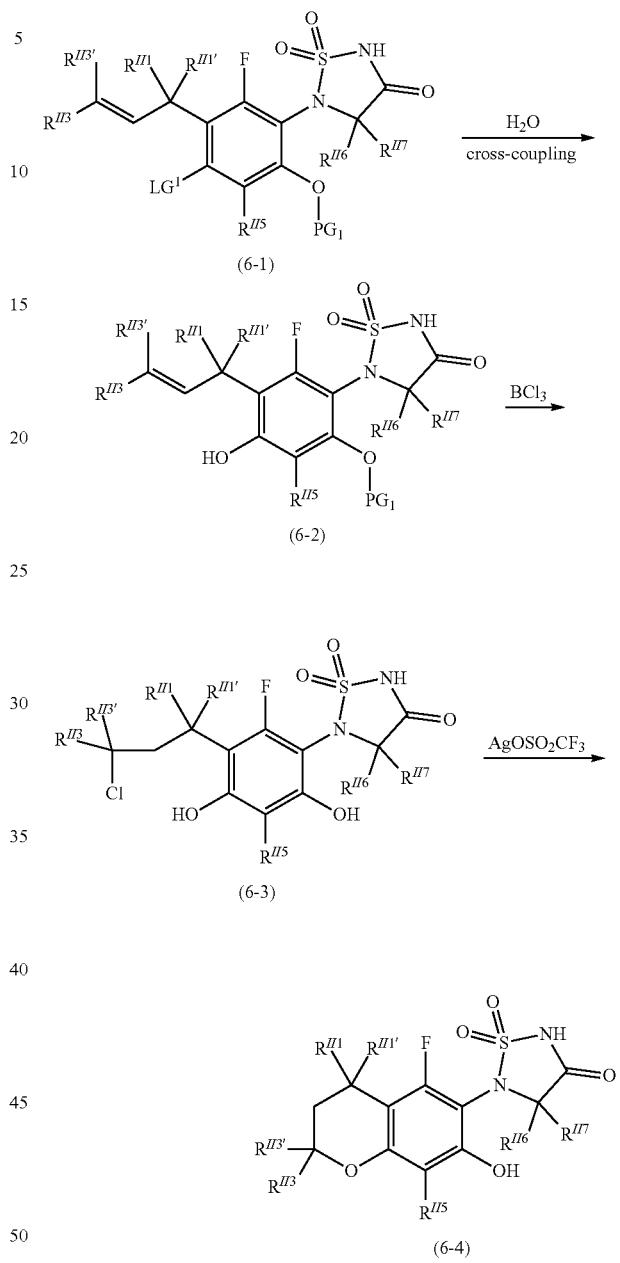

Scheme 6: Representative scheme for synthesis of exemplary compounds of the disclosure.

As shown in Scheme 5, compounds of formula (5-6) can be prepared from compounds of formula (5-1), wherein $LG^1$ is a leaving group such as chlorine, bromine, iodine or a sulfonate and $PG^1$ is a protecting group such as but not limited to benzyl. Compounds of formula (5-1) can be reacted with a base such as lithium 2,2,6,6-tetramethylpiperidine-1-ide in the presence of N,N,N',N'-tetramethylethylenediamine in a solvent such as cold tetrahydrofuran and then treated with allyl bromide, (5-2), to give compounds of formula (5-3). Compounds of formula (5-3) can be treated in a three-step hydroboration-oxidation sequence to give compounds of formula (5-4). Then, compounds of formula (5-4) can be reacted under appropriate palladium-catalyzed cross-coupling reaction conditions to give chromanes of formula (5-5). Compounds of formula (5-5) can be deprotected using methodologies known to one of skill in the art to give compounds of formula (5-6). When $PG^1$ is benzyl, treatment of compounds of formula (5-5) with boron trichloride in the presence of pentamethylbenzene in cold dichloromethane gives compounds of formula (5-6). Compounds of formula (5-6) are representative of compounds of formula (II).

As shown in Scheme 6, compounds of formula (6-4) can be prepared from compounds of formula (6-1), wherein $LG^1$ is a leaving group such as chlorine, bromine, iodine or a sulfonate and $PG^1$ is a protecting group such as but not limited to benzyl. Compounds of formula (6-1), prepared analogously to compounds of formula (5-3) in Scheme 5, can be cross-coupled with water to give compounds of formula (6-2). Compounds of formula (6-2) can be reacted with boron trichloride in the presence of pentamethylbenzene in cold dichloromethane gives compounds of formula (6-3). Compounds of formula (6-3) can be cyclized in the presence of a silver salt such as silver trifluoromethanesulfonate to give compounds of formula (6-4). Compounds of formula (6-4) are representative of compounds of formula (II).

Scheme 7: Representative scheme for synthesis of exemplary compounds of the disclosure.

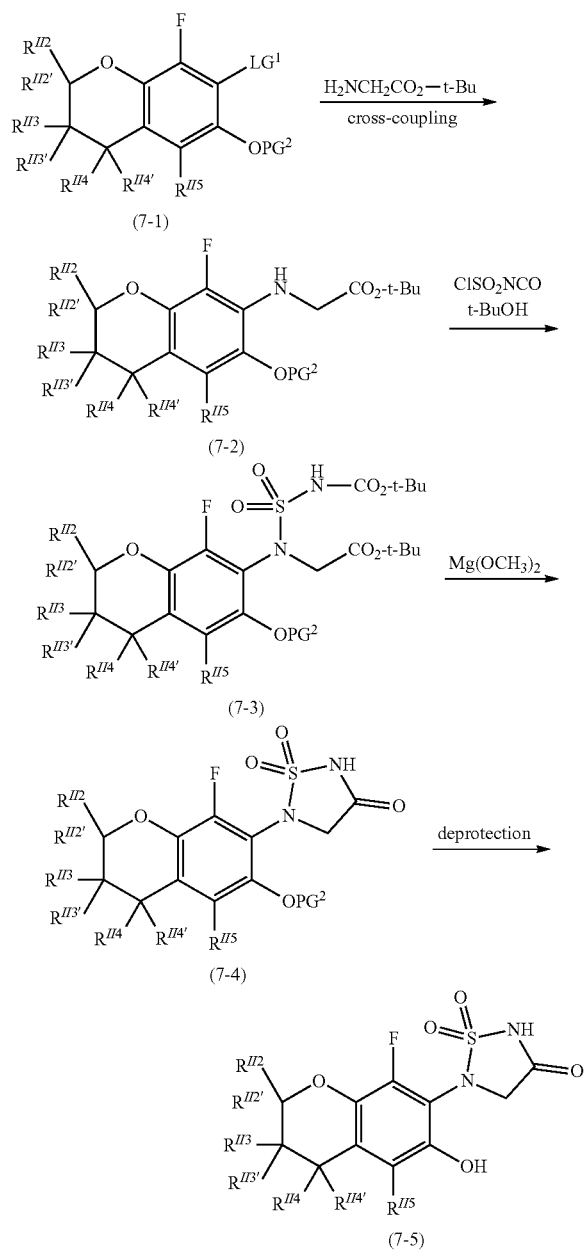

Scheme 8: Representative scheme for synthesis of exemplary compounds of the disclosure.

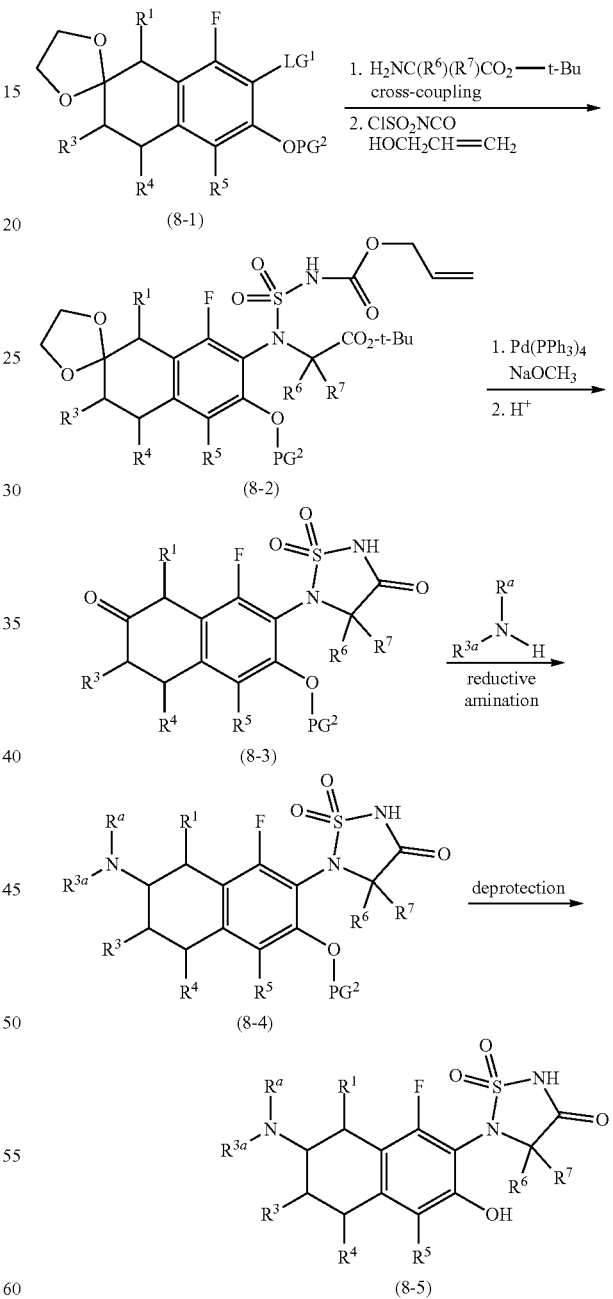

compounds of formula (7-5) by removal of the protecting group, $PG^2$, under conditions known to one of skill in the art and dependent upon the particular protecting group. When $PG^2$ is (methoxyethoxy)methyl, treatment with an acid such as 4 M HCl in dioxane gives compounds of formula (7-5). Compounds of formula (7-5) are representative of compounds of formula (II).

As shown in Scheme 7, compounds of formula (7-5) can be prepared from compounds of formula (7-1), wherein $LG^1$ is a leaving group such as chlorine, bromine, iodine or a sulfonate and $PG^2$ is a protecting group such as but not limited to (methoxyethoxy)methyl. Compounds of formula (7-1) can be cross-coupled with $H_2NCH_2CO_2$-t-Bu in the presence of a palladium catalyst, ligand, and base to give compounds of formula (7-2). Compounds of formula (7-2) can then be reacted with a preformed mixture of chlorosulfonyl isocyanate and tert-butanol in a solvent such as but not limited to cooled dichloromethane in the presence of a tertiary amine base such as triethylamine or diisopropylethylamine to give compounds of formula (7-3). Compounds of formula (7-3) can then be reacted with $Mg(OCH_3)_2$ in methanol in a heated solvent such as 2-methyltetrahydrofuran to give the cyclized compounds of formula (7-4). Compounds of formula (7-4) can then be converted to As shown in Scheme 8, compounds of formula (8-5) can be prepared from compounds of formula (8-1), wherein $LG^1$ is a leaving group such as chlorine, bromine, iodine or a sulfonate and $PG^2$ is a protecting group such as but not limited to (methoxyethoxy)methyl. Accordingly, compounds of formula (8-1) can be cross-coupled with amines, $H_2NC(R^6)(R^7)CO_2$-t-Bu, under conditions known to one of skill in the art. Subsequent treatment with a preformed mixture of chlorosulfonyl isocyanate and allyl alcohol in a solvent such as chilled dichloromethane gives compounds of formula (8-2). Treatment of compounds of formula (8-2) with tetrakis(triphenylphosphine)palladium(0) in the presence of a base such as sodium methoxide can give the corresponding $1\lambda^6,2,5$-thiadiazolidine-1,1,3-trione moiety. Then the dioxolane moiety can be removed by treatment under acidic conditions such as but not limited to formic acid to give compounds of formula (8-3). Compounds of formula (8-3) can be reductively aminated with amines, $(R^{3a})(R^a)$ NH wherein $R^{3a}$ is as described in Scheme 3, to give compounds of formula (8-4). Alternatively, $R^{3a}$ and $R^a$ and the nitrogen to which they are attached may be joined to form a 4-8 membered heterocycle which can be used to reductively aminate the compounds of formula (8-3). The protecting group, $PG^2$, can be removed known to one of skill in the art and dependent upon the particular protecting group to give compounds of formula (8-5). When $PG^2$ is (methoxyethoxy)methyl, treatment with an acid such as 4 M HCl in dioxane gives compounds of formula (8-5). Compounds of formula (8-5) are representative of compounds of formula (I).

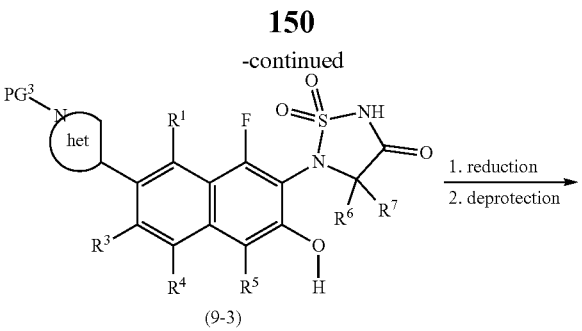

(9-3)

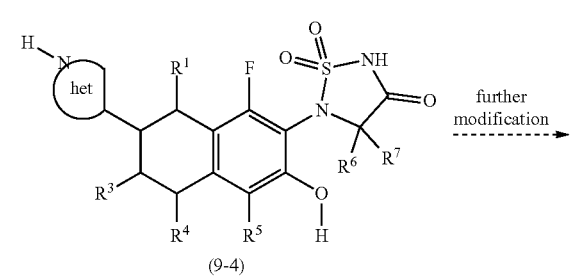

(9-4)

As shown in Scheme 9, compounds of formula (9-4) can be prepared from compounds of formula (2-1), wherein $LG^1$ is a leaving group such as chlorine, bromine, iodine or a sulfonate and $PG^1$ is a protecting group such as but not limited to benzyl. Compounds of formula (2-1) can be cross-coupled under palladium-catalyzed reaction conditions such as Suzuki reaction conditions with compounds of formula (9-1), wherein $—B(OR^{4b})_2$ represents a boronic acid or boronate, $PG^3$ is an amine protecting group such as tert-butoxycarbonyl, and "het" is a heterocyclyl containing a ring nitrogen, to give compounds of formula (9-2). Treatment under catalytic hydrogenation conditions saturates the heterocyclyl ring and removes the protecting group, $PG^1$, to give compounds of formula (9-3). Compounds of formula (9-3) can be reduced further with catalytic hydrogenation conditions, and the protecting group, $PG^3$, can be removed in a second step to give compounds of formula (9-4). When $PG^3$ is tert-butoxycarbonyl, treatment with an acid such as trifluoroacetic acid in dichloromethane is suitable for protecting group removal. Compounds of formula (9-4) are representative of compounds of formula (I). Compounds of formula (9-4) can be further modified such as by alkylation or acylation to give additional compounds of formula (I).

Scheme 9: Representative scheme for synthesis of exemplary compounds of the disclosure.

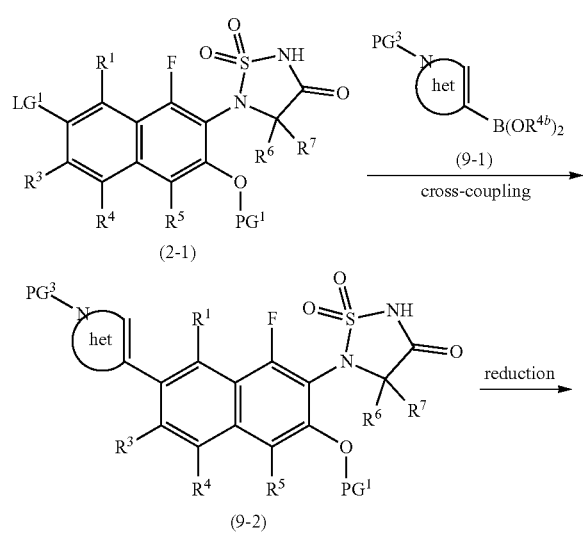

Scheme 10: Representative scheme for synthesis of exemplary compounds of the disclosure.

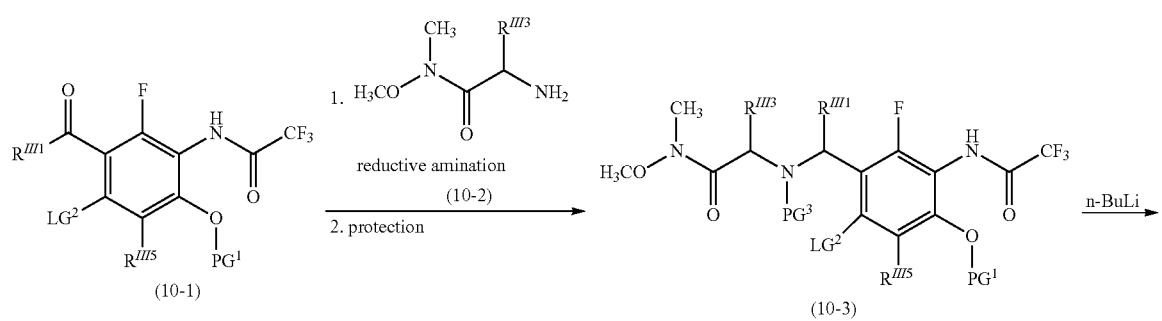

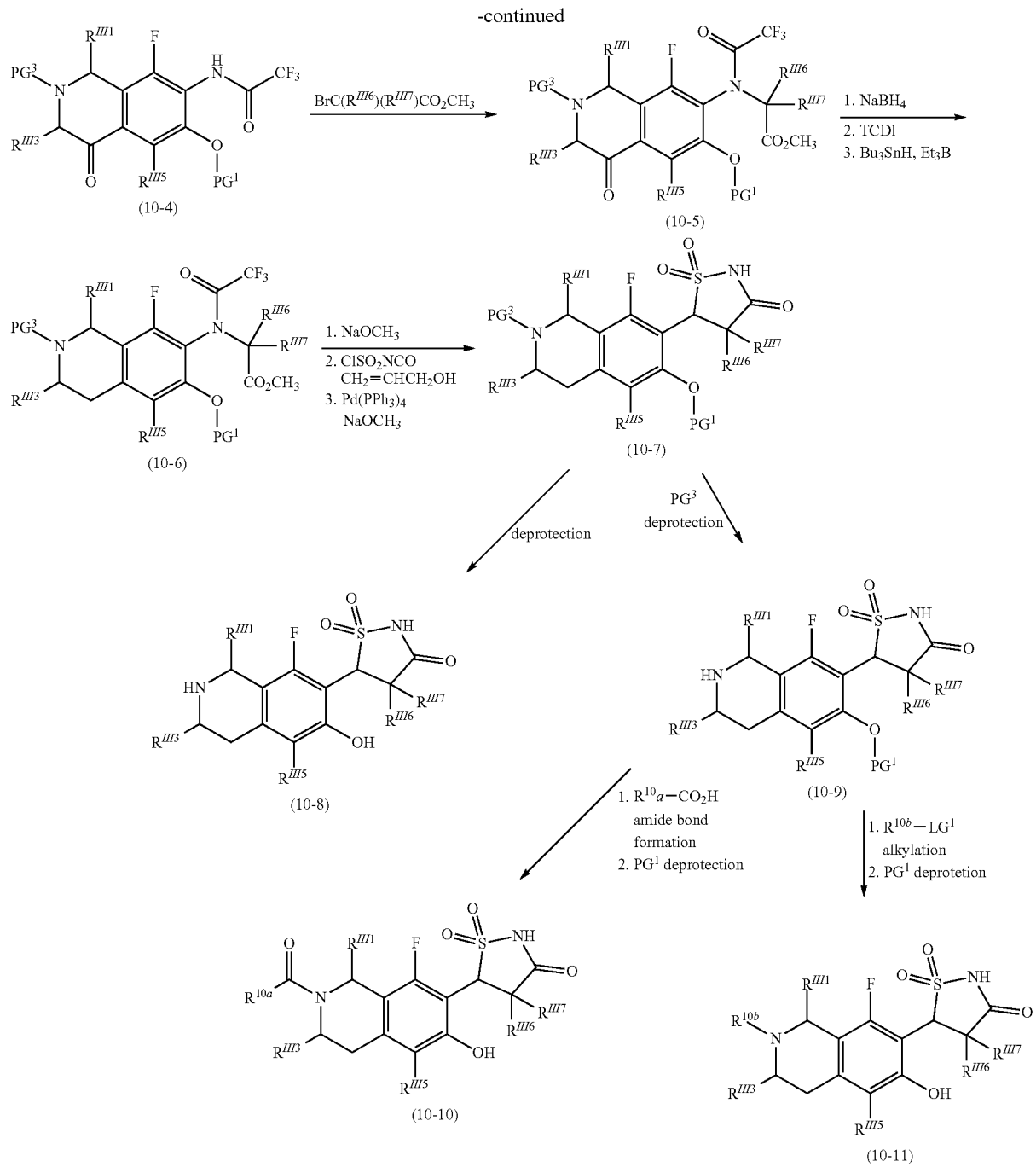

As shown in Scheme 10, compounds of formula (10-8), formula (10-10), and formula (10-11) can be prepared from compounds of formula (10-1), wherein $LG^2$ is a leaving group such as chlorine, bromine, or iodine and $PG^1$ is a protecting group such as but not limited to benzyl. Compounds of formula (10-1) can be reacted with compounds of formula (10-2) under reductive amination conditions. Subsequent protection of the formed amine with a nitrogen protecting group such as but not limited to tert-butoxycarbonyl provides compounds of formula (10-3). Compounds of formula (10-3) can be treated with n-butyllithium resulting in cyclization to give compounds of formula (10-4). The amide nitrogen of compounds of formula (10-4) can be alkylated with a bromoacetate, $BrC(R^{III6})(R^{III7})CO_2CH_3$, in the presence of a base such as but not limited to 1,2,2,6,6-pentamethylpiperidine in a heated solvent such as heated N,N-dimethylformamide to give compounds of formula (10-5). In a three-step process, the carbonyl can be reduced to the corresponding methylene. In the first step, treatment with a reductant such as sodium borohydride provides the corresponding alcohols. The second step is treatment with 1,1'-thiocarbonyldiimidazole (TCDI) in the presence of a base to give the corresponding 1H-imidazole-1-carbothioates. The 1H-imidazole-1-carbothioates can be treated tributyltin hydride and triethylborane in the third step with to give the tetrahydroisoquinolines of formula (10-6). Compounds of formula (10-6) can be treated with sodium methoxide in warmed methanol to remove the trifluoroacetyl moiety. Subsequent treatment with a preformed mixture of chlorosulfonyl isocyanate and allyl alcohol in a solvent such as chilled dichloromethane gives alloc-sulfonylureas. Treatment of the alloc-sulfonylureas with tetrakis(triphenylphosphine)palladium(0) in the presence of a base such as sodium methoxide can give the corresponding $1\lambda^6,2,5$-thiadiazolidine-1,1,3-trione moiety of compounds of formula (10-7). Simultaneous removal of protecting groups $PG^1$ and $PG^3$ give compounds of formula (10-8). When $PG^1$ is benzyl and $PG^3$ is tert-butoxycarbonyl, treatment with boron trichloride in the presence of 1,2,3,4,5-pentamethylbenzene in cold dichloromethane removes both the benzyl and tert-butoxycarbonyl groups. Alternatively, the protecting group, $PG^3$, can be selectively removed from compounds of formula (10-7) to give compounds of formula (10-9). When $PG^3$ is tert-butoxycarbonyl, treatment with an acid such as trifluoroacetic acid in dichloromethane gives compounds of formula (10-9). Compounds of formula (10-9) can be treated with carboxylic acids of formula $R^{10a}$—$CO_2H$, wherein $R^{10a}$ is optionally substituted $C_{1-6}$alkyl, under amide bond forming conditions, and then have $PG^1$ subsequently removed to give compounds of formula (10-10). One set of amide bond forming conditions involves treatment with 2-(1H-benzotriazole-1-yl)-1,1,3,3-tetramethylaminium tetrafluoroborate (TBTU) in the presence of a tertiary amine base such as diisopropylethylamine in a solvent such as dichloromethane. When $PG^1$ is benzyl, treatment with boron trichloride in the presence of 1,2,3,4,5-pentamethylbenzene in cold dichloromethane removes the benzyl protecting group. Compounds of formula (10-9) can also be alkylated with compounds of formula $R^{10b}$-$LG^1$, wherein $R^{10b}$ is optionally substituted $C_{1-6}$alkyl, optionally substituted —$C_{1-6}$alkylene-$C_{3-6}$cycloalkyl, optionally substituted $C_{1-6}$alkylene-phenyl, optionally substituted $C_{1-6}$alkylene-(4-6-membered)heterocyclyl and optionally substituted $C_{1-6}$alkylene-(5-6-membered)heteroaryl and $LG^1$ is a leaving group such as chlorine, bromine, iodine or a sulfonate, and then deprotected to give compounds of formula (10-11). One set of alkylation conditions involves treatment of compounds of formula (10-9) with compounds of formula $R^{10b}$-$LG^1$ in the presence of a base such as cesium carbonate in warmed acetonitrile. Then when $PG^1$ is benzyl, treatment with boron trichloride in the presence of 1,2,3,4,5-pentamethylbenzene in cold dichloromethane removes the benzyl protecting group and provides compounds of formula (10-11). Compounds of formula (10-8), formula (10-10), and formula (10-11) are representative of compounds of formula (III).

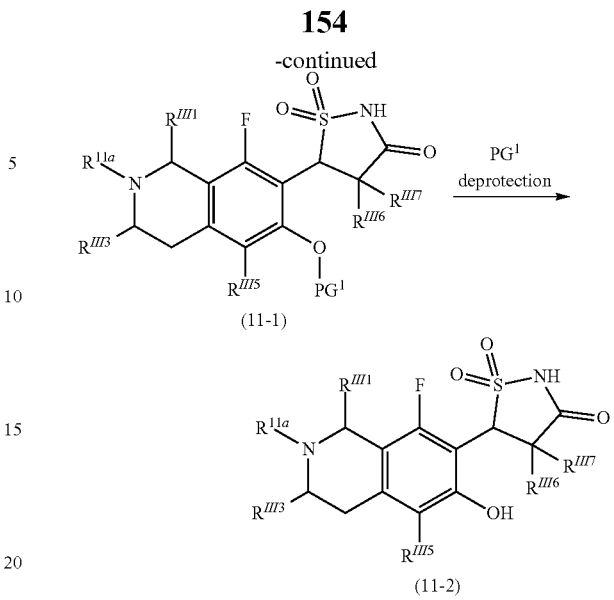

As shown in Scheme 11, compounds of formula (11-2) can be prepared from compounds of formula (10-9), wherein $PG^1$ is a protecting group such as but not limited to benzyl. Compounds of formula (10-9) can be reacted with compounds of formula $R^{11a}$=O under reductive amination conditions to give compounds of formula (11-1). $R^{11a}$ is optionally substituted $C_{1-6}$alkyl, $C_{2-6}$alkenyl, $C_{2-6}$alkynyl, $C_{3-6}$cycloalkyl, —$C_{1-6}$alkylene-$C_{3-7}$cycloalkyl, —$C_{1-6}$alkylene-phenyl, —$C_{1-6}$alkylene-4-6 membered heterocyclyl, —$C_{1-6}$alkylene-5-6 membered heteroaryl, 4-8 membered heterocycle, -(4-7 membered-heterocycle)-$C_{1-6}$alkylene-5-6 membered heteroaryl. $R^{11a}$ may be optionally substituted as described for $R^{III2}$. $R^{11a}$=O is the corresponding aldehyde or corresponding ketone of $C_{1-6}$alkyl, $C_{2-6}$alkenyl, $C_{2-6}$alkynyl, $C_{3-6}$cycloalkyl, H—$C_{1-6}$alkylene-$C_{3-7}$cycloalkyl, H—$C_{1-6}$alkylene-phenyl, H—$C_{1-6}$alkylene-4-6 membered heterocyclyl, H—$C_{1-6}$alkylene-5-6 membered heteroaryl, 4-8 membered heterocycle, H-(4-7 membered-heterocycle)-$C_{1-6}$alkylene-5-6 membered heteroaryl. Compounds of formula (11-1) can be deprotected using methods known to one of skill in the art and dependent upon the nature of $PG^1$ to give compounds of formula (11-1). When $PG^1$ is benzyl, treatment with boron trichloride in the presence of 1,2,3,4,5-pentamethylbenzene in cold dichloromethane removes the benzyl protecting group and provides compounds of formula (11-2). Alternatively, when $PG^1$ is benzyl, treatment under catalytic or transfer hydrogenation conditions removes the benzyl protecting group providing compounds of formula (11-2). Compounds of formula (11-1) and compounds of formula (11-2) can be further modified using methodologies known to one of skill in the art. Compounds of formula (11-2) are representative of compounds of formula (III).

Scheme 11: Representative scheme for synthesis of exemplary compounds of the disclosure.

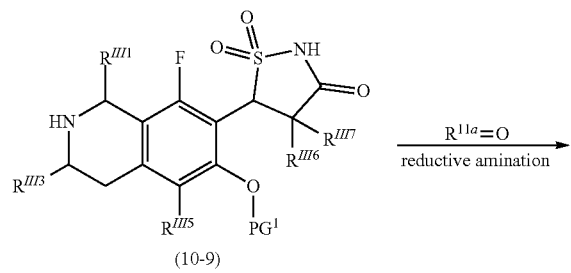

Scheme 12: Representative scheme for synthesis of exemplary compounds of the disclosure.

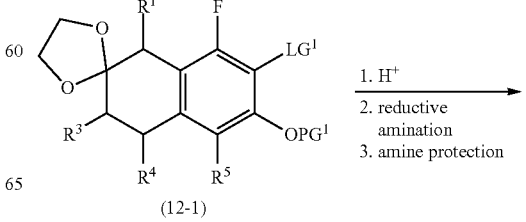

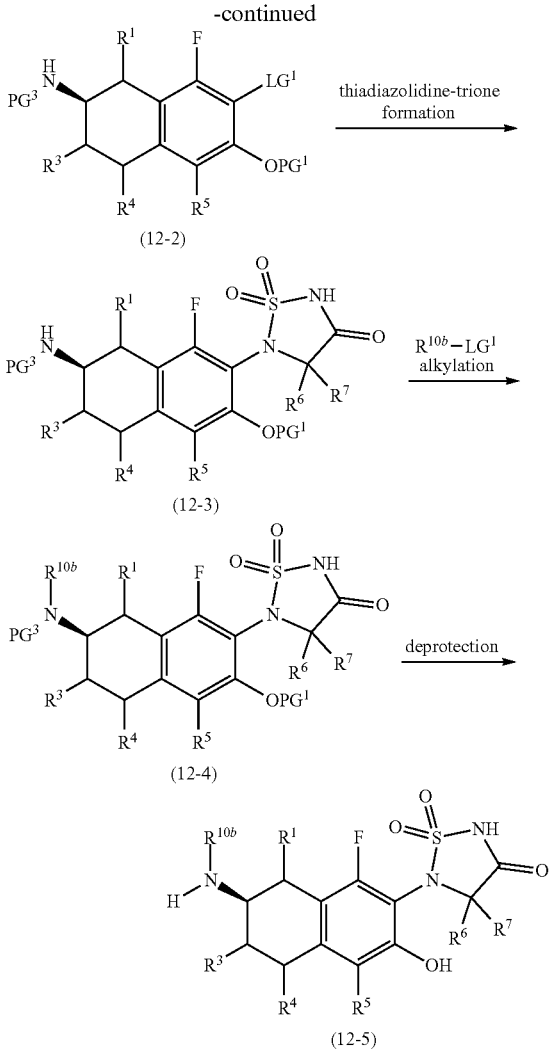

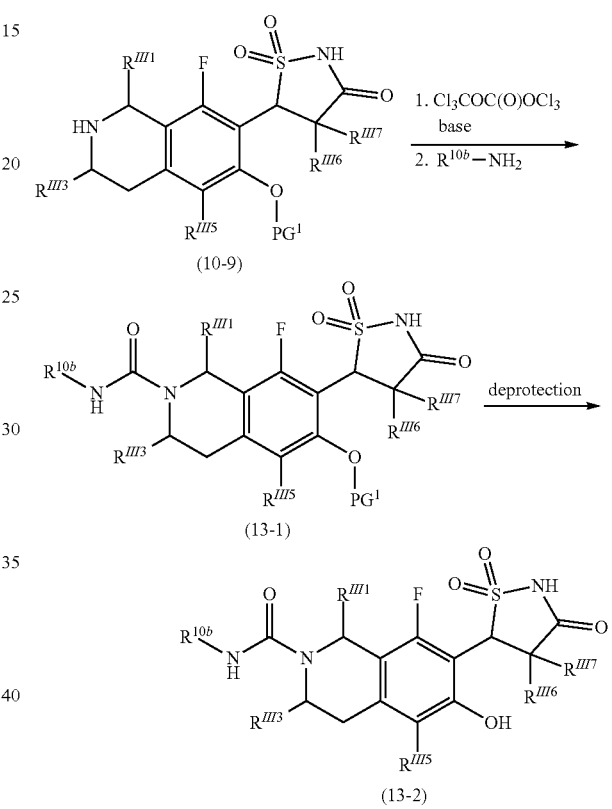

Scheme 13: Representative scheme for synthesis of exemplary compounds of the disclosure.

formula (12-4). Dependent on $PG^1$ and $PG^3$, the protecting groups of compounds of formula (12-4) can be removed stepwise or simultaneously to give compounds of formula (12-5). For example, when $PG^1$ is benzyl and $PG^3$ is benzyloxycarbonyl, treatment with boron trichloride in the presence of pentamethylbenzene in cold dichloromethane simultaneously removes both protecting groups. Compounds of formula (12-5) are representative of compounds of formula (I).

As shown in Scheme 12, compounds of formula (12-5) can be prepared from compounds of formula (12-1), wherein $R^{10b}$ is optionally substituted $C_{1-6}$alkyl, optionally substituted —$C_{1-6}$alkylene-$C_{3-6}$cycloalkyl, optionally substituted $C_{1-6}$alkylene-phenyl, optionally substituted $C_{1-6}$alkylene-(4-6-membered)heterocyclyl and optionally substituted $C_{1-6}$alkylene-(5-6-membered)heteroaryl. Compounds of formula (12-1), wherein $PG^1$ is a protecting group such as benzyl, can be converted to compound of formula (12-2) in a three-step process. The dioxolane of compounds of formula (12-1) can be removed under acidic conditions known to one of skill in the art. A reductive amination can introduce an amine moiety, —$NH_2$. The reductive amination can be done under conditions known to one of skill in the art. One stereoselective set of conditions include treatment with monobasic sodium phosphate, hydrochloric acid, sec-butylamine, pyridoxal-5-phosphate, and Codexis® ATA-025. The resulting amine can be protected as a benzyloxycarbonyl by treatment with benzyl chloroformate in the presence of a base forming a benzyloxycarbonyl, $PG^3$, protecting group. Compounds of formula (12-2) can then be transformed to compounds of formula (12-3) using the thiadiazolidine-trione forming sequence described in Scheme 8. Compounds of formula (12-2) can be alkylated with $R^{10b}$-$LG^1$ as described in Scheme 10 to give compounds of As shown in Scheme 13, compounds of formula (13-2) can be prepared from compounds of formula (10-9). Compounds of formula (10-9) can be reacted with triphosgene in the presence of a base such as but not limited to a tertiary amine. Subsequent treatment with an amine, $R^{10b}$—$NH_2$, wherein $R^{10b}$ is optionally substituted $C_{1-6}$alkyl, optionally substituted —$C_{1-6}$alkylene-$C_{3-6}$cycloalkyl, optionally substituted $C_{1-6}$alkylene-phenyl, optionally substituted $C_{1-6}$alkylene-(4-6-membered)heterocyclyl and optionally substituted $C_{1-6}$alkylene-(5-6-membered)heteroaryl, provides compounds of formula (13-1). Removal of the protecting group, $PG^1$, is accomplished using methodologies known to one of skill in the art and dependent upon $PG^1$. When $PG^1$ is benzyl, treatment with boron trichloride in the presence of 1,2,3,4,5-pentamethylbenzene in cold dichloromethane removes the benzyl protecting group and provides compounds of formula (13-2). Compounds of formula (13-2) are representative of compounds of formula (III).

Scheme 14: Representative scheme for synthesis of exemplary compounds of the disclosure.

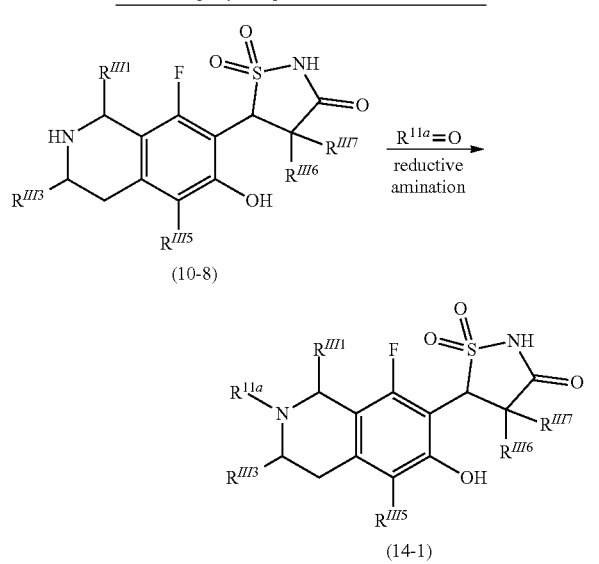

(10-8)

(14-1)

As shown in Scheme 14, compounds of formula (14-1) can be prepared from compounds of formula (10-8). Compounds of formula (10-8) can be reacted with compounds of formula $R^{11a}$=O under reductive amination conditions to give compounds of formula (14-1). $R^{11a}$ is optionally substituted $C_{1-6}$alkyl, $C_{2-6}$alkenyl, $C_{2-6}$alkynyl, $C_{3-6}$cycloalkyl, —$C_{1-6}$alkylene-$C_{3-7}$cycloalkyl, —$C_{1-6}$alkylene-phenyl, —$C_{1-6}$alkylene-4-6 membered heterocyclyl, —$C_{1-6}$alkylene-5-6 membered heteroaryl, 4-8 membered heterocycle, -(4-7 membered-heterocycle)-$C_{1-6}$alkylene-5-6 membered heteroaryl. $R^{11a}$ may be optionally substituted as described for $R^{III2}$. $R^{11a}$=O is the corresponding aldehyde or corresponding ketone of $C_{1-6}$alkyl, $C_{2-6}$alkenyl, $C_{2-6}$alkynyl, $C_{3-6}$cycloalkyl, H—$C_{1-6}$alkylene-$C_{3-7}$cycloalkyl, H—$C_{1-6}$alkylene-phenyl, H—$C_{1-6}$alkylene-4-6 membered heterocyclyl, H—$C_{1-6}$alkylene-5-6 membered heteroaryl, 4-8 membered heterocycle, H-(4-7 membered-heterocycle)-$C_{1-6}$alkylene-5-6 membered heteroaryl. The reductive amination can be conducted with conventional reagents such as sodium cyanoborohydride or sodium borohydride or the solid supported equivalents. Compounds of formula (14-1) can be further modified using methodologies known to one of skill in the art. Compounds of formula (14-1) are representative of compounds of formula (III).

Scheme 15: Representative scheme for synthesis of exemplary compounds of the disclosure.

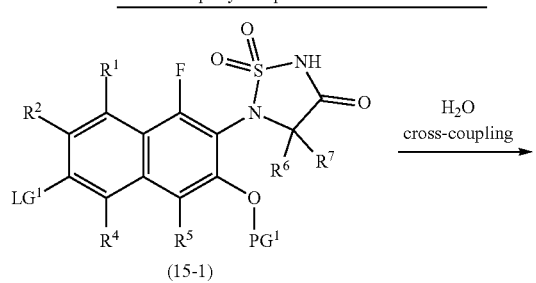

(15-1)

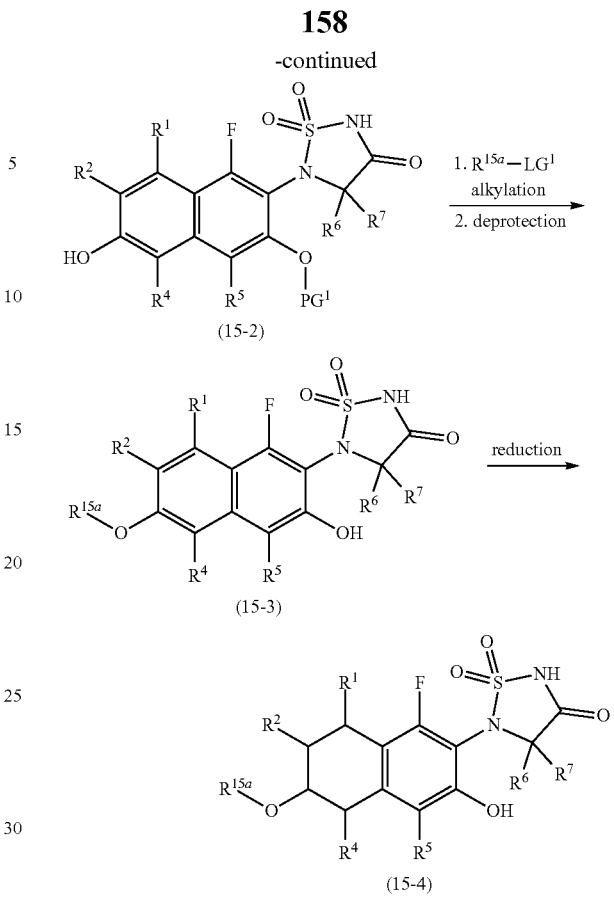

(15-2)

(15-3)

(15-4)

As shown in Scheme 15, compounds of formula (15-4) can be prepared from compounds of formula (15-1). Compounds of formula (15-1) can cross-coupled with water under palladium-catalyzed cross-coupling conditions including a catalyst or precatalyst, an optional ligand, a base such as cesium carbonate, and a heated solvent such as N,N-dimethylacetamide to give compounds of formula (15-2). Compounds of formula (15-2) can be alkylated with compounds of formula $R^{15a}$-$LG^1$, wherein $R^{15a}$ is optionally substituted $C_{1-6}$alkyl, optionally substituted —$C_{1-6}$alkylene-$C_{3-6}$cycloalkyl, optionally substituted $C_{1-6}$alkylene-phenyl, optionally substituted $C_{1-6}$alkylene-(4-6-membered)heterocyclyl and optionally substituted $C_{1-6}$alkylene-(5-6-membered)heteroaryl and $LG^1$ is a leaving group such as chlorine, bromine, iodine or a sulfonate, and then deprotected to give compounds of formula (15-3). One set of alkylation conditions involves treatment of compounds of formula (15-2) with compounds of formula $R^{15a}$-$LG^1$ in the presence of a base such as cesium carbonate in N,N-dimethylformamide. Then when $PG^1$ is benzyl, treatment with ammonium formate in ethanol in the presence of 10% palladium on carbon removes the benzyl protecting group and provides compounds of formula (15-3). Compounds of formula (15-3) can be reduced with hydrogen (approximately 120 psi) in the presence of 10% palladium on carbon in a solvent such as trifluoroethanol to give compounds of formula (15-4). Compounds of formula (15-4) are representative of compounds of formula (I).

Scheme 16: Representative scheme for synthesis of exemplary compounds of the disclosure.

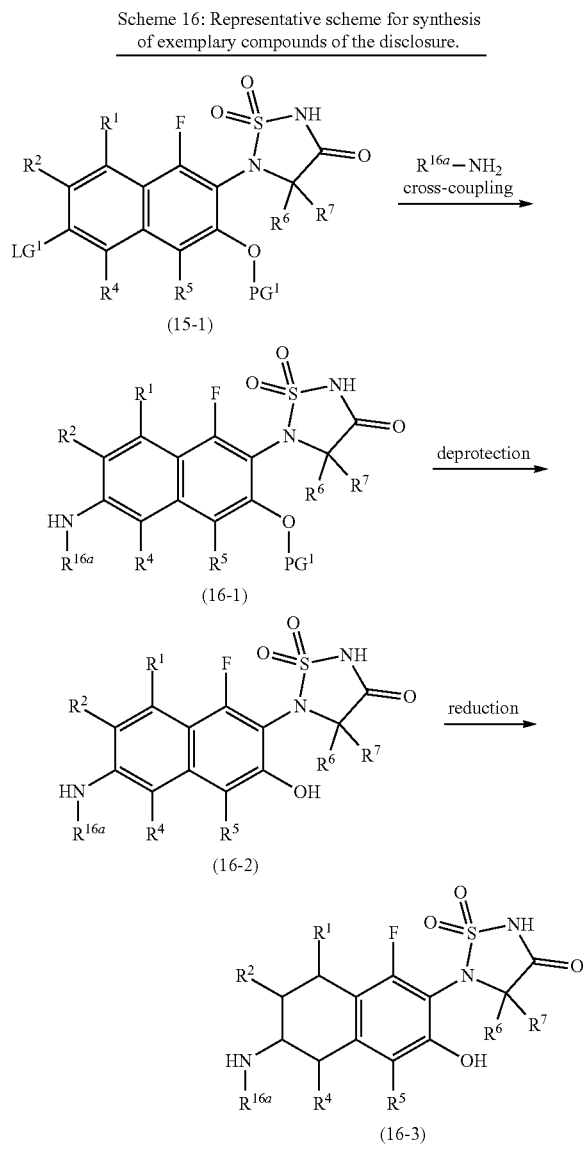

Scheme 17: Representative scheme for synthesis of exemplary compounds of the disclosure.

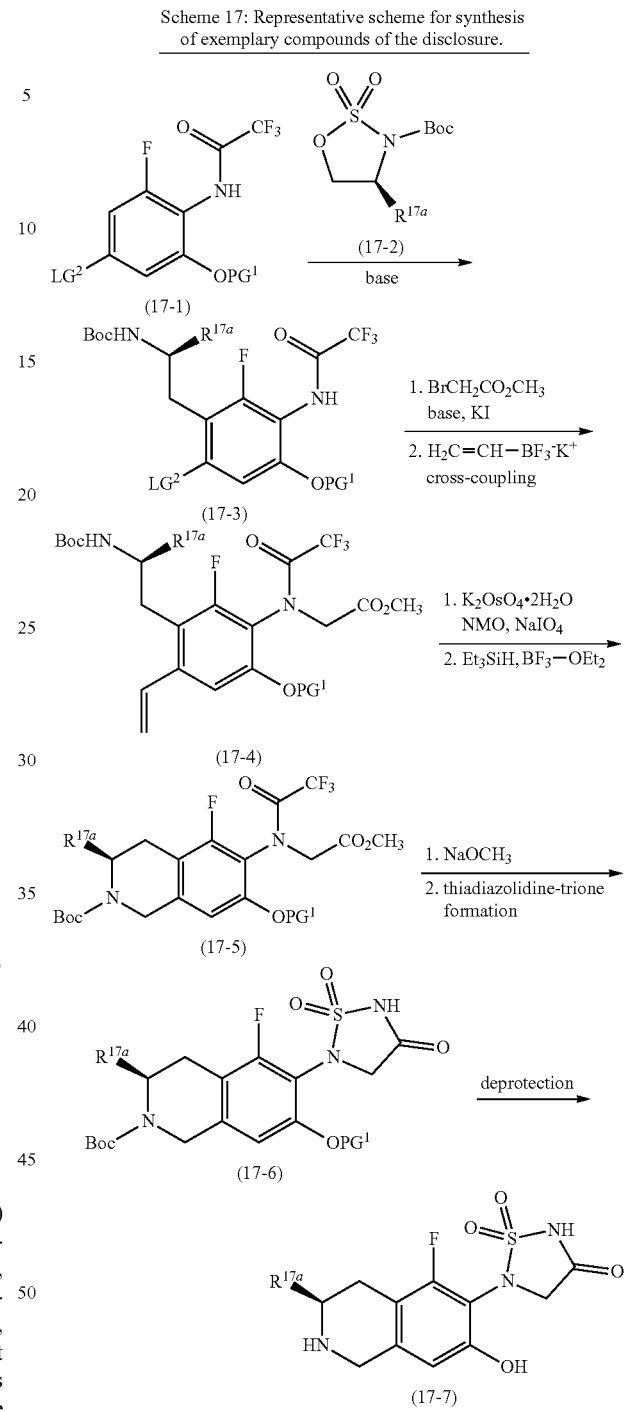

As shown in Scheme 16, compounds of formula (16-3) can be prepared from compounds of formula (15-1). Compounds of formula (15-1) can cross-coupled with amines, $R^{16a}$—$NH_2$, under palladium-catalyzed cross-coupling conditions including a catalyst or precatalyst, an optional ligand, a base such as cesium carbonate, and a heated solvent mixture such as N,N-dimethylacetamide to give compounds of formula (16-1). The protecting group, $PG^1$, can be removed under conditions known to one of skill in the art and dependent on the particular protecting group used. When $PG^1$ is benzyl, treatment with boron trichloride in the presence of pentamethylbenzene in cold dichloromethane or alternatively treatment under transfer hydrogenation conditions removes the protecting group giving compounds of formula (16-2). Compounds of formula (16-2) can be reduced with hydrogen (approximately 120 psi) in the presence of 10% palladium on carbon in a solvent such as trifluoroethanol to give compounds of formula (16-3). Compounds of formula (16-3) are representative of compounds of formula (I).

As shown in Scheme 17, compounds of formula (17-7) can be prepared from compounds of formula (17-1). Compounds of formula (17-1), wherein $LG^2$ is a leaving group such as chloro, bromo or iodo and $PG^1$ is a protecting group such as benzyl, can be treated with a base such lithium diisopropylamide and then with an oxathiazolidine 2,2-dioxide of formula (17-2), wherein Boc is tert-butoxycarbonyl and $R^{17a}$ is optionally substituted alkyl, optionally substituted —$C_{1-6}$alkylene-$C_{3-6}$cycloalkyl, or optionally substituted —$C_{1-6}$alkylene-4-6 membered heterocyclyl, to give compounds of formula (17-3). Compounds of formula (17-3) can be alkylated with methyl bromoacetate in the presence of a base and potassium iodide. Then cross-coupling with potassium vinyltrifluoroborate supplies compounds of formula (17-4). Compounds of formula (17-4) can be oxidized to the corresponding aldehyde with potassium osmate dihydrate in the presence of N-methylmorpholine N-oxide and sodium metaperiodate. The intermediate aldehyde can be cyclized with triethylsilane in the presence boron trifluoride diethyl etherate to give compounds of formula (17-5). The trifluoroacetamide group can be removed from compounds of formula (17-5) by treatment with sodium methoxide. The thiadiazolidine-trione can be formed following the steps described in Scheme 8 giving compounds of formula (17-6). The protecting groups, Boc and $PG^1$, can be removed from compounds of formula (17-6) simultaneously or stepwise dependent on $PG^1$ using conditions known to one of skill in the art to give compounds of formula (17-7). For example, when $PG^1$ is benzyl, transfer hydrogenation will selectively remove $PG^1$. Subsequent exposure to hydrochloric acid in dioxane will remove the tert-butoxycarbonyl protecting group. Compounds of formula (17-7) are representative of compounds of formula (I).

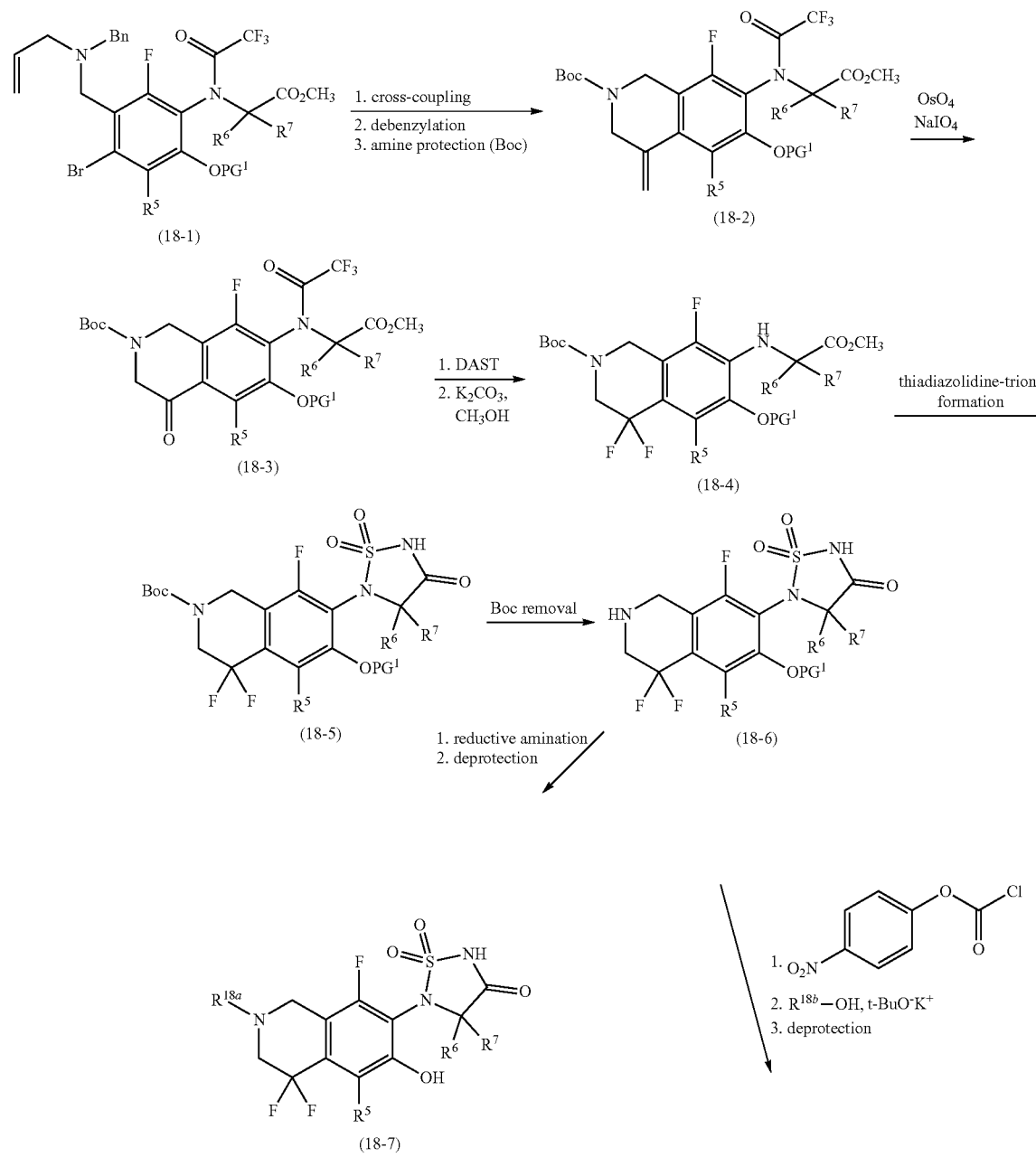

Scheme 18: Representative scheme for synthesis of exemplary compounds of the disclosure.

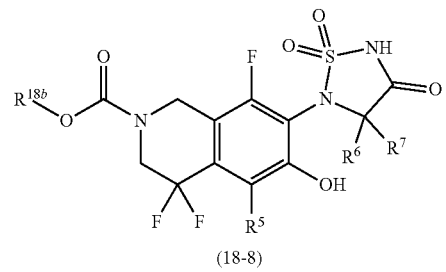

(18-8)

As shown in Scheme 18, compounds of formula (18-7) and compounds of formula (18-8) can be prepared from compounds of formula (18-1). Compounds of formula (18-1), wherein $PG^1$ is a protecting group such as benzyl, can be converted to compounds of formula (18-2) in a three-step process. Treating compounds of formula (18-1) under cross-coupling reaction conditions forms the bicyclic structure. The benzyl group can be selectively removed from the nitrogen of the tetrahydroisoquinoline by treatment with 1-chloroethyl chloroformate and 8-bis(dimethylamino) naphthalene in a solvent such as 1,2-dichloroethane. The exposed amine can be protected as the tert-butoxycarbonyl by treatment with di-tert-butyl dicarbonate in the presence of a base such as sodium bicarbonate in a solvent such as a mixture of tetrahydrofuran and water. Compounds of formula (18-2) can be oxidized with osmium tetroxide and sodium periodate to give the corresponding ketone, compounds of formula (18-3). Compounds of formula (18-3) can be treated with diethylaminosulfur trifluoride (DAST) to convert the ketone to the corresponding difluoromethylene. Subsequent treatment with potassium carbonate in methanol removes the trifluoroacetyl moiety to give compounds of formula (18-4). Compounds of formula (18-4) can be treated as described in Scheme 8 to construct the thiadiazolidine-trione giving compounds of formula (18-5). The tert-butoxycarbonyl protecting group can be removed from compounds of formula (18-5) by treatment under acidic conditions such as with trifluoroacetic acid in dichloromethane to give compounds of formula (18-6). Compounds of formula (18-6) can be reductively aminated and then deprotected using procedures known to one of skill in the art to give compounds of formula (18-7), wherein $R^{18a}$ is $C_{1-6}$alkyl, $C_{2-6}$alkenyl, $C_{2-6}$alkynyl, $C_{3-6}$cycloalkyl, 4-7 membered heterocyclyl, —$C_{1-6}$alkylene-$C_{3-8}$cycloalkyl, —$C_{1-6}$alkylene-phenyl, —$C_{1-6}$alkylene-4-7 membered heterocyclyl, or —$C_{1-6}$alkylene-5-6 membered heteroaryl. Compounds of formula (18-6) can also be transformed to compounds of formula (18-8). Compounds of formula (18-6) can be treated with 4-nitrophenyl carbonochloridate in the presence of a tertiary amine base. Then, treated with an alcohol, $R^{18b}$—OH, wherein $R^{18b}$ is optionally substituted $C_{1-6}$alkyl, in the presence of a base such as potassium tert-butoxide followed by removal of the $PG^1$ protecting group gives compounds of formula (18-8). Compounds of formula (18-7) and formula (18-8) are representative of compounds of formula (III).

Scheme 19: Representative scheme for synthesis of exemplary compounds of the disclosure.

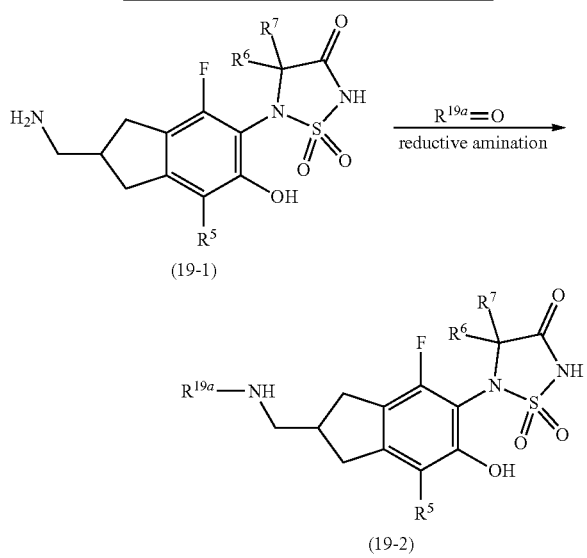

As shown in Scheme 19, compounds of formula (19-2) can be obtained from compounds of formula (19-1). Compounds of formula (19-1) can be prepared as described in the Examples. Compounds of formula (19-1) can be reductively aminated with an aldehyde or ketone ($R^{19a}$=O) under conditions known to one of skill in the art to give compounds of formula (19-2). $R^{19a}$ is —$C_{1-6}$alkyl, —$C_{1-6}$alkylene-N($R^a$)—$C_{1-6}$alkyl, —$C_{1-6}$alkylene-N($R^a$)—$C_{1-6}$alkylene-$C_{3-6}$cycloalkyl, $C_{3-6}$cycloalkyl, —$C_{1-6}$alkylene-$C_{3-6}$cycloalkyl, or —$C_{1-6}$alkylene-4-6 membered heterocyclyl, wherein each moiety may be optionally substituted. Compounds of formula (19-2) are representative of compounds of formula (I).

Pharmaceutical Compositions

The present disclosure provides pharmaceutical compositions comprising a compound disclosed herein, e.g., a compound of Formula (I), Formula (II) or Formula (III). In some embodiments, the pharmaceutical composition further comprises a pharmaceutically acceptable excipient. In some embodiments, a compound disclosed herein, e.g., a compound of Formula (I), Formula (II) or Formula (III), is provided in an effective amount in the pharmaceutical composition. In some embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing a disclosed compound (the "active ingredient") into association with a carrier and/or one or more other accessory ingredients, and then, if necessary and/or desirable, shaping and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of a compound disclosed herein, e.g., a compound of Formula (I), Formula (II) or Formula (III), the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) of a compound disclosed herein.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the disclosure are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present disclosure may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound disclosed herein may also be in micro-encapsulated form.

The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212, 162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, *J. Biomater Sci. Polym*. Ed. 7:623-645, 1995; as biodegradable and injectable gel formulations (see, e.g., *Gao Pharm. Res*. 12:857-863, 1995); or, as microspheres for oral administration (see, e.g., Eyles, *J. Pharm. Pharmacol*. 49:669-674, 1997). In another embodiment, the formulations of the compositions of the present disclosure can be delivered by the use of liposomes which fuse with the cellular membrane or are endocytosed, e.g., by employing receptor ligands attached to the liposome that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, J. Microencapsul. 13:293-306, 1996; Chonn,

*Curr. Opin. Biotechnol.* 6:698-708, 1995; Ostro, *J. Hosp. Pharm.* 46: 1576-1587, 1989). The compositions of the present disclosure can also be delivered as nanoparticles.

Alternatively, pharmaceutically acceptable compositions of the present disclosure may be administered in the form of suppositories for rectal administration. Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

In some embodiments, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein, e.g., a compound of Formula (I), Formula (II) or Formula (III) are typically formulated in dosage unit form, e.g., single unit dosage form, for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition disclosed herein can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Pharmaceutical compositions provided by the present disclosure include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., inhibiting the activity of a target molecule (e.g. PTPN2 and/or PTPN1), and/or reducing, eliminating, or slowing the progression of disease symptoms. Determination of a therapeutically effective amount of a compound disclosed herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods, compounds and compositions disclosed herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Also encompassed by the present are kits (e.g., pharmaceutical packs). The kits provided herein may be useful for preventing and/or treating a disease (e.g., cancer, type-2 diabetes, obesity, a metabolic disease, or other disease or condition described herein).

The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound disclosed herein. In certain embodiments, the kits are useful in preventing and/or treating a proliferative disease in a subject. In certain embodiments, the kits further include instructions for administering a disclosed compound to a subject to prevent and/or treat a disease described herein.

Methods of Treatment

The present disclosure features compounds, compositions, and methods comprising a compound disclosed herein, e.g., a compound of Formula (I), Formula (II) or Formula (III). In some embodiments, the compounds, compositions, and methods disclosed herein are used in the prevention or treatment of a disease, disorder, or condition. Exemplary diseases, disorders, or conditions include, but are not limited to cancer, type-2 diabetes, metabolic syndrome, obesity, or a metabolic disease.

Cancer

In some embodiments, a compound disclosed herein, e.g., a compound of Formula (I), Formula (II) or Formula (III) is used to treat cancer. As used herein, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In some embodiments, a compound disclosed herein, e.g., a compound of Formula (I), Formula (II) or Formula (III), is used to treat pancreatic cancer, breast cancer, multiple myeloma, cancers of secretory cells. For example certain methods herein treat cancer by decreasing or reducing or preventing the occurrence, growth, metastasis, or progression of cancer. In some embodiments, the methods described herein may be used to treat cancer by decreasing or eliminating a symptom of cancer. In some embodiments, a compound disclosed herein, e.g., a compound of Formula (I), Formula (II) or Formula (III), may be used as a single agent in a composition or in combination with another agent in a composition to treat a cancer described herein (e.g., pancreatic cancer, breast cancer, multiple myeloma, cancers of secretory cells).

In some embodiments, the compounds (compounds described herein, e.g., a compound of Formula (I), Formula (II) or Formula (III)) and compositions (e.g., compositions comprising a compound described herein, e.g., a compound of Formula (I), Formula (II) or Formula (III)) are used with a cancer immunotherapy (e.g., a checkpoint blocking antibody) to treat a subject (e.g., a human subject), e.g., suffering from a disease or disorder described herein (e.g., abnormal cell growth, e.g., cancer (e.g., a cancer described herein)). The methods described herein comprise administering a compound described herein, e.g., a compound of Formula (I), Formula (II) or Formula (III) and an immunotherapy to a subject having abnormal cell growth such as cancer. Exemplary immunotherapies include, but are not limited to the following.

In some embodiments, the immunotherapeutic agent is a compound (e.g., a ligand, an antibody) that inhibits the immune checkpoint blockade pathway. In some embodiments, the immunotherapeutic agent is a compound that inhibits the indoleamine 2,3-dioxygenase (IDO) pathway. In some embodiments, the immunotherapeutic agent is a compound that agonizes the STING pathway. Cancer immunotherapy refers to the use of the immune system to treat cancer. Three groups of immunotherapy used to treat cancer include cell-based, antibody-based, and cytokine therapies. All groups exploit cancer cells' display of subtly different structures (e.g., molecular structure; antigens, proteins, molecules, carbohydrates) on their surface that can be detected by the immune system. Cancer immunotherapy (e.g., anti-tumor immunotherapy or anti-tumor immunotherapeutics) includes but is not limited to, immune checkpoint antibodies (e.g., PD-1 antibodies, PD-L1 antibodies, PD-L2 antibodies, CTLA-4 antibodies, TIM3 antibodies, LAG3 antibodies, TIGIT antibodies); and cancer vaccines (e.g., anti-tumor vaccines or vaccines based on neoantigens such as a peptide or RNA vaccine).

Cell-based therapies (e.g., cancer vaccines), usually involve the removal of immune cells from a subject suffering from cancer, either from the blood or from a tumor. Immune cells specific for the tumor will be activated, grown, and returned to a subject suffering from cancer where the immune cells provide an immune response against the cancer. Cell types that can be used in this way are e.g., natural killer cells, lymphokine-activated killer cells, cytotoxic T-cells, dendritic cells, CAR-T therapies (e.g., chimeric antigen receptor T-cells which are T-cells engineered to target specific antigens), TIL therapy (e.g., administration of tumor-infiltrating lymphocytes), TCR gene therapy, protein vaccines, and nucleic acid vaccines. An exemplary cell-based therapy is Provenge. In some embodiments, the cell-based therapy is a CAR-T therapy.

Interleukin-2 and interferon-alpha are examples of cytokines, proteins that regulate and coordinate the behavior of the immune system.

Cancer Vaccines with Neoantigens

Neoantigens are antigens encoded by tumor-specific mutated genes. Technological innovations have made it possible to dissect the immune response to patient-specific neoantigens that arise as a consequence of tumor-specific mutations, and emerging data suggest that recognition of such neoantigens is a major factor in the activity of clinical immunotherapies. These observations indicate that neoantigen load may form a biomarker in cancer immunotherapy. Many novel therapeutic approaches are being developed that selectively enhance T cell reactivity against this class of antigens. One approach to target neoantigens is via cancer vaccine. These vaccines can be developed using peptides or RNA, e.g., synthetic peptides or synthetic RNA.

Antibody therapies are antibody proteins produced by the immune system and that bind to a target antigen on the surface of a cell. Antibodies are typically encoded by an immunoglobulin gene or genes, or fragments thereof. In normal physiology antibodies are used by the immune system to fight pathogens. Each antibody is specific to one or a few proteins, and those that bind to cancer antigens are used, e.g., for the treatment of cancer. Antibodies are capable of specifically binding an antigen or epitope (Fundamental Immunology, $3^{rd}$ Edition, Paul, W. E, ed., Raven Press, N.Y. (1993). Specific binding occurs to the corresponding antigen or epitope even in the presence of a heterogeneous population of proteins and other biologics. Specific binding of an antibody indicates that it binds to its target antigen or epitope with an affinity that is substantially greater than binding to irrelevant antigens. The relative difference in affinity is often at least 25% greater, more often at least 50% greater, most often at least 100% greater. The relative difference can be at least 2-fold, at least 5-fold, at least 10-fold, at least 25-fold, at least 50-fold, at least 100-fold, or at least 1000-fold, for example.

Exemplary types of antibodies include without limitation human, humanized, chimeric, monoclonal, polyclonal, single chain, antibody binding fragments, and diabodies. Once bound to a cancer antigen, antibodies can induce antibody-dependent cell-mediated cytotoxicity, activate the complement system, prevent a receptor interacting with its ligand or deliver a payload of chemotherapy or radiation, all of which can lead to cell death. Exemplary antibodies for the treatment of cancer include but are not limited to, Alemtuzumab, Bevacizumab, Bretuximab vedotin, Cetuximab, Gemtuzumab ozogamicin, Ibritumomab tiuxetan, Ipilimumab, Ofatumumab, Panitumumab, Rituximab, Tositumomab, Trastuzumab, Nivolumab, Pembrolizumab, Avelumab, durvalumab and pidilizumab.

Checkpoint Blocking Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a compound (e.g., an inhibitor or antibody) that inhibits the immune checkpoint blockade pathway. Immune checkpoint proteins, under normal physiological conditions, maintain self-tolerance (e.g., prevent autoimmunity) and protect tissues from damage when the immune system is responding to e.g., pathogenic infection. Immune checkpoint proteins can be dysregulated by tumors as an important immune resistance mechanism (Pardoll, *Nature Rev. Cancer*, 2012, 12, 252-264). Agonists of co-stimulatory receptors or antagonists of inhibitory signals (e.g., immune checkpoint proteins), provide an amplification of antigen-specific T-cell responses. Antibodies that block immune checkpoints do not target tumor cells directly but typically target lymphocyte receptors or their ligands to enhance endogenous antitumor activity.

Exemplary checkpoint blocking antibodies include but are not limited to, anti-CTLA-4, anti-PD-1, anti-LAG3 (e.g., antibodies against lymphocyte activation gene 3), and anti-TIM3 (e.g., antibodies against T-cell membrane protein 3). Exemplary anti-CTLA-4 antibodies include but are not limited to, ipilimumab and tremelimumab. Exemplary anti-PD-1 ligands include but are not limited to, PD-L1 (e.g., B7-H1 and CD274) and PD-L2 (e.g., B7-DC and CD273). Exemplary anti-PD-1 antibodies include but are not limited to, nivolumab (e.g., MDX-1106, BMS-936558, or ONO-4538)), CT-011, AMP-224, pembrolizumab (trade name Keytruda), and MK-3475. Exemplary PD-L1-specific antibodies include but are not limited to, BMS936559 (e.g., MDX-1105), MEDI4736 and MPDL-3280A. Exemplary checkpoint blocking antibodies also include but are not limited to, IMP321 and MGA271.

T-regulatory cells (e.g., CD4+, CD25+, or T-reg) are also involved in policing the distinction between self and non-self (e.g., foreign) antigens, and may represent an important mechanism in suppression of immune response in many cancers. T-reg cells can either emerge from the thymus (e.g., "natural T-reg") or can differentiate from mature T-cells under circumstances of peripheral tolerance induction (e.g., "induced T-reg"). Strategies that minimize the action of T-reg cells would therefore be expected to facilitate the immune response to tumors.

IDO Pathway Inhibitors

The IDO pathway regulates immune response by suppressing T cell function and enabling local tumor immune escape. IDO expression by antigen-presenting cells (APCs) can lead to tryptophan depletion, and resulting antigen-specific T cell energy and regulatory T cell recruitment. Some tumors even express IDO to shield themselves from the immune system. A compound that inhibits IDO or the IDO pathway activates the immune system to attack the cancer (e.g., tumor in a subject). Exemplary IDO pathway inhibitors include indoximod, epacadostat and EOS200271.

STING Pathway Agonists

Stimulator of interferon genes (STING) is an adaptor protein that plays an important role in the activation of type I interferons in response to cytosolic nucleic acid ligands. Evidence indicates involvement of the STING pathway in the induction of antitumor immune response. For example, activation of the STING-dependent pathway in cancer cells can result in tumor infiltration with immune cells and modulation of the anticancer immune response. STING agonists are being developed as a class of cancer therapeutics. Exemplary STING agonists include MK-1454 and ADU-S100.

Co-Stimulatory Antibodies

The methods described herein comprise, in some embodiments, treating a human subject suffering from a disease or disorder described herein, the method comprising administering a composition comprising a cancer immunotherapy (e.g., an immunotherapeutic agent). In some embodiments, the immunotherapeutic agent is a co-stimulatory inhibitor or antibody. In some embodiments, the methods described herein comprise depleting or activating anti-4-1BB, anti-OX40, anti-GITR, anti-CD27 and anti-CD40, and variants thereof.

Methods of the present disclosure contemplate single as well as multiple administrations of a therapeutically effective amount of a compound as described herein. Compounds, e.g., a compound as described herein, can be administered at regular intervals, depending on the nature, severity and extent of the subject's condition. In some embodiments, a compound described herein is administered in a single dose. In some embodiments, a compound described herein is administered in multiple doses.

Metabolic Diseases

In some embodiments, a compound disclosed herein, e.g., a compound of Formula (I), Formula (II) or Formula (III), is used to treat metabolic disease. As used herein, the term "metabolic disease" refers to a disease or condition affecting a metabolic process in a subject. Exemplary metabolic diseases that may be treated with a compound disclosed herein, e.g., a compound of Formula (I), Formula (II) or Formula (III), include non-alcoholic steatohepatitis (NASH), non-alcoholic fatty liver disease (NAFLD), liver fibrosis, obesity, heart disease, atherosclerosis, arthritis, cystinosis, diabetes (e.g., Type I diabetes, Type II diabetes, or gestational diabetes), metabolic syndrome, phenylketonuria, proliferative retinopathy, or Kearns-Sayre disease.

In some embodiments, a compound disclosed herein, e.g., a compound of Formula (I), Formula (II) or Formula (III), is used to treat a metabolic disease (e.g., a metabolic disease described herein) by decreasing or eliminating a symptom of the disease. In some embodiments, the method of treatment comprises decreasing or eliminating a symptom comprising elevated blood pressure, elevated blood sugar level, weight gain, fatigue, blurred vision, abdominal pain, flatulence, constipation, diarrhea, jaundice, and the like. In some embodiments, a compound disclosed herein, e.g., a compound of Formula (I), Formula (II) or Formula (III), may be used as a single agent in a composition or in combination with another agent in a composition to treat a metabolic disease.

In some embodiments, the compounds disclosed herein are provided as pharmaceutical compositions including a disclosed compound, e.g., of Formula (I), Formula (II) or Formula (III) and a pharmaceutically acceptable excipient. In embodiments of the method, a disclosed compound, e.g., of Formula (I), Formula (II) or Formula (III) is co-administered with a second agent (e.g. therapeutic agent). In other embodiments of the method, a disclosed compound, e.g., of Formula (I), Formula (II) or Formula (III) is co-administered with a second agent (e.g. therapeutic agent), which is administered in a therapeutically effective amount.

Combination Therapy

The present disclosure provides a pharmaceutical composition comprising a compound disclosed herein, e.g., a compound of Formula (I), Formula (II) or Formula (III), as well as a second agent (e.g. a second therapeutic agent). In some embodiments, the pharmaceutical composition includes a second agent (e.g. a second therapeutic agent) in a therapeutically effective amount. In some embodiments, the second agent is an agent for treating cancer, a metabolic disease (e.g., type-2 diabetes or obesity) or a disease or disorder favorably responsive to PTPN2 or PTPN1 inhibitor treatment.

The compounds described herein can be used in combination with one another, with other active agents known to be useful in treating cancer, a metabolic disease (e.g., type-2 diabetes or obesity) or a disease or disorder favorably responsive to PTPN2 or PTPN1 inhibitor treatment, or with adjunctive agents that may not be effective alone but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for a cancer, a metabolic disease (e.g., type-2 diabetes or obesity) or a disease or disorder favorably responsive to PTPN2 or PTPN1 inhibitor treatment. In embodiments, the second agent is an anti-cancer agent. In embodiments, the second agent is a chemotherapeutic. In embodiments, the second agent is an agent for treating a metabolic disease. In embodiments, the second agent is an anti-diabetic agent. In some embodiments, the second agent is an anti-obesity agent.

Anti-Cancer Agents

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anticancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK 1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iprop latin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol, i.e. paclitaxel), Taxotere, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and SC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-1 12378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A 1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tularik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{U1}$n, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{m}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$CU, $^{89}$Sr, $^{86}$Y, $^{87}$Y, $^{90}$Y, $^{105}$Rh, $^{m}$Ag, $^{m}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Synthetic Protocols

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures. General scheme relating to methods of making exemplary compounds of the disclosure are additionally described in the section entitled Methods of Making Exemplary Compounds.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Abbreviations

AcOH or HOAc for acetic acid; APCI for atmospheric pressure chemical ionization; 9-BBN for 9-borabicyclo[3.3.1]nonane; BrettPhos for 2-(dicyclohexylphosphino)3,6-dimethoxy-2',4',6'-triisopropyl-1,1'-biphenyl; BrettPhos Pd G3 precatalyst for [(2-di-cyclohexylphosphino-3,6-dimethoxy-2',4',6'-triisopropyl-1,1'-biphenyl)-2-(2'-amino-1,1'-biphenyl)]palladium(II) methanesulfonate; t-BuBrettPhos Pd G3 precatalyst for [2-(di-tert-butylphosphino)-2',4',6'-triisopropyl-3,6-dimethoxy-1,1'-biphenyl)-2-(2'-amino-1,1'-biphenyl)]palladium(II) methanesulfonate; DCM for dichloromethane; DMF for N,N-dimethylformamide; DMSO for dimethyl sulfoxide; ESI for electrospray ionization; HPLC for high performance liquid chromatography; i.d. for internal diameter; MS for mass spectrum; NMR for nuclear magnetic resonance; ppm for parts per million; psi for pounds per square inch; PTFE for polytetrafluoroethylene; RockPhos for 2-di(tert-butyl)phosphino-2',4',6'-triisopropyl-3-methoxy-6-methylbiphenyl; RockPhos Pd G3 precatalyst for [(2-di-tert-butylphosphino-3-methoxy-6-methyl-2',4',6'-triisopropyl-1,1'-biphenyl)-2-(2-aminobiphenyl)]palladium(II) methanesulfonate; SFC for supercritical fluid chromatography; TCDI for 1,1'-thiocarbonyldiimidazole; THF for tetrahydrofuran; TLC for thin layer chromatography; v/v for volume/volume; w/v for weight/volume; and w/w for weight/weight.

Example 1: 5-[1-fluoro-3-hydroxy-7-(3-methylbutoxy)-5,6,7,8-tetrahydronaphthalen-2-yl]-1$\lambda^6$,2,5-thiadiazolidine-1,1,3-trione (Compound 100)

Example 1A: Benzyl 3-(benzyloxy)-7-bromonaphthalene-2-carboxylate

A mixture of 7-bromo-3-hydroxy-2-naphthoic acid (100 g, 374 mmol) and cesium carbonate (366 g, 1123 mmol) in N,N-dimethylformamide (749 mL) was rapidly stirred for 5 minutes at 23° C. Thereafter, benzyl bromide (89.0 mL, 749 mmol) was added, and the internal temperature rose to 49° C. After 90 minutes, the light yellow mixture was poured into H$_2$O (1.5 L), and the resulting white precipitate was collected via filtration. The collected precipitate was washed sequentially with H$_2$O (3×1 L) and tert-butyl methyl ether/heptanes (1:2, 2×300 mL) and then dried in vacuo (15 mbar) at 45° C. to constant weight to afford the title compound (160.3 g, 358 mmol, 96% yield) as an off-white solid. MS (APCI$^+$) m/z 449 [M+H]$^+$.

Example 1B: 3-(benzyloxy)-7-bromonaphthalene-2-carboxylic Acid

To a mixture of the product of Example 1A (150.1 g, 336 mmol), water (746 mL), and methanol (1.49 L) was added lithium hydroxide monohydrate (28.2 g, 671 mmol). The thick slurry was agitated via overhead mechanical stirring and heated to an internal temperature of 70° C. After 3 hours, the mixture was cooled to room temperature in an ice bath and 6 M HCl (168 mL) was added over 5 minutes, causing an off-white solid to precipitate. The solid was collected via filtration and washed with H$_2$O (2×1 L), triturated with tert-butyl methyl ether (2×300 mL), and dried to constant weight in vacuo at 65° C. to afford the title compound (101.5 g, 284 mmol, 85% yield) as a white solid. MS (APCI$^+$) m/z 358 [M+H]$^+$.

Example 1C: 3-(benzyloxy)-7-bromonaphthalen-2-amine

To a suspension of the product of Example 1B (101 g, 283 mmol) in toluene (794 mL) and tert-butanol (794 mL) was added triethylamine (41.8 mL, 300 mmol). The hazy light yellow solution was heated to an internal temperature of 80° C. under nitrogen, and diphenyl phosphorazidate (64.4 mL, 300 mmol) was added dropwise over 90 minutes with the entire reaction behind a blast shield. After 5 hours, the reaction mixture was cooled to room temperature, diluted with H$_2$O (1.5 L), and extracted with ethyl acetate (2×400 mL). The combined organic layers were washed with brine (2×150 mL), dried over sodium sulfate, filtered and concentrated to give a white solid. The solid was carried forward to hydrolysis without further purification.

To the crude intermediate was added diethylenetriamine (253 mL, 2.34 mol). The heterogeneous suspension was heated to an internal temperature of 130° C. under nitrogen, at which time a homogeneous dark orange solution formed. After 13 hours, the mixture was cooled to room temperature in an ice bath, and H$_2$O (800 mL) was added slowly over 3 minutes, resulting in precipitation of a yellow solid and a concomitant exotherm to an internal temperature of 53° C. Once the heterogeneous suspension had cooled to room temperature, the crude solid was dissolved in CH$_2$Cl$_2$ (1.5 L), and the layers were separated. The aqueous layer was back-extracted with CH$_2$Cl$_2$ (3×150 mL). The combined organic layers were washed with brine (3×100 mL), dried over sodium sulfate, filtered, and the volatiles were removed in vacuo to afford an orange solid. The solid was combined with isopropanol (250 mL) to form a slurry that then was filtered. The resulting solid was again combined with isopropanol (2×100 mL), and solids were isolated via filtration. The solid was dried in vacuo (13 mbar) at 35° C. to afford the title compound (68.48 g, 209 mmol, 74% yield over two steps) as a white solid. MS (APCI$^+$) m/z 329 [M+H]$^+$.

Example 1D: Methyl {[3-(benzyloxy)-7-bromonaphthalen-2-yl]amino}acetate

To a mixture of the product of Example 1C (67.8 g, 207 mmol) and potassium carbonate (57.1 g, 413 mmol) in N,N-dimethylformamide (354 mL) and H$_2$O (1.861 mL, 103 mmol) was added methyl 2-bromoacetate (29.3 mL, 310 mmol). The suspension was vigorously stirred at room temperature for 5 minutes then heated to an internal temperature of 60° C. After 4 hours, the suspension was cooled to room temperature and partitioned between H$_2$O (400 mL) and ethyl acetate (400 mL). The aqueous layer was extracted with ethyl acetate (2×100 mL), and the combined organic layers were washed with saturated aqueous ammonium chloride (3×60 mL), dried over sodium sulfate, filtered, and concentrated to afford a pale beige solid. The solid was triturated with heptanes (100 mL), and the resulting beige solid was isolated via filtration, washed with additional heptanes (2×30 mL) and dried to constant weight in vacuo (15 mbar) at 35° C. to afford the title compound (68.52 g, 171 mmol, 83% yield) as an off-white solid. MS (APCI$^+$) m/z 401 [M+H]$^+$.

Example 1E: Methyl {[3-(benzyloxy)-7-bromo-1 fluoronaphthalen-2-yl]amino}acetate To a solution of the product of Example 1D (15 g, 37.5 mmol) in N,N-dimethylformamide (300 mL) at 2° C. was added a solution of 1-chloromethyl-4-fluoro-1,4-diazoniabicyclo[2.2.2]octane bis(tetrafluoroborate) (15.93 g, 45.0 mmol) in N,N-dimethylformamide (100 mL) over 5 minutes. The resulting solution was stirred for 15 minutes, and then quenched with a 0.33 M solution of sodium thiosulfate (300 mL, exothermic). The mixture was diluted with ethyl acetate (150 mL) and saturated aqueous ammonium chloride (75 mL) and stirred for 15 minutes at room temperature. The layers were separated, and the aqueous layer was extracted with ethyl acetate (3×75 mL). The combined organic layers were washed with saturated aqueous ammonium chloride (4×75 mL) and brine (75 mL), then dried over sodium sulfate, filtered and concentrated in vacuo to give an orange solid. Ethyl acetate (30 mL) was added to the crude solid, and the mixture was sonicated for 30 seconds. Then heptanes (150 mL) were slowly added via an addition funnel over 15 minutes. The resulting yellow solid was collected via filtration and washed with 33% v/v ethyl acetate in heptanes (3×60 mL). The solid was discarded, and the filtrate was concentrated in vacuo to give a yellow/orange solid, which was triturated with anhydrous ethanol (45 mL) heated to an internal temperature of 55° C. and stirred for 30 minutes, then slowly cooled to room temperature. The resulting yellow solid was collected by filtration, then washed with anhydrous ethanol (30 mL), and dried in vacuo (15 mbar) at 50° C. to constant weight to give the title compound (10.1 g, 24.25 mmol, 64.7% yield) as a pale yellow solid. $^1$H NMR (DMSO-$d_6$) δ ppm 7.79 (d, J=2.1 Hz, 1H), 7.65 (dd, J=8.7, 1.7 Hz, 1H), 7.56-7.51 (m, 2H), 7.46-7.35 (m, 3H), 7.38-7.31 (m, 2H), 7.28 (s, 1H), 5.64 (td, J=6.7, 2.5 Hz, 1H), 5.28 (s, 2H), 4.21 (dd, J=6.8, 4.0 Hz, 2H), 3.61 (s, 3H); MS (ESI$^+$) m/z 418, 420 [M+H]$^+$.

Example 1F: Methyl {[3-(benzyloxy)-7-bromo-1-fluoronaphthalen-2-yl](sulfamoyl)amino}acetate To a solution of chlorosulfonyl isocyanate (2.26 mL, 26.0 mmol) in dichloromethane (43.5 mL) at 0° C. was added tert-butanol (2.5 mL, 26.0 mmol) slowly so that the internal temperature remained below 10° C. After stirring for 30 minutes at 0° C., a preformed solution of the product of Example 1E (7.25 g, 17.34 mmol) and triethylamine (4.83 mL, 34.7 mmol) in dichloromethane (29.0 mL) was slowly added via addition funnel so that the internal temperature remained below 10° C. Upon complete addition, the addition funnel was rinsed with dichloromethane (12.5 mL). The resulting solution was stirred for 30 minutes at 0° C. and then was allowed to warm to room temperature. After 1 hour, the reaction mixture was quenched with H$_2$O (73 mL). The layers were separated, and the aqueous layer was extracted with dichloromethane (2×36 mL). The combined organic layers were washed with 1 M sodium bisulfate (2×73 mL). The aqueous washes were back extracted with dichloromethane (DCM) (36 mL), and the combined organic layers were dried over sodium sulfate, filtered and concentrated in vacuo to give an orange foam, which was used without purification. MS (APCI$^+$) m/z 541, 543 [M-tert-butyl+H]$^+$.

To a solution of the crude intermediate in dichloromethane (41 mL) was added trifluoroacetic acid (20 mL, 260 mmol), and the resulting dark solution was stirred at room temperature. After 30 minutes, the reaction was quenched by slow addition of saturated aqueous sodium bicarbonate (230 mL) via an addition funnel. The layers were separated, and the aqueous layer was extracted with dichloromethane (2×50 mL). The combined organic layers were concentrated to give an orange foam, which was suspended in dichloromethane (20 mL), and stirred for 5 minutes giving a slurry, which was diluted by dropwise addition of heptanes (40 mL) via an addition funnel. The resulting yellow solid was collected by filtration, washed with 25% v/v dichloromethane in heptanes (2×20 mL) and dried in vacuo (15 mbar) at 50° C. to constant weight to give the title compound (7.5 g, 15.05 mmol, 87% yield). $^1$H NMR (DMSO-$d_6$) δ ppm 8.11 (d, J=2.0 Hz, 1H), 7.84-7.80 (m, 1H), 7.67 (dd, J=8.8, 2.0 Hz, 1H), 7.58-7.53 (m, 2H), 7.44-7.36 (m, 3H), 7.36-7.30 (m, 1H), 7.07 (s, 2H), 5.26 (s, 2H), 4.47 (d, J=17.9 Hz, 1H), 4.31 (d, J=17.8 Hz, 1H), 3.54 (s, 3H); MS (ESI$^+$) m/z 497, 499 [M+H]$^+$.

Example 1G: 5-[3-(benzyloxy)-7-bromo-1-fluoronaphthalen-2-yl]-1λ$^6$,2,5-thiadiazolidine-1,1,3-trione To a solution of the product of Example 1F (24.14 g, 48.5 mmol) in tetrahydrofuran (THF) (241 mL) at room temperature was added a solution of sodium methoxide (16.65 mL, 72.8 mmol) (25 weight % in methanol) via syringe, and the resulting solution was stirred at room temperature. After 20 minutes, the reaction was quenched with 1 M hydrochloric acid (240 mL) and diluted with ethyl acetate (120 mL). The layers were separated, and the aqueous layer was extracted with ethyl acetate (2×120 mL). The combined organic layers were washed with a 4:1 mixture of brine and 1 M hydrochloric acid (120 mL), then dried over sodium sulfate, filtered and concentrated to 40 mL total volume to give a dark red solution, which was diluted with dichloromethane (75 mL) and concentrated to 40 mL of total volume. The resulting yellow suspension was diluted with dichloromethane (72 mL), and then slowly diluted with heptanes (72 mL). The suspension was sonicated for 30 seconds and stirred for 5 minutes at room temperature. The resulting white solid was collected via filtration, then washed with 25% v/v dichloromethane in heptanes (72 mL) and dried in vacuo (15 mbar) at 50° C. to constant weight to give the title compound (16.4 g, 35.2 mmol, 72.5% yield). $^1$H NMR (DMSO-$d_6$) δ ppm 8.16 (d, J=2.0 Hz, 1H), 7.87 (dd, J=8.9, 1.4 Hz, 1H), 7.74 (dd, J=8.8, 2.0 Hz, 1H), 7.54-7.48 (m, 3H), 7.47-7.29 (m, 3H), 5.28 (s, 2H), 4.54 (s, 2H); MS (ESI$^-$) m/z 463, 465 [M−H]$^-$.

Example 1H: 5-[3-(benzyloxy)-1-fluoro-7-hydroxynaphthalen-2-yl]-1λ$^6$,2,5-thiadiazolidine-1,1,3-trione, Ammonium Salt In a 500 mL round bottom flask were combined the product of Example 1G (9 g, 19.34 mmol), [(2-di-tert-butylphosphino-3-methoxy-6-methyl-2',4',6'-triisopropyl-1,1'-biphenyl)-2-(2-aminobiphenyl)]palladium(II) methanesulfonate (RockPhos Pd G3 precatalyst, 0.324 g, 0.387 mmol), and cesium carbonate (18.9 g, 58.0 mmol). The solids were placed under vacuum and stirred for 5 minutes, then the flask was filled with nitrogen and a preformed mixture of N,N-dimethylformamide (90 mL) and H$_2$O (1.045 mL, 58.0 mmol) was added. The resulting suspension was degassed by five vacuum/nitrogen backfills, and then heated to an internal temperature of 80° C. After 3 hours, the reaction mixture was cooled to room temperature, quenched by slow addition of 1 M hydrochloric acid (100 mL), and diluted with ethyl acetate (100 mL). The layers were separated, and the aqueous layer was extracted with ethyl acetate (2×50 mL). The combined organic layers were washed with saturated aqueous ammonium chloride (4×50 mL). The combined aqueous washes were back extracted with ethyl acetate (3×50 mL). The combined organic extracts were washed with a 4:1 mixture of brine and 1 M hydrochloric acid (50 mL), then dried over sodium sulfate, filtered, and concentrated to give a viscous, dark oil. The crude oil was dissolved in acetonitrile (9 mL), then tert-butyl methyl ether (180 mL) was added via addition funnel over 5 minutes with vigorous stirring. The resulting black solid was removed via filtration and washed with 50% v/v tert-butyl methyl ether in ethyl acetate (2×45 mL). The solid was discarded, and the filtrate was concentrated in vacuo. The resulting dark oil was diluted with methanol (9 mL), and then a solution of ammonia in methanol (2.76 mL, 7 M, 19.34 mmol) was added. The resulting solution was diluted by slow addition of 50% v/v ethyl acetate in heptanes (135 mL) via an addition funnel. The resulting solid was collected via filtration, then washed with the cold filtrate, followed by 50% v/v ethyl acetate in heptanes (45 mL), and dried in vacuo (15 mbar) at 50° C. to constant weight to give the title compound as an ammonium salt (6.33 g, 15.10 mmol, 78% yield). $^1$H NMR (DMSO-$d_6$) δ ppm 9.81 (s, 1H), 7.68 (dd, J=8.9, 1.4 Hz, 1H), 7.60-7.49 (m, 2H), 7.39-7.31 (m, 2H), 7.33-7.26 (m, 1H), 7.23 (s, 1H), 7.14 (d, J=2.5 Hz, 1H), 7.10 (dd, J=8.8, 2.5 Hz, 1H), 5.19 (s, 2H), 4.08 (s, 2H); MS (ESI$^-$) m/z 401 [M–H]$^-$.

Example 1I: 5-[3-(benzyloxy)-1-fluoro-7-(3-methylbutoxy)naphthalen-2-yl]-1λ$^6$,2,5-thiadiazolidine-1,1,3-trione A mixture of Example 1H (300 mg, 0.746 mmol) cesium carbonate (486 mg, 1.491 mmol) and 1-bromo-3-methylbutane (169 mg, 1.18 mmol) in N,N-dimethylformamide (DMF) (2 mL) was stirred at room temperature for 14 hours. To the reaction mixture, 2 N $Na_2CO_3$ (0.7 mL) and ethyl acetate (10 mL) were added resulting a suspension. The solid was collected by filtration to give the title compound (260 mg, 74% yield). $^1$H NMR (400 MHz, DMSO-$d_6$) δ ppm 7.74 (dd, J=9.1, 1.5 Hz, 1H), 7.59-7.52 (m, 2H), 7.41-7.22 (m, 5H), 7.19 (dd, J=9.0, 2.5 Hz, 1H), 5.22 (s, 2H), 4.12 (t, J=6.7 Hz, 2H), 4.08 (s, 2H), 1.83 (dp, J=13.3, 6.6 Hz, 1H), 1.68 (q, J=6.6 Hz, 2H), 0.96 (d, J=6.6 Hz, 6H); MS (APCI$^-$) m/z 471.4 [M–H]$^-$.

Example 1J: 5-[1-fluoro-3-hydroxy-7-(3-methylbutoxy)-5,6,7,8-tetrahydronaphthalen-2-yl]-1λ$^6$,2,5-thiadiazolidine-1,1,3-trione To a solution of Example 1I (140 mg, 0.296 mmol) in 2,2,2-trifluoroethanol (1.5 mL) was added 10% Pd/C (144 mg, 1.353 mmol) in a 20 mL Parr® Barnstead Hastelloy C reactor, and the mixture was stirred at 35° C. under 140 psi of hydrogen for 40 hours. Additional 10% Pd/C (140 mg, 1.316 mmol) was added with continued hydrogenation at 35° C. under 140 psi of hydrogen for 90 hours. The reaction mixture was filtered, concentrated and purified by preparative HPLC on Phenomenex® C8(2) Luna® 5 µm AXIA™ 150×30 mm column eluted with a gradient of acetonitrile (A) and 0.1% trifluoroacetic acid in water (B), at a flow rate of 50 mL/minute (0-0.5 min 5% A, 0.5-8.5 minutes linear gradient 05-100% A, 8.7-10.7 minutes 100% A, 10.7-11 minutes linear gradient 100-05% A) to give the title with an impurity. The title compound was further purified again by preparative HPLC on Phenomenex® C8(2) Luna® m AXIA™ 150×30 mm column eluted with a gradient of acetonitrile (A) and 0.1% trifluoroacetic acid in water (B) at a flow rate of 50 mL/minute (0-0.5 minute 5% A, 0.5-20.5 minutes linear gradient 05-100% A, 20.7-22.7 minutes 100% A, 22.7-23 minutes linear gradient 100-05% A) to give the title compound (12 mg, 0.031 mmol, 10.5% yield). $^1$H NMR (500 MHz, DMSO-$d_6$) δ ppm 10.00 (s, 1H), 6.47 (s, 1H), 4.35 (s, 2H), 3.70 (m, 1H), 3.48 (m, 2H), 2.82 (dd, J=16.4, 4.9 Hz, 1H), 2.74 (m, 1H), 2.68-2.58 (m, 1H), 2.50-2.43 (m, 1H), 1.90-1.81 (m, 1H), 1.79-1.70 (m, 1H), 1.64 (m, 1H), 1.38 (q, J=6.8 Hz, 2H), 0.86 (dd, J=6.7, 2.1 Hz, 6H); MS (APCI$^-$) m/z 385.3 [M–H]$^-$.

Example 2: 5-{7-[(2-cyclopropylethyl)amino]-1-fluoro-3-hydroxy-5,6,7,8-tetrahydronaphthalen-2-yl}-1λ$^6$,2,5-thiadiazolidine-1,1,3-trione (Compound 101)

Example 2A: 5-{3-(benzyloxy)-7-[(2-cyclopropylethyl)amino]-1-fluoronaphthalen-2-yl}-1λ$^6$,2,5-thiadiazolidine-1,1,3-trione In a 20 mL pressure release vial, the product from Example 1G (0.500 g, 1.075 mmol), cesium carbonate (1.050 g, 3.22 mmol), and [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3 precatalyst, 0.029 g, 0.032 mmol), and 2-(dicyclohexylphosphino)3,6-dimethoxy-2',4',6'-triisopropyl-1,1'-biphenyl (BrettPhos, 0.017 g, 0.032 mmol) were combined and placed under vacuum for 5 minutes. The vessel was then filled with nitrogen, and tert-amyl alcohol (10 mL) was added, followed by 2-cyclopropylethylamine (0.203 mL, 2.15 mmol). The mixture was placed under vacuum followed by nitrogen backfills for 5 cycles, was stirred for 10 minutes (became a suspension), and then was heated to 90° C. After 24 hours, the reaction mixture was cooled to room temperature and was then quenched with 1 M hydrochloric acid (8 mL). The aqueous layer was extracted with ethyl acetate (3×5 mL), and the combined organic layers were washed with a 4:1 mixture of brine and 1 M hydrochloric acid. The organic fraction was then dried over sodium sulfate, filtered and concentrated in vacuo. The crude oil was dissolved in acetonitrile and concentrated (2×5 mL) to give the title compound, which was used without purification for the next step. MS (APCI$^-$) m/z 468 [M–H]$^-$.

Example 2B: 5-{7-[(2-cyclopropylethyl)amino]-1-fluoro-3-hydroxynaphthalen-2-yl}-1λ$^6$,2,5-thiadiazolidine-1,1,3-trione To a suspension of the product from Example 2A (2.15 mmol) and pentamethylbenzene (0.637 g, 4.30 mmol) in dichloromethane (20 mL) at an internal temperature of −78° C. was added a solution of boron trichloride (12.9 mL, 12.89 mmol, 1 M in dichloromethane) slowly along the side of the flask so that the internal temperature remained below −65° C. After 5 minutes, the cooling bath was removed and the solution was allowed to warm. Upon reaching an internal temperature of 0° C., the reaction was re-cooled to −78° C. and was quenched with ethyl acetate (5 mL), followed by ethanol (5 mL). The mixture was warmed to room temperature and then concentrated in vacuo to give a solid. The solid was triturated with heptanes (3×10 mL), 1:1 heptanes/ethyl acetate (2×5 mL), and acetonitrile (2×3 mL) to give the title compound as a solid (0.654 g, 1.73 mmol, 80% yield). $^1$H NMR (DMSO-$d_6$) δ ppm 7.45 (dd, J=8.9, 1.6 Hz, 1H), 6.97 (dd, J=8.9, 2.3 Hz, 1H), 6.88 (d, J=1.4 Hz, 1H), 6.61 (d, J=2.2 Hz, 1H), 5.82 (t, J=5.5 Hz, 1H), 4.07 (s, 2H), 3.14 (td, J=7.0, 4.2 Hz, 2H), 1.51 (q, J=7.0 Hz, 2H), 0.84 (tdd, J=10.2, 7.5, 3.8 Hz, 1H), 0.50-0.37 (m, 2H), 0.14-0.06 (m, 2H); MS (ESI$^-$) m/z 378 [M–H]$^-$.

Example 2C: 2: 5-{7-[(2-cyclopropylethyl)amino]-1-fluoro-3-hydroxy-5,6,7,8-tetrahydronaphthalen-2-yl}-1$\lambda^6$,2,5-thiadiazolidine-1,1,3-trione In a Parr shaker, 10% palladium on carbon (0.443 g, 0.416 mmol) as a solid was added to a solution of the product from Example 2B (0.654 g, 1.725 mmol) in a mixture of acetic acid (6 mL) and methanol (3 mL). The reactor was purged with nitrogen and then was stirred under hydrogen (120 psi) at 25° C. until hydrogen uptake was complete (2 weeks). The reactor was purged with nitrogen, and the crude reaction mixture was filtered, washing the solid with methanol. The filtrate was then concentrated in vacuo to give a brown solid which was purified by reverse phase preparative HPLC, Waters XBridge™ C18 5 μm OBD column, 30×100 mm, flow rate 40 mL/minute, gradient of 5-60% CH$_3$OH in buffer (0.025 M aqueous ammonium bicarbonate, adjusted to pH 10 with ammonium hydroxide) observing at 210 nm, to give the title compound (0.114 g, 0.297 mmol, 14% yield). $^1$H NMR (501 MHz, DMSO-d$_6$) δ ppm 9.28 (s, 1H), 8.43 (s, 2H), 6.47 (s, 1H), 3.94 (d, J=1.6 Hz, 2H), 3.17 (d, J=3.0 Hz, 1H), 3.13-3.05 (m, 3H), 2.81 (dt, J=17.3, 4.7 Hz, 1H), 2.73 (ddd, J=17.1, 11.1, 5.3 Hz, 1H), 2.57-2.47 (m, 1H), 2.17 (dt, J=12.9, 4.1 Hz, 1H), 1.68 (qd, J=11.6, 5.5 Hz, 1H), 1.52 (q, J=7.2 Hz, 2H), 0.76 (ddd, J=12.5, 8.0, 4.9 Hz, 1H), 0.50-0.41 (m, 2H), 0.13 (q, J=4.9 Hz, 2H); MS (ESI$^-$) m/z 382 [M–H]$^-$.

Example 3: 5-{1-fluoro-3-hydroxy-7-[(3-methylbutyl)amino]-5,6,7,8-tetrahydronaphthalen-2-yl}-1$\lambda^6$,2,5-thiadiazolidine-1,1,3-trione (Compound 102)

Example 3A: 5-{3-(benzyloxy)-1-fluoro-7-[(3-methylbutyl)amino]naphthalen-2-yl}-1$\lambda^6$,2,5-thiadiazolidine-1,1,3-trione In a 20 mL pressure release vial, the product from Example 1G (0.500 g, 1.075 mmol), cesium carbonate (1.050 g, 3.22 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3 precatalyst, 0.029 g, 0.032 mmol), and 2-(dicyclohexylphosphino)3,6-dimethoxy-2',4',6'-triisopropyl-1,1'-biphenyl (BrettPhos, 0.017 g, 0.032 mmol) were combined and placed under vacuum for 5 minutes. The vessel was filled with nitrogen, then tert-amyl alcohol (10 mL) was added, followed by isoamylamine (0.25 mL, 2.149 mmol). The reaction mixture was degassed with 5 cycles under vacuum and nitrogen backfills, was stirred for 10 minutes, and then was heated to 90° C. After 24 hours, the reaction mixture was cooled to room temperature, and then was quenched with 1 M hydrochloric acid (8 mL). The aqueous layer was extracted with ethyl acetate (3×5 mL). The combined organic layers were washed with a 4:1 mixture of brine and 1 M hydrochloric acid, dried over sodium sulfate, filtered and concentrated in vacuo. The crude product was dissolved in acetonitrile and concentrated (2×5 mL) to give the title compound which was used without purification for the next step. MS (APCI$^-$) m/z 470 [M–H]$^-$.

Example 3B: 5-{1-fluoro-3-hydroxy-7-[(3-methylbutyl)amino]naphthalen-2-yl}-1$\lambda^6$,2,5-thiadiazolidine-1,1,3-trione To a suspension of the product from Example 3A (2.149 mmol theoretical) and pentamethylbenzene (0.637 g, 4.30 mmol) in dichloromethane (20 mL) at an internal temperature of –78° C. was added a solution of boron trichloride (12.9 mL, 12.9 mmol, 1 M in dichloromethane) slowly along the side of the flask so that the internal temperature remained below –65° C. After 5 minutes, the cooling bath was removed and the solution was allowed to warm. Upon reaching an internal temperature of 0° C., the reaction was re-cooled to –78° C., and then quenched with ethyl acetate (5 mL), followed by ethanol (5 mL). The mixture was warmed to room temperature, and then was concentrated in vacuo. The solid was triturated with heptanes (3×10 mL), then 1:1 heptanes/ethyl acetate (2×5 mL) and acetonitrile (2×3 mL) to give the title compound (0.475 g, 1.25 mmol, 58% yield). $^1$H NMR (DMSO-d$_6$) δ ppm 9.86 (s, 1H), 7.53 (d, J=8.9 Hz, 1H), 7.08 (dd, J=8.9, 2.3 Hz, 1H), 6.94 (s, 1H), 6.78 (s, 1H), 4.39 (s, 2H), 3.16-3.07 (m, 2H), 172 (dq, J=13.3, 6.7 Hz, 1H), 1.51 (q, J=7.1 Hz, 2H), 0.93 (d, J=6.7 Hz, 6H); MS (ESI$^-$) m/z 380 [M–H]$^-$.

Example 3C: 5-{1-fluoro-3-hydroxy-7-[(3-methylbutyl)amino]-5,6,7,8-tetrahydronaphthalen-2-yl}-1$\lambda^6$,2,5-thiadiazolidine-1,1,3-trione In a Parr shaker, 10% palladium on carbon (0.458 g, 0.430 mmol) was added to a solution of the product from Example 3B (0.4572 g, 1.199 mmol) in acetic acid (5 mL), the reactor was purged with nitrogen and then stirred under 120 psi of hydrogen gas at 25° C. until hydrogen uptake was complete (2 weeks). The reactor was purged with nitrogen, and the crude reaction mixture was filtered, washing the solid with methanol. The filtrate was then concentrated in vacuo, and the residue was purified by reverse phase preparative HPLC, Waters XBridge™ C18 5 μm OBD column, 30×100 mm, flow rate 40 mL/minute, gradient of 5-60% methanol in buffer (0.025 M aqueous ammonium bicarbonate, adjusted to pH 10 with ammonium hydroxide) observing at 210 nm, to give the title compound (0.143 g, 0.371 mmol, 31% yield). $^1$H NMR (501 MHz, DMSO-d$_6$) δ ppm 9.22 (s, 1H), 8.39 (br s, 2H), 6.47 (s, 1H), 3.93 (s, 2H), 3.43-3.35 (m, 1H), 3.09 (dd, J=16.0, 5.6 Hz, 1H), 3.03 (td, J=7.0, 2.1 Hz, 2H), 2.81 (dt, J=17.2, 4.7 Hz, 1H), 2.73 (ddd, J=17.0, 11.0, 5.3 Hz, 1H), 2.56-2.51 (m, 1H), 2.20-2.13 (m, 1H), 1.68 (ddt, J=17.2, 13.1, 6.0 Hz, 2H), 1.50 (dt, J=9.7, 6.8 Hz, 2H), 0.92 (d, J=6.6 Hz, 6H); MS (ESI$^-$) m/z 384 [M–H]$^-$.

Example 4: 5-{7-[(cyclopropylmethyl)amino]-1-fluoro-3-hydroxy-5,6,7,8-tetrahydronaphthalen-2-yl}-1$\lambda^6$,2,5-thiadiazolidine-1,1,3-trione (Compound 103)

Example 4A: 5-{3-(benzyloxy)-7-[(cyclopropylmethyl)amino]-1-fluoronaphthalen-2-yl}-1$\lambda^6$,2,5-thiadiazolidine-1,1,3-trione In a 20 mL pressure release vial, the product from Example 1G (0.50 g, 1.08 mmol), cesium carbonate (1.05 g, 3.22 mmol), [(2-di-cyclohexylphosphino-3,6-dimethoxy-2',4',6'-triisopropyl-1,1'-biphenyl)-2-(2'-amino-1,1'-biphenyl)] palladium(II) methanesulfonate (BrettPhos Pd G3 precatalyst, 0.029 g, 0.032 mmol), and 2-(dicyclohexylphosphino) 3,6-dimethoxy-2',4',6'-triisopropyl-1,1'-biphenyl (BrettPhos, 0.017 g, 0.032 mmol) were combined and placed under vacuum for 5 minutes. The vessel was then filled with nitrogen and tert-amyl alcohol (10 mL) was added, followed by cyclopropylmethylamine (0.19 mL, 2.15 mmol). The mixture was degassed with 5 cycles under vacuum and nitrogen backfills, was stirred for 10 minutes, and then was heated to 90° C. After 7 hours, the reaction mixture was cooled to room temperature and then quenched with 1 M hydrochloric acid (8 mL). The aqueous layer was extracted with ethyl acetate (3×5 mL). The combined organic layers were washed with a 4:1 mixture of brine and 1 M hydrochloric acid, then dried over sodium sulfate, filtered and concentrated in vacuo. The crude product was dissolved in acetonitrile and concentrated (2×5 mL) to give the title compound which was used without purification for the next step. MS (APCI⁻) m/z 454 [M−H]⁻.

Example 4B: 5-{7-[(cyclopropylmethyl)amino]-1-fluoro-3-hydroxynaphthalen-2-yl}-1λ⁶,2,5-thiadiazolidine-1,1,3-trione To a suspension of the product from Example 4A (1.075 mmol) in dichloromethane (10 mL) at an internal temperature of −78° C. was added a solution of boron trichloride (6.45 mL, 6.45 mmol, 1 M in dichloromethane) slowly along the side of the flask so that the internal temperature remained below −65° C. After 5 minutes, the cooling bath was removed and the solution was allowed to warm. Upon reaching an internal temperature of 0° C., the reaction was re-cooled to −78° C., and then quenched with ethyl acetate (5 mL), followed by ethanol (5 mL). The mixture was warmed to room temperature and then was concentrated in vacuo. The residue was triturated with heptanes (3×5 mL), then 1:1 heptanes/ethyl acetate (2×3 mL) and acetonitrile (2×3 mL) to give the title compound (0.129 g, 0.353 mmol, 33% yield). $^1$H NMR (DMSO-$d_6$) δ ppm 10.06 (s, 1H), 7.60 (d, J=8.9 Hz, 1H), 7.19 (dd, J=8.9, 2.3 Hz, 1H), 6.97 (d, J=4.8 Hz, 2H), 4.42 (s, 2H), 3.05 (d, J=6.8 Hz, 2H), 1.13-1.03 (m, 1H), 0.57-0.47 (m, 2H), 0.31-0.25 (m, 2H); MS (ESI⁻) m/z 364 [M−H]⁻.

Example 4C: 5-{7-[(cyclopropylmethyl)amino]-1-fluoro-3-hydroxy-5,6,7,8-tetrahydronaphthalen-2-yl}-1λ⁶,2,5-thiadiazolidine-1,1,3-trione In a Parr shaker, 10% palladium on carbon (0.122 g, 0.115 mmol) was added to a solution of the product from Example 4B (0.068 g, 0.187 mmol) in acetic acid (2 mL). The reactor was purged with nitrogen and then stirred under 120 psi of hydrogen gas at 25° C. until hydrogen uptake was complete (2 weeks). The reactor was purged with nitrogen, the crude reaction mixture was filtered, and the solid with washed with methanol. The filtrate was then concentrated in vacuo, and the residue was purified by reverse phase preparative HPLC, Waters XBridge™ C18 5 µm OBD column, 30×100 mm, flow rate 40 mL/minute, gradient of 5-30% methanol in buffer (0.025 M aqueous ammonium bicarbonate, adjusted to pH 10 with ammonium hydroxide) observing at 205 nm, to give the title compound as the ammonium salt (0.0046 g, 0.012 mmol, 6% yield). $^1$H NMR (501 MHz, DMSO-$d_6$) δ ppm 9.07 (s, 1H), 6.42 (s, 1H), 3.92 (d, J=1.6 Hz, 2H), 3.07-3.00 (m, 1H), 2.78-2.71 (m, 1H), 2.69-2.60 (m, 2H), 2.37-2.28 (m, 1H), 2.01-1.95 (m, 1H), 1.86-1.80 (m, 1H), 1.67-1.61 (m, 1H), 1.56-1.49 (m 1H), 0.87-0.80 (m, 1H), 0.49-0.44 (m, 2H), 0.23-0.18 (m, 2H); MS (ESI⁻) m/z 368 [M−H]⁻.

Example 5: 5-[(7R)-1-fluoro-3-hydroxy-7-methoxy-5,6,7,8-tetrahydronaphthalen-2-yl]-1λ⁶,2,5-thiadiazolidine-1,1,3-trione (Compound 104)

Example 5A: Benzyl 3-(benzyloxy)-7-methoxynaphthalene-2-carboxylate

A mixture of 3-hydroxy-7-methoxy-2-naphthoic acid (75 g, 344 mmol) and cesium carbonate (336 g, 1031 mmol) in N,N-dimethylformamide (687 mL) was rapidly stirred for 5 minutes at 23° C. Thereafter, benzyl bromide (84 mL, 705 mmol) was added. After 90 minutes, the mixture was poured into H₂O (1 L) and extracted with ethyl acetate (4×300 mL). The combined organic layers were washed with saturated aqueous ammonium chloride (3×100 mL), dried over sodium sulfate, filtered, and concentrated in vacuo to afford a brown solid. The crude solid was collected by filtration, slurried with tert-butyl methyl ether:heptanes (1:2, 3×100 mL), then dried in vacuo (12 mbar) at 40° C. to afford the title compound (122.5 g, 307 mmol, 89% yield) as a beige solid. MS (APCI⁺) m/z 399 [M+H]⁺.

Example 5B: 3-(benzyloxy)-7-methoxynaphthalene-2-carboxylic Acid

To a suspension of the product of Example 5A (122.5 g, 307 mmol) in methanol (780 mL) was added 6 M aqueous sodium hydroxide (154 mL, 922 mmol). The heterogeneous, brown slurry was agitated with an overhead mechanical stirrer and heated to an internal temperature of 68° C. After 15 minutes, the mixture was cooled to room temperature in an ice bath, and 6 M HCl (250 mL) was added over 5 minutes. The off-white solid was collected by filtration, washed with H₂O (3×500 mL), and dried to constant weight in vacuo at 65° C. to afford the title compound (84.1 g, 273 mmol, 89% yield) as a white solid. MS (APCI⁺) m/z 309 [M+H]⁺.

Example 5C: 3-(benzyloxy)-7-methoxynaphthalen-2-amine

To a suspension of the product of Example 5B (84.1 g, 273 mmol), in toluene (766 mL) and tert-butanol (766 mL) was added triethylamine (40.3 mL, 289 mmol). The homogeneous black solution was heated to an internal temperature of 80° C. under nitrogen, and diphenyl phosphorazidate (62.2 mL, 289 mmol) was added dropwise over 90 minutes with the entire reaction behind a blast shield. After 5 hours, the reaction was cooled to room temperature, diluted with H₂O (1.5 L), and extracted with ethyl acetate (3×150 mL). The combined organic layers were washed with brine (2×100 mL), dried over sodium sulfate, filtered and concentrated to give 180.1 g of a dark brown solid. The solid was carried forward to hydrolysis without further purification.

To the crude intermediate was added diethylenetriamine (475 mL, 4.40 mol). The heterogeneous suspension was heated to an internal temperature of 130° C. under nitrogen, at which time a homogeneous dark orange solution formed. After 16 hours, the mixture was cooled to room temperature in an ice bath, and H₂O (1.5 L) was added slowly over 3 minutes, resulting in precipitation of a yellow solid and a concomitant exotherm to an internal temperature of 62° C. Once the heterogeneous suspension had cooled to room temperature, the crude solid was dissolved in CH₂Cl₂ (1.5 L), and the layers were separated. The aqueous layer was back-extracted with CH₂Cl₂ (3×150 mL), and the combined organic layers were washed with brine (3×100 mL), dried over sodium sulfate, filtered, and concentrated in vacuo to afford 78.8 g of an orange solid. The solid was slurried with isopropanol (50 mL), collected via filtration, re-slurried with isopropanol (1×50 mL), and dried in vacuo (15 mbar) at 35° C. to afford the title compound (60.12 g, 215 mmol, 79% yield over two steps) as a yellow solid. MS (APCI⁺) m/z 280 [M+H]⁺.

Example 5D: Methyl {[3-(benzyloxy)-7-methoxynaphthalen-2-yl]amino}acetate

To a mixture of the product of Example 5C (59.2 g, 212 mmol) and potassium carbonate (58.6 g, 424 mmol) in N,N-dimethylformamide (363 mL) and $H_2O$ (1.91 mL, 106 mmol) was added methyl 2-bromoacetate (30.1 mL, 318 mmol). The suspension was vigorously stirred at room temperature for 5 minutes and then heated to an internal temperature of 60° C. After 70 minutes, the suspension was cooled to room temperature and diluted with $H_2O$ (600 mL) and ethyl acetate (500 mL). The aqueous layer was extracted with ethyl acetate (2×300 mL), and the combined organic layers were washed with saturated aqueous ammonium chloride (3×60 mL), dried over sodium sulfate, filtered, and concentrated to afford 104.3 g of a pale beige solid. The solid was triturated with heptanes (200 mL). The resulting beige solid was collected via filtration, washed with additional heptanes (2×30 mL), and dried in vacuo (15 mbar) at 35° C. to afford the title compound (72.27 g, 206 mmol, 97% yield) as an off-white solid. MS (APCI$^+$) m/z 352 [M+H]$^+$.

Example 5E: Methyl {[3-(benzyloxy)-1-fluoro-7-methoxynaphthalen-2-yl]amino}acetate To a mixture of the product of Example 5D (30.0 g, 85 mmol) and N-fluorobenzenesulfonimide (26.9 g, 85 mmol) was added tetrahydrofuran (THF) (854 mL), and the resulting homogeneous yellow solution was stirred at room temperature. After 90 minutes, residual oxidant was quenched by adding a solution of sodium thiosulfate pentahydrate (10.59 g, 42.7 mmol) in water (150 mL), and the mixture was stirred at room temperature for 30 minutes. Thereafter, ethyl acetate (600 mL) was added, the aqueous layer was separated, and the organic layer was washed with a solution of sodium carbonate (18.10 g, 171 mmol) in water (30 mL), followed by water:brine (1:1, 1×20 mL). The organic fraction was dried over sodium sulfate, filtered, and the concentrated in vacuo to afford a bright yellow/orange solid. The solids were triturated with tert-butyl methyl ether (300 mL), collected via filtration, and the filter cake (N-(phenylsulfonyl)benzenesulfonamide) was washed with tert-butyl methyl ether (2×100 mL). The filtrate was concentrated to afford 34.6 g of a dark red oil that was purified by flash chromatography (750 g $SiO_2$, heptanes to 20% ethyl acetate/heptanes) to afford the title compound (16.07 g, 43.5 mmol, 51% yield) as a yellow solid. MS (APCI$^+$) m/z 370 [M+H]$^+$.

Example 5F: Methyl {[3-(benzyloxy)-1-fluoro-7-methoxynaphthalen-2-yl](sulfamoyl)amino}acetate To a solution of chlorosulfonyl isocyanate (5.13 mL, 59.1 mmol) in dichloromethane (83 mL) at 0° C. was added tert-butanol (5.65 mL, 59.1 mmol) slowly so that the internal temperature remained less than 10° C. After stirring for 30 minutes at 0° C., a preformed solution of the product of Example 5E (14.55 g, 39.4 mmol) and triethylamine (10.98 mL, 79 mmol) in dichloromethane (68.9 mL) was added slowly via addition funnel so that the internal temperature remained below 10° C. Upon complete addition, the addition funnel was rinsed with dichloromethane (23 mL). The resulting solution was stirred for 30 minutes at 0° C., and then the reaction mixture was quenched with $H_2O$ (20 mL). The layers were separated, and the aqueous layer was extracted with dichloromethane (2×30 mL). The combined organic layers were washed with brine (1×30 mL), dried over sodium sulfate, filtered and concentrated in vacuo to give an orange oil. The residue was dissolved in ethyl acetate (200 mL) and washed with water:brine (1:1, 2×50 mL) to remove residual triethylamine hydrochloride. The organic layer was dried over sodium sulfate, filtered, and concentrated in vacuo to give methyl {[3-(benzyloxy)-1-fluoro-7-methoxynaphthalen-2-yl][(tert-butoxycarbonyl)sulfamoyl]amino}acetate which was used without purification.

To a solution of methyl {[3-(benzyloxy)-1-fluoro-7-methoxynaphthalen-2-yl][(tert-butoxycarbonyl)sulfamoyl]amino}acetate in dichloromethane (98 mL) was added trifluoroacetic acid (45.5 mL, 591 mmol), and the resulting dark solution was stirred at room temperature. After 20 minutes, the reaction was quenched by slow addition of saturated aqueous sodium bicarbonate (691 mL) via an addition funnel. The layers were separated, and the aqueous layer was extracted with dichloromethane (2×50 mL). The combined organic layers were concentrated to give a dark red oil; upon addition of tert-butyl methyl ether (60 mL), a yellow solid precipitated that was collected via filtration, washed with tert-butyl methyl ether (2×30 mL) and dried in vacuo (15 mbar) at 35° C. to give the title compound (13.23 g, 29.5 mmol, 75% yield over two steps) as a light yellow solid. MS (ESI$^+$) m/z 449 [M+H]$^+$.

Example 5G: 5-(1-fluoro-3-hydroxy-7-methoxynaphthalen-2-yl)-1$\lambda^6$,2,5-thiadiazolidine-1,1,3-trione To a solution of the product of Example 5F (13.23 g, 29.5 mmol) in tetrahydrofuran (THF) (355 mL) at room temperature was added solid potassium tert-butoxide (3.31 g, 29.5 mmol), and the resulting solution was stirred at room temperature. After 10 minutes, the reaction was quenched with 1 M hydrochloric acid (90 mL) and diluted with ethyl acetate (400 mL). The layers were separated, and the aqueous layer was extracted with ethyl acetate (2×120 mL). The combined organic layers were washed with brine (3×50 mL), then dried over sodium sulfate, filtered and concentrated. The crude 5-[3-(benzyloxy)-1-fluoro-7-methoxynaphthalen-2-yl]-1$\lambda^6$,2,5-thiadiazolidine-1,1,3-trione was used in the subsequent reaction without further purification.

A mixture of crude intermediate, 5-[3-(benzyloxy)-1-fluoro-7-methoxynaphthalen-2-yl]-1$\lambda^6$,2,5-thiadiazolidine-1,1,3-trione (12.28 g, 29.5 mmol) and pentamethylbenzene (13.11 g, 88 mmol) in dichloromethane (147 mL) was cooled to an internal temperature of −76° C. under an atmosphere of dry nitrogen. Subsequently, a 1 M solution of boron trichloride (59.0 mL, 59.0 mmol) in $CH_2Cl_2$ was added dropwise over 15 minutes, so as not to raise the internal temperature past −72° C. Over the course of the addition, the reaction turned dark brown and became homogeneous. Incomplete conversion was observed, and additional boron trichloride (2×5.90 mL, 2×5.90 mmol) was added, resulting in full conversion. The reaction was quenched at −75° C. with $CH_2Cl_2$:methanol (10:1, 140 mL) via cannula transfer under nitrogen over 15 minutes, then slowly warmed to room temperature over 20 minutes under nitrogen. The volatiles were removed in vacuo to afford a brown/tan solid, which was collected by filtration, and slurried with heptanes (5×40 mL) and $CH_2Cl_2$ (3×40 mL). The crude solid was suspended in isopropanol (75 mL), warmed until the material dissolved, then allowed to cool slowly to room temperature over 1 hour. The solid was collected by filtration, washed with heptanes (2×30 mL), and dried in vacuo (15 mbar) at 60° C. to afford 5.11 g of a white solid. The mother liquor was concentrated, and the process was repeated to give an additional 1.96 g of a white solid. The batches were combined to obtain the title compound (7.07 g, 21.67 mmol, 73.5% yield over two steps). $^1$H NMR (methanol-d$_4$) δ ppm 7.60 (dd, J=9.1, 1.5 Hz, 1H), 7.25 (d, J=2.6, 1H), 7.16 (dd, J=9.1, 2.6 Hz, 1H), 7.04 (s, 1H), 4.56 (s, 2H), 3.89 (s, 3H); MS (ESI$^-$) m/z 325 [M–H]$^-$.

Example 5H: 5-{3-[(benzyloxy)methoxy]-1-fluoro-7-methoxy-5,6,7,8-tetrahydronaphthalen-2-yl}-2-[(benzyloxy)methyl]-1λ$^6$,2,5-thiadiazolidine-1,1,3-trione A solution of the intermediate of Example 5G (785 mg, 1.89 mmol) in acetic acid (10 mL) was added to 10% Pd/C, dry (800 mg). The mixture was stirred for 46 hours at 200 psi hydrogen pressure and 25° C. After filtration, the filtrate was concentrated to a minimal volume. Toluene (5 mL) was added, the mixture was concentrated to minimal volume, and this was repeated a second time to remove residual acetic acid. The resulting solid was dried in a vacuum oven at 50° C., giving crude giving 5-(1-fluoro-3-hydroxy-7-methoxy-5,6,7,8-tetrahydronaphthalen-2-yl)-1λ$^6$,2,5-thiadiazolidine-1,1,3-trione containing a significant amount of des-OCH$_3$ byproduct. This mixture was used without purification in the next step. MS (ESI$^-$) m/z 329 [M–H]$^-$.

A solution of crude 5-(1-fluoro-3-hydroxy-7-methoxy-5,6,7,8-tetrahydronaphthalen-2-yl)-1λ$^6$,2,5-thiadiazolidine-1,1,3-trione from the previous step and dichloromethane (6.2 mL) was stirred at ambient temperature and N,N-diisopropylethylamine (0.988 mL, 5.66 mmol) was added. Benzyl chloromethyl ether (0.655 mL, 4.71 mmol) was added dropwise and stirring was continued at ambient temperature. After 1 hour, the reaction mixture was diluted with ethyl acetate (20 mL), washed with saturated aqueous NaHCO$_3$ (10 mL) and brine (2 mL), dried (Na$_2$SO$_4$), and concentrated. The residue was purified by flash chromatography (40 g SiO$_2$, heptanes to 50% tert-butyl methyl ether/heptanes, gradient elution) to afford the title compound (318 mg, 0.557 mmol, 30% yield over two steps). $^1$H NMR (501 MHz, DMSO-d$_6$) δ ppm 7.38-7.21 (m, 10H), 6.88 (s, 1H), 5.31 (s, 2H), 5.21 (s, 2H), 4.65 (s, 2H), 4.62 (s, 2H), 4.61 (s, 2H), 3.69 (dtd, J=7.5, 5.0, 2.6 Hz, 1H), 3.29 (s, 3H), 2.89-2.77 (m, 2H), 2.71 (dt, J=17.3, 6.2 Hz, 1H), 2.61 (dd, J=16.8, 5.8 Hz, 1H), 1.92-1.78 (m, 2H); MS (APCI$^+$) m/z 588 [M+H2O]$^+$.

Example 5I: 5-{(7R)-3-[(benzyloxy)methoxy]-1-fluoro-7-methoxy-5,6,7,8-tetrahydronaphthalen-2-yl}-2-[(benzyloxy)methyl]-1λ$^6$,2,5-thiadiazolidine-1,1,3-trione Racemic material from Example 5H was purified via preparative SFC, performed on a Waters SFC80Q system running under ChromScope™ software control. The preparative SFC system was equipped with a CO$_2$ pump, modifier pump, automated back pressure regulator (ABPR), UV detector, and 6-position fraction collector. The mobile phase comprised of supercritical CO$_2$ supplied by a dewar of bone-dry non-certified CO$_2$ pressurized to 350 psi with a modifier of methanol at a flow rate of 80 g/minute. The column was at ambient temperature, and the backpressure regulator was set to maintain 120 bar. The sample was loaded into the modifier stream in 1 mL (50 mg) injections. The mobile phase was held isocratically at 30% co-solvent: CO$_2$. Fraction collection was threshold triggered. The instrument was fitted with a Diacel CHIRALPAK® 30 cm column with dimensions 30 mm i.d.×250 mm length with 5 m particles. Earlier-eluting fractions containing desired product were combined and concentrated, giving the title compound (97 mg, 0.17 mmol, 31% yield). Later-eluting fractions containing the opposite enantiomer were concentrated and used in Example 10. Characterization data were identical to the product of Example 5H and absolute stereochemistry was arbitrarily assigned.

Example 5J: 5-[(7R)-1-fluoro-3-hydroxy-7-methoxy-5,6,7,8-tetrahydronaphthalen-2-yl]-1λ$^6$,2,5-thiadiazolidine-1,1,3-trione A solution of the product of Example 5I (94 mg, 0.17 mmol) in tetrahydrofuran (2 mL) was added to 20% Pd(OH)$_2$/C, wet (190 mg), and the mixture was stirred at 60 psi hydrogen and 25° C. for 18 hours. The mixture was filtered, and the filtrate was concentrated. The residue was purified by preparative HPLC on a Phenomenex® Luna® C8(2) 5 μm 100 Å AXIA™ column (30 mm×225 mm). A gradient of acetonitrile (A) and 0.1% trifluoroacetic acid in water (B) was used, at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A). Samples were injected in 1.5 mL dimethyl sulfoxide:methanol (1:1). A custom purification system was used consisting of the following modules: Waters LC4000 preparative pump; Waters 996 diode-array detector; Waters 717+autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan Navigator using 70:30 methanol: 10 mM NH$_4$OH (aqueous) at a flow rate of 0.8 mL/minute. Loop-injection mass spectra were acquired using a Finnigan Navigator running Navigator 1.8 software and a Gilson 215 liquid handler for fraction injection controlled by an Abbott developed Visual Basic application. Fractions containing product were combined and lyophilized, giving Example 5J (34 mg, 0.10 mmol, 63% yield). Characterization data were identical to the final product from Example 11 and absolute stereochemistry was arbitrarily assigned.

Example 6: 5-[7-(2-cyclopropylethyl)-1-fluoro-3-hydroxy-5,6,7,8-tetrahydronaphthalen-2-yl]-1λ$^6$,2,5-thiadiazolidine-1,1,3-trione (Compound 105)

Example 6A: 5-(7-bromo-1-fluoro-3-hydroxynaphthalen-2-yl)-1λ$^6$,2,5-thiadiazolidine-1,1,3-trione A dry 250 mL round bottom flask was charged with the product of Example 1G (4 g, 8.60 mmol) and 1,2,3,4,5-pentamethylbenzene (2.55 g, 17.2 mmol). The vessel was purged with dry nitrogen for 5 minutes and then charged with CH$_2$Cl$_2$ (80 mL). The cloudy white suspension was cooled to −78° C. and a 1 M solution of trichloroborane (25.8 mL, 25.8 mmol) in CH$_2$Cl$_2$ was added dropwise over 15 minutes. The reaction was allowed to stir for 30 minutes after the addition was complete and then was quenched at −78° C. with ethyl acetate (30 mL) followed by the rapid addition of methanol (5.22 mL). The mixture was then slowly warmed to ambient temperature over 20 minutes under nitrogen. The volatiles were removed under reduced pressure to afford an off-white solid. The solid was slurried with ethyl acetate/heptanes (1:1, 30 mL), stirred for 5 minutes, and then isolated via filtration. The resulting solid was slurried with additional ethyl acetate:heptanes (1:1, 2×5 mL), then heptanes (2×5 mL) and again isolated via filtration. The resulting solids were dried to constant weight to afford the title compound (2.9 g, 7.73 mmol, 90% yield) as a white solid. $^1$H NMR (501 MHz, DMSO-$d_6$) δ ppm 10.89 (s, 1H), 8.09 (d, J=2.0 Hz, 1H), 7.78 (dd, J=9.0, 1.3 Hz, 1H), 7.64 (dd, J=8.8, 2.0 Hz, 1H), 7.15 (s, 1H), 4.50 (s, 2H).

Example 6B: 5-{7-[(E)-2-cyclopropylethenyl]-1-fluoro-3-hydroxynaphthalen-2-yl}-1$\lambda^6$,2,5-thiadiazolidine-1,1,3-trione To a solution of the product of Example 6A (0.134 g, 0.36 mmol) was added dioxane:water (3:1, 3.6 mL, 0.1 M) followed by (E)-2-(2-cyclopropylvinyl)-4,4,5,5-tetramethyl-1,3,2-dioxaborolane (0.139 g, 0.714 mmol) and potassium carbonate (0.148 g, 1.072 mmol). This suspension was sparged with N2 for 10 minutes, and then 1,1'-bis(di-tert-butylphosphino)ferrocene palladium dichloride was added. Sparging was continued for 5 minutes, and then the biphasic suspension was heated at 80° C. for 12 hours. The mixture was allowed to cool to ambient temperature, and the volatiles were removed under reduced pressure. The resulting residue was purified over $SiO_2$ (0-25% methanol in ethyl acetate) to yield the title compound (0.048 g, 0.132 mmol, 37%). MS (ESI$^-$) m/z 361 [M−H]$^-$.

Example 6C: 5-[7-(2-cyclopropylethyl)-1-fluoro-3-hydroxy-5,6,7,8-tetrahydronaphthalen-2-yl]-1$\lambda^6$,2,5-thiadiazolidine-1,1,3-trione The product of Example 6B (0.048 g, 0.132 mmol) and trifluoroethanol (2 mL) were added to 10% Pd/C, dry (0.014 g, 0.132 mmol) in a 20 mL Parr® Barnstead Hastelloy C reactor. The mixture was allowed to stir for 86 hours under hydrogen (158 psi) at 25° C. The reaction mixture was filtered, and the filter-cake was washed with methanol. The filtrate was concentrated under reduced pressure to yield crude product which was purified by reverse phase HPLC (Phenomenex® C8(2) Luna® 5 μm AXIA™ 150×30 mm, acetonitrile in water (containing 0.1% trifluoroacetic acid) 3% to 100% gradient over 18 minutes (3 mL/minute to 100 mL/minute) to give the title compound (0.013 g, 27%). $^1$H NMR (400 MHz, DMSO-$d_6$) δ ppm 6.37 (s, 1H), 3.89 (s, 2H), 2.76-2.55 (m, 3H), 2.06-1.95 (m, 1H), 1.83-1.75 (m, 1H), 1.66-1.47 (m, 1H), 1.39 (q, J=7.0 Hz, 2H), 1.30-1.18 (m, 3H), 0.64 (pd, J=7.3, 3.7 Hz, 1H), 0.40-0.30 (m, 2H), −0.07 (d, J=4.5 Hz, 2H); MS (ESI$^-$) m/z 367 [M−H]$^-$.

Example 7: 5-[1-fluoro-3-hydroxy-7-(2-methoxyethoxy)-5,6,7,8-tetrahydronaphthalen-2-yl]-1$\lambda^6$,2,5-thiadiazolidine-1,1,3-trione (Compound 106)

Example 7A: 5-[3-(benzyloxy)-1-fluoro-7-(2-methoxyethoxy)naphthalen-2-yl]-1$\lambda^6$,2,5-thiadiazolidine-1,1,3-trione A mixture of the product of Example 1H (97 mg, 0.24 mmol), 1-bromo-2-methoxyethane (66.7 mg, 0.480 mmol) and cesium carbonate (180 mg, 0.552 mmol) in N,N-dimethylformamide (0.8 mL) was stirred at 75° C. for 40 minutes. The solution was filtered and concentrated under reduced pressure. The residue was purified by flash column chromatography on silica gel eluted with dichloromethane, then dichloromethane:methanol (10:1) to give the title compound (100 mg, 0.217 mmol, 90% yield). $^1$H NMR (400 MHz, DMSO-$d_6$) δ ppm 7.76 (d, J=8 Hz, 1H), 7.56 (d, J=8 Hz, 2H), 7.37 (t, J=8 Hz, 2H), 7.32 (m, 1H), 7.30 (br s, 1H), 7.25 (d, J=2 Hz, 1H), 7.21 (dd, J=8, 2 Hz, 1H), 5.21 (s, 2H), 4.21 (m, 2H), 4.08 (s, 2H), 3.72 (m, 2H), 3.33 (s, 3H); MS (ESI$^-$) m/z 459 [M−H]$^-$.

Example 7B: 5-[1-fluoro-3-hydroxy-7-(2-methoxyethoxy)-5,6,7,8-tetrahydronaphthalen-2-yl]-1$\lambda^6$,2,5-thiadiazolidine-1,1,3-trione A solution of Example 7A (320 mg, 0.695 mmol) in acetic acid (4 mL) was placed in a 20 mL Parr® Barnstead Hastelloy C reactor. 10% Pd/C, (320 mg, 3.01 mmol) was added, and the mixture was stirred at 25° C. under an atmosphere of 140 psi of hydrogen for 15 hours. The reaction mixture was filtered and concentrated. The residue was purified by preparative HPLC on a Phenomenex® C8(2) Luna® 5 μm AXIA™ 150×30 mm column eluted with acetonitrile (A) and 10 mM ammonium acetate in water (B) at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound (30 mg, 0.080 mmol, 11.53% yield). $^1$H NMR (400 MHz, DMSO-$d_6$) δ ppm 6.42 (d, J=1.4 Hz, 1H), 3.93 (s, 2H), 3.79-3.69 (m, 1H), 3.66-3.52 (m, 2H), 3.44 (t, J=4.8 Hz, 2H), 3.24 (s, 3H), 2.82 (dd, J=16.6, 4.9 Hz, 1H), 2.80-2.68 (m, 1H), 2.66-2.51 (m, 1H), 2.46 (dd, J=16.4, 6.4 Hz, 1H), 1.88-1.80 (m, 1H), 1.78-1.69 (m, 1H); MS (APCI$^-$) m/z 373.2 [M−H]$^-$.

Example 8: 5-[7-(cyclopropylmethoxy)-1-fluoro-3-hydroxy-5,6,7,8-tetrahydronaphthalen-2-yl]-1$\lambda^6$,2,5-thiadiazolidine-1,1,3-trione (Compound 107)

Example 8A: 5-[3-(benzyloxy)-7-(cyclopropylmethoxy)-1-fluoronaphthalen-2-yl]-1$\lambda^6$,2,5-thiadiazolidine-1,1,3-trione A mixture of Example 1H (300 mg, 0.746 mmol), cesium carbonate (486 mg, 1.491 mmol) and (bromomethyl)cyclopropane (151 mg, 1.118 mmol) in N,N-dimethyl formamide (DMF) (3 mL) was stirred at room temperature for 2 hours. Then 2 N $Na_2CO_3$ (1.5 mL) was added, and the reaction mixture was extracted with ethyl acetate (20 mL). The organic layer was discarded. The aqueous layer was acidified with 2 N HCl to pH 1-2 and extracted with ethyl acetate (3×25 mL). The combined organic fractions were washed with brine, dried over $Na_2SO_4$, and concentrated to give the title compound (230 mg, 0.504 mmol, 67.6% yield) which was used in the next step without further purification. $^1$H NMR (400 MHz, DMSO-$d_6$) δ ppm 7.77 (dd, J=9.0, 1.5 Hz, 1H), 7.52-7.41 (m, 2H), 7.40-7.27 (m, 4H), 7.25 (dd, J=9.0, 2.6 Hz, 1H), 7.20 (d, J=2.6 Hz, 1H), 5.20 (s, 2H), 4.46 (s, 2H), 3.92 (d, J=7.0 Hz, 2H), 1.31-1.17 (m, 1H), 0.61-0.50 (m, 2H), 0.38-0.29 (m, 2H); MS (APCI$^+$) m/z 457.0 [M+H]$^+$.

Example 8B: 5-[7-(cyclopropylmethoxy)-1-fluoro-3-hydroxy-5,6,7,8-tetrahydronaphthalen-2-yl]-1$\lambda^6$,2,5-thiadiazolidine-1,1,3-trione The title compound was prepared from Example 8A using the procedure described in Example 7B. $^1$H NMR (501 MHz, DMSO-$d_6$) δ ppm 6.42 (s, 1H), 3.93 (s, 2H), 3.73 (m, 1H), 3.31 (dd, J=6.8, 4.1 Hz, 2H), 2.82 (dd, J=16.5, 4.9 Hz, 1H), 2.73 (m, 1H), 2.65-2.52 (m, 1H), 2.45 (m, 1H), 1.85 (m, 1H), 1.71 (m, 1H), 1.04-0.93 (m, 1H), 0.48-0.39 (m, 2H), 0.16 (m, 2H). MS (APCI⁻) m/z 369.2 [M−H]⁻.

Example 9: 5-(1-fluoro-3-hydroxy-5,6,7,8-tetrahydronaphthalen-2-yl)-1λ⁶,2,5-thiadiazolidine-1,1,3-trione (Compound 108)

The product of Example 1H (1.0 g, 2.49 mmol) and acetic acid (16.2 mL) were added to 10% Pd/C, dry (1.0 g, 9.4 mmol) in a 25 mL Parr® Barnstead Hastelloy C reactor, and the mixture was stirred for 48 hours under hydrogen (140 psi) at 25° C. The mixture was then filtered through a pad of diatomaceous earth, and the volatiles were removed from the filtrate under reduced pressure to afford a crude residue (900 mg). A portion of the crude residue (600 mg) was purified by preparative HPLC [Waters XBridge™ C18 5 μm OBD column, 50×100 mm, flow rate 90 mL/minute, 3-100% gradient of acetonitrile in buffer (0.1% trifluoroacetic acid)] to give the title compound (23 mg, 0.077 mmol, 5% yield). $^1$H NMR (400 MHz, DMSO-d₆) δ ppm 6.46 (s, 1H), 4.33 (s, 2H), 2.67-2.60 (m, 2H), 2.56-2.51 (m, 2H), 1.69 (h, J=5.5, 4.8 Hz, 4H); MS (APCI⁻) m/z 299 [M−H]⁻.

Example 10: 5-[(7S)-1-fluoro-3-hydroxy-7-methoxy-5,6,7,8-tetrahydronaphthalen-2-yl]-1λ⁶,2,5-thiadiazolidine-1,1,3-trione (Compound 109)

Fractions from the later-eluting peak from Example 5I were concentrated, giving 5-{(7S)-3-[(benzyloxy)methoxy]-1-fluoro-7-methoxy-5,6,7,8-tetrahydronaphthalen-2-yl}-2-[(benzyloxy)methyl]-1λ⁶,2,5-thiadiazolidine-1,1,3-trione (88 mg, 0.15 mmol, 28% yield). This material was subjected to hydrogenolysis according to the procedure from Example 5J, giving the title compound (30 mg, 0.091 mmol, 60% yield). Characterization data were identical to the final product from Example 11 and absolute stereochemistry was arbitrarily assigned.

Example 11: 5-(1-fluoro-3-hydroxy-7-methoxy-5,6,7,8-tetrahydronaphthalen-2-yl)-1λ⁶,2,5-thiadiazolidine-1,1,3-trione (Compound 110)

A solution of the product of Example 5G (203 mg, 0.622 mmol) in acetic acid (2 mL) was added to 10% Pd/C, dry (209 mg). The mixture was stirred for 13 hours under 24 psi hydrogen pressure and 25° C. After filtration, the filtrate was concentrated to a minimal volume. The residue was purified by preparative HPLC on 2-coupled Phenomenex® C8(2) Luna® 5 μm AXIA™ 100 Å columns (30 mm×150 mm each). A gradient of acetonitrile (A) and 10 mM ammonium acetate in water (B) was used at a flow rate of 50 mL/minute (0-0.5 minute 5% A, 0.5-8.5 minutes linear gradient 05-100% A, 8.7-10.7 minutes 100% A, 10.7-11 minutes linear gradient 100-05% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. Fractions containing the desired product were concentrated and methanol (5 mL) was added. The slurry was sonicated and filtered. The collected solid was washed with methanol (2×1 mL) and dried in a vacuum oven at 50° C. giving the title compound (19.3 mg, 0.058 mmol, 9.4% yield). $^1$H NMR (501 MHz, methanol-d₄) δ ppm 6.48 (s, 1H), 4.56 (s, 1H), 4.24 (s, 2H), 3.72-3.64 (m, 1H), 3.40 (s, 3H), 2.93 (dd, J=16.7, 5.0 Hz, 1H), 2.84 (dt, J=17.2, 6.4 Hz, 1H), 2.69 (dt, J=17.0, 6.8 Hz, 1H), 2.59 (dd, J=16.6, 6.6 Hz, 1H), 2.02-1.93 (m, 1H), 1.82 (ddt, J=12.7, 8.0, 4.0 Hz, 1H); MS (ESI⁻) m/z 329 [M−H]⁻.

Example 12: 5-(5-fluoro-7-hydroxy-3,4-dihydro-2H-1-benzopyran-6-yl)-1λ⁶,2,5-thiadiazolidine-1,1,3-trione (Compound 111)

Example 12A: 1-(benzyloxy)-5-bromo-3-fluoro-2-nitrobenzene

To a suspension of 5-bromo-1,3-difluoro-2-nitrobenzene (40 g, 168 mmol) and benzyl alcohol (18.4 mL, 176 mmol) in tetrahydrofuran (800 mL) at −60° C. was added a solution of potassium tert-butoxide (176 mL, 176 mmol, 1 M in tetrahydrofuran) slowly along the side of the flask so that the internal temperature remained below −50° C. After complete addition, the mixture was stirred for 5 minutes, then was quenched with saturated aqueous ammonium chloride (40 mL), diluted with water (200 mL) and ethyl acetate (200 mL) and warmed to room temperature. The aqueous layer was extracted with ethyl acetate (200 mL). The combined organic fractions were washed with brine (160 mL), dried over anhydrous sodium sulfate, filtered and concentrated in vacuo to give a solid. Heptanes (500 mL) were added to the crude solid, the mixture was heated to an internal temperature of 65° C., then slowly cooled to room temperature, and the solids were collected by filtration. The solids were washed with the cold mother liquor and additional heptane (120 mL) and then were dried in a vacuum oven at 60° C. to constant weight to give 39.95 g of the title compound. The mother liquor was concentrated and then solids were precipitated from heptanes (100 mL) to give an additional 7.56 g of the title compound. Total recovery of the title compound was 47.5 g 146 mmol, 87% yield. $^1$H NMR (400 MHz, DMSO-d₆) δ ppm 7.63 (t, J=1.7 Hz, 1H), 7.57 (dd, J=9.3, 1.7 Hz, 1H), 7.46-7.32 (m, 5H), 5.36 (s, 2H).

Example 12B: 2-(benzyloxy)-4-bromo-6-fluoroaniline

To a suspension of the product from Example 12A (5.68 g, 17.4 mmol) and zinc dust (5.70 g, 87 mmol) in a mixture of tetrahydrofuran (56.8 mL) and methanol (56.8 mL) was added saturated aqueous ammonium chloride (28.4 mL) slowly via addition funnel so that the internal temperature remained below 30° C. After stirring vigorously for 1 hour, the mixture was filtered through Celite® (5 g), and the solids were washed with ethyl acetate (56.8 mL). The filtrate was washed with brine (56.8 mL), and then the aqueous layer was extracted with ethyl acetate (28.4 mL). The combined organic layers were washed with water (28.4 mL), then brine (22.7 mL), dried over anhydrous sodium sulfate, filtered and concentrated in vacuo to give the title compound (5.2 g, 17.5 mmol, 100% yield) which was used for the next step without purification. $^1$H NMR (400 MHz, DMSO-d₆) δ ppm 7.52-

7.45 (m, 2H), 7.43-7.36 (m, 2H), 7.36-7.30 (m, 1H), 6.99-6.93 (m, 2 h), 5.16 (s, 2H), 4.83 (s, 2H); MS (ESI⁺) m/z 296 [M+H]⁺.

Example 12C: N-(2-(benzyloxy)-4-bromo-6-fluorophenyl)-2,2,2-trifluoroacetamide

To a solution of the product from Example 12B (5.6 g, 18.96 mmol) and pyridine (2.30 mL, 28.4 mmol) in acetonitrile (56 mL) at an internal temperature below 16° C. was added trifluoroacetic anhydride (3.48 mL, 24.6 mmol) slowly. After 5 minutes, the reaction mixture was diluted with dichloromethane (56 mL) and water (56 mL). The aqueous layer was extracted with dichloromethane (28 mL), and the combined organic layers were washed with brine (28 mL), dried over anhydrous sodium sulfate, filtered and concentrated in vacuo to give the title compound (7.41 g, 18.9 mmol, 100% yield) which was used for the next step without purification. ¹H NMR (400 MHz, DMSO-$d_6$) δ ppm 11.04 (s, 1H), 7.45-7.29 (m, 8H), 5.24 (s, 2H); MS (ESI⁻) m/z 390 [M–H]⁻.

Example 12D: methyl 2-(N-(2-(benzyloxy)-4-bromo-6-fluorophenyl)-2,2,2-trifluoroacetamido)acetate To a suspension of the product from Example 12C (7.40 g, 18.9 mmol) and potassium carbonate (7.82 g, 56.6 mmol) in dimethylformamide (37 mL) was added methyl bromoacetate (2.09 mL, 22.6 mmol). The resulting suspension was heated to an internal temperature of 60° C. for 30 minutes, then cooled to room temperature and quenched with 1 M hydrochloric acid (74 mL). The crude aqueous mixture was extracted with ethyl acetate (74 mL, 2×37 mL), and the combined organic layers were washed with saturate aqueous ammonium chloride (2×37 mL), followed by brine (37 mL), dried over sodium sulfate, filtered and concentrated in vacuo to give the crude title compound (9.130 g, 19.67 mmol, 104% yield) which was used for the next step without purification assuming (100% yield). ¹H NMR (400 MHz, DMSO-$d_6$) δ ppm 7.47-7.30 (m, 7H), 5.25 (d, J=11.8 Hz, 1H), 5.21 (d, J=11.9 Hz, 1H), 4.52 (d, J=17.0 Hz, 1H), 4.29 (d, J=17.0 Hz, 1H), 3.60 (s, 3H); MS (ESI⁻) m/z 481 [M–H]⁻.

Example 12E: methyl 2-((2-(benzyloxy)-4-bromo-6-fluorophenyl)amino)acetate

To a solution of the product from Example 12D (8.76 g, 18.87 mmol) in methanol (76.8 mL) was added a solution of sodium methoxide (10.8 mL, 47.2 mmol, 25 weight % in methanol), and the resulting solution was heated to an internal temperature of 60° C. After 10 minutes, the reaction mixture was cooled to room temperature, diluted with ethyl acetate (87.6 mL), quenched with saturated aqueous ammonium chloride (17.5 mL) and diluted with water (43.8 mL). The aqueous layer was extracted with ethyl acetate (2×43.8 mL), and the combined organic layers were washed with brine (26.3 mL), dried over sodium sulfate, filtered and concentrated in vacuo to give the crude title compound (7.281 g, 19.77 mmol, 105% yield) that was used for the next step without purification, assuming 100% yield. ¹H NMR (400 MHz, DMSO-$d_6$) δ ppm 7.49-7.45 (m, 2H), 7.44-7.38 (m, 2H), 7.37-7.32 (m, 1H), 7.02-7.00 (m, 1H), 6.98 (dd, J=11.8, 2.2 Hz, 1H), 5.22 (td, J=6.9, 2.7 Hz, 1H), 5.16 (s, 2H), 4.04 (dt, J=7.0, 3.8 Hz, 2H), 3.59 (s, 3H); MS (ESI⁺) m/z 368 [M+H]⁺.

Example 12F: methyl 2-((2-(benzyloxy)-4-bromo-6-fluorophenyl)(N-(tert-butoxycarbonyl)sulfamoyl)amino)acetate To a solution of chlorosulfonyl isocyanate (2.46 mL, 28.3 mmol) in dichloromethane at 0° C. was added tert-butanol (2.71 mL, 28.3 mmol) slowly so that the internal temperature remained below 10° C. After stirring for 30 minutes, a preformed solution of the product from Example 12E (6.95 g, 18.88 mmol) and triethylamine (5.26 mL, 37.8 mmol) in dichloromethane (27.8 mL) were added dropwise via addition funnel so that the internal temperature did not rise above 10° C. After 30 minutes, the reaction mixture was warmed to room temperature and then quenched with water (70 mL). The layers were separated and the aqueous layer was extracted with dichloromethane (2×35 mL). The combined organic layers were washed with 1 M aqueous sodium bisulfate (40 mL), dried over sodium sulfate, filtered and concentrated in vacuo. The crude solid was precipitated from 1:1 heptanes/ethyl acetate (24 mL), washed with cold heptanes (21 mL) and dried in a vacuum oven at 60° C. to constant weight to give the title compound (9.8188 g, 17.94 mmol, 95% yield). ¹H NMR (400 MHz, DMSO-$d_6$) δ ppm 11.31 (s, 1H), 7.48-7.41 (m, 2H), 7.40-7.34 (m, 2H), 7.34-7.26 (m, 1H), 7.22 (dd, J=9.0, 2.1 Hz, 1H), 7.15 (t, J=1.8 Hz, 1H), 5.24 (d, J=13.0 Hz, 1H), 5.18 (d, J=13.0 Hz, 1H), 4.60 (d, J=17.8 Hz, 1H), 4.34 (d, J=17.8 Hz, 1H), 3.52 (s, 3H), 1.28 (s, 9H); MS (ESI⁻) m/z 545 [M–H]⁻.

Example 12G: methyl 2-((2-(benzyloxy)-4-bromo-6-fluorophenyl)(sulfamoyl)amino)acetate To a solution of the product from Example 12F (25.1 g, 45.9 mmol) in dichloromethane (100 mL) was added trifluoroacetic acid (53.0 mL, 688 mmol). After 30 minutes, the reaction was diluted with chloroform (125 mL) and concentrated in vacuo. The crude residue was diluted with ethyl acetate (150 mL) and quenched with saturated aqueous disodium phosphate (200 mL) to a final pH of 7. The layers were separated, and the aqueous layer was extracted with ethyl acetate (125 mL). The combined organic layers were washed with brine (75 mL), dried over sodium sulfate, filtered and concentrated to give the title compound (21.76 g, 48.7 mmol, 106% yield) as a thick yellow syrup, which was used for the next step without purification assuming 100% yield. ¹H NMR (500 MHz, DMSO-$d_6$) δ ppm 7.53-7.49 (m, 2H), 7.43-7.39 (m, 2H), 7.37-7.32 (m, 1H), 7.24-7.18 (m, 2H), 7.06 (s, 2H), 5.21 (s, 2H), 4.40 (d, J=17.8 Hz, 1H), 4.22 (d, J=17.8 Hz, 1H), 3.57 (s, 3H); MS (ESI⁺) m/z 447 [M+H]⁺.

Example 12H: 5-[2-(benzyloxy)-4-bromo-6-fluorophenyl]-1λ⁶,2,5-thiadiazolidine-1,1,3-trione To a solution of the product from Example 12G (29.769 g, 66.6 mmol) in tetrahydrofuran (300 mL) was added a solution of sodium methoxide (22.8 mL, 100 mmol, 25 weight % in methanol) slowly via syringe. After 30 minutes, the reaction was quenched with 1 M hydrochloric acid (150 mL), and extracted with ethyl acetate (3×150 mL). The combined organic layers were washed with brine (90 mL), dried over sodium sulfate, filtered and concentrated. The residue was dissolved in ethyl acetate (180 mL) by heating to 80° C. Heptanes (90 mL) were added dropwise via addition funnel while maintaining the temperature. Upon complete addition, the suspension was slowly cooled to room temperature, and the resulting solid collected by filtration and dried in a vacuum oven at 50° C. to constant weight to give the title compound (17.564 g, 42.3 mmol, 64% yield). $^{1}$H NMR (400 MHz, DMSO-$d_6$) δ ppm 7.53-7.46 (m, 2H), 7.40-7.25 (m, 3H), 7.22-7.15 (m, 2H), 7.13 (s, 4H), 5.19 (s, 2H), 3.95 (s, 2H); MS (ESI$^-$) m/z 414 [M−H]$^-$.

Example 12I: 5-[6-(benzyloxy)-4-bromo-2-fluoro-3-(prop-2-en-1-yl)phenyl]-1λ$^6$,2,5-thiadiazolidine-1,1,3-trione To a solution of 2,2,6,6-tetramethylpiperidine (0.474 mL, 3.13 mmol) in tetrahydrofuran (5 mL) at 0° C. was added a solution of n-butyllithium (1.2 mL, 3 mmol, 2.5 M in hexane) slowly over 5 minutes. The resulting solution was stirred for 30 minutes, then cooled to an internal temperature of −78° C., and a solution of the product from Example 12H (0.5 g, 1.204 mmol) in tetrahydrofuran (2.5 mL) was slowly added along the side of the flask so that the internal temperature remained below −65° C., followed by N,N,N',N'-tetramethylethylenediamine (0.200 mL, 1.325 mmol). The resulting red solution was stirred for 1 hour at −78° C., and then allyl bromide (0.11 mL, 1.271 mmol) was added via syringe. The resulting solution was allowed to slowly warm to room temperature overnight, then quenched with 1 M hydrochloric acid, and diluted with ethyl acetate. The layers were separated, and the aqueous layer was extracted with ethyl acetate (2×). The combined organic layers were washed with brine, dried over sodium sulfate, filtered and concentrated in vacuo. The residue was dissolved in dichloromethane, triethylamine (0.336 mL, 2.408 mmol) was added, and the crude material was loaded onto a 40 g Gold® Teledyne ISCO column, then purified by column chromatography with a gradient of 0-10% methanol in dichloromethane (with 0.1% triethylamine added) to give the title compound as a triethylamine salt (0.3915 g, 0.352 mmol, 29.2% yield). $^{1}$H NMR (400 MHz, DMSO-$d_6$) δ ppm 7.53-7.04 (m, 6H), 5.90-5.70 (m, 1H), 5.14 (s, 2H), 5.01 (dt, J=10.1, 1.7 Hz, 1H), 4.95 (dt, J=17.2, 1.9 Hz, 1H), 3.92 (s, 2H), 3.43-3.35 (m, 2H); MS (ESI$^-$) m/z 454 [M−H]$^-$.

Example 12J: 5-[6-(benzyloxy)-4-bromo-2-fluoro-3-(3-hydroxypropyl)phenyl]-1λ$^6$,2,5-thiadiazolidine-1,1,3-trione To a solution of the product from Example 12I (0.3910 g, 0.703 mmol, triethylamine salt) in tetrahydrofuran (7.8 mL) was added a solution of 9-borabicyclo[3.3.1]nonane (3.4 mL, 1.7 mmol, 0.5 M in tetrahydrofuran) slowly over 5 minutes. After 2 hours, the reaction mixture was cooled to 0° C. and 1 M aqueous sodium hydroxide (1.7 mL, 1.7 mmol) was added slowly so that the internal temperature remained below 6° C., followed by dropwise addition of aqueous hydrogen peroxide (0.301 mL, 4.92 mmol, 50 weight % in water) so that the internal temperature remained below 15° C. After 1 hour, the reaction mixture was quenched by adding 1 M hydrochloric acid, followed by 1 M aqueous sodium thiosulfate. The crude mixture was extracted with ethyl acetate (3×), and the combined organic layers were washed with brine, dried over sodium sulfate, filtered and concentrated in vacuo. The residue was dissolved in 1:1 dichloromethane/acetonitrile and triethylamine (0.196 mL, 1.405 mmol) was added, then the solution was loaded onto a 40 g Gold® Teledyne ISCO column and was purified by running a gradient of 0-10% methanol in dichloromethane (with 0.1% triethylamine added) to give the title compound as the triethylamine salt (0.2796 g, 0.487 mmol, 69.3% yield). $^{1}$H NMR (501 MHz, DMSO-$d_6$) δ ppm 7.51-7.44 (m, 2H), 7.39-7.27 (m, 3H), 7.23-7.14 (m, 1H), 4.54 (t, J=5.1 Hz, 1H), 5.16 (s, 2H), 3.96 (s, 2H), 3.44 (q, J=6.2 Hz, 2H), 2.66 (td, J=8.0, 2.1 Hz, 2H), 1.66-1.56 (m, 2H); MS (ESI$^-$) m/z 471 [M−H]$^-$.

Example 12K: 5-[7-(benzyloxy)-5-fluoro-3,4-dihydro-2H-1-benzopyran-6-yl]-1λ$^6$,2,5-thiadiazolidine-1,1,3-trione In a 20 mL pressure release vial, to a mixture of cesium carbonate (0.381 g, 1.170 mmol), 2-di(tert-butyl)phosphino-2',4',6'-triisopropyl-3-methoxy-6-methylbiphenyl (RockPhos, 9 mg, 0.019 mmol), and [(2-di-tert-butylphosphino-3-methoxy-6-methyl-2',4',6'-triisopropyl-1,1'-biphenyl)-2-(2-aminobiphenyl)]palladium(II) methanesulfonate (RockPhos Pd G3 precatalyst, 16 mg, 0.019 mmol) was added a suspension of the product from Example 12J (0.224 g, 0.390 mmol, triethylamine salt) in N,N-dimethylacetamide (6.5 mL). The resulting suspension was degassed by 5 cycles of vacuum and nitrogen backfills, and then heated to 100° C. After 4 hours the reaction mixture was cooled to room temperature and quenched with 1 M hydrochloric acid. The crude mixture was extracted with ethyl acetate (3×). Then the combined organic layers were washed with saturated aqueous ammonium chloride (3×) and brine. The combined aqueous layers were back extracted with ethyl acetate, and the combined organic layers were dried over sodium sulfate, filtered and concentrated in vacuo to give the crude title compound as an orange oil, which was used for the next step without purification. MS (APCI$^-$) m/z 391 [M−H]$^-$.

Example 12L: 5-(5-fluoro-7-hydroxy-3,4-dihydro-2H-1-benzopyran-6-yl)-1λ$^6$,2,5-thiadiazolidine-1,1,3-trione To a suspension of the product of Example 12K (0.191 g, 0.487 mmol) and pentamethylbenzene (0.144 g, 0.973 mmol) in dichloromethane (3.8 mL) at −78° C. was added a solution boron trichloride (1.46 mL, 1.46 mmol, 1 M in dichloromethane) slowly along the side of the flask so that the internal temperature did not rise above −70° C. Upon complete addition, the cooling bath was removed, and the reaction mixture was allowed to warm to 0° C., then re-cooled to −78° C. and quenched with ethyl acetate (2 mL), followed by ethanol (2 mL) and warmed to room temperature. The crude reaction mixture was concentrated in vacuo to give a residue which was triturated with heptanes (3×5 mL) and 1:1 heptanes/ethyl acetate (2×5 mL). The solid was further purified by reverse phase preparative HPLC on a Phenomenex® Luna® C8(2) 5 μm 100 Å AXIA™ column (30 mm×75 mm) using a gradient of acetonitrile (A) and 10 mM ammonium acetate in water (B), at a flow rate of 50 mL/minute (0-1.0 minute 5% A, 1.0-8.5 minutes linear gradient 5-100% A, 8.5-11.5 minutes 100% A, 11.5-12.0 minutes linear gradient 95-5% A) to give the title compound as the ammonium salt (13.0 mg, 0.041 mmol, 8.4% yield). $^{1}$H NMR (400 MHz, DMSO-$d_6$) δ ppm 6.08 (d, J=1.8 Hz, 1H), 4.07 (dd, J=5.9, 4.2 Hz, 2H), 3.89 (s, 2H), 2.55 (t, J=6.4 Hz, 2H), 1.86 (qd, J=6.4, 4.1 Hz, 2H); MS (ESI$^-$) m/z 301 [M−H]$^-$.

Example 13: 5-(5-fluoro-7-hydroxy-2,2-dimethyl-3,4-dihydro-2H-1-benzopyran-6-yl)-1λ$^6$,2,5-thiadiazolidine-1,1,3-trione (Compound 112)

Example 13A: 5-[6-(benzyloxy)-4-bromo-2-fluoro-3-(3-methylbut-2-en-1-yl)phenyl]-1λ$^6$,2,5-thiadiazolidine-1,1,3-trione To a solution of 2,2,6,6-tetramethylpiperidine (0.949 mL, 6.26 mmol) in tetrahydrofuran (10 mL) at 0° C. was added a solution of n-butyllithium (1.2 mL, 3 mmol, 2.5 M in hexane) slowly over 5 minutes. The resulting solution was stirred for 30 minutes then cooled to an internal temperature of −78° C., and a solution of the product from Example 12H (1.0 g, 2.4 mmol) in tetrahydrofuran (5 mL) was added slowly along the side of the flask so that the internal temperature remained below −65° C., followed by N,N,N', N'-tetramethylethylenediamine (0.400 mL, 2.65 mmol). The resulting solution was stirred for 1 hour at −78° C., and then 1-bromo-3-methylbut-2-ene (0.623 mL, 4.82 mmol, 90% purity) was added via syringe. The resulting solution was allowed to slowly warm to room temperature overnight, then quenched with 1 M hydrochloric acid, and diluted with ethyl acetate. The layers were separated, and the aqueous layer was extracted with ethyl acetate (2×). The combined organic layers were washed with brine, dried over sodium sulfate, filtered and concentrated in vacuo. The residue was dissolved in dichloromethane, triethylamine (0.336 mL, 2.408 mmol) was added, and the material was loaded onto a 80 g Gold® Teledyne ISCO column, then purified by column chromatography with a gradient of 0-10% methanol in dichloromethane (with 0.1% triethylamine added) to give the title compound as a triethylamine salt (0.5033 g, 0.861 mmol, 35.8% yield). $^1$H NMR (400 MHz, DMSO-d$_6$) δ ppm 7.65-7.08 (m, 6H), 5.74 (s, 1H), 5.19 (s, 2H), 3.96 (s, 2H), 3.40-3.33 (m, 2H), 1.73 (s, 3H), 1.65 (s, 3H); MS (ESI$^-$) m/z 483 [M−H]$^-$.

Example 13B: 5-[6-(benzyloxy)-2-fluoro-4-hydroxy-3-(3-methylbut-2-en-1-yl)phenyl]-1λ$^6$,2,5-thiadiazolidine-1,1,3-trione In a 20 mL pressure release vial, cesium carbonate (0.785 g, 2.41 mmol), 2-di(tert-butyl)phosphino-2',4',6'-triisopropyl-3-methoxy-6-methylbiphenyl (RockPhos, 19 mg, 0.040 mmol), and [(2-di-tert-butylphosphino-3-methoxy-6-methyl-2',4',6'-triisopropyl-1,1'-biphenyl)-2-(2-aminobiphenyl)]palladium(II) methanesulfonate (RockPhos Pd G3 precatalyst, 34 mg, 0.040 mmol) were added to a suspension of the product from Example 13A (0.4693 g, 0.803 mmol, triethylamine salt) in N,N-dimethylacetamide (9.4 mL) followed by water (0.145 mL, 8.03 mmol). The resulting suspension was degassed by putting the vial under vacuum and then backfilling with nitrogen through 5 cycles. The reaction mixture was then heated to 90° C. After 7 hours the reaction mixture was cooled to room temperature and quenched with 1 M hydrochloric acid. The crude mixture was extracted with ethyl acetate (3×), then the combined organic layers were washed with saturated aqueous ammonium chloride (3×) and brine. The combined aqueous layers were back extracted with ethyl acetate, and the combined organic layers were dried over sodium sulfate, filtered and concentrated in vacuo. The residue was dissolved in dichloromethane, triethylamine (0.336 mL, 2.408 mmol) was added, and the crude material was loaded onto a 24 g Gold® Teledyne ISCO column, then purified by column chromatography with a gradient of 0-10% methanol in dichloromethane (with 0.1% triethylamine added) to give the title compound as a triethylamine salt (0.5033 g, 0.861 mmol, 35.8% yield). $^1$H NMR (400 MHz, DMSO-d$_6$) δ ppm 7.55-7.43 (m, 3H), 7.34 (ddt, J=10.1, 7.5, 2.7 Hz, 3H), 7.31-7.20 (m, 2H), 6.34 (d, J=1.5 Hz, 1H), 5.04 (s, 2H), 3.89 (s, 2H), 3.36-3.30 (m, 2H), 1.68 (d, J=1.3 Hz, 3H), 1.62 (d, J=1.5 Hz, 3H); MS (ESI$^-$) m/z 419 [M−H]$^-$.

Example 13C: 5-[3-(3-chloro-3-methylbutyl)-2-fluoro-4,6-dihydroxyphenyl]-1λ$^6$,2,5-thiadiazolidine-1,1,3-trione To a suspension of the product of Example 13B (0.2428 g, 0.465 mmol) and pentamethylbenzene (0.138 g, 0.931 mmol) in dichloromethane (5 mL) at −78° C. was added a solution boron trichloride (2.79 mL, 2.79 mmol, 1 M in dichloromethane) slowly along the side of the flask so that the internal temperature did not rise above −70° C. Upon complete addition, the cooling bath was removed and the reaction mixture was allowed to warm to 0° C. Then the mixture was re-cooled to −78° C. and quenched with ethyl acetate (1 mL) followed by ethanol (1 mL) and warmed to room temperature. The crude reaction mixture was concentrated in vacuo, and the residue was triturated with heptanes (3×5 mL) to give the title compound which was used without further purification for the next step. MS (APCI$^-$) m/z 365 [M−H]$^-$.

Example 13D: 5-(5-fluoro-7-hydroxy-2,2-dimethyl-3,4-dihydro-2H-1-benzopyran-6-yl)-1λ$^6$,2,5-thiadiazolidine-1,1,3-trione To a solution of the product of Example 13C (0.171 g, 0.465 mmol) in acetonitrile (5 mL) was added silver trifluoromethanesulfonate (0.239 g, 0.931 mmol), and the resulting suspension was heated to an internal temperature of 80° C. After 15 hours, the mixture was cooled to room temperature, diluted with methanol and filtered through diatomaceous earth. The solid was washed extensively with 1:1 methanol/acetonitrile, and the filtrate was concentrated in vacuo. The residue was purified by reverse phase preparative HPLC, Waters XBridge™ C18 5 m OBD column, 50×100 mm, flow rate 100 mL/minute, gradient of 5-40% acetonitrile in buffer (0.025 M aqueous ammonium bicarbonate, adjusted to pH 10 with ammonium hydroxide) observing at 210 nm to give the title compound as the ammonium salt (0.009 g, 0.026 mmol, 5.57% yield). $^1$H NMR (400 MHz, DMSO-d$_6$) δ ppm 6.04 (d, J=1.8 Hz, 1H), 3.89 (s, 2H), 2.55 (t, J=6.8 Hz, 2H), 1.71 (t, J=6.8 Hz, 2H), 1.25 (s, 6H); MS (ESI$^-$) m/z 329 [M−H]$^-$.

Example 14: 5-(8-fluoro-6-hydroxy-2,2-dimethyl-3,4-dihydro-2H-1-benzopyran-7-yl)-1λ$^6$,2,5-thiadiazolidine-1,1,3-trione (Compound 113)

Example 14A: 2-fluoro-4-methoxy-1-((2-methylbut-3-yn-2-yl)oxy)benzene

To a solution of 3-chloro-3-methyl-1-butyne (1.9 mL, 16 mmol) and 2-fluoro-4-methoxyphenol (3.9 mL, 35 mmol) in N,N-dimethylformamide (35 mL) at ambient temperature was added potassium iodide (9.93 g, 59.8 mmol), potassium carbonate (9.72 g, 70.4 mmol) and copper(I) iodide (0.134 g, 0.704 mmol). An exotherm of 5° C. to 10° C. (internal) was noted. The reaction mixture was heated to 65° C. After 2.5 hours, an additional 1 equivalent of 3-chloro-3-methyl-1-butyne was added and stirring was continued at 65° C. After 4 hours, the reaction mixture was cooled to ambient temperature, and water and ethyl acetate were added; followed by additional stirring for 20 minutes. The layers were separated, and the organic phase was washed with water and brine, dried (Na$_2$SO$_4$), filtered and concentrated. The residue was passed through a plug of SiO$_2$ (50 mm) in a glass funnel (140 mm diameter) eluted with 30% tert-butyl methyl ether: heptanes (1500 mL). The filtrate was concentrated, and the residue was further purified by chromatography (330 g SiO$_2$; elution with 0% to 20% tert-butyl methyl ether:heptanes) to provide 5.91 g (81%) of the title compound. $^1$H NMR (400 MHz, CDCl$_3$) δ ppm 7.31 (t, J=9.1 Hz, 1H), 6.65 (dd, J=12.1, 3.0 Hz, 1H), 6.59 (ddd, J=8.9, 3.0, 1.4 Hz, 1H), 3.77 (s, 3H), 2.50 (s, 1H), 1.62 (s, 6H).

Example 14B:
8-fluoro-6-methoxy-2,2-dimethyl-2H-chromene

To a solution of Example 14A (15.2 g, 73.0 mmol) in 1,2-dichloroethane (100 mL) at ambient temperature was added triphenylphosphinegold(I) bis(trifluoromethanesulfonyl)imidate (0.540 g, 0.730 mmol). After 3 hours, the mixture was treated with an additional 170 mg of gold catalyst and stirred overnight. The dark mixture was concentrated, and the residue was placed on top of a 750 g SiO$_2$ column and eluted with 0% to 60% CH$_2$Cl$_2$:heptanes to provide an oil after concentration. The residue was taken up in 200 mL of CH$_2$Cl$_2$, treated with MgSO$_4$ (5 g) and decolorizing charcoal (22 g), and stirred for 90 minutes. The mixture was filtered through a plug of diatomaceous earth, and the filtrate was concentrated to provide 10.83 g (71%) of the title compound. $^1$H NMR (400 MHz, CDCl$_3$) δ ppm 6.53 (dd, J=12.2, 2.8 Hz, 1H), 6.35 (dd, J=2.9, 1.5 Hz, 1H), 6.28 (dd, J=9.8, 1.7 Hz, 1H), 5.69 (d, J=9.9 Hz, 1H), 3.74 (s, 3H), 1.45 (s, 6H).

Example 14C:
8-fluoro-6-methoxy-2,2-dimethylchromane

A solution of Example 14B (6.60 g, 28.5 mmol) in tetrahydrofuran (70 mL) was added to 5% Pd/C (7.19 g, 31.5 mmol) in a 250 mL pressure bottle at ambient temperature. Then the mixture was shaken for 1.2 hours under hydrogen (50 psi). The mixture was filtered, and the filtrate was concentrated to give the title compound (6.1 g) of 90% purity. $^1$H NMR (501 MHz, CDCl$_3$) δ ppm 6.54 (ddd, J=12.7, 2.9, 1.4 Hz, 1H), 6.39 (dt, J=2.9, 1.6 Hz, 1H), 3.84-3.63 (m, 3H), 2.76 (app t, J=6.6 Hz, 2H), 1.81 (app t, J=6.8, 2H), 1.44-1.29 (m, 6H).

Example 14D: 8-fluoro-6-((2-methoxyethoxy)methoxy)-2,2-dimethylchromane

To a solution of Example 14C (2.00 g, 9.51 mmol) in CH$_2$Cl$_2$ (40 mL) at −10° C. was added 1 M BBr$_3$ in CH$_2$Cl$_2$ (47.6 mL, 47.6 mmol). After 4 hours, the mixture was carefully quenched with methanol added down the inside of the flask keeping the internal temperature below 10° C. Once the exotherm ceased, excess methanol (150 mL) was added, the ice bath was removed, and the mixture was allowed to warm to ambient temperature. The mixture was concentrated in a 60° C. water bath, and the resulting residue was concentrated again from methanol (2×). The phenol, 8-fluoro-2,2-dimethylchroman-6-ol, was used without further purification. $^1$H NMR (400 MHz, methanol-d$_4$) δ ppm 6.36 (ddd, J=12.2, 2.1, 1.4 Hz, 1H), 6.31 (ddt, J=2.7, 1.8, 1.0 Hz, 1H), 2.72 (app t, J=6.7, 0.9 Hz, 2H), 1.79 (app t, J=6.8 Hz, 2H), 1.30 (s, 6H).

To a solution of 8-fluoro-2,2-dimethylchroman-6-ol (1.8 g, 9.2 mmol) in tetrahydrofuran (40 mL) at ambient temperature was added 1 M potassium 2-methylpropan-2-olate in tetrahydrofuran (13.7 mL, 13.7 mmol). After 15 minutes, 1-(chloromethoxy)-2-methoxyethane (1.6 mL, 14 mmol) was added and stirring was continued for 15 minutes. The mixture was quenched with ammonium chloride (saturated aqueous), transferred to a separatory funnel with water (100 mL) and ethyl acetate (100 mL), and shaken. The organic phase was washed with 1 M HCl (100 mL), saturated NaHCO$_3$ (100 mL), water (100 mL) and brine (50 mL), dried (Na$_2$SO$_4$), filtered and concentrated. The residue was purified by chromatography to remove baseline impurities (220 g SiO$_2$, elution with 50% to 100% tert-butyl methyl ether: heptanes) to provide the title compound in 85% yield. $^1$H NMR (400 MHz, CDCl$_3$) δ ppm 6.68 (ddt, J=12.4, 2.9, 0.7 Hz, 1H), 6.57 (ddt, J=2.6, 1.7, 1.0 Hz, 1H), 5.16 (s, 2H), 3.87-3.76 (m, 2H), 3.63-3.51 (m, 2H), 3.39 (s, 3H), 2.80-2.71 (m, 2H), 1.80 (t, J=6.8 Hz, 2H), 1.36 (s, 6H).

Example 14E: 8-fluoro-7-iodo-6-((2-methoxyethoxy)methoxy)-2,2-dimethylchromane

To a solution of Example 14D (2.28 g, 8.02 mmol) and tetramethylethylenediamine (2.4 mL, 16 mmol) in tetrahydrofuran (50 mL) at −66° C. was added 1.4 M s-BuLi in cyclohexane (8.0 mL, 11 mmol) at such a rate as to keep the internal temperature <−60° C. Stirring was continued for 3 hours. To this mixture was added 12 in tetrahydrofuran (6.7 mL, 16.84 mmol). After 15 minutes, the reaction was allowed to warm to ambient temperature. The reaction was quenched with saturated NH$_4$Cl, transferred to a separatory funnel with water and ethyl acetate, and shaken with saturated sodium bisulfite. The organic phase washed with 1 M HCl, saturated NaHCO$_3$, water and brine, then dried (Na$_2$SO$_4$), filtered and concentrated to provide the title compound (94% yield). $^1$H NMR (400 MHz, DMSO-d$_6$) δ ppm 6.77 (dd, J=2.0, 1.1 Hz, 1H), 5.22 (s, 2H), 3.81-3.72 (m, 2H), 3.53-3.43 (m, 2H), 3.24 (s, 3H), 2.79-2.64 (m, 2H), 1.77 (m, 2H), 1.29 (s, 6H).

Example 14F: tert-butyl ({8-fluoro-6-[(2-methoxyethoxy)methoxy]-2,2-dimethyl-3,4-dihydro-2H-1-benzopyran-7-yl}amino)acetate To a solution of Example 14E (3.00 g, 7.31 mmol) and tert-butyl 2-aminoacetate (1.2 mL, 8.8 mmol) in dioxane (50 mL) at ambient temperature was added cesium carbonate (4.77 g, 14.6 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3, 0.663 g, 0.731 mmol) and 2-(dicyclohexylphosphino) 3,6-dimethoxy-2',4',6'-triisopropyl-1,1'-biphenyl (BrettPhos, 0.393 g, 0.731 mmol). The mixture was degassed (3× vacuum/purge N2); then heated to 98° C. After 90 minutes, less than 10% converted. Additional BrettPhos (0.1 equivalent) and BrettPhos Pd G3 (0.1 equivalent) were added and heating was continued. After 2 hours, the reaction was complete. The reaction mixture was concentrated, and the residue was partitioned between water and ethyl acetate (emulsion). The organic phase was washed with an additional portion of water (emulsion) and brine then concentrated. The residue was purified by chromatography (220 g SiO$_2$, elution with 0% to 50% ethyl acetate:heptanes) to provide 2.56 g (67%) of the title compound. $^1$H NMR (500 MHz, CDCl$_3$) δ ppm 6.60 (dt, J=2.1, 0.9 Hz, 1H), 5.20 (s, 2H), 4.41 (td, J=6.2, 2.6 Hz, 1H), 3.96 (dd, J=6.0, 2.1 Hz, 2H), 3.90-3.79 (m, 2H), 3.63-3.52 (m, 2H), 3.39 (s, 3H), 2.66 (m, 2H), 1.77 (m, 2H), 1.45 (s, 9H), 1.34 (s, 6H).

Example 14G: tert-butyl ([(tert-butoxycarbonyl)sulfamoyl]{8-fluoro-6-[(2-methoxyethoxy)methoxy]-2,2-dimethyl-3,4-dihydro-2H-1-benzopyran-7-yl}amino)acetate To a solution of sulfurisocyanatidic chloride (0.80 mL, 9.3 mmol) in CH$_2$Cl$_2$ (20 mL) at −5° C. was added 2-methylpropan-2-ol (0.89 mL, 9.3 mmol). After 30 minutes, a solution of Example 14F (2.56 g, 6.19 mmol) and triethylamine (1.7 mL, 12 mmol) in $CH_2Cl_2$ (20 mL) was added, and the mixture was stirred for 1 hour. The reaction mixture was transferred to a separatory funnel with $CH_2Cl_2$ and washed with brine. The organic phase was concentrated, and the residue was taken up in tert-butyl methyl ether and washed with water (emulsion) and brine, then dried ($Na_2SO_4$), filtered and concentrated to give 3.32 g (81%) of the title compound in 90% purity. $^1H$ NMR (501 MHz, DMSO-$d_6$) δ ppm 6.82-6.77 (m, 1H), 5.22 (d, J=7.0 Hz, 1H), 5.15 (d, J=7.0 Hz, 1H), 4.66 (d, J=17.4 Hz, 1H), 4.12 (d, J=17.4 Hz, 1H), 3.79-3.67 (m, 2H), 3.47 (t, J=4.8 Hz, 2H), 3.24 (s, 3H), 2.74 (app t, J=6.8 Hz, 2H), 1.77 (app t, J=6.9 Hz, 2H), 1.43 (d, J=10.7 Hz, 9H), 1.32 (s, 9H), 1.30 (s, 3H), 1.27 (s, 3H).

Example 14H: 5-(8-fluoro-6-hydroxy-2,2-dimethyl-3,4-dihydro-2H-1-benzopyran-7-yl)-1$λ^6$,2,5-thiadiazolidine-1,1,3-trione To a solution of Example 14G (1.78 g, 3.00 mmol) in 2-methyltetrahydrofuran (30 mL) at ambient temperature was added 6% $Mg(OCH_3)_2$ in $CH_3OH$ (15.9 mL, 9.01 mmol), and the mixture was heated to 65° C. After 36 hours, the reaction mixture was cooled to ambient temperature and filtered through diatomaceous earth (elution with 2-methyltetrahydrofuran). The filtrate was concentrated and filtered again through a Whatman polytetrafluoroethylene (PTFE) membrane filter (0.45 micron×25 mm; elution with 2-methyltetrahydrofuran), concentrated, to give 5-{8-fluoro-6-[(2-methoxyethoxy)methoxy]-2,2-dimethyl-3,4-dihydro-2H-1-benzopyran-7-yl}-1$λ^6$,2,5-thiadiazolidine-1,1,3-trione that was used directly in the next reaction. MS (ESI$^-$) m/z 325 [M−H]$^-$.

To a neat sample of 5-{8-fluoro-6-[(2-methoxyethoxy)methoxy]-2,2-dimethyl-3,4-dihydro-2H-1-benzopyran-7-yl}-1$λ^6$,2,5-thiadiazolidine-1,1,3-trione (0.040 g, 0.096 mmol) at ambient temperature was added 4 M HCl in dioxane (0.5 mL, 2 mmol). After 1 hour, the reaction mixture was triturated with ether, sonicated and filtered to provide 3.3 mg (10%) of the title compound. $^1H$ NMR (501 MHz, DMSO-$d_6$) δ ppm 9.74 (s, 1H), 6.42 (d, J=2.0 Hz, 1H), 3.57 (s, 2H), 2.63 (app t, J=6.7 Hz, 2H), 1.73 (app t, J=6.7 Hz, 2H), 1.26 (s, 6H).

Example 15: 5-(1,4-difluoro-3-hydroxy-7-methoxy-5,6,7,8-tetrahydronaphthalen-2-yl)-1$λ^6$,2,5-thiadiazolidine-1,1,3-trione (Compound 114)

Example 15A: 5-[3-(benzyloxy)-7-bromo-1,4-difluoronaphthalen-2-yl]-1$λ^6$,2,5-thiadiazolidine-1,1,3-trione To a mixture of the product of Example 1F (300 mg, 0.603 mmol) in N,N-dimethylformamide (6.73 mL) was added Selectfluor® (256 mg, 0.724 mmol), and the solution was heated to 65° C. After 90 minutes, the mixture was cooled to room temperature, and the excess oxidant was quenched with a solution of sodium thiosulfate pentahydrate (404 mg, 1.63 mmol) in water (3.3 mL). After stirring for 15 minutes, water (10 mL) was added, and the mixture was extracted with ethyl acetate (3×10 mL). The combined organic fractions were washed with saturated aqueous ammonium chloride (2×10 mL) and brine (1×10 mL), dried over sodium sulfate, filtered, and concentrated in vacuo to afford methyl {[3-(benzyloxy)-7-bromo-1,4-difluoronaphthalen-2-yl](sulfamoyl)amino}acetate as a viscous, orange oil that was used in the next step without further purification. MS (APCI$^+$) m/z 516 [M+H]$^+$.

To a solution of methyl {[3-(benzyloxy)-7-bromo-1,4-difluoronaphthalen-2-yl](sulfamoyl)amino}acetate from the previous reaction in tetrahydrofuran (2.69 mL) at room temperature was added a solution of sodium methoxide (207 μL, 0.905 mmol) (25 weight % in methanol) via syringe, and the resulting solution was stirred at room temperature. After 5 minutes, the reaction was quenched with 1 M hydrochloric acid (3 mL) and diluted with ethyl acetate (3 mL). The layers were separated, and the aqueous layer was extracted with ethyl acetate (3×1 mL). The combined organic layers were washed with water (2×1 mL), saturated aqueous ammonium chloride (2×1 mL) and brine (1×1 mL) then dried over sodium sulfate, filtered and concentrated. The residue was purified via flash column chromatography (24 g $SiO_2$, $CH_2Cl_2$ to 10% methanol/$CH_2Cl_2$) to afford the title compound along with minor, inseparable impurities. The product was carried on to the next step without further purification. MS (APCI$^+$) m/z 484 [M+H]$^+$.

Example 15B: 5-[3-(benzyloxy)-1,4-difluoro-7-methoxynaphthalen-2-yl]-1$λ^6$,2,5-thiadiazolidine-1,1,3-trione A mixture of the product of Example 15A (301 mg, 0.623 mmol), [(2-di-tert-butylphosphino-3-methoxy-6-methyl-2',4',6'-triisopropyl-1,1'-biphenyl)-2-(2-aminobiphenyl)]palladium(II) methanesulfonate (RockPhos Pd G3 precatalyst, 16.1 mg, 0.019 mmol), and cesium carbonate (609 mg, 1.87 mmol) were placed under vacuum and stirred for 5 minutes, then the flask was filled with nitrogen and a preformed mixture of N,N-dimethylformamide (3.11 mL) and anhydrous methanol (126 μL, 3.11 mmol) was added. The resulting suspension was degassed by five vacuum/nitrogen backfills, and then heated to an internal temperature of 80° C. After 15 minutes, the reaction mixture was cooled to room temperature, quenched by the slow addition of 1 M hydrochloric acid (5 mL), and diluted with ethyl acetate (5 mL). The layers were separated, and the aqueous layer was extracted with ethyl acetate (2×5 mL). The combined organic layers were washed with saturated aqueous ammonium chloride (4×5 mL), then dried over sodium sulfate, filtered, and concentrated. The residue was purified via flash column chromatography (12 g $SiO_2$, $CH_2Cl_2$ to 10% methanol/$CH_2Cl_2$) to afford the title compound along with minor, inseparable impurities. The product was carried on to the next step without further purification. MS (APCI$^+$) m/z 435 [M+H]$^+$.

Example 15C: 5-(1,4-difluoro-3-hydroxy-7-methoxynaphthalen-2-yl)-1$λ^6$,2,5-thiadiazolidine-1,1,3-trione A mixture of the product of Example 15B (38.7 mg, 0.089 mmol) and pentamethylbenzene (39.6 mg, 0.267 mmol) in dichloromethane (445 μL) was cooled to an internal temperature of −76° C. under an atmosphere of dry nitrogen. Subsequently, a 1 M solution of boron trichloride (178 μL, 0.178 mmol) in $CH_2Cl_2$ was added dropwise over 15 minutes, so as not to raise the internal temperature past −72° C. After 15 minutes, the reaction was quenched at −75° C. with $CH_2Cl_2$/methanol (10:1, 230 μL) via cannula transfer under nitrogen. The mixture was then slowly warmed to room temperature under nitrogen. The volatiles were removed in vacuo to afford a brown solid that was purified via HPLC (Phenomenex® Luna® 10 μM C18(2) 100 Å, AXIA™ (00G-4253-U0-AX) column, 250×30 mm, flow rate 50 mL/minute, 5-95% gradient of acetonitrile in buffer (0.025 M aqueous ammonium acetate) to give the title compound (10.3 mg, 0.030 mmol, 34% yield). $^1$H NMR (400 MHz, methanol-$d_4$) δ ppm 7.84 (dd, J=9.3, 1.4 Hz, 1H), 7.30 (t, J=1.5 Hz, 1H), 7.23 (dd, J=9.3, 2.5 Hz, 1H), 4.41 (s, 2H), 3.91 (s, 3H); MS (ESI$^-$) m/z 343 [M−H]$^-$.

Example 15D: 5-(1,4-difluoro-3-hydroxy-7-methoxy-5,6,7,8-tetrahydronaphthalen-2-yl)-1λ$^6$,2,5-thiadiazolidine-1,1,3-trione To a mixture of 10% Pd—C(23.18 mg, 0.218 mmol) in ethanol (10 mL) was added Example 15C (50 mg, 0.109 mmol) at 25° C., and the mixture was then stirred for 24 hours at 60° C. under H2 (140 psi). The mixture was filtered, and the filtrate was concentrated under a stream of N2 at 25° C. to give the crude product. The reaction was repeated on the same scale. The crude products from both reactions were combined, and purified by preparative HPLC on a Welch Ultimate® AQ-C18 column 150*30 mm*5 μm eluted with 5-100% acetonitrile in water with 0.075% trifluoroacetic acid at a flow rate of 25 mL/minute to give the title compound (2 mg, 2% yield). $^1$H NMR (400 MHz, methanol-$d_4$) δ ppm 4.32 (s, 2H), 3.62 (m, 1H), 3.30 (s, 3H), 2.88-2.69 (m, 2H), 2.60 (m, 2H), 1.99-1.70 (m, 2H); MS (ESI$^+$) m/z 366.0 [M+18]$^+$.

Example 16: 5-(7-{[2-(azetidin-1-yl)ethyl]amino}-1-fluoro-3-hydroxy-5,6,7,8-tetrahydronaphthalen-2-yl)-1λ$^6$,2,5-thiadiazolidine-1,1,3-trione (Compound 115)

Example 16A: 5-[7-{[2-(azetidin-1-yl)ethyl]amino}-3-(benzyloxy)-1-fluoronaphthalen-2-yl]-1λ$^6$,2,5-thiadiazolidine-1,1,3-trione A mixture of 5-[3-(benzyloxy)-7-bromo-1-fluoronaphthalen-2-yl]-1λ$^6$,2,5-thiadiazolidine-1,1,3-trione (Example 1G, 93 mg, 0.2 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3, 10.88 mg, 0.012 mmol), 2-(dicyclohexylphosphino)3,6-dimethoxy-2',4',6'-triisopropyl-1,1'-biphenyl (BrettPhos, 6.44 mg, 0.012 mmol), cesium carbonate (195 mg, 0.600 mmol) and 2-(azetidin-1-yl)ethanamine (40.1 mg, 0.400 mmol) in 2-methylbutan-2-ol (2 mL) was sparged and filled with nitrogen five times. Then the mixture was heated at 105° C. for 3 hours. The mixture was cooled to room temperature, and CH$_2$Cl$_2$/CH$_3$OH (10:1, 50 mL) was added to the mixture, followed by 4 M HCl in dioxane (0.2 mL). The mixture was filtered, the filtrate was concentrated, and the residue was purified by flash column chromatography on silica gel (12 g) eluted with CH$_2$Cl$_2$/CH$_3$OH (0 to 65%) to afford the title compound (85 mg, 0.175 mmol, 88% yield) as a solid. MS (ESI$^-$) m/z 424 [M−H]$^-$.

Example 16B: 5-(7-{[2-(azetidin-1-yl)ethyl]amino}-1-fluoro-3-hydroxynaphthalen-2-yl)-1λ$^6$,2,5-thiadiazolidine-1,1,3-trione To a mixture of Example 16A (85 mg, 0.175 mmol) and 1,2,3,4,5-pentamethylbenzene (59.8 mg, 0.403 mmol) in CH$_2$Cl$_2$ (5 mL) at −78° C. was added trichloroborane (1754 μL, 1.754 mmol). The mixture was stirred at −78° C. for 5 minutes, and then warmed to 0° C. for 30 minutes. The mixture was quenched with ethanol (4 mL), and then concentrated. The residue was washed with CH$_2$Cl$_2$ (4×4 mL) and dried to afford the title compound (73 mg, 0.169 mmol, 97% yield) as an HCl salt. $^1$H NMR (500 MHz, DMSO-$d_6$) δ ppm 10.38 (br s, 1H), 10.12 (br s, 1H), 7.55 (br d, J=8 Hz, 1H), 7.03 (dd, J=8, 2 Hz, 1H), 6.97 (s, 1H), 6.75 (d, J=2 Hz, 1H), 4.50 (s, 2H), 4.11 (m, 2H), 4.06 (m, 2H), 3.37 (m, 4H), 2.40 (m, 1H), 2.25 (m, 1H). MS (ESI$^-$) m/z 393 [M−H]$^-$.

Example 16C 5-(7-{[2-(azetidin-1-yl)ethyl]amino}-1-fluoro-3-hydroxy-5,6,7,8-tetrahydronaphthalen-2-yl)-1λ$^6$,2,5-thiadiazolidine-1,1,3-trione To Example 16B (72 mg, 0.167 mmol) in acetic acid (4 mL) was added 10% Pd/C (216 mg, 2.16 mmol). The mixture was stirred for 5 days at room temperature under hydrogen (110 psi). Then methanol (20 mL) was added, and the mixture was filtered. The filtrate was concentrated, and the residue was purified by preparative HPLC [YMC Tri-Art™ C18 Hybrid 20 μm column, 25×150 mm, flow rate 80 mL/minute, 5-60% gradient of acetonitrile in buffer (0.025 M aqueous ammonium bicarbonate, adjusted to pH 10 with ammonium hydroxide)] to afford the title compound (4 mg, 0.01 mmol, 6% yield). $^1$H NMR (500 MHz, DMSO-$d_6$) δ ppm 6.43 (s, 1H), 3.92 (s, 2H), 3.41 (t, J=8 Hz, 2H), 3.17 (1H), 2.97 (m, 1H), 2.91 (m, 1H), 2.71 (m, 6H), 2.32 (m, 1H), 2.08 (m, 2H), 1.97 (m, 2H), 1.52 (m, 1H); MS (ESI$^+$) m/z 39 [M+H]$^+$.

Example 17: 5-{1-fluoro-3-hydroxy-7-[(3,3,3-trifluoropropyl)amino]-5,6,7,8-tetrahydronaphthalen-2-yl}-1λ$^6$,2,5-thiadiazolidine-1,1,3-trione (Compound 116)

Example 17A: 5-{3-(benzyloxy)-1-fluoro-7-[(3,3,3-trifluoropropyl)amino]naphthalen-2-yl}-1λ$^6$,2,5-thiadiazolidine-1,1,3-trione A mixture of 5-[3-(benzyloxy)-7-bromo-1-fluoronaphthalen-2-yl]-1×$^6$,2,5-thiadiazolidine-1,1,3-trione (Example 1G, 170 mg, 0.365 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3, 23.18 mg, 0.026 mmol), 2-(dicyclohexylphosphino)3,6-dimethoxy-2',4',6'-triisopropyl-1,1'-biphenyl (BrettPhos, 23.53 mg, 0.044 mmol), cesium carbonate (357 mg, 1.096 mmol) and 3,3,3-trifluoropropan-1-amine (66.1 mg, 0.585 mmol) in 2-methylbutan-2-ol (6 mL) was sparged and filled with N2 five times, and then the mixture was heated at 105° C. for 2 hours. The mixture was cooled to room temperature, and CH$_2$Cl$_2$/CH$_3$OH (10:1, 50 mL) was added to the mixture, followed by 4 M HCl in dioxane (0.2 mL). The mixture was filtered, the filtrate was concentrated, and the residue was purified by flash column chromatography on silica gel (12 g) eluted with CH$_2$Cl$_2$/CH$_3$OH (0 to 65%) to afford the title compound (159 mg, 0.32 mmol, 87% yield). MS (ESI$^-$) m/z 496 [M−H]$^-$.

Example 17B: 5-{1-fluoro-3-hydroxy-7-[(3,3,3-trifluoropropyl)amino]naphthalen-2-yl}-1λ$^6$,2,5-thiadiazolidine-1,1,3-trione To a mixture of Example 17A (158 mg, 0.318 mmol) and 1,2,3,4,5-pentamethylbenzene (108 mg, 0.731 mmol) in CH$_2$Cl$_2$ (5 mL) at −78° C. was added trichloroborane (3176 μL, 3.18 mmol). The mixture was stirred at −78° C. for 5 minutes, and then warmed to 0° C. for 20 minutes. The mixture was quenched with ethanol (4 mL) and concentrated. The residue was washed with heptane (4×4 mL), and the resulting solid was dissolved in $CH_3OH$ (5 mL), and purified by preparative HPLC [YMC TriArt™ C18 Hybrid 20 m column, 25×150 mm, flow rate 80 mL/minute, 5-70% gradient of $CH_3OH$ in water (0.01% trifluoroacetic acid) to afford the title compound (100 mg, 0.318 mmol, 77% yield). $^1H$ NMR (500 MHz, DMSO-$d_6$) δ ppm 9.81 (br s, 1H), 7.53 (br d, J=8 Hz, 1H), 7.01 (dd, J=8, 2 Hz, 1H), 6.95 (s, 1H), 6.68 (d, J=2 Hz, 1H), 4.40 (s, 2H), 3.37 (t, J=8 Hz, 2H), 2.59 (m, 2H); MS (ESI$^-$) m/z 496 [M−H]$^-$.

Example 17C: 5-{1-fluoro-3-hydroxy-7-[(3, 3,3-trifluoropropyl)amino]-5,6,7,8-tetrahydronaphthalen-2-yl}-1$\lambda^6$,2,5-thiadiazolidine-1,1,3-trione To Example 17B (80 mg, 0.196 mmol) in acetic acid (3 mL) was added 5% Pd/C (wet, 160 mg, 0.7 mmol). The mixture was stirred at room temperature for 2 days under hydrogen (110 psi). Then $CH_3OH$ (20 mL) was added, and the mixture was filtered. The filtrate was concentrated, and the residue was purified by preparative HPLC [YMC TriArt™ C18 Hybrid 20 μm column, 25×150 mm, flow rate 80 mL/minute, 5-90% gradient of acetonitrile in buffer (0.025 M aqueous ammonium bicarbonate, adjusted to pH 10 with ammonium hydroxide)] to afford the title compound (8.5 mg, 0.021 mmol, 10.5% yield). $^1H$ NMR (500 MHz, DMSO-$d_6$) δ ppm 9.15 (br s, 1H), 7.10 (br s, 1H), 6.46 (s, 1H), 3.93 (s, 2H), 3.20 (m, 2H), 3.04 (m, 2H), 2.77 (m, 2H), 2.63 (m, 2H), 2.10 (m, 1H), 1.52 (m, 2H); MS (ESI$^-$) m/z 410 [M−H]$^-$.

Example 18: 5-{(7S)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione (Compound 117)

Example 18A: 5-{1-fluoro-3-[(2-methoxyethoxy)methoxy]-7-[(3-methylbutyl)amino]-5,6,7,8-tetrahydronaphthalen-2-yl}-1$\lambda^6$,2,5-thiadiazolidine-1,1,3-trione To a solution of the product from Example 22I (0.9659 g, 1.92 mmol) and isoamylamine (0.251 g, 2.88 mmol) in acetonitrile (19.2 mL) at room temp was added sodium cyanoborohydride (0.145 g, 2.3 mmol). After 18 h, the reaction mixture was diluted with acetonitrile (10 mL), quenched with ammonium hydroxide (0.436 mL, 23 mmol), and then added water (2 mL). Subsequently, Celite® (5 g) was added, and the mixture was concentrated in vacuo. The residue was purified by reverse phase chromatography by dry loading onto an Teledyne ISCO 100 g C18 column, running a gradient of 5-50% methanol in buffer (0.025 M ammonium bicarbonate in water acidified to pH 7 by adding dry ice) to give the title compound (0.4694 g, 0.991 mmol, 51.7% yield). $^1H$ NMR (400 MHz, DMSO-$d_6$) δ ppm 8.42 (s, 2H), 6.77 (d, J=1.4 Hz, 1H), 5.21 (s, 2H), 3.93 (d, J=1.1 Hz, 2H), 3.77-3.70 (m, 2H), 3.48-3.42 (m, 3H), 3.23 (s, 3H), 3.13 (dd, J=16.5, 5.6 Hz, 1H), 3.03 (dd, J=9.6, 6.2 Hz, 2H), 2.92-2.72 (m, 2H), 2.62-2.51 (m, 1H), 2.22-2.15 (m, 1H), 1.79-1.60 (m, 2H), 1.50 (dt, J=10.6, 7.0 Hz, 2H), 0.93 (s, 3H), 0.91 (s, 3H); MS (APCI$^+$) 474 [M+H]$^+$.

Example 18B: 5-{(7S)-1-fluoro-3-[(2-methoxyethoxy)methoxy]-7-[(3-methylbutyl)amino]-5,6,7,8-tetrahydronaphthalen-2-yl}-1$\lambda^6$,2,5-thiadiazolidine-1,1,3-trione The product of Example 18A (205.7 mg, 0.434 mmol) was separated by preparative chiral SFC. Preparative SFC was performed on a THAR/Waters SFC80 system running under SuperChrom™ software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a dewar of bone-dry non-certified $CO_2$ pressurized to 350 psi with a modifier of methanol (0.1% triethylamine) at a flow rate of 70 g/minute. The column was at ambient temperature and the backpressure regulator was set to maintain 100 bar. The sample was dissolved in methanol:dimethyl sulfoxide(70:30) at a concentration of 5 mg/mL. The sample was loaded into the modifier stream in 2 mL (10 mg) injections. The mobile phase was held isocratically at 45% cosolvent:$CO_2$. Fraction collection was time triggered. The instrument was fitted with a CHIRALPAK® IC column with dimensions 21 mm i.d.×250 mm length with 5 μm particles. The earlier eluting enantiomer peak gave the title compound (69.9 mg, 0.148 mmol, 68% recovery). $^1H$ NMR and MS data were identical to those from Example 18A.

Example 18C: 5-{(7S)-1-fluoro-3-hydroxy-7-[(3-methylbutyl)amino]-5,6,7,8-tetrahydronaphthalen-2-yl}-1$\lambda^6$,2,5-thiadiazolidine-1,3-trione (Compound 117)

To a suspension of the product of Example 18B (20 mg, 0.042 mmol) in acetonitrile (0.8 mL) was added a solution of hydrogen chloride (0.053 mL, 0.211 mmol, 4 M in dioxane). After 2 hours, the solid was collected by filtration, rinsed with acetonitrile (0.5 mL) and dried in a vacuum oven at 50° C. to give the title compound (9.5 mg, 58.4% yield). $^1H$ NMR and MS data were identical to those from Example 3.

Example 19: 5-{(7R)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione (Compound 118)

Example 19A: 5-{(7R)-1-fluoro-3-[(2-methoxyethoxy)methoxy]-7-[(3-methylbutyl)amino]-5,6,7,8-tetrahydronaphthalen-2-yl}-1$\lambda^6$,2,5-thiadiazolidine-1,1,3-trione The product of Example 18A (205.7 mg, 0.434 mmol) was separated by preparative chiral SFC. Preparative SFC was performed on a THAR/Waters SFC80 system running under SuperChrom™ software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a dewar of bone-dry non-certified $CO_2$ pressurized to 350 psi with a modifier of methanol (0.1% triethylamine) at a flow rate of 70 g/minute. The column was at ambient temperature and the backpressure regulator was set to maintain 100 bar. The sample was dissolved in methanol:dimethyl sulfoxide (70:30) at a concentration of 5 mg/mL. The sample was loaded into the modifier stream in 2 mL (10 mg) injections. The mobile phase was held isocratically at 45% cosolvent:$CO_2$. Fraction collection was time triggered. The instrument was fitted with a CHIRALPAK® IC column with dimensions 21 mm i.d.×250 mm length with m particles. The later eluting enantiomer peak gave the title compound (60.3 mg, 0.127 mmol, 58.6% recovery). $^1H$ NMR and MS data were identical to those from Example 18A. Crystals suitable for X-ray crystallography were grown by slow evaporation of a solution in methanol. X-ray crystallographic analysis showed the absolute stereochemistry to be (R).

Example 19B: 5-{(7R)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione (Compound 117)

To a suspension of the product of Example 19A (60 mg, 0.127 mmol) in acetonitrile (1.2 mL) was added a solution of hydrogen chloride (0.158 mL, 0.634 mmol, 4 M in dioxane). After 2 hours, the reaction was diluted with acetonitrile (1 mL), quenched with ammonium hydroxide (0.014 mL, 0.760 mmol), and then diluted with water (0.5 mL). Celite® (1 g) was added and the resulting suspension concentrated. The crude residue was dry loaded onto a 100 g C18 column, and purified by reverse phase liquid chromatography, flow rate 60 mL/minute, gradient of 10-50% (10 column volumes) then 50-100% (6 column volumes), then flushing at 100% (1 column volume) methanol in buffer (0.025 M ammonium bicarbonate in water acidified to pH 7 with dry ice) observing at 206 nM, to give the title compound (33.3 mg, 0.086 mmol, 68.2% yield). $^1$H NMR and MS data were identical to the product of Example 3.

Example 20: 5-{7-[(3,3-difluorocyclobutyl)methoxy]-1-fluoro-3-hydroxy-5,6,7,8-tetrahydronaphthalen-2-yl}-1$\lambda^6$,2,5-thiadiazolidine-1,1,3-trione (Compound 119)

Example 20A: 5-{3-(benzyloxy)-7-[(3,3-difluorocyclobutyl)methoxy]-1-fluoronaphthalen-2-yl}-1$\lambda^6$,2,5-thiadiazolidine-1,1,3-trione Example 1H (511 mg, 1.270 mmol), 3-(bromomethyl)-1,1-difluorocyclobutane (470 mg, 2.54 mmol), and cesium carbonate (1241 mg, 3.81 mmol) were combined in N,N-dimethylformamide (DMF) (5 mL). The reaction was heated overnight at 50° C. The material was diluted with 1 M HCl (aqueous) and extracted with ethyl acetate. The organic fraction was washed with saturated NH$_4$Cl (2×) and brine. Organic layer was dried over Na$_2$SO$_4$ and concentrated in vacuo. The residue was purified using silica gel chromatography (0-10% methanol in dichloromethane) to give the title compound (409 mg, 64% yield). $^1$H NMR (400 MHz, DMSO-d$_6$) δ ppm 7.79 (dd, J=9.0, 1.5 Hz, 1H), 7.55-7.45 (m, 2H), 7.43-7.19 (m, 6H), 5.20 (s, 2H), 4.47 (s, 2H), 4.14 (d, J=6.3 Hz, 2H), 2.81-2.49 (m, 5H).

Example 20B: 5-{7-[(3,3-difluorocyclobutyl)methoxy]-1-fluoro-3-hydroxynaphthalen-2-yl}-1$\lambda^6$,2,5-thiadiazolidine-1,1,3-trione Example 20A (406 mg, 0.802 mmol) in tetrahydrofuran (THF) (4.0 mL) was added to 5% Pd/C (wet JM #9) (108 mg, 0.451 mmol) in a 20 mL RS10 Hastelloy C reactor. The reactor was purged with argon. The mixture was stirred at 1200 RPM under 65 psi of hydrogen at 25° C. After 16.3 hours, the reactor was vented. The hydrogen uptake had ceased between 9-10 hours. The mixture was filtered through a filter funnel with a polyethylene frit packed with diatomaceous earth as a tetrahydrofuran (THF) (4.0 mL) solution. The catalyst was washed successive with methanol (2×) and again with THF. The combined filtrate and washes were concentrated by rotary evaporation. The residue was placed under house vacuum for 10 minutes to give a foam. The material was triturated with dichloromethane/heptanes to afford a solid that was collected by filtration and dried under reduced pressure (267 mg, 80% yield). $^1$H NMR (400 MHz, DMSO-d$_6$) δ ppm 7.68 (dd, J=9.0, 1.5 Hz, 1H), 7.24-7.13 (m, 2H), 7.03 (s, 1H), 4.43 (s, 2H), 4.11 (d, J=6.3 Hz, 2H), 2.80-2.48 (m, 5H); MS (ESI$^-$) m/z 414.9 [M–H]$^-$.

Example 20C: 5-{7-[(3,3-difluorocyclobutyl)methoxy]-1-fluoro-3-hydroxy-5,6,7,8-tetrahydronaphthalen-2-yl}-1$\lambda^6$,2,5-thiadiazolidine-1,1,3-trione Example 20B (100 mg, 0.240 mmol) in acetic acid (AcOH) (2.0 mL) was added to 10% Pd/C, dry (26.9 mg, 0.025 mmol) in a 20 mL RS10 Hastelloy C reactor. The reactor was purged with nitrogen, and the mixture was stirred under 130 psi of hydrogen at 25° C. for 42.75 hours. The reactor was vented, and the reaction mixture was filtered, but the reaction was deemed incomplete. The filtrate was combined with 5% Pd/C (wet JM #9) (377 mg, 1.289 mmol) and repressurized under hydrogen (119 psi) for 95.6 hours and then under hydrogen (136 psi) for an additional 24.56 hours. The mixture was filtered through a filter funnel with a polyethylene frit packed with diatomaceous earth rinsed with methanol. The filtrate was concentrated, and the residue was purified by reverse-phase preparative HPLC on a Phenomenex® Luna® C8(2) 5 m 100 Å AXIA™ column (50 mm×30 mm). A gradient of acetonitrile (A) and 0.1% ammonium acetate in water (B) was used, at a flow rate of 40 mL/minute (0-0.5 minutes 25% A, 0.5-8.0 minutes linear gradient 25-100% A, 8.0-9.0 minutes 100% A, 9.0-9.1 minutes linear gradient 100-25% A, 9.1-10.0 minutes 25% A), to provide the title compound (10.2 mg, 10% yield). $^1$H NMR (500 MHz, 9:1 v/v DMSO-d$_6$/D$_2$O) δ ppm 6.43 (s, 1H), 3.99 (s, 2H), 3.80-3.71 (m, 1H), 3.56-3.44 (m, 2H), 2.84-2.53 (m, 5H), 2.45 (dd, J=J=16.5, 6.2 Hz, 1H), 2.33-2.18 (m, 3H), 1.92-1.79 (m, 1H), 1.79-1.67 (m, 1H); MS (ESI$^-$) m/z 418.9 [M–H]$^-$.

Example 21: 5-{1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione (Compound 120)

The title compound was prepared using the methodologies described in Example 17 substituting 4,4,4-trifluorobutan-1-amine for 3,3,3-trifluoropropan-1-amine. $^1$H NMR (400 MHz, DMSO-d$_6$) δ ppm 9.18 (br s, 1H), 7.26 (br s, 1H), 6.47 (s, 1H), 3.93 (s, 2H), 3.07 (m, 4H), 2.77 (m, 2H), 2.41 (m, 2H), 2.21 (m, 1H), 1.84 (m, 2H), 1.68 (m, 2H); MS (ESI$^-$) m/z 424 [M–H].

Example 22: 5-{1-fluoro-3-hydroxy-7-[(4-methoxy-3,3-dimethylbutyl)amino]-5,6,7,8-tetrahydronaphthalen-2-yl}-1$\lambda^6$,2,5-thiadiazolidine-1,1,3-trione (Compound 121)

Example 22A: 6-bromo-8-fluoro-3,4-dihydronaphthalen-2(1H)-one

To a slurry of 4-bromo-2-fluorophenylacetic acid (10.0 g, 42.9 mmol) in dichloroethane (100 mL) at room temperature was added N,N-dimethylformamide (5 drops) followed by 2 M oxalyl chloride in dichloromethane (23.6 mL, 47.2 mmol). After 90 minutes, the reaction was complete and used directly in the next reaction without concentration or further workup. A small sample was taken for analytical analysis. $^1$H NMR (400 MHz, DMSO-$d_6$) δ ppm 7.51 (td, J=9.4, 2.0 Hz, 1H), 7.40-7.26 (m, 2H), 3.63 (s, 2H).

To a solution of aluminum trichloride (7.44 g, 55.8 mmol) in dichloromethane (200 mL) at −10° C. was added the acid chloride solution from above at such a rate as to maintain the internal temperature below −2° C. Stirring was continued for 15 minutes. To the mixture was introduced a gentle stream of ethylene (internal temperature at −4° C.). After 1 hour, the gas flow was shut off, and the mixture was stirred an additional 10 minutes at −2° C. The reaction was slowly quench with ice water via 2 mL pipet aliquots until the internal temperature stopped rising (approximately 16 to 20 mL water added; internal temperature at 10° C.). Then additional water (500 mL) was added, the ice bath was removed, and the mixture was stirred for 10 minutes to final internal temperature of 20° C. The mixture was transferred to a separatory funnel, and the organic phase washed with brine; then dried (Na$_2$SO$_4$), filtered and concentrated to provide 12.6 g of the title compound which was used for the next step without purification. A small sample was taken for analytical analysis. $^1$H NMR (500 MHz, methanol-$d_4$) δ ppm 7.11 (dd, J=2.0, 1.1 Hz, 1H), 7.06 (dd, J=9.2, 1.9 Hz, 1H), 2.82 (m, 2H), 1.97 (m, 2H).

Example 22B: 6'-bromo-8'-fluoro-3',4'-dihydro-1'H-spiro[[1,3]dioxolane-2,2'-naphthalene]

To a solution of the product from Example 22A (10.4 g, 42.9 mmol) and ethylene glycol (14.5 mL, 257 mmol) in toluene (100 mL) at room temperature was added 4-methylbenzenesulfonic acid hydrate (1.63 g, 8.58 mmol); the flask was fitted with a Dean-Stark trap and heated to reflux. After 1 hour, the reaction was cooled to room temperature, transferred to a separatory funnel with ethyl acetate (500 mL) and washed with saturated aqueous sodium bicarbonate (2×300 mL), water (200 mL) and brine (200 mL). The organic fraction was then dried (Na$_2$SO$_4$), filtered and concentrated. The residue was purified by chromatography (750 g silica; 1 hour gradient elution from 0% to 20% ethyl acetate:heptanes) to provide 8.74 g (42.9 mmol, 90% pure, 63.8% yield) of the title compound. $^1$H NMR (400 MHz, DMSO-$d_6$) δ ppm 7.29 (dd, J=9.2, 1.9 Hz, 1H), 7.23 (dd, J=2.0, 1.0 Hz, 1H), 4.00-3.90 (m, 4H), 2.91 (app t, J=6.7 Hz, 2H), 2.76 (s, 2H), 1.85 (app t, J=6.7 Hz, 2H).

Example 22C 8'-fluoro-3',4'-dihydro-1'H-spiro[[1,3]dioxolane-2,2'-naphthalen]-6'-ol To a solution of the product of Example 22B (12.1 g, 42.2 mmol), water (3.8 mL, 210 mmol) and cesium carbonate (28 g, 84 mmol) in N,N-dimethylacetamide (100 mL) at room temperature was added t-BuBrettPhos Pd G3 precatalyst (1.4 g, 1.7 mmol). The reaction was degassed (3× vacuum/purge with nitrogen) followed by heating to 90° C. After 90 minutes, the reaction was cooled to room temperature and transferred to a separatory funnel with water (200 mL) and ethyl acetate (600 mL). To this was added 1 M hydrochloric acid (500 mL) to adjust the aqueous phase to pH to 3. The layers were separated, and the organic phase was washed with water (3×400 mL) and brine (1×400 mL); then dried (Na$_2$SO$_4$), filtered and concentrated. Two reaction batches were combined and purified by chromatography (750 g silica; gradient elution 0% to 40% ethyl acetate:0.1% triethylamine in heptanes) to provide 9.34 g (41.8 mmol, 49%) of the title compound. $^1$H NMR (400 MHz, DMSO-$d_6$) δ ppm 9.52 (s, 1H), 6.36 (d, J=9.2 Hz, 2H), 3.99-3.87 (m, 4H), 2.80 (t, J=6.7 Hz, 2H), 2.68 (s, 2H), 1.80 (t, J=6.7 Hz, 2H); MS (ESI$^-$) m/z 223 [M−H]$^-$.

Example 22D: 8'-fluoro-6'-[(2-methoxyethoxy)methoxy]-3',4'-dihydro-1'H-spiro[[1,3]dioxolane-2,2'-naphthalene]

To a solution of the product from Example 22C (3.6628 g, 16.34 mmol) and 2-methoxyethoxymethyl chloride (2.77 mL, 24.5 mmol) in tetrahydrofuran (72 mL) at room temperature was added N,N-diisopropylethylamine (5.71 mL, 32.7 mmol). The resulting solution was then heated to an internal temperature of 60° C. After 24 hours, the reaction mixture was cooled to room temperature, diluted with ethyl acetate (36 mL) and water (36 mL), and the layers were separated. The aqueous layer was extracted with ethyl acetate (2×25 mL). The combined organic layers were washed with 1 M aqueous sodium bisulfate (36 mL) followed by brine (18 mL), dried over sodium sulfate, filtered and concentrated in vacuo. The residue was loaded onto an 80 g silica gel column in dichloromethane and purified by running a gradient of 0-30% ethyl acetate in heptanes containing 0.1% triethylamine to give the title compound (2.9903 g, 9.57 mmol, 58.6% yield). $^1$H NMR (500 MHz, CDCl$_3$) δ ppm 6.64 (dd, J=2.5, 1.1 Hz, 1H), 6.61 (dd, J=11.0, 2.4 Hz, 1H), 5.20 (s, 2H), 4.08-3.98 (m, 4H), 3.83-3.76 (m, 2H), 3.59-3.52 (m, 2H), 3.38 (s, 3H), 2.96 (t, J=6.7 Hz, 2H), 2.85 (s, 2H), 1.96-1.89 (m, 2H); MS (APCI$^+$) m/z 237 [M−(OCH$_2$CH$_2$OCH$_3$)]$^+$.

Example 22E: 8'-fluoro-7'-iodo-6'-[(2-methoxyethoxy)methoxy]-3',4'-dihydro-1'H-spiro[[1,3]dioxolane-2,2'-naphthalene]

To a solution of 2,2,6,6-tetramethylpiperidine (4.30 mL, 25.3 mmol) in tetrahydrofuran (100 mL) at 0° C. was added a solution of n-butyllithium (9.49 mL, 23.72 mmol, 2.5 M in hexane) dropwise so that the internal temperature remained below 7° C. After 30 minutes, the solution was cooled to an internal temperature of −74° C., and then a solution of the product of Example 22D (4.94 g, 15.82 mmol) in tetrahydrofuran (25 mL) was added slowly along the side of the flask at a rate so that the internal temperature remained below −70° C., followed by dropwise addition of N,N,N',N'-tetramethylethylenediamine (3.58 mL, 23.72 mmol). The resulting solution was stirred for 2 hours at −78° C., then a solution of iodine (8.03 g, 31.6 mmol) in tetrahydrofuran (25 mL) was added dropwise so that the internal temperature remained below −65° C. Upon complete addition, the reaction mixture was allowed to warm to 0° C. The resulting suspension was quenched with a 1:1 mixture of saturated aqueous ammonium chloride and 1 M aqueous sodium thiosulfate (50 mL), stirred for 5 minutes at room temperature, and then extracted with ethyl acetate (50 mL, 2×25 mL). The combined organic layers were washed with water (50 mL), and brine (20 mL), then dried over sodium sulfate, filtered and partially concentrated in vacuo to approximately 50 mL of total volume. Silica (20 g) was added, and the resulting suspension was concentrated in vacuo. The resulting yellow powder was dry loaded onto a 120 g silica gel column, and eluted with a gradient of 0-30% ethyl acetate in heptanes containing 0.1% triethylamine to give the title compound (5.6776 g, 12.96 mmol, 82% yield). $^1$H NMR (400 MHz, CDCl$_3$) δ ppm 6.73 (d, J=1.4 Hz, 1H), 5.30 (s, 2H), 4.09-3.97 (m, 4H), 3.88-3.76 (m, 2H), 3.60-3.52 (m, 2H), 3.38 (s, 3H), 2.96 (t, J=6.7 Hz, 2H), 2.88 (s, 2H), 1.92 (t, J=6.7 Hz, 2H); MS (APCI⁺) m/z 363 [M-(OCH₂CH₂OCH₃)]⁺.

Example 22F: tert-butyl ({8'-fluoro-6'-[(2-methoxyethoxy)methoxy]-3',4'-dihydro-1'H-spiro[[1,3]dioxolane-2,2'-naphthalen]-7'-yl}amino)acetate In a 500 mL round-bottom flask were combined cesium carbonate (7.70 g, 23.63 mmol), BrettPhos (0.127 g, 0.236 mmol), BrettPhos Pd G3 precatalyst (0.214 g, 0.236 mmol) and the product from Example 22E (5.1776 g, 11.81 mmol). The flask was placed under vacuum for 5 minutes, and refilled with nitrogen. 1,4-Dioxane (104 mL) was added followed by tert-butyl 2-aminoacetate (1.94 mL, 14.18 mmol). The resulting suspension was degassed by 5×vacuum/nitrogen backfills, stirred for 5 minutes at room temperature, and then heated to an internal temperature of 90° C. After 2 hours, the mixture was cooled to below 40° C. and another portion of BettPhos (0.127 g, 0.236 mmol) and BrettPhos Pd G3 precatalyst (0.214 g, 0.236 mmol) were added. The resultant mixture was degassed by 3× vacuum/nitrogen backfills and then heating to 90° C. was resumed. After 90 minutes, the reaction mixture was cooled to below 40° C. and another portion of BettPhos (0.127 g, 0.236 mmol) and BrettPhos Pd G3 precatalyst (0.214 g, 0.236 mmol) were added. The mixture was degassed by 3× vacuum/nitrogen backfills and heating to 90° C. was again resumed. After 24 hours, the reaction mixture was cooled to room temperature and quenched with saturated aqueous ammonium chloride (15 mL), diluted with water (35 mL), and extracted with ethyl acetate (50 mL, 2×25 mL). The combined organic layers were washed with brine (20 mL), dried over sodium sulfate, filtered and concentrated in vacuo. The residue was loaded onto an 80 g silica gel column in dichloromethane and eluted with a gradient of 0-50% ethyl acetate in heptanes containing 0.1% triethylamine to give the title compound (4.4284 g, 10.03 mmol, 85% yield). $^1$H NMR (400 MHz, CDCl₃) δ ppm 6.80-6.55 (m, 1H), 5.25 (s, 2H), 4.36 (td, J=6.0, 2.8 Hz, 1H), 4.09-3.97 (m, 4H), 3.93 (dd, J=6.1, 2.0 Hz, 2H), 3.86-3.80 (m, 2H), 3.62-3.51 (m, 2H), 3.39 (s, 3H), 2.88 (t, J=6.7 Hz, 2H), 2.83 (s, 2H), 1.89 (t, J=6.7 Hz, 2H), 1.45 (s, 9H); MS (ESI⁺) m/z 442 [M+H]⁺.

Example 22G: tert-butyl [{8'-fluoro-6'-[(2-methoxyethoxy)methoxy]-3',4'-dihydro-1'H-spiro[[1,3]dioxolane-2,2'-naphthalen]-7'-yl}({[(prop-2-en-1-yl)oxy]carbonyl}sulfamoyl)amino]acetate To a solution of chlorosulfonyl isocyanate (1.42 mL, 16.29 mmol) in dichloromethane (48 mL) at 0° C. was added allyl alcohol (1.11 mL, 16.29 mmol) dropwise so that the internal temperature remained below 10° C. After 30 minutes, a preformed solution of the product of Example 22F (4.7953 g, 10.86 mmol) and N,N-diisopropylethylamine (3.79 mL, 21.72 mmol) in dichloromethane (24 mL) was added slowly so that the internal temperature remained below 10° C. After 30 minutes, the reaction mixture was quenched with water (48 mL), stirred for 5 minutes, and then the layers were separated. The aqueous layer was extracted with dichloromethane (2×24 mL). The combined organic layers were washed with 1 M aqueous sodium bisulfate (24 mL), and then the new aqueous layer was back extracted with dichloromethane (15 mL). The combined organic layers were dried over sodium sulfate, filtered and concentrated in vacuo to give the title compound, which was used for the next step without purification. $^1$H NMR (400 MHz, DMSO-d₆) δ ppm 11.46 (s, 1H), 6.81 (s, 1H), 5.91 (ddt, J=17.2, 10.6, 5.3 Hz, 1H), 5.37-5.28 (m, 1H), 5.25 (d, J=7.1 Hz, 1H), 5.22 (d, J=9.8 Hz, 1H), 5.14 (d, J=6.8 Hz, 1H), 4.70 (d, J=17.5 Hz, 1H), 4.63-4.48 (m, 4H), 4.08 (d, J=17.6 Hz, 1H), 4.01-3.88 (m, 4H), 3.72 (qt, J=11.2, 4.7 Hz, 2H), 3.46 (t, J=4.7 Hz, 2H), 3.23 (s, 3H), 2.87 (t, J=6.7 Hz, 2H), 2.71 (s, 2H), 1.84 (t, J=6.6 Hz, 2H), 1.33 (s, 9H); MS (ESI⁺) m/z 622 [M+NH₄]⁺.

Example 22H: 5-{8'-fluoro-6'-[(2-methoxyethoxy)methoxy]-3',4'-dihydro-1'H-spiro[[1,3]dioxolane-2,2'-naphthalen]-7'-yl}-1$\lambda^6$,2,5-thiadiazolidine-1,1,3-trione To a solution of the product of Example 22G (6.57 g, 10.87 mmol) in methanol (117 mL) was added tetrakis(triphenylphosphine)palladium(0) (0.251 g, 0.217 mmol). The resulting suspension was degassed by 5× vacuum/nitrogen backfills, then a solution of sodium methoxide (14.9 mL, 65.2 mmol, 25 w % in methanol) was added and the resulting suspension was heated to an internal temperature of 60° C. After 1 hour, the mixture was cooled to room temperature, diluted with ethyl acetate (66 mL), and partially concentrated to approximately 33 mL total volume to remove methanol. The resulting suspension was diluted with ethyl acetate (66 mL) and quenched with 1 M hydrochloric acid (70 mL, final pH<3). The aqueous layer was extracted with ethyl acetate (2×33 mL). The combined organic layers were washed with brine (19 mL), dried over sodium sulfate, filtered through Celite® (5 g disposable frit) and concentrated in vacuo. The residue was chased with acetonitrile (33 mL) and concentrated to give the title compound (4.6781 g, 10.48 mmol, 96% yield), which was used for the next step without further purification. $^1$H NMR (400 MHz, DMSO-d₆) δ ppm 6.83 (d, J=1.5 Hz, 1H), 5.25 (s, 2H), 4.35 (s, 2H), 3.99-3.86 (m, 4H), 3.81-3.69 (m, 2H), 3.50-3.39 (m, 2H), 3.23 (s, 3H), 2.89 (t, J=6.7 Hz, 2H), 2.74 (s, 2H), 1.85 (t, J=6.6 Hz, 2H); MS (ESI⁻) m/z 445 [M–H]⁻.

Example 22I: 5-{1-fluoro-3-[(2-methoxyethoxy)methoxy]-7-oxo-5,6,7,8-tetrahydronaphthalen-2-yl}-1$\lambda^6$,2,5-thiadiazolidine-1,1,3-trione, Triethylamine Salt The product of Example 22H (2.6869 g, 6.02 mmol) was suspended in formic acid (13.4 mL, 307 mmol, 88%), quickly becoming a yellow suspension. After 15 minutes, the reaction mixture was diluted with a slow addition of brine (54 mL). The aqueous mixture was extracted with a 2:1 mixture of ethyl acetate and acetonitrile (3×27 mL). The combined organic layers were washed with brine (2×13 mL), dried over sodium sulfate, and filtered. To the crude solution was added triethylamine (2.52 mL, 18.06 mmol) and silica (10 g), and the resulting suspension was concentrated in vacuo. The resulting yellow powder was dry loaded onto an 80 g silica gel column and eluted with a gradient of 0-20% methanol in dichloromethane containing 0.2% triethylamine to give the title compound (3.2400 g, 6.02 mmol, 100% yield) as a hygroscopic yellow solid. $^1$H NMR (400 MHz, DMSO-d₆) δ ppm 6.93 (d, J=1.5 Hz, 1H), 5.24 (s, 2H), 3.94 (s, 1H), 3.80-3.71 (m, 2H), 3.50-3.41 (m, 3H), 3.23 (s, 2H), 3.17 (s, 3H), 3.02 (dd, J=7.6, 5.9 Hz, 2H), 2.56-2.40 (m, 2H); MS (ESI⁺) m/z 420 [M+NH₄]⁺.

Example 22J: 5-{1-fluoro-3-hydroxy-7-[(4-methoxy-3,3-dimethylbutyl)amino]-5,6,7,8-tetrahydronaphthalen-2-yl}-1$\lambda^6$,2,5-thiadiazolidine-1,1,3-trione To a solution of the product from Example 22I (0.100 g, 0.186 mmol) and 4-methoxy-3,3-dimethylbutan-1-amine (0.037 g, 0.279 mmol) in acetonitrile (2 mL) at room temperature was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column, eluted with a gradient of 5-100% methanol in buffer (0.025 M ammonium bicarbonate in water acidified to pH 7 by adding dry ice) to give the title compound (0.0221 g, 0.051 mmol, 27.7% yield). $^1$H NMR (400 MHz, DMSO-$d_6$) δ ppm 9.21 (br s, 1H), 8.41 (br s, 2H), 6.47 (d, J=1.5 Hz, 1H), 3.93 (s, 2H), 3.49-3.39 (m, 2H), 3.27 (s, 3H), 3.15-3.07 (m, 1H), 3.06 (s, 2H), 3.04-2.96 (m, 2H), 2.87-2.64 (m, 2H), 2.20-2.13 (m, 1H), 1.68 (dq, J=11.2, 5.7 Hz, 1H), 1.62-1.53 (m, 2H), 0.90 (s, 6H); MS (ESI$^+$) m/z 430 [M+H]$^+$.

Example 23: 5-{1-fluoro-3-hydroxy-7-[(3-methoxy-3-methylbutyl)amino]-5,6,7,8-tetrahydronaphthalen-2-yl}-1λ$^6$,2,5-thiadiazolidine-1,1,3-trione (Compound 122)

To a solution of the product from Example 22I (0.100 g, 0.186 mmol) and 4-methoxy-3-(3-methoxy-3-methylbutyl) amine (0.033 g, 0.279 mmol) in acetonitrile (2 mL) at room temperature was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0162 g, 0.039 mmol, 21% yield). $^1$H NMR (400 MHz, DMSO-$d_6$) δ ppm 9.21 (s, 1H), 8.42 (s, 2H), 6.47 (d, J=1.4 Hz, 1H), 3.94 (s, 2H), 3.47-3.40 (m, 1H), 3.11 (s, 3H), 3.09-3.00 (m, 2H), 2.87-2.64 (m, 2H), 2.59-2.50 (m, 1H), 2.20-2.12 (m, 1H), 1.83-1.75 (m, 2H), 1.69 (qd, J=11.2, 5.7 Hz, 1H), 1.15 (s, 6H); MS (ESI$^+$) m/z 416 [M+H]$^+$.

Example 24: 5-{1-fluoro-3-hydroxy-7-[(4,4,4-trifluoro-3,3-dimethylbutyl)amino]-5,6,7,8-tetrahydronaphthalen-2-yl}-1λ$^6$,2,5-thiadiazolidine-1,1,3-trione (Compound 123)

To a solution of the product from Example 22I (0.100 g, 0.186 mmol) and 4,4,4-trifluoro-3,3-dimethylbutan-1-amine (0.043 g, 0.279 mmol) in acetonitrile (2 mL) at room temperature was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0200 g, 0.044 mmol, 23.8% yield). $^1$H NMR (400 MHz, DMSO-$d_6$) δ ppm 9.20 (s, 1H), 8.44 (s, 2H), 6.47 (d, J=1.3 Hz, 1H), 3.93 (s, 2H), 3.45 (s, 2H), 3.15-3.05 (m, 3H), 2.90-2.64 (m, 2H), 2.59-2.44 (m, 1H), 2.15 (t, J=9.5 Hz, 1H), 1.81 (dd, J=11.4, 5.9 Hz, 2H), 1.76-1.62 (m, 1H), 1.14 (s, 6H); MS (ESI$^+$) m/z 454 [M+H]$^+$.

Example 25: 5-[1-fluoro-3-hydroxy-7-({2-[1-(trifluoromethyl)cyclopropyl]ethyl}amino)-5,6,7,8-tetrahydronaphthalen-2-yl]-1λ$^6$,2,5-thiadiazolidine-1,1,3-trione (Compound 124)

To a solution of the product from Example 22I (0.100 g, 0.186 mmol) and 2-[1-(trifluoromethyl)cyclopropyl]ethan-1-amine hydrochloride (0.053 g, 0.279 mmol) in acetonitrile (2 mL) at room temperature was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0161 g, 0.036 mmol, 19.2% yield). $^1$H NMR (400 MHz, DMSO-$d_6$) δ ppm 9.21 (br s, 1H), 8.44 (br s, 2H), 6.47 (d, J=1.4 Hz, 1H), 3.93 (s, 2H), 3.50-3.39 (m, 1H), 3.16-3.02 (m, 3H), 2.86-2.64 (m, 2H), 2.57-2.51 (m, 1H), 2.17-2.09 (m, 1H), 1.91 (dd, J=10.4, 6.5 Hz, 2H), 1.75-1.62 (m, 1H), 1.01-0.90 (m, 2H), 0.90-0.83 (m, 2H); MS (ESI$^+$) m/z 452 [M+H]$^+$.

Example 26: 5-{7-[(2,2-difluoro-2-phenylethyl)amino]-1-fluoro-3-hydroxy-5,6,7,8-tetrahydronaphthalen-2-yl}-1λ$^6$,2,5-thiadiazolidine-1,1,3-trione (Compound 125)

A mixture of the product of Example 22I (110 mg, 0.218 mmol), 2,2-difluoro-2-phenylethanamine, hydrochloric acid salt (85 mg, 0.437 mmol), triethylamine (66.3 mg, 0.655 mmol) and sodium cyanoborohydride (27.5 mg, 0.437 mmol) in acetonitrile (2.5 mL) was stirred at room temperature for 18 hours, then 4 N HCl solution in dioxane (0.983 mL) was added slowly. The mixture was stirred at room temperature for 30 minutes and then concentrated. The resulting residue was dissolved in methanol and water (10:1 ratio, 5 mL), and purified by preparative HPLC [YMC TriArt™ C18 Hybrid 20 μm column, 25×150 mm, flow rate 80 mL/minute, 0-65% gradient of methanol in buffer (0.025 M aqueous ammonium bicarbonate, adjusted to pH 10 with ammonium hydroxide)] to afford the title compound (54 mg, 0.119 mmol, 54% yield). $^1$H NMR (500 MHz, DMSO-$d_6$) δ ppm 9.04 (br s, 1H), 7.60 (m, 2H), 7.52 (m, 3H), 6.41 (s, 1H), 3.92 (s, 2H), 3.52 (m, 2H), 3.17 (m, 1H), 2.95 (m, 1H), 2.73 (m, 1H), 2.62 (m, 1H), 2.33 (m, 1H), 2.02 (m, 1H), 1.50 (m, 1H); MS (ESI$^-$) m/z 454 [M−H]$^-$.

Example 27: 5-{7-[(3-cyclopropyl-2,2-difluoropropyl)amino]-1-fluoro-3-hydroxy-5,6,7,8-tetrahydronaphthalen-2-yl}-1λ$^6$,2,5-thiadiazolidine-1,1,3-trione (Compound 126)

The title compound was prepared using the methodologies described in Example 26 substituting 3-cyclopropyl-2,2-difluoropropan-1-amine, hydrochloric acid salt for 2,2-difluoro-2-phenylethanamine, hydrochloric acid salt. $^1$H NMR (500 MHz, DMSO-$d_6$) δ ppm 9.09 (br s, 1H), 6.44 (s, 1H), 3.93 (s, 2H), 3.40 (m, 2H), 3.02 (m, 2H), 2.78 (m, 1H), 2.69 (m, 1H), 2.40 (m, 1H), 2.14 (m, 1H), 1.92 (m, 2H), 1.58 (m, 1H), 0.81 (m, 1H), 0.50 (m, 2H), 0.18 (m, 2H); MS (ESI⁻) m/z 432 [M–H]⁻.

Example 28: 5-{1-fluoro-3-hydroxy-7-[(3-hydroxy-3-methylbutyl)amino]-5,6,7,8-tetrahydronaphthalen-2-yl}-1λ⁶,2,5-thiadiazolidine-1,1,3-trione (Compound 127)

To a solution of the product from Example 22I (0.107 g, 0.199 mmol) and 4-amino-2-methylbutan-2-ol (0.033 mL, 0.298 mmol) in acetonitrile (2 mL) at room temperature was added sodium cyanoborohydride (0.015 g, 0.238 mmol). After 19 hours, a solution of HCl (0.497 mL, 1.987 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.04679 g, 0.117 mmol, 58.7% yield). ¹H NMR (400 MHz, DMSO-d₆) δ ppm 6.41 (s, 1H), 3.94 (s, 2H), 2.93-2.56 (m, 6H), 2.21 (dd, J=15.3, 8.1 Hz, 1H), 1.90 (dd, J=11.9, 6.0 Hz, 1H), 1.53 (t, J=7.2 Hz, 2H), 1.45 (dt, J=13.4, 7.5 Hz, 1H), 1.09 (s, 6H); MS (ESI⁺) m/z 402 [M+H]⁺.

Example 29: 5-{1-fluoro-3-hydroxy-7-[methyl(3-methylbutyl)amino]-5,6,7,8-tetrahydronaphthalen-2-yl}-1λ⁶,2,5-thiadiazolidine-1,1,3-trione (Compound 128)

To a solution of the product from Example 22I (0.100 g, 0.186 mmol) and methyl(3-methylbutyl)amine hydrochloride (0.038 g, 0.279 mmol) in acetonitrile (2 mL) at room temperature was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0106 g, 0.027 mmol, 14.3% yield). ¹H NMR (400 MHz, DMSO-d₆) δ ppm 9.40 (br s, 1H), 9.22 (s, 1H), 6.47 (d, J=1.4 Hz, 1H), 3.94 (s, 2H), 3.62 (br s, 1H), 3.21-3.08 (m, 2H), 3.06-2.96 (m, 1H), 2.90-2.69 (m, 6H), 2.15 (br d, J=11.5 Hz, 1H), 1.68-1.48 (m, 3H), 0.92 (d, J=6.3 Hz, 6H); MS (ESI⁺) m/z 400 [M+H]⁺.

Example 30: 5-{1-fluoro-3-hydroxy-7-[(4-methylpentyl)amino]-5,6,7,8-tetrahydronaphthalen-2-yl}-1λ⁶,2,5-thiadiazolidine-1,1,3-trione (Compound 129)

To a solution of the product from Example 22I (0.100 g, 0.186 mmol) and 4-methylpentan-1-amine (0.028 g, 0.279 mmol) in acetonitrile (2 mL) at room temp was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0105 g, 0.026 mmol, 14.2% yield). ¹H NMR (400 MHz, DMSO-d₆) δ ppm 9.20 (s, 1H), 8.31 (br s, 2H), 6.47 (d, J=1.4 Hz, 1H), 3.93 (s, 2H), 3.08 (dd, J=16.0, 5.5 Hz, 1H), 3.03-2.95 (m, 2H), 2.77 (qt, J=17.4, 8.2 Hz, 2H), 2.57-2.43 (m, 1H), 2.20-2.10 (m, 1H), 1.72-1.60 (m, 1H), 1.63-1.50 (m, 2H), 1.28-1.13 (m, 2H), 0.89 (d, J=6.6 Hz, 6H); MS (ESI⁺) m/z 400 [M+H]⁺.

Example 31: 5-(1-fluoro-3-hydroxy-7-{[4,4,4-trifluoro-3-hydroxy-3-(trifluoromethyl)butyl]amino}-5,6,7,8-tetrahydronaphthalen-2-yl)-1λ⁶,2,5-thiadiazolidine-1,1,3-trione (Compound 130)

To a solution of the product from Example 22I (0.100 g, 0.186 mmol) and 4-amino-1,1,1-trifluoro-2-(trifluoromethyl)butan-2-ol (0.059 g, 0.0.279 mmol) in acetonitrile (2 mL) at room temperature was added sodium cyanoborohydride (0.014 g, 0.223 mmol). After 3 hours, a solution of HCl (0.462 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0354 g, 0.069 mmol, 37.4% yield). ¹H NMR (400 MHz, DMSO-d₆) δ ppm 9.19 (s, 1H), 8.43 (br s, 2H), 7.07 (br s, 1H), 6.47 (s, 1H), 3.94 (s, 2H), 3.19 (t, J=7.8 Hz, 2H), 3.04 (dd, J=16.2, 5.3 Hz, 1H), 2.76 (qt, J=17.4, 5.4 Hz, 2H), 2.54-2.43 (m, 1H), 2.29-2.21 (m, 2H), 2.08 (d, J=13.1 Hz, 1H), 1.66 (qd, J=10.5, 5.3 Hz, 1H); MS (ESI⁺) m/z 510 [M+H]⁺.

Example 32: 5-(1-fluoro-3-hydroxy-7-{[4,4,4-trifluoro-3-(trifluoromethyl)butyl]amino}-5,6,7,8-tetrahydronaphthalen-2-yl)-1λ⁶,2,5-thiadiazolidine-1,1,3-trione (Compound 131)

To a solution of the product from Example 22I (0.100 g, 0.186 mmol) and 4,4,4-trifluoro-3-(trifluoromethyl)butan-1-amine hydrochloride (0.064 g, 0.279 mmol) in acetonitrile (2 mL) at room temperature was added sodium cyanoborohydride (0.014 g, 0.223 mmol). After 3 hours, a solution of HCl (0.464 mL, 1.857 mmol, 4 M in dioxane) was added dropwise (vigorous gas evolution). After 90 minutes, the reaction mixture was diluted with acetonitrile (3 mL) and water (1 mL). Celite® (1 g) was added, and the mixture was concentrated in vacuo. The resultant mixture was dry loaded onto a Teledyne ISCO 100 g reverse-phase C18 column eluted with a gradient of 5-100% methanol in buffer (0.025 M ammonium bicarbonate in water acidified to pH 7 by adding dry ice) to give the title compound (0.0177 g, 0.036 mmol, 19.3% yield). ¹H NMR (400 MHz, DMSO-d₆) δ ppm 9.24 (s, 1H), 8.59 (br s, 2H), 6.48 (s, 1H), 4.23 (ddt, J=11.1, 8.5, 4.5 Hz, 1H), 3.94 (s, 2H), 3.50 (s, 1H), 3.21 (t, J=8.2 Hz, 2H), 3.06 (dd, J=16.0, 5.4 Hz, 1H), 2.78 (qt, J=17.4, 8.4 Hz, 2H), 2.60-2.43 (m, 1H), 2.21-2.06 (m, 3H), 1.71 (qd, J=10.7, 5.4 Hz, 1H); MS (ESI⁺) m/z 510 [M+H]⁺.

Example 33: 5-{7-[(2,2-difluoropropyl)amino]-1-fluoro-3-hydroxy-5,6,7,8-tetrahydronaphthalen-2-yl}-1λ⁶,2,5-thiadiazolidine-1,1,3-trione (Compound 132)

The title compound was prepared using the methodologies described in Example 17 substituting 2,2-difluoropropan-1-amine for 3,3,3-trifluoropropan-1-amine. $^1$H NMR (400 MHz, DMSO-d$_6$) δ ppm 9.15 (br s, 1H), 6.44 (s, 1H), 3.93 (s, 2H), 3.47 (m, 2H), 3.04 (m, 1H), 2.79 (m, 1H), 2.68 (m, 1H), 2.52 (m, 1H), 2.41 (m, 1H), 2.11 (m, 1H), 1.71 (t, J=19 Hz, 3H), 1.59 (m, 1H); MS (ESI$^-$) m/z 392 [M−H]$^-$.

Example 34: 5-{(7R)-7-[(2-cyclopropylethyl)amino]-1-fluoro-3-hydroxy-5,6,7,8-tetrahydronaphthalen-2-yl}-1λ$^6$,2,5-thiadiazolidine-1,1,3-trione (Compound 133)

The product of Example 2 (100 mg, 0.261 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a dewar of bone-dry non-certified CO$_2$ pressurized to 350 psi with a modifier of methanol (0.1% triethylamine) at a flow rate of 70 g/minute. The column was at ambient temperature and the backpressure regulator was set to maintain 100 bar. The sample was dissolved in methanol:dimethyl sulfoxide (70:30) at a concentration of 5 mg/mL. The sample was loaded into the modifier stream in 2 mL (10 mg) injections. The mobile phase was held isocratically at 45% cosolvent:CO$_2$. Fraction collection was time triggered. The instrument was fitted with a CHIRALPAK® IC column with dimensions 21 mm i.d.×250 mm length with 5 μm particles. The later eluting enantiomer peak gave the title compound (26 mg, 0.068 mmol, 52% recovery). $^1$H NMR and MS data were identical to those from Example 2. Absolute stereochemistry was tentatively assigned in analogy to the chromatography elution order to the product of Example 19.

Example 35: 5-{(7S)-7-[(2-cyclopropylethyl)amino]-1-fluoro-3-hydroxy-5,6,7,8-tetrahydronaphthalen-2-yl}-1λ$^6$,2,5-thiadiazolidine-1,1,3-trione (Compound 134)

The product of Example 2 (100 mg, 0.261 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a dewar of bone-dry non-certified CO$_2$ pressurized to 350 psi with a modifier of methanol (0.1% triethylamine) at a flow rate of 70 g/minute. The column was at ambient temperature and the backpressure regulator was set to maintain 100 bar. The sample was dissolved in methanol:dimethyl sulfoxide (70:30) at a concentration of 5 mg/mL. The sample was loaded into the modifier stream in 2 mL (10 mg) injections. The mobile phase was held isocratically at 45% cosolvent:CO$_2$. Fraction collection was time triggered. The instrument was fitted with a CHIRALPAK® IC column with dimensions 21 mm i.d.×250 mm length with m particles. The earlier eluting enantiomer peak gave the title compound (25.7 mg, 0.067 mmol, 51.4% recovery). $^1$H NMR and MS data were identical to those from Example 2. Absolute stereochemistry was tentatively assigned in analogy to the chromatography elution order to the product of Example 18.

Example 36: 5-(1-fluoro-3-hydroxy-7-{[2-(pyridin-2-yl)ethyl]amino}-5,6,7,8-tetrahydronaphthalen-2-yl)-1λ$^6$,2,5-thiadiazolidine-1,1,3-trione (Compound 135)

The title compound was prepared using the methodologies described in Example 26 substituting 2-(pyridin-2-yl)ethanamine for 2,2-difluoro-2-phenylethanamine, hydrochloric acid salt. $^1$H NMR (500 MHz, DMSO-d$_6$) δ ppm 8.51 (dd, J=6, 2 Hz, 1H), 7.74 (dt, J=2, 7 Hz, 1H), 7.31 (br d, J=7 Hz, 1H), 7.26 (dd, J=7, 6 Hz, 1H), 6.41 (s, 1H), 3.92 (s, 2H), 3.13 (t, J=7 Hz, 2H), 2.99 (m, 2H), 2.88 (m, 2H), 2.73 (m, 1H), 2.62 (m, 1H), 2.23 (m, 1H), 1.89 (m, 1H), 1.46 (m, 1H); MS (ESI$^-$) m/z 419 [M−1]$^-$.

Example 37: 5-{(7RS)-1-fluoro-3-hydroxy-7-[(3RS)-pyrrolidin-3-yl]-5,6,7,8-tetrahydronaphthalen-2-yl}-1λ$^6$,2,5-thiadiazolidine-1,1,3-trione (Compound 136)

Example 37A: tert-butyl 3-[6-(benzyloxy)-8-fluoro-7-(1,1,4-trioxo-1λ$^6$,2,5-thiadiazolidin-2-yl)naphthalen-2-yl]-2,5-dihydro-1H-pyrrole-1-carboxylate To the product of Example 1G in dioxane (20 mL) was added tert-butyl 3-(4,4,5,5-tetramethyl-1,3,2-dioxaborolan-2-yl)-2,5-dihydro-1H-pyrrole-1-carboxylate (3.05 g, 10.32 mmol) and 1 M sodium carbonate (12.90 mL, 25.8 mmol). Tetrakis(triphenylphosphine)palladium(0) (497 mg, 0.43 mmol) was added, and the reaction mixture was sparged with N2 for 5 minutes. The mixture was then heated at 100° C. overnight. The reaction mixture was cooled down to room temperature, and the volatiles were removed under reduced pressure. The residue was subjected to column chromatography (dry loading with diatomaceous earth, 5% CH$_3$OH in CH$_2$Cl$_2$) to afford the title compound (3.75 g, 6.77 mmol, 79% yield) as a yellow solid. $^1$H NMR (500 MHz, DMSO-d$_6$) δ ppm 7.87-7.80 (m, 2H), 7.75 (d, J=12.7 Hz, 1H), 7.60-7.52 (m, 2H), 7.41-7.35 (m, 3H), 7.35-7.28 (m, 1H), 6.59-6.52 (m, 1H), 5.27 (s, 2H), 4.53 (d, J=7.7 Hz, 2H), 4.26 (d, J=12.0 Hz, 2H), 4.09 (s, 2H), 1.47 (d, J=10.6 Hz, 9H); MS (APCI$^-$) m/z 551 [M−H]$^-$.

Example 37B: tert-butyl 3-[8-fluoro-6-hydroxy-7-(1,1,4-trioxo-1λ$^6$,2,5-thiadiazolidin-2-yl)naphthalen-2-yl]pyrrolidine-1-carboxylate To the product of Example 37A (2.76 g, 4.99 mmol) and tetrahydrofuran (THF) (10 mL) was added 5% Pd/C (2.8 g, 12.26 mmol) in a 20 mL Parr® Barnstead Hastelloy C reactor, and the resultant mixture was stirred for 68 hours under hydrogen (61 psi) at 25° C. The volatiles were removed under the reduced pressure, and the crude residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) used over 15 minutes, at a flow rate of 25 mL/minute] to afford the titled compound (1.7 g, 3.65 mmol, 73.3% yield). $^1$H NMR (400 MHz, DMSO-d$_6$) δ ppm 7.74-7.67 (m, 2H), 7.44 (dd, J=8.6, 1.7 Hz, 1H), 7.05 (d, J=1.3 Hz, 1H), 4.10 (s, 2H), 3.75 (dd, J=10.4, 7.5 Hz, 1H), 3.55-3.44 (m, 2H), 3.37-3.21 (m, 2H), 2.25 (s, 1H), 2.02 (s, 1H), 1.42 (d, J=4.3 Hz, 9H); MS (APCI$^-$) m/z 464 [M−H]$^-$.

Example 37C: tert-butyl 3-[8-fluoro-6-hydroxy-7-(1,1,4-trioxo-1λ$^6$,2,5-thiadiazolidin-2-yl)-1,2,3,4-tetrahydronaphthalen-2-yl]pyrrolidine-1-carboxylate The product of Example 37B (420 mg, 0.902 mmol) and acetic acid (9 mL) were added to 5% Pd/C (840 mg, 3.68 mmol) in a 50 mL Hastelloy C reactor, and the reaction mixture as stirred for 18 hours under hydrogen (110 psi) without external heating. Subsequently, 10% Pd(OH)$_2$/C (420 mg, 1.495 mmol) was added to the reactor, and the hydrogenation reaction was continued under hydrogen (110 psi) for an additional 20 hours at room temperature. After filtration, the volatiles were removed under reduced pressure to give the titled compound, which was used in the next step without purification. MS (APCI$^-$) m/z 468 [M–H]$^-$.

Example 37D: 5-{(RS)-1-fluoro-3-hydroxy-7-[(3RS)-pyrrolidin-3-yl]-5,6,7,8-tetrahydronaphthalen-2-yl}-1$\lambda^6$,2,5-thiadiazolidine-1,1,3-trione The product of Example 37C (100 mg, 0.213 mmol) was dissolved in dichloromethane (DCM) (1 mL) and trifluoroacetic acid (1 mL) and stirred at ambient temperature. After 30 minutes, the volatiles were removed under reduced pressure, and the residue was subjected to preparative HPLC [Phenomenex® C8(2) Luna® 5 µm AXIA™ 150×30 mm column eluted with a gradient of acetonitrile (A) and 0.1% trifluoroacetic acid in water (B) at a flow rate of 50 mL/minute (0-0.5 minute 5% A, 0.5-20.5 minutes linear gradient 05-100% A, 20.7-22.7 minutes 100% A, 22.7-23 minutes linear gradient 100-05% A)] to afford the titled compound (stereochemistry arbitrarily assigned) and the diastereomer, Example 39. $^1$H NMR (400 MHz, DMSO-d$_6$) δ ppm 8.95 (s, 1H), 8.56 (s, 2H), 6.39 (s, 1H), 3.89 (s, 2H), 3.41-3.33 (m, 1H), 3.13-3.02 (m, 1H), 2.81 (t, J=10.3 Hz, 1H), 2.72 (dd, J=16.6, 5.0 Hz, 1H), 2.68-2.54 (m, 2H), 2.21-1.98 (m, 3H), 1.78 (d, J=12.8 Hz, 1H), 1.65-1.55 (m, 3H), 1.30 (qd, J=11.3, 5.5 Hz, 1H); MS (APCI$^+$) m/z 370 [M+H]+; retention time=14.6 minutes.

Example 38: 5-{(7RS)-7-[(3RS)-1-(cyclopropanesulfonyl)pyrrolidin-3-yl]-1-fluoro-3-hydroxy-5,6,7,8-tetrahydronaphthalen-2-yl}-1$\lambda^6$,2,5-thiadiazolidine-1,1,3-trione (Compound 137)

The crude product of Example 37C (100 mg, 0.213 mmol) was dissolved in dichloromethane (DCM) (1 mL) and trifluoroacetic acid (1 mL). After stirring for 30 minutes, the volatiles were removed under reduced pressure, and the crude 5-[1-fluoro-3-hydroxy-7-(pyrrolidin-3-yl)-5,6,7,8-tetrahydronaphthalen-2-yl]-1$\lambda^6$,2,5-thiadiazolidine-1,1,3-trione trifluoroacetate was subjected to the next reaction without purification.

To a solution of the crude 5-[1-fluoro-3-hydroxy-7-(pyrrolidin-3-yl)-5,6,7,8-tetrahydronaphthalen-2-yl]-1$\lambda^6$,2,5-thiadiazolidine-1,1,3-trione trifluoroacetate in methylene chloride (DCM) (2 mL) was added cyclopropanesulfonyl chloride (0.055 mL, 0.541 mmol) at room temperature followed by Hunig's base (N,N-diisopropylethylamine) (0.142 mL, 0.812 mmol). The reaction mixture was stirred overnight at room temperature. The volatiles were removed under reduced pressure, and the crude residue was partitioned between water (5 mL) and ethyl acetate (5 mL). The organic layer was separated, volatiles were removed under reduced pressure, and the crude residue was subjected to preparative HPLC [Phenomenex® C8(2) Luna® 5 µm AXIA™ 150×30 mm column eluted with a gradient of acetonitrile (A) and 0.1% trifluoroacetic acid in water (B) at a flow rate of 50 mL/minute (0-0.5 minute 5% A, 0.5-20.5 minutes linear gradient 05-100% A, 20.7-22.7 minutes 100% A, 22.7-23 minutes linear gradient 100-05% A)] to afford the title compound (stereochemistry arbitrarily assigned) and the diastereomer, Example 40. $^1$H NMR (500 MHz, DMSO-d$_6$) δ ppm 9.97 (s, 1H), 6.47 (s, 1H), 4.34 (s, 2H), 3.54 (dd, J=9.6, 7.4 Hz, 1H), 3.45-3.38 (m, 1H), 3.26 (td, J=9.7, 6.3 Hz, 1H), 3.02 (t, J=9.5 Hz, 1H), 2.81-2.64 (m, 3H), 2.54 (s, 2H), 2.21 (dd, J=16.5, 10.5 Hz, 1H), 2.17-2.01 (m, 2H), 1.94-1.88 (m, 1H), 1.67-1.52 (m, 2H), 1.32 (qd, J=11.5, 5.2 Hz, 1H), 0.98-0.92 (m, 4H); MS (APCI$^-$) m/z 472 [M–H]$^-$; retention time=15.4 minutes.

Example 39: 5-{(7RS)-1-fluoro-3-hydroxy-7-[(3SR)-pyrrolidin-3-yl]-5,6,7,8-tetrahydronaphthalen-2-yl}-1$\lambda^6$,2,5-thiadiazolidine-1,1,3-trione (Compound 138)

This compound was purified as described in Example 37 to provide the diastereomeric title compound (stereochemistry arbitrarily assigned). $^1$H NMR (400 MHz, DMSO-d$_6$) δ ppm 9.14 (s, 1H), 8.68 (broad, 1H), 8.65-8.58 (broad, 1H), 6.44 (s, 1H), 3.99 (s, 2H), 3.32-3.20 (m, 2H), 3.16-3.04 (m, 1H), 2.93-2.83 (m, 1H), 2.78-2.58 (m, 3H), 2.25-2.09 (m, 3H), 1.92-1.84 (m, 1H), 1.65-1.55 (m, 2H), 1.41-1.29 (m, 1H). MS (APCI$^+$) m/z 370 [M+H]+; retention time=15.8 minutes.

Example 40: 5-{(7RS)-7-[(3SR)-1-(cyclopropanesulfonyl)pyrrolidin-3-yl]-1-fluoro-3-hydroxy-5,6,7,8-tetrahydronaphthalen-2-yl}-1$\lambda^6$,2,5-thiadiazolidine-1,1,3-trione (Compound 139)

This compound was purified as described in Example 38 to provide the diastereomeric title compound (stereochemistry arbitrarily assigned). $^1$H NMR (400 MHz, DMSO-d$_6$) δ ppm 9.94 (s, 1H), 6.47 (s, 1H), 4.33 (s, 2H), 3.57 (dd, J=9.8, 7.5 Hz, 1H), 3.46-3.38 (m, 1H), 3.26 (td, J=9.7, 6.2 Hz, 1H), 3.00 (t, J=9.3 Hz, 1H), 2.82-2.58 (m, 4H), 2.25-2.05 (m, 1H), 2.10 (s, 2H), 1.80 (d, J=12.8 Hz, 1H), 1.69-1.50 (m, 2H), 1.34 (tq, J=11.3, 5.5 Hz, 1H), 1.01-0.92 (m, 4H); MS (APCI$^-$) m/z 472 [M–H]; retention time=14.8 minutes.

Example 41: 5-{7-[1-(cyclopropylmethyl)pyrrolidin-3-yl]-1-fluoro-3-hydroxy-5,6,7,8-tetrahydronaphthalen-2-yl}-1$\lambda^6$,2,5-thiadiazolidine-1,1,3-trione (Compound 140)

The crude product of example 37C (100 mg, 0.213 mmol) was dissolved in dichloromethane (DCM) (1 mL) and trifluoroacetic acid (1 mL). After stirring for 30 minutes at ambient temperature, the volatiles were removed under reduced pressure, and the crude 5-[1-fluoro-3-hydroxy-7-(pyrrolidin-3-yl)-5,6,7,8-tetrahydronaphthalen-2-yl]-1$\lambda^6$,2,5-thiadiazolidine-1,1,3-trione trifluoroacetate was subjected to next reaction without purification. The crude 5-[1-fluoro-3-hydroxy-7-(pyrrolidin-3-yl)-5,6,7,8-tetrahydronaphthalen-2-yl]-1$\lambda^6$,2,5-thiadiazolidine-1,1,3-trione trifluoroacetate was dissolved in N,N-dimethylformamide (DMF) (3 mL) followed by addition of sodium carbonate (57.4 mg, 0.541 mmol). After stirring for 5 minutes, cyclopropanecarbaldehyde (56.9 mg, 0.812 mmol) and acetic acid (0.077 mL, 1.354 mmol) were added, and the mixture was stirred for 5 minutes at room temperature. Sodium cyanoborohydride (102 mg, 1.624 mmol) was then added. The reaction mixture was stirred at ambient temperature for two hours. The mixture was then partitioned between water (5 mL) and ethyl acetate (5 mL). The aqueous layer was separated and then extracted with ethyl acetate (2×3 mL). The combined organic layers were washed with saturated aqueous ammonium chloride (5 mL) and dried over sodium sulfate. The volatiles were removed under reduced pressure, and the crude residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) used over 15 minutes, at a flow rate of 25 mL/minute] to afford the title compound (22 mg, 0.052 mmol, 19% yield) as an inseparable mixture of diastereomers with the ratio of 1.7:1. MS (APCI$^-$) m/z 422 [M−H]$^-$.

Example 42: 5-(1-fluoro-3-hydroxy-7-{[2-(1H-pyrazol-1-yl)ethyl]amino}-5,6,7,8-tetrahydronaphthalen-2-yl)-1λ$^6$,2,5-thiadiazolidine-1,1,3-trione (Compound 141)

The title compound was prepared using the methodologies described in Example 26 substituting 2-(1H-pyrazol-1-yl)ethanamine, hydrochloric acid for 2,2-difluoro-2-phenylethanamine, hydrochloric acid salt. $^1$H NMR (500 MHz, DMSO-d$_6$) δ ppm 9.10 (s, 1H), 7.79 (d, J=2 Hz, 1H), 7.50 (d, J=2 Hz, 1H), 6.44 (s, 1H), 6.27 (m, 1H), 4.32 (m, 2H), 3.92 (s, 2H), 3.29 (m, 2H), 3.17 (m, 1H), 2.97 (m, 1H), 2.75 (m, 1H), 2.67 (m, 1H), 2.40 (m, 1H), 2.01 (m, 1H), 1.59 (m, 1H); MS (ESI$^-$) m/z 408 [M−1]$^-$.

Example 43: 5-[1-fluoro-3-hydroxy-7-(4,4,4-trifluorobutoxy)-5,6,7,8-tetrahydronaphthalen-2-yl]-1λ$^6$,2,5-thiadiazolidine-1,1,3-trione (Compound 142)

The title compound was prepared using the methodologies described in Example 1 substituting 1,1,1-trifluoro-4-iodobutane for 1-bromo-3-methylbutane. Purification by preparative HPLC [YMC TriArt™ C18 Hybrid 20 μm column, 25×150 mm, flow rate 80 mL/minute, 0-55% gradient of CH$_3$OH in buffer (0.025 M aqueous ammonium bicarbonate, adjusted to pH 10 with ammonium hydroxide)] afforded the title compound (38 mg, 0.086 mmol, 46% yield) as an ammonium salt. $^1$H NMR (500 MHz, DMSO-d$_6$) δ ppm 9.00 (br s, 1H), 7.09 (br s, 4H), 6.42 (s, 1H), 3.93 (s, 2H), 3.73 (m, 1H), 3.53 (m, 2H), 2.84 (m, 1H), 2.74 (m, 1H), 2.62 (m, 1H), 2.45 (m, 1H), 2.27 (m, 2H), 1.88 (m, 1H), 1.72 (m, 3H); MS (ESI$^-$) m/z 425 [M−1]$^-$.

Example 44: 5-(8-fluoro-6-hydroxy-1,2,3,4-tetrahydroisoquinolin-7-yl)-1λ$^6$,2,5-thiadiazolidine-1,1,3-trione (Compound 143)

Example 44A: N-[6-(benzyloxy)-4-bromo-2-fluoro-3-formylphenyl]-2,2,2-trifluoroacetamide A solution of diisopropylamine (4.80 mL, 33.7 mmol) in tetrahydrofuran (21 mL) was cooled to an internal temperature of −73° C., and n-butyllithium (14.0 mL, 33.7 mmol, 2.5 M in hexanes) was added over 10 minutes. The mixture was stirred for 5 minutes, warmed to 0° C., stirred for 10 minutes, and then re-cooled to −73° C. A solution of N-(2-(benzyloxy)-4-bromo-6-fluorophenyl)-2,2,2-trifluoroacetamide (the compound from Example 12C) (6.00 g, 15.3 mmol) in tetrahydrofuran (41 mL) was cooled to an internal temperature of −76° C., and the lithium diisopropylamide solution prepared above was added at a rate such that the internal temperature did not exceed −70° C. After aging for 75 minutes, a solution of N,N-dimethylformamide (4.74 mL, 185 mmol) in tetrahydrofuran (15 mL) was added at a rate such that the internal temperature did not exceed −68° C. After 20 minutes, the reaction was quenched with saturated aqueous ammonium chloride (30 mL), warmed to room temperature, and partitioned between ethyl acetate (2×50 mL) and water (50 mL). The combined organic extracts were washed with saturated aqueous ammonium chloride (4×20 mL), dried over sodium sulfate, then filtered and concentrated under reduced pressure to afford a viscous oil that was immediately purified by flash chromatography on silica gel [80 g SiO$_2$, gradient from heptanes→30% ethyl acetate/heptanes, 60 mL/minute] to afford the title compound (3.58 g, 8.42 mmol, 55.6% yield). $^1$H NMR (400 MHz, DMSO-d$_6$) δ ppm 11.21 (br s, 1H), 10.10 (d, J=1.1 Hz, 1H), 7.55 (d, J=1.4 Hz, 1H), 7.48-7.27 (m, 5H), 5.38 (s, 2H); MS (APCI$^+$) m/z 421 [M+H]$^+$.

Example 44B: tert-butyl {[4-(benzyloxy)-6-bromo-2-fluoro-3-(2,2,2-trifluoroacetamido)phenyl]methyl}{2-[methoxy(methyl)amino]-2-oxoethyl}carbamate To a solution of 2-amino-N-methoxy-N-methylacetamide hydrobromide (5.86 g, 29.5 mmol) in methanol (89 mL) was added triethylamine (4.11 mL, 29.5 mmol). After 5 minutes, acetic acid (0.766 mL, 13.39 mmol) was added followed by a solution of N-[6-(benzyloxy)-4-bromo-2-fluoro-3-formylphenyl]-2,2,2-trifluoroacetamide (11.25 g, 26.8 mmol) in methanol (89 mL). After 20 minutes, sodium triacetoxyborohydride (11.35 g, 53.6 mmol) was added in one portion, and the reaction mixture was stirred at room temperature for 2 hours. Thereafter, a solution of 2-amino-N-methoxy-N-methylacetamide hydrobromide (1.40 g, 7.03 mmol) and triethylamine (1.20 mL, 8.61 mmol) in methanol (15 mL) was added followed by sodium triacetoxyborohydride (3.00 g, 14.2 mmol). After 25 minutes, the reaction was poured into water (200 mL) and extracted into ethyl acetate (2×100 mL). The combined organic extracts were dried over sodium sulfate, filtered and concentrated under reduced pressure to give 15.48 g of a viscous residue. This was dissolved in dichloromethane (179 mL) and triethylamine (4.11 mL, 29.5 mmol) was added followed by di-tert-butyl dicarbonate (6.43 g, 29.5 mmol), and the reaction mixture was stirred at room temperature. After 14 hours, water (100 mL) was added, and the mixture was extracted into ethyl acetate (2×50 mL). The combined organic layers were dried over sodium sulfate, then filtered and concentrated under reduced pressure to afford 18.7 g of a viscous oil that was purified by flash chromatography on silica gel [220 g SiO$_2$, heptanes→50% ethyl acetate/heptanes, 150 mL/minute] to afford the title compound (12.1 g, 19.4 mmol, 72.4% yield). MS (APCI$^+$) m/z 624 [M+H]$^+$.

Example 44C: tert-butyl 6-(benzyloxy)-8-fluoro-4-oxo-7-(2,2,2-trifluoroacetamido)-3,4-dihydroisoquinoline-2(1H)-carboxylate A solution of tert-butyl {[4-(benzyloxy)-6-bromo-2-fluoro-3-(2,2,2-trifluoroacetamido)phenyl]methyl}{2-[methoxy(methyl)amino]-2-oxoethyl}carbamate (11.0 g, 17.7 mmol) in tetrahydrofuran (142 mL) was cooled to an internal temperature of −75° C., and n-butyllithium (15.1 mL, 36.3 mmol, 2.5 M in hexanes) was added at a rate such that the internal temperature did not exceed −70° C. After 5 minutes, the reaction was quenched with saturated aqueous ammonium chloride (20 mL), warmed to room temperature, and partitioned between ethyl acetate (150 mL) and water (100 mL). The aqueous layer was back-extracted with ethyl acetate (1×50 mL), and the combined organic extracts were dried over sodium sulfate, then filtered and concentrated under reduced pressure to afford 10.2 g of a viscous oil that was purified by flash chromatography on silica gel [120 g SiO$_2$, heptanes→30% ethyl acetate/heptanes, 85 mL/minute] to afford the title compound (6.44 g, 13.4 mmol, 68.6% yield). $^1$H NMR (400 MHz, CDCl$_3$) δ ppm 7.80 (s, 1H), 7.53 (d, J=1.5 Hz, 1H), 7.49-7.31 (m, 5H), 5.19 (s, 2H), 4.78 (s, 2H), 4.33 (s, 2H), 1.49 (s, 9H); MS (ESI$^-$) m/z 481 [M–H]$^-$.

Example 44D: tert-butyl 6-(benzyloxy)-8-fluoro-7-[(2-methoxy-2-oxoethyl) (trifluoroacetyl)amino]-4-oxo-3,4-dihydroisoquinoline-2(1H)-carboxylate To a solution of tert-butyl 6-(benzyloxy)-8-fluoro-4-oxo-7-(2,2,2-trifluoroacetamido)-3,4-dihydroisoquinoline-2(1H)-carboxylate (1.50 g, 3.11 mmol) in anhydrous N,N-dimethylformamide (7.8 mL) was added 1,2,2,6,6-pentamethylpiperidine (1.13 mL, 6.22 mmol) and methyl bromoacetate (0.372 mL, 4.04 mmol), and the reaction was heated to an internal temperature of 60° C. After 1 hour, the mixture was cooled to room temperature and partitioned between ethyl acetate (25 mL) and saturated aqueous ammonium chloride (20 mL). The organic layer was further washed with saturated aqueous ammonium chloride (4×20 mL), dried over sodium sulfate, then filtered and concentrated under reduced pressure to give 2.11 g of an orange oil that was purified by flash chromatography on silica gel [24 g SiO$_2$, heptanes→25% ethyl acetate/heptanes, 35 mL/minute] to afford the title compound (1.29 g, 2.33 mmol, 74.9% yield). MS (APCI$^+$) m/z 574 [M+NH$_4$]$^+$.

Example 44E: tert-butyl 6-(benzyloxy)-8-fluoro-4-[(1H-imidazole-1-carbothioyl)oxy]-7-[(2-methoxy-2-oxoethyl) (trifluoroacetyl)amino]-3,4-dihydroisoquinoline-2(1H)-carboxylate To a solution of tert-butyl 6-(benzyloxy)-8-fluoro-7-[(2-methoxy-2-oxoethyl)(trifluoroacetyl)amino]-4-oxo-3,4-dihydroisoquinoline-2(1H)-carboxylate (1.29 g, 2.33 mmol) in anhydrous tetrahydrofuran (23 mL) was added sodium borohydride (0.088 g, 2.33 mmol) in one portion. After 5 minutes, the reaction was diluted with ethyl acetate (20 mL) and quenched with saturated aqueous ammonium chloride (2 mL). The aqueous layer was back-extracted with ethyl acetate (1×20 mL), and the combined organic layers were dried over sodium sulfate, then filtered and concentrated under reduced pressure to give 1.26 g of an oil. The oil was dissolved in dichloromethane (23 mL) and 4-dimethylaminopyridine (0.085 g, 0.698 mmol) was added followed by 1,1'-thiocarbonyldiimidazole (0.539 g, 3.02 mmol). After 45 minutes, the reaction was directly concentrated to give an oil that was immediately purified by flash chromatography on silica gel [24 g SiO$_2$, heptanes→25% acetone/heptanes, 35 mL/minute, detect at 216 nm] to afford the title compound (1.03 g, 1.54 mmol, 66.3% yield over two steps). MS (APCI$^+$) m/z 667 [M+H]$^+$.

Example 44F: tert-butyl 6-(benzyloxy)-8-fluoro-7-[(2-methoxy-2-oxoethyl) (trifluoroacetyl)amino]-3,4-dihydroisoquinoline-2(1H)-carboxylate To a solution of tert-butyl 6-(benzyloxy)-8-fluoro-4-[(1H-imidazole-1-carbothioyl)oxy]-7-[(2-methoxy-2-oxoethyl) (trifluoroacetyl)amino]-3,4-dihydroisoquinoline-2(1H)-carboxylate (1.029 g, 1.54 mmol) and benzene (26 mL) was added tributyltin hydride (0.457 mL, 1.70 mmol). To the mixture was added a solution of triethylborane (1.70 mL, 1.70 mmol, 1.0 M in tetrahydrofuran) in one portion, and the reaction was stirred at room temperature. After 8 minutes, the reaction was concentrated to 1.5 mL and directly purified by flash chromatography on silica gel [24 g SiO$_2$, heptanes→20% acetone/heptanes, 35 mL/minute, detect at 208 nm] to afford the title compound (0.705 g, 1.30 mmol, 85% yield). MS (ESI$^-$) m/z 539 [M–H]$^-$.

Example 44G: tert-butyl 6-(benzyloxy)-8-fluoro-7-[(2-methoxy-2-oxoethyl)amino]-3,4-dihydroisoquinoline-2(1H)-carboxylate To a solution of tert-butyl 6-(benzyloxy)-8-fluoro-7-[(2-methoxy-2-oxoethyl)(trifluoroacetyl)amino]-3,4-dihydroisoquinoline-2(1H)-carboxylate (0.660 g, 1.22 mmol) in anhydrous methanol (8.1 mL) was added sodium methoxide (0.70 mL, 3.05 mmol, 25% w/w in methanol), and the reaction was heated to an internal temperature of 50° C. After 2 hours, the reaction was cooled to room temperature and quenched with saturated aqueous ammonium chloride (10 mL). The mixture was partitioned between ethyl acetate (30 mL) and water (10 mL), the aqueous layer was back-extracted with ethyl acetate (2×5 mL), and the combined organic extracts were dried over sodium sulfate, then filtered and concentrated under reduced pressure. To remove adventitious water, the residue was dissolved in ethyl acetate (20 mL), washed with brine (1×10 mL), dried over sodium sulfate, then filtered and concentrated under reduced pressure. To afford 0.702 g of an oil that was purified by flash chromatography on silica gel [12 g SiO$_2$, heptanes→25% acetone/heptanes, 30 mL/minute, detect at 208 nm] to afford the title compound (0.412 g, 0.927 mmol, 71.1% yield). MS (ESI$^+$) m/z 445 [M+H]$^+$.

Example 44H: tert-butyl 6-(benzyloxy)-8-fluoro-7-(1,1,4-trioxo-1λ$^6$,2,5-thiadiazolidin-2-yl)-3,4-dihydroisoquinoline-2(1H)-carboxylate To a solution of chlorosulfonyl isocyanate (0.121 mL, 1.39 mmol) in dichloromethane (4.6 mL) at an internal temperature of 0° C. was added allyl alcohol (0.095 mL, 1.39 mmol) at a rate such that the internal temperature did not exceed 7° C. After 30 minutes, a preformed solution of tert-butyl 6-(benzyloxy)-8-fluoro-7-[(2-methoxy-2-oxoethyl)amino]-3,4-dihydroisoquinoline-2(1H)-carboxylate (0.425 g, 0.927 mmol) and N,N-diisopropylethylamine (0.324 mL, 1.854 mmol) in dichloromethane (4.6 mL) was added at a rate such that the internal temperature did not exceed 7° C. After 30 minutes, the reaction was quenched with water (48 mL) and stirred for 5 minutes. Then the layers were separated, and the aqueous layer was extracted with dichloromethane (2×24 mL). The combined organic extracts were dried over sodium sulfate, filtered and concentrated to give 0.530 g of a foam, which was used without purification in the next step.

A solution of the above alloc-sulfonylurea (0.473 g, 0.778 mmol) in anhydrous methanol (8.6 mL) was degassed via sub-surface nitrogen sparging for 15 minutes. Thereafter, tetrakis(triphenylphosphine)palladium(0) (0.018 g, 0.016 mmol) was added followed by a solution of sodium methoxide (1.07 mL, 4.67 mmol, 25% w/w in methanol), and the reaction mixture was heated to a mantle temperature of 60° C. After 15 minutes, the mixture was cooled to room temperature, quenched with 1 M HCl (1 mL), and partitioned between ethyl acetate (4 mL) and water (3 mL). The aqueous layer was extracted with ethyl acetate (2×1 mL), and the combined organic extracts were washed with brine (1×5 mL), dried over sodium sulfate, filtered, and concen- Example 44I. 5-(8-fluoro-6-hydroxy-1,2,3,4-tetrahydroisoquinolin-7-yl)-1λ⁶,2,5-thiadiazolidine-1,1,3-trione A suspension of tert-butyl 6-(benzyloxy)-8-fluoro-7-(1,1,4-trioxo-1λ⁶,2,5-thiadiazolidin-2-yl)-3,4-dihydroisoquinoline-2(1H)-carboxylate (37.7 mg, 0.077 mmol) and 1,2,3,4,5-pentamethylbenzene (34.1 mg, 0.230 mmol) in dichloromethane (0.76 mL) was cooled to −78° C., and a solution of boron trichloride (153 μL, 0.153 mmol, 1.0 M in dichloromethane) was added dropwise over 5 minutes. After 15 minutes, the reaction was quenched with anhydrous methanol (31.0 μL, 0.767 mmol) and warmed to room temperature under nitrogen. The volatiles were removed to afford a solid that was triturated with heptane (3×1 mL) and dichloromethane (2×1 mL). The crude material was thereafter dissolved in water (2 mL), filtered through a plug of cotton to remove a yellow residue, and purified by reverse-phase HPLC [Luna® 10 μM C18(2) 100 Å, AX (00G-4253-U0-AX) column, 250×30 mm, 50 mL/minute, 1 injection, 5%→95% CH$_3$CN/H$_2$O (with pure, unbuffered water) over 15 minutes, monitored/collected at 205 nm]. The product eluted with the solvent front and was thereafter lyophilized (0.031 mbar) for 8 hours to afford the title compound (9.3 mg, 0.031 mmol, 40.2% yield). $^1$H NMR (400 MHz, DMSO-d$_6$) δ ppm 10.49 (br s, 1H), 9.34 (br s, 2H), 6.64 (s, 1H), 4.33 (s, 2H), 4.14 (app t, J=3.8 Hz, 2H); 3.32 (app q, J=5.7 Hz, 2H), 2.94 (t, J=5.9 Hz, 2H); MS (ESI⁻) m/z 300 [M−H]⁻.

Example 45: 5-[8-fluoro-6-hydroxy-2-(4-methylpentanoyl)-1,2,3,4-tetrahydroisoquinolin-7-yl]-1λ⁶,2,5-thiadiazolidine-1,1,3-trione (Compound 144)

Example 45A: 5-[6-(benzyloxy)-8-fluoro-2-(4-methylpentanoyl)-1,2,3,4-tetrahydroisoquinolin-7-yl]-1λ⁶,2,5-thiadiazolidine-1,1,3-trione To a solution of tert-butyl 6-(benzyloxy)-8-fluoro-7-(1,1,4-trioxo-1λ⁶,2,5-thiadiazolidin-2-yl)-3,4-dihydroisoquinoline-2(1H)-carboxylate (50 mg, 0.102 mmol) in dichloromethane (2.0 mL) was added trifluoroacetic acid (118 μL, 1.53 mmol). After 90 minutes, the reaction mixture was directly concentrated, the substrate was suspended in dichloromethane (1.0 mL) and N,N-diisopropylethylamine (71.1 μL, 0.407 mmol) was added, resulting in a homogeneous solution. Subsequently, 2-(1H-benzotriazole-1-yl)-1,1,3,3-tetramethylaminium tetrafluoroborate (TBTU) (35.9 mg, 0.112 mmol) was added followed by 4-methylvaleric acid (13.0 mg, 0.112 mmol), and the reaction was stirred at room temperature. After 20 minutes, additional N,N-diisopropylethylamine (71.1 μL, 0.407 mmol) was dispensed. After 5 minutes, the reaction mixture was diluted with dichloromethane (2 mL), quenched with 1 M HCl (2 mL), and extracted into dichloromethane (2×2 mL). The combined organic extracts were washed with brine (1×2 mL), dried over sodium sulfate, filtered, and concentrated to give a yellow oil that was immediately purified by flash chromatography on silica gel [4 g SiO$_2$, heptanes→95% acetone/heptanes, 18 mL/minute, monitor at 205 nm] to afford the title compound (35.0 mg, 0.071 mmol, 69.9% yield). MS (APCI⁺) m/z 490 [M+H]⁺.

trated to afford the title compound (314 mg, 0.639 mmol, 82% yield). MS (ESI⁻) m/z 490 [M−H]⁻.

Example 45B: 5-(8-fluoro-6-hydroxy-2-(4-methylpentanoyl)-1,2,3,4-tetrahydroisoquinolin-7-yl)-1,2,5-thiadiazolidin-3-one 1,1-dioxide A suspension of 5-[6-(benzyloxy)-8-fluoro-2-(4-methylpentanoyl)-1,2,3,4-tetrahydroisoquinolin-7-yl]-1λ⁶,2,5-thiadiazolidine-1,1,3-trione (74.7 mg, 0.153 mmol) and 1,2,3,4,5-pentamethylbenzene (67.9 mg, 0.458 mmol) in dichloromethane (1.5 mL) was cooled to −78° C., and a solution of boron trichloride (305 μL, 0.305 mmol, 1.0 M in dichloromethane) was added dropwise over 5 minutes. After 15 minutes, the reaction was quenched with anhydrous methanol (61.7 μl, 1.53 mmol) and warmed to room temperature under nitrogen. The volatiles were removed to afford a solid that was triturated with heptane (3×1 mL). The crude material was thereafter dissolved in dimethyl sulfoxide (2 mL) and purified by reverse-phase HPLC [Luna® 10 μM C18(2) 100 Å, AX (00G-4253-U0-AX) column, 250×30 mm, 50 mL/minute, 1 injection, 5%→95% CH$_3$CN/H$_2$O (buffer containing 29.4 g ammonium acetate in 18 L water) over 15 minutes, monitored/collected at 205 nm] to afford the title compound (21.6 mg, 0.054 mmol, 35.4% yield). $^1$H NMR (400 MHz, DMSO-d$_6$) δ 60:40 mixture of rotamers at 27° C.) δ ppm 6.51 (br s, 1H), 4.51 (s, 0.8H), 4.46 (s, 1.2H), 3.94 (s, 0.8H), 3.93 (s, 1.2H), 3.63 (q, J=5.7 Hz, 2H), 2.76 (t, J=5.9 Hz, 1.2H) 2.64 (t, J=5.9 Hz, 0.8H), 2.38 (q, J=8.2 Hz, 2H), 1.55 (sept, J=6.8 Hz, 1H), 1.40 (m, 2H), 0.87 (d, J=6.6 Hz, 4H), 0.86 (d, J=6.6 Hz, 2H); MS (APCI⁺) m/z 400 [M+H]⁺.

Example 46: 5-[8-fluoro-6-hydroxy-2-(4-methylpentyl)-1,2,3,4-tetrahydroisoquinolin-7-yl]-1λ⁶,2,5-thiadiazolidine-1,1,3-trione (Compound 145)

To a solution of tert-butyl 6-(benzyloxy)-8-fluoro-7-(1,1,4-trioxo-1λ⁶,2,5-thiadiazolidin-2-yl)-3,4-dihydroisoquinoline-2(1H)-carboxylate (60 mg, 0.122 mmol) in dichloromethane (1.1 mL) was added trifluoroacetic acid (141 μl, 1.83 mmol). After 25 minutes, the reaction mixture was directly concentrated, suspended in acetonitrile (1.4 mL), and potassium carbonate (84 mg, 0.610 mmol) was added followed by 1-bromo-4-methylpentane (40.3 mg, 0.244 mmol), and the reaction mixture was heated to 60° C. After 16 hours, the mixture was cooled to room temperature, filtered through a 0.45 μm Whatman PTFE syringe filter, and the volatiles were removed to afford a residue that was suspended with 1,2,3,4,5-pentamethylbenzene (46.0 mg, 0.310 mmol) in dichloromethane (1.0 mL) and cooled to −78° C. A solution of boron trichloride (207 μL, 0.207 mmol, 1.0 M in dichloromethane) was added dropwise over 5 minutes. After 15 minutes, additional boron trichloride (1.86 mL, 1.86 mmol, 1.0 M in dichloromethane) was dispensed. After 15 minutes, the reaction was quenched with anhydrous ethanol (302 μL, 5.17 mmol) and warmed to room temperature under nitrogen. The volatiles were removed to afford a solid that was triturated with heptane (3×1 mL). The crude material was thereafter dissolved in methanol (2.5 mL) and purified by reverse-phase HPLC [Luna® 10 μM C18(2) 100 Å, AX (00G-4253-U0-AX) column, 250×30 mm, 50 mL/minute, 1 injection, 5%→95% CH$_3$CN/H$_2$O (with pure, unbuffered water) over 15 minutes, monitored/collected at 205 nm] to afford the title compound (9.1 mg, 0.024 mmol, 19.7% yield). $^1$H NMR (400 MHz, DMSO-d$_6$) δ ppm 9.64 (br s, 2H), 6.58 (s, 1H), 4.28 (m, 2H), 3.47 (m, 2H), 3.15 (m, 2H), 2.96 (m, 2H), 1.69 (pent, J=8.0

Hz, 2H), 1.55 (sept, J=6.8 Hz, 1H), 1.17 (q, J=7.1 Hz, 2H), 0.86 (d, J=6.4 Hz, 6H); MS (APCI⁺) m/z 386 [M+H]⁺.

Example 47: 5-{(7R)-1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione (Compound 146)

Example 21 (76 mg, 0.179 mmol) was separated by preparative chiral SFC. Preparative SFC was performed on a THAR/Waters SFC80 system running under Super-Chrom™ software control. The preparative SFC system was equipped with an 8-way preparative column switcher, $CO_2$ pump, modifier pump, automated back pressure regulator (ABPR), UV detector, and 6-position fraction collector. The mobile phase was comprised of supercritical $CO_2$ supplied by a Dewar of bone-dry non-certified $CO_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide (70:30) at a concentration of 2 mg/mL. The sample was loaded into the modifier stream in 2 mL (4 mg) injections. The mobile phase was held isocratically at 45% cosolvent:$CO_2$. Fraction collection was time triggered. The instrument was fitted with a CHIRALPAK® IC column with dimensions 21 mm i.d.×250 mm length with 5 m particles. The later eluting enantiomer peak gave the title compound (21 mg, 0.049 mmol, 27.6% yield). ¹H NMR (500 MHz, DMSO-d₆) δ ppm 9.09 (br s, 1H), 6.45 (s, 1H), 3.93 (s, 2H), 3.07 (m, 4H), 2.74 (m, 2H), 2.37 (m, 2H), 2.03 (m, 1H), 1.76 (m, 2H), 1.58 (m, 2H); MS (ESI⁻) m/z 424 [M–H]⁻.

Example 48: 5-{(7S)-1-fluoro-3-hydroxy-7-[(4,4,4-trifluorobutyl)amino]-5,6,7,8-tetrahydronaphthalen-2-yl}-1$\lambda^6$,2,5-thiadiazolidine-1,1,3-trione (Compound 147)

The title compound was prepared using the methodologies described in Example 47. The first eluting enantiomer peak gave the title compound (5 mg, 0.012 mmol, 6.6% yield). ¹H NMR (500 MHz, DMSO-d₆) δ ppm 9.18 (br s, 1H), 7.26 (br s, 1H), 6.47 (s, 1H), 3.93 (s, 2H), 3.07 (m, 4H), 2.77 (m, 2H), 2.41 (m, 2H), 2.21 (m, 1H), 1.84 (m, 2H), 1.68 (m, 2H); MS (ESI⁻) m/z 424 [M–H]⁻.

Example 49: 5-[(7R)-1-fluoro-3-hydroxy-7-({2-[1-(trifluoromethyl)cyclopropyl]ethyl}amino)-5,6,7,8-tetrahydronaphthalen-2-yl]-1$\lambda^6$,2,5-thiadiazolidine-1,1,3-trione (Compound 148)

To a solution of the product from Example 22I (1.12 g, 2.23 mmol) and 2-[1-(trifluoromethyl)cyclopropyl]ethan-1-amine hydrochloride (0.634 g, 3.35 mmol) in acetonitrile (22 mL) at room temperature was added sodium cyanoborohydride (0.168 g, 2.68 mmol). After 18 hours, the reaction mixture was quenched with ammonium hydroxide (0.506 mL, 26.8 mmol), and diluted with acetonitrile (10 mL) and water (2 mL). Celite® (5 g) was added, and the mixture was concentrated in vacuo. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give 5-{1-fluoro-3-[(2-methoxyethoxy)methoxy]-7-({2-[1-(trifluoromethyl)cyclopropyl]ethyl}amino)-5,6,7,8-tetrahydronaphthalen-2-yl}-1$\lambda^6$,2,5-thiadiazolidine-1,1,3-trione (0.1414 g, 0.262 mmol, 11.8% yield). ¹H NMR (400 MHz, DMSO-d₆) δ ppm 8.44 (br s, 2H), 6.77 (s, 1H), 5.21 (s, 2H), 3.98-3.86 (m, 2H), 3.77-3.70 (m, 2H), 3.50-3.42 (m, 4H), 3.23 (s, 3H), 3.17-3.09 (m, 3H), 2.86-2.76 (m, 2H), 2.58 (dd, J=16.4, 9.6 Hz, 1H), 2.16 (d, J=12.0 Hz, 1H), 1.92 (dd, J=10.4, 6.3 Hz, 2H), 1.70 (td, J=11.2, 10.4, 4.8 Hz, 2H), 1.01-0.94 (m, 2H), 0.94-0.85 (m, 3H); MS (APCI⁺) m/z 540 [M+H]⁺.

Earlier eluting fractions gave the alcohol byproduct 5-{1-fluoro-7-hydroxy-3-[(2-methoxyethoxy)methoxy]-5,6,7,8-tetrahydronaphthalen-2-yl}-1$\lambda^6$,2,5-thiadiazolidine-1,1,3-trione (0.303 g, 0.75 mmol, 32% yield) as the ammonium salt. MS (APCI⁺) m/z 422 [M+NH₄]⁺.

Racemic 5-{(1-fluoro-3-[(2-methoxyethoxy)methoxy]-7-({2-[1-(trifluoromethyl)cyclopropyl]ethyl}amino)-5,6,7,8-tetrahydronaphthalen-2-yl}-1$\lambda^6$,2,5-thiadiazolidine-1,1,3-trione (0.1414 g, 0.262 mmol) was separated by chiral SFC. Preparative SFC was performed on a THAR/Waters SFC80 system running under SuperChrom™ software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a Dewar of bone-dry non-certified $CO_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide (70:30) at a concentration of 5 mg/mL. The sample was loaded into the modifier stream in 2 mL (10 mg) injections. The mobile phase was held isocratically at 45% cosolvent:$CO_2$. Fraction collection was time triggered. The instrument was fitted with a CHIRALPAK® IC column with dimensions 21 mm i.d.× 250 mm length with 5 μm particles. The later eluting enantiomer peak gave 5-[(7R)-1-fluoro-3-[(2-methoxyethoxy)methoxy]-7-({2-[1-(trifluoromethyl)cyclopropyl]ethyl}amino)-5,6,7,8-tetrahydronaphthalen-2-yl]-1$\lambda^6$,2,5-thiadiazolidine-1,1,3-trione (54.4 mg, 0.101 mmol, 77% recovery). ¹H NMR and MS data were identical to those of the racemic material. The absolute configuration was assigned by analogy to the chromatography elution order to the product of Example 19.

To a suspension of 5-[(7R)-1-fluoro-3-[(2-methoxyethoxy)methoxy]-7-({2-[1-(trifluoromethyl)cyclopropyl]ethyl}amino)-5, 6,7,8-tetrahydronaphthalen-2-yl]-1$\lambda^6$,2,5-thiadiazolidine-1,1,3-trione (54.4 mg, 0.101 mmol) in acetonitrile (1.1 mL) was added a solution of hydrogen chloride (0.126 mL, 0.504 mmol, 4 M in dioxane). After 2.5 hours, the reaction was diluted with acetonitrile (1 mL), quenched with ammonium hydroxide (0.023 mL, 1.210 mmol), and then diluted with water (0.5 mL). Celite® (1 g) was added, and the resulting suspension concentrated. The crude residue was dry loaded onto a 100 g C18 column, and purified by reversed-phase liquid chromatography, flow rate 60 mL/minute, gradient of 10-50% (10 column volumes) then 50-100% (6 column volumes), then flushing at 100% (1 column volume) methanol in buffer (0.025 M ammonium bicarbonate in water acidified to pH 7 with dry ice) observing at 206 nM, to give the title compound (25.7 mg, 0.057 mmol, 57% yield). ¹H NMR and MS data were identical to the product of Example 25.

Example 50: 8-fluoro-6-hydroxy-7-(1,1,4-trioxo-1$\lambda^6$,2,5-thiadiazolidin-2-yl)-1,2,3,4-tetrahydronaphthalen-2-yl Phenylcarbamate (Compound 149)

To a solution of the alcohol byproduct from Example 49, 5-{1-fluoro-7-hydroxy-3-[(2-methoxyethoxy)methoxy]-5,6, 7,8-tetrahydronaphthalen-2-yl}-1$\lambda^6$,2,5-thiadiazolidine-1,1,3-trione (50 mg, 0.118 mmol) and 4-dimethylaminopyridine (1.2 mg, 9.9 mol) in N,N-dimethylformamide (1 mL) was added phenyl isocyanate (0.02 mL, 0.183 mmol). After 20 hours, the reaction mixture was filtered through a glass microfiber frit, directly loaded onto a Teledyne ISCO 50 g reversed-phase C18 column and eluted with a gradient of 10-100% methanol in buffer (0.025 M ammonium bicarbonate in water acidified to pH 7 by adding dry ice) to give 8-fluoro-6-[(2-methoxyethoxy)methoxy]-7-(1,1,4-trioxo-1$\lambda^6$,2,5-thiadiazolidin-2-yl)-1,2,3,4-tetrahydronaphthalen-2-yl phenylcarbamate (0.0238 g, 0.044 mmol, 45.9% yield). MS (APCI$^+$) m/z 541 [M+NH$_4$]$^+$.

To a suspension of 8-fluoro-6-[(2-methoxyethoxy)methoxy]-7-(1,1,4-trioxo-1$\lambda^6$,2,5-thiadiazolidin-2-yl)-1,2,3,4-tetrahydronaphthalen-2-yl phenylcarbamate (0.022 g, 0.042 mmol) in acetonitrile (0.45 mL) was added a solution of hydrogen chloride (0.053 mL, 0.210 mmol, 4 M in dioxane). After 1.5 hours, the reaction was diluted with acetonitrile (1 mL), quenched with ammonium hydroxide (0.005 mL, 0.252 mmol), and then diluted with water (0.5 mL). Celite® (1 g) was added and the resulting suspension concentrated. The crude residue was dry loaded onto a 50 g C18 column, and purified by reversed-phase liquid chromatography, flow rate 60 mL/minute, gradient of 10-100% methanol in buffer (0.025 M ammonium bicarbonate in water acidified to pH 7 with dry ice) observing at 206 nM, to give the title compound (12.2 mg, 0.028 mmol, 67% yield). $^1$H NMR (400 MHz, DMSO-d$_6$) δ ppm 9.65 (s, 1H), 9.11 (s, 1H), 7.46 (d, J=8.0 Hz, 2H), 7.31-7.21 (m, 2H), 6.99-6.94 (m, 2H), 6.48 (s, 1H), 5.17-5.10 (m, 1H), 4.01-3.87 (m, 2H), 3.09 (q, J=7.3 Hz, 2H), 2.93 (dd, J=16.9, 4.8 Hz, 1H), 2.89-2.64 (m, 3H); MS (APCI$^-$) m/z 434 [M−H]$^-$.

Example 51: 4-{[8-fluoro-6-hydroxy-7-(1,1,4-trioxo-1$\lambda^6$,2,5-thiadiazolidin-2-yl)-1,2,3,4-tetrahydronaphthalen-2-yl]amino}-2,2-dimethylbutanenitrile (Compound 150)

To a solution of the product from Example 22I (0.200 g, 0.397 mmol) and 4-amino-2,2-dimethylbutanenitrile (0.074 mL, 0.596 mmol) in acetonitrile (4 mL) at room temperature was added sodium cyanoborohydride (0.030 g, 0.477 mmol). After 19 hours, a solution of hydrogen chloride (0.5 mL, 1.99 mmol, 4 M in dioxane) was added dropwise (vigorous gas evolution). After 1 hour, the reaction mixture was quenched with ammonium hydroxide (0.045 mL, 2.38 mmol), and then diluted with acetonitrile (3 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice). The chromatographically purified material was further purified by trituration with acetonitrile (4 mL) to give the title compound (0.011 g, 0.027 mmol, 7% yield). $^1$H NMR (400 MHz, DMSO-d$_6$) δ ppm 9.21 (s, 1H), 6.47 (s, 1H), 3.94 (s, 2H), 3.17-3.04 (m, 3H), 2.86-2.66 (m, 3H), 2.55-2.49 (m, 1H), 2.15 (d, J=12.3 Hz, 1H), 1.88 (dd, J=11.1, 5.8 Hz, 2H), 1.68 (tt, J=11.3, 5.6 Hz, 1H), 1.37 (s, 6H); MS (APCI$^+$) m/z 411 [M+H]$^+$.

Example 52: 5-{1-fluoro-3-hydroxy-7-[(4,4,4-trifluoro-3-hydroxybutyl)amino]-5,6,7,8-tetrahydronaphthalen-2-yl}-1$\lambda^6$,2,5-thiadiazolidine-1,1,3-trione (Compound 151)

To a solution of the product from Example 22I (0.20 g, 0.397 mmol) and 4-amino-1,1,1-trifluorobutan-2-ol hydrochloride (0.107 g, 0.596 mmol) in acetonitrile (4 mL) at room temperature was added sodium cyanoborohydride (0.030 g, 0.477 mmol). After 19 hours, a solution of hydrogen chloride (0.496 mL, 1.99 mmol, 4 M in dioxane) was added dropwise (vigorous gas evolution). After 1 hour, the reaction mixture was quenched with ammonium hydroxide (0.045 mL, 2.38 mmol), and then diluted with acetonitrile (3 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.048 g, 0.109 mmol, 27% yield). $^1$H NMR (400 MHz, DMSO-d$_6$) δ ppm 8.95 (s, 1H), 7.10 (br s, 2H), 6.41 (d, J=1.5 Hz, 1H), 4.81 (d, J=3.8 Hz, 1H), 4.21-4.09 (m, 1H), 3.93 (s, 2H), 3.93-3.84 (m, 1H), 3.57-3.43 (m, 1H), 3.13-3.02 (m, 1H), 2.76 (dt, J=17.3, 5.8 Hz, 2H), 2.67-2.51 (m, 1H), 2.35 (dd, J=16.5, 7.3 Hz, 1H), 1.80 (ddd, J=12.1, 8.6, 5.5 Hz, 1H), 2.04-1.50 (m, 3H); MS (APCI$^+$) m/z 442 [M+H]$^+$.

Example 53: 5-{1-fluoro-3-hydroxy-7-[(4,4,4-trifluoro-3-methoxybutyl)amino]-5,6,7,8-tetrahydronaphthalen-2-yl}-1$\lambda^6$,2,5-thiadiazolidine-1,1,3-trione (Compound 152)

To a solution of the product from Example 22I (0.20 g, 0.397 mmol) and 4,4,4-trifluoro-3-methoxybutan-1-amine (0.082 mL, 0.596 mmol) in acetonitrile (4 mL) at room temperature was added sodium cyanoborohydride (0.030 g, 0.477 mmol). After 19 hours, a solution of hydrogen chloride (0.496 mL, 1.99 mmol, 4 M in dioxane) was added dropwise (vigorous gas evolution). After 1 hour, the reaction mixture was quenched with ammonium hydroxide (0.045 mL, 2.383 mmol), and then diluted with acetonitrile (3 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.016 g, 0.034 mmol, 9% yield). $^1$H NMR (400 MHz, DMSO-d$_6$) δ ppm 9.16 (s, 1H), 6.44 (d, J=1.4 Hz, 1H), 3.90 (s, 2H), 3.88 (d, J=7.3 Hz, 1H), 3.48 (s, 3H), 3.47-3.38 (m, 1H), 3.34-3.28 (m, 1H), 3.09-2.93 (m, 2H), 2.89-2.56 (m, 3H), 2.17-2.05 (m, 1H), 2.00-1.47 (m, 3H); MS (APCI$^+$) m/z 456 [M+H]$^+$.

Example 54: 5-[8-fluoro-6-hydroxy-2-(5,5,5-trifluoropentyl)-1,2,3,4-tetrahydroisoquinolin-7-yl]-1$\lambda^6$,2,5-thiadiazolidine-1,1,3-trione (Compound 153)

Example 54A: 5-[6-(benzyloxy)-8-fluoro-1,2,3,4-tetrahydroisoquinolin-7-yl]-1$\lambda^6$,2,5-thiadiazolidine-1,1,3-trione, Trifluoroacetate Trifluoroacetic acid (0.1 mL, 1.34 mmol, 15.0 equivalents) was added to a suspension of tert-butyl 6-(benzyloxy)-8-fluoro-7-(1,1,4-trioxo-1$\lambda^6$,2,5-thiadiazolidin-2-yl)-3,4-dihydroisoquinoline-2(1H)-carboxylate, the product of Example 44H (44 mg, 0.09 mmol, 1 equivalent), in dichloromethane (0.45 mL) at 23° C. The reaction mixture was stirred for 30 minutes at 23° C. The product mixture was then diluted with ether (1.0 mL) at 23° C. A precipitate immediately formed. The diluted mixture was concentrated under a stream of nitrogen. The titled compound obtained was used without further purification. MS (APCI$^+$) m/z 433 [M+H+CH$_3$CN]$^+$.

Example 54B: 5-[6-(benzyloxy)-8-fluoro-2-(5, 5,5-trifluoropentyl)-1,2,3,4-tetrahydroisoquinolin-7-yl]-1λ$^6$,2,5-thiadiazolidine-1,1,3-trione A suspension of 5-[6-(benzyloxy)-8-fluoro-1,2,3,4-tetrahydroisoquinolin-7-yl]-1λ$^6$,2,5-thiadiazolidine-1,1,3-trione, trifluoroacetate, the product of Example 54A (nominally 0.09 mmol, 1 equivalent), potassium carbonate (62 mg, 0.45 mmol, 5.0 equivalents), and 5,5,5-trifluoropentyl 4-methylbenzenesulfonate (40 mg, 0.14 mmol, 1.5 equivalents; Erdeljac, N., et al. *Chem. Commun*, 2018, 54, 12002-12005) in acetonitrile (0.45 mL) was heated to 60° C. with stirring for 19 hours. The reaction mixture was then cooled to 23° C. The cooled reaction mixture was diluted sequentially with aqueous hydrogen chloride solution (1.0 M, 0.5 mL), water (0.5 mL), and dimethyl sulfoxide (1.0 mL). The diluted mixture was purified by reversed-phase flash column chromatography (100 g RediSep Rf Gold® C18 column, elution with a gradient of 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute). The title compound obtained (44 mg) was used in the following step without further purification. MS (APCI$^+$) m/z 516 [M+H]$^+$.

Example 54C: 5-[8-fluoro-6-hydroxy-2-(5, 5,5-trifluoropentyl)-1,2,3,4-tetrahydroisoquinolin-7-yl]-1λ$^6$,2,5-thiadiazolidine-1,1,3-trione A solution of boron trichloride in dichloromethane (1.0 M, 0.9 mL, 0.90 mmol, 11.3 equivalents) was added to a suspension of the product of Example 54B (nominally 44 mg, 0.08 mmol, 1 equivalent) and pentamethylbenzene (37 mg, 0.25 mmol, 3.0 equivalents) in dichloromethane (0.85 mL) at −78° C. The reaction mixture was stirred for 4 hours at −78° C. The reaction mixture was then diluted with methanol (0.5 mL) at −78° C. The diluted mixture was warmed over 15 minutes to 23° C. The warmed mixture was concentrated. The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (14 mg, 41% yield, two steps). $^1$H NMR (400 MHz, DMSO-d$_6$) δ ppm 6.52 (s, 1H), 4.10 (q, J=5.2 Hz, 1H), 3.94 (2, 2H), 3.17 (d, J=5.1 Hz, 2H), 2.86 (app bs, 2H), 2.35-2.23 (m, 2H), 1.71 (app bs, 2H), 1.59-1.47; MS (APCI$^+$) m/z 426 [M+H]$^+$.

Example 55: 5-(1-fluoro-3-hydroxy-7-{(3-methylbutyl)[(pyridin-2-yl)methyl]amino}-5,6,7,8-tetrahydronaphthalen-2-yl)-1λ$^6$,2,5-thiadiazolidine-1,1,3-trione (Compound 154)

To a solution of the product from Example 22I (0.3492 g, 0.693 mmol) and 2-(aminomethyl)pyridine (0.192 mL, 1.66 mmol) in acetonitrile (7 mL) at room temperature was added sodium cyanoborohydride (0.087 g, 1.39 mmol). After 19 hours, isovaleraldehyde (0.299 mL, 2.77 mmol) was added. After 6 hours, a solution of hydrogen chloride (1.73 mL, 6.93 mmol, 4 M in dioxane) was added dropwise (vigorous gas evolution). After 1 hour, the reaction mixture was quenched with ammonium hydroxide (0.157 mL, 8.32 mmol), and then diluted with acetonitrile (4 mL) and water (2 mL). Celite® (2 g) was added, and the mixture was concentrated in vacuo. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice). Later eluting fractions were combined and concentrated to give the title compound (0.163 g, 0.341 mmol, 49% yield). $^1$H NMR (400 MHz, DMSO-d$_6$) δ ppm 9.21 (s, 1H), 8.66 (d, J=5.2 Hz, 1H), 7.92 (td, J=7.7, 1.9 Hz, 1H), 7.58 (d, J=7.8 Hz, 1H), 7.49-7.41 (m, 1H), 6.46 (s, 1H), 4.64-4.46 (m, 2H), 3.93 (s, 2H), 3.75-3.58 (m, 1H), 3.49-3.40 (m, 1H), 3.27-3.06 (m, 3H), 2.90-2.68 (m, 4H), 1.86-1.77 (m, 1H), 1.59-1.41 (m, 3H), 0.83 (d, J=2.2 Hz, 3H), 0.81 (d, J=2.2 Hz, 3H); MS (APCI$^+$) m/z 477 [M+H]$^+$.

Example 56: 5-(1-fluoro-3-hydroxy-7-{[(pyridin-2-yl)methyl]amino}-5,6,7,8-tetrahydronaphthalen-2-yl)-1λ$^6$,2,5-thiadiazolidine-1,1,3-trione (Compound 155)

To a solution of the product from Example 22I (0.3492 g, 0.693 mmol) and 2-(aminomethyl)pyridine (0.192 mL, 1.66 mmol) in acetonitrile (7 mL) at room temperature was added sodium cyanoborohydride (0.087 g, 1.387 mmol). After 19 hours, isovaleraldehyde (0.299 mL, 2.77 mmol) was added. After 6 hours, a solution of hydrogen chloride (1.73 mL, 6.93 mmol, 4 M in dioxane) was added dropwise (vigorous gas evolution). After 1 hour, the reaction mixture was quenched with ammonium hydroxide (0.157 mL, 8.32 mmol), and then diluted with acetonitrile (4 mL) and water (2 mL). Celite® (2 g) was added, and the mixture was concentrated in vacuo. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice). Early eluting fractions were combined and concentrated to give the title compound (0.0972 g, 0.239 mmol, 34.5% yield). $^1$H NMR (400 MHz, DMSO-d$_6$) showed a mixture of rotamers, data for the major rotamer are δ ppm 9.37 (s, 1H), 9.21 (s, 2H), 8.57 (td, J=5.0, 1.7 Hz, 1H), 7.84 (td, J=7.7, 1.8 Hz, 1H), 7.49-7.41 (m, 1H), 7.35 (dt, J=8.0, 4.2 Hz, 1H), 6.43 (s, 1H), 5.03-4.87 (m, 2H), 4.38-4.24 (m, 1H), 4.00-3.78 (m, 2H), 3.45 (dd, J=5.9, 3.7 Hz, 1H), 3.00-2.53 (m, 3H), 2.33 (s, 2H), 1.89-1.62 (m, 2H); MS (APCI$^+$) m/z 477 [M+H]$^+$.

Example 57: 5-{1-fluoro-3-hydroxy-7-[(4,4,4-trifluoro-2-hydroxybutyl)amino]-5,6,7,8-tetrahydronaphthalen-2-yl}-1λ$^6$,2,5-thiadiazolidine-1,1,3-trione (Compound 156)

To a solution of the product from Example 22I (0.302 g, 0.600 mmol) and 1-amino-4,4,4-trifluoro-butan-2-ol (0.1 g, 0.699 mmol) in acetonitrile (6 mL) at room temperature was added sodium cyanoborohydride (0.045 g, 0.715 mmol). After 18 hours, a solution of hydrogen chloride (1.19 mL, 4.77 mmol, 4 M in dioxane) was added dropwise (vigorous gas evolution). After 2 hours, the reaction mixture was quenched with ammonium hydroxide (0.068 mL, 3.57 mmol), and then diluted with acetonitrile (3 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0694 g, 0.157 mmol, 26.4% yield). $^1$H NMR (500 MHz, DMSO-$d_6$) δ ppm 9.26 (s, 1H), 8.65 (br s, 2H), 6.46 (s, 1H), 5.84 (s, 1H), 4.15 (s, 1H), 4.12-4.08 (m, 1H), 3.94 (d, J=1.2 Hz, 2H), 3.50-3.39 (m, 1H), 3.22-3.17 (m, 1H), 3.15-2.99 (m, 2H), 2.86-2.67 (m, 2H), 2.64-2.41 (m, 2H), 2.23-2.12 (m, 1H), 1.79-1.62 (m, 1H); MS (APCI$^+$) m/z 442 [M+H]$^+$.

Example 58: 5-(7-{[2-(difluoromethoxy)ethyl]amino}-1-fluoro-3-hydroxy-5,6,7,8-tetrahydronaphthalen-2-yl)-1$\lambda^6$,2,5-thiadiazolidine-1,1,3-trione (Compound 157)

To a solution of the product from Example 22I (0.302 g, 0.600 mmol) and 2-(difluoromethoxy)ethan-1-amine (0.1 g, 0.900 mmol) in acetonitrile (6 mL) at room temperature was added sodium cyanoborohydride (0.045 g, 0.715 mmol). After 18 hours, a solution of hydrogen chloride (1.191 mL, 4.77 mmol, 4 M in dioxane) was added dropwise (vigorous gas evolution). After 2 hours, the reaction mixture was quenched with ammonium hydroxide (0.068 mL, 3.57 mmol), and then diluted with acetonitrile (3 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0604 g, 0.148 mmol, 24.6% yield). $^1$H NMR (500 MHz, DMSO-$d_6$) δ ppm 9.29 (s, 1H), 8.79 (br s, 2H), 6.80 (t, J=75.2 Hz, 1H), 6.48 (d, J=1.3 Hz, 1H), 4.17-4.08 (m, 2H), 3.96 (d, J=2.1 Hz, 2H), 3.52-3.44 (m, 1H), 3.39 (t, J=5.2 Hz, 2H), 3.16-3.08 (m, 1H), 2.83 (dt, J=17.2, 4.6 Hz, 1H), 2.75 (ddd, J=17.0, 11.4, 5.4 Hz, 1H), 2.61-2.53 (m, 1H), 2.23-2.16 (m, 1H), 1.72 (qd, J=11.7, 5.4 Hz, 1H); MS (APCI$^+$) m/z 410 [M+H]$^+$.

Example 59: 5-(8-fluoro-6-hydroxy-2-pentanimidoyl-1,2,3,4-tetrahydroisoquinolin-7-yl)-1$\lambda^6$,2,5-thiadiazolidine-1,1,3-trione (Compound 158)

Example 59A: 5-[6-(benzyloxy)-8-fluoro-2-pentanimidoyl-1,2,3,4-tetrahydroisoquinolin-7-yl]-1$\lambda^6$,2,5-thiadiazolidine-1,1,3-trione N,N-Diisopropylethylamine (0.15 mL, 0.84 mmol, 5.5 equivalents) was added to a suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate, the product of Example 54A (nominally 0.15 mmol, 1 equivalent) and ethyl pentanimidate hydrochloride (50 mg, 0.31 mmol, 2.0 equivalent; Goebel, M, et al. *ChemMedChem* 2009, 4, 1136-1142) in acetonitrile (0.75 mL) at 23° C. The reaction vessel was sealed, and the sealed vessel was placed in a heating block that had been preheated to 60° C. The reaction mixture was stirred for 18 hours at 60° C. The reaction mixture was then cooled to 23° C. Additional ethyl pentanimidate hydrochloride (150 mg, 0.93 mmol, 6.0 equivalents) and N,N-diisopropylethylamine (0.40 mL, 2.29 mmol, 15.0 equivalents) were added at 23° C. The reaction vessel was sealed, and the sealed vessel was placed in a heating block that had been preheated to 60° C. The reaction mixture was stirred for 3 hours at 60° C. and then cooled to 23° C. The cooled mixture was diluted sequentially with aqueous hydrogen chloride solution (1.0 M, 3.0 mL) and dimethyl sulfoxide (3.0 mL). The diluted mixture was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute). The title compound (146 mg) was used in the following step without further purification. MS (APCI$^+$) m/z 475 [M+H]$^+$.

Example 59B: 5-(8-fluoro-6-hydroxy-2-pentanimidoyl-, 2, 3,4-tetrahydroisoquinolin-7-yl)-1$\lambda^6$,2,5-thiadiazolidine-1,1,3-trione A solution of boron trichloride in dichloromethane (1.0 M, 0.31 mL, 0.31 mmol, 1.0 equivalent) was added to a suspension of pentamethylbenzene (141 mg, 0.92 mmol, 3.0 equivalents) and the product of Example 59A (nominally 146 mg, 0.307 mmol, 1 equivalent) in dichloromethane (3.0 mL) at −78° C. The reaction mixture was stirred for 15 minutes at −78° C. Additional boron trichloride solution in dichloromethane (1.0 M, 0.35 mL, 0.35 mmol, 1.17 equivalents) was added at −78° C. The reaction mixture was stirred for 30 minutes at −78° C. Additional boron trichloride solution in dichloromethane (1.0 M, 0.40 mL, 0.40 mmol, 1.33 equivalents) was added at −78° C. The reaction mixture was stirred for 30 minutes at −78° C. The mixture was then diluted sequentially with ethyl acetate (1.5 mL) and ethanol (1.5 mL) at −78° C. The diluted mixture was warmed over 15 minutes to 23° C. The warmed mixture was concentrated. The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (12 mg, 0.031 mmol, 10% yield, two steps). $^1$H NMR (500 MHz, DMSO-$d_6$) δ ppm 6.47 (s, 1H), 4.51 (s, 2H), 4.19 (d, J=17.5 Hz, 1H), 3.75-3.61 (m, 2H), 3.23 (d, J=17.5 Hz, 1H), 2.82 (t, J=5.9 Hz, 2H), 2.58 (t, J=7.9 Hz, 2H), 1.56-1.48 (m, 2H), 1.41-1.31 (m, 2H), 0.91 (t, J=7.9 Hz, 2H); MS (APCI$^+$) m/z 385 [M+H]$^+$.

Example 60: 5-[2-(3-cyclopropylpropyl)-8-fluoro-6-hydroxy-1,2,3,4-tetrahydroisoquinolin-7-yl]-1$\lambda^6$,2,5-thiadiazolidine-1,1,3-trione (Compound 159)

Example 60A: 5-[6-(benzyloxy)-2-(3-cyclopropylpropyl)-8-fluoro-1,2,3,4-tetrahydroisoquinolin-7-yl]-1$\lambda^6$,2,5-thiadiazolidine-1,1,3-trione A suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate, the product of Example 54A (nominally 0.15 mmol, 1 equivalent), potassium carbonate (106 mg, 0.77 mmol, 5.0 equivalents), and 3-cyclopropylpropyl 4-methylbenzenesulfonate (60 mg, 0.23 mmol, 1.5 equivalents; Wagner, P J, et al. *J. Am. Chem. Soc.* 1981, 103, 3837-3841) in acetonitrile (0.80 mL) was sealed in a 4 mL vial. The sealed vessel was placed in a heating block that had been preheated to 60° C. The reaction mixture was stirred for 18 hours at 60° C. The reaction mixture was then cooled to 23° C. The cooled mixture was diluted with dimethyl sulfoxide (3.0 mL). The diluted mixture was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (68 mg, 0.14 mmol, 93% yield, two steps). MS (APCI$^+$) m/z 474 [M+H]$^+$.

Example 60B: 5-[2-(3-cyclopropylpropyl)-8-fluoro-6-hydroxy-1,2,3,4-tetrahydroisoquinolin-7-yl]-1$\lambda^6$,2,5-thiadiazolidine-1,1,3-trione A solution of boron trichloride in dichloromethane (1.0 M, 0.14 mL, 0.14 mmol, 1.0 equivalents) was added suspension of the product of Example 60A (65 mg, 0.14 mmol, 1 equivalent) and pentamethylbenzene (61 mg, 0.41 mmol, 3.0 equivalents) in dichloromethane (1.4 mL) at −78° C. The reaction mixture was stirred for 15 minutes at −78° C. Additional boron trichloride solution in dichloromethane (1.0 M, 0.30 mL, 0.30 mmol, 2.1 equivalents) was added at −78° C. The reaction mixture was stirred for 15 minutes at −78° C. and then diluted with methanol (0.5 mL) at −78° C. The diluted mixture was warmed over 15 minutes to 23° C. The warmed product mixture was concentrated. The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute). The fractions containing product were combined and the combined fractions were concentrated. The residue obtained was repurified using the same chromatography conditions to furnish the title compound (5 mg, 0.013 mmol, 9% yield). $^1$H NMR (500 MHz, DMSO-d$_6$) δ ppm 6.33 (s, 1H), 3.95 (s, 2H), 2.69-2.62 (m, 2H), 2.59-2.54 (m, 2H), 2.49-2.44 (m, 2H), 1.59 (p, J=7.4 Hz, 2H), 1.24-1.13 (m, 4H), 0.74-0.65 (m, 1H), 0.40-0.36 (m, 2H), 0.02--0.01 (m, 2H). MS (APCI$^+$) m/z 384 [M+H]$^+$.

Example 61: 5-[2-(2-azaspiro[3.3]heptan-6-yl)-8-fluoro-6-hydroxy-1,2,3,4-tetrahydroisoquinolin-7-yl]-1$\lambda^6$,2,5-thiadiazolidine-1,1,3-trione (Compound 160)

Example 61A: 5-[6-(benzyloxy)-8-fluoro-1,2,3,4-tetrahydroisoquinolin-7-yl]-1$\lambda^6$,2,5-thiadiazolidine-1,1,3-trione A vial containing a suspension of tert-butyl 6-(benzyloxy)-8-fluoro-7-(1,1,4-trioxo-1$\lambda^6$,2,5-thiadiazolidin-2-yl)-3,4-dihydroisoquinoline-2(1H)-carboxylate (0.200 g, 0.407 mmol, Example 44H) in dichloromethane (1.4 mL) was cooled to 0° C. Then 2,2,2-trifluoroacetic acid (0.19 mL, 2.4 mmol) was added dropwise and the cooling bath was subsequently removed. After 2 hours, the reaction mixture was concentrated under reduced pressure. The residue was azeotroped with toluene (3×3 mL) and then passed through an SCX-2 cartridge (loaded and eluted initially with methanol/dichloromethane (1:1) and then eluted with a 2 M solution of ammonia in methanol) to give the title compound (0.159 g, 0.406 mmol, 100% yield). $^1$H NMR (400 MHz, DMSO-d$_6$) δ ppm 7.49 (dd, J=7.0, 1.6 Hz, 2H), 7.38-7.32 (m, 2H), 7.32-7.27 (m, 1H), 6.86 (s, 1H), 5.15 (s, 2H), 4.18 (s, 2H), 3.96 (s, 2H), 3.36-3.31 (m, 2H), 2.94 (t, J=6.2 Hz, 2H); MS (ESI$^+$) m/z 433.2 [M+CH$_3$CN+H]+; MS (ESI$^-$) m/z 390.2 [M−H]$^-$.

Example 61B: tert-butyl 6-[6-(benzyloxy)-8-fluoro-7-(1,1,4-trioxo-1$\lambda^6$,2,5-thiadiazolidin-2-yl)-3,4-dihydroisoquinolin-2(1H)-yl]-2-azaspiro[3.3]heptane-2-carboxylate To a vial were added 5-[6-(benzyloxy)-8-fluoro-1,2,3,4-tetrahydroisoquinolin-7-yl]-1$\lambda^6$,2,5-thiadiazolidine-1,1,3-trione (0.040 g, 0.10 mmol, Example 61A), tert-butyl 6-oxo-2-azaspiro[3.3]heptane-2-carboxylate (0.024 g, 0.11 mmol), and dichloromethane (0.34 mL). The resulting suspension was stirred at ambient temperature for 10 minutes, then sodium triacetoxyhydroborate (0.043 g, 0.20 mmol) was added. After 16 hours, the reaction mixture was diluted with saturated aqueous sodium bicarbonate and stirred for 20 minutes. Next, water was added, and the mixture was extracted with dichloromethane (4×20 mL). The organic phases were combined, washed sequentially with 50% aqueous sodium chloride and brine, dried over sodium sulfate, and concentrated under reduced pressure to give the title compound. This material was used without further purification. MS (ESI$^+$) m/z 587.0 [M+H]+; MS (ESI$^-$) m/z 585.2 [M−H]$^-$.

Example 61C: tert-butyl 6-[8-fluoro-6-hydroxy-7-(1,1,4-trioxo-1$\lambda^6$,2,5-thiadiazolidin-2-yl)-3,4-dihydroisoquinolin-2(1H)-yl]-2-azaspiro[3.3]heptane-2-carboxylate To a 20 mL Barnstead Hast C reactor containing 5% palladium on carbon (0.120 g, 0.525 mmol) were added tert-butyl 6-[6-(benzyloxy)-8-fluoro-7-(1,1,4-trioxo-1$\lambda^6$,2,5-thiadiazolidin-2-yl)-3,4-dihydroisoquinolin-2(1H)-yl]-2-azaspiro[3.3]heptane-2-carboxylate (theoretically 0.10 mmol, Example 61B) and tetrahydrofuran (2 mL). The resulting mixture was stirred at ambient temperature for 2.7 hours under an atmosphere of hydrogen at 50 psi. The catalyst was then removed by filtration and washed with methanol. The filtrate was concentrated under reduced pressure to give the title compound (0.033 g, 0.066 mmol). This material was used without further purification. MS (ESI$^+$) m/z 497.2 [M+H]+; MS (ESI$^-$) m/z 495.2 [M−H]$^-$.

Example 61D: 5-[2-(2-azaspiro[3.3]heptan-6-yl)-8-fluoro-6-hydroxy-1,2,3,4-tetrahydroisoquinolin-7-yl]-1$\lambda^6$,2,5-thiadiazolidine-1,1,3-trione A vial containing a suspension of tert-butyl 6-[8-fluoro-6-hydroxy-7-(1,1,4-trioxo-1$\lambda^6$,2,5-thiadiazolidin-2-yl)-3,4-dihydroisoquinolin-2(1H)-yl]-2-azaspiro[3.3]heptane-2-carboxylate (0.033 g, 0.066 mmol, Example 61C) in dichloromethane (0.22 mL) was cooled to 0° C. Then 2,2,2-trifluoroacetic acid (0.031 mL, 0.40 mmol) was added dropwise and the cooling bath was subsequently removed. After 1 hour, the reaction mixture was concentrated under reduced pressure. The residue was azeotroped with toluene (3×3 mL) and purified using reversed-phase preparative HPLC [Waters XBridge™ RP18 column, 5 m, 30×100 mm, flow rate 40 mL/minute, 5-70% gradient of methanol in water (buffered with 0.025 M aqueous ammonium bicarbonate, adjusted to pH 10 with ammonium hydroxide)]. Product-containing fractions were combined and concentrated under reduced pressure. The residue was passed through an SCX-2 cartridge (loaded and eluted initially with methanol/dichloromethane (1:1) and then eluted with a 2 M solution of ammonia in methanol) to give the title compound (5.0 mg, 0.013 mmol, 13% yield over three steps). $^1$H NMR (400 MHz, DMSO-d$_6$) δ ppm 6.44 (s, 1H), 3.98 (s, 2H), 3.94

(s, 2H), 3.87 (s, 2H), 3.28 (s, 2H), 2.76 (p, J=7.6 Hz, 1H), 2.67 (t, J=5.8 Hz, 2H), 2.49-2.40 (m, 2H), 2.43-2.36 (m, 1H), 2.14-1.95 (m, 2H); MS (ESI$^+$) m/z 397.2 [M+H]$^+$.

Example 62: 5-[8-fluoro-6-hydroxy-2-(6,6,6-trifluorohexyl)-1,2,3,4-tetrahydroisoquinolin-7-yl]-1$\lambda^6$,2,5-thiadiazolidine-1,1,3-trione (Compound 161)

Example 62A: 5-[6-(benzyloxy)-8-fluoro-2-(6, 6,6-trifluorohexyl)-1,2,3,4-tetrahydroisoquinolin-7-yl]-1$\lambda^6$,2,5-thiadiazolidine-1,1,3-trione A suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate, the product of Example 54A (nominally 0.25 mmol, 1 equivalent), triethylamine (0.18 mL, 1.3 mmol, 5.0 equivalents), and 6-bromo-1,1,1-trifluorohexane (86 mg, 0.38 mmol, 1.5 equivalents) in acetonitrile (1.3 mL) was sealed in a 4 mL vial. The sealed vessel was placed in a heating block that had been preheated to 60° C. The reaction mixture was stirred for 18 hours at 60° C. and then cooled to 23° C. The cooled mixture was concentrated. The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (53 mg, 0.10 mmol, 39% yield). MS (APCI$^+$) m/z 530 [M+H]$^+$.

Example 62B: 5-[8-fluoro-6-hydroxy-2-(6, 6,6-trifluorohexyl)-1,2,3,4-tetrahydroisoquinolin-7-yl]-1$\lambda^6$, 2,5-thiadiazolidine-1,1,3-trione A solution of boron trichloride in dichloromethane (1.0 M, 1.0 mL, 1.0 mmol, 10.0 equivalents) was added slowly down the side of the flask to a suspension of the product of Example 62A (53 mg, 0.10 mmol, 1 equivalent) and pentamethylbenzene (48 mg, 0.33 mmol, 3.3 equivalents) in dichloromethane (1.5 mL) at −78° C. The reaction mixture was stirred for 30 minutes at −78° C. and then was then slowly diluted with ethanol (0.8 mL) at −78° C. The diluted mixture was warmed over 30 minutes to 23° C. and concentrated. The residue obtained was triturated with heptanes (3×5 mL). The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (8.6 mg, 20% yield). $^1$H NMR (500 MHz, DMSO-d$_6$) δ ppm 9.59 (bs, 1H), 6.55 (s, 1H), 3.94 (s, 2H), 3.25-2.83 (m, 6H), 2.34-2.20 (m, 2H), 1.76-1.66 (m, 2H), 1.53 (p, J=7.2 Hz, 2H), 1.39 (p, J=7.7 Hz, 2H). MS (APCI$^+$) m/z 440 [M+H]$^+$.

Example 63: 5-{2-[(3,3-difluorocyclobutyl)methyl]-8-fluoro-6-hydroxy-1,2,3,4-tetrahydroisoquinolin-7-yl}-1$\lambda^6$,2,5-thiadiazolidine-1,1,3-trione (Compound 162)

Example 63A: 5-{6-(benzyloxy)-2-[(3,3-difluorocyclobutyl)methyl]-8-fluoro-, 2,3,4-tetrahydroisoquinolin-7-yl}-1$\lambda^6$,2,5-thiadiazolidine-1,1,3-trione A suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate, the product of Example 54A (nominally 0.25 mmol, 1 equivalent), potassium carbonate (176 mg, 1.27 mmol, 5.0 equivalents), and 3-(bromomethyl)-1,1-difluorocyclobutane (61 mg, 0.33 mmol, 1.3 equivalents) in acetonitrile (1.3 mL) was sealed in a 4 mL vial. The sealed vessel was placed in a heating block that had been preheated to 60° C. The reaction mixture was stirred for 18 hours at 60° C. and then cooled to 23° C. The cooled mixture was filtered through a plug of diatomaceous earth (1.0 cm×0.5 cm). The filter cake was rinsed with acetonitrile (5×1.0 mL). The filtrates were combined, and the combined filtrates were passed through a 0.45 μm PTFE membrane Whatman® syringe filter. The filtrate was concentrated. The residue obtained was used without further purification in the following step. MS (APCI$^+$) m/z 496 [M+H]$^+$.

Example 63B: 5-{2-[(3,3-difluorocyclobutyl)methyl]-8-fluoro-6-hydroxy-1,2,3,4-tetrahydroisoquinolin-7-yl}-1$\lambda^6$,2,5-thiadiazolidine-1,1,3-trione A solution of boron trichloride in dichloromethane (1.0 M, 2.0 mL, 2.0 mmol, 7.9 equivalents) was added slowly down the side of the flask to a suspension of the product of Example 63A (nominally 0.25 mmol, 1 equivalent) and pentamethylbenzene (122 mg, 0.92 mmol, 3.3 equivalents) in dichloromethane (2.0 mL) at −78° C. The reaction mixture was stirred for 30 minutes at −78° C. and was then slowly diluted with ethanol (0.8 mL) at −78° C. The diluted mixture was warmed over 30 minutes to 23° C. and concentrated. The residue obtained was triturated with heptanes (3×5 mL). The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (8 mg, 0.020 mmol, 8% yield, three steps). $^1$H NMR (500 MHz, DMSO-d$_6$) δ ppm 9.71 (bs, 1H), 6.58 (s, 1H), 4.52-4.08 (m, 2H), 3.96 (s, 2H), 3.11-2.63 (m, 6H); MS (APCI$^+$) m/z 406 [M+H]$^+$.

Example 64: 5-[2-(azetidin-3-yl)-8-fluoro-6-hydroxy-1,2,3,4-tetrahydroisoquinolin-7-yl]-1$\lambda^6$,2,5-thiadiazolidine-1,1,3-trione (Compound 163)

Example 64A: tert-butyl 3-[6-(benzyloxy)-8-fluoro-7-(1,1,4-trioxo-1$\lambda^6$,2,5-thiadiazolidin-2-yl)-3,4-dihydroisoquinolin-2(1H)-yl]azetidine-1-carboxylate To a vial were added 5-[6-(benzyloxy)-8-fluoro-1,2,3,4-tetrahydroisoquinolin-7-yl]-1$\lambda^6$,2,5-thiadiazolidine-1,1,3-trione (0.045 g, 0.12 mmol, Example 61A), tert-butyl 3-oxoazetidine-1-carboxylate (0.022 g, 0.13 mmol), and dichloromethane (0.38 mL). The suspension was stirred at ambient temperature for 10 minutes, then sodium triacetoxyhydroborate (0.049 g, 0.23 mmol) was added. After 14 hours, more tert-butyl 3-oxoazetidine-1-carboxylate (0.022 g, 0.13 mmol) and sodium triacetoxyhydroborate (0.049 g, 0.23 mmol) were added. After 4 additional hours, the reaction mixture was diluted with saturated aqueous sodium bicarbonate and stirred for 20 minutes. Next, water was added, and the mixture was extracted with dichloromethane (4×20 mL). The organic phases were combined, washed sequentially with 50% aqueous sodium chloride and brine, dried over sodium sulfate, and concentrated under reduced pressure to give the title compound. This material was used without further purification. MS (ESI⁺) m/z 588.1 [M+CH₃CN+H]+; MS (ESI⁻) m/z 545.2 [M−H]⁻.

Example 64B: tert-butyl 3-[8-fluoro-6-hydroxy-7-(1,1,4-trioxo-1λ⁶,2,5-thiadiazolidin-2-yl)-3,4-dihydroisoquinolin-2(1H)-yl]azetidine-1-carboxylate To a 20 mL Barnstead Hast C reactor containing 5% palladium on carbon (0.057 g, 0.25 mmol) were added tert-butyl 3-[6-(benzyloxy)-8-fluoro-7-(1,1,4-trioxo-1λ⁶,2,5-thiadiazolidin-2-yl)-3,4-dihydroisoquinolin-2(1H)-yl]azetidine-1-carboxylate (theoretically 0.12 mmol, Example 64A) and tetrahydrofuran (2 mL). The resulting mixture was stirred at ambient temperature for 1.8 hours under an atmosphere of hydrogen at 100 psi. The catalyst was then removed by filtration and washed with methanol. The filtrate was concentrated under reduced pressure and purified using reversed-phase preparative HPLC [Waters XBridge™ RP18 column, 5 μm, 30×100 mm, flow rate 40 mL/minute, 5-70% gradient of acetonitrile in water (buffered with 0.025 M aqueous ammonium bicarbonate, adjusted to pH 10 with ammonium hydroxide)] to afford the title compound (0.019 g, 0.042 mmol, 36% yield over two steps). ¹H NMR (500 MHz, methanol-d₄) δ ppm 7.26 (d, J=1.3 Hz, 1H), 4.76 (s, 2H), 4.71 (s, 2H), 4.16 (s, 2H), 4.10 (s, 1H), 3.51 (t, J=5.9 Hz, 2H), 3.37-3.30 (m, 4H), 2.15 (s, 9H); MS (ESI⁺) m/z 456.9 [M+H]⁺.

Example 64C: 5-[2-(azetidin-3-yl)-8-fluoro-6-hydroxy-1,2,3,4-tetrahydroisoquinolin-7-yl]-1λ⁶,2,5-thiadiazolidine-1,1,3-trione A vial containing a solution of tert-butyl 3-[8-fluoro-6-hydroxy-7-(1,1,4-trioxo-1λ⁶,2,5-thiadiazolidin-2-yl)-3,4-dihydroisoquinolin-2(1H)-yl]azetidine-1-carboxylate (0.019 g, 0.042 mmol, Example 64B) in dichloromethane (0.21 mL) was cooled to 0° C. Then 2,2,2-trifluoroacetic acid (0.019 mL, 0.25 mmol) was added dropwise and the resulting mixture stirred at 0° C. After 1 hour, more 2,2,2-trifluoroacetic acid (0.019 mL, 0.25 mmol) was added and the cooling bath was removed. After an additional 1.5 hours, the reaction mixture was passed through an SCX-2 cartridge (loaded and eluted initially with methanol/dichloromethane (1:1) and then eluted with a 2 M solution of ammonia in methanol) to give the title compound (5.5 mg, 0.015 mmol, 37% yield). ¹H NMR (500 MHz, DMSO-d₆) δ ppm 8.78 (s, 3H), 6.47 (d, J=1.3 Hz, 1H), 4.04 (dd, J=10.9, 7.3 Hz, 2H), 3.97-3.89 (m, 4H), 3.48 (p, J=7.0 Hz, 1H), 3.41 (s, 2H), 2.73 (t, J=5.9 Hz, 2H), 2.55 (t, J=5.8 Hz, 2H); MS (APCI⁺) m/z 357.4 [M+H]⁺.

Example 65: 5-(8-fluoro-6-hydroxy-2-{2-[(propan-2-yl)amino]ethyl}-1,2,3,4-tetrahydroisoquinolin-7-yl)-1λ⁶,2,5-thiadiazolidine-1,1,3-trione (Compound 164)

Example 65A: 5-[6-(benzyloxy)-8-fluoro-1,2,3,4-tetrahydroisoquinolin-7-yl]-1λ⁶,2,5-thiadiazolidine-1,1,3-trione To a solution of the product of Example 44H (133 mg, 0.271 mmol) in dichloromethane (5 mL) was added trifluoroacetic acid (617 mg, 5.41 mmol). The mixture was stirred at room temperature for 1 hour and concentrated under reduced pressure to give the title compound as a trifluoroacetic acid salt (137 mg, 0.271 mmol, 100% yield). MS (ESI⁻) m/z 390 [M−H]⁻.

Example 65B: tert-butyl {2-[6-(benzyloxy)-8-fluoro-7-(1,1,4-trioxo-1λ⁶,2,5-thiadiazolidin-2-yl)-3,4-dihydroisoquinolin-2(1H)-yl]ethyl}propan-2-yl-carbamate A mixture of the product of Example 65A (138 mg, 0.274 mmol), triethylamine (139 mg, 1.370 mmol), tert-butyl isopropyl(2-oxoethyl)carbamate (60.7 mg, 0.301 mmol) and sodium triacetoxyborohydride (232 mg, 1.096 mmol) in acetonitrile and methanol (4:1, 1.5 mL) was stirred at room temperature for 1.5 hours. The mixture was quenched with methanol/water (1:2, 2 mL) and filtered. The filtrate was concentrated under reduced pressure and the residue was purified by preparative HPLC [YMC TriArt™ C18 Hybrid 20 μm column, 25×150 mm, flow rate 80 mL/minute, 0-80% gradient of methanol in buffer (0.025 M aqueous ammonium bicarbonate, adjusted to pH 10 with ammonium hydroxide)] to give the title compound (79 mg, 0.137 mmol, 50% yield). MS (ESI⁻) m/z 575 [M−H]⁻.

Example 65C: 5-[6-(benzyloxy)-8-fluoro-2-{2-[(propan-2-yl)amino]ethyl}-1,2,3,4-tetrahydroisoquinolin-7-yl]-1λ⁶,2,5-thiadiazolidine-1,1,3-trione To a solution of the product of Example 65B (73 mg, 0.127 mmol) in dichloromethane (3 mL) was added trifluoroacetic acid (722 mg, 6.33 mmol). The mixture was stirred at room temperature for 1 hour and concentrated under reduced pressure to give the title compound (75 mg, 0.127 mmol, 100% yield) as a trifluoroacetic acid salt. MS (ESI⁻) m/z 475 [M−H]⁻.

Example 65D: 5-(8-fluoro-6-hydroxy-2-{2-[(propan-2-yl)amino]ethyl}-1,2,3,4-tetrahydroisoquinolin-7-yl)-1λ⁶,2,5-thiadiazolidine-1,1,3-trione To a mixture of 1,2,3,4,5-pentamethylbenzene (55.0 mg, 0.371 mmol) and the product of Example 65C (73 mg, 0.124 mmol) in dichloromethane (3 mL) at −78° C. was added trichloroborane (1.48 mL, 1.48 mmol, 1 M in dichloromethane). The mixture was stirred at −78° C. for 10 minutes, then at −20° C. for 20 minutes. The mixture was quenched with ethanol (2 mL) and concentrated under reduced pressure. The residue was washed with heptane (4×4 mL) and dichloromethane (6×3 mL) and dried under reduced pressure to give the title compound (33 mg, 0.066 mmol, 53% yield). ¹H NMR (500 MHz, DMSO-d₆) δ ppm 11.16 (br s, 1H), 10.40 (br s, 1H), 9.10 (br s, 2H), 6.65 (s, 1H), 4.30-4.60 (m, 2H), 4.27 (s, 2H), 3.40-3.54 (m, 4H), 3.15-3.30 (m, 4H), 3.07 (m, 1H), 1.28 (d, J=7 Hz, 6H); MS (ESI⁻) m/z 385 [M−H]⁻.

Example 66: 5-{2-[(azetidin-3-yl)methyl]-8-fluoro-6-hydroxy-1,2,3,4-tetrahydroisoquinolin-7-yl}-1λ⁶,2,5-thiadiazolidine-1,1,3-trione (Compound 165)

Example 66A: tert-butyl 3-{[6-(benzyloxy)-8-fluoro-7-(1,1,4-trioxo-1λ⁶,2,5-thiadiazolidin-2-yl)-3,4-dihydroisoquinolin-2(1H)-yl]methyl}azetidine-1-carboxylate To a vial were added 5-[6-(benzyloxy)-8-fluoro-1,2,3,4-tetrahydroisoquinolin-7-yl]-1λ⁶,2,5-thiadiazolidine-1,1,3-trione (0.045 g, 0.12 mmol, Example 61A), tert-butyl 3-formylazetidine-1-carboxylate (0.023 g, 0.13 mmol), and dichloromethane (0.38 mL). The suspension was stirred at ambient temperature for 10 minutes, then sodium triacetoxyhydroborate (0.049 g, 0.23 mmol) was added. After 14 hours, the reaction mixture was diluted with saturated aqueous sodium bicarbonate and stirred for 20 minutes. Next, water was added, and the mixture was extracted with dichloromethane (4×20 mL). The organic phases were combined, washed sequentially with 50% aqueous sodium chloride and brine, dried over sodium sulfate, and concentrated under reduced pressure to give the title compound. This material was used without further purification. MS (ESI$^+$) m/z 561.1 [M+H]$^+$.

Example 66B: tert-butyl 3-{[8-fluoro-6-hydroxy-7-(1,1,4-trioxo-1$\lambda^6$,2,5-thiadiazolidin-2-yl)-3,4-dihydroisoquinolin-2(1H)-yl]methyl}azetidine-1-carboxylate To a 20 mL Barnstead Hast C reactor containing 5% palladium on carbon (0.067 g, 0.29 mmol) were added tert-butyl 3-{[6-(benzyloxy)-8-fluoro-7-(1,1,4-trioxo-1$\lambda^6$,2,5-thiadiazolidin-2-yl)-3,4-dihydroisoquinolin-2(1H)-yl]methyl}azetidine-1-carboxylate (theoretically 0.12 mmol, Example 66A) and tetrahydrofuran (2 mL). The resulting mixture was stirred at ambient temperature for 2.4 hours under an atmosphere of hydrogen at 100 psi. The catalyst was then removed by filtration and washed with methanol. The filtrate was concentrated under reduced pressure and purified using reversed-phase preparative HPLC [Waters XBridge™ RP18 column, 5 m, 30×100 mm, flow rate 40 mL/minute, 5-70% gradient of acetonitrile in water (buffered with 0.025 M aqueous ammonium bicarbonate, adjusted to pH 10 with ammonium hydroxide)] to afford the title compound (0.023 g, 0.049 mmol, 43% yield over two steps). $^1$H NMR (500 MHz, methanol-d$_4$) δ ppm 6.60-6.56 (m, 1H), 4.22 (s, 2H), 4.10 (t, J=8.5 Hz, 2H), 3.97 (s, 2H), 3.71 (d, J=8.4 Hz, 2H), 3.24 (d, J=7.3 Hz, 2H), 3.19-3.13 (m, 2H), 3.11-3.02 (m, 1H), 2.99 (t, J=6.1 Hz, 2H), 1.43 (s, 9H); MS (ESI$^+$) m/z 471.1 [M+H]+; MS (ESI$^-$) m/z 469.1 [M−H]$^-$.

Example 66C: 5-{2-[(azetidin-3-yl)methyl]-8-fluoro-6-hydroxy-1,2,3,4-tetrahydroisoquinolin-7-yl}-1$\lambda^6$,2,5-thiadiazolidine-1,1,3-trione A vial containing a suspension of tert-butyl 3-{[8-fluoro-6-hydroxy-7-(1,1,4-trioxo-1$\lambda^6$,2,5-thiadiazolidin-2-yl)-3,4-dihydroisoquinolin-2(1H)-yl]methyl}azetidine-1-carboxylate (0.023 g, 0.049 mmol, Example 66B) in acetonitrile (0.24 mL) was cooled to 0° C. A solution of hydrogen chloride (2.0 M in diethyl ether, 0.098 mL, 0.20 mmol) was added dropwise, and the cooling bath was subsequently removed. After 1 hour, a second portion of hydrogen chloride (2.0 M in diethyl ether, 0.098 mL, 0.20 mmol) was added along with a few drops of water. After an additional 2.5 hours, the mixture was concentrated under reduced pressure and purified using reversed-phase HPLC [Waters XBridge™ RP18 column, 5 m, 30×100 mm, flow rate 40 mL/minute, 5-70% gradient of methanol in water (buffered with 0.025 M aqueous ammonium bicarbonate, adjusted to pH 10 with ammonium hydroxide)]. Product-containing fractions were combined and concentrated under reduced pressure. The residue was passed through an SCX-2 cartridge (loaded and eluted initially with methanol/dichloromethane(1:1) and then eluted with a 2 M solution of ammonia in methanol) to give the title compound (8.7 mg, 0.023 mmol, 48% yield). $^1$H NMR (400 MHz, DMSO-d$_6$) δ ppm 6.44 (d, J=1.3 Hz, 1H), 4.00 (dd, J=10.5, 8.5 Hz, 2H), 3.93 (s, 2H), 3.67 (dd, J=10.4, 7.0 Hz, 2H), 3.42 (s, 2H), 3.07 (p, J=7.7 Hz, 1H), 2.71 (dd, J=14.9, 6.6 Hz, 4H), 2.61 (t, J=5.7 Hz, 2H); MS (APCI$^+$) m/z 371.4 [M+H]$^+$.

Example 67: 5-{2-[(azetidin-3-yl)methyl]-8-fluoro-6-hydroxy-1,2,3,4-tetrahydroisoquinolin-7-yl}-1$\lambda^6$,2,5-thiadiazolidine-1,1,3-trione (Compound 166)

Example 67A: 6'-(benzyloxy)-8'-fluoro-3',4'-dihydro-1'H-spiro[[1,3]dioxolane-2,2'-naphthalene]

To a solution of the product from Example 22B (100 g, 348 mmol) and benzyl alcohol (50.5 mL, 488 mmol) in dioxane (200 mL) was added sodium tert-butoxide (40.2 g, 418 mmol), N,N'-diphenethyloxalamide (1.032 g, 3.48 mmol) and copper (I) iodide (0.663 g, 3.48 mmol). The resulting mixture was degassed (3× vacuum/purge with nitrogen) and then heated to 80° C. After 48 hours, water (1 L) was added, and the resulting mixture was cooled to ambient temperature. The mixture was filtered, and the solid was washed with water (200 mL). The filtrate was extracted with ethyl acetate (3×500 mL). The organic layers were combined, dried over anhydrous sodium sulfate, filtered and concentrated in vacuo. The residue was dissolved in dichloromethane (1 L) and filtered through Celite® (100 g). The filtrate was concentrated in vacuo. The resulting solid was triturated with isopropanol (200 mL) to give 85 g (244 mmol, 78% yield) of the title compound. $^1$H NMR (400 MHz, CDCl$_3$) δ ppm 7.46-7.28 (m, 5H), 6.74-6.60 (m, 2H), 5.07 (s, 2H), 4.00-3.88 (m, 4H), 2.86 (t, J=6.7 Hz, 2H), 2.72 (s, 2H), 1.83 (t, J=6.7 Hz, 2H); MS (APCI$^+$) m/z 315 [M+H]$^+$.

Example 67B: 6'-(benzyloxy)-7'-bromo-8'-fluoro-3',4'-dihydro-1'H-spiro[[1,3]dioxolane-2,2'-naphthalene]

To a solution of 2,2,6,6-tetramethylpiperidine (164 mL, 964 mmol) in tetrahydrofuran (500 mL) at 0° C. was added a solution of n-butyllithium (360 mL, 2.5 M in hexane, 900 mL) slowly over 40 minutes. After stirring for 30 minutes, the reaction mixture was diluted with tetrahydrofuran (500 mL) and cooled to −78° C. A solution of the product of Example 67A (202.11 g, 643 mmol) in tetrahydrofuran (500 mL) was added slowly over 30 minutes so that the internal temperature remained below −70° C. After 2 hours, 1,2-dibromo-1,1,2,2-tetrafluoroethane (92 mL, 772 mmol) was added slowly so that the internal temperature remained below −60° C. Upon complete addition the reaction mixture was warmed to −10° C., then was quenched with saturated aqueous ammonium chloride (500 mL) and diluted with water (1.5 L) and ethyl acetate (2 L). The layers were separated, and the organic layer was washed with 1 M hydrochloric acid, saturated aqueous sodium bicarbonate, and brine (500 mL), then dried over anhydrous sodium sulfate, filtered and concentrated in vacuo. The resulting residue was diluted with isopropanol (500 mL), and then heated to 50° C. and slowly cooled to ambient temperature. The resulting solid was collected by filtration to give the title compound (130.3 g, 331 mmol, 51.5% yield). $^1$H NMR (400 MHz, CDCl$_3$) δ ppm 7.50-7.28 (m, 5H), 6.53 (d, J=1.6 Hz, 1H), 5.12 (s, 2H), 4.10-3.97 (m, 4H), 2.93 (t, J=6.7 Hz, 2H), 2.89 (s, 2H), 1.92 (t, J=6.7 Hz, 2H); MS (APCI$^+$) m/z 393 [M+H]$^+$.

Example 67C: tert-butyl {[6'-(benzyloxy)-8'-fluoro-3',4'-dihydro-1'H-spiro[[1,3]dioxolane-2,2'-naphthalen]-7'-yl]amino}acetate To a suspension of the product from Example 67B (14.17 g, 36 mmol), cesium carbonate (35.2 g, 108 mmol), BrettPhos (0.387 g, 0.721 mmol), and BrettPhos Pd G3 precatalyst (0.653 g, 0.721 mmol) in 1,4-dioxane (280 mL) was added tert-butyl glycinate (7.39 mL, 54.1 mmol). The resulting suspension was degassed (5× vacuum/purge with nitrogen), and then heated to 90° C. After 16 hours, the reaction mixture was cooled to below 30° C., and additional BrettPhos Pd G3 precatalyst was added (0.653 g, 0.721 mmol). The reaction mixture was degassed (5× vacuum/purge with nitrogen), and then heating to 90° C. was resumed. After 7 hours, the reaction mixture was cooled to below 30° C., and additional BrettPhos Pd G3 precatalyst was added (0.653 g, 0.721 mmol). The reaction mixture was degassed (5× vacuum/purge with nitrogen), then heating to 90° C. was resumed. After 16 hours, the reaction mixture was cooled to below 30° C., and additional BrettPhos Pd G3 precatalyst was added (0.328 g, 0.362 mmol). The reaction mixture was degassed (5× vacuum/purge with nitrogen), then heating to 90° C. was resumed. After 4 hours, the reaction mixture was cooled to ambient temperature, quenched with saturated aqueous ammonium chloride (70 mL), and diluted with water (70 mL) and ethyl acetate (140 mL). The layers were separated, and the aqueous layer was extracted with ethyl acetate (2×70 mL). The organic layers were combined, washed with brine (42 mL), dried over anhydrous sodium sulfate and filtered. Silica (35 g) was added to the filtrate, and the mixture was concentrated in vacuo to a powder, which was dry loaded onto a 220 g gold Teledyne ISCO silica column, and purified by running a gradient of 0-40% ethyl acetate in heptanes with 0.1% triethylamine added to give 12.44 g (28.1 mmol, 78% yield) of the title compound. $^1$H NMR (400 MHz, CDCl$_3$) δ ppm 7.50-7.27 (m, 5H), 6.45 (d, J=1.4 Hz, 1H), 5.06 (s, 2H), 4.42 (s, 1H), 4.10-3.97 (m, 5H), 3.97-3.91 (m, 2H), 2.88 (t, J=6.8 Hz, 2H), 2.84 (s, 2H), 1.90 (t, J=6.6 Hz, 2H), 1.44 (s, 9H); MS (APCI$^+$) m/z 444 [M+H]$^+$.

Example 67D: tert-butyl {[6'-(benzyloxy)-8'-fluoro-3',4'-dihydro-1'H-spiro[[1,3]dioxolane-2,2'-naphthalen]-7'-yl]({[(prop-2-en-1-yl)oxy]carbonyl}sulfamoyl)amino}acetate To a solution of chlorosulfonyl isocyanate (3.65 mL, 42.1 mmol) in dichloromethane (124 mL), was added allyl alcohol (2.86 mL, 42.1 mmol) dropwise. After 30 minutes, a preformed solution of the product of Example 67C (12.44 g, 28.1 mmol) and N,N-diisopropylethylamine (9.8 mL, 56.1 mmol) in dichloromethane (62 mL) was added slowly via an addition funnel. After 45 minutes, the reaction mixture was quenched with water (125 mL) and stirred for 5 minutes. The layers were separated, and the aqueous layer was extracted with dichloromethane (2×62 mL). The organic layers were combined, washed with 1 M aqueous sodium bisulfate (62 mL), dried over anhydrous sodium sulfate, filtered and concentrated in vacuo to give the title compound, which was used without purification for the next step. MS (APCI$^+$) m/z 624 [M+NH$_4$]$^+$.

Example 67E: 5-[6'-(benzyloxy)-8'-fluoro-3',4'-dihydro-1'H-spiro[[1,3]dioxolane-2,2'-naphthalen]-7'-yl]-1λ$^6$,2,5-thiadiazolidine-1,1,3-trione To a solution of the crude product of Example 67D (17.0 g, 28.1 mmol) in methanol (340 mL) was added tetrakis(triphenylphosphine)palladium(0) (0.648 g, 0.561 mmol), followed by a solution of sodium methoxide (38.5 mL, 25 weight % in methanol, 168 mmol). The resulting mixture was degassed (3× vacuum/nitrogen purge), and then heated to 60° C. After 1 hour, the reaction mixture was cooled to ambient temperature, quenched with 1 M hydrochloric acid (190 mL), diluted with ethyl acetate (85 mL) and partially concentrated in vacuo to remove methanol. The resulting biphasic mixture was extracted with ethyl acetate (3×85 mL). The organic layers were combined, washed with brine (51 mL), dried over anhydrous sodium sulfate, filtered through Celite® (5 g) and concentrated in vacuo. The residue was suspended in tert-butyl methyl ether (85 mL), heated to boiling, and then cooled to ambient temperature. The resulting solid was collected by filtration, washed with the cold filtrate and then with cold tert-butyl methyl ether (34 mL), and dried in a vacuum oven at 50° C. to give 7.95 g (17.72 mmol, 63.2% yield) of the title compound. MS (APCI$^+$) m/z 449 [M+H]$^+$.

Example 67F: 5-[3-(benzyloxy)-1-fluoro-7-oxo-5,6,7,8-tetrahydronaphthalen-2-yl]-1λ$^6$,2,5-thiadiazolidine-1,1,3-trione The product from Example 67E (1.5 g, 3.34 mmol) was suspended in 88% formic acid (7.5 mL, 196 mmol). After 45 minutes, the reaction mixture was diluted with drop-wise addition of brine (15 mL). The resulting solid was collected by filtration, washed with water (4×7.5 mL) and dried in a vacuum oven at 50° C. to give 1.33 g (3.30 mmol, 99% yield) of the title compound. $^1$H NMR (400 MHz, DMSO-d$_6$) δ ppm 7.47 (d, J=6.8 Hz, 2H), 7.45-7.28 (m, 3H), 7.05 (s, 1H), 5.19 (s, 2H), 4.40 (s, 2H), 3.47 (s, 2H), 3.06 (t, J=6.7 Hz, 2H), 2.50 (t, J=6.7 Hz, 2H); MS (APCI$^+$) m/z 422 [M+NH$_4$]$^+$.

Example 67G: 5-{3-(benzyloxy)-7-[(4,4-difluorobutyl)amino]-1-fluoro-5,6,7,8-tetrahydronaphthalen-2-yl}-1λ$^6$,2,5-thiadiazolidine-1,3-trione To a solution of the product of Example 67F (0.5 g, 1.24 mmol) in ethanol (10 mL) was added 4,4-difluorobutan-1-amine hydrochloride (0.270 g, 1.86 mmol) followed by triethylamine (0.517 mL, 3.71 mmol). After 30 minutes, sodium cyanoborohydride (0.093 g, 1.48 mmol) was added as a solid. The mixture was allowed to stir for 16 hours, and then was quenched with ammonium hydroxide (0.14 mL, 7.42 mmol) and diluted with acetonitrile (10 mL) and water (2 mL). Celite® (5 g) was added, and the mixture was concentrated in vacuo to give a powder. The resultant mixture was dry loaded onto a Teledyne ISCO 275 g reversed-phase C18 column eluted with a gradient of 10-100% methanol in buffer (0.025 M ammonium bicarbonate in water acidified to pH 7 by adding dry ice) to give the title compound (0.386 g, 0.776 mmol, 63% yield. MS (APCI$^+$) m/z 498 [M+H]$^+$.

Example 67H: 5-{2-[(azetidin-3-yl)methyl]-8-fluoro-6-hydroxy-1,2,3,4-tetrahydroisoquinolin-7-yl}-1λ$^6$,2,5-thiadiazolidine-1,1,3-trione To a suspension of the product of Example 67G (0.386 g, 0.776 mmol) and pentamethylbenzene (0.230 g, 1.55 mmol) in dichloromethane (7.7 mL) at −78° C. was added a solution of boron trichloride (4.66 mL, 1 M in dichloromethane, 4.66 mmol) slowly along the side of the flask. The resulting mixture was stirred for 5 minutes, then warmed to an internal temperature of 0° C., then cooled to −78° C. and quenched with ethyl acetate (4 mL) followed by ethanol (4 mL). The reaction mixture was warmed to ambient temperature and concentrated in vacuo. The residue was triturated with heptanes (3×8 mL), 1:1 ethyl acetate/heptanes (2×4 mL), dichloromethane (2×4 mL) and acetonitrile (3×4 mL), and then dried in a vacuum oven at 50° C. to give the title compound as an HCl salt (0.297 g, 0.669 mmol, 86% yield). $^1$H NMR (400 MHz, DMSO-$d_6$) δ ppm 10.17 (br s, 1H), 9.00 (br s, 2H), 6.54 (s, 1H), 6.15 (tt, J=56.6, 4.2 Hz, 1H), 4.32 (s, 2H), 3.48-3.40 (m, 1H), 316-3.02 (m, 3H), 2.88-2.70 (m, 2H), 2.61 (dd, J=16.1, 10.0 Hz, 1H), 2.24-2.16 (m, 1H), 2.09-1.86 (m, 2H), 1.84-1.67 (m, 3H); MS (APCI$^+$) m/z 408 [M+H]$^+$.

Example 68: 5-(1-fluoro-3-hydroxy-7-{(3-methylbutyl)[2-(pyridin-2-yl)ethyl]amino}-5,6,7,8-tetrahydronaphthalen-2-yl)-1$\lambda^6$,2,5-thiadiazolidine-1,1,3-trione (Compound 167)

To a solution of the product from Example 22I (0.3 g, 0.596 mmol) and 2-(2-aminoethyl)pyridine (0.107 mL, 0.894 mmol) in acetonitrile (6 mL) at room temperature was added sodium cyanoborohydride (0.075 g, 1.191 mmol). After 18 hours, isovaleraldehyde (0.257 mL, 2.383 mmol) was added. After 23 hours, a solution of hydrogen chloride (1.489 mL, 5.96 mmol, 4 M in dioxane) was added dropwise (vigorous gas evolution). After 4 hours, the reaction mixture was quenched with ammonium hydroxide (0.090 mL, 4.77 mmol) and then diluted with acetonitrile (4 mL) and water (2 mL). Celite® (2 g) was added, and the mixture was concentrated in vacuo. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give the title compound (0.0363 g, 0.074 mmol, 12.4% yield). $^1$H NMR (400 MHz, DMSO-$d_6$) δ ppm 9.17 (s, 1H), 8.51 (dd, J=4.8, 1.7 Hz, 1H), 7.75 (tt, J=7.2, 3.6 Hz, 1H), 7.62 (s, 2H), 7.37 (d, J=7.8 Hz, 1H), 7.27 (dd, J=7.5, 4.8 Hz, 1H), 6.44 (s, 1H), 3.90 (s, 2H), 3.81-3.65 (m, 1H), 3.62-3.50 (m, 2H), 3.25-3.16 (m, 2H), 3.07-2.97 (m, 1H), 2.84-2.73 (m, 2H), 2.20-2.10 (m, 1H), 1.86-1.75 (m, 1H), 163-1.51 (m, 3H), 1.48-1.33 (m, 1H), 0.86 (d, J=5.7 Hz, 6H); MS (APCI$^+$) m/z 491 [M+H]$^+$.

Example 69: 5-{8-fluoro-6-hydroxy-2-[(spiro[2.3]hexan-5-yl)methyl]-1,2,3,4-tetrahydroisoquinolin-7-yl}-1$\lambda^6$,2,5-thiadiazolidine-1,1,3-trione (Compound 168)

Example 69A: 5-{6-(benzyloxy)-8-fluoro-2-[(spiro[2.3]hexan-5-yl)methyl]-1,2,3,4-tetrahydroisoquinolin-7-yl}-1$\lambda^6$,2,5-thiadiazolidine-1,1,3-trione A suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate, the product of Example 54A (nominally 0.25 mmol, 1 equivalent), potassium carbonate (175 mg, 1.27 mmol, 5.0 equivalents), and 5-(bromomethyl)spiro[2.3]hexane (89 mg, 0.51 mmol, 2.0 equivalents) in acetonitrile (1.7 mL) was sealed in a 4 mL vial. The sealed vessel was placed in a heating block that had been preheated to 60° C. The reaction mixture was stirred for 18 hours at 60° C. and then cooled to 23° C. The cooled mixture was filtered through a plug of diatomaceous earth (1.0 cm×0.5 cm). The filter cake was rinsed with acetonitrile (5×1.0 mL). The filtrates were combined, and the combined filtrates were concentrated. The residue obtained was used without further purification in the following step. MS (APCI$^+$) m/z 486 [M+H]$^+$.

Example 69B: 5-{8-fluoro-6-hydroxy-2-[(spiro[2.3]hexan-5-yl)methyl]-1,2,3,4-tetrahydroisoquinolin-7-yl}-1$\lambda^6$,2,5-thiadiazolidine-1,1,3-trione A solution of boron trichloride in dichloromethane (1.0 M, 1.5 mL, 1.5 mmol, 6.0 equivalents) was added slowly down the side of the flask to a suspension of the product of Example 69A (nominally 0.25 mmol, 1 equivalent) and pentamethylbenzene (113 mg, 0.76 mmol, 3.0 equivalents) in dichloromethane (1.3 mL) at −78° C. The reaction mixture was stirred for 30 minutes at −78° C. and then slowly diluted with ethanol (0.8 mL) at −78° C. The diluted mixture was warmed over 30 minutes to 23° C. and concentrated. The residue obtained was triturated with heptanes (3×5 mL). The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (12 mg, 0.030 mmol, 12% yield, three steps). $^1$H NMR (500 MHz, DMSO-$d_6$) δ ppm 9.68 (bs, 1H), 6.56 (s, 1H), 3.94 (s, 2H), 3.16-2.83 (m, 4H), 2.22-2.01 (m, 4H), 0.33-0.33 (m, 4H). MS (APCI$^+$) m/z 396 [M+H]$^+$.

Example 70: 5-(1-fluoro-3-hydroxy-7-{[2-(trifluoromethoxy)ethyl]amino}-5,6,7,8-tetrahydronaphthalen-2-yl)-1$\lambda^6$,2,5-thiadiazolidine-1,1,3-trione (Compound 169)

The title compound was prepared using the methodologies described in Example 26 substituting 2-(trifluoromethoxy)ethanamine, hydrochloric acid for 2,2-difluoro-2-phenylethanamine, hydrochloric acid. $^1$H NMR (500 MHz, DMSO-$d_6$) δ ppm 9.20 (br s, 1H), 8.92 (br s, 4H), 6.47 (s, 1H), 4.35 (m, 2H), 3.93 (s, 2H), 3.41 (m, 2H), 3.07 (m, 1H), 2.75 (m, 2H), 2.55 (m, 2H), 2.15 (m, 1H), 1.69 (m, 1H); MS (ESI$^-$) m/z 426 [M−H]$^-$.

Example 71: 5-[8-fluoro-6-hydroxy-2-(3-hydroxy-3-methylbutyl)-1,2,3,4-tetrahydroisoquinolin-7-yl]-1$\lambda^6$,2,5-thiadiazolidine-1,1,3-trione (Compound 170)

Example 71A: 5-[6-(benzyloxy)-8-fluoro-2-(3-hydroxy-3-methylbutyl)-1,2,3,4-tetrahydroisoquinolin-7-yl]-1$\lambda^6$,2,5-thiadiazolidine-1,1,3-trione A mixture of the product of Example 65A (139 mg, 0.275 mmol), 4-bromo-2-methylbutan-2-ol (59.7 mg, 0.358 mmol) and cesium carbonate (448 mg, 1.375 mmol) in N,N-dimethylformamide (1.5 mL) was stirred at 70° C. for 2.5 hours and then at room temperature for 3 days. The mixture was quenched with methanol/water (2:1, 5 mL) and filtered. The filtrate was concentrated under reduced pressure and the residue was purified by preparative HPLC [YMC TriArt™ C18 Hybrid 5 μm column, 50×100 mm, flow rate 140 mL/minute, 5-65% gradient of methanol in water (0.1% trifluoroacetic acid)] to give the title compound (53 mg, 0.090 mmol, 33% yield). MS (ESI$^-$) m/z 476 [M−H]$^-$.

Example 71B: 5-[8-fluoro-6-hydroxy-2-(3-hydroxy-3-methylbutyl)-1,2,3,4-tetrahydroisoquinolin-7-yl]-1$\lambda^6$,2,5-thiadiazolidine-1,1,3-trione To a mixture of 1,2,3,4,5-pentamethylbenzene (50.1 mg, 0.338 mmol) and Example 71A (50 mg, 0.085 mmol) in dichloromethane (3 mL) at −78° C. was added trichloroborane (0.93 mL, 0.930 mmol, 1 M in dichloromethane). The mixture was stirred at −78° C. for 10 minutes, then at −20° C. for 30 minutes. The mixture was quenched with ethanol (3 mL) and concentrated under reduced pressure. The residue was washed with heptane (4×4 mL), dichloromethane (6×3 mL) and dried under reduced pressure to give the title compound (39 mg, 0.078 mmol, 92% yield). $^1$H NMR (500 MHz, DMSO-$d_6$) δ ppm 10.48 (br s, 1H), 10.34 (br s, 1H), 6.66 (s, 1H), 4.45 (m, 1H), 4.32 (s, 2H), 4.12 (m, 1H), 3.69 (m, 2H), 3.29 (m, 3H), 3.14 (m, 1H), 2.99 (m, 1H), 1.88 (t, J=7 Hz, 2H), 1.16 (s, 6H); MS (ESI$^+$) m/z 388 [M+H]$^+$.

Example 72: 3-hydroxybutyl 8-fluoro-6-hydroxy-7-(1,1,4-trioxo-1$\lambda^6$,2,5-thiadiazolidin-2-yl)-3,4-dihydroisoquinoline-2(1H)-carboxylate (Compound 171)

Example 72A: 3-hydroxybutyl 6-(benzyloxy)-8-fluoro-7-(1,1,4-trioxo-1$\lambda^6$,2,5-thiadiazolidin-2-yl)-3,4-dihydroisoquinoline-2(1H)-carboxylate To a solution of the product of Example 44H (116 mg, 0.236 mmol) in dichloromethane (5 mL) was added trifluoroacetic acid (538 mg, 4.72 mmol). The mixture was stirred at room temperature for 1 hour. The mixture was concentrated under reduced pressure to give the intermediate, 6-(benzyloxy)-8-fluoro-7-(1,1,4-trioxo-1$\lambda^6$,2,5-thiadiazolidin-2-yl)-3,4-dihydroisoquinoline-2(1H)-carboxylic acid. To the said intermediate was added 4-bromobutan-2-ol (45.1 mg, 0.295 mmol) and cesium carbonate (384 mg, 1.180 mmol) in N,N-dimethylformamide (1 mL). The mixture was stirred at 50° C. for 18 hours and was cooled to room temperature. The mixture was diluted with ethyl acetate (80 mL), washed with 0.2 N aqueous HCl solution (15 mL) and brine (2×15 mL) and dried over anhydrous sodium sulfate. The mixture was filtered and concentrated under reduced pressure. The residue was dissolved in methanol/N,N-dimethylformamide (2:1, 3 mL) and purified by preparative HPLC [YMC TriArt™ C18 Hybrid 20 µm column, 25×150 mm, flow rate 80 mL/minute, 0-70% gradient of methanol in buffer (0.025 M aqueous ammonium bicarbonate, adjusted to pH 10 with ammonium hydroxide)] to give the title compound (25 mg, 0.048 mmol, 20.2% yield) as an ammonium salt. $^1$H NMR (500 MHz, DMSO-$d_6$) δ ppm 7.53 (br s, 4H), 6.48 (s, 1H), 4.52 (m, 1H), 4.37 (s, 2H), 4.07 (m, 2H), 3.92 (s, 2H), 3.68 (m, 1H), 3.52 (m, 2H), 2.67 (m, 2H), 1.60 (m, 2H), 1.04 (d, J=7 Hz, 3H); MS (ESI$^-$) m/z 506 [M−H]$^-$.

Example 72B: 3-hydroxybutyl 8-fluoro-6-hydroxy-7-(1,1,4-trioxo-1$\lambda^6$,2,5-thiadiazolidin-2-yl)-3,4-dihydroisoquinoline-2(1H)-carboxylate To a mixture of 1,2,3,4,5-pentamethylbenzene (16.65 mg, 0.112 mmol) and the product of Example 72A (19 mg, 0.037 mmol) in dichloromethane (2 mL) at −78° C. was added trichloroborane (0.441 mL, 0.441 mmol, 1 M in dichloromethane). The mixture was stirred at −78° C. for 10 minutes then at −20° C. for 20 minutes. The mixture was quenched with ethanol (3 mL) and concentrated under reduced pressure. The residue was washed with heptane (4×4 mL) and dichloromethane (6×3 mL). The resulting residue was dissolved in methanol/N,N-dimethylformamide (2:1, 3 mL) and was purified by preparative HPLC [YMC TriArt™ C18 Hybrid 20 µm column, 25×150 mm, flow rate 80 mL/minute, 0-50% gradient of methanol in buffer (0.025 M aqueous ammonium bicarbonate, adjusted to pH 10 with ammonium hydroxide)] to give the title compound (10 mg, 0.023 mmol, 61.5% yield). $^1$H NMR (500 MHz, DMSO-$d_6$) δ ppm 7.53 (br s, 4H), 6.48 (s, 1H), 4.52 (m, 1H), 4.37 (s, 2H), 4.07 (m, 2H), 3.92 (s, 2H), 3.68 (m, 1H), 3.52 (m, 2H), 2.67 (m, 2H), 1.60 (m, 2H), 1.04 (d, J=7 Hz, 3H); MS (ESP) m/z 416 [M−H]$^-$.

Example 73: 5-{1-fluoro-3-hydroxy-7-[3-(propan-2-yl)pyrrolidin-1-yl]-5,6,7,8-tetrahydronaphthalen-2-yl}-1$\lambda^6$,2,5-thiadiazolidine-1,1,3-trione (Compound 172)

To a solution of the product of Example 67F (0.1 g, 0.247 mmol) in ethanol (2 mL) was added 3-(propan-2yl)pyrrolidine hydrochloride (0.056 g, 0.371 mmol), followed by triethylamine (0.103 mL, 0.742 mmol). After 30 minutes, sodium cyanoborohydride (0.019 g, 0.297 mmol) was added as a solid. After 16 hours, the reaction mixture was quenched with ammonium hydroxide (0.028 mL, 1.48 mmol), then diluted with acetonitrile (2 mL) and water (1 mL). Celite® (1 g) was added and the mixture was concentrated in vacuo to give a powder. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-1-fluoro-7-[3-(propan-2-yl)pyrrolidin-1-yl]-5,6,7,8-tetrahydronaphthalen-2-yl}-1$\lambda^6$,2,5-thiadiazolidine-1,1,3-trione (0.08 g, 0.159 mmol, 64.4% yield). MS (APCI$^+$) m/z 502 [M+H]$^+$.

To a suspension of 5-{3-(benzyloxy)-1-fluoro-7-[3-(propan-2-yl)pyrrolidin-1-yl]-5,6,7,8-tetrahydronaphthalen-2-yl}-1$\lambda^6$,2,5-thiadiazolidine-1,1,3-trione (0.08 g, 0.159 mmol) and pentamethylbenzene (0.047 g, 0.319 mmol) in dichloromethane (2.9 mL) at −78° C. was added a solution of boron trichloride (0.96 mL, 1 M in dichloromethane, 0.96 mmol) slowly along the side of the flask. The resulting mixture was stirred for 5 minutes, then warmed to an internal temperature of 0° C., then cooled to −78° C. and quenched with ethyl acetate (1 mL), followed by ethanol (1 mL). The reaction mixture was warmed to ambient temperature and concentrated in vacuo. The residue was triturated with heptanes (3×2 mL), 1:1 ethyl acetate/heptanes (2×2 mL), dichloromethane (2×2 mL) and acetonitrile (2×1 mL), and then dried in a vacuum oven at 50° C. to give the title compound as an HCl salt (0.0493 g, 0.110 mmol, 69.1% yield). $^1$H NMR (400 MHz, DMSO-$d_6$) δ ppm 10.85 (s, 1H), 10.15 (s, 1H), 6.54 (s, 1H), 4.32 (d, J=1.6 Hz, 2H), 3.73-3.52 (m, 1H), 3.52-3.42 (m, 2H), 3.37-3.04 (m, 3H), 2.92-2.82 (m, 1H), 2.81-2.66 (m, 3H), 2.37-2.20 (m, 1H), 2.16-1.91 (m, 2H), 1.85-1.62 (m, 1H), 1.62-1.48 (m, 1H), 0.95-0.87 (m, 6H); MS (APCI$^+$) m/z 412 [M+H]$^+$.

Example 74: 5-{7-[(2-cyclohexylethyl)amino]-1-fluoro-3-hydroxy-5,6,7,8-tetrahydronaphthalen-2-yl}-1$\lambda^6$,2,5-thiadiazolidine-1,1,3-trione (Compound 173)

To a solution of the product of Example 67F (0.1 g, 0.247 mmol) in ethanol (2 mL) was added 2-cyclohexylethanamine (0.047 g, 0.371 mmol). After 30 minutes, sodium cyanoborohydride (0.019 g, 0.297 mmol) was added as a solid. After 16 hours, the reaction mixture was quenched with ammonium hydroxide (0.028 mL, 1.484 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025

M ammonium bicarbonate in water acidified to pH 7 by adding dry ice) to give 5-{3-(benzyloxy)-7-[(2-cyclohexylethyl)amino]-1-fluoro-5,6,7,8-tetrahydronaphthalen-2-yl}-1$\lambda^6$,2,5-thiadiazolidine-1,1,3-trione (0.0517 g, 0.100 mmol, 40.5% yield). MS (APCI$^+$) m/z 516 [M+H]$^+$.

To a suspension of 5-{3-(benzyloxy)-7-[(2-cyclohexylethyl)amino]-1-fluoro-5,6,7,8-tetrahydronaphthalen-2-yl}-1$\lambda^6$,2,5-thiadiazolidine-1,1,3-trione (0.0517 g, 0.100 mmol) and pentamethylbenzene (0.030 g, 0.201 mmol) in dichloromethane (2 mL) at −78° C. was added a solution of boron trichloride (0.602 mL, 1 M in dichloromethane, 0.602 mmol) slowly along the side of the flask. The resulting mixture was stirred for 5 minutes, then was warmed to an internal temperature of 0° C., then was cooled to −78° C. and quenched with ethyl acetate (1 mL), followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), and then dried in a vacuum oven at 50° C. to give the title compound as an HCl salt (0.0452 g, 0.098 mmol, 98% yield). $^1$H NMR (400 MHz, DMSO-d$_6$) δ ppm 10.17 (s, 1H), 8.97 (tq, J=12.0, 6.1 Hz, 2H), 6.54 (s, 1H), 4.31 (s, 2H), 3.44-3.35 (m, 1H), 3.13 (dd, J=15.9, 5.5 Hz, 1H), 3.01 (dq, J=12.4, 6.4 Hz, 2H), 2.82 (dt, J=17.1, 4.5 Hz, 1H), 2.73 (ddd, J=17.3, 11.4, 5.4 Hz, 1H), 2.61 (dd, J=16.0, 10.1 Hz, 1H), 2.25-2.18 (m, 1H), 1.80-1.58 (m, 6H), 1.61-1.51 (m, 2H), 1.35 (td, J=8.7, 7.0, 3.7 Hz, 1H), 1.18 (dddd, J=24.2, 15.2, 12.2, 6.2 Hz, 3H), 0.92 (q, J=11.8 Hz, 2H); MS (APCI$^+$) m/z 426 [M+H]$^+$.

Example 75: 5-{7-[(3,3-dimethylbutyl)amino]-1-fluoro-3-hydroxy-5,6,7,8-tetrahydronaphthalen-2-yl}-1$\lambda^6$,2,5-thiadiazolidine-1,1,3-trione (Compound 174)

To a solution of the product of Example 67F (0.1 g, 0.247 mmol) in ethanol (2 mL) was added 3,3-dimethylbutylamine (0.038 g, 0.371 mmol). After 30 minutes sodium cyanoborohydride (0.019 g, 0.297 mmol) was added as a solid. After 16 hours, the reaction mixture was quenched with ammonium hydroxide (0.028 mL, 1.48 mmol), and then was diluted with acetonitrile (2 mL) and water (1 mL). Celite® (1 g) was added, and the mixture was concentrated in vacuo to give a white powder. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-7-[(3,3-dimethylbutyl)amino]-1-fluoro-5,6,7,8-tetrahydronaphthalen-2-yl}-1$\lambda^6$,2,5-thiadiazolidine-1,1,3-trione (0.0714 g, 0.146 mmol, 59% yield). MS (APCI$^+$) m/z 490 [M+H]$^+$.

To a suspension of 5-{3-(benzyloxy)-7-[(3,3-dimethylbutyl)amino]-1-fluoro-5,6,7,8-tetrahydronaphthalen-2-yl}-1$\lambda^6$,2,5-thiadiazolidine-1,1,3-trione (0.0714 g, 0.146 mmol) and pentamethylbenzene (0.043 g, 0.292 mmol) in dichloromethane (2.14 mL) at −78° C. was added a solution of boron trichloride (0.875 mL, 1 M in dichloromethane, 0.875 mmol) slowly along the side of the flask. The resulting mixture was stirred for 5 minutes, then warmed to an internal temperature of 0° C., then was cooled to −78° C. and quenched with ethyl acetate (1 mL), followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), then dried in a vacuum oven at 50° C. to give the title compound as an HCl salt (0.0573 g, 0.131 mmol, 90% yield). $^1$H NMR (600 MHz, DMSO-d$_6$) δ ppm 10.08 (s, 1H), 8.91 (dt, J=29.1, 5.8 Hz, 2H), 6.53 (s, 1H), 4.29 (s, 2H), 3.42 (s, 1H), 3.14 (dd, J=15.9, 5.5 Hz, 1H), 3.00 (dq, J=12.3, 6.4 Hz, 2H), 2.83 (dt, J=17.3, 4.5 Hz, 1H), 2.74 (ddd, J=17.3, 11.6, 5.5 Hz, 1H), 2.61 (dd, J=15.9, 10.4 Hz, 1H), 2.25-2.20 (m, 1H), 1.73 (qd, J=11.8, 5.3 Hz, 1H), 1.60-1.54 (m, 2H), 0.93 (s, 9H); MS (APCI$^+$) m/z 400 [M+H]$^+$.

Example 76: 5-[7-(butylamino)-1-fluoro-3-hydroxy-5,6,7,8-tetrahydronaphthalen-2-yl]-1$\lambda^6$,2,5-thiadiazolidine-1,1,3-trione (Compound 175)

To a solution of the product of Example 67F (0.1 g, 0.247 mmol) in ethanol (2 mL) was added butylamine (0.037 mL, 0.371 mmol). After 30 minutes, sodium cyanoborohydride (0.019 g, 0.297 mmol) was added as a solid. After 16 hours, the reaction mixture was quenched with ammonium hydroxide (0.028 mL, 1.484 mmol), and then diluted with acetonitrile (2 mL) and water (1 mL). Celite® (1 g) was added, and the mixture was concentrated in vacuo to give a powder. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-[3-(benzyloxy)-7-(butylamino)-1-fluoro-5,6,7,8-tetrahydronaphthalen-2-yl]-1$\lambda^6$,2,5-thiadiazolidine-1,1,3-trione (0.0803 g, 0.174 mmol, 70.4% yield). MS (APCI$^+$) m/z 462 [M+H]$^+$.

To a suspension of 5-[3-(benzyloxy)-7-(butylamino)-1-fluoro-5,6,7,8-tetrahydronaphthalen-2-yl]-1$\lambda^6$,2,5-thiadiazolidine-1,1,3-trione (0.0803 g, 0.174 mmol) and pentamethylbenzene (0.052 g, 0.348 mmol) in dichloromethane (1.6 mL) at −78° C. was added a solution of boron trichloride (1.04 mL, 1.04 mmol, 1 M in dichloromethane) slowly along the side of the flask. The resulting mixture was stirred for 5 minutes, then warmed to an internal temperature of 0° C., and then cooled to −78° C. and quenched with ethyl acetate (1 mL), followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), and then dried in a vacuum oven at 50° C. to give the title compound as an HCl salt (0.0665 g, 0.163 mmol, 94% yield). $^1$H NMR (600 MHz, DMSO-d$_6$) δ ppm 10.12 (s, 1H), 8.90 (ddd, J=22.0, 12.4, 6.5 Hz, 2H), 6.53 (s, 1H), 4.30 (s, 2H), 3.46-3.35 (m, 1H), 3.12 (dd, J=16.0, 5.6 Hz, 1H), 3.00 (dq, J=12.5, 6.6 Hz, 2H), 2.82 (dt, J=17.2, 4.5 Hz, 1H), 2.74 (ddd, J=17.2, 11.4, 5.5 Hz, 1H), 2.60 (dd, J=16.1, 10.2 Hz, 1H), 2.24-2.17 (m, 1H), 1.73 (qd, J=11.8, 4.7 Hz, 1H), 1.63 (dq, J=12.7, 8.1, 7.5 Hz, 2H), 1.37 (h, J=7.4 Hz, 2H), 0.91 (t, J=7.3 Hz, 3H); MS (APCI$^+$) m/z 372 [M+H]$^+$.

Example 77: 5-{(7S)-1-fluoro-3-hydroxy-7-[(4,4,4-trifluoro-3,3-dimethylbutyl)amino]-5,6,7,8-tetrahydronaphthalen-2-yl}-1$\lambda^6$,2,5-thiadiazolidine-1,1,3-trione (Compound 176)

The product of Example 24 (0.299 g, 0.660 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified $CO_2$ pressurized to 350 psi with a modifier of methanol (0.1% triethylamine) at a flow rate of 80 g/minute. The column was at ambient temperature and the back pressure regulator was set to maintain 100 bar. The sample was dissolved in methanol at a concentration of 15 mg/mL. The sample was loaded into the modifier stream in 0.25 mL (3.75 mg) injections. The mobile phase was held isocratically at 40% cosolvent:$CO_2$. Fraction collection was time triggered. The instrument was fitted with a CHIRALPAK® IC column with dimensions 21 mm i.d.×250 mm length with 5 µm particles. The earlier eluting enantiomer peak gave the title compound (0.1069 mg, 0.236 mmol, 17.4% recovery). $^1$H NMR and MS data were identical to those from Example 24. Absolute stereochemistry was assigned in analogy to the chromatographic elution order of the product of Example 18.

Example 78: 5-{(7R)-1-fluoro-3-hydroxy-7-[(4,4,4-trifluoro-3,3-dimethylbutyl)amino]-5,6,7,8-tetrahydronaphthalen-2-yl}-1$\lambda^6$,2,5-thiadiazolidine-1,1,3-trione (Compound 177)

The product of Example 24 (0.2993 g, 0.660 mmol) was separated by preparative chiral SFC. Preparative SFC was performed on a THAR/Waters SFC80 system running under SuperChrom™ software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a Dewar of bone-dry non-certified $CO_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol at a concentration of 15 mg/mL. The sample was loaded into the modifier stream in 0.25 mL (3.75 mg) injections. The mobile phase was held isocratically at 40% cosolvent:$CO_2$. Fraction collection was time triggered. The instrument was fitted with a CHIRALPAK® IC column with dimensions 21 mm i.d.×250 mm length with 5 µm particles. The later eluting enantiomer peak gave the title compound (0.0723 mg, 0.159 mmol, 48.3% recovery). $^1$H NMR and MS data were identical to those from Example 24. Absolute stereochemistry was assigned in analogy to the chromatographic elution order of the product of Example 19.

Example 79: 5-{7-[(2-cyclopentylethyl)amino]-1-fluoro-3-hydroxy-5,6,7,8-tetrahydronaphthalen-2-yl}-1$\lambda^6$,2,5-thiadiazolidine-1,1,3-trione (Compound 178)

To a solution of the product of Example 67F (0.05 g, 0.124 mmol) in ethanol (1 mL) was added 2-cyclopentylethanamine (0.021 g, 0.185 mmol). After 30 minutes, sodium cyanoborohydride (0.009 g, 0.148 mmol) was added as a solid. After 16 hours, the reaction mixture was quenched with ammonium hydroxide (0.014 mL, 0.742 mmol) and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-7-[(2-cyclopentylethyl)amino]-1-fluoro-5,6,7,8-tetrahydronaphthalen-2-yl}-1$\lambda^6$,2,5-thiadiazolidine-1,1,3-trione (0.0338 g, 0.067 mmol, 54.5% yield) as an off-white (beige) solid. MS (APCI$^+$) m/z 502 [M+H]$^+$.

To a suspension of 5-{3-(benzyloxy)-7-[(2-cyclopentylethyl)amino]-1-fluoro-5,6,7,8-tetrahydronaphthalen-2-yl}-1$\lambda^6$,2,5-thiadiazolidine-1,1,3-trione (0.0338 g, 0.067 mmol) and pentamethylbenzene (0.020 g, 0.135 mmol) in dichloromethane (1.4 mL) at −78° C. was added a solution of boron trichloride (0.404 mL, 0.404 mmol, 1 M in dichloromethane) slowly along the side of the flask. The resulting mixture was stirred for 5 minutes, then warmed to an internal temperature of 0° C., and then was cooled to −78° C. and quenched with ethyl acetate (1 mL), followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), then dried in a vacuum oven at 50° C. to give the title compound as an HCl salt (0.0264 g, 0.059 mmol, 87% yield). $^1$H NMR (500 MHz, DMSO-d$_6$) δ ppm 10.16 (s, 1H), 9.00-8.82 (m, 2H), 6.53 (s, 1H), 4.32 (s, 2H), 3.41 (s, 1H), 3.12 (dd, J=16.0, 5.5 Hz, 1H), 3.00 (dq, J=12.0, 6.3 Hz, 2H), 2.83 (dt, J=16.9, 4.4 Hz, 1H), 2.74 (ddd, J=17.1, 11.4, 5.4 Hz, 1H), 2.60 (dd, J=16.1, 10.2 Hz, 1H), 2.24-2.18 (m, 1H), 1.89-1.44 (m, 9H), 1.20-1.05 (m, 2H); MS (APCI$^+$) m/z 412 [M+H]$^+$.

Example 80: 5-[2-(2-cyclohexylethyl)-8-fluoro-6-hydroxy-1,2,3,4-tetrahydroisoquinolin-7-yl]-1$\lambda^6$,2,5-thiadiazolidine-1,1,3-trione (Compound 179)

Example 80A: 5-[6-(benzyloxy)-2-(2-cyclohexylethyl)-8-fluoro-1,2,3,4-tetrahydroisoquinolin-7-yl]-1$\lambda^6$,2,5-thiadiazolidine-1,1,3-trione A suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate, the product of Example 54A (nominally 0.25 mmol, 1 equivalent), potassium carbonate (176 mg, 1.27 mmol, 5.0 equivalents), and (2-bromoethyl)cyclohexane (99 mg, 0.51 mmol, 2.0 equivalents) in acetonitrile (0.8 mL) was sealed in a 4 mL vial. The sealed vessel was placed in a heating block that had been preheated to 60° C. The reaction mixture was stirred for 18 hours at 60° C. and then cooled to 23° C. The cooled product mixture was filtered through a plug of diatomaceous earth (1.0 cm×0.5 cm). The filter cake was rinsed with acetonitrile (5×1.0 mL). The filtrates were combined, and the combined filtrates were concentrated. The residue obtained was used without further purification in the following step. MS (APCI$^+$) n/z 502 [M+H]$^+$.

Example 80B: 5-[2-(2-cyclohexylethyl)-8-fluoro-6-hydroxy-1,2,3,4-tetrahydroisoquinolin-7-yl]-1$\lambda^6$,2,5-thiadiazolidine-1,1,3-trione A solution of boron trichloride in dichloromethane (1.0 M, 2.5 mL, 2.5 mmol, 10.0 equivalents) was added slowly down the side of the flask to a suspension of the product of Example 80A (nominally 0.25 mmol, 1 equivalent) and pentamethylbenzene (113 mg, 0.76 mmol, 3.0 equivalents) in dichloromethane (1.3 mL) at −78° C. The reaction mixture was stirred for 15 minutes at −78° C. The reaction mixture was then placed in an ice bath at 0° C. and stirred for 1.5 hours at 0° C. The mixture was then slowly diluted with ethanol (0.8 mL) at −78° C. The diluted mixture was warmed over 30 minutes to 23° C. and concentrated. The residue obtained was triturated with heptanes (3×5 mL). The residue obtained was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (32 mg, 0.078 mmol, 31% yield, three steps). $^1$H NMR (400 MHz, DMSO-d$_6$) δ ppm 9.69 (bs, 1H), 6.58 (s, 1H), 4.57-3.94 (m, 2H), 3.78 (s, 2H), 3.28-3.14 (m, 4H), 3.00 (s, 2H), 1.75-1.57 (m, 7H), 1.38-1.07 (m, 4H), 1.00-0.89 (m, 2H); MS (APCI$^+$) m/z 412 [M+H]$^+$.

Example 81: 5-{1-fluoro-3-hydroxy-7-[(2-hydroxyethyl)amino]-5,6,7,8-tetrahydronaphthalen-2-yl}-1λ$^6$,2,5-thiadiazolidine-1,1,3-trione (Compound 180)

To a solution of the product of Example 67F (0.05 g, 0.124 mmol) in ethanol (1 mL) was added 2-aminoethyl isopropyl ether (0.019 g, 0.185 mmol). After 30 minutes, sodium cyanoborohydride (0.009 g, 0.148 mmol) was added as a solid. After 16 hours, the reaction mixture was quenched with ammonium hydroxide (0.014 mL, 0.742 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-[3-(benzyloxy)-1-fluoro-7-({2-[(propan-2-yl)oxy]ethyl}amino)-5,6,7,8-tetrahydronaphthalen-2-yl]-1λ$^6$,2,5-thiadiazolidine-1,1,3-trione (0.0390 g, 0.079 mmol, 64.2% yield). MS (APCI$^+$) m/z 492 [M+H]$^+$.

To a suspension of 5-[3-(benzyloxy)-1-fluoro-7-({2-[(propan-2-yl)oxy]ethyl}amino)-5,6,7,8-tetrahydronaphthalen-2-yl]-1λ$^6$,2,5-thiadiazolidine-1,1,3-trione (0.0390 g, 0.079 mmol) and pentamethylbenzene (0.024 g, 0.159 mmol) in dichloromethane (1.6 mL) at −78° C. was added a solution of boron trichloride (0.476 mL, 1 M in dichloromethane, 0.476 mmol) slowly along the side of the flask. The resulting mixture was stirred for 5 minutes, then warmed to an internal temperature of 0° C., and then was cooled to −78° C. and quenched with ethyl acetate (1 mL), followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), and then dried in a vacuum oven at 50° C. to give the title compound as an HCl salt (0.0262 g, 0.073 mmol, 92% yield). $^1$H NMR (400 MHz, DMSO-d$_6$) δ ppm 10.22 (s, 1H), 9.07-8.97 (m, 2H), 6.55 (s, 1H), 4.34 (s, 2H), 3.72 (t, J=5.2 Hz, 2H), 3.44 (s, 1H), 3.19-3.06 (m, 5H), 2.89-2.78 (m, 1H), 2.80-2.67 (m, 1H), 2.62 (dd, J=16.0, 10.4 Hz, 1H), 2.28-2.20 (m, 1H), 1.74 (qd, J=11.8, 5.4 Hz, 1H); MS (APCI$^+$) m/z 360 [M+H]$^+$.

Example 82: 5-{1-fluoro-3-hydroxy-7-[2-(propan-2-yl)morpholin-4-yl]-5,6,7,8-tetrahydronaphthalen-2-yl}-1λ$^6$,2,5-thiadiazolidine-1,1,3-trione (Compound 181)

To a solution of the product of Example 67F (0.05 g, 0.124 mmol) in ethanol (1 mL) was added 2-isopropylmorpholine (0.024 g, 0.185 mmol). After 30 minutes, sodium cyanoborohydride (0.009 g, 0.148 mmol) was added as a solid. After 16 hours, the reaction mixture was quenched with ammonium hydroxide (0.014 mL, 0.742 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-1-fluoro-7-[2-(propan-2-yl)morpholin-4-yl]-5,6,7,8-tetrahydronaphthalen-2-yl}-1λ$^6$,2,5-thiadiazolidine-1,1,3-trione (0.0321 g, 0.062 mmol, 50.2% yield). MS (APCI$^+$) m/z 518 [M+H]$^+$.

A suspension of 5-{3-(benzyloxy)-1-fluoro-7-[2-(propan-2-yl)morpholin-4-yl]-5,6,7,8-tetrahydronaphthalen-2-yl}-1λ$^6$,2,5-thiadiazolidine-1,1,3-trione (0.0321 g, 0.062 mmol) and 10% palladium hydroxide on carbon (0.064 g, 0.228 mmol, 50 weight % in water) in tetrahydrofuran (3 mL) was stirred for 22 hours under 100 psi of hydrogen. After filtration, Celite® (1 g) was added, and the mixture was concentrated in vacuo. The resultant mixture was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.0025 g, 0.00585 mmol, 9.4% yield). $^1$H NMR (400 MHz, DMSO-d$_6$) δ ppm 9.05 (br s, 1H), 7.15 (br s, 1H), 6.44 (s, 1H), 3.93 (s, 2H), 3.89 (d, J=9.4 Hz, 1H), 3.61-3.45 (m, 2H), 2.89-2.74 (m, 4H), 2.75-2.63 (m, 2H), 2.58-2.46 (m, 1H), 2.12-2.00 (m, 1H), 1.67 (q, J=6.9 Hz, 1H), 1.58 (s, 1H), 0.90 (d, J=6.8 Hz, 3H), 0.88 (d, J=6.7 Hz, 3H); MS (APCI$^+$) m/z 428 [M+H]$^+$.

Example 83: 5-{1-fluoro-3-hydroxy-7-[(2R)-2-(propan-2-yl)morpholin-4-yl]-5,6,7,8-tetrahydronaphthalen-2-yl}-1λ$^6$,2,5-thiadiazolidine-1,1,3-trione (Compound 182)

To a solution of the product of Example 67F (0.05 g, 0.124 mmol) in ethanol (1 mL) was added (R)-2-isopropylmorpholine (0.024 g, 0.185 mmol). After 30 minutes, sodium cyanoborohydride (0.009 g, 0.148 mmol) was added as a solid. After 16 hours, the reaction mixture was quenched with ammonium hydroxide (0.014 mL, 0.742 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-1-fluoro-7-[(2R)-2-(propan-2-yl)morpholin-4-yl]-5,6,7,8-tetrahydronaphthalen-2-yl}-1λ$^6$,2,5-thiadiazolidine-1,1,3-trione (0.027 g, 0.052 mmol, 42.3% yield). MS (APCI$^+$) m/z 518 [M+H]$^+$.

A suspension of 5-{3-(benzyloxy)-1-fluoro-7-[(2R)-2-(propan-2-yl)morpholin-4-yl]-5,6,7,8-tetrahydronaphthalen-2-yl}-1λ$^6$,2,5-thiadiazolidine-1,1,3-trione (0.0271 g, 0.052 mmol) and 10% palladium hydroxide on carbon (0.055 g, 0.196 mmol, 50 weight % in water) in a mixture of water (0.5 mL) and tetrahydrofuran (4 mL) was stirred for 20.5 hours under 113 psi of hydrogen. After filtration, Celite® (1 g) was added, and the mixture was concentrated in vacuo. The resultant mixture was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.011 g, 0.026 mmol, 49.1% yield). $^1$H NMR (400 MHz, DMSO-d$_6$) δ ppm 9.05

(br s, 1H), 7.15 (br s, 1H), 6.44 (s, 1H), 3.93 (s, 2H), 3.89 (d, J=9.4 Hz, 1H), 3.61-3.45 (m, 2H), 2.89-2.74 (m, 4H), 2.75-2.63 (m, 2H), 2.58-2.46 (m, 1H), 2.12-2.00 (m, 1H), 1.67 (q, J=6.9 Hz, 1H), 1.58 (s, 1H), 0.90 (d, J=6.8 Hz, 3H), 0.88 (d, J=6.7 Hz, 3H); MS (APCI$^+$) m/z 428 [M+H]$^+$.

Example 84: 5-{8-fluoro-6-hydroxy-2-[(pyrrolidin-2-yl)methyl]-1,2,3,4-tetrahydroisoquinolin-7-yl}-1$\lambda^6$,2,5-thiadiazolidine-1,1,3-trione (Compound 183)

Example 84A: 5-(8-fluoro-6-hydroxy-1,2,3,4-tetrahydroisoquinolin-7-yl)-1,2,5-thiadiazolidin-3-one 1,1-dioxide The product of Example 44H (200 mg, 0.41 mmol) and tetrahydrofuran (5 mL) were added to 10% Pd(OH)$_2$/C wet (114 mg, 0.41 mmol) in a 20 mL Barnstead Hast C reactor, and the mixture was stirred at 25° C. for 19 hours under 65 psi of hydrogen. Additional Pd/C (5%, wet JM #9) (400 mg, 1.75 mmol) was added, and the reaction mixture was stirred at 30° C. for an additional 19 hours under 65 psi of hydrogen. The mixture was filtered through a pad of diatomaceous earth, the volatiles were removed from the filtrate under reduced pressure, and the crude tert-butyl 8-fluoro-6-hydroxy-7-(1,1,4-trioxo-1$\lambda^6$,2,5-thiadiazolidin-2-yl)-3,4-dihydroisoquinoline-2(1H)-carboxylate was carried to the next step without purification. MS (APCI$^-$) m/z 400 [M−H]$^-$.

To a solution of the crude tert-butyl 8-fluoro-6-hydroxy-7-(1,1,4-trioxo-1$\lambda^6$,2,5-thiadiazolidin-2-yl)-3,4-dihydroisoquinoline-2(1H)-carboxylate in methylene chloride (3 mL) was added trifluoroacetic acid (3 mL). The reaction mixture was stirred for 1 hour at room temperature. The volatiles were removed under reduced pressure, and the residue was subjected to preparative HPLC [Phenomenex® Luna® C18 (2) 5 μm 100 Å AXIA™ column (250 mm×25 mm). 30-100% gradient of acetonitrile (A) and 0.1% trifluoroacetic acid in water (B) used over 15 minutes, at a flow rate of 25 mL/minute] to give a trifluoroacetic acid salt of the title compound (80 mg, 0.19 mmol, 47% yield over two steps). MS (APCI$^+$) m/z 302 [M+H]$^+$.

Example 84B: 5-{8-fluoro-6-hydroxy-2-[(pyrrolidin-2-yl)methyl]-1,2,3,4-tetrahydroisoquinolin-7-yl}-1$\lambda^6$,2,5-thiadiazolidine-1,1,3-trione The trifluoroacetic acid salt of the product of Example 84A (40 mg, 0.096 mmol) was dissolved in N,N-dimethylformamide (2 mL) followed by addition of sodium carbonate (28.1 mg, 0.266 mmol). After stirring for 5 minutes, tert-butyl 2-formylpyrrolidine-1-carboxylate (52.9 mg, 0.266 mmol) and acetic acid (0.038 mL, 0.664 mmol) were added and the mixture was stirred for 5 minutes at room temperature. Sodium cyanoborohydride (25.0 mg, 0.4 mmol) was then added, and the mixture was stirred at room temperature overnight. The volatiles were removed under reduced pressure and the crude tert-butyl 2-{[8-fluoro-6-hydroxy-7-(1,1,4-trioxo-1$\lambda^6$,2,5-thiadiazolidin-2-yl)-3,4-dihydroisoquinolin-2(1H)-yl]methyl}pyrrolidine-1-carboxylate was subjected to the next step without purification. MS (APCI$^-$) m/z 483 [M−H]$^-$.

To a solution of the crude tert-butyl 2-{[8-fluoro-6-hydroxy-7-(1,1,4-trioxo-1$\lambda^6$,2,5-thiadiazolidin-2-yl)-3,4-dihydroisoquinolin-2(1H)-yl]methyl}pyrrolidine-1-carboxylate in methylene chloride (3 mL) was added trifluoroacetic acid (3 mL). The reaction mixture was stirred for 1 hour at room temperature. The volatiles were removed under reduced pressure, and the residue was subjected to preparative HPLC [Phenomenex® Luna C18(2) 5 μm 100 Å AXIA™ column (250 mm×25 mm). 30-100% gradient of acetonitrile (A) and 0.1% trifluoroacetic acid in water (B) used over 15 minutes, at a flow rate of 25 mL/minute] to give the title compound as a trifluoroacetic acid salt (28 mg, 0.056 mmol, 58% yield over two steps). $^1$H NMR (400 MHz, DMSO-d$_6$) δ ppm 9.15 (s, 1H), 6.63 (s, 1H), 4.31-4.27 (m, 1H), 4.26 (s, 2H), 4.19-4.11 (m, 1H), 4.10-4.01 (m, 1H), 3.47-3.32 (m, 4H), 3.28-3.22 (m, 2H), 3.02 (t, J=6.1 Hz, 2H), 2.26-2.13 (m, 1H), 2.05-1.81 (m, 2H), 1.66 (dq, J=12.9, 8.4 Hz, 1H); MS (APCI$^+$) m/z 385 [M+H]$^+$.

Example 85: 5-{8-fluoro-6-hydroxy-2-[(pyridin-2-yl)methyl]-1,2,3,4-tetrahydroisoquinolin-7-yl}-1$\lambda^6$,2,5-thiadiazolidine-1,1,3-trione (Compound 184)

The trifluoroacetic acid salt of the product of Example 84A (40 mg, 0.096 mmol) was dissolved in N,N-dimethylformamide (2 mL) followed by addition of sodium carbonate (28.1 mg, 0.266 mmol). After stirring for 5 minutes, 2-pyridinecarboxaldehyde (28.4 mg, 0.266 mmol) and acetic acid (0.038 mL, 0.66 mmol) were added, and the mixture was stirred for 5 minutes at room temperature. Sodium cyanoborohydride (25.0 mg, 0.4 mmol) was then added. The mixture was stirred at room temperature for two hours. The volatiles were removed under reduced pressure, and the residue was subjected to preparative HPLC [Phenomenex® Luna® C18(2) 5 μm 100 Å AXIA™ column (250 mm×25 mm). 30-100% gradient of acetonitrile (A) and 0.1% trifluoroacetic acid in water (B) used over 15 minutes, at a flow rate of 25 mL/minute] to give the title compound as a trifluoroacetic acid salt (21 mg, 0.039 mmol, 41% yield). $^1$H NMR (500 MHz, DMSO-d$_6$) δ ppm 10.30 (s, 1H), 8.72 (ddd, J=4.8, 1.8, 0.9 Hz, 1H), 7.97 (td, J=7.7, 1.8 Hz, 1H), 7.60 (dt, J=7.8, 1.1 Hz, 1H), 7.52 (ddd, J=7.7, 4.9, 1.2 Hz, 1H), 6.64-6.60 (m, 1H), 4.66 (s, 2H), 4.38 (s, 2H), 4.22 (s, 2H), 3.52 (t, J=6.2 Hz, 2H), 3.05 (t, J=6.3 Hz, 2H); MS (APCI$^+$) m/z 393 [M+H]$^+$.

Example 86: 5-{7-[(2-cyclobutylethyl)amino]-1-fluoro-3-hydroxy-5,6,7,8-tetrahydronaphthalen-2-yl}-1$\lambda^6$,2,5-thiadiazolidine-1,1,3-trione (Compound 185)

To a solution of the product of Example 67F (0.05 g, 0.124 mmol) in ethanol (1 mL) was added 2-cyclobutylethan-1-amine (0.018 g, 0.185 mmol). After 30 minutes, sodium cyanoborohydride (0.009 g, 0.148 mmol) was added as a solid. After 16 hours, the reaction mixture was quenched with ammonium hydroxide (0.014 mL, 0.742 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-7-[(2-cyclobutylethyl)amino]-1-fluoro-5,6,7,8-tetrahydronaphthalen-2-yl}-1$\lambda^6$,2,5-thiadiazolidine-1,1,3-trione (0.0378 g, 0.078 mmol, 62.7% yield). MS (APCI$^+$) m/z 488 [M+H]$^+$.

To a suspension of 5-{3-(benzyloxy)-7-[(2-cyclobutylethyl)amino]-1-fluoro-5,6,7,8-tetrahydronaphthalen-2-yl}-1$\lambda^6$,2,5-thiadiazolidine-1,1,3-trione (0.0378 g, 0.078 mmol) and pentamethylbenzene (0.023 g, 0.155 mmol) in dichloromethane (1.6 mL) at −78° C. was added a solution of boron trichloride (0.465 mL, 0.465 mmol, 1 M in dichloromethane) slowly along the side of the flask. The resulting mixture was stirred for 5 minutes, then warmed to an internal temperature of 0° C., and then was cooled to −78° C. and quenched with ethyl acetate (1 mL), followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), and then dried in a vacuum oven at 50° C. to give the title compound as an HCl salt (0.0320 g, 0.074 mmol, 95% yield). $^1$H NMR (400 MHz, DMSO-d$_6$) δ ppm 10.16 (s, 1H), 8.99-8.82 (m, 2H), 6.53 (s, 1H), 4.32 (s, 2H), 3.43-3.35 (m, 1H), 3.11 (dd, J=16.0, 5.5 Hz, 1H), 2.94-2.84 (m, 2H), 2.83-2.65 (m, 2H), 2.60 (dd, J=16.1, 10.1 Hz, 1H), 2.32 (h, J=7.7 Hz, 1H), 2.24-2.16 (m, 1H), 2.12-1.96 (m, 3H), 1.93-1.57 (m, 7H); MS (APCI$^+$) m/z 398 [M+H]$^+$.

Example 87: 5-[1-fluoro-3-hydroxy-7-({2-[(propan-2-yl)oxy]ethyl}amino)-5,6,7,8-tetrahydronaphthalen-2-yl]-1λ$^6$,2,5-thiadiazolidine-1,1,3-trione (Compound 186)

To a solution of the product of Example 67F (0.05 g, 0.124 mmol) in ethanol (1 mL) was added 2-aminoethyl isopropyl ether (0.019 g, 0.185 mmol). After 30 minutes, sodium cyanoborohydride (0.009 g, 0.148 mmol) was added as a solid. After 16 hours, the reaction mixture was quenched with ammonium hydroxide (0.014 mL, 0.742 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-[3-(benzyloxy)-1-fluoro-7-({2-[(propan-2-yl)oxy]ethyl}amino)-5,6,7,8-tetrahydronaphthalen-2-yl]-1λ$^6$,2,5-thiadiazolidine-1,1,3-trione (0.0426 g, 0.087 mmol, 70.1% yield). MS (APCI$^+$) m/z 492 [M+H]$^+$.

A suspension of 5-[3-(benzyloxy)-1-fluoro-7-({2-[(propan-2-yl)oxy]ethyl}amino)-5,6,7,8-tetrahydronaphthalen-2-yl]-1λ$^6$,2,5-thiadiazolidine-1,1,3-trione (0.0426 g, 0.087 mmol) and 10% palladium hydroxide on carbon (0.085 g, 0.303 mmol, 50 weight % in water) in a mixture of water (0.5 mL) and tetrahydrofuran (5 mL) was stirred for 20.5 hours under 160 psi of hydrogen. After filtration, Celite® (1 g) was added and the mixture was concentrated in vacuo. The resultant mixture was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.0204 g, 0.051 mmol, 58.6% yield). $^1$H NMR (500 MHz, DMSO-d$_6$) δ ppm 9.24 (s, 1H), 8.36 (br s, 2H), 6.46 (s, 1H), 3.93 (d, J=1.8 Hz, 2H), 3.62 (dt, J=8.4, 5.7 Hz, 3H), 3.43-3.34 (m, 1H), 3.18 (q, J=5.0 Hz, 2H), 3.08 (dd, J=15.8, 5.4 Hz, 1H), 2.80 (dt, J=17.1, 4.4 Hz, 1H), 2.71 (ddd, J=17.2, 11.5, 5.5 Hz, 1H), 2.57-2.50 (m, 1H), 2.16 (dd, J=11.0, 5.1 Hz, 1H), 1.68 (qd, J=11.7, 5.3 Hz, 1H), 1.14 (d, J=6.1 Hz, 6H); MS (APCI$^+$) m/z 402 [M+H]$^+$.

Example 88: 5-{1-fluoro-3-hydroxy-7-[(2-hydroxy-3-methylbutyl)amino]-5,6,7,8-tetrahydronaphthalen-2-yl}-1λ$^6$,2,5-thiadiazolidine-1,1,3-trione (Compound 187)

To a solution of the product of Example 67F (0.1 g, 0.247 mmol) in ethanol (2 mL) was added 1-amino-3-methylbutan-2-ol (0.038 g, 0.371 mmol). After 30 minutes, sodium cyanoborohydride (0.019 g, 0.297 mmol) was added as a solid. After 16 hours, the reaction mixture was quenched with ammonium hydroxide (0.028 mL, 1.484 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-1-fluoro-7-[(2-hydroxy-3-methylbutyl)amino]-5,6,7,8-tetrahydronaphthalen-2-yl}-1λ$^6$,2,5-thiadiazolidine-1,1,3-trione (0.0583 g, 0.119 mmol, 48% yield). MS (APCI$^+$) m/z 492 [M+H]$^+$.

A suspension of 5-{3-(benzyloxy)-1-fluoro-7-[(2-hydroxy-3-methylbutyl)amino]-5,6,7,8-tetrahydronaphthalen-2-yl}-1λ$^6$,2,5-thiadiazolidine-1,1,3-trione (0.0583 g, 0.119 mmol) and 5% palladium hydroxide on carbon (0.0201 g, 0.084 mmol, 44.4 weight % in water) in a mixture of N,N-dimethylformamide (0.5 mL), tetrahydrofuran (2 mL) and water (0.5 mL) was stirred for 18 hours under 50 psi of hydrogen. After filtration, Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0324 g, 0.081 mmol, 68.1% yield). $^1$H NMR (400 MHz, DMSO-d$_6$) δ ppm 9.22 (br s, 1H), 8.48 (br s, 2H), 6.46 (s, 1H), 5.28 (br s, 1H), 3.94 (s, 2H), 3.57-3.49 (m, 2H), 3.45-3.35 (m, 1H), 3.20-3.05 (m, 2H), 2.96-2.65 (m, 3H), 2.66-2.50 (m, 1H), 2.20 (dd, J=29.2, 12.1 Hz, 1H), 1.81-1.60 (m, 2H), 0.91 (d, J=2.8 Hz, 3H), 0.89 (d, J=2.9 Hz, 3H); MS (APCI$^+$) m/z 402 [M+H]$^+$.

Example 89: 5-{7-[(2-cyclopropyl-2-hydroxyethyl)amino]-1-fluoro-3-hydroxy-5,6,7,8-tetrahydronaphthalen-2-yl}-1λ$^6$,2,5-thiadiazolidine-1,1,3-trione (Compound 188)

To a solution of the product of Example 67F (0.1 g, 0.247 mmol) in ethanol (2 mL) was added 2-amino-1-cyclopropylethan-1-ol (0.038 g, 0.371 mmol). After 30 minutes, sodium cyanoborohydride (0.019 g, 0.297 mmol) was added as a solid. After 16 hours, the reaction mixture was quenched with ammonium hydroxide (0.028 mL, 1.484 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-{3-(benzyloxy)-7-[(2-cyclopropyl-2-hydroxyethyl)amino]-1-fluoro-5,6,7,8-tetrahydronaphthalen-2-yl}-1λ$^6$,2,5-thiadiazolidine-1,1,3-trione (0.0909 g, 0.186 mmol, 75% yield). MS (APCI$^+$) m/z 490 [M+H]$^+$.

A suspension of 5-{3-(benzyloxy)-7-[(2-cyclopropyl-2-hydroxyethyl)amino]-1-fluoro-5,6,7,8-tetrahydronaphthalen-2-yl}-1λ$^6$,2,5-thiadiazolidine-1,1,3-trione (0.0909 g, 0.186 mmol) and 5% palladium hydroxide on carbon (0.030 g, 0.125 mmol, 44.4 weight % in water) in a mixture of N,N-dimethylformamide (1 mL) and tetrahydrofuran (2 mL) was stirred for 18 hours under 50 psi of hydrogen. After filtration, Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0230 g, 0.058 mmol, 31% yield). $^1$H NMR (500 MHz, DMSO-$d_6$) δ ppm 9.24 (s, 1H), 8.53 (s, 2H), 6.46 (s, 1H), 5.47 (d, J=5.1 Hz, 1H), 3.99-3.88 (m, 2H), 3.52-3.36 (m, 2H), 3.25-2.98 (m, 5H), 2.88-2.67 (m, 1H), 2.62-2.52 (m, 1H), 2.23 (d, J=12.0 Hz, 1H), 2.16 (d, J=12.6 Hz, 1H), 1.84-1.54 (m, 1H), 0.95-0.84 (m, 1H), 0.51-0.41 (m, 2H), 0.35 (ddt, J=8.8, 4.9, 1.8 Hz, 1H), 0.32-0.22 (m, 1H); MS (APCI$^+$) m/z 400 [M+H]$^+$.

Example 90: 5-(1-fluoro-3-hydroxy-7-{[3-(trimethylsilyl)propyl]amino}-5,6,7,8-tetrahydronaphthalen-2-yl)-1λ$^6$,2,5-thiadiazolidine-1,1,3-trione (Compound 189)

To a solution of the product of Example 67F (0.1 g, 0.247 mmol) in ethanol (2 mL) was added (3-aminopropyl)trimethylsilane (0.049 g, 0.371 mmol). After 30 minutes, sodium cyanoborohydride (0.019 g, 0.297 mmol) was added as a solid. After 16 hours, the reaction mixture was quenched with ammonium hydroxide (0.028 mL, 1.484 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-[3-(benzyloxy)-1-fluoro-7-{[3-(trimethyl silyl)propyl]amino}-5,6,7,8-tetrahydronaphthalen-2-yl]-1λ$^6$,2,5-thiadiazolidine-1,1,3-trione (0.0917 g, 0.176 mmol, 71.4% yield). MS (APCI$^+$) m/z 520 [M+H]$^+$.

A suspension of 5-[3-(benzyloxy)-1-fluoro-7-{[3-(trimethylsilyl)propyl]amino}-5,6,7,8-tetrahydronaphthalen-2-yl]-1λ$^6$,2,5-thiadiazolidine-1,1,3-trione (0.0917 g, 0.176 mmol) and 5% palladium hydroxide on carbon (0.049 g, 0.204 mmol, 44.4 weight % in water) in a mixture of N,N-dimethylformamide (1 mL) and tetrahydrofuran (2 mL) was stirred for 18 hours under 50 psi of hydrogen. After filtration, Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0271 g, 0.063 mmol, 35.8% yield). $^1$H NMR (500 MHz, DMSO-$d_6$) δ ppm 9.22 (s, 1H), 8.36 (s, 2H), 6.49-6.44 (m, 1H), 3.93 (s, 2H), 3.56-3.35 (m, 1H), 3.08 (dd, J=16.1, 5.5 Hz, 1H), 3.00 (dd, J=8.9, 6.7 Hz, 2H), 2.85-2.66 (m, 2H), 2.60-2.46 (m, 1H), 2.18-2.10 (m, 1H), 1.75-1.53 (m, 3H), 0.59-0.50 (m, 2H), 0.02 (s, 9H); MS (APCI$^+$) m/z 430 [M+H]$^+$.

Example 91: 5-[1-fluoro-3-hydroxy-7-({3-[hydroxy(dimethyl)silyl]propyl}amino)-5,6,7,8-tetrahydronaphthalen-2-yl]-1λ$^6$,2,5-thiadiazolidine-1,1,3-trione (Compound 190)

To a solution of the product of Example 67F (0.1 g, 0.247 mmol) in ethanol (2 mL) was added 3-(ethoxydimethylsilyl)propylamine (0.060 g, 0.371 mmol). After 30 minutes sodium cyanoborohydride (0.019 g, 0.297 mmol) was added as a solid. After 16 hours, the reaction mixture was quenched with ammonium hydroxide (0.028 mL, 1.484 mmol), and then diluted with acetonitrile (2 mL) and water (1 mL). Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-[3-(benzyloxy)-1-fluoro-7-({3-[hydroxy(dimethyl)silyl]propyl}amino)-5,6,7,8-tetrahydronaphthalen-2-yl]-1λ$^6$,2,5-thiadiazolidine-1,1,3-trione (0.0419 g, 0.080 mmol, 16.9% yield). MS (APCI$^+$) m/z 522 [M+H]$^+$.

A suspension of 5-[3-(benzyloxy)-1-fluoro-7-({3-[hydroxy(dimethyl)silyl]propyl}amino)-5,6,7,8-tetrahydronaphthalen-2-yl]1λ$^6$,2,5-thiadiazolidine-1,1,3-trione (0.0419 g, 0.080 mmol) and 5% palladium hydroxide on carbon (0.0143 g, 0.060 mmol, 44.4 weight % in water) in a mixture of N,N-dimethylformamide (2 mL) and tetrahydrofuran (2 mL) was stirred for 18 hours under 50 psi of hydrogen. After filtration, Celite® (1 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0205 g, 0.048 mmol, 59.1% yield). $^1$H NMR (400 MHz, DMSO-$d_6$) δ ppm 9.92 (br s, 1H), 8.91 (br s, 2H), 6.51 (s, 1H), 4.22 (s, 2H), 3.42 (br s, 1H), 3.12 (dd, J=15.6, 5.5 Hz, 1H), 3.06-2.94 (m, 2H), 2.91-2.71 (m, 1H), 2.62 (dd, J=16.1, 10.1 Hz, 1H), 2.27-2.15 (m, 1H), 1.78-1.65 (m, 3H), 0.63-0.54 (m, 2H), 0.10 (s, 6H); MS (APCI$^+$) m/z 432 [M+H]$^+$.

Example 92: 5-[8-fluoro-6-hydroxy-2-(pyridin-2-yl)-1,2,3,4-tetrahydroisoquinolin-7-yl]-1λ$^6$,2,5-thiadiazolidine-1,1,3-trione (Compound 191)

Example 92A: 5-[6-(benzyloxy)-8-fluoro-2-(pyridin-2-yl)-1,2,3,4-tetrahydroisoquinolin-7-yl]-1λ$^6$,2,5-thiadiazolidine-1,1,3-trione A solution of n-butyllithium in hexanes (2.3 M, 0.24 mL, 0.55 mmol, 2.2 equivalents) was added dropwise to a suspension of 5-[6-(benzyloxy)-8-fluoro-1,2,3,4-tetrahydroisoquinolin-7-yl]-1λ$^6$,2,5-thiadiazolidine-1,1,3-trione, trifluoroacetate, the product of Example 54A (nominally 0.25 mmol, 1 equivalent) in tetrahydrofuran (1.5 mL) at 0° C. The reaction vessel was immediately removed from the cooling bath and the mixture was stirred for 10 minutes at 23° C. 2-Fluoropyridine (0.03 mL, 0.35 mmol, 1.4 equivalents) was added to the reaction mixture at 23° C. and the resultant mixture was stirred for 30 minutes at 23° C. The reaction vessel was then sealed, and the sealed vessel was placed in a heating block that had been preheated to 60° C. The reaction mixture was stirred for 19 hours at 60° C. Liquid chromatography-mass spectrometric analysis of the reaction mixture indicated no reaction had occurred. The reaction mixture was concentrated. The residue obtained was dissolved in dimethyl sulfoxide (0.6 mL). Additional 2-fluoropyridine (0.06 mL, 0.70 mmol, 2.8 equivalents) was added at 23° C. The reaction vessel was sealed, and the sealed vessel was placed in a heating block that had been preheated to 100° C. The reaction mixture was stirred for 20 hours at 100° C. and then cooled to 23° C. Additional 2-fluoropyridine (0.06 mL, 0.70 mmol, 2.8 equivalents) and N,N-diisopropylethylamine (0.13 mL, 0.76 mmol, 3.0 equivalents) were added at 23° C. The reaction vessel was sealed, and the sealed vessel was placed in a heating block that had been preheated to 100° C. The reaction mixture was stirred for 26 hours at 100° C. and then cooled to 23° C. The mixture was diluted with aqueous ammonium hydroxide solution (30% w/v, 1.0 mL) and the diluted mixture was purified by reversed-phase flash column chromatography (100 g RediSep Rf Gold® C18 column, elution with a gradient from 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute). The fractions containing product were collected and concentrated (~63 mg). The residue obtained was used in the following step without further purification. MS (APCI$^+$) m/z 469 [M+H]$^+$.

Example 92B: 5-[8-fluoro-6-hydroxy-2-(pyridin-2-yl)-1,2,3,4-tetrahydroisoquinolin-7-yl]-1$\lambda^6$,2,5-thiadiazolidine-1,1,3-trione A solution of boron trichloride in dichloromethane (1.0 M, 0.80 mL, 0.80 mmol, 5.95 equivalents) was added to a suspension of the product of Example 92A (nominally 63 mg, 0.13 mmol, 1 equivalent) and pentamethylbezene (51 mg, 0.34 mmol, 2.6 equivalents) in dichloromethane (1.0 mL) at −78° C. The reaction mixture was stirred for 2 minutes at −78° C. The reaction vessel was then removed from the cooling bath and placed in an ice bath at 0° C. The reaction mixture was stirred for 20 minutes at 0° C. The product mixture was then cooled over 10 minutes to −78° C. and diluted with ethanol (1.5 mL). The diluted mixture was concentrated under a stream of nitrogen. The residue obtained was triturated with heptanes (2×3.0 mL). The residue obtained was dissolved in 25% methanol-acetonitrile (v/v, 7.0 mL) and ethyl acetate (~4 mL) was slowly added. A suspension resulted. The mother liquor was decanted, and the residue obtained was triturated with 15% ethyl acetate-40% pentane-45% acetonitrile mixture (v/v/v, 5 mL) to furnish the title compound (12 mg, 0.032 mmol, 24% yield). $^1$H NMR (400 MHz, DMSO-d$_6$) δ ppm 10.13 (bs, 1H), 8.08 (dd, J=5.9, 1.9 Hz, 1H), 7.91 (s, 1H), 6.89 (t, J=6.7 Hz, 1H), 6.67 (s, 1H), 4.67 (s, 2H), 4.23 (s, 2H) 3.84 (t, J=5.8 Hz, 1H), 2.90 (t, J=5.8 Hz, 1H); MS (APCI$^+$) m/z 379 [M+H]$^+$.

Example 93: 5-{2-[2-(3,3-difluorocyclobutyl)ethyl]-8-fluoro-6-hydroxy-1,2,3,4-tetrahydroisoquinolin-7-yl}-1$\lambda^6$,2,5-thiadiazolidine-1,1,3-trione (Compound 192)

Example 93A: 5-[6-(benzyloxy)-8-fluoro-1,2,3,4-tetrahydroisoquinolin-7-yl]-1$\lambda^6$,2,5-thiadiazolidine-1,1,3-trione, Trifluoroacetic Acid Salt A vial containing a suspension of tert-butyl 6-(benzyloxy)-8-fluoro-7-(1,1,4-trioxo-1$\lambda^6$,2,5-thiadiazolidin-2-yl)-3,4-dihydroisoquinoline-2(1H)-carboxylate (0.125 g, 0.254 mmol, Example 44H) in dichloromethane (0.85 mL) was cooled to 0° C. Then 2,2,2-trifluoroacetic acid (0.20 mL, 2.5 mmol) was added dropwise and the cooling bath was subsequently removed. After 3 hours, the reaction mixture was concentrated under reduced pressure. The residue was azeotroped with toluene (3×3 mL) to give the title compound. This material was used without further purification. MS (APCI$^+$) m/z 433.4 [M+CH$_3$CN+H]$^+$.

Example 93B: 5-{6-(benzyloxy)-2-[2-(3,3-difluorocyclobutyl)ethyl]-8-fluoro-1,2,3,4-tetrahydroisoquinolin-7-yl}-1$\lambda^6$,2,5-thiadiazolidine-1,1,3-trione To a vial containing 5-[6-(benzyloxy)-8-fluoro-1,2,3,4-tetrahydroisoquinolin-7-yl]-1$\lambda^6$,2,5-thiadiazolidine-1,1,3-trione trifluoroacetate (theoretically 0.254 mmol, Example 93A) were added potassium carbonate (0.176 g, 1.27 mmol) and acetonitrile (0.64 mL). Next, a solution of 2-(3,3-difluorocyclobutyl)ethyl 4-methylbenzenesulfonate (0.111 g, 0.381 mmol, Example 93D) in a minimum volume of acetonitrile (approximately 0.050 mL) was added. The vial was capped, and the mixture was heated to 60° C. After 18 hours, the reaction mixture was cooled to ambient temperature and filtered over a thin pad of diatomaceous earth. The filtrate was concentrated under reduced pressure and purified using silica gel chromatography [4 g column, 0-20% gradient of methanol in dichloromethane, then 50% methanol in dichloromethane] to give the title compound (0.073 g, 0.14 mmol, 56% yield over two steps). MS (APCI$^+$) m/z 510.5 [M+H]$^+$.

Example 93C: 5-{2-[2-(3,3-difluorocyclobutyl)ethyl]-8-fluoro-6-hydroxy-1,2,3,4-tetrahydroisoquinolin-7-yl}-1$\lambda^6$,2,5-thiadiazolidine-1,1,3-trione To a 20 mL Barnstead Hast C reactor containing 10% palladium hydroxide on carbon (0.140 g, 0.498 mmol) were added 55-{6-(benzyloxy)-2-[2-(3,3-difluorocyclobutyl)ethyl]-8-fluoro-1,2,3,4-tetrahydroisoquinolin-7-yl}-1$\lambda^6$,2,5-thiadiazolidine-1,1,3-trione (0.071 g, 0.14 mmol, Example 93B) and tetrahydrofuran (6 mL). The resulting mixture was stirred at ambient temperature for 21.2 hours under an atmosphere of hydrogen at >160 psi. The catalyst was then removed by filtration and washed with methanol. The filtrate was concentrated under reduced pressure and purified using reversed-phase preparative HPLC [Waters XBridge™ RP18 column, m, 30×100 mm, flow rate 40 mL/minute, 5-70% gradient of methanol in water (buffered with 0.025 M aqueous ammonium bicarbonate, adjusted to pH 10 with ammonium hydroxide)]. Product-containing fractions were combined and concentrated under reduced pressure. The residue was passed through an SCX-2 cartridge (loaded and eluted initially with methanol/dichloromethane(1:1) and then eluted with a 2 M solution of ammonia in methanol) to give the title compound (0.018 g, 0.043 mmol, 31% yield). $^1$H NMR (400 MHz, DMSO-d$_6$) δ ppm 9.37 (br s, 1H), 7.07 (br s, 1H), 6.48 (s, 1H), 3.91 (s, 2H), 3.80 (br s, 2H), 2.98 (br s, 2H), 2.84-2.75 (br m, 4H), 2.71-2.57 (m, 2H), 2.37-2.16 (m, 2H), 2.16-1.98 (m, 1H), 1.79 (q, J=7.6 Hz, 2H); MS (APCI$^+$) m/z 420.3 [M+H]$^+$.

Example 93D: 2-(3,3-difluorocyclobutyl)ethyl 4-methylbenzenesulfonate

A vial containing a solution of 2-(3,3-difluorocyclobutyl) ethanol (0.340 g, 2.50 mmol) and triethylamine (0.45 mL, 3.2 mmol) in dichloromethane (12.5 mL) was cooled to 0° C. Then 4-methylbenzenesulfonic anhydride (0.978 g, 3.00 mmol) was added in one portion and the cooling bath was subsequently removed. After 18 hours, the reaction mixture was concentrated under reduced pressure. The residue was suspended in diethyl ether (100 mL) and washed sequentially with 1 M hydrochloric acid (75 mL), saturated aqueous sodium bicarbonate (75 mL), and brine. The organic phase was then dried over magnesium sulfate and concentrated under reduced pressure. The residue was purified using silica gel chromatography [4 g column, 0-50% gradient of ethyl acetate in heptanes, then 100% ethyl acetate] to afford 2-(3,3-difluorocyclobutyl)ethyl 4-methylbenzenesulfonate (0.595 g, 2.05 mmol, 82% yield). $^1$H NMR (500 MHz, CDCl$_3$) δ ppm 7.83-7.75 (m, 2H), 7.39-7.33 (m, 2H), 4.01 (t, J=6.1 Hz, 2H), 2.69-2.55 (m, 2H), 2.46 (s, 3H), 2.24-2.05 (m, 3H), 1.88-1.80 (m, 2H).

Example 94: 5-{8-fluoro-6-hydroxy-2-[2-(pyrrolidin-1-yl)ethyl]-1,2,3,4-tetrahydroisoquinolin-7-yl}-1λ$^6$,2,5-thiadiazolidine-1,1,3-trione (Compound 193)

Example 94A: 5-{6-(benzyloxy)-8-fluoro-2-[2-(pyrrolidin-1-yl)ethyl]-1,2,3,4-tetrahydroisoquinolin-7-yl}-1λ$^6$,2,5-thiadiazolidine-1,1,3-trione To a vial containing 5-[6-(benzyloxy)-8-fluoro-1,2,3,4-tetrahydroisoquinolin-7-yl]-1λ$^6$,2,5-thiadiazolidine-1,1,3-trione, trifluoroacetic acid salt (theoretically 0.254 mmol, Example 93A) were added acetonitrile (0.85 mL), potassium carbonate (0.176 g, 1.27 mmol), and 1-(2-bromoethyl)pyrrolidine hydrobromide (0.099 g, 0.38 mmol). The vial was capped, and the mixture was heated to 60° C. After 22 hours, a second portion of 1-(2-bromoethyl)pyrrolidine hydrobromide (0.099 g, 0.38 mmol) was added. After 42 hours total reaction time, the mixture was cooled to ambient temperature, filtered over diatomaceous earth, and concentrated under reduced pressure. The residue was partially purified using silica gel chromatography [4 g column, 0-40% gradient of methanol (containing 1% ammonium hydroxide) in dichloromethane] to give the title compound (0.066 g, 0.14 mmol) along with some impurities. This material was used without further purification. MS (APCI$^+$) m/z 488.4 [M+H]$^+$.

Example 94B: 5-{8-fluoro-6-hydroxy-2-[2-(pyrrolidin-1-yl)ethyl]-1,2,3,4-tetrahydroisoquinolin-7-yl}-1λ$^6$,2,5-thiadiazolidine-1,1,3-trione To a 20 mL Barnstead Hast C reactor containing 10% palladium hydroxide on carbon (0.120 g, 0.427 mmol) were added impure 5-{6-(benzyloxy)-8-fluoro-2-[2-(pyrrolidin-1-yl)ethyl]-1,2,3,4-tetrahydroisoquinolin-7-yl}-1λ$^6$,2,5-thiadiazolidine-1,1,3-trione (0.066 g, 0.14 mmol) and tetrahydrofuran (2 mL). The resulting mixture was stirred at ambient temperature for 20.6 hours under an atmosphere of hydrogen at 110 psi. The catalyst was then removed by filtration and washed with methanol. The filtrate was concentrated under reduced pressure and purified using reversed-phase preparative HPLC [Waters XBridge™ RP18 column, 5 μm, 30×100 mm, flow rate 40 mL/minute, 5-70% gradient of methanol in water (buffered with 0.025 M aqueous ammonium bicarbonate, adjusted to pH 10 with ammonium hydroxide)]. Product-containing fractions were combined and concentrated under reduced pressure. The residue was passed through an SCX-2 cartridge (loaded and eluted initially with methanol/dichloromethane(1:1) and then eluted with a 2 M solution of ammonia in methanol) to give the title compound (9.0 mg, 0.020 mmol, 8% yield over three steps) with a purity of approximately 90%, as determined by $^1$H NMR analysis. $^1$H NMR (500 MHz, DMSO-d$_6$) δ ppm 9.25 (s, 1H), 6.47 (s, 1H), 3.95 (s, 2H), 3.55 (s, 2H), 3.35 (t, J=5.8 Hz, 2H), 3.27 (t, J=6.7 Hz, 4H), 2.78 (2 overlapping multiplets, 4H), 2.71 (t, J=5.8 Hz, 2H), 1.96-1.88 (m, 4H); MS (APCI$^+$) m/z 399.4 [M+H]$^+$.

Example 95: 5-{2-[2-(3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione (Compound 194)

Example 95A: 5-{6-(benzyloxy)-2-[2-(3,5-dimethyl-1H-pyrazol-4-yl)ethyl]-8-fluoro-1,2,3,4-tetrahydroisoquinolin-7-yl}-1λ$^6$,2,5-thiadiazolidine-1,1,3-trione To a vial containing 5-[6-(benzyloxy)-8-fluoro-1,2,3,4-tetrahydroisoquinolin-7-yl]-1λ$^6$,2,5-thiadiazolidine-1,1,3-trione, trifluoroacetic acid salt (theoretically 0.407 mmol, Example 93A) were added acetonitrile (1.0 mL), potassium carbonate (0.281 g, 2.04 mmol), and 4-(2-bromoethyl)-3,5-dimethyl-1H-pyrazole (0.124 g, 0.611 mmol). The vial was capped, and the mixture was heated to 60° C. After 14 hours, a second portion of 4-(2-bromoethyl)-3,5-dimethyl-1H-pyrazole (0.124 g, 0.611 mmol) was added along with more potassium carbonate (0.141 g, 1.02 mmol). After 62 hours total reaction time, the reaction mixture was cooled to ambient temperature, diluted with dichloromethane, and filtered over diatomaceous earth. The filtrate was concentrated under reduced pressure. The residue was first purified using silica gel chromatography [12 g column, 0-50% gradient of methanol in dichloromethane] and then using reversed-phase chromatography [12 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.070 g, 0.14 mmol, 34% yield over two steps). $^1$H NMR (400 MHz, DMSO-d$_6$) δ ppm 12.01 (br s, 1H), 7.51 (dd, J=8.1, 6.4 Hz, 2H), 7.40-7.26 (2 overlapped multiplets, 3H), 6.88 (s, 1H), 5.16 (s, 2H), 4.29 (s, 2H), 3.97 (s, 2H), 3.43 (br s, 2H), 3.12 (t, J=8.4 Hz, 2H), 3.04 (t, J=6.1 Hz, 2H), 2.77 (dd, J=10.5, 6.3 Hz, 2H), 2.14 (s, 6H); MS (APCI$^+$) m/z 514.4 [M+H]$^+$.

Example 95B: 5-{2-[2-(3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione To a 20 mL Barnstead Hast C reactor containing 10% palladium hydroxide on carbon (0.037 g, 0.13 mmol) were added 5-{6-(benzyloxy)-2-[2-(3,5-dimethyl-1H-pyrazol-4-yl)ethyl]-8-fluoro-1,2,3,4-tetrahydroisoquinolin-7-yl}-1λ$^6$,2,5-thiadiazolidine-1,1,3-trione (0.067 g, 0.13 mmol, Example 95A) and tetrahydrofuran (4 mL). The resulting mixture was stirred at ambient temperature for 20 hours under an atmosphere of hydrogen at 60 psi. The catalyst was then removed by filtration and washed with methanol. The filtrate was concentrated under reduced pressure, and the residue was purified using reversed-phase chromatography [30 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.023 g, 0.054 mmol, 42% yield). $^1$H NMR (500 MHz, DMSO-d$_6$) δ ppm 12.04 (s, 1H), 9.64 (s, 1H), 6.57 (s, 1H), 4.24 (s, 2H), 3.95 (s, 2H), 3.36 (br s, 2H), 3.10 (t, J=8.2 Hz, 2H), 2.99 (t, J=6.2 Hz, 2H), 2.74 (dd, J=10.1, 6.7 Hz, 2H), 2.13 (s, 6H); MS (APCI$^+$) m/z 424.1 [M+H]$^+$.

Example 96: N-[8-fluoro-6-hydroxy-7-(1,1,4-trioxo-1λ$^6$,2,5-thiadiazolidin-2-yl)-1,2,3,4-tetrahydronaphthalen-2-yl]-3-methylbutanimidamide (Compound 195)

To a solution of the product of Example 67F (0.2 g, 0.495 mmol) in ethanol (4 mL) was added ammonium acetate (0.0762 g, 9.89 mmol). After 30 minutes, sodium cyanoborohydride (0.037 g, 0.148 mmol) was added as a solid. After 16 hours, the reaction mixture was diluted with acetonitrile (2 mL) and water (1 mL). Celite® (2 g) was added, and the mixture was concentrated in vacuo to give a white powder. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give 5-[7-amino-3-(benzyloxy)-1-fluoro-5,6,7,8-tetrahydronaphthalen-2-yl]-1$\lambda^6$,2,5-thiadiazolidine-1,1,3-trione (0.0771 g, 0.190 mmol, 38.5% yield). MS (APCI$^+$) m/z 406 [M+H]$^+$.

To a solution of 5-[7-amino-3-(benzyloxy)-1-fluoro-5,6,7,8-tetrahydronaphthalen-2-yl]-1$\lambda^6$,2,5-thiadiazolidine-1,1,3-trione (0.0340 g, 0.084 mmol) and methyl 3-methylbutanecarboximidate hydrochloride (0.019 g, 0.126 mmol) in N,N-dimethylformamide (0.7 mL) at 0° C. was added N,N-diisopropylamine (0.044 mL, 0.252 mmol). After complete addition, the reaction mixture was heated to 60° C. After 17 hours, the reaction mixture was cooled to room temperature and directly purified by loading onto a Teledyne ISCO 50 g reversed-phase C18 column and eluted with a gradient of 10-100% methanol in buffer (0.025 M ammonium bicarbonate in water acidified to pH 7 by adding dry ice) to give N-[6-(benzyloxy)-8-fluoro-7-(1,1,4-trioxo-1$\lambda^6$,2,5-thiadiazolidin-2-yl)-1,2,3,4-tetrahydronaphthalen-2-yl]-3-methylbutanimidamide (0.0300 g, 0.061 mmol, 73.2% yield). MS (APCI$^+$) m/z 489 [M+H]$^+$.

To a suspension N-[6-(benzyloxy)-8-fluoro-7-(1,1,4-trioxo-1$\lambda^6$,2,5-thiadiazolidin-2-yl)-1,2,3,4-tetrahydronaphthalen-2-yl]-3-methylbutanimidamide (0.0300 g, 0.061 mmol) and pentamethylbenzene (0.018 g, 0.123 mmol) in dichloromethane (1.2 mL) at −78° C. was added a solution of boron trichloride (0.368 mL, 0.368 mmol, 1 M in dichloromethane) slowly along the side of the flask. The resulting mixture was stirred for 5 minutes, then warmed to an internal temperature of 0° C., and then cooled to −78° C. and quenched with ethyl acetate (1 mL) followed by ethanol (1 mL). The reaction mixture was warmed to ambient temperature and concentrated in vacuo. The crude solid was triturated with heptanes (3×2 mL), 1:1 ethyl acetate/heptanes (2×2 mL), dichloromethane (2×2 mL) and acetonitrile (2×1 mL), and then dried in a vacuum oven at 50° C. to give the title compound (0.0126 g, 0.032 mmol, 51.5% yield). $^1$H NMR (400 MHz, DMSO-d$_6$) δ ppm 9.11 (br s, 4H), 6.47 (s, 1H), 3.97-3.90 (m, 2H), 3.92-3.83 (m, 1H), 3.00 (dd, J=16.1, 5.3 Hz, 1H), 2.86-2.72 (m, 2H), 2.45 (dd, J=16.1, 9.1 Hz, 1H), 2.27 (d, J=7.6 Hz, 2H), 2.02 (hept, J=7.0 Hz, 1H), 1.98-1.91 (m, 1H), 1.72 (dtd, J=12.4, 9.9, 6.2 Hz, 1H), 0.92 (d, J=6.5 Hz, 6H); MS (APCI$^+$) m/z 399 [M+H]$^+$.

Example 97: 5-{8-fluoro-6-hydroxy-2-[3-(oxan-4-yl)propyl]-1,2,3,4-tetrahydroisoquinolin-7-yl}-1$\lambda^6$,2,5-thiadiazolidine-1,1,3-trione (Compound 196)

Example 97A: 5-{6-(benzyloxy)-8-fluoro-2-[3-(oxan-4-yl)propyl]-1,2,3,4-tetrahydroisoquinolin-7-yl}-1$\lambda^6$,2,5-thiadiazolidine-1,1,3-trione To a vial containing 5-[6-(benzyloxy)-8-fluoro-1,2,3,4-tetrahydroisoquinolin-7-yl]-1$\lambda^6$,2,5-thiadiazolidine-1,1,3-trione trifluoroacetate (theoretically 0.10 mmol, Example 93A) were added potassium carbonate (0.070 g, 0.51 mmol) and acetonitrile (0.26 mL). Next, 4-(3-bromopropyl)tetrahydro-2H-pyran (0.032 g, 0.15 mmol) dissolved in a minimum volume of acetonitrile (approximately 0.050 mL) was added. The vial was capped, and the mixture was heated to 60° C. After 18 hours, the reaction mixture was cooled to ambient temperature and filtered over a thin pad of diatomaceous earth. The filtrate was concentrated under reduced pressure and purified using silica gel chromatography [4 g column, 0-20% gradient of methanol in dichloromethane, then 50% methanol in dichloromethane] to give the title compound (0.050 g, 0.096 mmol, 94% yield over two steps). $^1$H NMR (600 MHz, DMSO-d$_6$-D$_2$O) δ ppm 7.51-7.45 (m, 2H), 7.38-7.31 (m, 2H), 7.31-7.27 (m, 1H), 6.81 (s, 1H), 5.12 (s, 2H), 3.97 (s, 2H), 3.92 (br s, 2H), 3.81 (ddd, J=11.6, 4.5, 1.8 Hz, 2H), 3.26 (td, J=11.7, 2.1 Hz, 2H), 3.08 (br s, 2H), 2.91 (br s, 4H), 1.69-1.60 (m, 2H), 1.57 (dd, J=12.4, 1.7 Hz, 2H), 1.51-1.43 (m, 1H), 1.23 (q, J=7.3 Hz, 2H), 1.17-1.08 (m, 2H); MS (APCI$^+$) m/z 518.4 [M+H]$^+$.

Example 97B: 5-{8-fluoro-6-hydroxy-2-[3-(oxan-4-yl)propyl]-1,2,3,4-tetrahydroisoquinolin-7-yl}-1$\lambda^6$,2,5-thiadiazolidine-1,1,3-trione To a 20 mL Barnstead Hast C reactor containing 10% palladium hydroxide on carbon (0.100 g, 0.356 mmol) were added 5-{6-(benzyloxy)-8-fluoro-2-[3-(oxan-4-yl)propyl]-1,2,3,4-tetrahydroisoquinolin-7-yl}-1$\lambda^6$,2,5-thiadiazolidine-1,1,3-trione (0.100 g, 0.193 mmol) and tetrahydrofuran (4 mL). The resulting mixture was stirred at ambient temperature for 22.1 hours under an atmosphere of hydrogen at 60 psi. The catalyst was then removed by filtration and washed with methanol. The filtrate was concentrated under reduced pressure and purified using silica gel chromatography [4 g column, 0-50% gradient of methanol (containing 1% ammonium hydroxide) in dichloromethane]. Product-containing fractions were combined and concentrated under reduced pressure. The residue was passed through an SCX-2 cartridge (loaded and eluted initially with methanol/dichloromethane(1:1) and then eluted with a 2 M solution of ammonia in methanol) to give the title compound (0.035 g, 0.082 mmol, 42% yield). $^1$H NMR (500 MHz, pyridine-d$_5$) δ ppm 6.80 (s, 1H), 4.63 (s, 2H), 4.05 (s, 2H), 3.97 (dd, J=10.7, 3.4 Hz, 2H), 3.33 (td, J=11.7, 2.1 Hz, 2H), 3.11 (t, J=5.9 Hz, 2H), 2.96 (t, J=6.0 Hz, 2H), 2.87 (dd, J=9.0, 6.6 Hz, 2H), 1.73 (tt, J=10.1, 6.6 Hz, 2H), 1.50 (ddd, J=12.6, 3.9, 1.8 Hz, 2H), 1.38 (dtq, J=14.6, 7.0, 3.4 Hz, 1H), 1.29-1.19 (m, 3H), 1.21-1.14 (m, 1H); MS (APCI$^+$) m/z 428.4 [M+H]$^+$.

Example 98: 5-[1-fluoro-3-hydroxy-7-(3-hydroxy-3-methylbutoxy)-5,6,7,8-tetrahydronaphthalen-2-yl]-1$\lambda^6$,2,5-thiadiazolidine-1,1,3-trione (Compound 197)

Example 98A: 5-[3-(benzyloxy)-1-fluoro-7-(3-hydroxy-3-methylbutoxy)naphthalen-2-yl]-1$\lambda^6$,2,5-thiadiazolidine-1,1,3-trione A mixture of the product of Example 1H (100 mg, 0.249 mmol), 4-bromo-2-methylbutan-2-ol (49.8 mg, 0.298 mmol) and Cs2CO$_3$ (162 mg, 0.497 mmol) in N,N-dimethylformamide (1 mL) was stirred at ambient temperature for 14 hours. The mixture was diluted with ethyl acetate and 0.2 N HCl (15 mL). The organic layer was separated, washed with brine, dried over Na$_2$SO$_4$, and concentrated to give the title compound which was used in the next step without further purification. MS (APCI⁻) m/z 487.5 [M−H]⁻.

Example 98B: 5-[1-fluoro-3-hydroxy-7-(3-hydroxy-3-methylbutoxy)naphthalen-2-yl]-1$\lambda^6$,2,5-thiadiazolidine-1,1,3-trione A solution of the product of Example 98A (120 mg, 0.246 mmol) in tetrahydrofuran (6 mL) was added to a 20 mL Barnstead Hastelloy C reactor charged with 5% Pd/C, wet (145 mg, 0.681 mmol). The mixture was stirred under hydrogen at 150 psi pressure for 25 hours at 25° C. The reaction mixture was filtered, the filtrate was concentrated, and the residue was triturated with dichloromethane to give the title compound (65 mg, 0.163 mmol, 66% yield). $^1$H NMR (400 MHz, DMSO-d$_6$) δ ppm 10.22 (s, 1H), 7.70 (dd, J=9.1, 1.5 Hz, 1H), 7.22 (d, J=2.5 Hz, 1H), 7.16 (dd, J=9.0, 2.6 Hz, 1H), 7.06 (s, 1H), 4.45 (s, 2H), 4.19 (t, J=7.2 Hz, 2H), 1.90 (t, J=7.2 Hz, 2H), 1.19 (s, 6H); MS (APCI⁻) m/z 397.7 [M−H]⁻.

Example 98C: 5-[1-fluoro-3-hydroxy-7-(3-hydroxy-3-methylbutoxy)-5,6,7,8-tetrahydronaphthalen-2-yl]-1$\lambda^6$,2,5-thiadiazolidine-1,1,3-trione A solution of the product of Example 98B (118 mg, 0.296 mmol) in acetic acid (4 mL) was added to a 20 mL Barnstead Hastelloy C reactor charged with 10% palladium hydroxide on carbon (120 mg, 0.427 mmol). The mixture was stirred under 182 psi of hydrogen at 25° C. for 20 hours. The mixture was filtered and the filtrate was concentrated under reduced pressure. The residue was purified by preparative HPLC [YMC TriArt™ C18 Hybrid 20 μm column, 25×150 mm, flow rate 80 mL/minute, 0-50% gradient of methanol in buffer (0.025 M aqueous ammonium bicarbonate, adjusted to pH 10 with ammonium hydroxide)] to give the title compound (49 mg, 0.117 mmol, 39% yield). $^1$H NMR (500 MHz, DMSO-d$_6$) δ ppm 8.91 (br s, 1H), 7.20 (br s, 4H), 6.41 (br s, 1H), 4.20 (s, 1H), 3.94 (s, 2H), 3.70 (m, 1H), 3.57 (m, 2H), 2.77 (m, 2H), 2.46-2.61 (m, 2H), 1.70-1.87 (m, 2H), 1.65 (t, J=8 Hz, 2H), 1.09 (s, 6H); MS (ESI⁻) m/z 401 [M−H]⁻.

Example 99: 5-[(7R)-7-amino-1-fluoro-3-hydroxy-5,6,7,8-tetrahydronaphthalen-2-yl]-1$\lambda^6$,2,5-thiadiazolidine-1,1,3-trione (Compound 198)

Example 99A: 7'-bromo-8'-fluoro-6'-[(2-methoxyethoxy)methoxy]-3',4'-dihydro-1'H-spiro[[1,3]dioxolane-2,2'-naphthalene]

To a solution of 2,2,6,6-tetramethylpiperidine (4.35 mL, 25.6 mmol) in tetrahydrofuran (50 mL) at <2° C. (internal temperature) was added a solution of n-butyllithium (9.61 mL, 24.01 mmol, 2.5 M in hexane) slowly (internal temperature <7° C.). The reaction mixture was stirred for 30 minutes, then cooled to an internal temperature of <−75° C. A solution of the product of Example of 22D (5.00 g, 16.01 mmol) in tetrahydrofuran (25.00 mL) was added slowly down the side of the flask (internal temperature <−67° C.), followed by N,N,N',N'-tetramethylethylenediamine (3.62 mL, 24.01 mmol). The reaction mixture was stirred for 90 minutes while maintaining the internal temperature below −75° C., then a solution of 1,2-dibromotetrachloroethane (7.82 g, 24.01 mmol) in tetrahydrofuran (12.50 mL) was added slowly down the center of the flask (internal temperature <−65° C.). After complete addition, the reaction mixture was stirred for 5 minutes, and then the cooling bath was removed. After reaching 10° C., the reaction mixture was quenched with 50% 1.0 M aqueous sodium thiosulfate solution-saturated aqueous ammonium chloride solution (50 mL) and extracted with ethyl acetate (50 mL, 2×25 mL). The combined organic layers were washed with brine (15 mL)m dried over sodium sulfate, filtered, and concentrated to ca 80 mL total volume. Silica gel (~10 g) was added and the mixture was concentrated to give a powder. The residue obtained was purified by flash column chromatography (120 g RediSep Rf Gold® silica column, elution with a gradient from 0-50% ethyl acetate-0.1% triethylamine-heptanes mixture to give the title compound (4.89 g, 12.50 mmol, 78% yield). $^1$H NMR (500 MHz, CDCl$_3$) δ ppm 6.79 (br s, 1H), 5.30 (s, 2H), 4.07-3.99 (m, 4H), 3.87-3.82 (m, 2H), 3.58-3.53 (m, 2H), 3.38 (s, 3H), 2.97-2.91 (t, J=6.7 Hz, 2H), 2.88 (s, 2H), 1.92 (t, J=6.7 Hz, 2H).

Example 99B: 7-bromo-8-fluoro-6-[(2-methoxyethoxy)methoxy]-3,4-dihydronaphthalen-2(1H)-one The product of Example 99A (4.74 g, 12.12 mmol, 1 equivalent) was suspended in 88% formic acid (w/v, 26.0 mL, 606.0 mmol, 50.0 equivalents) at 23° C. and stirred for 20 minutes. The product mixture was then carefully poured into a stirring mixture of saturated aqueous sodium bicarbonate solution (350 mL) and ethyl acetate (400 mL) at 23° C. The resulting biphasic mixture was stirred for 20 minutes at 23° C. The mixture was then transferred to a separatory funnel and the layers that formed were separated. The aqueous layer was extracted with ethyl acetate (2×100 mL). The organic layers were combined, and the combined organic layers were washed sequentially with saturated aqueous sodium bicarbonate solution (6×100 mL), water (100 mL), and saturated aqueous sodium chloride solution (100 mL). The washed organic layer was dried over magnesium sulfate. The dried solution was filtered through a diatomaceous earth plug (2.0 cm×8.0 cm). The filter cake was rinsed with ethyl acetate (50 mL). The filtrates were combined and concentrated. The residue obtained was reconcentrated once from ether (15 mL) and once from pentane (15 mL) to give the title compound (4.18 g, 12.0 mmol, 99% yield). $^1$H NMR (400 MHz, CDCl$_3$) δ ppm 6.91 (s, 1H), 5.35 (s, 2H), 3.91-3.86 (m, 2H), 3.60-3.52 (m, 4H), 3.38 (s, 3H), 3.09-2.99 (m, 2H), 2.62-2.56 (m, 2H).

Example 99C: (2R)-7-bromo-8-fluoro-6-[(2-methoxyethoxy)methoxy]-N-[(1S)-1-(naphthalen-1-yl)ethyl]-1,2,3,4-tetrahydronaphthalen-2-amine A 250 mL round-bottom flask was charged with the product of Example 99B (3.84 g, 11.06 mmol, 1 equivalent) and deoxygenated methanol (previously sparged with nitrogen for 30 minutes, 110 mL). The reaction vessel was then sealed with a rubber septum. The reaction mixture was further deoxygenated by brief subjection to vacuum (10-20 s) and backfilling with nitrogen (×2). (S)-1-(Naphthalen-1-yl)ethanamine (1.86 g, 11.06 mmol, 1.0 equivalent) was then added dropwise to the solution under nitrogen at 23° C. A deep red mixture resulted. The reaction vessel was then placed in a heating block that had been preheated to 70° C. and stirred for 1 hour. A transparent orange solution resulted within 30 minutes. The block temperature was then increased to 80° C. with continued stirring for an additional 2 hours. Additional (S)-1-(naphthalen-1-yl)ethanamine (330 mg, 1.93 mmol, 0.2 equivalent) was added at 80° C. with continued stirring for an additional 1 hour. The reaction mixture was then placed in a cooling bath at −20° C. (brine-ice) and stirred for 20 minutes. The reaction vessel was briefly unsealed and sodium borohydride (1.26 g, 33.20 mmol, 3.0 equivalents) was added to the suspension in one portion at −20° C. The reaction vessel was resealed, and the reaction mixture was stirred for 30 minutes at −20° C. The product mixture was then diluted sequentially with saturated aqueous ammonium chloride solution (50 mL), water (50 mL), and ethyl acetate (150 mL). The aqueous layer was extracted with ethyl acetate (3×150 mL). The organic layers were combined, and the combined organic layers were washed with brine (2×75 mL). The washed organic layers were dried over sodium sulfate. The dried solution was filtered through a diatomaceous earth plug (2.0 cm×8.0 cm). The filter cake was rinsed with ethyl acetate (50 mL). The filtrates were combined and concentrated. The residue obtained was dissolved in 75% dichloromethane-ethyl acetate (100 mL). Diatomaceous earth (11 g) was added to the solution and the mixture was concentrated. The residue obtained was purified by flash column chromatography (120 g RediSep Rf Gold® silica column, eluted with a gradient from 0-10% methanol-dichloromethane). The fractions containing product were collected and the combined fractions were concentrated. The residue obtained was dissolved in dichloromethane (100 mL). Diatomaceous earth (24 g) was added to the solution and the mixture was concentrated. The residue obtained was reconcentrated from pentane (100 mL). The residue obtained was purified by flash column chromatography (120 g RediSep Rf Gold® silica column, eluted with a gradient from 0-80% ethyl acetate-heptanes, then from 80-100% ethyl acetate-heptanes) to furnish the title compound (2.87 g, 5.70 mmol, 52% yield). MS (APCI$^+$) m/z 502 [M+H]$^+$.

Example 99D: tert-butyl {[(7R)-1-fluoro-3-[(2-methoxyethoxy)methoxy]-7-{[(1S)-1-(naphthalen-1-yl)ethyl]amino}-5,6,7,8-tetrahydronaphthalen-2-yl]amino}acetate A 250 mL round-bottom flask was charged with a solution of the product of Example 99C (2.87 g, 5.71 mmol, 1 equivalent) in 1,4-dioxane (60 mL) and tert-butyl glycinate (1.2 mL, 8.78 mmol, 1.5 equivalents), BrettPhos (61 mg, 0.11 mmol, 2.0 mol %), BrettPhos Pd G3 (104 mg, 0.11 mmol, 2.0 mol %), and cesium carbonate (5.58 g, 17.13 mmol, 3.0 equivalents). The reaction vessel was outfitted with a reflux condenser and a rubber septum. The reaction mixture was briefly subjected to vacuum (5-15 seconds) and backfilled with nitrogen (×5). The reaction vessel was then placed in a heating block that had been preheated to 100° C. The reaction mixture was stirred for 14 hours at 100° C. then cooled over 30 minutes to 23° C. Additional BrettPhos Pd G3 (146 mg, 0.16 mmol, 2.8 mol %) was added. The reaction mixture was sealed and deoxygenated by nitrogen backfills as above (×5). The reaction vessel was then placed in a heating block that had been preheated to 100° C. The reaction mixture was stirred for 4 hours at 100° C. and then cooled over 30 minutes to 23° C. Additional BrettPhos Pd G3 (110 mg, 0.11 mmol, 2.0 mol %) was added. The reaction mixture was sealed and deoxygenated by nitrogen backfills as above (×5). The reaction vessel was then placed in a heating block that had been preheated to 100° C. The reaction mixture was stirred for 16 hours at 100° C. and then cooled over 30 minutes to 23° C. The cooled mixture was poured into a stirring mixture of saturated aqueous ammonium chloride solution (100 mL) and ethyl acetate (300 mL). The resulting biphasic mixture was stirred for 10 minutes. The mixture was then transferred to a separatory funnel and the layers that formed were separated. The aqueous layer was extracted with ethyl acetate (3×100 mL). The organic layers were combined, and the combined organic layers were washed with saturated aqueous sodium chloride solution (100 mL). The washed organic layer was dried over sodium sulfate. The dried solution was filtered, and the filtrate was concentrated. The residue obtained was dissolved in ethyl acetate (100 mL). Diatomaceous earth (25 g) was added to the solution and the mixture was concentrated. The residue obtained was purified by flash column chromatography (120 g RediSep Rf Gold® silica column, eluted with a gradient from 0-80% ethyl acetate-heptanes, then from 80-100% ethyl acetate-heptanes) to furnish the title compound (2.32 g, 4.2 mmol, 74% yield). MS (APCI$^+$) m/z 553 [M+H]$^+$.

Example 99E: tert-butyl ({(7R)-7-amino-1-fluoro-3-[(2-methoxyethoxy)methoxy]-5,6,7,8-tetrahydronaphthalen-2-yl}amino)acetate A suspension of the product of Example 99D (2.32 g, 4.20 mmol, 1 equivalent) and 10% palladium hydroxide-on-carbon (1.30 g, 4.6 mmol, 1.1 equivalents, 50% wet) in tetrahydrofuran (50 mL) was stirred in a stainless-steel Parr reactor under hydrogen (50 psi) for 34 hours at 23° C. The product mixture was then filtered, and the filtrate was concentrated. The residue obtained was used in the following step without further purification. MS (APCI$^+$) m/z 399 [M+H]$^+$.

Example 99F: tert-butyl ({(7R)-7-[(tert-butoxycarbonyl)amino]-1-fluoro-3-[(2-methoxyethoxy)methoxy]-5,6,7,8-tetrahydronaphthalen-2-yl}amino)acetate 4-Dimethylaminopyridine (56 mg, 0.46 mmol, 12.3 mol %) was added to a solution of the product of Example 99E (nominally 3.73 mmol, 1 equivalent) and di-tert-butyldicarbonate (900 mg, 4.12 mmol, 1.1 equivalents) in dichloromethane (20 mL) at 23° C. The reaction mixture was stirred for 16 hours at 23° C. The mixture was diluted sequentially with saturated aqueous ammonium chloride solution (30 mL), water (50 mL), and ethyl acetate (150 mL). The aqueous layer was extracted with ethyl acetate (2×75 mL). The organic layers were combined, and the combined organic layers were washed with saturated aqueous sodium chloride solution (50 mL). The washed organic layer was dried over sodium sulfate. The dried solution was filtered, and the filtrate was concentrated. The residue obtained was purified by flash column chromatography (80 g RediSep Rf Gold® silica column, elution with a gradient from 0-100% ethyl acetate-heptanes) to furnish the title compound (1.57 g, 3.15 mmol, 84% yield, two steps). MS (APCI$^+$) m/z 499 [M+H]$^+$.

Example 99G: tert-butyl [{(7R)-7-[(tert-butoxycarbonyl)amino]-1-fluoro-3-[(2-methoxyethoxy)methoxy]-5,6,7,8-tetrahydronaphthalen-2-yl}({[(prop-2-en-1-yl)oxy]carbonyl}sulfamoyl)amino]acetate Allyl alcohol (0.28 mL, 4.07 mmol, 1.5 equivalents) was added dropwise to a solution of chlorosulfonyl isocyanate (0.35 mL, 4.07 mmol, 1.5 equivalents) in dichloromethane (6 mL) at 0° C. The reaction mixture was stirred for 30 minutes at 0° C. A solution of the product of Example 99F (1.35 g, 2.71 mmol, 1 equivalents) and N,N-diisopropylethylamine (0.95 mL, 5.42 mmol, 2.0 equivalents) in dichloromethane (5 mL) was then added slowly down the side of the flask at 0° C. The reaction mixture was stirred for 30 minutes at 0° C. and then diluted with water (5 mL). The mixture was then transferred to a separatory funnel and the layers that formed were separated. The aqueous layer was extracted with dichloromethane (2×10 mL). The organic layers were combined, and the combined organic layers were washed with aqueous sodium bisulfate solution (1.0 M, 10 mL). The combined aqueous layers were reextracted with dichloromethane (3×5 mL). The organic layers were combined, and the combined organic layers were washed with brine (10 mL). The washed organic layer was dried over sodium sulfate. The dried solution was filtered, and the filtrate was concentrated. The residue obtained was used without further purification.

Example 99H: tert-butyl [(2R)-8-fluoro-6-[(2-methoxyethoxy)methoxy]-7-(1,1,4-trioxo-1$\lambda^6$,2,5-thiadiazolidin-2-yl)-1,2,3,4-tetrahydronaphthalen-2-yl]carbamate A solution of tetrakis(triphenylphosphine)palladium(0) (94 mg, 0.08 mmol, 3.0 mol %), the product of Example 99G (nominally 2.71 mmol, 1 equivalent), and sodium methoxide (25 weight % in methanol, 3.8 mL, 16.5 mmol, 6.1 equivalents) in methanol (30 mL) was deoxygenated by brief subjection to vacuum and nitrogen backfill (×3). The reaction vessel was then placed in a heating block that had been preheated to 70° C. The reaction mixture was stirred for 1.5 hours at 70° C. The product mixture was then cooled to 23° C. The cooled product mixture was concentrated. The concentrated mixture was dissolved in 16% acetonitrile-ethyl acetate mixture (v/v, 60 mL), and aqueous hydrochloric acid solution (1.0 M, 25.0 mL). The resulting biphasic mixture was stirred for 5 minutes. The biphasic mixture was then transferred to a separatory funnel and the layers that formed were separated. The aqueous layer was extracted with 10% acetonitrile-ethyl acetate mixture (v/v, 3×15 mL). The organic layers were combined, and the combined organic layers were washed with brine (2×5 mL). The washed organic layer was dried over sodium sulfate. The dried solution was filtered through a plug of diatomaceous earth (2.0 cm×6.0 cm). Diatomaceous earth (~15 g) was added to the filtrates and the mixture was concentrated. The residue obtained was purified by reversed-phase flash column chromatography (275 g RediSep Rf Gold® C18 column, elution with a gradient from 5-100% [v/v] methanol-0.025 M aqueous ammonium bicarbonate solution [acidified with solid carbon dioxide] over 10 column volumes, then isocratic elution with 100% methanol for 3 column volumes, flow rate=125 mL/minute, $\lambda$=214, 254) to furnish the title compound (900 mg, 1.78 mmol, 66% yield, two steps). MS (APCI$^+$) m/z 404 [M+H—C(O)OC(CH$_3$)$_3$]$^+$.

Example 99I. 5-[(7R)-7-amino-1-fluoro-3-hydroxy-5,6,7,8-tetrahydronaphthalen-2-yl]-1$\lambda^6$,2,5-thiadiazolidine-1,1,3-trione, Hydrochloride Salt A solution of hydrogen chloride in dioxane (4.0 M, 0.1 mL, 0.40 mmol, 6.1 equivalents) was added to a solution of the product of Example 99H (33.0 mg, 0.066 mmol, 1 equivalent) in acetonitrile (0.2 mL) at 23° C. A precipitate immediately resulted. The reaction mixture was stirred for 1 hour at 23° C. The reaction mixture was then diluted with ether (1.0 mL) and additional precipitate immediately resulted. The precipitate was allowed to settle, and the supernatant was removed. The residue obtained was triturated with 10% acetonitrile-ethyl acetate mixture (v/v, 3×1.0 mL). $^1$H NMR analysis of the residue obtained in this way indicated the presence of starting material. The residue was suspended in a solution of hydrogen chloride in dioxane (4.0 M, 0.4 mL, 1.60 mmol, 24.2 equivalents) at 23° C. The reaction mixture was stirred for 4 hours at 23° C. The product mixture was then concentrated to furnish the title compound (21.0 mg, 0.060 mmol, 91% yield). $^1$H NMR (400 MHz, CDCl$_3$) δ ppm 997 (bs, 1H), 6.51 (s, 1H), 4.24 (s, 2H), 3.76-3.63 (m, 1H), 3.01 (dd, J=16.0, 5.5 Hz, 1H), 2.86-2.72 (m, 2H), 2.11-2.01 (m, 1H), 1.77-1.64 (m, 1H); MS (APCI$^+$) m/z 316 [M+H]$^+$.

Example 100: 5-{(7R)-7-[(4,4-difluorobutyl)amino]-1-fluoro-3-hydroxy-5,6,7,8-tetrahydronaphthalen-2-yl}-1$\lambda^6$,2,5-thiadiazolidine-1,1,3-trione (Compound 199)

The product of Example 67 (0.3470 g, 0.782 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide (90:10) at a concentration of 10 mg/mL. The sample was loaded into the modifier stream in 0.4 mL (4 mg) injections. The mobile phase was held isocratically at 35% cosolvent:CO$_2$. Fraction collection was time triggered. The instrument was fitted with a CHIRAL-PAK® IC column with dimensions 21 mm i.d.×250 mm length with 5 μm particles. The earlier eluting enantiomer peak gave the title compound (0.1043 g, 0.256 mmol, 65.5% recovery). $^1$H NMR (400 MHz, DMSO-d$_6$) δ ppm 9.18 (s, 1H), 8.35 (s, 2H), 6.44 (s, 1H), 6.12 (tt, J=56.6, 4.2 Hz, 1H), 3.90 (s, 2H), 3.09-2.99 (m, 3H), 2.82-2.63 (m, 2H), 2.10 (d, J=12.0 Hz, 1H), 2.00-1.82 (m, 2H), 1.66 (ddt, J=27.2, 11.2, 6.7 Hz, 3H); MS (APCI$^+$) m/z 408 [M+H]$^+$.

Example 101: 5-{(7R)-7-[(2-cyclopentylethyl)amino]-1-fluoro-3-hydroxy-5,6,7,8-tetrahydronaphthalen-2-yl}-1$\lambda^6$,2,5-thiadiazolidine-1,1,3-trione (Compound 200)

Example 101A: 6-(benzyloxy)-7-bromo-8-fluoro-3,4-dihydronaphthalen-2(1H)-one

The product of Example 67B (33.31 g, 73.1 mmol) was suspended in 88% formic acid (70 mL). After 1.5 hours, the mixture was diluted with water (400 mL). The resulting solid was collected by filtration, washed with water (800 mL) and dried in a vacuum oven at 30° C. to give the title compound (26.84 g, 71.7 mmol, 98% yield) as a monohydrate. $^1$H NMR (500 MHz, DMSO-d$_6$) δ ppm 7.49 (ddt, J=7.7, 1.4, 0.7 Hz, 2H), 7.45-7.39 (m, 2H), 7.37-7.32 (m, 1H), 7.09-7.05 (m, 1H), 5.23 (s, 2H), 3.50 (d, J=1.1 Hz, 2H), 3.08-3.01 (m, 2H), 2.48 (s, 2H).

Example 101B: (2R)-6-(benzyloxy)-7-bromo-8-fluoro-1,2,3,4-tetrahydronaphthalen-2-amine hydrochloride To a solution of monobasic sodium phosphate (38.2 g, 318 mmol) in water (0.95 L) was added concentrated hydrochloric acid (175 mL), followed by portion-wise addition of sec-butylamine (235 mL, 2326 mmol). The pH was adjusted to 6.5 by addition of concentrated hydrochloric acid. After cooling the mixture to 30° C., pyridoxal-5-phosphate (0.625 g, 286 mmol) was added, and 100 mL of the buffer solution was removed for use below. To the remaining buffer solution was slowly added a solution of the product of Example 101A (118 g, 338 mmol) in dimethyl sulfoxide (0.95 L) while maintaining the pH between 7.25 and 7.75 by addition of either concentrated hydrochloric acid or 50% aqueous sec-butylamine. Upon complete addition, a dispersion of Codexis® ATA-025 (12 g) in the 100 mL of buffer from above was added and the resulting mixture was heated to 40° C. while maintaining the pH between 7.25 and 7.75 by addition of either concentrated hydrochloric acid or 50% aqueous sec-butylamine. After 24 hours, the reaction mixture was cooled to 10° C. and filtered. The solid was triturated with water (2×250 mL) followed by acetonitrile (2×250 mL), and then dried in a vacuum oven at 40° C. to give the title compound (126 g, 91% potency by HPLC, 327 mmol, 96.9% potency adjusted yield). Analytical HPLC conditions: Supelco Acentis® Express C18 column, 4.6× 150 mm, 2.7 micron, held at 35° C., eluting with a gradient of 30 to 90% acetonitrile in 0.1% perchloric acid in water over 6 minutes, holding at 90% acetonitrile for 1 minute then back to 30% acetonitrile over 0.1 minutes; $^1$H NMR (500 MHz, CD$_3$OD) δ ppm 7.50-7.44 (m, 2H), 7.41-7.34 (m, 2H), 7.34-7.27 (m, 1H), 6.78-6.73 (m, 1H), 5.16 (d, J=3.8 Hz, 2H), 3.61-3.50 (m, 1H), 3.21 (ddt, J=16.1, 5.7, 1.7 Hz, 1H), 2.99-2.84 (m, 2H), 2.65 (dd, J=16.3, 9.8 Hz, 1H), 2.21 (dddd, J=14.5, 7.3, 4.2, 1.7 Hz, 1H), 1.84 (dddd, J=12.7, 11.1, 10.2, 6.3 Hz, 1H); MS (APCI$^+$) m/z 350 [M+H]$^+$.

Example 101C: benzyl [(2R)-6-(benzyloxy)-7-bromo-8-fluoro-1,2,3,4-tetrahydronaphthalen-2-yl]carbamate To a solution of the product of Example 101B (2 g, 5.17 mmol) in a mixture of tetrahydrofuran (20 mL) and water (10 mL) was added 1 M aqueous sodium hydroxide (10.35 mL, 10.35 mmol), followed by benzyl chloroformate (1.811 mL, 3 M in toluene, 5.43 mL) dropwise. After 10 minutes the reaction mixture was extracted with ethyl acetate (3×10 mL). The organic layers were combined, washed with brine (10 mL), dried over anhydrous sodium sulfate, filtered and concentrated. The residue was dissolved in boiling ethyl acetate (10 mL), and the solution was diluted by dropwise addition of heptanes (12 mL) and then slowly cooled to room temperature. The solid was collected by filtration, washed with 1:1 ethyl acetate/heptanes (10 mL) and dried in a vacuum oven at 50° C. to give the title compound (1.8513 g, 3.82 mmol, 74% yield). $^1$H NMR (400 MHz, DMSO-d$_6$) δ ppm 7.47-7.23 (m, 9H), 6.85 (s, 1H), 6.81 (s, 1H), 5.14 (s, 2H), 5.00 (s, 2H), 3.82-3.57 (m, 1H), 2.91 (dd, J=16.5, 5.3 Hz, 1H), 2.84-2.76 (m, 1H), 2.79-2.66 (m, 1H), 2.47-2.39 (m, 1H), 1.94-1.86 (m, 1H), 1.67-1.55 (m, 1H); MS (APCI$^+$) m/z 484 [M+H]$^+$.

Example 101D: (R)-tert-butyl 2-((3-(benzyloxy)-7-(((benzyloxy)carbonyl)amino)-1-fluoro-5,6,7,8-tetrahydronaphthalen-2-yl)amino)acetate To a suspension of the product of Example 101C (2.0876 g, 4.31 mmol), cesium carbonate (4.21 g, 12.93 mmol), BrettPhos (0.093 g, 0.172 mmol), and BrettPhos Pd G3 precatalyst (0.078 g, 0.086 mmol) in dioxane (41.8 mL) was added tert-butyl 2-aminoacetate (0.883 mL, 6.47 mmol). The resulting mixture was degassed by 5 vacuum/nitrogen backfills, stirred for 5 minutes and then heated to 90° C. After 3 hours, the mixture was cooled to below 30° C., BrettPhos Pd G3 precatalyst (0.078 g, 0.086 mmol) was added, and the mixture was degassed by 3 vacuum/nitrogen backfills and stirred for 5 minutes and then heated to 90° C. After 16 hours, the mixture was cooled to below 30° C., BrettPhos Pd G3 precatalyst (0.078 g, 0.086 mmol) was added, and the mixture was degassed by 3 vacuum/nitrogen backfills stirred for 5 minutes and then heated to 90° C. After 3.5 hours, the mixture was cooled to below 30° C., BrettPhos Pd G3 precatalyst (0.078 g, 0.086 mmol) was added, the mixture was degassed by 3 vacuum/nitrogen backfills stirred for 5 minutes and then heated to 90° C. After 3 hours, the reaction mixture was cooled to ambient temperature and quenched with saturated aqueous ammonium chloride (20 mL), diluted with water (10 mL) and extracted with ethyl acetate (20 mL, 2×10 mL). The organic layers were combined, washed with brine (10 mL), dried over anhydrous sodium sulfate, and filtered. Silica (10 g) was added to the filtrate, and the resulting mixture was concentrated in vacuo to give a yellow powder. The resultant mixture was dry loaded onto an 80 g Teledyne ISCO RediSep Rf Gold® column and eluted with a gradient of 0-35% ethyl acetate in heptanes with 0.1% triethylamine added to give the title compound (1.7647 g, 3.30 mmol, 77% yield). $^1$H NMR (400 MHz, DMSO-d$_6$) δ ppm 7.50-7.43 (m, 2H), 7.38 (s, 1H), 7.43-7.31 (m, 6H), 7.31 (s, 1H), 6.57 (s, 1H), 5.07 (s, 2H), 5.03 (s, 2H), 4.76 (td, J=6.8, 2.7 Hz, 1H), 3.88 (dd, J=6.9, 2.6 Hz, 2H), 3.69-3.57 (m, 1H), 2.86 (dd, J=16.4, 5.5 Hz, 1H), 2.75-2.66 (m, 2H), 2.36 (dd, J=16.5, 9.7 Hz, 1H), 1.95-1.87 (m, 1H), 1.60-1.48 (m, 1H), 1.34 (s, 9H); MS (APCI$^+$) m/z 535 [M+H]$^+$.

Early fractions gave the hydrodehalogenation byproduct benzyl [(2R)-6-(benzyloxy)-8-fluoro-1,2,3,4-tetrahydronaphthalen-2-yl]carbamate (0.1848 g, 0.456 mmol, 10.6% yield). $^1$H NMR (500 MHz, DMSO-d$_6$) δ ppm 7.49-7.39 (m, 3H), 7.42-7.34 (m, 6H), 7.37-7.28 (m, 2H), 6.68 (dd, J=11.5, 2.4 Hz, 1H), 6.62 (d, J=2.5 Hz, 1H), 5.06 (s, 2H), 5.03 (s, 2H), 3.69 (s, 1H), 2.90 (dd, J=16.5, 5.6 Hz, 1H), 2.80 (tt, J=16.6, 5.5 Hz, 2H), 2.39 (dd, J=16.6, 9.6 Hz, 1H), 1.93 (dd, J=12.7, 4.1 Hz, 1H), 1.59 (dtd, J=12.3, 10.5, 5.7 Hz, 1H); MS (APCI$^+$) m/z 406 [M+H]$^+$. Crystals suitable for X-ray crystallography of the hydrodehalogenation byproduct were grown from slow evaporation of a solution in methanol. X-ray crystallographic analysis confirmed the absolute stereochemistry to be (R).

Example 101E: tert-butyl {[(7R)-3-(benzyloxy)-7-{[(benzyloxy)carbonyl]amino}-1-fluoro-5,6,7,8-tetrahydronaphthalen-2-yl]({[(prop-2-en-1-yl)oxy]carbonyl}sulfamoyl)amino}acetate To a solution of chlorosulfonyl isocyanate (0.430 mL, 4.95 mmol) in dichloromethane (17.6 mL) at 0° C. was added allyl alcohol (0.337 mL, 4.95 mmol) dropwise. After 30 minutes, a preformed solution of the product of Example 101D (1.7647 g, 3.30 mmol), and N,N-diisopropylamine (1.73 mL, 9.90 mmol) in dichloromethane (17.6 mL) was slowly added along the side of the flask. After 45 minutes, the reaction was quenched with water (18 mL) and the layers were separated. The aqueous layer was extracted with dichloromethane (2×9 mL). The organic layers were combined and washed with 1 M aqueous sodium bisulfate (9 mL). The sodium bisulfate layer was extracted with dichloromethane (9 mL). The organic layers were combined and dried over anhydrous sodium sulfate, filtered and concentrated in vacuo to give the title compound which was used for the next reaction without purification. $^1$H NMR (400 MHz, DMSO-$d_6$) δ ppm 11.49 (d, J=3.5 Hz, 1H), 7.47-7.24 (m, 10H), 6.73 (s, 1H), 5.69 (ddtd, J=17.4, 10.7, 5.5, 1.5 Hz, 1H), 5.23-5.05 (m, 3H), 5.07-4.95 (m, 6H), 4.59 (dd, J=17.3, 3.0 Hz, 1H), 4.28-4.18 (m, 1H), 4.21-4.07 (m, 2H), 3.74-3.54 (m, 1H), 2.87 (dd, J=16.7, 5.4 Hz, 1H), 2.81-2.68 (m, 1H), 2.38 (dd, J=16.5, 9.6 Hz, 1H), 1.97-1.87 (m, 1H), 1.29 (d, J=3.0 Hz, 9H); MS (APCI$^+$) m/z 642 [M-tert-butyl+H]$^+$.

Example 101F: benzyl [(2R)-6-(benzyloxy)-8-fluoro-7-(1,1,4-trioxo-1λ$^6$,2,5-thiadiazolidin-2-yl)-1,2,3,4-tetrahydronaphthalen-2-yl]carbamate To a suspension of the product of Example 101E (2.306 g, 3.30 mmol) and tetrakis(triphenylphosphine)palladium(0) (0.076 g, 0.066 mmol) in methanol (23 mL) was added a solution of sodium methoxide (5.29 mL, 25 weight % in methanol, 23.13 mmol), and the resulting mixture was heated to 60° C. After 1.5 hours, the reaction mixture was cooled to ambient temperature, quenched 1 M hydrochloric acid (23 mL), diluted with ethyl acetate (23 mL) and partially concentrated to remove methanol. The crude aqueous mixture was extracted with 2-methyltetrahydrofuran (3×23 mL). The organic layers were combined, washed with brine (10 mL), dried over sodium sulfate, filtered through Celite® (5 g) and concentrated in vacuo. The residue was dissolved in acetonitrile (23 mL), Celite® (5 g) was added and the mixture was concentrated. The resulting mixture was dry loaded onto a 40 g Teledyne ISCO RediSep Rf Gold® column and eluted with a gradient of 0-100% acetonitrile in dichloromethane to give the title compound (1.3459 g, 2.494 mmol, 75% yield). $^1$H NMR (600 MHz, DMSO-$d_6$) δ ppm 7.51-7.39 (m, 3H), 7.39-7.34 (m, 6H), 7.34-7.28 (m, 2H), 6.82 (s, 1H), 5.12 (s, 2H), 5.08-5.00 (m, 2H), 4.38 (d, J=0.8 Hz, 2H), 3.74-3.70 (m, 1H), 2.95-2.75 (m, 3H), 2.44 (dd, J=16.6, 9.3 Hz, 1H), 1.97-1.91 (m, 1H), 1.62 (dtd, J=12.5, 10.4, 5.5 Hz, 1H); MS (APCI$^+$) m/z 540 [M+H]$^+$.

Example 101G: benzyl [(2R)-6-(benzyloxy)-8-fluoro-7-(1,1,4-trioxo-1λ$^6$,2,5-thiadiazolidin-2-yl)-1,2,3,4-tetrahydronaphthalen-2-yl](2-cyclopentylethyl)carbamate, Ammonium Salt To a solution of the product of Example 101F (0.1 g, 0.185 mmol) in N,N-dimethylformamide (1 mL) was added potassium carbonate (0.026 g, 0.185 mmol) followed by (2-bromoethyl)cyclopentane (0.051 mL, 0.371 mmol). After stirring for 5 minutes, a suspension of potassium tert-butoxide (0.042 g, 0.371 mmol) in N,N-dimethylformamide (1 mL) was added dropwise over 30 minutes. After 90 minutes, additional (2-bromoethyl)cyclopentane (0.30 mL, 0.219 mmol) was added followed by a suspension of potassium tert-butoxide (0.042 g, 0.371 mmol) in N,N-dimethylformamide (1 mL) over 30 minutes. After 1 hour, the reaction mixture was diluted with water (1 mL) and filtered through a glass microfiber frit. The resulting solution was directly purified by loading onto a Teledyne ISCO 100 g reversed-phase C18 column eluted with a gradient of 10-100% methanol in buffer (0.025 M ammonium bicarbonate in water acidified to pH 7 by adding dry ice) to give the title compound (0.0501 g, 0.036 mmol, 41.4% yield). MS (APCI$^+$) m/z 653 [M+NH$_4$]$^+$.

Example 101H: 5-{(7R)-7-[(2-cyclopentylethyl)amino]-1-fluoro-3-hydroxy-5,6,7,8-tetrahydronaphthalen-2-yl}-1λ$^6$,2,5-thiadiazolidine-1,1,3-trione To a suspension the product of Example 101G (0.0300 g, 0.061 mmol) and pentamethylbenzene (0.018 g, 0.123 mmol) in dichloromethane (1.2 mL) at −78° C. was added a solution of boron trichloride (0.368 mL, 0.368 mmol, 1 M in dichloromethane) slowly along the side of the flask. The resulting mixture was stirred for 5 minutes, then warmed to an internal temperature of 0° C., and then cooled to −78° C. and quenched with ethyl acetate (1 mL) followed by ethanol (1 mL). The reaction mixture was warmed to ambient temperature and concentrated in vacuo. The residue was triturated with heptanes (3×2 mL), 1:1 ethyl acetate/heptanes (2×2 mL), and dichloromethane (2×2 mL). The crude solid was dissolved in methanol (5 mL), Celite® (1 g) was added, and the mixture was concentrated. The resultant mixture was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.0203 g, 0.049 mmol, 64.3% yield). $^1$H NMR (400 MHz, DMSO-$d_6$) δ ppm 9.21 (br s, 1H), 8.47 (br s, 2H), 6.47 (s, 1H), 3.93 (s, 2H), 3.45-3.38 (m, 1H), 3.09 (dd, J=16.0, 5.4 Hz, 1H), 3.01 (dd, J=10.0, 6.1 Hz, 2H), 2.85-2.65 (m, 2H), 2.57-2.46 (m, 1H), 2.16 (dd, J=11.5, 5.1 Hz, 1H), 1.88-1.42 (m, 9H), 1.18-1.05 (m, 2H); MS (APCI$^+$) m/z 412 [M+H]$^+$.

Example 102: 5-{(7R)-7-[(2-cyclobutylethyl)amino]-1-fluoro-3-hydroxy-5,6,7,8-tetrahydronaphthalen-2-yl}-1λ$^6$,2,5-thiadiazolidine-1,1,3-trione (Compound 201)

Example 102A: 2-cyclobutylethyl 4-methylbenzenesulfonate

To a solution of 2-cyclobutylethanol (0.5 g, 4.99 mmol), 4-dimethylaminopyridine (0.030 g, 0.250 mmol), and p-toluenesulfonyl chloride (1.047 g, 5.49 mmol) in dichloromethane (20 mL) at 0° C. was added N,N-diisopropylethylamine (1.308 mL, 7.49 mmol). After 30 minutes, the reaction mixture was warmed to ambient temperature. After 19 hours, the reaction was quenched with water (10 mL), and the layers were separated. The aqueous layer was extracted with dichloromethane (2×2 mL). The organic layers were combined, washed with 1 M aqueous sodium bisulfate (2 mL), dried over anhydrous sodium sulfate, filtered through a silica plug (1 g) and concentrated in vacuo to give the title compound (0.8254 g, 3.25 mmol, 65% yield). $^1$H NMR (400 MHz, CDCl$_3$) δ ppm 7.82-7.74 (m, 2H), 7.39-7.31 (m, 2H), 3.95 (t, J=6.6 Hz, 2H), 2.45 (s, 3H), 2.31 (dt, J=15.7, 7.9 Hz, 1H), 2.11-1.92 (m, 2H), 1.92-1.73 (m, 2H), 1.72 (q, J=6.7 Hz, 2H), 1.63-1.49 (m, 2H); MS (APCI$^+$) m/z 255 [M+H]$^+$.

Example 102B: benzyl [(2R)-6-(benzyloxy)-8-fluoro-7-(1,1,4-trioxo-1λ$^6$,2,5-thiadiazolidin-2-yl)-1,2,3,4-tetrahydronaphthalen-2-yl](2-cyclobutylethyl)carbamate, Ammonium Salt To a solution of the product of Example 101F (0.1 g, 0.185 mmol) and the product of Example 102A (0.1615 g, 0.635 mmol) in N,N-dimethylformamide (1 mL) was added a suspension of potassium tert-butoxide (0.104 g, 0.927 mmol) in N,N-dimethylformamide (2 mL) dropwise over 30 minutes. After 1 hour, the reaction mixture was diluted with water (1 mL) and filtered through a glass microfiber frit. The resulting solution was directly purified by loading onto a Teledyne ISCO 50 g reversed-phase C18 column eluted with a gradient of 10-100% methanol in buffer (0.025 M ammonium bicarbonate in water acidified to pH 7 by adding dry ice) to give the title compound as the ammonium salt (0.0577 g, 0.090 mmol, 48.7% yield). MS (APCI$^+$) m/z 639 [M+NH$_4$]$^+$.

Example 102C: 5-{(7R)-7-[(2-cyclobutylethyl)amino]-1-fluoro-3-hydroxy-5,6,7,8-tetrahydronaphthalen-2-yl}-1λ$^6$,2,5-thiadiazolidine-1,1,3-trione A suspension of the product of Example 102B (0.0501 g, 0.078 mmol) and 10% palladium hydroxide on carbon (0.05 g, 50 weight % in water, 0.0178 mmol) in tetrahydrofuran (4 mL) was stirred for 19 hours under 60 psi of hydrogen. After filtration, Celite® (1 g) was added, and the mixture was concentrated in vacuo. The resultant mixture was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.0051 g, 0.013 mmol, 16.4% yield). $^1$H NMR (400 MHz, DMSO-d$_6$) δ ppm 9.18 (br s, 1H), 8.26 (br s, 2H), 6.46 (s, 1H), 3.93 (s, 2H), 3.40-3.30 (m, 1H), 3.06 (dd, J=16.0, 5.4 Hz, 1H), 2.88 (dd, J=9.8, 6.2 Hz, 2H), 2.83-2.65 (m, 2H), 2.51-2.46 (m, 1H), 2.32 (hept, J=7.8 Hz, 1H), 2.16-2.00 (m, 3H), 1.92-1.75 (m, 2H), 1.75-1.56 (m, 5H); MS (APCI$^+$) m/z 398 [M+H]$^+$.

Example 103: 5-[(7R)-7-{[2-(3,3-difluorocyclobutyl)ethyl]amino}-1-fluoro-3-hydroxy-5,6,7,8-tetrahydronaphthalen-2-yl]-1λ$^6$,2,5-thiadiazolidine-1,1,3-trione (Compound 202)

Example 103A: 2-(3,3-difluorocyclobutyl)ethyl 4-methylbenzenesulfonate

To a solution of 2-(3,3-difluorocyclobutyl)ethanol (0.340 g, 2.496 mmol), and triethylamine (0.42 mL, 3.24 mmol) in dichloromethane (12.5 mL) ad 0° C. was added 4-methylbenzenesulfonic anhydride (0.978 mL, 3.00 mmol). After 30 minutes the reaction was warmed to ambient temperature. After 19 hours, the reaction mixture was concentrated in vacuo. The residue was partitioned between diethyl ether (100 mL) and 1 M hydrochloric acid (75 mL). The layers were separated, and the organic layer was washed with saturated aqueous sodium bicarbonate (75 mL), and brine (10 mL). The organic layer was dried over anhydrous magnesium sulfate, filtered and concentrated in vacuo. The residue was purified by loading onto a 40 g Teledyne ISCO RediSep Rf Gold® column and eluting with a gradient of 0-50% ethyl acetate in heptanes to give the title compound (0.595 g, 2.049 mmol, 82% yield). $^1$H NMR (400 MHz, CDCl$_3$) δ ppm 7.83-7.75 (m, 2H), 7.39-7.33 (m, 2H), 4.01 (t, J=6.1 Hz, 2H), 2.69-2.54 (m, 2H), 2.46 (s, 3H), 2.24-2.05 (m, 3H), 1.88-1.80 (m, 2H).

Example 103B: benzyl [(2R)-6-(benzyloxy)-8-fluoro-7-(1,1,4-trioxo-1λ$^6$,2,5-thiadiazolidin-2-yl)-1,2,3,4-tetrahydronaphthalen-2-yl][2-(3,3-difluorocyclobutyl)ethyl]carbamate To a solution of the product of Example 101F (0.1 g, 0.185 mmol) and the product of Example 103A (0.140 g, 0.482 mmol) in N,N-dimethylformamide (1 mL) was added a suspension of potassium tert-butoxide (0.104 g, 0.927 mmol) in N,N-dimethylformamide (2 mL) dropwise over 30 minutes. After 1 hour, the reaction mixture was diluted with water (1 mL) and filtered through a glass microfiber frit. The filtrate was directly purified by loading onto a Teledyne ISCO 50 g reversed-phase C18 column eluted with a gradient of 10-100% methanol in buffer (0.025 M ammonium bicarbonate in water acidified to pH 7 by adding dry ice) to give the title compound as the ammonium salt (0.0488 g, 0.072 mmol, 39% yield). MS (APCI$^+$) m/z 676 [M+NH$_4$]$^+$.

Example 103C: 5-[(7R)-7-{[2-(3,3-difluorocyclobutyl)ethyl]amino}-1-fluoro-3-hydroxy-5,6,7,8-tetrahydronaphthalen-2-yl]-1λ$^6$,2,5-thiadiazolidine-1,1,3-trione A suspension of the product of Example 103B (0.0488 g, 0.072 mmol) and 10% palladium hydroxide on carbon (0.05 g, 50 weight % in water, 0.0.178 mmol) in tetrahydrofuran (4 mL) was stirred for 20 hours under 60 psi of hydrogen. After filtration, Celite® (1 g) was added and the mixture was concentrated in vacuo. The resultant mixture was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.0093 g, 0.021 mmol, 29.7% yield). $^1$H NMR (400 MHz, DMSO-d$_6$) δ ppm 9.15 (s, 1H), 8.17 (s, 2H), 6.46 (s, 1H), 3.93 (s, 2H), 3.46-3.33 (m, 1H), 3.05 (dd, J=15.9, 5.3 Hz, 1H), 2.92 (t, J=7.8 Hz, 2H), 2.86-2.62 (m, 4H), 2.52-2.43 (m, 1H), 2.36-2.07 (m, 4H), 1.78 (q, J=7.6 Hz, 2H), 1.64 (qd, J=11.4, 7.8 Hz, 1H); MS (APCI$^+$) m/z 434 [M+H]$^+$.

Example 104: 5-{(7R)-1-fluoro-3-hydroxy-7-[(3-methylpentyl)amino]-5,6,7,8-tetrahydronaphthalen-2-yl}-1λ$^6$,2,5-thiadiazolidine-1,1,3-trione (Compound 203)

Example 104A: 3-methylpentyl 4-methylbenzenesulfonate

To a solution of 3-methylpentan-1-ol (0.534 mL, 4.3 mmol), 4-dimethylaminopyridine (0.053 g, 0.430 mmol), and N,N-diisopropylethylamine (2.253 g, 1.667 mmol) in dichloromethane (10 mL) at 0° C. was added p-toluenesulfonyl chloride (0.902, 4.73 mmol). After 30 minutes the reaction was warmed to ambient temperature. After 19 hours, the reaction was quenched with water (5 mL), and the layers were separated. The aqueous layer was extracted with dichloromethane (2×2 mL). The organic layers were combined, washed with 1 M aqueous sodium bisulfate (2 mL), dried over anhydrous sodium sulfate, filtered through a silica plug (1 g) and concentrated in vacuo to give the title compound (0.8135 g, 3.17 mmol, 73.8% yield). $^1$H NMR (600 MHz, CDCl$_3$) δ ppm 7.82-7.77 (m, 2H), 7.39-7.32 (m, 2H), 4.11-4.01 (m, 2H), 2.45 (d, J=0.7 Hz, 3H), 1.72-1.63 (m, 1H), 1.48-1.37 (m, 2H), 1.32-1.22 (m, 1H), 1.16-1.06 (m, 1H), 0.86-0.77 (m, 6H); MS (APCI$^+$) m/z 257 [M+H]$^+$.

Example 104B: benzyl [(2R)-6-(benzyloxy)-8-fluoro-7-(1,1,4-trioxo-1λ$^6$,2,5-thiadiazolidin-2-yl)-1,2,3,4-tetrahydronaphthalen-2-yl](3-methylpentyl) carbamate To a solution of the product of Example 101F (0.1 g, 0.185 mmol) and the product of Example 104A (0.143 g, 0.556 mmol) in N,N-dimethylformamide (1 mL) was added a suspension of potassium tert-butoxide (0.104 g, 0.927 mmol) in N,N-dimethylformamide (2 mL) dropwise over 30 minutes. After 1 hour, the reaction mixture was diluted with water (1 mL) and filtered through a glass microfiber frit. The resulting solution was directly purified by loading onto a Teledyne ISCO 50 g reversed-phase C18 column eluted with a gradient of 10-100% methanol in buffer (0.025 M ammonium bicarbonate in water acidified to pH 7 by adding dry ice) to give the title compound as the ammonium salt (0.0723 g, 0.113 mmol, 60.9% yield). MS (APCI$^+$) m/z 641 [M+NH$_4$]$^+$.

Example 104C: 5-{(7R)-1-fluoro-3-hydroxy-7-[(3-methylpentyl)amino]-5,6,7,8-tetrahydronaphthalen-2-yl}-1λ$^6$,2,5-thiadiazolidine-1,1,3-trione To a suspension the product of Example 104B (0.0723 g, 0.113 mmol) and pentamethylbenzene (0.033 g, 0.226 mmol) in dichloromethane (3.6 mL) at −78° C. was added a solution of boron trichloride (1.128 mL, 1 M in dichloromethane, 1.128 mmol) slowly along the side of the flask. The resulting mixture was stirred for 5 minutes, then warmed to an internal temperature of 0° C., and then cooled to −78° C. and quenched with ethyl acetate (1 mL) followed by ethanol (1 mL). The mixture was warmed to ambient temperature and concentrated in vacuo. The residue was triturated with heptanes (3×2 mL), 1:1 ethyl acetate/heptanes (2×2 mL), and dichloromethane (2×2 mL). The crude solid was dissolved in methanol (5 mL), and Celite® (1 g) was added. The mixture was concentrated. The resultant mixture was dry loaded onto a Teledyne ISCO 50 g reversed-phase C18 column eluted with a gradient of 10-100% methanol in buffer (0.025 M ammonium bicarbonate in water acidified to pH 7 by adding dry ice) to give the title compound (0.0146 g, 0.037 mmol, 32.4% yield). $^1$H NMR (400 MHz, DMSO-d$_6$) δ ppm 9.19 (br s, 1H), 8.39 (br s, 2H), 6.47 (s, 1H), 3.94 (s, 2H), 3.47-3.37 (m, 1H), 3.18-2.93 (m, 3H), 2.86-2.66 (m, 2H), 2.57-2.46 (m, 1H), 2.20-2.12 (m, 1H), 1.74-1.56 (m, 2H), 1.52-1.27 (m, 3H), 1.26-1.10 (m, 1H), 0.92-0.83 (m, 6H); MS (APCI$^+$) m/z 400 [M+H]$^+$.

Example 105: 5-{(7R)-7-[(3-ethylpentyl)amino]-1-fluoro-3-hydroxy-5,6,7,8-tetrahydronaphthalen-2-yl}-1λ$^6$,2,5-thiadiazolidine-1,1,3-trione (Compound 204)

Example 105A: 3-ethylpentyl 4-methylbenzenesulfonate

To a solution of 3-ethylpentan-1-ol (0.5 mL, 4.3 mmol), 4-dimethylaminopyridine (0.053 g, 0.430 mmol), and N,N-diisopropylethylamine (2.253 g, 1.667 mmol) in dichloromethane (10 mL) at 0° C. was added p-toluenesulfonyl chloride (0.902, 4.73 mmol). After 30 minutes the reaction mixture was warmed to ambient temperature. After 19 hours, the reaction was quenched with water (5 mL), and the layers were separated. The aqueous layer was extracted with dichloromethane (2×2 mL). The organic layers were combined, washed with 1 M aqueous sodium bisulfate (2 mL), dried over anhydrous sodium sulfate, filtered through a silica plug (1 g) and concentrated in vacuo to give the title compound (0.9158 g, 3.39 mmol, 79% yield). $^1$H NMR (600 MHz, CDCl$_3$) δ ppm 7.82-7.77 (m, 2H), 7.37-7.32 (m, 2H), 4.05 (t, J=6.9 Hz, 2H), 2.45 (s, 3H), 1.61-1.56 (m, 2H), 1.36-1.12 (m, 5H), 0.78 (t, J=7.3 Hz, 6H); MS (APCI$^+$) m/z 271 [M+H]$^+$.

Example 105B: benzyl [(2R)-6-(benzyloxy)-8-fluoro-7-(1,1,4-trioxo-1λ$^6$,2,5-thiadiazolidin-2-yl)-1,2,3,4-tetrahydronaphthalen-2-yl](3-ethylpentyl)carbamate To a solution of the product of Example 101F (0.1 g, 0.185 mmol) and the product of Example 105A (0.150 g, 0.556 mmol) in N,N-dimethylformamide (1 mL) was added a suspension of potassium tert-butoxide (0.104 g, 0.927 mmol) in N,N-dimethylformamide (2 mL) dropwise over 30 minutes. After 1 hour, the reaction mixture was diluted with water (1 mL) and filtered through a glass microfiber frit. The resulting solution was directly purified by loading onto a Teledyne ISCO 50 g reversed-phase C18 column eluted with a gradient of 10-100% methanol in buffer (0.025 M ammonium bicarbonate in water acidified to pH 7 by adding dry ice) to give the title compound as the ammonium salt (0.0305 g, 0.047 mmol, 25.1% yield). MS (APCI$^+$) m/z 655 [M+NH$_4$]$^+$.

Example 105C: 5-{(7R)-7-[(3-ethylpentyl)amino]-1-fluoro-3-hydroxy-5,6,7,8-tetrahydronaphthalen-2-yl}-1λ$^6$,2,5-thiadiazolidine-1,1,3-trione To a suspension the product of Example 105B (0.0305 g, 0.047 mmol) and pentamethylbenzene (0.014 g, 0.093 mmol) in dichloromethane (3.6 mL) at −78° C. was added a solution of boron trichloride (0.466 mL, 1 M in dichloromethane, 0.466 mmol) slowly along the side of the flask. The resulting mixture was stirred for 5 minutes, then warmed to an internal temperature of 0° C., then cooled to −78° C. and quenched with ethyl acetate (1 mL) followed by ethanol (1 mL). The reaction mixture was warmed to ambient temperature and concentrated in vacuo. The residue was triturated with heptanes (3×2 mL), 1:1 ethyl acetate/heptanes (2×2 mL), and dichloromethane (2×2 mL). The crude solid was dissolved in methanol (5 mL). Celite® (1 g) was added to the mixture, and the resultant mixture was concentrated. The residue was dry loaded onto a Teledyne ISCO 50 g reversed-phase C18 column eluted with a gradient of 10-100% methanol in buffer (0.025 M ammonium bicarbonate in water acidified to pH 7 by adding dry ice) to give the title compound (0.0156 g, 0.038 mmol, 81% yield). $^1$H NMR (400 MHz, DMSO-d$_6$) δ ppm 9.23 (br s, 1H), 8.49 (br s, 2H), 6.47 (d, J=1.4 Hz, 1H), 3.96-3.91 (m, 2H), 3.51-3.37 (m, 1H), 3.10 (dd, J=16.0, 5.4 Hz, 1H), 3.05-2.97 (m, 2H), 2.86-2.66 (m, 2H), 2.59-2.51 (m, 1H), 2.21-2.13 (m, 1H), 1.69 (qd, J=11.4, 5.6 Hz, 1H), 1.60-1.54 (m, 2H), 1.35-1.26 (m 5H), 0.85 (t, J=7.0 Hz, 6H); MS (APCI$^+$) m/z 414 [M+H]$^+$.

Example 106: 8-fluoro-6-hydroxy-N-(3-methylbutyl)-7-(1,1,4-trioxo-1λ$^6$,2,5-thiadiazolidin-2-yl)-3,4-dihydroisoquinoline-2(1H)-carboxamide (Compound 205)

Example 106A: 4-nitrophenyl Isopentylcarbamate

A solution of 3-methylbutan-1-amine (105 mg, 1.2 mmol) in dichloromethane (1 mL) was added dropwise to a stirred solution of 4-nitrophenyl chloroformate (242 mg, 1.200 mmol) and triethylamine (182 mg, 1.800 mmol) in dichloromethane (3 mL) at 0° C. The reaction mixture was allowed to warm to room temperature and was maintained at room temperature for 18 hours. The reaction mixture was then diluted with ethyl acetate (60 mL), washed with 0.2 N aqueous HCl solution (15 mL) and brine (2×15 ml), dried over anhydrous sodium sulfate, filtered and concentrated under reduced pressure. The residue was purified by flash column chromatography on silica gel (40 g) eluted with heptane/ethyl acetate (0 to 20%) to give the title compound (205 mg, 0.813 mmol, 68% yield). $^1$H NMR (500 MHz, DMSO-d$_6$) δ ppm 8.26 (dd, J=8, 2 Hz, 2H), 8.02 (m, 1H), 7.39 (dd, J=8, 2 Hz, 2H), 3.11 (dt, J=8, 7 Hz, 2H), 1.62 (m, 1H), 1.38 (m, 2H), 0.89 (d, J=7 Hz, 6H).

Example 106B: 6-(benzyloxy)-8-fluoro-N-(3-methylbutyl)-7-(1,1,4-trioxo-1λ$^6$,2,5-thiadiazolidin-2-yl)-3,4-dihydroisoquinoline-2(1H)-carboxamide A mixture of the product of Example 65A (122 mg, 0.18 mmol), the product of Example 106A (59.0 mg, 0.234 mmol), and potassium carbonate (87 mg, 0.630 mmol) in N,N-dimethylformamide (0.8 mL) was stirred at 60° C. for 1 hour. The mixture was cooled to room temperature, 0.5 N aqueous HCl solution (1.6 mL) and N,N-dimethylformamide (1 mL) were added. The solution was filtered, and the filtrate was concentrated under reduced pressure. The residue was purified by preparative HPLC [YMC TriArt™ C18 Hybrid 20 μm column, 25×150 mm, flow rate 80 mL/minute, 10-75% gradient of methanol in buffer (0.025 M aqueous ammonium bicarbonate, adjusted to pH 10 with ammonium hydroxide)] to give the title compound (76 mg, 0.146 mmol, 81% yield). MS (ESI$^-$) m/z 503 [M–H]$^-$.

Example 106C: 8-fluoro-6-hydroxy-N-(3-methylbutyl)-7-(1,1,4-trioxo-1λ$^6$,2,5-thiadiazolidin-2-yl)-3,4-dihydroisoquinoline-2(1H)-carboxamide To a mixture of 1,2,3,4,5-pentamethylbenzene (57.1 mg, 0.385 mmol) and Example 106B (67 mg, 0.128 mmol) in dichloromethane (3 mL) at –78° C. was added trichloroborane (1.927 mL, 1.93 mmol, 1 M in dichloromethane). The mixture was stirred at –78° C. for 20 minutes, then at 0° C. for 30 minutes. The mixture was quenched with ethanol (2 mL) and concentrated under reduced pressure. The residue was washed with heptane (3×2 mL) and dichloromethane (2×2 mL) and dried under reduced pressure. The resulting residue was dissolved in methanol/N,N-dimethylformamide (1:1, 3 mL) and purified by preparative HPLC [YMC TriArt™ C18 Hybrid 20 μm column, 25×150 mm, flow rate 80 mL/minute, 5-55% gradient of methanol in buffer (0.025 M aqueous ammonium bicarbonate, adjusted to pH 10 with ammonium hydroxide)] to give the title compound (36 mg, 0.083 mmol, 65% yield). $^1$H NMR (600 MHz, DMSO-d$_6$) δ ppm 9.23 (br s, 1H), 6.57 (t, J=5.4 Hz, 1H), 6.49 (s, 1H), 4.35 (s, 2H), 3.94 (s, 2H), 3.49 (t, J=5.8 Hz, 2H), 3.05 (m, 2H), 2.64 (t, J=5.8 Hz, 2H), 1.56 (m, 1H), 1.31 (m, 2H), 0.86 (d, J=6.6 Hz, 6H); MS (ESI$^-$) m/z 413 [M–H]$^-$.

Example 107: 8-fluoro-6-hydroxy-N-(2-methylpropyl)-7-(1,1,4-trioxo-1λ$^6$,2,5-thiadiazolidin-2-yl)-3,4-dihydroisoquinoline-2(1H)-carboxamide (Compound 206)

The title compound was prepared using the methodologies described in Example 106 substituting 2-methylpropan-1-amine for 3-methylbutan-1-amine. $^1$H NMR (600 MHz, DMSO-d$_6$) δ ppm 10.22 (br s, 1H), 6.67 (m, 1H), 6.56 (br s, 1H), 4.38 (s, 2H), 4.35 (s, 2H), 2.86 (m, 2H), 2.67 (t, J=6 Hz, 2H), 1.70 (m, 1H), 0.88 (m, 2H), 0.81 (d, J=7 Hz, 6H); MS (ESI$^-$) m/z 399 [M–H]$^-$.

Example 108: 5-{8-fluoro-6-hydroxy-2-[3-(pyridin-3-yl)propyl]-1,2,3,4-tetrahydroisoquinolin-7-yl}-1λ$^6$,2,5-thiadiazolidine-1,1,3-trione (Compound 207)

The title compound was prepared using the methodologies described in Example 71 substituting 3-(3-bromopropyl)pyridine, hydrobromic acid for 4-bromo-2-methylbutan-2-ol. $^1$H NMR (500 MHz, DMSO-d$_6$) δ ppm 10.31 (br s, 2H), 8.77 (br s, 1H), 8.71 (d, J=7 Hz, 1H), 8.36 (d, J=8 Hz, 1H), 7.88 (dd, J=8, 7 Hz, 1H), 6.59 (s, 1H), 4.41 (br s, 2H), 4.16 (s, 2H), 3.23 (m, 4H), 2.98-3.08 (m, 2H), 2.83 (m, 2H), 2.13 (m, 2H); MS (ESI$^-$) m/z 419 [M–H]$^-$.

Example 109: 5-{2-[(3,5-dimethyl-1,2-oxazol-4-yl)methyl]-8-fluoro-6-hydroxy-1,2,3,4-tetrahydroisoquinolin-7-yl}-1λ$^6$,2,5-thiadiazolidine-1,1,3-trione (Compound 208)

Example 109A: 5-{6-(benzyloxy)-2-[(3,5-dimethyl-1,2-oxazol-4-yl)methyl]-8-fluoro-1,2,3,4-tetrahydroisoquinolin-7-yl}-1λ$^6$,2,5-thiadiazolidine-1,1,3-trione To a vial containing 5-[6-(benzyloxy)-8-fluoro-1,2,3,4-tetrahydroisoquinolin-7-yl]-1λ$^6$,2,5-thiadiazolidine-1,1,3-trione, trifluoroacetic acid salt (theoretically 0.10 mmol, Example 93A) were added acetonitrile (0.34 mL), 4-(chloromethyl)-3,5-dimethylisoxazole (0.022 g, 0.15 mmol), and potassium carbonate (0.070 g, 0.51 mmol). The vial was then heated to 50° C. After 90 minutes, the reaction mixture was cooled to ambient temperature and filtered over diatomaceous earth with the aid of dichloromethane/methanol (9:1 v/v). The filtrate was concentrated under reduced pressure, and the residue was purified using silica gel chromatography [4 g column, 0-20% gradient of methanol in dichloromethane] to give the title compound (0.041 g, 0.082 mmol, 80% yield). $^1$H NMR (400 MHz, DMSO-d$_6$) δ ppm 7.53-7.45 (m, 2H), 7.38-7.31 (m, 2H), 7.31-7.26 (m, 1H), 6.72 (s, 1H), 5.10 (s, 2H), 3.94 (s, 2H), 3.45 (s, 2H), 3.43 (s, 2H), 2.73 (t, J=5.8 Hz, 2H), 2.57 (t, J=5.8 Hz, 2H), 2.35 (s, 3H), 2.17 (s, 3H); MS (APCI$^+$) m/z 501.3 [M+H]$^+$.

Example 109B: 5-{2-[(3,5-dimethyl-1,2-oxazol-4-yl)methyl]-8-fluoro-6-hydroxy-1,2,3,4-tetrahydroisoquinolin-7-yl}-1λ$^6$,2,5-thiadiazolidine-1,1,3-trione, Ammonium Salt A vial containing a suspension of 5-{6-(benzyloxy)-2-[(3,5-dimethyl-1,2-oxazol-4-yl)methyl]-8-fluoro-1,2,3,4-tetrahydroisoquinolin-7-yl}-1λ$^6$,2,5-thiadiazolidine-1,1,3-trione (0.076 g, 0.15 mmol, Example 109A) and 1,2,3,4,5-pentamethylbenzene (0.068 g, 0.46 mmol) in dichloromethane (1.5 mL) was cooled to –78° C. with stirring under an atmosphere of nitrogen. Next, trichloroborane (1.0 M in dichloromethane, 1.2 mL, 1.2 mmol) was added slowly. The resulting brownish mixture was stirred at –78° C. for 10 minutes, and then the dry ice-acetone bath was replaced with an ice-water bath. After 10 minutes, the mixture was recooled to –78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure, and then the residue was co-evaporated with ethanol (2×5 mL). The residue was purified using reversed-phase chromatography [60 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound as the corresponding ammonium salt (0.048 g, 0.11 mmol, 74% yield). $^1$H NMR (600 MHz, DMSO-d$_6$) δ ppm 9.28 (br s, 1H), 7.27-6.85 (m, 3H), 6.48 (s, 1H), 3.93 (s, 2H), 3.55 (br s, 4H), 2.85-2.68 (br s, 4H), 2.38 (s, 3H), 2.20 (s, 3H); MS (APCI$^+$) m/z 411.3 [M+H]$^+$.

Example 110: 5-{8-fluoro-6-hydroxy-2-[2-(1,3,5-trimethyl-1H-pyrazol-4-yl)ethyl]-1,2,3,4-tetrahydroisoquinolin-7-yl}-1λ$^6$,2,5-thiadiazolidine-1,1,3-trione (Compound 209)

Example 110A: 5-(6-(benzyloxy)-8-fluoro-2-(2-(1,3,5-trimethyl-1H-pyrazol-4-yl)ethyl)-1,2,3,4-tetrahydroisoquinolin-7-yl)-1,2,5-thiadiazolidin-3-one 1,1-dioxide To a vial containing the product of Example 93A (theoretically 0.10 mmol) were added 1,2-dichloroethane (0.31 mL) and triethylamine (0.028 mL, 0.20 mmol). The mixture was stirred for 5 minutes. A solution of 2-(1,3,5-trimethyl-1H-pyrazol-4-yl)acetaldehyde (0.023 g, 0.15 mmol, Example 110C) in 1,2-dichloroethane (0.20 mL) was then added and the resulting suspension was stirred at ambient temperature. After 10 minutes, sodium triacetoxyhydroborate (0.054 g, 0.26 mmol) was added. After 12 hours, the reaction mixture was poured into saturated aqueous sodium bicarbonate (20 mL) with the aid of dichloromethane. The resulting biphasic mixture was stirred for 20 minutes. The layers were then separated, and the aqueous phase was extracted with dichloromethane (2×20 mL). The organic phases were combined, washed with brine, dried over sodium sulfate, and concentrated under reduced pressure. The residue was purified using silica gel chromatography [4 g column, 0-25% gradient of methanol in dichloromethane] to give the title compound (0.049 g, 0.093 mmol, 91% yield). MS (APCI$^+$) m/z 528.4 [M+H]$^+$.

Example 110B: 5-{8-fluoro-6-hydroxy-2-[2-(1,3,5-trimethyl-1H-pyrazol-4-yl)ethyl]-1,2,3,4-tetrahydroisoquinolin-7-yl}-1λ$^6$,2,5-thiadiazolidine-1,1,3-trione A vial containing a suspension of 5-(6-(benzyloxy)-8-fluoro-2-(2-(1,3,5-trimethyl-1H-pyrazol-4-yl)ethyl)-1,2,3,4-tetrahydroisoquinolin-7-yl)-1,2,5-thiadiazolidin-3-one 1,1-dioxide (0.049 g, 0.093 mmol, Example 110A) and 1,2,3,4,5-pentamethylbenzene (0.041 g, 0.28 mmol) in dichloromethane (0.93 mL) was cooled to −78° C. with stirring under an atmosphere of nitrogen. Next, trichloroborane (1.0 M in dichloromethane) (0.74 mL, 0.74 mmol) was added slowly. The resulting brownish mixture was stirred at −78° C. for 10 minutes, and then the dry ice-acetone bath was replaced with an ice-water bath. After 10 minutes, the mixture was recooled to −78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [60 g Biotage® Sfär C18 Duo 100 Å 30 µm column, 10-100% gradient of methanol in water (buffered with 0.025 M aqueous ammonium bicarbonate, adjusted to pH 7 with dry ice)] to give the title compound (0.027 g, 0.062 mmol, 67% yield). $^1$H NMR (500 MHz, DMSO-d$_6$-D$_2$O) δ ppm 6.59 (s, 1H), 4.27 (br s, 2H), 4.02 (s, 2H), 3.55 (s, 3H), 3.43 (br s, 2H), 3.13 (dd, J=8.9, 6.2 Hz, 2H), 3.05-2.94 (m, 2H), 2.74 (dd, J=10.6, 6.4 Hz, 2H), 2.12 (s, 3H), 2.05 (s, 3H); MS (APCI$^+$) m/z 438.3 [M+H]$^+$.

Example 110C:
2-(1,3,5-trimethyl-1H-pyrazol-4-yl)acetaldehyde

To a flask were added 2-(1,3,5-trimethyl-1H-pyrazol-4-yl)ethanol (0.050 g, 0.32 mmol) and dichloromethane (1.6 mL). The white suspension was stirred at ambient temperature and Dess-Martin periodinane (0.206 g, 0.486 mmol) was added in portions. After 2 hours, the solid materials were removed by filtration over diatomaceous earth with the aid of dichloromethane. The filtrate was concentrated under reduced pressure. The residue was treated with tert-butyl methyl ether (20 mL) and filtered over diatomaceous earth. The filtrate was stirred with 0.1 M sodium thiosulfate/saturated aqueous sodium bicarbonate (1:1 v/v) (20 mL) for 15 minutes. The layers were then separated, and the aqueous phase was extracted with tert-butyl methyl ether (2×15 mL). The organic phases were combined, washed with water, brine, dried over sodium sulfate, and concentrated under reduced pressure. The residue was purified using silica gel chromatography [4 g column, 0-50% gradient of acetonitrile in dichloromethane] to give the title compound (0.032 g, 0.21 mmol, 65% yield). $^1$H NMR (600 MHz, DMSO-d$_6$) δ ppm 9.48 (t, J=2.1 Hz, 1H), 3.62 (s, 3H), 3.44 (d, J=2.1 Hz, 2H), 2.09 (s, 3H), 1.98 (s, 3H).

Example 111: 5-{8-fluoro-6-hydroxy-2-[2-(pyrimidin-5-yl)ethyl]-1,2,3,4-tetrahydroisoquinolin-7-yl}-1λ$^6$,2,5-thiadiazolidine-1,1,3-trione (Compound 210)

Example 111A: 2-(pyrimidin-5-yl)ethyl 4-methylbenzenesulfonate

4-Dimethylaminopyridine (4.9 mg, 0.040 mmol, 5.0 mol %) was added to a solution of p-toluenesulfonyl chloride (161.0 mg, 0.846 mmol, 1.1 equivalents), 2-(pyrimidin-5-yl)ethanol (100.0 mg, 0.806 mmol, 1 equivalent), and triethylamine (0.34 mL, 2.42 mmol, 3.0 equivalents) in dichloromethane (4.0 mL) at 23° C. The reaction mixture was stirred for 19 hours at 23° C. The reaction mixture was then diluted sequentially with ethyl acetate (25 mL), saturated aqueous sodium bicarbonate solution (3 mL), and water (3 mL). The resulting biphasic mixture was transferred to a separatory funnel and the layers that formed were separated. The organic layer was washed with saturated aqueous sodium chloride solution (5 mL). The washed organic layer was dried over sodium sulfate. The dried solution was filtered, and the filtrate was concentrated. The residue obtained was dissolved in 2% ethyl acetate-ether (v/v, 2 mL) and diluted with pentane (5 mL). A white precipitate formed. The suspension was filtered through a plug of diatomaceous earth (0.5 cm×1.0 cm). The filter cake was rinsed with ether (3×3 mL). The filtrates were combined, and the combined filtrates were concentrated. The title compound obtained was used without further purification in the following step.

Example 111B: 5-{6-(benzyloxy)-8-fluoro-2-[2-(pyrimidin-5-yl)ethyl]-1,2,3,4-tetrahydroisoquinolin-7-yl}-1λ$^6$,2,5-thiadiazolidine-1,1,3-trione, Ammonia Salt A suspension of the product of Example 111A (80.0 mg, 0.29 mmol, 1.4 equivalents), 5-[6-(benzyloxy)-8-fluoro-1,2, 3,4-tetrahydroisoquinolin-7-yl]-1λ⁶,2,5-thiadiazolidine-1,1,3-trione, trifluoroacetate (nominally 0.203 mmol, 1 equivalent, Example 54A), and potassium carbonate (80.0 mg, 0.58 mmol, 2.9 equivalents) in acetonitrile (0.8 mL) was placed in a heating block that had been preheated to 70° C. The reaction mixture was stirred for 18 hours at 70° C. The reaction mixture was cooled to 23° C. The cooled reaction mixture was diluted with dimethyl sulfoxide (1 mL) and water (0.5 mL). The diluted mixture was purified by reversed-phase flash column chromatography (50 g RediSep® Gold C18 column, eluted with a gradient from 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (52 mg, 52% yield, two steps). MS (APCI⁺) m/z 498 [M+H]⁺.

Example 111C: 5-{8-fluoro-6-hydroxy-2-[2-(pyrimidin-5-yl)ethyl]-1,2,3,4-tetrahydroisoquinolin-7-yl}-1λ⁶,2,5-thiadiazolidine-1,1,3-trione A solution of boron trichloride in dichloromethane (1.0 M, 0.65 mL, 0.65 mmol, 6.2 equivalents) was added to a suspension of the product of Example 111B (52 mg, 0.105 mmol, 1 equivalent) in dichloromethane (0.53 mL) at −78° C. The reaction vessel was immediately transferred to a cooling bath at 0° C. The reaction mixture was stirred for 15 minutes at 0° C. The reaction vessel was then transferred to a cooling bath at −78° C. Additional boron trichloride in dichloromethane (1.0 M, 1.00 mL, 1.00 mmol, 9.5 equivalents) was added at −78° C. The reaction vessel was immediately removed from its cooling bath and warmed over 1.5 hours to 23° C. The reaction vessel was transferred to a cooling bath at −78° C. and cooled over 30 minutes to −78° C. The reaction mixture was diluted slowly with ethanol (2.5 mL) at −78° C. The diluted mixture was warmed over 15 minutes to 23° C. The warmed mixture was concentrated. The residue obtained was triturated sequentially with 1% methanol-dichloromethane (v/v, 1.0 mL), ethyl acetate (2.0 mL), 30% acetone-heptanes (2.0 mL), and heptanes (2.0 mL) to furnish the title compound (36 mg, 0.088 mmol, 84% yield). ¹H NMR (400 MHz, DMSO-d₆) δ ppm 11.28 (bs, 1H), 9.11 (s, 1H), 8.81 (s, 2H), 6.70 (s, 1H), 4.58-4.19 (m, 5H), 3.60-3.48 (m, 2H), 3.39-3.24 (m, 4H), 3.10-2.96 (m, 1H); MS (APCI⁺) m/z 408 [M+H]⁺.

Example 112: 5-{2-[2-(3,5-dimethyl-1,2-oxazol-4-yl)ethyl]-8-fluoro-6-hydroxy-1,2,3,4-tetrahydroisoquinolin-7-yl}-1λ⁶,2,5-thiadiazolidine-1,1,3-trione (Compound 211)

Example 112A: 5-{6-(benzyloxy)-2-[2-(3,5-dimethyl-1,2-oxazol-4-yl)ethyl]-8-fluoro-1,2,3,4-tetrahydroisoquinolin-7-yl}-1λ⁶,2,5-thiadiazolidine-1,1,3-trione To a vial containing the product of Example 93A (theoretically 0.203 mmol) were added 1,2-dichloroethane (0.61 mL) and triethylamine (0.057 mL, 0.41 mmol). The mixture was stirred for 5 minutes. A solution of 2-(3,5-dimethylisoxazol-4-yl)acetaldehyde (0.042 g, 0.31 mmol, Example 112C) in 1,2-dichloroethane (0.41 mL) was then added and the resulting suspension was stirred at ambient temperature. After 10 minutes, sodium triacetoxyhydroborate (0.108 g, 0.508 mmol) was added. After 12 hours, the reaction mixture was poured into saturated aqueous sodium bicarbonate (20 mL) with the aid of dichloromethane. The resulting biphasic mixture was stirred for 20 minutes. The layers were then separated, and the aqueous phase was extracted with dichloromethane (2×20 mL). The organic phases were combined, washed with brine, dried over sodium sulfate, and concentrated under reduced pressure. The residue was purified using silica gel chromatography [12 g column, 0-25% gradient of methanol in dichloromethane] to give the title compound (0.088 g, 0.17 mmol, 84% yield). MS (APCI⁺) m/z 515.3 [M+H]⁺.

Example 112B: 5-{2-[2-(3,5-dimethyl-1,2-oxazol-4-yl)ethyl]-8-fluoro-6-hydroxy-1,2,3,4-tetrahydroisoquinolin-7-yl}-1λ⁶,2,5-thiadiazolidine-1,1,3-trione A vial containing a suspension of 5-{6-(benzyloxy)-2-[2-(3,5-dimethyl-1,2-oxazol-4-yl)ethyl]-8-fluoro-1,2,3,4-tetrahydroisoquinolin-7-yl}-1λ⁶,2,5-thiadiazolidine-1,1,3-trione (0.085 g, 0.17 mmol) and 1,2,3,4,5-pentamethylbenzene (0.073 g, 0.50 mmol) in dichloromethane (1.7 mL) was cooled to −78° C. with stirring under an atmosphere of nitrogen. Next, trichloroborane (1.0 M in dichloromethane) (1.3 mL, 1.3 mmol) was added slowly. The resulting brownish mixture was stirred at −78° C. for 10 minutes, and then the dry ice-acetone bath was replaced with an ice-water bath. After 10 minutes, the mixture was recooled to −78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [100 g Isco RediSep Rf Gold® C18 column, 10-100% gradient of methanol in water (buffered with 0.025 M aqueous ammonium bicarbonate, adjusted to pH 7 with dry ice)] to give the title compound (0.039 g, 0.092 mmol, 56% yield). ¹H NMR (600 MHz, DMSO-d₆-D₂O) δ ppm 6.59 (s, 1H), 4.16 (br s, 2H), 3.97 (s, 2H), 3.40-3.17 (br m, 4H), 3.05-2.92 (m, 2H), 2.78 (t, J=8.3 Hz, 2H), 2.33 (s, 3H), 2.19 (s, 3H); MS (ESI⁺) m/z 424.9 [M+H]⁺.

Example 112C: 2-(3,5-dimethylisoxazol-4-yl)acetaldehyde

To a flask were added 2-(3,5-dimethylisoxazol-4-yl)ethanol (0.200 g, 1.42 mmol) and dichloromethane (7.1 mL). The white suspension was stirred at ambient temperature and Dess-Martin periodinane (0.721 g, 1.70 mmol) was added in portions. After 2 hours, the solid materials were removed by filtration over diatomaceous earth with the aid of tert-butyl methyl ether. The filtrate was concentrated under reduced pressure. The residue was treated with tert-butyl methyl ether (50 mL) and filtered over diatomaceous earth. The filtrate was stirred with 0.1 M sodium thiosulfate/saturated aqueous sodium bicarbonate (1:1 v/v) (50 mL) for 15 minutes. The layers were then separated, and the aqueous phase was extracted with tert-butyl methyl ether (2×50 mL). The organic phases were combined, washed with water and brine, dried over sodium sulfate, and concentrated under reduced pressure to give the title compound (0.061 g, 0.44 mmol, 31% yield). ¹H NMR (600 MHz, CDCl₃) δ ppm 9.66 (t, J=1.8 Hz, 1H), 3.41 (d, J=1.7 Hz, 2H), 2.33 (s, 3H), 2.18 (s, 3H).

Example 113: 5-{2-[(3,5-dimethyl-1H-pyrazol-4-yl)methyl]-8-fluoro-6-hydroxy-1,2,3,4-tetrahydroisoquinolin-7-yl}-1λ⁶,2,5-thiadiazolidine-1,1,3-trione (Compound 212)

Example 113A: 5-{6-(benzyloxy)-2-[(3,5-dimethyl-1H-pyrazol-4-yl)methyl]-8-fluoro-1,2,3,4-tetrahydroisoquinolin-7-yl}-1λ⁶,2,5-thiadiazolidine-1,1,3-trione To a vial containing the product of Example 93A (theoretically 0.15 mmol) were added 1,2-dichloroethane (0.77 mL) and triethylamine (0.043 mL, 0.31 mmol). The resulting mixture was stirred for 5 minutes, then 3,5-dimethyl-1H-pyrazole-4-carbaldehyde (0.028 g, 0.23 mmol, Example 113C) was added. After 10 minutes, sodium triacetoxyhydroborate (0.081 g, 0.38 mmol) was added. After 13 hours, the reaction mixture was poured into saturated aqueous sodium bicarbonate (20 mL) with the aid of dichloromethane. The resulting biphasic mixture was stirred for 20 minutes. The layers were then separated, and the aqueous phase was extracted with dichloromethane (2×20 mL). The organic phases were combined, washed with brine, dried over sodium sulfate, and concentrated under reduced pressure. The residue was purified using reversed-phase chromatography [100 g Isco RediSep Rf Gold® C18 column, 10-100% gradient of methanol in water (buffered with 0.025 M aqueous ammonium bicarbonate, adjusted to pH 7 with dry ice)] to give the title compound (0.045 g, 0.090 mmol, 59% yield). $^1$H NMR (400 MHz, DMSO-d$_6$-D$_2$O) δ ppm 7.44 (d, J=7.3 Hz, 2H), 7.37-7.30 (m, 2H), 7.30-7.23 (m, 1H), 6.85 (s, 1H), 5.12 (s, 2H), 4.22 (br s, 4H), 4.00 (s, 2H), 3.34 (br s, 2H), 3.02 (br s, 2H), 2.20 (s, 6H); MS (APCI$^+$) m/z 500.4 [M+H]$^+$.

Example 113B: 5-{2-[(3,5-dimethyl-1H-pyrazol-4-yl)methyl]-8-fluoro-6-hydroxy-1,2,3,4-tetrahydroisoquinolin-7-yl}-1λ⁶,2,5-thiadiazolidine-1,1,3-trione A vial containing a suspension of 5-{6-(benzyloxy)-2-[(3,5-dimethyl-1H-pyrazol-4-yl)methyl]-8-fluoro-1,2,3,4-tetrahydroisoquinolin-7-yl}-1λ⁶,2,5-thiadiazolidine-1,1,3-trione (0.044 g, 0.088 mmol, Example 113A) and 1,2,3,4,5-pentamethylbenzene (0.039 g, 0.26 mmol) in dichloromethane (0.88 mL) was cooled to −78° C. with stirring under an atmosphere of nitrogen. Next, trichloroborane (1.0 M in dichloromethane) (0.71 mL, 0.71 mmol) was added slowly. The resulting brownish mixture was stirred at −78° C. for 10 minutes, and then the dry ice-acetone bath was replaced with an ice-water bath. After 10 minutes, the mixture was recooled to −78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [60 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.023 g, 0.056 mmol, 64% yield). $^1$H NMR (600 MHz, DMSO-d$_6$-D$_2$O) δ ppm 6.55 (s, 1H), 4.05 (br s, 4H), 3.97 (s, 2H), 3.24 (br s, 2H), 2.92 (br s, 2H), 2.18 (s, 6H); MS (APCI$^+$) m/z 410.3 [M+H]$^+$.

Example 113C: 3,5-dimethyl-1H-pyrazole-4-carbaldehyde

To a flask were added (3,5-dimethyl-1H-pyrazol-4-yl)methanol (0.188 g, 1.49 mmol) and dichloromethane (7.5 mL). The white suspension was stirred at ambient temperature and Dess-Martin periodinane (0.948 g, 2.24 mmol) was added in portions. After 2 hours, the solid materials were removed by filtration over diatomaceous earth with the aid of tert-butyl methyl ether. The filtrate was concentrated under reduced pressure. The residue was treated with tert-butyl methyl ether (50 mL) and filtered over diatomaceous earth. The filtrate was stirred with 0.1 M sodium thiosulfate/saturated aqueous sodium bicarbonate (1:1 v/v) (50 mL) for 15 minutes. The layers were then separated, and the aqueous phase was extracted with tert-butyl methyl ether (2×50 mL). The organic phases were combined, washed with water, brine, dried over sodium sulfate, and concentrated under reduced pressure to give the title compound (0.085 g, 0.69 mmol, 46% yield). $^1$H NMR (400 MHz, CDCl$_3$) δ ppm 9.97 (s, 1H), 2.52 (s, 6H).

Example 114: 5-{8-fluoro-6-hydroxy-2-[(1,3,5-trimethyl-1H-pyrazol-4-yl)methyl]-1,2,3,4-tetrahydroisoquinolin-7-yl}-1λ⁶,2,5-thiadiazolidine-1,1,3-trione (Compound 213)

Example 114A: 5-{6-(benzyloxy)-8-fluoro-2-[(1,3,5-trimethyl-1H-pyrazol-4-yl)methyl]-1,2,3,4-tetrahydroisoquinolin-7-yl}-1λ⁶,2,5-thiadiazolidine-1,1,3-trione To a vial containing the product of Example 93A (theoretically 0.15 mmol) were added 1,2-dichloroethane (0.77 mL) and triethylamine (0.043 mL, 0.31 mmol). The mixture was stirred for 5 minutes, then 1,3,5-trimethyl-1H-pyrazole-4-carbaldehyde (0.032 g, 0.23 mmol) was added. After 10 minutes, sodium triacetoxyhydroborate (0.081 g, 0.38 mmol) was added. After 13 hours, the reaction mixture was poured into saturated aqueous sodium bicarbonate (20 mL) with the aid of dichloromethane. The resulting biphasic mixture was stirred for 20 minutes. The layers were then separated, and the aqueous phase was extracted with dichloromethane (2×20 mL). The organic phases were combined, washed with brine, dried over sodium sulfate, and concentrated under reduced pressure. The residue was purified using reversed-phase chromatography [100 g Isco RediSep Rf Gold® C18 column, 10-100% gradient of methanol in water (buffered with 0.025 M aqueous ammonium bicarbonate, adjusted to pH 7 with dry ice)] to give the title compound (0.050 g, 0.097 mmol, 64% yield). $^1$H NMR (600 MHz, DMSO-d$_6$-D2O) δ ppm 7.48-7.42 (m, 2H), 7.36-7.30 (m, 2H), 7.30-7.24 (m, 1H), 6.84 (s, 1H), 5.12 (s, 2H), 4.17 (br s, 4H), 3.99 (s, 2H), 3.63 (s, 3H), 3.27 (br s, 2H), 2.98 (br s, 2H), 2.22 (s, 3H), 2.14 (s, 3H); MS (APCI$^+$) m/z 514.4 [M+H]$^+$.

Example 114B: 5-{8-fluoro-6-hydroxy-2-[(1,3,5-trimethyl-1H-pyrazol-4-yl)methyl]-1,2,3,4-tetrahydroisoquinolin-7-yl}-1λ⁶,2,5-thiadiazolidine-1,1,3-trione A vial containing a suspension of 5-{6-(benzyloxy)-8-fluoro-2-[(1,3,5-trimethyl-1H-pyrazol-4-yl)methyl]-1,2,3,4-tetrahydroisoquinolin-7-yl}-1λ⁶,2,5-thiadiazolidine-1,1,3-trione (0.047 g, 0.092 mmol, Example 114A) and 1,2,3,4,5-pentamethylbenzene (0.041 g, 0.28 mmol) in dichloromethane (0.92 mL) was cooled to −78° C. with stirring under an atmosphere of nitrogen. Next, trichloroborane (1.0 M in dichloromethane) (0.73 mL, 0.73 mmol) was added slowly. The resulting brownish mixture was stirred at −78° C. for 10 minutes, and then the dry ice-acetone bath was replaced with an ice-water bath. After 10 minutes, the mixture was recooled to −78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [60 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.028 g, 0.066 mmol, 72% yield). $^1$H NMR (600 MHz, pyridine-d$_5$) δ ppm 6.77 (s, 1H), 4.66 (s, 2H), 3.78 (s, 2H), 3.67 (s, 2H), 3.63 (s, 3H), 2.83 (s, 4H), 2.39 (s, 3H), 2.15 (s, 3H); MS (APCI$^+$) m/z 424.2 [M+H]$^+$.

Example 114C:
1,3,5-trimethyl-1H-pyrazole-4-carbaldehyde

To a flask were added (1,3,5-trimethyl-1H-pyrazol-4-yl)methanol (0.209 g, 1.49 mmol) and dichloromethane (7.5 mL). The white suspension was stirred at ambient temperature and Dess-Martin periodinane (0.759 g, 1.79 mmol) was added in portions. After 2 hours, the solid materials were removed by filtration over diatomaceous earth with the aid of tert-butyl methyl ether. The filtrate was concentrated under reduced pressure. The residue was treated with tert-butyl methyl ether (50 mL) and filtered over diatomaceous earth. The filtrate was stirred with 0.1 M sodium thiosulfate/saturated aqueous sodium bicarbonate (1:1 v/v) (50 mL) for 15 minutes. The layers were then separated, and the aqueous phase was extracted with tert-butyl methyl ether (2×50 mL). The organic phases were combined, washed with water and brine, dried over sodium sulfate, and concentrated under reduced pressure to give the title compound (0.101 g, 0.731 mmol, 49% yield). $^1$H NMR (600 MHz, CDCl$_3$) δ ppm 9.89 (s, 1H), 3.73 (s, 3H), 2.50 (s, 3H), 2.42 (s, 3H).

Example 115: 5-{8-fluoro-6-hydroxy-2-[2-(oxan-4-yl)ethyl]-1,2,3,4-tetrahydroisoquinolin-7-yl}-1λ$^6$,2,5-thiadiazolidine-1,1,3-trione (Compound 214)

Example 115A: 5-{6-(benzyloxy)-8-fluoro-2-[2-(oxan-4-yl)ethyl]-1,2,3,4-tetrahydroisoquinolin-7-yl}-1λ$^6$,2,5-thiadiazolidine-1,1,3-trione To a vial containing the product of Example 93A (theoretically 0.15 mmol) were added 1,2-dichloroethane (0.77 mL) and triethylamine (0.043 mL, 0.31 mmol). The mixture was stirred for 5 minutes, then 2-(tetrahydro-2H-pyran-4-yl)acetaldehyde (0.029 g, 0.23 mmol) was added. After 10 minutes, sodium triacetoxyhydroborate (0.081 g, 0.38 mmol) was added. After 14 hours, the reaction mixture was poured into saturated aqueous sodium bicarbonate (20 mL) with the aid of dichloromethane. The resulting biphasic mixture was stirred for 20 minutes. The layers were then separated, and the aqueous phase was extracted with dichloromethane (2×20 mL). The organic phases were combined, washed with brine, dried over sodium sulfate, and concentrated under reduced pressure to give the title compound. This material was used without further purification. MS (APCI$^+$) m/z 504.3 [M+H]$^+$.

Example 115B: 5-{8-fluoro-6-hydroxy-2-[2-(oxan-4-yl)ethyl]-1,2,3,4-tetrahydroisoquinolin-7-yl}-1λ$^6$,2,5-thiadiazolidine-1,1,3-trione A flask containing a suspension of 5-{6-(benzyloxy)-8-fluoro-2-[2-(oxan-4-yl)ethyl]-1,2,3,4-tetrahydroisoquinolin-7-yl}-1λ$^6$,2,5-thiadiazolidine-1,1,3-trione (theoretically 0.15 mmol) and 1,2,3,4,5-pentamethylbenzene (0.068 g, 0.46 mmol) in dichloromethane (1.5 mL) was cooled to −78° C. with stirring under an atmosphere of nitrogen. Next, trichloroborane (1.0 M in dichloromethane) (1.2 mL, 1.2 mmol) was added slowly. The resulting brownish mixture was stirred at −78° C. for 15 minutes, and then the dry ice-acetone bath was replaced with an ice-water bath. After 15 minutes, the mixture was recooled to −78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.026 g, 0.064 mmol, 42% yield). $^1$H NMR (400 MHz, DMSO-d$_6$-D$_2$O) δ ppm 6.58 (s, 1H), 4.18 (s, 2H), 3.99 (s, 2H), 3.79 (dd, J=11.1, 3.4 Hz, 2H), 3.40-3.30 (m, 2H), 3.25 (td, J=11.7, 1.9 Hz, 2H), 3.21-3.13 (m, 2H), 2.97 (t, J=6.2 Hz, 2H), 1.69-1.60 (m, 2H), 1.60-1.47 (m, 3H), 1.25-1.09 (m, 2H); MS (APCI$^+$) m/z 414.3 [M+H]$^+$.

Example 116: 5-[2-(2-cyclohexyl-2-hydroxyethyl)-8-fluoro-6-hydroxy-1,2,3,4-tetrahydroisoquinolin-7-yl]-1λ$^6$,2,5-thiadiazolidine-1,1,3-trione (Compound 215)

Example 116A: 5-[6-(benzyloxy)-2-(2-cyclohexyl-2-hydroxyethyl)-8-fluoro-1,2,3,4-tetrahydroisoquinolin-7-yl]-1λ$^6$,2,5-thiadiazolidine-1,1,3-trione, Ammonia Salt A suspension of 5-[6-(benzyloxy)-8-fluoro-1,2,3,4-tetrahydroisoquinolin-7-yl]-1λ$^6$,2,5-thiadiazolidine-1,1,3-trione, trifluoroacetate (nominally 0.19 mmol, 1 equivalent, Example 54A), sodium perchlorate (96 mg, 0.78 mmol, 4.0 equivalents), and 2-cyclohexyloxirane (50 mg, 0.39 mmol, 2.0 equivalents) in acetonitrile (0.5 mL) was stirred for 66 hours at 23° C. Additional sodium perchlorate (114 mg, 0.93 mmol, 4.8 equivalents) was added at 23° C. The reaction mixture was stirred for 5 hours at 23° C. The mixture was diluted then with water (0.5 mL) and dimethyl sulfoxide (1.0 mL). The diluted mixture was purified by reversed-phase flash column chromatography (100 g RediSep Gold® C18 column, eluted with a gradient from 10-100% [v/v]methanol-0.025 M aqueous ammonium bicarbonate solution [acidified with solid carbon dioxide] over 10 column volumes, then isocratically eluted with 100% methanol for 3 column volumes, flow rate=80 mL/minute) to furnish the title compound (37 mg, 0.069 mmol, 37% yield). MS (APCI$^+$) m/z 518 [M+H]$^+$.

Example 116B: 5-[2-(2-cyclohexyl-2-hydroxyethyl)-8-fluoro-6-hydroxy-1,2,3,4-tetrahydroisoquinolin-7-yl]-1λ$^6$,2,5-thiadiazolidine-1,1,3-trione A solution of boron trichloride in dichloromethane (1.0 M, 1.07 mL, 1.07 mmol, 15.0 equivalents) was added to a suspension of the product of Example 116A (52 mg, 0.071 mmol, 1 equivalent) in dichloromethane (0.7 mL) at −78° C. The reaction vessel was immediately transferred to a cooling bath at 0° C. The reaction mixture was stirred for 40 minutes at 0° C. The reaction vessel was then transferred to a cooling bath at −78° C. and cooled over 10 minutes to −78° C. The reaction mixture was diluted sequentially with ethyl acetate (1.0 mL) and ethanol (1.0 mL) slowly at −78° C. The diluted mixture was warmed over 15 minutes to 23° C. The warmed mixture was concentrated. The residue obtained was triturated with 20% acetone-heptanes (3×2.0 mL) to furnish the title compound (9.0 mg, 0.021 mmol, 30% yield). $^1$H NMR (400 MHz, DMSO-d$_6$) δ ppm 6.73 (s, 1H), 4.52 (s, 2H), 4.21-4.08 (m, 2H), 3.64-3.45 (m, 3H), 2.96 (dt, J=10.9, 5.6 Hz, 2H), 1.80-0.89 (m, 13H); MS (APCI$^+$) m/z 428 [M+H]$^+$.

Example 117: 5-[8-fluoro-6-hydroxy-2-(2-methoxyethyl)-1,2,3,4-tetrahydroisoquinolin-7-yl]-1λ$^6$,2,5-thiadiazolidine-1,1,3-trione (Compound 216)

Example 117A: 5-[6-(benzyloxy)-8-fluoro-2-(2-methoxyethyl)-1,2,3,4-tetrahydroisoquinolin-7-yl]-1λ$^6$,2,5-thiadiazolidine-1,1,3-trione To a vial containing a suspension of the product of Example 65A (150 mg, 0.297 mmol) in acetonitrile (1.5 ml) was added potassium carbonate (205 mg, 1.484 mmol), and the mixture was stirred at ambient temperature for 10 minutes. Then, 1-bromo-2-methoxyethane (0.028 mL, 0.298 mmol) was added, and the mixture was heated to 50° C. for 40 hours. The solution was cooled to room temperature and then filtered over diatomaceous earth eluted sequentially with acetonitrile and methanol. The filtrate was concentrated under reduced pressure. The residue was filtered through a glass microfiber frit and rinsed with a minimal amount of methanol. The resulting solution was purified by reversed-phase HPLC [Waters XBridge™ RP18 column, 5 jam, 30×100 mm, flow rate 40 mL/minute, 5-100% gradient of acetonitrile in buffer 0.025 M aqueous ammonium bicarbonate, adjusted to pH 10 with ammonium hydroxide)] to give the title compound (93 mg, 0.207 mmol, 69.7% yield). MS (APCI$^+$) m/z 450 [M+H]$^+$.

Example 117B: 5-[8-fluoro-6-hydroxy-2-(2-methoxyethyl)-1,2,3,4-tetrahydroisoquinolin-7-yl]-1λ$^6$,2,5-thiadiazolidine-1,1,3-trione Trichloroborane (1.0 M in dichloromethane, 1068 μL, 1.068 mmol) was added dropwise to a vial containing a suspension of the product of Example 117A (60 mg, 0.133 mmol) and 1,2,3,4,5-pentamethylbenzene (59.4 mg, 0.400 mmol) in dichloromethane (0.929 ml) cooled to −78° C. The resulting mixture was stirred at −78° C. for 15 minutes, then at 0° C. for 45 minutes, and then at ambient temperature for 1.5 hours. The mixture was cooled back to −78° C., diluted with dichloromethane (5 mL), and quenched with the addition of ethyl acetate (3 mL) and ethanol (3 mL). The mixture was then warmed to ambient temperature and stirred for an additional 15 minutes. The mixture was diluted with ethanol and concentrated under reduced pressure. The residue was filtered through a glass microfiber frit and rinsed with a minimal amount of methanol. The resulting solution was purified by reversed-phase HPLC [Waters XBridge™ RP18 column, 5 jam, 30×100 mm, flow rate 40 mL/minute, 5-100% gradient of acetonitrile in buffer 0.025 M aqueous ammonium bicarbonate, adjusted to pH 10 with ammonium hydroxide)] to give the ammonium salt of the title compound (24.1 mg, 0.067 mmol, 50.2% yield). $^1$H NMR (600 MHz, DMSO-d$_6$/D$_2$O) δ ppm 7.36 (s, 3H), 6.61 (d, J=4.8 Hz, 1H), 4.24 (s, 2H), 3.99 (s, 2H), 3.76 (t, J=5.0 Hz, 2H), 3.38 (s, 4H), 3.33 (s, 3H), 3.02 (s, 2H); MS (APCI$^+$) m/z 360.33 [M+H]$^+$.

Example 118: 5-[8-fluoro-6-hydroxy-2-(3-methoxypropyl)-1,2,3,4-tetrahydroisoquinolin-7-yl]-1λ$^6$,2,5-thiadiazolidine-1,1,3-trione (Compound 217)

Example 118A: 5-[6-(benzyloxy)-8-fluoro-2-(3-methoxypropyl)-1,2,3,4-tetrahydroisoquinolin-7-yl]-1λ$^6$,2,5-thiadiazolidine-1,1,3-trione To a vial containing a suspension of the product of Example 65A (100 mg, 0.198 mmol) in acetonitrile (1.5 ml) was added potassium carbonate (137 mg, 0.989 mmol) and 1-bromo-3-methoxypropane (0.033 mL, 0.297 mmol). The mixture was stirred at 60° C. for 4 hours. The solution was filtered over a pad of diatomaceous earth with excess acetonitrile and concentrated under reduced pressure. The residue was then filtered through a glass microfiber frit rinsed with a minimal amount of methanol. The resulting solution was purified by reversed-phase HPLC [Waters XBridge™ RP18 column, 5 μm, 30×100 mm, flow rate 40 mL/minute, 5-100% gradient of acetonitrile in buffer 0.025 M aqueous ammonium bicarbonate, adjusted to pH 10 with ammonium hydroxide)] to give the title compound (40.4 mg, 0.087 mmol, 44.1% yield). MS (APCI$^+$) m/z 464 [M+H]$^+$.

Example 118B: 5-[8-fluoro-6-hydroxy-2-(3-methoxypropyl)-1,2,3,4-tetrahydroisoquinolin-7-yl]-1λ$^6$,2,5-thiadiazolidine-1,1,3-trione Trichloroborane (1.0 M in dichloromethane, 604 μL, 0.604 mmol) was added dropwise to a vial containing a suspension of the product of Example 118A (35 mg, 0.076 mmol) and 1,2,3,4,5-pentamethylbenzene (33.6 mg, 0.227 mmol) in dichloromethane (755 μL) cooled to −78° C. The resulting mixture was stirred at −78° C. for 15 minutes, and then at 0° C. for 15 minutes. The mixture was cooled back to −78° C., diluted with dichloromethane (5 mL), and quenched with ethyl acetate (3 mL) and ethanol (3 mL). The mixture was warmed to ambient temperature and stirred for 15 minutes. The mixture was diluted with ethanol and concentrated under reduced pressure. The residue was filtered through a glass microfiber frit rinsed with a minimal amount of methanol. The resulting filtrate was purified by reversed-phase HPLC [Waters XBridge™ RP18 column, 5 μm, 30×100 mm, flow rate 40 mL/minute, 5-100% gradient of acetonitrile in buffer 0.025 M aqueous ammonium bicarbonate, adjusted to pH 10 with ammonium hydroxide)] to give the title compound as the ammonium salt (23.7 mg, 0.058 mmol, 77% yield). $^1$H NMR (500 MHz, DMSO-d$_6$/D$_2$O) δ ppm 7.31 (s, 6H), 6.59 (s, 1H), 4.13 (s, 4H), 3.98 (s, 2H), 3.41 (t, J=5.9 Hz, 2H), 3.23 (s, 3H), 2.98 (s, 2H), 1.97 (s, 2H); MS (APCI$^+$) m/z 374 [M+H]$^+$.

Example 119: 5-[2-(3-aminopropyl)-8-fluoro-6-hydroxy-1,2,3,4-tetrahydroisoquinolin-7-yl]-1$\lambda^6$,2,5-thiadiazolidine-1,1,3-trione (Compound 218)

Example 119A: tert-butyl {3-[6-(benzyloxy)-8-fluoro-7-(1,1,4-trioxo-1$\lambda^6$,2,5-thiadiazolidin-2-yl)-3,4-dihydroisoquinolin-2(1H)-yl]propyl}carbamate, Ammonia Salt Triethylamine (0.12 mL, 0.86 mmol, 3.4 equivalents) was added to a suspension of the 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.25 mmol, 1 equivalent, Example 54A) in acetonitrile (0.80 mL) at 23° C. The reaction mixture was stirred for 30 minutes at 23° C. A solution of tert-butyl (3-oxopropyl)carbamate (57 mg, 0.33 mmol, 1.3 equivalents) in acetonitrile (0.3 mL) was added at 23° C. The reaction mixture was stirred for 3 minutes at 23° C. Sodium triacetoxyborohydride (135 mg, 0.64 mmol, 2.5 equivalents) was added in one portion at 23° C. The reaction mixture was stirred for 1.5 hours at 23° C. The reaction mixture was diluted sequentially with aqueous sodium bisulfate solution (1.0 mL, CAUTION: gas evolution) and dimethyl sulfoxide (1.0 mL). The diluted mixture was purified by reversed-phase flash column chromatography (50 g RediSep Rf Gold® C18 column, eluted with a gradient from 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (70 mg, 0.12 mmol, 50% yield, two steps). MS (APCI$^+$) m/z 549 [M+H]$^+$.

Example 119B: 5-[2-(3-aminopropyl)-8-fluoro-6-hydroxy-1,2,3,4-tetrahydroisoquinolin-7-yl]-1$\lambda^6$,2,5-thiadiazolidine-1,1,3-trione, bis(hydrochloride) Salt A solution of boron trichloride in dichloromethane (1.0 M, 2.06 mL, 2.06 mmol, 14.5 equivalents) was added to a suspension of the product of Example 119A (78 mg, 0.142 mmol, 1 equivalent) in dichloromethane (1.4 mL) at −78° C. The reaction vessel was immediately transferred to a cooling bath at 0° C. The reaction mixture was stirred for 30 minutes at 0° C. The reaction vessel was then transferred to a cooling bath at −78° C. and cooled over 15 minutes to −78° C. Additional boron trichloride in dichloromethane (1.0 M, 1.00 mL, 1.00 mmol, 9.5 equivalents) was added at −78° C. The reaction vessel was immediately removed from its cooling bath and warmed over 1.5 hours to 23° C. The reaction vessel was transferred to a cooling bath at −78° C. and cooled over 15 minutes to −78° C. The reaction mixture was diluted sequentially with ethyl acetate (1.0 mL) and ethanol (1.0 mL) slowly at −78° C. The diluted mixture was warmed over 15 minutes to 23° C. The warmed mixture was concentrated. The residue obtained was triturated successively with ethanol (3×1.0 mL), acetonitrile (1.0 mL), and ethyl acetate (1.0 mL) to furnish the title compound (55 mg, 0.13 mmol, 90% yield). $^1$H NMR (600 MHz, DMSO-d$_6$) δ ppm 10.89 (bs, 1H), 10.13 (bs, 1H), 6.63 (s, 1H), 4.46-4.36 (m, 1H), 4.17-4.08 (m, 3H), 3.71-3.58 (m, 2H), 3.32-3.13 (m, 4H), 2.99-2.86 (m, 2H), 2.19-2.07 (m, 2H); MS (APCI$^+$) m/z 359 [M+H]$^+$.

Example 120: 5-{8-fluoro-6-hydroxy-2-[3-(piperidin-4-yl)propyl]-1,2,3,4-tetrahydroisoquinolin-7-yl}-1$\lambda^6$,2,5-thiadiazolidine-1,1,3-trione (Compound 219)

Example 120A: tert-butyl 4-{3-[6-(benzyloxy)-8-fluoro-7-(1,1,4-trioxo-1$\lambda^6$,2,5-thiadiazolidin-2-yl)-3,4-dihydroisoquinolin-2(1H)-yl]propyl}piperidine-1-carboxylate Triethylamine (0.100 mL, 0.718 mmol) was added to a suspension of the product of Example 65A (182 mg, 0.359 mmol) in dichloromethane (1 mL) and the resultant mixture was stirred at ambient temperature for 5 minutes. tert-Butyl 4-(3-oxopropyl)piperidine-1-carboxylate (130 mg, 0.539 mmol) in dichloromethane (1 mL) was then added, and the resultant mixture was allowed to stir for a further 10 minutes. Then, sodium triacetoxyhydroborate (190 mg, 0.898 mmol) was added, and the reaction mixture was stirred at ambient temperature for 48 hours. The reaction mixture was then diluted with dichloromethane and stirred with saturated sodium bicarbonate (20 mL) for 20 minutes. The mixture was extracted with dichloromethane, dried over sodium sulfate, filtered, and concentrated under reduced pressure. The residue was purified by reversed-phase column chromatography (60 g Biotage® Sfär C18 Duo 100 Å 30 µm column, flow rate 50 mL/minute, 10 to 100% methanol in water [buffered with 0.025 M aqueous ammonium bicarbonate, adjusted to pH 7 with CO$_2$ (s)]) to give the title compound (73.4 mg, 0.119 mmol, 33.1% yield). MS (APCI$^+$) m/z 618 [M+H]$^+$.

Example 120B: 5-{8-fluoro-6-hydroxy-2-[3-(piperidin-4-yl)propyl]-1,2,3,4-tetrahydroisoquinolin-7-yl}-1$\lambda^6$,2,5-thiadiazolidine-1,1,3-trione Trichloroborane (1.0 M in dichloromethane, 778 µL, 0.778 mmol) was added dropwise to a vial containing a suspension of the product of Example 120A (60 mg, 0.097 mmol) and 1,2,3,4,5-pentamethylbenzene (43.3 mg, 0.292 mmol) in dichloromethane (973 µL) cooled to −78° C. The resulting mixture was stirred at −78° C. for 15 minutes, and then at 0° C. for 15 minutes. The mixture was cooled back to −78° C., diluted with dichloromethane (5 mL), and quenched with ethyl acetate (3 mL) and ethanol (3 mL). The mixture was then warmed to ambient temperature and stirred for 15 minutes. The mixture was diluted with ethanol and concentrated under reduced pressure. The residue was filtered through a glass microfiber frit rinsed with a minimal amount of methanol. The filtrate was purified by reversed-phase HPLC [Waters XBridge™ RP18 column, 5 jam, 30×100 mm, flow rate 40 mL/minute, 5-100% gradient of acetonitrile in buffer 0.025 M aqueous ammonium bicarbonate, adjusted to pH 10 with ammonium hydroxide)] to give the title compound (10.5 mg, 0.025 mmol, 25.3% yield). $^1$H NMR (400 MHz, DMSO-d$_6$/D$_2$O) δ ppm 6.56 (s, 1H), 3.99 (s, 2H), 3.28-3.20 (m, 2H), 3.16 (s, 3H), 2.92 (s, 3H), 2.82 (td, J=12.8, 3.0 Hz, 2H), 1.87-1.76 (m, 3H), 1.67 (s, 2H), 1.54 (s, 1H), 1.32-1.17 (m, 5H); MS (APCI$^+$) m/z 427 [M+H]$^+$.

Example 121: 5-[8-fluoro-6-hydroxy-2-(3-methylbutyl)-1,2,3,4-tetrahydroisoquinolin-7-yl]-1$\lambda^6$,2,5-thiadiazolidine-1,1,3-trione (Compound 220)

Example 121A: 5-[6-(benzyloxy)-8-fluoro-2-(3-methylbutyl)-1,2,3,4-tetrahydroisoquinolin-7-yl]-1$\lambda^6$,2,5-thiadiazolidine-1,1,3-trione, Ammonia Salt Triethylamine (0.11 mL, 0.79 mmol, 3.1 equivalents) and isovaleraldehyde (0.04 mL, 0.37 mmol, 1.5 equivalents)

were added in succession to a suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.254 mmol, 1 equivalent, Example 54A) in acetonitrile (0.6 mL) at 23° C. The reaction mixture was stirred for 5 minutes at 23° C. Significant dissolution of suspended reactants was observed within 1 minute of addition of isovaleraldehyde. Sodium triacetoxyborohydride (75 mg, 0.36 mmol, 1.4 equivalents) was added in one portion at 23° C. The reaction mixture was stirred for 1 hour at 23° C. The reaction mixture was diluted with saturated aqueous ammonium chloride solution (0.5 mL) and dimethyl sulfoxide (3.0 mL). The diluted mixture was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (82 mg, 0.17 mmol, 70% yield, two steps); MS (APCI$^+$) m/z 462 [M+H]$^+$.

Example 121B: 5-[8-fluoro-6-hydroxy-2-(3-methylbutyl)-1,2,3,4-tetrahydroisoquinolin-7-yl]-1$\lambda^6$,2,5-thiadiazolidine-1,1,3-trione, Hydrochloride Salt A solution of boron trichloride in dichloromethane (1.0 M, 1.80 mL, 1.80 mmol, 10.1 equivalents) was added to a suspension of the product of Example 121A (82 mg, 0.178 mmol, 1 equivalent) in dichloromethane (1.0 mL) at −78° C. The reaction vessel was immediately transferred to a cooling bath at 0° C. The reaction mixture was stirred for 30 minutes at 0° C. The reaction vessel was then transferred to a cooling bath at −78° C. and cooled over 15 minutes to −78° C. The reaction mixture was diluted slowly ethanol (1.0 mL) at −78° C. The diluted mixture was warmed over 15 minutes to 23° C. The warmed mixture was concentrated. The residue obtained was triturated successively with ethanol (3×1.0 mL), acetonitrile (1.0 mL), and ethyl acetate (1.0 mL) to furnish the title compound (8.0 mg, 0.016 mmol, 11% yield). $^1$H NMR (400 MHz, DMSO-d$_6$) δ ppm 10.33 (bs, 1H), 9.84 (bs, 1H), 6.61 (s, 1H), 4.46 (d, J=15.2 Hz, 1H), 4.20 (s, 2H), 4.13 (dd, J=15.5, 7.8 Hz, 1H), 3.31-2.93 (m, 6H), 1.71-1.56 (m, 3H), 0.92 (d, J=5.5 Hz); MS (APCI$^+$) m/z 372 [M+H]$^+$.

Example 122: tert-butyl 8-fluoro-6-hydroxy-7-(1,1,4-trioxo-1$\lambda^6$,2,5-thiadiazolidin-2-yl)-3,4-dihydroisoquinoline-2(1H)-carboxylate (Compound 221)

To a 20 mL Barnstead Hast C reactor containing 5% palladium on carbon (0.140 g, 0.613 mmol) were added tert-butyl 6-(benzyloxy)-8-fluoro-7-(1,1,4-trioxo-1$\lambda^6$,2,5-thiadiazolidin-2-yl)-3,4-dihydroisoquinoline-2(1H)-carboxylate (0.075 g, 0.15 mmol, Example 44H) and tetrahydrofuran (4 mL). The resulting mixture was stirred at 50° C. for 25 hours under an atmosphere of hydrogen at 64 psi. The catalyst was then removed by filtration and washed with methanol. The filtrate was concentrated under reduced pressure and purified using reversed-phase chromatography [120 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound as the corresponding ammonium salt, along with some impurities. This mixture was repurified using reversed-phase chromatography [30 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound as the corresponding ammonium salt (0.023 g, 0.055 mmol, 36% yield). $^1$H NMR (600 MHz, DMSO-d$_6$-D$_2$O) δ ppm 6.51 (s, 1H), 4.34 (s, 2H), 3.97 (s, 2H), 3.49 (t, J=5.8 Hz, 2H), 2.66 (t, J=5.9 Hz, 2H), 1.39 (s, 9H); MS (ESI$^-$) m/z 400.1 [M−H]$^-$.

Example 123: 5-{8-fluoro-6-hydroxy-2-[(7-oxabicyclo[2.2.1]heptan-2-yl)methyl]-1,2,3,4-tetrahydroisoquinolin-7-yl}-1$\lambda^6$,2,5-thiadiazolidine-1,1,3-trione (Compound 222)

Example 123A: 5-{6-(benzyloxy)-8-fluoro-2-[(7-oxabicyclo[2.2.1]heptan-2-yl)methyl]-1,2,3,4-tetrahydroisoquinolin-7-yl}-1$\lambda^6$,2,5-thiadiazolidine-1,1,3-trione, Ammonia Salt Triethylamine (0.21 mL, 1.50 mmol, 3.0 equivalents) and 7-oxabicyclo[2.2.1]heptane-2-carbaldehyde (82 mg, 0.65 mmol, 1.3 equivalents) were added in succession to a suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.5 mmol, 1 equivalent, Example 54A) in acetonitrile (1.0 mL) at 23° C. The reaction mixture was stirred for 5 minutes at 23° C. Sodium triacetoxyborohydride (138 mg, 0.65 mmol, 1.3 equivalents) was added in one portion at 23° C. The reaction mixture was stirred for 18 hours at 23° C. The reaction mixture was diluted with saturated aqueous ammonium chloride solution (0.6 mL) and dimethyl sulfoxide (3.0 mL). The diluted mixture was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (224 mg, 0.432 mmol, 89% yield, two steps). MS (APCI$^+$) min 502 [M+H]$^+$.

Example 123B: 5-{8-fluoro-6-hydroxy-2-[(7-oxabicyclo[2.2.1]heptan-2-yl)methyl]-1,2,3,4-tetrahydroisoquinolin-7-yl}-1$\lambda^6$,2,5-thiadiazolidine-1,1,3-trione, Ammonia Salt A suspension of palladium-on-carbon (10 weight %, 42 mg, 0.04 mmol, 10.0 mol %), ammonium formate (126 mg, 1.99 mmol, 5.0 equivalents), and the product of Example 123A (200 mg, 0.399 mmol, 1 equivalent) in ethanol (2.0 mL) was stirred for 3 hours at 23° C. The reaction mixture was filtered through a plug of diatomaceous earth (1.0 cm×0.5 cm). The filter cake was rinsed with methanol (3×1.0 mL). The filtrates were combined and concentrated. The residue obtained was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (130 mg, 0.30 mmol, 76% yield). $^1$H NMR (500 MHz, DMSO-d$_6$) δ ppm 9.66 (bs, 1H), 6.56 (s, 1H), 4.61-4.39 (m, 2H), 4.03 (s, 2H), 3.11-2.77 (m, 2H), 2.45-2.21 (m, 1H), 1.80-1.66 (m, 1H), 1.62-1.25 (m, 5H); MS (APCI$^+$) m/z 412 [M+H]$^+$.

Example 124: 5-{7-[(3,3-difluoropropyl)amino]-1-fluoro-3-hydroxy-5,6,7,8-tetrahydronaphthalen-2-yl}-1λ⁶,2,5-thiadiazolidine-1,1,3-trione (Compound 223)

Example 124A: 5-{3-(benzyloxy)-7-[(3,3-difluoropropyl)amino]-1-fluoro-5,6,7,8-tetrahydronaphthalen-2-yl}-12l, 2,5-thiadiazolidine-1,1,3-trione To a suspension of the product of Example 67F (0.5294 g, 1.309 mmol) and 3,3-difluoropropan-1-amine hydrochloride (0.254 g, 1.931 mmol) in ethanol (10 mL) was added triethylamine (0.550 mL, 3.93 mmol). After 30 minutes, sodium cyanoborohydride (0.099 g, 1.571 mmol) was added as a solid. After 16 hours, the reaction mixture was quenched with ammonium hydroxide (0.150 mL, 7.85 mmol), and the resultant mixture was diluted with acetonitrile (10 mL) and water (2 mL). Celite® (4 g) was added, and the mixture was concentrated in vacuo to give a white powder. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give the title compound (0.3947 g, 0.816 mmol, 62.4% yield). MS (APCI⁺) m/z 484 [M+H]⁺.

Example 124B: 5-{7-[(3,3-difluoropropyl)amino]-1-fluoro-3-hydroxy-5,6,7,8-tetrahydronaphthalen-2-yl}-1λ⁶,2,5-thiadiazolidine-1,1,3-trione To a suspension of 5-{3-(benzyloxy)-7-[(3,3-difluoropropyl)amino]-1-fluoro-5,6,7,8-tetrahydronaphthalen-2-yl}-1λ⁶,2,5-thiadiazolidine-1,1,3-trione (0.3947 g, 0.816 mmol) and pentamethylbenzene (0.225 g, 1.518 mmol) in dichloromethane (8 mL) and 1,2-dichloroethane (4 mL) at −78° C. was added a solution of boron trichloride (9.10 mL, 1 M in dichloromethane, 9.10 mmol) slowly along the side of the flask. The resulting mixture was stirred for 5 minutes, then warmed to an internal temperature of 0° C., then cooled to −78° C. and quenched sequentially with ethyl acetate (4 mL) and ethanol (4 mL). The reaction mixture was warmed to ambient temperature and concentrated in vacuo. The crude solid was triturated with heptanes (3×5 mL), 1:1 ethyl acetate/heptanes (2×5 mL) and dichloromethane (2×5 mL) to give a residue, which was dissolved in methanol (20 mL). Celite® (3 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.1798 g, 0.457 mmol, 60.2% yield). ¹H NMR (600 MHz, DMSO-d₆) δ ppm 9.26 (s, 1H), 8.41 (s, 2H), 6.47 (s, 1H), 6.23 (tt, J=56.0, 4.3 Hz, 1H), 3.94 (s, 2H), 3.43 (br s, 1H), 3.17 (t, J=7.8 Hz, 2H), 3.07 (dd, J=16.0, 5.5 Hz, 1H), 2.85-2.68 (m, 2H), 2.56-2.50 (m, 1H), 2.30-2.16 (m, 2H), 2.16-2.10 (m, 1H), 1.69 (qd, J=11.2, 5.5 Hz, 1H); MS (APCI⁺) m/z 394 [M+H]⁺.

Example 125: 5-(8-fluoro-6-hydroxy-2-{1-[(1,3,5-trimethyl-1H-pyrazol-4-yl)methyl]azetidin-3-yl}-1,2,3,4-tetrahydroisoquinolin-7-yl)-1λ⁶,2,5-thiadiazolidine-1,1,3-trione (Compound 224)

Example 125A: tert-butyl 3-[6-(benzyloxy)-8-fluoro-7-(1,1,4-trioxo-1λ⁶,2,5-thiadiazolidin-2-yl)-3,4-dihydroisoquinolin-2(1H)-yl]azetidine-1-carboxylate, Ammonium Salt To a vial containing the product of Example 93A (theoretically 0.407 mmol) were added 1,2-dichloroethane (2.0 mL) and triethylamine (0.11 mL, 0.81 mmol). The mixture was stirred for 10 minutes, then tert-butyl 3-oxoazetidine-1-carboxylate (0.105 g, 0.611 mmol) was added. After 30 minutes, sodium triacetoxyhydroborate (0.216 g, 1.02 mmol) was added. After 12 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×30 mL). The organic phases were combined, washed with brine, dried over sodium sulfate, and concentrated under reduced pressure. The residue was purified using reversed-phase chromatography [120 g Agela Claricep™ spherical C18 100 Å 40-60 µm column, 10-100% gradient of methanol in water (buffered with 0.025 M aqueous ammonium bicarbonate, adjusted to pH 7 with dry ice)] to give the title compound as the corresponding ammonium salt (0.207 g, 0.367 mmol, 90% yield). ¹H NMR (400 MHz, DMSO-d₆-D₂O) δ ppm 7.49-7.43 (m, 2H), 7.36-7.31 (m, 2H), 7.31-7.25 (m, 1H), 6.76 (s, 1H), 5.09 (s, 2H), 3.98 (s, 2H), 3.95 (s, 2H), 3.81 (s, 2H), 3.54 (s, 2H), 3.45 (s, 1H), 2.80 (d, J=6.0 Hz, 2H), 2.68 (s, 2H), 1.35 (s, 9H); MS (APCI⁺) m/z 588.3 [M+CH₃CN+H]⁺.

Example 125B: 5-[2-(azetidin-3-yl)-6-(benzyloxy)-8-fluoro-1,2,3,4-tetrahydroisoquinolin-7-yl]-1λ⁶,2,5-thiadiazolidine-1,1,3-trione, trifluoroacetic Acid Salt A vial containing a suspension of tert-butyl 3-[6-(benzyloxy)-8-fluoro-7-(1,1,4-trioxo-1λ⁶,2,5-thiadiazolidin-2-yl)-3,4-dihydroisoquinolin-2(1H)-yl]azetidine-1-carboxylate, ammonium salt (0.180 g, 0.319 mmol) in dichloromethane (1.1 mL) was cooled to 0° C. Then 2,2,2-trifluoroacetic acid (0.25 mL, 3.2 mmol) was added dropwise and the cooling bath was subsequently removed. After 1 hour, the reaction mixture was concentrated under reduced pressure. The residue was azeotroped with toluene (2×1 mL) and then co-evaporated with methanol (1 mL) to give the title compound. This material was used without further purification. MS (APCI⁺) m/z 447.3 [M+H]⁺.

Example 125C: 5-[6-(benzyloxy)-8-fluoro-2-{1-[(1,3,5-trimethyl-1H-pyrazol-4-yl)methyl]azetidin-3-yl}-1,2,3,4-tetrahydroisoquinolin-7-yl]-1λ⁶,2,5-thiadiazolidine-1,1,3-trione To a vial containing 5-[2-(azetidin-3-yl)-6-(benzyloxy)-8-fluoro-1,2,3,4-tetrahydroisoquinolin-7-yl]-1λ⁶,2,5-thiadiazolidine-1,1,3-trione, trifluoroacetic acid salt (theoretically 0.319 mmol) were added 1,2-dichloroethane (1.6 mL) and triethylamine (0.089 mL, 0.64 mmol). The mixture was stirred for 10 minutes, then 1,3,5-trimethyl-1H-pyrazole-4-carbaldehyde (0.066 g, 0.48 mmol) was added. After 30 minutes, sodium triacetoxyhydroborate (0.169 g, 0.798 mmol) was added. After 37 hours, more 1,3,5-trimethyl-1H-pyrazole-4-carbaldehyde (0.066 g, 0.48 mmol) was added, followed 15 minutes later by more sodium triacetoxyhydroborate (0.169 g, 0.798 mmol). Forty-two hours later, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×30 mL). The organic phases were combined, washed with brine, dried over sodium sulfate, and concentrated under reduced pressure. The residue was purified using reversed-phase chromatography [120 g Agela Claricep™ spherical C18 100 Å 40-60

μm column, 10-100% gradient of methanol in water (buffered with 0.025 M aqueous ammonium bicarbonate, adjusted to pH 7 with dry ice)] to give the title compound (0.057 g, 0.10 mmol, 32% yield over two steps). $^1$H NMR (400 MHz, DMSO-$d_6$) δ ppm 9.58 (br s, 1H), 7.53-7.44 (m, 2H), 7.37-7.31 (m, 2H), 7.31-7.22 (m, 1H), 6.75 (s, 1H), 5.11 (s, 2H), 4.17 (2 overlapping singlets, 3H), 4.04 (br s, 2H), 3.98 (s, 2H), 3.81 (br s, 1H), 3.64 (s, 3H), 3.47 (s, 2H), 3.40 (br s, 1H), 2.78 (t, J=5.8 Hz, 2H), 2.59 (t, J=5.8 Hz, 2H), 2.26 (s, 3H), 2.16 (s, 3H); MS (APCI$^+$) m/z 569.4 [M+H]$^+$.

Example 125D: 5-(8-fluoro-6-hydroxy-2-{1-[(1,3,5-trimethyl-1H-pyrazol-4-yl)methyl]azetidin-3-yl}-1,2,3,4-tetrahydroisoquinolin-7-yl)-1$\lambda^6$,2,5-thiadiazolidine-1,1,3-trione To a 20 mL Barnstead Hast C reactor containing 5% palladium on carbon (0.80 g, 3.5 mmol) were added 5-[6-(benzyloxy)-8-fluoro-2-{1-[(1,3,5-trimethyl-1H-pyrazol-4-yl)methyl]azetidin-3-yl}-1,2,3,4-tetrahydroisoquinolin-7-yl]-1$\lambda^6$,2,5-thiadiazolidine-1,1,3-trione (0.070 g, 0.12 mmol) and tetrahydrofuran (4 mL). The resulting mixture was stirred at 25° C. for 42 hours under an atmosphere of hydrogen at 45 psi. The catalyst was then removed by filtration and washed with methanol. The filtrate was concentrated under reduced pressure and purified using reversed-phase chromatography [60 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.011 g, 0.024 mmol, 19% yield). $^1$H NMR (400 MHz, DMSO-$d_6$) δ ppm 9.21 (s, 1H), 6.47 (s, 1H), 4.11 (s, 2H), 4.07-3.98 (m, 2H), 3.94 (s, 2H), 3.82 (br s, 2H), 3.64 (s, 3H), 3.41 (s, 3H), 2.73 (t, J=5.4 Hz, 2H), 2.56 (t, J=5.4 Hz, 2H), 2.25 (s, 3H), 2.15 (s, 3H); MS (APCI$^+$) m/z 479.3 [M+H]$^+$.

Example 126: 5-{8-fluoro-6-hydroxy-2-[2-(7-oxabicyclo[2.2.1]heptan-2-yl)ethyl]-1,2,3,4-tetrahydroisoquinolin-7-yl}-1$\lambda^6$,2,5-thiadiazolidine-1,1,3-trione (Compound 225)

Example 126A: 2-(7-oxabicyclo[2.2.1]heptan-2-yl)acetaldehyde

A solution of potassium tert-butoxide in tetrahydrofuran (1.0 M, 1.0 mL, 1.0 mmol, 1.1 equivalents) was added to a suspension of (methoxymethyl)triphenylphosphonium chloride (326 mg, 0.95 mmol, 1.0 equivalent) in tetrahydrofuran (5 mL) at 0° C. The reaction mixture was stirred for 5 minutes at 0° C. A solution of 7-oxabicyclo[2.2.1]heptane-2-carbaldehyde (120 mg, 0.95 mmol, 1 equivalent) in tetrahydrofuran (1.0 mL) was added at 0° C. The reaction mixture was stirred for 5 minutes at 0° C. Thin layer chromatography analysis indicated consumption of starting material (new spot: $R_f$=0.60, 3:1 heptanes:ethyl acetate, developed with 2,4-dinitrophenylhydrazine). Aqueous hydrochloric acid solution (1.0 M, 4.0 mL, 4.0 mmol, 4.2 equivalents) was added at 0° C. The reaction mixture was immediately removed from its cooling bath, and the reaction mixture was stirred for 20 hours at 23° C. The reaction mixture was then diluted sequentially with ether (15 mL) and pentane (10 mL). The diluted mixture was stirred for 10 minutes. The resulting biphasic mixture was then transferred to a separatory funnel and the layers that formed were separated. The organic layer was washed sequentially with saturated aqueous sodium bicarbonate solution (5 mL) and saturated aqueous sodium chloride solution (5 mL). The washed organic layer was dried over sodium sulfate. The dried solution was filtered, and the filtrate was concentrated. The residue obtained was extracted with 50% ether-pentane mixture (v/v, 5.0 mL). The supernatant was filtered through a silica plug (1.5 cm×0.5 cm). The filter cake was washed with 50% ether-pentane mixture (v/v, 3×1 mL). The filtrates were combined and concentrated. The residue obtained was used without further purification. $R_f$=0.18, 3:1 heptanes:ethyl acetate, developed with 2,4-dinitrophenylhydrazine).

Example 126B: 5-{6-(benzyloxy)-8-fluoro-2-[2-(7-oxabicyclo[2.2.1]heptan-2-yl)ethyl]-1,2,3,4-tetrahydroisoquinolin-7-yl}-1$\lambda^6$,2,5-thiadiazolidine-1,1,3-trione, Ammonia Salt Sodium triacetoxyborohydride (97 mg, 0.46 mmol, 1.2 equivalents) was added in one portion to a suspension of the product of Example 126A (nominally 0.95 mmol, 2.5 equivalents), triethylamine (0.16 mL, 1.14 mmol, 3.0 equivalents), and 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.38 mmol, 1 equivalent, Example 54A) in acetonitrile (1.5 mL) at 23° C. The reaction mixture was stirred for 5 hours at 23° C. The reaction mixture was then diluted with saturated aqueous ammonium chloride (0.5 mL) and dimethyl sulfoxide (1.0 mL). The diluted mixture was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (80 mg, 0.15 mmol, 41% yield). MS (APCI$^+$) m/z 516 [M+H]$^+$.

Example 126C: 5-{8-fluoro-6-hydroxy-2-[2-(7-oxabicyclo[2.2.1]heptan-2-yl)ethyl]-1,2,3,4-tetrahydroisoquinolin-7-yl}-1$\lambda^6$,2,5-thiadiazolidine-1,3-trione, Ammonia Salt A suspension of palladium-on-carbon (10 weight %, 16 mg, 0.016 mmol, 10.0 mol %), ammonium formate (49 mg, 0.78 mmol, 5.0 equivalents), and the product of Example 126B (80 mg, 0.155 mmol, 1 equivalent) in ethanol (1.5 mL) was stirred for 2 hours at 23° C. The reaction mixture was filtered through a plug of diatomaceous earth (1.0 cm×0.5 cm). The filter cake was rinsed with methanol (3×1.0 mL). The filtrates were combined and concentrated. The residue obtained was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (42 mg, 0.095 mmol, 61% yield). 1H NMR (400 MHz, DMSO-$d_6$) δ ppm 9.70 (bs, 1H), 9.59 (bs, 1H), 6.57 (s, 1H), 4.50 (t, J=5.0 Hz, 1H), 4.44 (t, J=5.3 Hz, 0.5H)*, 4.38 (t, J=4.8 Hz, 0.5H)*, 4.26 (d, 4.6 Hz, 0.5H)*, 4.13 (bs, 0.5H)*, 3.94 (s, 2H), 3.67 (bs, 0.5H), 3.24-3.08 (m, 1H), 2.98 (bs, 2H), 1.96-1.36 (m, 8H), 1.26-1.19 (m, 0.5H)*, 0.96 (dd, J=11.4, 4.61 Hz, 0.5H)*. * denotes isomeric resonances. MS (APCI$^-$) m/z 424 [M−H]$^-$.

Example 127: 5-(2-{2-[1-(2,2-difluoroethyl)-3,5-dimethyl-1H-pyrazol-4-yl]ethyl}-4,4,8-trifluoro-6-hydroxy-1,2,3,4-tetrahydroisoquinolin-7-yl)-1$\lambda^6$,2,5-thiadiazolidine-1,1,3-trione (Compound 226)

Example 127A: ethyl 3-acetyl-4-oxopentanoate

To a mixture of NaH (4.19 g, 105 mmol) in tetrahydrofuran (240 mL) was added pentane-2,4-dione (10 g, 100 mmol) dropwise at 0° C. The mixture was stirred for 1 hour at 0° C. under N2. A solution of ethyl 2-bromoacetate (16.68 g, 100 mmol) in tetrahydrofuran (60 mL) was added dropwise to the mixture at 20° C. and the mixture was stirred for 18 hours under N2. The mixture was quenched with saturated NH$_4$Cl (200 mL), and the mixture was extracted with ethyl acetate (3×200 mL). The combined organic layers were washed with brine (200 mL), dried over Na$_2$SO$_4$, and concentrated to give the title compound (~20 g) that was used in the subsequent step without further purification. MS (ESI$^+$) m/z 187 [M+H]$^+$.

Example 127B: ethyl 2-(3,5-dimethyl-1H-pyrazol-4-yl)acetate

To a solution of the product of Example 127A (10.5 g) in methanol (100 mL) was added hydrazine hydrate (2.96 g, 59.2 mmol) at 20° C. The mixture was stirred for 3 hours at 20° C. The mixture was concentrated under reduced pressure. Then the crude mixture was diluted with water (100 mL) and extracted with ethyl acetate (3×50 mL). The combined organic phases were washed with brine (50 mL), dried over Na$_2$SO$_4$ and concentrated under reduced pressure to give the title compound (7.091 g, 38.9 mmol, 74% yield for two steps). $^1$H NMR (400 MHz, DMSO-d$_6$) δ ppm 1.05-1.35 (m, 5H) 1.96-2.27 (m, 6H) 3.25-3.48 (m, 2H) 3.95-4.24 (m, 2H).

Example 127C: ethyl 2-(1-(2,2-difluoroethyl)-3,5-dimethyl-1H-pyrazol-4-yl)acetate To a solution of the product of Example 127B (2.55 g, 14.0 mmol) in tetrahydrofuran (20 mL) was added potassium 2-methylpropan-2-olate (2.120 g, 18.89 mmol) at 20° C. and the mixture was stirred for 10 minutes. Then 2,2-difluoroethyl trifluoromethanesulfonate (8.09 g, 37.8 mmol) was added to the mixture at 0° C. The mixture was stirred for 12 hours at 20° C. The mixture was diluted with water (50 mL) and extracted with ethyl acetate (3×20 mL). The combined organic phases were washed with brine (3×10 mL), dried over Na$_2$SO$_4$ and concentrated under reduced pressure to give the title compound (3.2 g, 13.0 mmol, 93% yield). $^1$H NMR (400 MHz, DMSO-d$_6$) δ ppm 2.14 (s, 3H) 2.42 (t, J=7.32 Hz, 2H) 2.50 (br s, 5H) 3.28-3.41 (m, 5H) 4.39 (td, J=14.95, 3.75 Hz, 2H) 4.55-4.70 (m, 1H) 6.08-6.44 (m, 1H).

Example 127D: 2-(1-(2,2-difluoroethyl)-3,5-dimethyl-1H-pyrazol-4-yl)ethanol To a solution of the product of Example 127C (2.8 g, 11.4 mmol) in tetrahydrofuran (30 mL) was added LiAlH$_4$ (0.665 g, 17.51 mmol) in portions at 0° C. under N2. The mixture was stirred for 1 hour at 0° C. under N2. Water (0.7 mL), an aqueous solution of NaOH (0.7 mL, 15% in water) and water (2.1 mL) were added successively to the mixture at 0° C. After 10 minutes, the mixture was filtered and concentrated under reduced pressure to give the title compound (1.8 g, 8.8 mmol, 77% yield), which was used for the next step without purification. $^1$H NMR (400 MHz, DMSO-d$_6$) δ ppm 2.14 (s, 3H) 2.42 (t, J=7.32 Hz, 2H) 2.50 (br s, 5H) 3.28-3.41 (m, 5H) 4.39 (td, J=14.95, 3.75 Hz, 2H) 4.55-4.70 (m, 1H) 6.08-6.44 (m, 1H).

Example 127E: 2-(1-(2,2-difluoroethyl)-3,5-dimethyl-1H-pyrazol-4-yl)acetaldehyde To a solution of the product of Example 127D (100 mg, 0.441 mmol) in dichloromethane (2 mL) was added Dess-Martin periodinane (1,1,1-tris(acetyloxy)-1,1-dihydro-1,2-benzodioxol-3-(1H)-one) (280 mg, 0.661 mmol) at 20° C. The mixture was stirred for 1 hour at 20° C. The mixture was filtered, and the filtrate was concentrated under reduced pressure. The residue was purified by preparative thin-layer chromatography (ethyl acetate) to give the title compound (20 mg, 0.099 mmol, yield 20%). $^1$H NMR (400 MHz, CDCl$_3$) δ ppm 2.11-2.29 (m, 6H) 3.33-3.46 (m, 2H) 4.30-4.42 (m, 2H) 5.88-6.25 (m, 1H) 9.59 (t, J=2.25 Hz, 1H).

Example 127F: methyl 2-(N-(3-((benzylamino)methyl)-6-(benzyloxy)-4-bromo-2-fluorophenyl)-2,2,2-trifluoroacetamido)acetate To a solution of phenylmethanamine (16.16 g, 151 mmol) in dichloromethane (350 mL) was added a solution of the product of Example 44A (55 g, 101 mmol) in dichloromethane (600 mL) at 0° C. dropwise. The mixture was stirred for 30 minutes at 20° C. Acetic acid (0.288 mL, 5.03 mmol) and sodium triacetoxyborohydride (32.0 g, 151 mmol) were added to the mixture successively at 20° C. The resulting mixture was stirred for 12 hours at 20° C. One additional vial on 55 g scale was set up as described above. The mixtures were combined and diluted with water (800 mL), extracted with ethyl acetate (3×500 mL). The organic phases were combined, dried over Na$_2$SO$_4$ and concentrated under reduced pressure. The residue was purified by flash column chromatography (petroleum ether:ethyl acetate=20:1) to give the title compound (100 g, 171 mmol, yield 77%). $^1$H NMR (400 MHz, CDCl$_3$) δ ppm 3.67 (s, 3H) 3.71-3.82 (m, 2H) 3.87-4.06 (m, 3H) 4.61 (d, J=16.88 Hz, 1H) 4.89-5.21 (m, 2H) 7.10 (s, 1H) 7.30-7.52 (m, 10H).

Example 127G: Methyl {[6-(benzyloxy)-3-{[benzyl(prop-2-en-1-yl)amino]methyl}-4-bromo-2-fluorophenyl](trifluoroacetyl)amino}acetate To a solution of the product of Example 127F (47.5 g, 73.3 mmol) in N,N-dimethylformamide (500 mL) was added 3-bromoprop-1-ene (13.30 g, 110 mmol) and K2CO$_3$ (30.4 g, 220 mmol) at 20° C. The mixture was stirred for 12 hours at 40° C. Two additional reactions on 5 g and 47.5 g scale, respectively, were set up as described above. The reaction mixtures were combined, diluted with brine (1000 mL) and extracted with ethyl acetate (3×1000 mL). The combined organic phases were dried over Na$_2$SO$_4$ and concentrated under reduced pressure. The residue was purified by flash column chromatography (petroleum ether:ethyl acetate=20:1) to give the title compound (97 g, 0.156 mol, 91% yield). $^1$H NMR (400 MHz, CDCl$_3$) δ ppm 3.08 (d, J=6.48 Hz, 2H) 3.51-3.62 (m, 1H) 3.59 (d, J=2.08 Hz, 1H) 3.65 (s, 3H) 3.68-3.82 (m, 2H) 3.97 (d, J=16.75 Hz, 1H) 4.56 (d, J=16.75 Hz, 1H) 4.97-5.28 (m, 4H) 5.94 (ddt, J=17.04, 10.35, 6.48, 6.48 Hz, 1H) 7.08 (d, J=1.71 Hz, 1H) 7.27 (m, 11H).

Example 127H: Methyl {[2-benzyl-6-(benzyloxy)-8-fluoro-4-methylidene-1,2,3,4-tetrahydroisoquinolin-7-yl](trifluoroacetyl)amino}acetate To a solution of the product of Example 127G (30 g, 46.3 mmol) in toluene (300 mL) were added chloro(2-dicyclohexylphosphino-2',6'-dimethoxy-1,1'-biphenyl)[2-(2'-amino-1,1'-biphenyl)]palladium(II) (SPhos Pd G2, 3.34 g, 4.63 mmol) and $Cs_2CO_3$ (45.2 g, 139 mmol) at 20° C. The mixture was heated at 100° C. for 4 days. Two additional reactions on 30 g scale were run as described above. The reactions mixtures were combined, filtered and diluted with water (1000 mL). Then the mixture was extracted with ethyl acetate (3×500 mL). The combined organic layers were washed with brine (500 mL), dried over $Na_2SO_4$, filtered and concentrated under reduced pressure. The residue was purified by flash column chromatography (petroleum ether:ethyl acetate=10:1) to give the title compound (44 g, 81.1 mmol, 52.8% yield). $^1H$ NMR (400 MHz, $CDCl_3$) δ ppm 3.26-3.45 (m, 2H) 3.62-3.82 (m, 7H) 3.99 (d, J=16.88 Hz, 1H) 4.65 (d, J=16.76 Hz, 1H) 5.01-5.19 (m, 3H) 5.59 (s, 1H) 7.09 (d, J=1.00 Hz, 1H) 7.28-7.46 (m, 10H).

Example 127I: Methyl {[6-(benzyloxy)-8-fluoro-4-methylidene-1,2,3,4-tetrahydroisoquinolin-7-yl](trifluoroacetyl)amino}acetate To a solution of the product of Example 127H (10.5 g, 17.42 mmol) and 1,8-bis(dimethylamino)naphthalene (3.73 g, 17.42 mmol) in 1,2-dichloroethane (200 mL) was added 1-chloroethyl chloroformate (3.74 g, 26.1 mmol) dropwise at 0° C. The mixture was stirred for 1 hour at 20° C. The solvent was removed under reduced pressure. The residue was diluted with methanol (200 mL). The mixture was stirred for 1 hour at 55° C. One additional reaction on 2 g scale and three addition reactions on 10.5 g scale were run as describe above. The reaction mixtures were combined and concentrated under reduced pressure to give crude title compound (78 g), which was used for next step without further purification. MS (ESI⁺) m/z 453 [M+H]⁺.

Example 127J: tert-butyl 6-(benzyloxy)-8-fluoro-7-[(2-methoxy-2-oxoethyl) (trifluoroacetyl)amino]-4-methylidene-3,4-dihydroisoquinoline-2(1H)-carboxylate To a solution of the product of Example 127I (35 g, 69.6 mmol) in tetrahydrofuran (350 mL) and water (70 mL) were added sodium bicarbonate (11.70 g, 139 mmol) and di-tert-butyl dicarbonate (19.40 mL, 84 mmol) successively at 0° C. The mixture was stirred for 1 hour at 20° C. Two additional reactions on 8 g and 35 g scales were run as describe above. The reaction mixtures were combined, diluted with water (1500 mL) and extracted with ethyl acetate (3×500 mL). The combined organic layers were washed with brine (300 mL), dried over $Na_2SO_4$, filtered and concentrated under reduced pressure. The residue was purified by flash column chromatography (petroleum ether:ethyl acetate=20:1) to give the title compound (38 g, 68.8 mmol, 89% yield). $^1H$ NMR (400 MHz, $CDCl_3$) δ ppm 1.49 (s, 8H), 3.59-3.74 (m, 3H), 3.92-4.06 (m, 1H), 4.10-4.31 (m, 2H), 4.49-4.74 (m, 3H), 5.04-5.18 (m, 2H), 5.26 (br s, 1H), 5.46-5.61 (m, 1H), 7.04 (s, 1H), 7.33-7.48 (m, 6H).

Example 127K: tert-butyl 6-(benzyloxy)-8-fluoro-7-[(2-methoxy-2-oxoethyl) (trifluoroacetyl)amino]-4-oxo-3,4-dihydroisoquinoline-2(1H)-carboxylate To a solution of the product of Example 127J (10 g, 16.29 mmol) in water (20 mL) and tetrahydrofuran (100 mL) were added osmium tetroxide (0.511 mL, 0.4 mmol/L in tertiary butanol) and sodium periodate (10.45 g, 48.9 mmol) successively at 20° C. The mixture was stirred for 1 hour at 20° C. One additional reaction on 2 g scale and three addition reactions on 10.5 g scale were run as describe above. The reaction mixtures were combined, quenched with saturated $Na_2S_2O_3$ (200 mL), and extracted with ethyl acetate (3×200 mL). The combined organic layers were washed with brine (100 mL), dried over $Na_2SO_4$, filtered and concentrated under reduced pressure. The residue was purified by flash column chromatography (petroleum ether:ethyl acetate=20:1) to give the title compound (14.5 g, 26.2 mmol, 37.4% yield). $^1H$ NMR (400 MHz, DMSO-$d_6$) δ ppm 1.29-1.44 (m, 9H), 3.63 (s, 3H), 4.30-4.44 (m, 2H), 4.47-4.66 (m, 2H), 4.74 (br d, J=15.51 Hz, 2H), 5.24-5.45 (m, 2H), 7.42 (br d, J=2.75 Hz, 4H), 7.54 (s, 1H).

Example 127L: tert-butyl 6-(benzyloxy)-4,4,8-trifluoro-7-[(2-methoxy-2-oxoethyl)(trifluoroacetyl)amino]-3,4-dihydroisoquinoline-2(1H)-carboxylate To a solution of the product of Example 127K (3 g, 4.87 mmol) in dichloromethane (30 mL) was added diethylaminosulfur trifluoride (DAST, 30 mL, 227 mmol) at 0° C. The mixture was stirred for 12 hours at 40° C. Five additional reactions on 0.5 g, 2 g and 3 g (three reactions) scale were run as describe above. The reaction mixtures were combined and quenched with saturated $NaHCO_3$(800 mL) at 20° C. The mixture was then diluted with water (500 mL) and extracted with ethyl acetate (3×300 mL). The combined organic layers were washed with brine (200 mL), dried over $Na_2SO_4$, filtered and concentrated under reduced pressure. The residue was purified by flash column chromatography (petroleum ether:ethyl acetate=20:1) to give the title compound (9.5 g, 16.5 mmol, 56.7% yield). $^1H$ NMR (400 MHz, $CDCl_3$) δ ppm 1.44-1.55 (m, 9H), 3.60-3.74 (m, 3H), 3.86-3.96 (m, 1H), 4.13 (q, J=7.09 Hz, 2H), 4.45-4.59 (m, 1H), 4.66 (br d, J=16.88 Hz, 2H), 5.08-5.24 (m, 2H), 7.18 (br s, 1H), 7.31-7.48 (m, 5H).

Example 127M tert-butyl 6-(benzyloxy)-4,4,8-trifluoro-7-[(2-methoxy-2-oxoethyl)amino]-3,4-dihydroisoquinoline-2(1H)-carboxylate To a solution of the product of Example 127L (9 g, 14.05 mmol) in methanol (90 mL) was added $K_2CO_3$ (3.88 g, 28.1 mmol) at 20° C. The mixture was stirred for 1 hour at 20° C. Two additional reactions on 0.5 g and 4.5 g scales were run as describe above. The reaction mixtures were combined, diluted with water (200 mL), and extracted with ethyl acetate (3×200 mL). The combined organic layers were washed with brine (100 mL), dried over $Na_2SO_4$, filtered and concentrated under reduced pressure to give the title compound (7.9 g, 16.4 mmol, 90% yield) which was used for the next step without further purification. $^1H$ NMR (400 MHz, $CDCl_3$) δ ppm 1.51 (s, 9H), 3.75 (s, 3H), 3.97 (br t, J=10.82 Hz, 2H), 4.06-4.26 (m, 2H), 4.59 (br s, 2H), 4.77 (br s, 1H), 5.13 (s, 2H), 6.86-7.10 (m, 1H), 7.31-7.53 (m, 5H).

Example 127N: tert-butyl 6-(benzyloxy)-4,4,8-trifluoro-7-[(2-methoxy-2-oxoethyl) ({[(prop-2-en-1-yl)oxy]carbonyl}sulfamoyl)amino]-3,4-dihydroisoquinoline-2(1H)-carboxylate To a solution of chlorosulfonyl isocyanate (0.854 mL, 9.83 mmol) in dichloromethane (5 mL) was added allyl alcohol (0.669 mL, 9.83 mmol) dropwise at 0° C. The mixture was stirred for 30 minutes at 0° C. A solution of the product of Example 127M (3.5 g, 6.56 mmol) and N,N-diisopropylethylamine (2.290 mL, 13.11 mmol) in dichloromethane (5 mL) was added to the above mixture dropwise at 0° C. The mixture was stirred for 30 minutes at 0° C. The mixture was diluted with water (10 mL). The organic phase was separated, dried over $Na_2SO_4$ and concentrated under reduced pressure to give the title compound (6 g, crude), which was used for the next step without further purification. MS (ESI$^+$) m/z 666 [M+Na]$^+$.

Example 127O: tert-butyl 6-(benzyloxy)-4,4,8-trifluoro-7-(1,1,4-trioxo-1λ$^6$,2,5-thiadiazolidin-2-yl)-3,4-dihydroisoquinoline-2(1H)-carboxylate To a solution of the product of Example 127N (6 g, 6.53 mmol) in anhydrous methanol (5 mL) was added $K_2CO_3$ (2.98 g, 21.53 mmol) and tetrakis(triphenylphosphine)palladium (O) (0.226 g, 0.196 mmol) at 20° C. under $N_2$. The mixture was stirred at 20° C. under $N_2$ for 12 hours. The mixture was filtered, and the filtrate was diluted with water (20 mL), adjusted to pH=3 with aqueous HCl (1 mol/L) and extracted with ethyl acetate (3×20 mL). The combined organic layers were washed with brine (30 mL), dried over $Na_2SO_4$, filtered and concentrated under reduced pressure. The residue was purified by flash column chromatography (ethyl acetate:methanol=10:1) to give the title compound (2.1 g, 4.0 mmol, yield 53.2%). $^1$H NMR (400 MHz, DMSO-$d_6$) δ ppm 1.33-1.50 (m, 1H), 1.45 (s, 8H), 3.19 (s, 2H), 3.76-4.03 (m, 1H), 4.04-4.21 (m, 4H), 4.58 (br s, 2H), 5.24 (s, 2H), 7.20 (s, 1H), 7.26-7.42 (m, 1H), 7.31-7.42 (m, 1H), 7.31-7.42 (m, 1H), 7.31-7.42 (m, 1H), 7.52 (d, J=7.13 Hz, 2H); MS (ESI$^-$) m/z 526 [M–H]$^-$.

Example 127P: 5-[6-(benzyloxy)-4,4,8-trifluoro-1,2,3,4-tetrahydroisoquinolin-7-yl]-1λ$^6$,2,5-thiadiazolidine-1,1,3-trione To a solution of the product of Example 127O (200 mg, 0.341 mmol) in dichloromethane (3 mL) was added trifluoroacetic acid (1 mL) dropwise at 0° C. The mixture was stirred for 1 hour at 20° C. The mixture was concentrated under reduced pressure to give the title compound as a trifluoroacetic acid salt (160 mg, 99% yield), which was used in the next step without further purification. MS (ESI$^-$) m/z 426 [M–H]$^-$.

Example 127Q: 5-[6-(benzyloxy)-2-{2-[1-(2,2-difluoroethyl)-3,5-dimethyl-1H-pyrazol-4-yl]ethyl}-4,4,8-trifluoro-1,2,3,4-tetrahydroisoquinolin-7-yl]-1λ$^6$,2,5-thiadiazolidine-1,1,3-trione To a solution of the product of Example 127P (150 mg, 0.316 mmol) in 1,2-dichloroethane (2 mL) was added triethylamine (0.088 mL, 0.632 mmol) followed by a solution of the product of Example 127E (106 mg, 0.474 mmol) in 1,2-dchloroethane (2 mL) at 20° C. After 10 minutes, sodium triacetoxyborohydride (167 mg, 0.790 mmol) was added and the mixture was stirred at 20° C. for 12 hours. The mixture was diluted with saturated $NaHCO_3$(10 mL) and extracted with ethyl acetate (3×10 mL). The combined organic layers were washed with brine (10 mL), dried over $Na_2SO_4$, filtered and concentrated under reduced pressure. The residue was purified by flash column chromatography (petroleum ether:ethyl acetate=10:1 to 1:1) to give the title compound (90 mg, 0.15 mmol, 41.8% yield). MS (ESI$^-$) m/z 612 [M–H]$^-$.

Example 127R: 5-(2-{2-[1-(2,2-difluoroethyl)-3,5-dimethyl-1H-pyrazol-4-yl]ethyl}-4,4,8-trifluoro-6-hydroxy-1,2,3,4-tetrahydroisoquinolin-7-yl)-1λ$^6$,2,5-thiadiazolidine-1,1,3-trione To a mixture of the product of Example 127Q (90 mg, 0.132 mmol) in dichloromethane (1 mL) was added pentamethylbenzene (58.7 mg, 0.396 mmol) at 20° C. The mixture was cooled to −78° C. under $N_2$ before borontrichloride (1.056 mL, 1.056 mmol) was added. The mixture was then stirred for 10 minutes at −78° C. and 1 hour at 0° C. The reaction was then quenched at −78° C. by adding ethyl acetate (3 mL) and ethanol (3 mL) dropwise. The mixture was concentrated under reduced pressure to give the crude product which was purified by preparative HPLC on a Phenomenex® C18 Gemini-NX 3 μm 150×30 mm column eluted with a gradient of acetonitrile (A) and 10 mM $NH_4HCO_3$ in water (B) at a flow rate of 25 mL/minute (0-8 minute linear gradient 30-60% A, 8-10 minutes 100% A) to give the title compound (3.3 mg, 0.006 mmol, 4.6% yield). $^1$H NMR (400 MHz, methanol-$d_4$) δ ppm 2.22 (br d, J=19.14 Hz, 6H) 2.70 (br s, 4H) 3.24 (br s, 2H) 3.78 (br s, 2H) 4.23-4.46 (m, 4H) 5.83-6.24 (m, 1H) 7.01 (br s, 1H); MS (ESI$^-$) m/z 522 [M–H]$^-$.

Example 128: 5-(4-{[8-fluoro-6-hydroxy-7-(1,1,4-trioxo-1λ$^6$,2,5-thiadiazolidin-2-yl)-3,4-dihydroisoquinolin-2(1H)-yl]methyl}-3,5-dimethyl-1H-pyrazol-1-yl)-2,2-dimethylpentanenitrile (Compound 227)

Example 128A: 5-(4-{[6-(benzyloxy)-8-fluoro-7-(1,1,4-trioxo-1λ$^6$,2,5-thiadiazolidin-2-yl)-3,4-dihydroisoquinolin-2(1H)-yl]methyl}-3,5-dimethyl-1H-pyrazol-1-yl)-2,2-dimethylpentanenitrile To a vial containing the product of Example 93A (theoretically 0.15 mmol) were added 1,2-dichloroethane (0.77 mL) and triethylamine (0.043 mL, 0.31 mmol). The mixture was stirred for 10 minutes, then 5-(4-formyl-3,5-dimethyl-1H-pyrazol-1-yl)-2,2-dimethylpentanenitrile (0.054 g, 0.23 mmol) was added. After 30 minutes, sodium triacetoxyhydroborate (0.081 g, 0.38 mmol) was added. After 14 hours, the reaction mixture was poured into saturated aqueous sodium bicarbonate (25 mL) with the aid of dichloromethane. The resulting biphasic mixture was stirred for 20 minutes. The layers were then separated, and the aqueous phase was extracted with dichloromethane (4×15 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.081 g, 0.13 mmol, 87% yield). $^1$H NMR (600 MHz, DMSO-$d_6$) δ ppm 9.50 (br s, 1H), 7.50-7.45 (m, 2H), 7.38-7.31 (m, 2H), 7.31-7.22 (m, 1H), 6.89 (s, 1H), 5.17 (s, 2H), 4.48 (br d, J=15.0 Hz, 1H), 4.38 (br d, J=14.0 Hz, 1H), 4.24 (br d, J=13.6 Hz, 1H), 4.17 (br d, J=13.6 Hz, 1H), 4.04-3.99 (m, 2H), 3.99-3.91 (m, 2H), 3.58 (br s, 1H), 3.30 (br s, 1H), 3.03 (br s, 2H), 2.30 (s, 3H), 2.20 (s, 3H), 1.93-1.75 (m, 2H), 1.62-1.43 (m, 2H), 1.28 (s, 6H); MS (APCI$^+$) m/z 609.4 [M+H]$^+$.

Example 128B: 5-(4-{[8-fluoro-6-hydroxy-7-(1,1,4-trioxo-1λ$^6$,2,5-thiadiazolidin-2-yl)-3,4-dihydroisoquinolin-2(1H)-yl]methyl}-3,5-dimethyl-1H-pyrazol-1-yl)-2,2-dimethylpentanenitrile A vial containing a suspension of 5-(4-{[6-(benzyloxy)-8-fluoro-7-(1,1,4-trioxo-1λ$^6$,2,5-thiadiazolidin-2-yl)-3,4-dihydroisoquinolin-2(1H)-yl]methyl}-3,5-dimethyl-1H-pyrazol-1-yl)-2,2-dimethylpentanenitrile (0.077 g, 0.13 mmol, Example 128A) and 1,2,3,4,5-pentamethylbenzene (0.056 g, 0.38 mmol) in dichloromethane (1.3 mL) was cooled to −78° C. with stirring under an atmosphere of nitrogen. Next, trichloroborane (1.0 M in dichloromethane) (1.0 mL, 1.0 mmol) was added slowly. The resulting mixture was stirred at −78° C. for 10 minutes, and then the dry ice-acetone bath was replaced with an ice-water bath. After 60 minutes, the mixture was recooled to −78° C. and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.059 g, 0.11 mmol, 90% yield). $^1$H NMR (600 MHz, DMSO-d$_6$) δ ppm 9.73 (br s, 1H), 9.61 (s, 1H), 6.55 (s, 1H), 4.14 (br s, 4H), 4.00 (t, J=7.2 Hz, 2H), 3.93 (s, 2H), 3.26 (br s, 2H), 2.96 (t, J=5.4 Hz, 2H), 2.28 (s, 3H), 2.18 (s, 3H), 1.87-1.79 (m, 2H), 1.55-1.47 (m, 2H), 1.28 (s, 6H); MS (APCI$^+$) m/z 519.2 [M+H]$^+$.

Example 129: 5-{8-fluoro-6-hydroxy-2-[(piperidin-4-yl)methyl]-1,2,3,4-tetrahydroisoquinolin-7-yl}-1λ$^6$,2,5-thiadiazolidine-1,1,3-trione (Compound 228)

Example 129A: tert-butyl 4-{[6-(benzyloxy)-8-fluoro-7-(1,1,4-trioxo-1λ$^6$,2,5-thiadiazolidin-2-yl)-3,4-dihydroisoquinolin-2(1H)-yl]methyl}piperidine-1-carboxylate Triethylamine (0.083 ml, 0.594 mmol) was added to the product of Example 65A (150 mg, 0.297 mmol) in dichloromethane (1 mL), and the mixture was stirred at ambient temperature for 5 minutes. tert-Butyl 4-formylpiperidine-1-carboxylate (130 mg, 0.610 mmol) in dichloromethane (1 mL) was then added, and the resultant mixture was stirred for a further 10 minutes. Then sodium triacetoxyhydroborate (157 mg, 0.742 mmol) was added, and the reaction mixture was stirred at ambient temperature for 15 hours. The reaction mixture was diluted with dichloromethane and stirred with saturated sodium bicarbonate (20 mL) for 20 minutes. The mixture was extracted with dichloromethane, dried over sodium sulfate, filtered, and concentrated under reduced pressure. The residue was purified by reversed-phase column chromatography (60 g Biotage® Sfär C18 Duo 100 Å 30 μm column, flow rate 50 mL/minute, 10 to 100% methanol in water [buffered with 0.025 M aqueous ammonium bicarbonate, adjusted to pH 7 with CO$_2$ (s)]) twice to give the title compound (111.7 mg, 0.190 mmol, 63.9% yield). MS (APCI$^+$) m/z 590 [M+H]$^+$.

Example 129B: 5-{8-fluoro-6-hydroxy-2-[(piperidin-4-yl)methyl]-1,2,3,4-tetrahydroisoquinolin-7-yl}-1λ$^6$,2,5-thiadiazolidine-1,1,3-trione Trichloroborane (1.0 M in dichloromethane, 679 μL, 0.679 mmol) was added to a vial containing a suspension of the product of Example 129A (50 mg, 0.085 mmol) and 1,2,3,4,5-pentamethylbenzene (37.8 mg, 0.255 mmol) in dichloromethane (849 μL) cooled to −78° C. The resulting mixture was stirred at −78° C. for 30 minutes and then quenched with ethanol (4 mL). The mixture was then warmed to ambient temperature and stirred for 15 minutes. The mixture was concentrated under reduced pressure, and the residue was purified by reversed-phase column chromatography (120 g Agela Technologies Claricep™ Flash C18 100 Å 40-60 m column, flow rate 50 mL/minute, 10 to 100% methanol in water [buffered with 0.025 M aqueous ammonium bicarbonate, adjusted to pH 7 with CO$_2$ (s)]) to give the title compound (6.5 mg, 0.016 mmol, 19.2% yield). $^1$H NMR (600 MHz, DMSO-d$_6$) δ ppm 6.44 (s, 1H), 3.93 (s, 2H), 3.41 (s, 2H), 3.23 (dt, J=12.7, 3.4 Hz, 2H), 2.86 (td, J=12.6, 2.9 Hz, 2H), 2.71 (t, J=5.8 Hz, 2H), 2.60 (t, J=5.8 Hz, 2H), 2.34 (d, J=7.0 Hz, 2H), 1.94-1.86 (m, 2H), 1.84 (d, J=3.6 Hz, 1H), 1.28-1.18 (m, 2H); MS (APCI$^+$) m/z 399 [M+H]$^+$.

Example 130: 5-{8-fluoro-6-hydroxy-2-[3-(morpholin-4-yl)propyl]-1,2,3,4-tetrahydroisoquinolin-7-yl}-1λ$^6$,2,5-thiadiazolidine-1,1,3-trione (Compound 229)

Example 130A: 5-{6-(benzyloxy)-8-fluoro-2-[3-(morpholin-4-yl)propyl]-1,2,3,4-tetrahydroisoquinolin-7-yl}-1λ$^6$,2,5-thiadiazolidine-1,1,3-trione To a vial containing a suspension of the product of Example 65A (150 mg, 0.297 mmol) in acetonitrile (2.5 mL) was added potassium carbonate (205 mg, 1.484 mmol) and 3-morpholinopropyl methanesulfonate (133 mg, 0.594 mmol). The reaction mixture was heated to 60° C. for 2 hours. The reaction mixture was filtered over a pad of diatomaceous earth eluted sequentially with acetonitrile and methanol, and the filtrate was concentrated under reduced pressure. The residue was purified by reversed-phase column chromatography (120 g Agela Technologies Claricep™ Flash C18 100 Å 40-60 μm column, flow rate 50 mL/minute, 10 to 100% methanol in water [buffered with 0.025 M aqueous ammonium bicarbonate, adjusted to pH 7 with CO$_2$ (s)]) to give the title compound (43.2 mg, 0.083 mmol, 28.1% yield). $^1$H NMR (600 MHz, DMSO-d$_6$) δ ppm 7.52-7.47 (m, 2H), 7.35 (dd, J=8.2, 6.7 Hz, 2H), 7.32-7.26 (m, 1H), 6.77 (s, 1H), 5.12 (s, 2H), 3.95 (s, 2H), 3.67 (s, 4H), 2.88-2.85 (m, 3H), 2.77-2.65 (m, 11H), 1.85 (s, 2H); MS (APCI$^+$) m/z 519 [M+H]$^+$.

Example 130B: 5-{8-fluoro-6-hydroxy-2-[3-(morpholin-4-yl)propyl]-1,2,3,4-tetrahydroisoquinolin-7-yl}-1λ$^6$,2,5-thiadiazolidine-1,1,3-trione Trichloroborane (1.0 M in dichloromethane, 614 μL, 0.614 mmol) was added to a vial containing a suspension of the product of Example 130A and 1,2,3,4,5-pentamethylbenzene (34.1 mg, 0.230 mmol) in dichloromethane (767 μL) cooled to −78° C. The resulting mixture was stirred at −78° C. for 1 hour, and then at 0° C. for 30 minutes. The mixture was cooled back to −78° C. and quenched with ethanol (4 mL). The mixture was then allowed to warm to ambient temperature and stirred for 15 minutes. The mixture was then concentrated under reduced pressure. The residue was purified by reversed-phase column chromatography (120 g Agela Technologies Claricep™ Flash C18 100 Å 40-60 μm column, flow rate 50 mL/minute, 10 to 100% methanol in water [buffered with 0.025 M aqueous ammonium bicarbonate, adjusted to pH 7 with $CO_2$ (s)]) to give the title compound (19.7 mg, 0.046 mmol, 59.9% yield). $^1$H NMR (600 MHz, DMSO-$d_6$) δ ppm 9.39 (s, 1H), 6.52 (s, 1H), 3.94 (s, 2H), 3.83 (s, 2H), 3.67 (d, J=4.8 Hz, 4H), 3.01 (s, 2H), 2.88-2.84 (m, 3H), 2.82 (s, 5H), 2.77 (s, 2H), 1.90 (t, J=7.2 Hz, 2H); MS (APCI$^+$) m/z 429 [M+H]$^+$.

Example 131: 5-{8-fluoro-6-hydroxy-2-[2-(piperidin-4-yl)ethyl]-1,2,3,4-tetrahydroisoquinolin-7-yl}-1$\lambda^6$,2,5-thiadiazolidine-1,1,3-trione (Compound 230)

Example 131A: tert-butyl 4-{2-[6-(benzyloxy)-8-fluoro-7-(1,1,4-trioxo-1$\lambda^6$,2,5-thiadiazolidin-2-yl)-3,4-dihydroisoquinolin-2(1H)-yl]ethyl}piperidine-1-carboxylate Triethylamine (0.083 mL, 0.594 mmol) was added to 5-[6-(benzyloxy)-8-fluoro-1,2,3,4-tetrahydroisoquinolin-7-yl]-1$\lambda^6$,2,5-thiadiazolidine-1,1,3-trione 2,2,2-trifluoroacetate (150 mg, 0.297 mmol, Example 54A) in dichloromethane (5 mL) and the mixture was stirred at ambient temperature for 5 minutes. tert-Butyl 4-(2-oxoethyl)piperidine-1-carboxylate (130 mg, 0.572 mmol) was then added and the mixture was stirred for a further 10 minutes. Then, sodium triacetoxyhydroborate (157 mg, 0.742 mmol) was added, and the reaction mixture was stirred at ambient temperature for 16 hours. The reaction mixture was diluted with dichloromethane (5 mL) and stirred with saturated sodium bicarbonate (20 mL) for 20 minutes. The mixture was extracted with dichloromethane. The organic fractions were dried over sodium sulfate, filtered, and concentrated under reduced pressure. The residue was purified by reversed-phase column chromatography (120 g Agela Technologies Claricep™ Flash C18 100 Å 40-60 μm column, flow rate 50 mL/minute, 10 to 100% methanol in water [buffered with 0.025 M aqueous ammonium bicarbonate, adjusted to pH 7 with $CO_2$ (s)]) to give the title compound (173.2 mg, 0.287 mmol, 97% yield). MS (APCI$^+$) m/z 603 [M+H]$^+$.

Example 131B: 5-{8-fluoro-6-hydroxy-2-[2-(piperidin-4-yl)ethyl]-1,2,3,4-tetrahydroisoquinolin-7-yl}-1$\lambda^6$,2,5-thiadiazolidine-1,1,3-trione Trichloroborane (1.0 M in dichloromethane, 929 μL, 0.929 mmol) was added to a vial containing a suspension of the product of Example 131A (51.7 mg, 0.348 mmol) in dichloromethane (1161 μL) cooled to −78° C. The mixture was stirred at −78° C. for 10 minutes and then at 0° C. for 20 minutes. The reaction mixture was cooled back to −78° C. and quenched with the addition of ethyl acetate (3 mL) and ethanol (3 mL). The mixture was then allowed to warm to ambient temperature and stirred further for 15 minutes. The mixture was concentrated under reduced pressure and purified by reversed-phase column chromatography (120 g Agela Technologies Claricep™ Flash C18 100 Å 40-60 μm column, flow rate 50 mL/minute, 10 to 100% methanol in water [buffered with 0.025 M aqueous ammonium bicarbonate, adjusted to pH 7 with $CO_2$ (s)]) to give the title compound (10.3 mg, 0.025 mmol, 21.5% yield). $^1$H NMR (400 MHz, DMSO-$d_6$) δ ppm 6.44 (s, 1H), 3.93 (s, 2H), 3.21 (d, J=12.8 Hz, 3H), 2.82 (t, J=12.5 Hz, 2H), 2.70 (d, J=5.7 Hz, 2H), 2.59 (t, J=6.0 Hz, 2H), 1.82 (d, J=13.6 Hz, 2H), 1.62 (s, 2H), 1.47 (q, J=7.5, 7.1 Hz, 2H), 1.30-1.29 (m, 3H); MS (APCI$^+$) m/z 413 [M+H]$^+$.

Example 132: 5-(8-fluoro-6-hydroxy-2-{2-[(1s,3r)-3-(trifluoromethoxy)cyclobutyl]ethyl}-1,2,3,4-tetrahydroisoquinolin-7-yl)-1$\lambda^6$,2,5-thiadiazolidine-1,1,3-trione (Compound 231)

Example 132A: 5-[6-(benzyloxy)-8-fluoro-2-{2-[(1s,3r)-3-(trifluoromethoxy)cyclobutyl]ethyl}-1,2,3,4-tetrahydroisoquinolin-7-yl]-1$\lambda^6$,2,5-thiadiazolidine-1,1,3-trione, Ammonia Salt A suspension of the product of Example 135H (120.0 mg, 0.356 mmol, 1.4 equivalents), 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.254 mmol, 1 equivalent, Example 54A), and potassium carbonate (176 mg, 1.27 mmol, 5.0 equivalents) in acetonitrile (0.8 mL) was placed in a heating block that had been preheated to 60° C. The reaction mixture was stirred for 18 hours at 60° C. The reaction mixture was cooled to 23° C. The cooled reaction mixture was diluted with dimethyl sulfoxide (1 mL) and saturated aqueous ammonium chloride solution (0.5 mL). The diluted mixture was purified by reversed-phase flash column chromatography (50 g RediSep® Gold C18 column, eluted with a gradient from 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (35 mg, 0.061 mmol, 25% yield, two steps). MS (APCI$^+$) m/z 558 [M+H]$^+$.

Example 132B: 5-(8-fluoro-6-hydroxy-2-{2-[(1s,3r)-3-(trifluoromethoxy)cyclobutyl]ethyl}-1,2,3,4-tetrahydroisoquinolin-7-yl)-1$\lambda^6$,2,5-thiadiazolidine-1,1,3-trione, Ammonia Salt A suspension of palladium-on-carbon (10 weight %, 6.7 mg, 0.006 mmol, 10.0 mol %), ammonium formate (20 mg, 0.314 mmol, 5.0 equivalents), and the product of Example 132A (35 mg, 0.063 mmol, 1 equivalent) in ethanol (1.0 mL) was stirred for 2 hours at 23° C. Additional ammonium formate (58 mg, 0.920 mmol, 14.6 equivalents) was added at 23° C. The reaction mixture was stirred for 30 minutes at 23° C. Additional palladium-on-carbon (10 weight %, 15.0 mg, 0.014 mmol, 22.3 mol %) was added at 23° C. The reaction mixture was stirred for 1 hour at 23° C. Water (0.2 mL) was added at 23° C. The reaction vessel was then placed in a heating block that had been preheated to 40° C. The reaction mixture was stirred for 1 hour at 40° C. The reaction mixture was then cooled to 23° C. The cooled mixture was filtered through a plug of diatomaceous earth (1.0 cm×0.5 cm). The filter cake was rinsed with methanol (3×1.0 mL). The filtrates were combined and concentrated. The residue obtained was purified by reversed-phase flash column chromatography (5.5 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=13 mL/minute) to furnish the title compound (20 mg, 0.041 mmol, 66% yield). $^1$H NMR (500 MHz, DMSO-$d_6$) δ ppm 9.67 (bs, 1H), 6.57 (s, 1H), 4.68 (p, J=7.4 Hz, 1H), 4.56-4.02 (m, 2H), 3.94 (s, 2H), 3.79-3.46 (m, 1H), 3.24-2.89 (m, 5H), 1.88 (app s, 5H); MS (APCI$^+$) m/z 468 [M+H]$^+$.

Example 133: 5-{8-fluoro-6-hydroxy-2-[3-(4-methylpiperazin-1-yl)propyl]-1,2,3,4-tetrahydroisoquinolin-7-yl}-1$\lambda^6$,2,5-thiadiazolidine-1,1,3-trione (Compound 232)

Example 133A: 5-{6-(benzyloxy)-8-fluoro-2-[3-(4-methylpiperazin-1-yl)propyl]-1,2,3,4-tetrahydroisoquinolin-7-yl}-1$\lambda^6$,2,5-thiadiazolidine-1,1,3-trione To a vial containing a suspension of the product of Example 65A in acetonitrile (2 mL) (150 mg, 0.297 mmol) was added potassium carbonate (205 mg, 1.484 mmol), and 1-(3-bromopropyl)-4-methylpiperazine 2 hydrobromic acid (162 mg, 0.297 mmol) and the mixture was stirred at 60° C. for 3 hours. The solution was filtered over a pad of diatomaceous earth eluted with acetonitrile. The filtrate was concentrated under reduced pressure. The product was purified by reversed-phase column chromatography (120 g Agela Technologies Claricep™ Flash C18 100 Å 40-60 µm column, flow rate 50 mL/minute, 10 to 100% methanol in water [buffered with 0.025 M aqueous ammonium bicarbonate, adjusted to pH 7 with $CO_2$ (s)]) to give the title compound (49.1 mg, 0.092 mmol, 31.1% yield). MS (APCI$^+$) m/z 532 [M+H]$^+$.

Example 133B: 5-{8-fluoro-6-hydroxy-2-[3-(4-methylpiperazin-1-yl)propyl]-1,2,3,4-tetrahydroisoquinolin-7-yl}-1$\lambda^6$,2,5-thiadiazolidine-1,1,3-trione Trichloroborane (1.0 M in dichloromethane, 584 µL, 0.584 mmol) was added to a vial containing a suspension of the product of Example 133A (38.8 mg, 0.073 mmol) and 1,2,3,4,5-pentamethylbenzene (32.5 mg, 0.219 mmol) in dichloromethane (730 µL) cooled to −78° C. The mixture was stirred at −78° C. for 10 minutes, and then at 0° C. for 20 minutes. The mixture was cooled back to −78° C., diluted with dichloromethane (2 mL), and quenched via the successive addition of ethyl acetate (3 mL) and ethanol (3 mL). The mixture was warmed to room temperature and stirred for 15 minutes. The mixture was diluted with ethanol and concentrated under reduced pressure. The compound was purified by reversed-phase column chromatography (60 g Biotage® Sfär C18 Duo 100 Å 30 µm column, flow rate 50 mL/minute, 10 to 100% methanol in water [buffered with 0.025 M aqueous ammonium bicarbonate, adjusted to pH 7 with $CO_2$ (s)]) to give the title compound (16.8 mg, 0.038 mmol, 52.1% yield). $^1$H NMR (500 MHz, DMSO-$d_6$) δ ppm 9.21 (s, 1H), 6.46 (s, 1H), 3.94 (s, 2H), 3.50 (s, 2H), 3.17 (s, 1H), 2.80 (s, 8H), 2.75 (d, J=6.2 Hz, 2H), 2.75-2.54 (m, 6H), 2.46 (s, 3H), 1.75 (p, J=7.2 Hz, 2H); MS (APCI$^+$) m/z 442 [M+H]$^+$.

Example 134: 5-(8-fluoro-6-hydroxy-2-{2-[(propan-2-yl)oxy]ethyl}-1,2,3,4-tetrahydroisoquinolin-7-yl)-1$\lambda^6$,2,5-thiadiazolidine-1,1,3-trione (Compound 233)

Example 134A: 5-[6-(benzyloxy)-8-fluoro-2-{2-[(propan-2-yl)oxy]ethyl}-1,2,3,4-tetrahydroisoquinolin-7-yl]-1$\lambda^6$,2,5-thiadiazolidine-1,1,3-trione To a vial containing a suspension of the product of Example 65A (100 mg, 0.198 mmol) in acetonitrile (2 mL) was added potassium carbonate (137 mg, 0.989 mmol). The resultant solution was stirred at ambient temperature for 10 minutes. Then 2-isopropoxyethyl methanesulfonate (54.1 mg, 0.297 mmol) dissolved in acetonitrile (0.5 mL) was added, and the resulting mixture was heated to 60° C. for 17 hours. The solution was filtered over a pad of diatomaceous earth eluted with acetonitrile and methanol. The filtrate was concentrated under reduced pressure. The product was purified by reversed-phase column chromatography (120 g Agela Technologies Claricep™ Flash C18 100 Å 40-60 µm column, flow rate 50 mL/minute, 10 to 100% methanol in water [buffered with 0.025 M aqueous ammonium bicarbonate, adjusted to pH 7 with $CO_2$ (s)]) to give the title compound (16.2 mg, 0.034 mmol, 17.15% yield). MS (APCI$^+$) m/z 478 [M+H]$^+$.

Example 134B: 5-(8-fluoro-6-hydroxy-2-{2-[(propan-2-yl)oxy]ethyl}-1,2,3,4-tetrahydroisoquinolin-7-yl)-1$\lambda^6$,2,5-thiadiazolidine-1,1,3-trione Trichloroborane (1.0 M in dichloromethane, 271 µL, 0.271 mmol) was added to a vial containing a suspension of the product of Example 134A (16.2 mg, 0.034 mmol) and 1,2,3,4,5-pentamethylbenzene (15.09 mg, 0.102 mmol) in dichloromethane (339 µL) cooled to −78° C. The resulting mixture was stirred at −78° C. for 30 minutes. The mixture was diluted with ethanol (1 mL) and then warmed to ambient temperature and stirred further for 15 minutes. The mixture was concentrated under reduced pressure, and the residue was purified by reversed-phase column chromatography (60 g Biotage® Sfär C18 Duo 100 Å 30 µm column, 10 to 100% methanol in water [buffered with 0.025 M aqueous ammonium bicarbonate, adjusted to pH 7 with $CO_2$ (s)]) to give the title compound (5.6 mg, 0.014 mmol, 42.6% yield). $^1$H NMR (500 MHz, DMSO-$d_6$) δ ppm 9.59 (s, 1H), 6.55 (s, 1H), 4.14 (s, 2H), 3.94 (s, 2H), 3.72 (t, J=5.1 Hz, 2H), 3.63 (p, J=6.1 Hz, 1H), 3.25 (s, 2H), 2.95 (t, J=6.2 Hz, 2H), 1.13 (d, J=6.1 Hz, 6H); MS (APCI$^+$) m/z 388 [M+H]$^+$.

Example 135: 5-[1-fluoro-3-hydroxy-7-({2-[(1s,3r)-3-(trifluoromethoxy)cyclobutyl]ethyl}amino)-5,6,7,8-tetrahydronaphthalen-2-yl]-1$\lambda^6$,2,5-thiadiazolidine-1,1,3-trione (Compound 234)

Example 135A: benzyl (1s,3s)-3-(trifluoromethoxy)cyclobutane-1-carboxylate

To a mixture of solid silver trifluoromethanesulfonate (394 g, 1536 mmol), 1-chloromethyl-4-fluoro-1,4-diazoniabicyclo[2.2.2]octane bis(tetrafluoroborate) (204 g, 576 mmol) and potassium fluoride (89.2 g, 1536 mmol) was added a solution of benzyl (1s,3s)-3-hydroxycyclobutane-1-carboxylate (88 g, 90% purity by $^1$H NMR, 384 mmol) in ethyl acetate (1800 mL), followed by 2-fluoropyridine (132 mL, 1536 mmol) and (trifluoromethyl)trimethylsilane (274 g, 960 mmol) dropwise. After 36 hours, the reaction mixture was filtered through Celite® and concentrated in vacuo to give the crude product, which was purified by column chromatography eluting with a 20:1 mixture of petroleum ether and ethyl acetate to give the title compound (90 g, 90% purity by $^1$H NMR, 295 mmol, 76.8% yield). $^1$H NMR (400 MHz, CDCl$_3$) δ ppm 7.43-7.32 (m, 5H), 5.15 (s, 2H), 4.58 (p, J=7.5 Hz, 1H), 2.87-2.70 (m, 1H), 2.65 (dtd, J=9.6, 7.3, 2.6 Hz, 2H), 2.60-2.49 (m, 2H), 1.27 (t, J=7.1 Hz, 1H).

Example 135B: (1s,3s)-3-(trifluoromethoxy)cyclobutane-1-carboxylic Acid

To a solution of the product of Example 135A (90 g, 90% purity by $^1$H NMR, 295 mmol) in tetrahydrofuran (500 mL) was added palladium(II) hydroxide on carbon (30 g, 214 mmol) and the reaction mixture was placed under a hydrogen gas atmosphere (15 psi). After 1 hour, the reaction mixture was vented and then filtered through Celite®. The filtrate was concentrated in vacuo. The residue was purified by column chromatography eluting with a 20:1 mixture of petroleum ether and ethyl acetate to give the title compound (60 g, 90% purity by $^1$H NMR, 293 mmol, 99% yield). $^1$H NMR (400 MHz, CDCl$_3$) δ ppm 11.66 (br s, 1H), 4.60 (p, J=7.4 Hz, 1H), 2.85-2.62 (m, 3H), 2.61-2.49 (m, 2H).

Example 135C: [(1s,3s)-3-(trifluoromethoxy)cyclobutyl]methanol

To a solution of the product of Example 135B (30.0 g, 90% purity by $^1$H NMR, 146 mmol) in tetrahydrofuran (600 mL) at 0° C. was added lithium aluminum hydride (6.68 g, 176 mmol) portion-wise. After 30 minutes, the reaction was quenched with water (5 mL) and stirred for 5 minutes, then 15% aqueous sodium hydroxide (5 mL) was added, followed by water (15 mL). The mixture was filtered through Celite®, and the filtrate was concentrated in vacuo. The residue was purified by column chromatography eluting with a 20:1 mixture of petroleum ether and ethyl acetate to give the title compound (17.00 g, 90% purity by $^1$H NMR, 90 mmol, 61.6% yield). $^1$H NMR (400 MHz, CDCl$_3$) δ ppm 4.57 (p, J=7.4 Hz, 1H), 3.65 (d, J=5.5 Hz, 2H), 2.55-2.37 (m, 2H), 2.19-1.93 (m, 3H), 1.43 (br s, 1H).

Example 135D: [(1s,3s)-3-(trifluoromethoxy)cyclobutyl]methyl 4-methylbenzene-1-sulfonate To a solution of the product of Example 135C (17 g, 90 mmol, 90% purity) in dichloromethane (400 mL) at 0° C. was added triethylamine (21.84 g, 216 mmol), followed by 4-toluenesulfonyl chloride (25.7 g, 135 mmol) portion-wise. After 12 hours, the reaction mixture was diluted with water (200 mL) and extracted with dichloromethane (3×100 mL). The combined organic layers were dried over anhydrous sodium sulfate, filtered and concentrated in vacuo. The residue was purified by column eluting with a 20:1 mixture of petroleum ether and ethyl acetate to give the title compound (28.00 g, 86.3 mmol, 95.9% yield). $^1$H NMR (400 MHz, CDCl$_3$) δ ppm 7.80 (d, J=8.3 Hz, 2H), 7.37 (d, J=8.1 Hz, 2H), 4.52 (p, J=7.5 Hz, 1H), 4.01 (d, J=6.0 Hz, 2H), 2.52-2.38 (m, 5H), 2.31-2.17 (m, 1H), 2.04-1.88 (m, 2H).

Example 135E: [(1s,3r)-3-(trifluoromethoxy)cyclobutyl]acetonitrile

To a solution of the product of Example 135D (19 g, 55.7 mmol) in dimethyl sulfoxide (200 mL) was added sodium cyanide (3.27 g, 66.8 mmol). After 12 hours, the reaction was diluted with water (100 mL) and extracted with ethyl acetate (3×100 mL). The combined organic layers were dried over sodium sulfate, filtered and concentrated in vacuo to give the title compound (10.6 g, 90% purity by $^1$H NMR, 49.2 mmol, 88.3% yield), which was used for the next step without purification. $^1$H NMR (400 MHz, CDCl$_3$) δ ppm 4.54 (p, J=7.4 Hz, 1H), 2.72-2.60 (m, 2H), 2.52 (d, J=6.4 Hz, 2H), 2.31-2.17 (m, 1H), 2.14-2.05 (m, 2H).

Example 135F: [(1s,3s)-3-(trifluoromethoxy)cyclobutyl]acetic Acid

To a solution of the product of Example 135E (10.6 g, 90% purity by $^1$H NMR, 49.2 mmol) in a mixture of water (90 mL) and methanol (90 mL) was added sodium hydroxide (39.4 g, 985 mmol), and the resulting mixture was heated to 100° C. After 12 hours, the reaction mixture was cooled to ambient temperature, diluted with water (100 mL) and washed with ethyl acetate (200 mL). The aqueous layer was adjusted to pH 3 by addition of 1 M hydrochloric acid and then extracted with ethyl acetate (3×150 mL). The combined organic layers were dried over anhydrous sodium sulfate, filtered and concentrated in vacuo to give the title compound (12 g, 48.5 mmol, 80% purity, 98% yield), which was used without purification in the next step. $^1$H NMR (400 MHz, CDCl$_3$) δ ppm 4.53 (p, J=7.5 Hz, 1H), 2.62 (dtd, J=9.6, 7.0, 3.1 Hz, 2H), 2.53 (d, J=7.4 Hz, 2H), 2.33-2.19 (m, 1H), 2.02-1.90 (m, 2H).

Example 135G: 2-[(1s,3r)-3-(trifluoromethoxy)cyclobutyl]ethan-1-ol

To a solution of the product of Example 135F (11 g, 80% purity by $^1$H NMR, 44.4 mmol) in tetrahydrofuran (110 mL) at 0° C. was added a solution of borane tetrahydrofuran complex (89 mL, 1 M in tetrahydrofuran, 89 mmol) portion-wise. After 30 minutes the reaction mixture was warmed to room temperature and stirred for 12 hours, then quenched with methanol (100 mL). The mixture was concentrated in vacuo, and the residue was purified by column chromatography eluting with a 20:1 mixture of petroleum ether and ethyl acetate to give the title compound (7.50 g, 38.7 mmol, 91.7% yield). $^1$H NMR (400 MHz, CDCl$_3$) δ ppm 4.51 (p, J=7.4 Hz, 1H), 3.62 (t, J=6.5 Hz, 2H), 2.59-2.48 (m, 2H), 2.04-1.93 (m, 1H), 1.93-1.83 (m, 2H), 1.72 (q, J=6.8 Hz, 2H), 1.42-1.21 (m, 1H).

Example 135H: 2-[(1s,3r)-3-(trifluoromethoxy)cyclobutyl]ethyl 4-methylbenzene-1-sulfonate To a solution of the product of Example 135G (3.50 g, 18.06 mmol) in dichloromethane (30 mL) at 0° C. was added triethylamine (6.04 mL, 43.3 mmol), followed by p-toluenesulfonyl chloride (5.16 g, 27.1 mmol) portion-wise. After 12 hours, the reaction was quenched with water (30 mL) and the aqueous layer was extracted with ethyl acetate (3×20 mL). The combined organic layers were dried over anhydrous sodium sulfate, filtered and concentrated in vacuo. The residue was purified by column chromatography eluting with a 20:1 mixture of petroleum ether and ethyl acetate to give the title compound (5.74 g, 14.93 mmol, 93.9% yield). $^1$H NMR (400 MHz, CDCl$_3$) δ ppm 7.79 (d, J=8.3 Hz, 2H), 7.36 (d, J=8.0 Hz, 2H), 4.46 (p, J=7.4 Hz, 1H), 3.99 (t, J=6.1 Hz, 2H), 2.54-2.37 (m, 5H), 1.99-1.87 (m, 1H), 1.86-1.75 (m, 4H).

Example 135I. 2-[(1s,3r)-3-(trifluoromethoxy)cyclobutyl]ethan-1-amine

To a solution of the product of Example 135H (0.5487 g, 1.622 mmol) and di-tert-butyl iminodicarboxylate (3.88 g, 1.784 mmol) in N,N-dimethylformamide (5.5 mL) was added cesium carbonate (0.793 g, 2.43 mmol), and the resulting mixture was heated to 60° C. After 17 hours, the mixture was cooled to ambient temperature, quenched with saturated aqueous ammonium chloride (2.25 mL), diluted with water (5.5 mL) and extracted with ethyl acetate (3×5.5 mL). The combined organic layers were washed with saturated aqueous ammonium chloride (3×5.5 mL) and brine (2.25 mL), then dried over anhydrous sodium sulfate, filtered and concentrated in vacuo. The residue was dissolved in ethyl acetate (5.5 mL) and a solution of hydrogen chloride (5.5 mL, 4 M in dioxane, 22 mmol) was added. After 3 days the mixture was concentrated, then ethyl acetate (5.5 mL) was added. The resulting solid was collected by filtration, washed with ethyl acetate (2.25 mL) and dried in a vacuum oven at 50° C. to give the title compound as the hydrochloride salt (0.285 g, 1.298 mmol, 80% yield). $^1$H NMR (500 MHz, methanol-d$_4$) δ ppm 4.62 (p, J=7.4 Hz, 1H), 2.89-2.82 (m, 2H), 2.63-2.53 (m, 2H), 2.10-1.83 (m, 3H), 1.83-1.73 (m, 2H); MS (APCI$^+$) m/z 184 [M+H]$^+$.

Example 135J: 5-[3-(benzyloxy)-1-fluoro-7-({2-[(1s,3r)-3-(trifluoromethoxy)cyclobutyl]ethyl}amino)-5,6,7,8-tetrahydronaphthalen-2-yl]-1λ$^6$,2,5-thiadiazolidine-1,1,3-trione To a solution of the product of Example 67F (0.350 g, 0.865 mmol) in ethanol (6 mL) was added triethylamine (0.362 mL, 2.60 mmol), followed by the product of Example 135I (0.285 g, 1.298 mmol). After 30 minutes sodium cyanoborohydride (0.065 g, 1.039 mmol) was added as a solid. After 16 hours, the reaction mixture was quenched with ammonium hydroxide (0.088 mL, 5.19 mmol), then diluted with acetonitrile (10 mL) and water (2 mL). Celite® (4 g) was added and the mixture was concentrated in vacuo to give a powder. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give the title compound (0.3830 g, 0.670 mmol, 77.0% yield). MS (APCI$^+$) m/z 572 [M+H]$^+$.

Example 135K: 5-[1-fluoro-3-hydroxy-7-({2-[(1s,3r)-3-(trifluoromethoxy)cyclobutyl]ethyl}amino)-5,6,7,8-tetrahydronaphthalen-2-yl]-1λ$^6$,2,5-thiadiazolidine-1,1,3-trione To a suspension of the product of Example 135J (0.3830 g, 0.670 mmol) and pentamethylbenzene (0.199 g, 1.34 mmol) in dichloromethane (7.6 mL) at −78° C. was added a solution of boron trichloride (4.02 mL, 1 M in dichloromethane, 4.02 mmol) slowly along the side of the flask. The resulting mixture was stirred for 5 minutes, then warmed to an internal temperature of 0° C., then cooled to −78° C. and quenched with ethyl acetate (4 mL) followed by ethanol (4 mL). The reaction mixture was warmed to ambient temperature and concentrated in vacuo. The crude solid was triturated with heptanes (3×8 mL), 1:1 ethyl acetate/heptanes (2×8 mL) and dichloromethane (2×8 mL) to give a tar, which was dissolved in methanol (20 mL). Celite® (3 g) was added and the mixture was concentrated in vacuo to give a powder. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.2012 g, 0.418 mmol, 62.4% yield). $^1$H NMR (400 MHz, DMSO-d$_6$) δ ppm 9.25 (s, 1H), 8.49 (br s, 2H), 6.47 (s, 1H), 4.68 (p, J=7.2 Hz, 1H), 3.94 (s, 2H), 3.47-3.32 (m, 3H), 3.08 (dd, J=15.9, 5.4 Hz, 1H), 2.99-2.91 (m, 2H), 2.77 (qt, J=16.8, 7.8 Hz, 2H), 2.57-2.51 (m, 1H), 2.19-2.11 (m, 1H), 1.99-1.81 (m, 3H), 1.82-1.72 (m, 2H), 1.68 (dh, J=11.4, 5.7 Hz, 1H); MS (APCI$^+$) m/z 482 [M+H]$^+$.

Example 136: 5-(1-fluoro-3-hydroxy-7-{[(1s,3s)-3-(trifluoromethoxy)cyclobutyl]amino}-5,6,7,8-tetrahydronaphthalen-2-yl)-1λ$^6$,2,5-thiadiazolidine-1,1,3-trione (Compound 235)

Example 136A: tert-butyl [(1s,3s)-3-(trifluoromethoxy)cyclobutyl]carbamate

To a solution of the product of Example 135B (12 g, 58.7 mmol, 90% purity) in toluene was added triethylamine (16.35 mL, 117 mmol), followed by diphenylphosphoryl azide (18.96 mL, 88 mmol). After 30 minutes, tert-butanol (360 mL) was added and the resulting mixture was heated to 110° C. After 18 hours, the reaction mixture was cooled to ambient temperature and then concentrated in vacuo. The residue was purified by column chromatography eluting with a 10:1 mixture of petroleum ether and ethyl acetate to give the title compound (16.00 g, 80% purity by $^1$H NMR, 50.2 mmol). $^1$H NMR (400 MHz, CDCl$_3$) δ ppm 4.58 (br s, 1H), 4.29 (p, J=7.2 Hz, 1H), 3.75 (br s, 1H), 2.76 (br d, J=6.8 Hz, 1H), 2.08-1.91 (m, 1H), 1.37 (s, 9H).

Example 136B: (1s,3s)-3-(trifluoromethoxy)cyclobutan-1-amine

To a solution of hydrogen chloride (320 mL, 4 M in ethyl acetate, 1280 mmol) was added the product of Example 136A (14 g, 80% purity by $^1$H NMR, 50.2 mmol). After 4 hours, the reaction mixture was concentrated in vacuo. The residue was triturated with methyl tert-butyl ether (25 mL) to give the title compound as the hydrochloride salt (8.1 g, 42.3 mmol, 84.2% yield). $^1$H NMR (400 MHz, DMSO-d$_6$) δ ppm 8.38 (br s, 3H), 4.66 (p, J=7.2 Hz, 1H), 3.28-3.35 (m, 1H), 2.65-2.78 (m, 2H), 2.30-2.45 (m, 2H); MS (ESI$^+$) m/z 156 [M+H]$^+$.

Example 136C: 5-[3-(benzyloxy)-1-fluoro-7-{[(1s,3s)-3-(trifluoromethoxy)cyclobutyl]amino}-5,6,7,8-tetrahydronaphthalen-2-yl]-1λ$^6$,2,5-thiadiazolidine-1,1,3-trione To a solution of the product of Example 67F (0.285 g, 0.705 mmol) in ethanol (5.7 mL) was added triethylamine (0.295 mL, 2.12 mmol), followed by the product of Example 136B (0.2025 g, 1.057 mmol). After 30 minutes sodium cyanoborohydride (0.053 g, 0.846 mmol) was added as a solid. After 16 hours, the reaction mixture was quenched with ammonium hydroxide (0.080 mL, 4.23 mmol), then diluted with acetonitrile (10 mL) and water (2 mL). Celite® (4 g) was added, and the mixture was concentrated in vacuo to give a powder. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give the title compound (0.2553 g, 0.470 mmol, 66.6% yield). MS (APCI$^+$) m/z 544 [M+H]$^+$.

Example 136D: 5-(1-fluoro-3-hydroxy-7-{[(1s,3s)-3-(trifluoromethoxy)cyclobutyl]amino}-5,6,7,8-tetrahydronaphthalen-2-yl)-1λ$^6$,2,5-thiadiazolidine-1,1,3-trione To a suspension of the product of example 136C (0.2553 g, 0.470 mmol) and pentamethylbenzene (0.139 g, 0.939 mmol) in dichloromethane (5 mL) at −78° C. was added a solution of boron trichloride (2.82 mL, 1 M in dichloromethane, 2.82 mmol) slowly along the side of the flask. The resulting mixture was stirred for 5 minutes, then warmed to an internal temperature of 0° C., then cooled to −78° C. and quenched with ethyl acetate (2.5 mL) followed by ethanol (2.5 mL). The reaction mixture was warmed to ambient temperature and concentrated in vacuo. The crude solid was triturated with heptanes (3×5 mL), 1:1 ethyl acetate/heptanes (2×5 mL) and dichloromethane (2×5 mL) to give a solid, which was dissolved in methanol (20 mL). Celite® (3 g) was added, and the mixture was concentrated in vacuo to give a powder. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.1761 g, 0.388 mmol, 83.0% yield). $^1$H NMR (500 MHz, DMSO-$d_6$) δ ppm 9.13 (s, 1H), 7.13 (br s, 2H), 6.45 (s, 1H), 4.60 (p, J=7.3 Hz, 1H), 3.94 (s, 2H), 3.5-3.3 (m, 1H), 3.12 (s, 1H), 2.91 (dd, J=16.2, 5.3 Hz, 1H), 2.81-2.63 (m, 4H), 2.36 (dd, J=16.5, 9.4 Hz, 1H), 2.21 (s, 2H), 1.95 (d, J=25.7 Hz, 1H), 1.56 (dt, J=15.8, 10.8 Hz, 1H); MS (APCI$^+$) m/z 454 [M+H]$^+$.

Example 137: 5-(8-fluoro-6-hydroxy-2-{1-[(1,3,5-trimethyl-1H-pyrazol-4-yl)methyl]piperidin-4-yl}-1,2,3,4-tetrahydroisoquinolin-7-yl)-1$\lambda^6$,2,5-thiadiazolidine-1,1,3-trione (Compound 236)

Example 137A: tert-butyl 4-[6-(benzyloxy)-8-fluoro-7-(1,1,4-trioxo-1$\lambda^6$,2,5-thiadiazolidin-2-yl)-3,4-dihydroisoquinolin-2(1H)-yl]piperidine-1-carboxylate To a vial containing 5-[6-(benzyloxy)-8-fluoro-1,2,3,4-tetrahydroisoquinolin-7-yl]-1$\lambda^6$,2,5-thiadiazolidine-1,1,3-trione 2,2,2-trifluoroacetate (theoretically 0.407 mmol) were added 1,2-dichloroethane (2.0 mL) and triethylamine (0.11 mL, 0.81 mmol). The mixture was stirred for 10 minutes, then tert-butyl 4-oxopiperidine-1-carboxylate (0.122 g, 0.611 mmol) was added. After 60 minutes, sodium triacetoxyhydroborate (0.216 g, 1.02 mmol) was added. After 96 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×30 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.177 g, 0.308 mmol, 76% yield over two steps). $^1$H NMR (600 MHz, DMSO-$d_6$) δ ppm 9.75 (br s, 1H), 7.52-7.47 (m, 2H), 7.38-7.32 (m, 2H), 7.33-7.27 (m, 1H), 6.89 (s, 1H), 5.17 (s, 2H), 4.36 (s, 2H), 4.09 (s, 2H), 3.96 (d, J=8.6 Hz, 2H), 3.72 (br s, 1H), 3.63-3.57 (m, 1H), 3.32-3.21 (m, 1H), 3.04 (br s, 2H), 2.77 (br s, 2H), 2.11 (br s, 1H), 2.03 (br s, 1H), 1.65 (br s, 1H), 1.56 (br s, 1H), 1.41 (s, 9H); MS (APCI$^+$) m/z 575.3 [M+H]$^+$.

Example 137B: 5-[6-(benzyloxy)-8-fluoro-2-(piperidin-4-yl)-1,2,3,4-tetrahydroisoquinolin-7-yl]-1$\lambda^6$,2,5-thiadiazolidine-1,1,3-trione 2,2,2-trifluoroacetate A vial containing a suspension of tert-butyl 4-[6-(benzyloxy)-8-fluoro-7-(1,1,4-trioxo-1$\lambda^6$,2,5-thiadiazolidin-2-yl)-3,4-dihydroisoquinolin-2(1H)-yl]piperidine-1-carboxylate (0.161 g, 0.280 mmol) in dichloromethane (0.93 mL) was cooled to 0° C. Then 2,2,2-trifluoroacetic acid (0.22 mL, 2.8 mmol) was added dropwise, and the cooling bath was subsequently removed. After 1 hour, the reaction mixture was concentrated under reduced pressure. The residue was azeotroped with toluene (2×1 mL) and then co-evaporated with methanol (1 mL) to give the title compound. This material was used without further purification. MS (APCI$^+$) m/z 475.3 [M+H]$^+$.

Example 137C: 5-[6-(benzyloxy)-8-fluoro-2-{1-[(1,3,5-trimethyl-1H-pyrazol-4-yl)methyl]piperidin-4-yl}-1,2,3,4-tetrahydroisoquinolin-7-yl]-1$\lambda^6$,2,5-thiadiazolidine-1,1,3-trione To a vial containing 5-[6-(benzyloxy)-8-fluoro-2-(piperidin-4-yl)-1,2,3,4-tetrahydroisoquinolin-7-yl]-1$\lambda^6$,2,5-thiadiazolidine-1,1,3-trione 2,2,2-trifluoroacetate (theoretically 0.280 mmol) were added 1,2-dichloroethane (1.4 mL) and triethylamine (0.078 mL, 0.56 mmol). The mixture was stirred for 10 minutes, then 1,3,5-trimethyl-1H-pyrazole-4-carbaldehyde (0.058 g, 0.42 mmol) was added. After 30 minutes, sodium triacetoxyhydroborate (0.148 g, 0.700 mmol) was added. After 18 hours, more 1,3,5-trimethyl-1H-pyrazole-4-carbaldehyde (0.058 g, 0.42 mmol) was added, followed 15 minutes later by more sodium triacetoxyhydroborate (0.148 g, 0.700 mmol). Twenty-four hours later, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×30 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.120 g, 0.201 mmol, 72% yield over two steps). $^1$H NMR (500 MHz, DMSO-$d_6$-$D_2$O) δ ppm 7.47-7.42 (m, 2H), 7.36-7.30 (m, 2H), 7.30-7.23 (m, 1H), 6.71 (s, 1H), 5.07 (s, 2H), 3.99 (s, 2H), 3.94 (br s, 2H), 3.61 (s, 3H), 3.59 (br s, 2H), 3.35 (br s, 2H), 2.85 (br s, 2H), 2.73 (br s, 5H), 2.20 (s, 3H), 2.12 (s, 3H), 2.05-1.94 (br m, 2H), 1.79-1.60 (br m, 2H); MS (APCI$^+$) m/z 597.4 [M+H]$^+$.

Example 137D: 5-(8-fluoro-6-hydroxy-2-{1-[(1,3,5-trimethyl-1H-pyrazol-4-yl)methyl]piperidin-4-yl}-1,2,3,4-tetrahydroisoquinolin-7-yl)-1$\lambda^6$,2,5-thiadiazolidine-1,1,3-trione A vial containing a suspension of 5-[6-(benzyloxy)-8-fluoro-2-{1-[(1,3,5-trimethyl-1H-pyrazol-4-yl)methyl]piperidin-4-yl}-1,2,3,4-tetrahydroisoquinolin-7-yl]-1$\lambda^6$,2,5-thiadiazolidine-1,1,3-trione (0.110 g, 0.184 mmol) and 1,2,3,4,5-pentamethylbenzene (0.082 g, 0.55 mmol) in dichloromethane (1.8 mL) was cooled to −78° C. with stirring under an atmosphere of nitrogen. Next, trichloroborane (1.0 M in dichloromethane) (1.5 mL, 1.5 mmol) was added slowly. The resulting brownish mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Biotage® Sfär C18 Duo 100 Å 30 µm column, 10-100% gradient of methanol in water (buffered with 0.025 M aqueous ammonium bicarbonate, adjusted to pH 7 with dry ice)] to give the title compound (0.072 g, 0.14 mmol, 77% yield). $^1$H NMR (600 MHz, DMSO-d$_6$) δ ppm 9.18 (s, 1H), 8.86 (br s, 1H), 6.45 (s, 1H), 3.99 (br s, 2H), 3.93 (s, 2H), 3.65 (s, 3H), 3.60 (br s, 2H), 3.34 (br s, 2H), 3.17 (br s, 1H), 2.85 (br s, 2H), 2.81-2.64 (br m, 4H), 2.25 (s, 3H), 2.15 (s, 3H), 2.05-1.96 (br m, 2H), 1.77-1.67 (br m, 2H); MS (APCI$^+$) m/z 507.4 [M+H]$^+$.

Example 138: 5-(8-fluoro-6-hydroxy-2-{2-[(1,3,5-trimethyl-1H-pyrazol-4-yl)methyl]-2-azaspiro[3.3]heptan-6-yl}-1,2,3,4-tetrahydroisoquinolin-7-yl)-1λ$^6$,2,5-thiadiazolidine-1,1,3-trione (Compound 237)

Example 138A: tert-butyl 6-[6-(benzyloxy)-8-fluoro-7-(1,1,4-trioxo-1λ$^6$,2,5-thiadiazolidin-2-yl)-3,4-dihydroisoquinolin-2(1H)-yl]-2-azaspiro[3.3]heptane-2-carboxylate To a vial containing 5-[6-(benzyloxy)-8-fluoro-1,2,3,4-tetrahydroisoquinolin-7-yl]-1λ$^6$,2,5-thiadiazolidine-1,1,3-trione 2,2,2-trifluoroacetate (Example 93A, theoretically 0.407 mmol) were added 1,2-dichloroethane (2.0 mL) and triethylamine (0.11 mL, 0.81 mmol). The mixture was stirred for 10 minutes, then tert-butyl 6-oxo-2-azaspiro[3.3]heptane-2-carboxylate (0.129 g, 0.611 mmol) was added. After 30 minutes, sodium triacetoxyhydroborate (0.216 g, 1.02 mmol) was added. After 12 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×30 mL). The organic phases were combined, washed with brine, dried over sodium sulfate, and concentrated under reduced pressure. The residue was purified using reversed-phase chromatography [120 g Agela Claricep™ spherical C18 100 Å 40-60 µm column, 10-100% gradient of methanol in water (buffered with 0.025 M aqueous ammonium bicarbonate, adjusted to pH 7 with dry ice)] to give the title compound (0.220 g, 0.375 mmol, 92% yield over two steps). $^1$H NMR (500 MHz, DMSO-d$_6$) δ ppm 10.00 (br s, 1H), 7.52-7.46 (m, 2H), 7.39-7.32 (m, 2H), 7.32-7.26 (m, 1H), 6.90 (s, 1H), 5.16 (s, 2H), 4.37 (br s, 1H), 4.02 (br s, 1H), 3.99-3.94 (m, 2H), 3.90 (s, 2H), 3.81 (s, 2H), 3.74 (br s, 1H), 3.51 (br s, 1H), 3.13 (br s, 1H), 3.01 (s, 2H), 2.58 (br t, J=8.9 Hz, 2H), 2.43 (br s, 2H), 1.37 (s, 9H); MS (APCI$^+$) m/z 587.3 [M+H]$^+$.

Example 138B: 5-[2-(2-azaspiro[3.3]heptan-6-yl)-6-(benzyloxy)-8-fluoro-1,2,3,4-tetrahydroisoquinolin-7-yl]-1λ$^6$,2,5-thiadiazolidine-1,1,3-trione 2,2,2-trifluoroacetate A vial containing a suspension of tert-butyl 6-[6-(benzyloxy)-8-fluoro-7-(1,1,4-trioxo-1λ$^6$,2,5-thiadiazolidin-2-yl)-3,4-dihydroisoquinolin-2(1H)-yl]-2-azaspiro[3.3]heptane-2-carboxylate (0.082 g, 0.14 mmol) in dichloromethane (0.47 mL) was cooled to 0° C. Then 2,2,2-trifluoroacetic acid (0.11 mL, 1.4 mmol) was added dropwise, and the cooling bath was subsequently removed. After 3 hours, the reaction mixture was concentrated under reduced pressure. The residue was azeotroped with toluene (2×1 mL) and then co-evaporated with methanol (1 mL) to give the title compound. This material was used without further purification. MS (APCI$^+$) m/z 487.1 [M+H]$^+$.

Example 138C: 5-[6-(benzyloxy)-8-fluoro-2-{2-[(1,3,5-trimethyl-1H-pyrazol-4-yl)methyl]-2-azaspiro[3.3]heptan-6-yl}-1,2,3,4-tetrahydroisoquinolin-7-yl]-1λ$^6$,2,5-thiadiazolidine-1,1,3-trione To a vial containing 5-[2-(2-azaspiro[3.3]heptan-6-yl)-6-(benzyloxy)-8-fluoro-1,2,3,4-tetrahydroisoquinolin-7-yl]-1λ$^6$,2,5-thiadiazolidine-1,1,3-trione 2,2,2-trifluoroacetate (theoretically 0.14 mmol) were added 1,2-dichloroethane (0.70 mL) and triethylamine (0.039 mL, 0.28 mmol). The mixture was stirred for 10 minutes, then 1,3,5-trimethyl-1H-pyrazole-4-carbaldehyde (0.029 g, 0.21 mmol) was added. After 30 minutes, sodium triacetoxyhydroborate (0.074 g, 0.35 mmol) was added. After 18 hours, more 1,3,5-trimethyl-1H-pyrazole-4-carbaldehyde (0.029 g, 0.21 mmol) was added, followed 15 minutes later by more sodium triacetoxyhydroborate (0.074 g, 0.35 mmol). Twenty-two hours later, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×30 mL). The organic phases were combined, washed with brine, dried over sodium sulfate, and concentrated under reduced pressure. The residue was purified using reversed-phase chromatography [60 g Biotage® Sfär C18 Duo 100 Å 30 µm column, 10-100% gradient of methanol in water (buffered with 0.025 M aqueous ammonium bicarbonate, adjusted to pH 7 with dry ice)] to give the title compound (0.054 g, 0.089 mmol, 64% yield over two steps). $^1$H NMR (500 MHz, DMSO-d$_6$-D$_2$O) δ ppm 7.49-7.43 (m, 2H), 7.36-7.30 (m, 2H), 7.30-7.24 (m, 1H), 6.71 (s, 1H), 5.07 (s, 2H), 4.00 (s, 2H), 3.97 (s, 2H), 3.95 (s, 2H), 3.83 (s, 2H), 3.60 (s, 3H), 3.30 (s, 2H), 2.80 (p, J=7.6 Hz, 1H), 2.71 (t, J=5.9 Hz, 2H), 2.46 (t, J=5.9 Hz, 2H), 2.42-2.36 (m, 2H), 2.21 (s, 3H), 2.11 (s, 3H), 2.09-2.03 (br m, 2H); MS (APCI$^+$) m/z 609.3 [M+H]$^+$.

Example 138D: 5-(8-fluoro-6-hydroxy-2-{2-[(1,3,5-trimethyl-1H-pyrazol-4-yl)methyl]-2-azaspiro[3.3]heptan-6-yl}-1,2,3,4-tetrahydroisoquinolin-7-yl)-1λ$^6$,2,5-thiadiazolidine-1,1,3-trione A vial was charged with 5-[6-(benzyloxy)-8-fluoro-2-{2-[(1,3,5-trimethyl-1H-pyrazol-4-yl)methyl]-2-azaspiro[3.3]heptan-6-yl}-1,2,3,4-tetrahydroisoquinolin-7-yl]-1λ$^6$,2,5-thiadiazolidine-1,1,3-trione (0.053 g, 0.088 mmol), ammonium formate (0.028 g, 0.44 mmol), and 10% palladium on carbon (0.009 g, 0.009 mmol). The vial was capped and purged with nitrogen. Next, ethanol (0.44 mL) was added and the mixture was heated to 60° C. After 16 hours, the mixture was cooled to ambient temperature and filtered over diatomaceous earth with the aid of methanol. The filtrate was concentrated under reduced pressure. The residue was purified using reversed-phase chromatography [120 g Biotage® Sfär C18 Duo 100 Å 30 µm column, 10-100% gradient of methanol in water (buffered with 0.025 M aqueous ammonium bicarbonate, adjusted to pH 7 with dry ice)] to give the title compound (0.012 g, 0.023 mmol, 27% yield). $^1$H NMR (600 MHz, DMSO-d$_6$-D$_2$O) δ ppm 6.62 (s, 1H), 4.65 (d, J=15.3 Hz, 1H), 4.48 (d, J=15.2 Hz, 1H), 4.24 (s, 1H), 4.04-3.96 (m, 2H), 3.83-3.77 (m, 1H), 3.65 (dt, J=13.6, 7.4 Hz, 1H), 3.54 (s, 3H), 3.53-3.50 (m, 1H), 3.42-3.37 (m, 1H), 3.37 (s, 2H), 3.18-3.04 (m, 2H), 2.65 (s, 2H), 2.19 (t, J=10.0 Hz, 1H), 2.10 (s, 3H), 2.07-2.03 (m, 3H), 2.03 (s, 3H); MS (ESI$^+$) m/z 518.9 [M+H]$^+$.

Example 139: 5-(2-{2-[1-(difluoromethyl)-3,5-dimethyl-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione (Compound 238)

Example 139A: 5-[6-(benzyloxy)-2-{2-[1-(difluoromethyl)-3,5-dimethyl-1H-pyrazol-4-yl]ethyl}-8-fluoro-1,2,3,4-tetrahydroisoquinolin-7-yl]-1$\lambda^6$,2,5-thiadiazolidine-1,1,3-trione To a vial containing 5-[6-(benzyloxy)-8-fluoro-1,2,3,4-tetrahydroisoquinolin-7-yl]-1$\lambda^6$,2,5-thiadiazolidine-1,1,3-trione 2,2,2-trifluoroacetate (Example 93A, theoretically 0.15 mmol) were added 1,2-dichloroethane (0.77 mL) and triethylamine (0.043 mL, 0.31 mmol). The mixture was stirred for 5 minutes, then 2-(1-(difluoromethyl)-3,5-dimethyl-1H-pyrazol-4-yl)acetaldehyde (0.043 g, 0.23 mmol) was added. After 30 minutes, sodium triacetoxyhydroborate (0.081 g, 0.38 mmol) was added. After 16 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.040 g, 0.070 mmol, 46% yield over two steps). $^1$H NMR (600 MHz, DMSO-d$_6$) δ ppm 9.89 (br s, 1H), 7.67 (t, J=58.2 Hz, 1H), 7.52-7.48 (m, 2H), 7.38-7.33 (m, 2H), 7.32-7.28 (m, 2H), 6.91 (s, 1H), 5.17 (s, 2H), 4.63 (br s, 1H), 4.25 (br s, 1H), 3.98 (s, 2H), 3.81 (br s, 1H), 3.32 (br s, 3H), 3.07 (s, 2H), 2.85 (t, J=8.6 Hz, 2H), 2.36 (s, 3H), 2.19 (s, 3H); MS (APCI$^+$) m/z 564.3 [M+H]$^+$.

Example 139B: 5-(2-{2-[1-(difluoromethyl)-3,5-dimethyl-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione A vial containing a suspension of 5-[6-(benzyloxy)-2-{2-[1-(difluoromethyl)-3,5-dimethyl-1H-pyrazol-4-yl]ethyl}-8-fluoro-1,2,3,4-tetrahydroisoquinolin-7-yl]-1$\lambda^6$,2,5-thiadiazolidine-1,1,3-trione (0.038 g, 0.067 mmol) and 1,2,3,4,5-pentamethylbenzene (0.030 g, 0.20 mmol) in dichloromethane (0.67 mL) was cooled to −78° C. with stirring under an atmosphere of nitrogen. Next, trichloroborane (1.0 M in dichloromethane) (0.54 mL, 0.54 mmol) was added slowly. The resulting brownish mixture was stirred at −78° C. for 10 minutes, and then the dry ice-acetone bath was replaced with an ice-water bath. After 60 minutes, the mixture was recooled to −78° C., diluted with dichloromethane (5 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [60 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound (0.031 g, 0.065 mmol, 97% yield). $^1$H NMR (500 MHz, DMSO-d$_6$-D$_2$O) δ ppm 7.57 (t, J=58.2 Hz, 1H), 6.60 (s, 1H), 4.23 (br s, 2H), 3.99 (s, 2H), 3.23 (t, J=8.5 Hz, 2H), 3.03 (t, J=6.2 Hz, 2H), 2.83 (dd, J=10.1, 7.0 Hz, 2H), 2.32 (s, 3H), 2.16 (s, 3H). Note: Two non-exchangeable protons are unaccounted for; MS (APCI$^+$) m/z 474.2 [M+H]$^+$.

Example 139C: 2-(1-(difluoromethyl)-3,5-dimethyl-1H-pyrazol-4-yl)ethan-1-ol

To a vial were added 2-(3,5-dimethyl-1H-pyrazol-4-yl)ethan-1-ol (0.282 g, 2.01 mmol), potassium fluoride (0.234 g, 4.03 mmol), and acetonitrile (8.1 mL). The resulting suspension was stirred at ambient temperature under an atmosphere of nitrogen. Next, a solution of diethyl (bromodifluoromethyl)phosphonate (0.538 g, 2.01 mmol) in acetonitrile (2.0 mL) was added dropwise. The resulting mixture was stirred at ambient temperature. After 20 hours, the mixture was filtered over diatomaceous earth and concentrated under reduced pressure. The residue was purified using silica gel chromatography [12 g column, 0-100% gradient of ethyl acetate in heptanes] to give the title compound (0.377 g, 1.98 mmol, 98% yield). $^1$H NMR (600 MHz, CDCl$_3$) δ ppm 7.09 (t, J=59.3 Hz, 1H), 3.69 (td, J=6.7, 5.6 Hz, 2H), 2.62 (t, J=6.7 Hz, 2H), 2.36 (s, 3H), 2.20 (t, J=1.1 Hz, 3H), 1.53 (t, J=5.7 Hz, 1H); MS (APCI$^+$) m/z 191.7 [M+H]$^+$.

Example 139D: 2-(1-(difluoromethyl)-3,5-dimethyl-1H-pyrazol-4-yl)acetaldehyde

To a flask were added 2-(1-(difluoromethyl)-3,5-dimethyl-1H-pyrazol-4-yl)ethan-1-ol (0.360 g, 1.89 mmol) and dichloromethane (9.5 mL). The suspension was stirred at ambient temperature and Dess-Martin periodinane (1.20 g, 2.84 mmol) was added in portions. After 2 hours, the solid materials were removed by filtration over diatomaceous earth with the aid of tert-butyl methyl ether. The filtrate was concentrated under reduced pressure. The residue was treated with tert-butyl methyl ether (50 mL) and stirred with 0.1 M sodium thiosulfate/saturated aqueous sodium bicarbonate (1:1 v/v) (50 mL) for 15 minutes. The layers were then separated, and the aqueous phase was extracted with tert-butyl methyl ether (3×20 mL). The organic phases were combined, washed with brine, dried over magnesium sulfate/sodium sulfate (1:1 w/w), and concentrated under reduced pressure to give the title compound (0.348 g, 1.85 mmol, 98% yield). $^1$H NMR (400 MHz, CDCl$_3$) δ ppm 9.62 (t, J=2.0 Hz, 1H), 7.12 (t, J=59.3 Hz, 1H), 3.44 (d, J=2.1 Hz, 2H), 2.34 (s, 3H), 2.16 (s, 3H); MS (APCI$^+$) m/z 189.7 [M+H]$^+$.

Example 140: 5-{2-[2-(bicyclo[2.2.1]heptan-1-yl)ethyl]-8-fluoro-6-hydroxy-1,2,3,4-tetrahydroisoquinolin-7-yl}-1$\lambda^6$,2,5-thiadiazolidine-1,1,3-trione (Compound 239)

Example 140A: 2-(bicyclo[2.2.1]heptan-1-yl)acetaldehyde

Dess-Martin periodinane (275 mg, 0.648 mmol, 1.0 equivalent) was added to a solution of 2-(bicyclo[2.2.1]heptan-1-yl)ethanol (91 mg, 0.648 mmol, 1 equivalent) in dichloromethane (3.3 mL) at 23° C. The reaction mixture was stirred for 1.5 hours at 23° C. The reaction mixture was then partitioned between saturated aqueous sodium bicarbonate solution (5 mL), saturated aqueous sodium thiosulfate solution (5 mL), ether (25 mL), and pentane (3 mL). The organic layer was washed with saturated aqueous sodium chloride solution (3 mL). The washed organic layer was dried over sodium sulfate. The dried solution was filtered, and the filtrate was concentrated. The residue obtained was suspended in ether (3 mL) and the suspension was filtered through a plug of diatomaceous earth (1.0 cm×0.5 cm). The filter cake was rinsed with ether (3×1.0 mL). The filtrates were combined and concentrated. The title compound obtained was used without further purification in the following step.

Example 140B: 5-{6-(benzyloxy)-2-[2-(bicyclo [2.2.1]heptan-1-yl)ethyl]-8-fluoro-1,2,3,4-tetrahydroisoquinolin-7-yl}-1$\lambda^6$,2,5-thiadiazolidine-1,1,3-trione, Ammonia Salt Sodium triacetoxyborohydride (97 mg, 0.46 mmol, 1.2 equivalents) was added in one portion to a suspension of the product of Example 140A (nominally 0.648 mmol, 2.0 equivalents), triethylamine (0.14 mL, 0.972 mmol, 3.0 equivalents), and 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.324 mmol, 1 equivalent, Example 54A) in acetonitrile (0.75 mL) at 23° C. The reaction mixture was stirred for 18 hours at 23° C. The reaction mixture was then diluted with saturated aqueous ammonium chloride (0.5 mL), water (0.5 mL), and dimethyl sulfoxide (2.0 mL). The diluted mixture was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (45 mg, 0.085 mmol, 27% yield). MS (APCI$^+$) m/z 514 [M+H]$^+$.

Example 140C: 5-{2-[2-(bicyclo[2.2.1]heptan-1-yl) ethyl]-8-fluoro-6-hydroxy-1,2,3,4-tetrahydroisoquinolin-7-yl}-1$\lambda^6$,2,5-thiadiazolidine-1,1,3-trione, Ammonia Salt A suspension of palladium-on-carbon (10 weight %, 9.3 mg, 0.009 mmol, 10.0 mol %), ammonium formate (28 mg, 0.438 mmol, 5.0 equivalents), and the product of Example 140B (45 mg, 0.088 mmol, 1 equivalent) in ethanol (0.5 mL) was sealed in a one dram vial with a pressure-relieving screw cap. The sealed vessel was placed in a heating block that had been preheated to 50° C. The reaction mixture was stirred for 1 hour at 50° C. The reaction mixture was then cooled to 23° C. The cooled mixture was filtered through a plug of diatomaceous earth (1.0 cm×0.5 cm). The filter cake was rinsed with methanol (3×1.0 mL). The filtrates were combined and concentrated. The residue obtained was purified by reversed-phase flash column chromatography (5.5 g RediSep Rf Gold® C18 column, eluted with a gradient of 10-100% [v/v]methanol-0.025 M aqueous ammonium bicarbonate solution [acidified with solid carbon dioxide] over 10 column volumes, then isocratically eluted with 100% methanol for 3 column volumes, flow rate=13 mL/minute) to furnish the title compound (22 mg, 0.05 mmol, 57% yield). $^1$H NMR (500 MHz, DMSO-d$_6$) δ ppm 9.65 (bs, 1H), 6.57 (s, 1H), 4.60-4.06 (m, 1H), 3.94 (s, 2H), 3.79-3.49 (m, 1H)*, 3.23 (app bs, 2H), 2.97 (app bs), 2.16 (s, 1H), 2.14-1.88 (m, 2H), 1.66-1.54 (m, 2H), 1.43-1.32 (m, 2H), 1.32-1.20 (m, 4H), 1.17 (s, 2H); MS (APCI$^+$) m: 424 [M+H]$^+$.

Example 141: 5-[7-amino-1-fluoro-3-hydroxy-7-(prop-2-en-1-yl)-5,6,7,8-tetrahydronaphthalen-2-yl]-1$\lambda^6$,2,5-thiadiazolidine-1,1,3-trione (Compound 240)

Example 141A: N'-[6-(benzyloxy)-8-fluoro-7-(1,1,4-trioxo-1$\lambda^6$,2,5-thiadiazolidin-2-yl)-3,4-dihydronaphthalen-2(1H)-ylidene]benzohydrazide To a suspension of the product of example 67F (1.0207 g, 2.52 mmol) in ethanol (20 mL) was added benzohydrazide (0.412 g, 3.03 mmol), and the resulting suspension was stirred vigorously. After 20 minutes, the mixture was diluted with water (40 mL), sonicated for 1 minute, and stirred vigorously for 5 minutes. The resulting solid was collected by filtration, washed with water (3×10 mL) and dried in a vacuum oven at 50° C. to give the title compound (1.1295 g, 2.162 mmol, 86% yield). $^1$H NMR showed a mixture of E/Z isomers and rotamers. MS (APCI$^+$) m/z 523 [M+H]$^+$.

Example 141B: N'-[6-(benzyloxy)-8-fluoro-2-(prop-2-en-1-yl)-7-(1,1,4-trioxo-1$\lambda^6$,2,5-thiadiazolidin-2-yl)-1,2,3,4-tetrahydronaphthalen-2-yl]benzohydrazide To a solution of allyltrichlorosilane (1 mL, 6.90 mmol) in 1,2-dichloroethane (20 mL) at 0° C. was added triethylamine (1.742 mL, 12.5 mmol), followed by dropwise addition of 2-(methylamino)ethanol (0.5 mL, 6.25 mmol). After 30 minutes, the mixture was warmed to ambient temperature. After 20 hours, the mixture was filtered through Celite® (1.5 g), and the solid was rinsed with 1,2-dichloroethane (3 mL). The filtrate was transferred to a 25 mL volumetric flask and diluted to a total volume of 25 mL, giving a theoretical 0.25 M concentration of 2-allyl-2-chloro-3-methyl-1,3,2-oxazasilolidine.

To a suspension of the product of Example 141A (0.5623 g, 1.076 mmol) in 1,2-dichloroethane (11 mL) was added triethylamine (0.150 mL, 1.076 mmol). After 3 minutes, a solution of 2-allyl-2-chloro-3-methyl-1,3,2-oxazasilolidine (6.03 mL, 0.25 M in 1,2-dichloroethane, 1.507 mmol) was added, and the resulting mixture was degassed by three vacuum/nitrogen backfills. After 18 hours, the reaction was quenched with methanol (3 mL) and diluted with acetonitrile (11 mL). Celite® (3 g) was added, and the mixture was concentrated in vacuo. The resultant residue was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound as the ammonium salt (0.1761 g, 0.388 mmol, 83.0% yield). $^1$H NMR (500 MHz, DMSO-d$_6$) δ ppm 9.85 (s, 1H), 7.87-7.82 (m, 2H), 7.70-7.54 (m, 1H), 7.57-7.43 (m, 5H), 7.40-7.33 (m, 2H), 7.35-7.27 (m, 1H), 6.73 (s, 1H), 6.07 (ddt, J=16.4, 10.7, 7.3 Hz, 1H), 5.23 (s, 1H), 5.13-5.05 (m, 4H), 3.97 (d, J=2.7 Hz, 2H), 2.95 (dt, J=17.3, 6.6 Hz, 1H), 2.68 (d, J=7.2 Hz, 1H), 2.64 (s, 1H), 2.57 (s, 1H), 2.23 (d, J=7.3 Hz, 2H), 1.80 (dt, J=13.2, 6.5 Hz, 1H), 1.65 (dt, J=13.2, 6.4 Hz, 1H); MS (APCI⁺) m/z 565 [M+H]⁺.

Example 141C: 5-[7-amino-3-(benzyloxy)-1-fluoro-7-(prop-2-en-1-yl)-5,6,7,8-tetrahydronaphthalen-2-yl]-1λ⁶,2,5-thiadiazolidine-1,1,3-trione To a thoroughly degassed (5× vacuum/nitrogen backfills) solution of the product of Example 141B (0.200 g, 0.344 mmol) in a mixture of tetrahydrofuran (2 mL) and methanol (2 mL) was added a solution of samarium (II) iodide (10.32 mL, 0.1 M in tetrahydrofuran, 1.032 mmol) slowly over 3 minutes. After 20 minutes, the reaction mixture was diluted with water (2 mL) and acetonitrile (8 mL). Celite® (2 g) was added, and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0770 g, 0.173 mmol, 50.3% yield). MS (APCI⁺) m/z 446 [M+H]⁺.

Example 141D: 5-[7-amino-1-fluoro-3-hydroxy-7-(prop-2-en-1-yl)-5,6,7,8-tetrahydronaphthalen-2-yl]-1λ⁶,2,5-thiadiazolidine-1,1,3-trione To a suspension of the product of Example 141C (0.0770 g, 0.173 mmol) and pentamethylbenzene (0.051 g, 0.346 mmol) in dichloromethane (3 mL) at −78° C. was added a solution of boron trichloride (2.074 mL, 1 M in dichloromethane, 2.074 mmol) slowly along the side of the flask. The resulting mixture was stirred for 5 minutes, then warmed to an internal temperature of 0° C., then cooled to −78° C. and quenched with ethyl acetate (1 mL) followed by ethanol (1 mL). The reaction mixture was warmed to ambient temperature and concentrated in vacuo. The crude solid was triturated with heptanes (3×3 mL), 1:1 ethyl acetate/heptanes (2×3 mL), dichloromethane (2×3 mL) and acetonitrile (2×3 mL) to give a solid, which was dissolved in 1:1 dimethyl sulfoxide/methanol (6 mL). The resultant solution was filtered through a 0.45 m PTFE frit, directly loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.0238 g, 0.067 mmol, 38.7% yield). ¹H NMR (600 MHz, DMSO-d₆) δ ppm 9.27 (s, 1H), 7.85 (s, 3H), 6.50 (s, 1H), 5.91 (ddt, J=17.5, 10.2, 7.4 Hz, 1H), 5.27-5.19 (m, 2H), 3.95 (d, J=13.1 Hz, 1H), 3.92 (d, J=13.1 Hz, 1H), 2.82-2.70 (m, 3H), 2.67 (d, J=16.8 Hz, 1H), 2.40-2.36 (m, 2H), 1.84 (hept, J=6.6 Hz, 2H); MS (APCI⁺) m/z 356 [M+H]⁺.

Example 142: N'-[8-fluoro-6-hydroxy-2-propyl-7-(1,1,4-trioxo-1λ⁶,2,5-thiadiazolidin-2-yl)-1,2,3,4-tetrahydronaphthalen-2-yl]benzohydrazide (Compound 241)

A suspension of the product of example 141B (0.200 g, 0.344 mmol) and 10% palladium hydroxide on carbon (0.4 g, 46.6 w % in water, 1.752 mmol) in a mixture of tetrahydrofuran (1.786 mL) and methanol (4.47 mL) was stirred for 16 hours under 60 psi of hydrogen. After filtration, Celite® (2 g) was added and the mixture was concentrated in vacuo. The resultant mixture was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound as the ammonium salt (0.0700 g, 0.142 mmol, 41.2% yield). ¹H NMR (500 MHz, DMSO-d₆) δ ppm 9.78 (s, 1H), 9.02 (s, 1H), 7.85-7.80 (m, 2H), 7.58-7.51 (m, 1H), 7.48 (dd, J=8.2, 6.7 Hz, 2H), 7.29-6.94 (m, 4H), 6.46 (s, 1H), 5.18 (s, 1H), 3.95 (s, 2H), 2.88 (dt, J=17.5, 6.2 Hz, 1H), 2.64-2.54 (m, 2H), 2.54-2.44 (m, 1H), 1.78-1.71 (m, 1H), 1.69-1.62 (m, 1H), 1.51-1.41 (m, 2H), 1.44-1.32 (m, 2H), 0.86 (t, J=6.9 Hz, 3H); MS (APCI⁺) m/z 477 [M+H]⁺.

Example 143: 5-[8-fluoro-6-hydroxy-2-(3-hydroxybutyl)-1,2,3,4-tetrahydroisoquinolin-7-yl]-1λ⁶,2,5-thiadiazolidine-1,1,3-trione (Compound 242)

Example 143A: 5-{6-(benzyloxy)-2-[3-(benzyloxy)butyl]-8-fluoro-1,2,3,4-tetrahydroisoquinolin-7-yl}-1λ⁶,2,5-thiadiazolidine-1,1,3-trione Triethylamine (0.055 ml, 0.396 mmol) was added to a vial containing a suspension of the product of Example 65A (100 mg, 0.198 mmol) in dichloromethane (1 mL) and the mixture was stirred at ambient temperature for 5 minutes. 3-(Benzyloxy)butanal (35.3 mg, 0.198 mmol) in dichloromethane (1 mL) was then added and the mixture was allowed to stir for a further 10 minutes. Then sodium triacetoxyhydroborate (105 mg, 0.495 mmol) was added, and the reaction mixture was stirred at ambient temperature for 14 hours. Then the reaction mixture was stirred with saturated sodium bicarbonate (20 mL) for 20 minutes. The mixture was extracted with dichloromethane. The organic fractions were dried over sodium sulfate, filtered, and concentrated under reduced pressure. The residue was purified by reversed-phase column chromatography (120 g Agela Technologies Claricep™ Flash C18 100 Å 40-60 µm column, flow rate 50 mL/minute, 10 to 100% methanol in water [buffered with 0.025 M aqueous ammonium bicarbonate, adjusted to pH 7 with CO₂ (s)]) to give the title compound (44.9 mg, 0.081 mmol, 41.0% yield). MS (APCI⁺) m/z 554 [M+H]⁺.

Example 143B: 5-[8-fluoro-6-hydroxy-2-(3-hydroxybutyl)-1,2,3,4-tetrahydroisoquinolin-7-yl]-1λ⁶,2,5-thiadiazolidine-1,1,3-trione Trichloroborane (1.0 M in dichloromethane, 539 µL, 0.539 mmol) was added to a vial containing a suspension of the product of Example 143A (37.3 mg, 0.067 mmol) and 1,2,3,4,5-pentamethylbenzene (30.0 mg, 0.202 mmol) in dichloromethane (674 µL) cooled to −78° C. The mixture was stirred at −78° C. for 10 minutes, and then at 0° C. for 20 minutes. The reaction was cooled back to −78° C. and quenched with the successive addition of ethyl acetate (2 mL) and ethanol (2 mL). The mixture was warmed to ambient temperature and stirred further for 15 minutes. The mixture was concentrated under reduced pressure, and the residue was purified by reversed-phase column chromatography (60 g Biotage® Sfär C18 Duo 100 Å 30 µm column, 10 to 100% methanol in water [buffered with 0.025 M aqueous ammonium bicarbonate, adjusted to pH 7 with CO₂ (s)]) to give the title compound (14.3 mg, 0.038 mmol, 56.8% yield). ¹H NMR (500 MHz, DMSO-d₆) δ ppm 9.62 (s, 1H), 6.56 (s, 1H), 4.17 (s, 2H), 3.94 (s, 2H), 3.71 (ddd, J=8.1, 6.1, 3.9 Hz, 1H), 3.24-3.09 (m, 2H), 2.97 (d, J=6.2 Hz, 2H), 1.80 (td, J=11.7, 9.9, 4.9 Hz, 1H), 1.72 (dddd, J=13.2, 10.1, 8.1, 5.6 Hz, 1H), 1.46 (s, 2H), 1.12 (d, J=6.2 Hz, 3H); MS (APCI⁺) m/z 374 [M+H]⁺.

Example 144: 5-(8-fluoro-6-hydroxy-2-{2-[1-(trifluoromethyl)cyclopropyl]ethyl}-1,2,3,4-tetrahydroisoquinolin-7-yl)-1λ⁶,2,5-thiadiazolidine-1,1,3-trione (Compound 243)

Example 144A: 2-(1-(trifluoromethyl)cyclopropyl)acetaldehyde 2-(1-(Trifluoromethyl)cyclopropyl)ethanol (106.2 mg, 0.689 mmol) was dissolved in dichloromethane (2 mL) and cooled to 0° C. After which, pyridinium chlorochromate (297 mg, 1.378 mmol) was added. The reaction mixture was stirred at ambient temperature for 3 hours. The reaction mixture was filtered over a plug of silica washed with dichloromethane. The filtrate was concentrated under reduced pressure to give the title compound (105 mg, 0.689 mmol, 63% yield) that was used without further purification. $^1$H NMR (600 MHz, CDCl$_3$) δ ppm 9.88-9.75 (m, 1H), 2.55 (d, J=2.4 Hz, 2H), 1.19-1.16 (m, 2H), 0.83-0.74 (m, 2H).

Example 144B: 5-[6-(benzyloxy)-8-fluoro-2-{2-[1-(trifluoromethyl)cyclopropyl]ethyl}-1,2,3,4-tetrahydroisoquinolin-7-yl]-1λ⁶,2,5-thiadiazolidine-1,1,3-trione Triethylamine was added to a vial containing a suspension of the product of Example 65A (110 mg, 0.218 mmol) in dichloromethane (1 mL) and stirred at ambient temperature for 5 minutes. Then, the product of Example 144A (51.5 mg, 0.339 mmol) dissolved in dichloromethane (1 mL) was added and stirred at ambient temperature for 10 minutes. Thereafter, sodium triacetoxyhydroborate (115 mg, 0.544 mmol) was added and the reaction mixture was stirred at ambient temperature for 3 days. The reaction mixture was diluted with methanol (10 mL) and concentrated under reduced pressure. The residue was purified by reversed-phase column chromatography (120 g Agela Technologies Claricep™ Flash C18 100 Å 40-60 μm column, flow rate 50 mL/minute, 10 to 100% methanol in water [buffered with 0.025 M aqueous ammonium bicarbonate, adjusted to pH 7 with CO$_2$ (s)]) to give the title compound (78.3 mg, 0.040 mmol, 68.2% yield). MS (APCI$^+$) m/z 528 [M+H]$^+$.

Example 144C: 5-(8-fluoro-6-hydroxy-2-{2-[1-(trifluoromethyl)cyclopropyl]ethyl}-1,2,3,4-tetrahydroisoquinolin-7-yl)-1λ⁶,2,5-thiadiazolidine-1,1,3-trione Trichloroborane (1.0 M in dichloromethane, 1.190 mL, 1.187 mmol) was added to a vial containing a suspension of the product of Example 144B (78.3 mg, 0.148 mmol) and 1,2,3,4,5-pentamethylbenzene (66 mg, 0.445 mmol) in dichloromethane (1.48 mL) cooled to −78° C. The mixture was stirred at −78° C. for 10 minutes and then at 0° C. for 20 minutes. The mixture was cooled back to −78° C. and quenched with the successive addition of ethyl acetate (2 mL) and ethanol (2 mL). The mixture was then warmed to ambient temperature and stirred further for 15 minutes. The mixture was concentrated under reduced pressure, and the residue was purified by reversed-phase column chromatography (60 g Biotage® Sfär C18 Duo 100 Å 30 μm column, 10 to 100% methanol in water [buffered with 0.025 M aqueous ammonium bicarbonate, adjusted to pH 7 with CO$_2$ (s)]) to give the title compound (33.6 mg, 0.077 mmol, 51.8% yield). $^1$H NMR (500 MHz, DMSO-d$_6$/D$_2$O) δ ppm 6.58 (s, 1H), 4.30-4.07 (m, 2H), 3.99 (s, 2H), 3.30 (s, 4H), 3.02-2.91 (m, 2H), 2.06-1.96 (m, 2H), 0.98-0.95 (m, 2H), 0.85-0.82 (m, 2H); MS (APCI$^+$) m/z 438 [M+H]$^+$.

Example 145: 5-[8-fluoro-6-hydroxy-2-(3-hydroxypropyl)-1,2,3,4-tetrahydroisoquinolin-7-yl]-1λ⁶,2,5-thiadiazolidine-1,1,3-trione (Compound 244)

Example 145A: 5-[6-(benzyloxy)-8-fluoro-2-{3-[(propan-2-yl)oxy]propyl}-1,2,3,4-tetrahydroisoquinolin-7-yl]-1λ⁶,2,5-thiadiazolidine-1,1,3-trione To a vial containing a suspension of the product of Example 65A in acetonitrile (2 mL) (125 mg, 0.247 mmol) was added potassium carbonate (171 mg, 1.237 mmol) and 3-isopropoxypropyl methanesulfonate (87 mg, 0.445 mmol). The mixture was stirred at 60° C. for 6 hours. The reaction mixture was filtered over a plug of diatomaceous earth with acetonitrile and methanol, and the filtrate was concentrated under reduced pressure. The product was purified by reversed-phase column chromatography (60 g Biotage® Sfär C18 Duo 100 Å 30 μm column, flow rate 50 mL/minute, 10 to 100% methanol in water [buffered with 0.025 M aqueous ammonium bicarbonate, adjusted to pH 7 with CO$_2$ (s)]) to give the title compound (91.7 mg, 0.187 mmol, 75% yield). MS (APCI$^+$) m/z 492 [M+H]$^+$.

Example 145B: 5-[8-fluoro-6-hydroxy-2-(3-hydroxypropyl)-1,2,3,4-tetrahydroisoquinolin-7-yl]-1λ⁶,2,5-thiadiazolidine-1,1,3-trione Trichloroborane (1.0 M in dichloromethane, 1492 μL, 1.492 mmol) was added to a vial containing a suspension of the product of Example 145A (91.7 mg, 0.187 mmol) and 1,2,3,4,5-pentamethylbenzene (83 mg, 0.560 mmol) in dichloromethane (1865 μL) cooled to −78° C. The mixture was stirred at −78° C. for 10 minutes, and then at 0° C. for 1 hour. The mixture was cooled back to −78° C. and quenched with the successive addition of ethyl acetate (2 mL) and ethanol (2 mL). The mixture was then warmed to ambient temperature and stirred further for 15 minutes. The mixture was concentrated under reduced pressure, and the residue was purified by reversed-phase column chromatography (60 g Biotage® Sfär C18 Duo 100 Å 30 μm column, flow rate 50 mL/minute, 10 to 100% methanol in water [buffered with 0.025 M aqueous ammonium bicarbonate, adjusted to pH 7 with CO$_2$ (s)]) to give the title compound (28.1 mg, 0.078 mmol, 41.9% yield). $^1$H NMR (400 MHz, DMSO-d$_6$/D$_2$O) δ ppm 6.60 (s, 1H), 4.43-4.05 (m, 3H), 3.96 (s, 2H), 3.51 (t, J=5.9 Hz, 2H), 3.27 (s, 2H), 3.01 (s, 2H), 1.89 (p, J=6.3 Hz, 2H); MS (APCI$^+$) m/z 360 [M+H]$^+$.

Example 146: 5-{2-[(2S)-2-aminopropyl]-8-fluoro-6-hydroxy-1,2,3,4-tetrahydroisoquinolin-7-yl}-1λ⁶,2,5-thiadiazolidine-1,1,3-trione (Compound 2245)

Example 146A: tert-butyl {(2S)-1-[6-(benzyloxy)-8-fluoro-7-(1,1,4-trioxo-1λ⁶,2,5-thiadiazolidin-2-yl)-3,4-dihydroisoquinolin-2(1H)-yl]propan-2-yl}carbamate To a vial containing 5-[6-(benzyloxy)-8-fluoro-1,2,3,4-tetrahydroisoquinolin-7-yl]-1λ⁶,2,5-thiadiazolidine-1,1,3-trione 2,2,2-trifluoroacetate (Example 93A, theoretically 0.305 mmol) were added potassium carbonate (0.211 g, 1.53 mmol), tert-butyl (S)-4-methyl-1,2,3-oxathiazolidine-3-carboxylate 2,2-dioxide (0.109 g, 0.458 mmol), acetonitrile (0.57 mL), and water (0.19 mL). The vial was capped, and the mixture was heated to 60° C. After 16 hours, the reaction mixture was cooled to ambient temperature and treated with 1.0 M hydrochloric acid (6.1 mL, 6.1 mmol). The resulting mixture was stirred for 27 hours at ambient temperature. After this time, water (30 mL) was added and the mixture was extracted with ethyl acetate (4×30 mL). The organic phases were combined, washed with brine, dried over sodium sulfate, and concentrated under reduced pressure to give the title compound. This material was used without further purification. MS (ESI⁻) m/z 547.1 [M–H]⁻.

Example 146B: 5-{2-[(2S)-2-aminopropyl]-8-fluoro-6-hydroxy-1,2,3,4-tetrahydroisoquinolin-7-yl}-1$\lambda^6$,2,5-thiadiazolidine-1,1,3-trione A flask containing a suspension of tert-butyl {(2S)-1-[6-(benzyloxy)-8-fluoro-7-(1,1,4-trioxo-1$\lambda^6$,2,5-thiadiazolidin-2-yl)-3,4-dihydroisoquinolin-2(1H)-yl]propan-2-yl}carbamate (theoretically 0.305 mmol) and 1,2,3,4,5-pentamethylbenzene (0.136 g, 0.915 mmol) in dichloromethane (3.1 mL) was cooled to –78° C. with stirring under an atmosphere of nitrogen. Next, trichloroborane (1.0 M in dichloromethane) (3.1 mL, 3.1 mmol) was added slowly. The resulting brownish mixture was stirred at –78° C. for 10 minutes, and then the dry ice-acetone bath was removed, and the mixture allowed to warm to ambient temperature. After 3 hours, the mixture was recooled to –78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Biotage® Sfär C18 Duo 100 Å 30 µm column, 10-100% gradient of methanol in water (buffered with 0.025 M aqueous ammonium bicarbonate, adjusted to pH 7 with dry ice)] to give the title compound (0.044 g, 0.12 mmol, 40% yield over three steps). $^1$H NMR (600 MHz, DMSO-d$_6$) δ ppm 6.46 (s, 1H), 4.01-3.88 (m, 2H), 3.61 (d, J=14.7 Hz, 1H), 3.47-3.39 (m, 2H), 2.80-2.69 (m, 3H), 2.64-2.59 (m, 1H), 2.58-2.52 (m, 1H), 2.52-2.47 (m, 1H), 1.15 (d, J=6.5 Hz, 3H); MS (ESI⁺) m/z 359.0 [M+H]⁺.

Example 147: 5-{2-[(2R)-2-aminopropyl]-8-fluoro-6-hydroxy-1,2,3,4-tetrahydroisoquinolin-7-yl}-1$\lambda^6$,2,5-thiadiazolidine-1,1,3-trione (Compound 246)

Example 147A: tert-butyl {(2R)-1-[6-(benzyloxy)-8-fluoro-7-(1,1,4-trioxo-1$\lambda^6$,2,5-thiadiazolidin-2-yl)-3,4-dihydroisoquinolin-2(1H)-yl]propan-2-yl}carbamate To a vial containing 5-[6-(benzyloxy)-8-fluoro-1,2,3,4-tetrahydroisoquinolin-7-yl]-1$\lambda^6$,2,5-thiadiazolidine-1,1,3-trione 2,2,2-trifluoroacetate (Example 93A, theoretically 0.305 mmol) were added potassium carbonate (0.211 g, 1.53 mmol), tert-butyl (R)-4-methyl-1,2,3-oxathiazolidine-3-carboxylate 2,2-dioxide (0.109 g, 0.458 mmol), acetonitrile (0.57 mL), and water (0.19 mL). The vial was capped, and the mixture was heated to 60° C. After 16 hours, the reaction mixture was cooled to ambient temperature and treated with 1.0 M hydrochloric acid (6.1 mL, 6.1 mmol). The resulting mixture was stirred for 27 hours at ambient temperature. After this time, water (30 mL) was added and the mixture was extracted with ethyl acetate (4×30 mL). The organic phases were combined, washed with brine, dried over sodium sulfate, and concentrated under reduced pressure to give the title compound. This material was used without further purification. MS (ESI⁻) m/z 547.1 [M–H]⁻.

Example 147B: 5-{2-[(2R)-2-aminopropyl]-8-fluoro-6-hydroxy-1,2,3,4-tetrahydroisoquinolin-7-yl}-1$\lambda^6$,2,5-thiadiazolidine-1,1,3-trione A flask containing a suspension of tert-butyl {(2R)-1-[6-(benzyloxy)-8-fluoro-7-(1,1,4-trioxo-1$\lambda^6$,2,5-thiadiazolidin-2-yl)-3,4-dihydroisoquinolin-2(1H)-yl]propan-2-yl}carbamate (theoretically 0.305 mmol) and 1,2,3,4,5-pentamethylbenzene (0.136 g, 0.915 mmol) in dichloromethane (3.1 mL) was cooled to –78° C. with stirring under an atmosphere of nitrogen. Next, trichloroborane (1.0 M in dichloromethane) (3.1 mL, 3.1 mmol) was added slowly. The resulting brownish mixture was stirred at –78° C. for 10 minutes, and then the dry ice-acetone bath was removed, and the mixture allowed to warm to ambient temperature. After 3 hours, the mixture was recooled to –78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Biotage® Sfär C18 Duo 100 Å 30 µm column, 10-100% gradient of methanol in water (buffered with 0.025 M aqueous ammonium bicarbonate, adjusted to pH 7 with dry ice)] to give the title compound (0.036 g, 0.090 mmol, 30% yield over three steps) with a purity of approximately 90%, as determined by $^1$H NMR analysis. $^1$H NMR (600 MHz, DMSO-d$_6$) δ ppm 6.48 (s, 1H), 4.03-3.93 (m, 2H), 3.60 (d, J=14.7 Hz, 1H), 3.47-3.38 (m, 2H), 2.80-2.68 (m, 3H), 2.63-2.57 (m, 1H), 2.57-2.53 (m, 1H), 2.53-2.47 (m, 1H), 1.16 (d, J=6.4 Hz, 3H); MS (ESI⁺) m/z 359.1 [M+H]⁺.

Example 148: 5-{8-fluoro-6-hydroxy-2-[2-(piperazin-1-yl)ethyl]-1,2,3,4-tetrahydroisoquinolin-7-yl}-1$\lambda^6$,2,5-thiadiazolidine-1,1,3-trione (Compound 247)

Example 148A: tert-butyl 4-{2-[6-(benzyloxy)-8-fluoro-7-(1,1,4-trioxo-1$\lambda^6$,2,5-thiadiazolidin-2-yl)-3,4-dihydroisoquinolin-2(1H)-yl]ethyl}piperazine-1-carboxylate To a vial containing a suspension of the product of Example 65A (150 mg, 0.297 mmol) in acetonitrile (2 mL) was added potassium carbonate (205 mg, 1.484 mmol) and the mixture was stirred at ambient temperature for 15 minutes. Thereafter, tert-butyl 4-(2-bromoethyl)piperazine-1-carboxylate (131 mg, 0.445 mmol) was added, and the mixture was stirred at 50° C. for 34 hours. The solution was filtered over a pad of diatomaceous earth eluted with excess acetonitrile, and the filtrate was concentrated under reduced pressure. The product was purified by reversed-phase column chromatography (120 g Agela Technologies Claricep™ Flash C18 100 Å 40-60 µm column, flow rate 50 mL/minute, 10 to 100% methanol in water [buffered with 0.025 M aqueous ammonium bicarbonate, adjusted to pH 7 with $CO_2$ (s)]) to give the title compound (45.4 mg, 0.075 mmol, 25.3% yield). MS (APCI$^+$) m/z 604 [M+H]$^+$.

Example 148B: 5-{8-fluoro-6-hydroxy-2-[2-(piperazin-1-yl)ethyl]-1,2,3,4-tetrahydroisoquinolin-7-yl}-1$\lambda^6$,2,5-thiadiazolidine-1,1,3-trione Trichloroborane (1.0 M in dichloromethane, 464 μL, 0.464 mmol) was added to a vial containing a suspension of the product of Example 148A (35 mg, 0.058 mmol) and 1,2,3,4,5-pentamethylbenzene (25.8 mg, 0.174 mmol) in dichloromethane (580 μL) cooled to −78° C. The mixture was stirred at −78° C. for 10 minutes, and then at 0° C. for 10 minutes. The mixture was cooled back to −78° C., diluted with dichloromethane (2 mL), and quenched with ethanol (3 mL). The mixture was then stirred at ambient temperature for 15 minutes. The mixture was concentrated under reduced pressure, and the residue was purified by reversed-phase column chromatography (60 g Biotage® Sfär C18 Duo 100 Å 30 μm column, flow rate 50 mL/minute, 10 to 100% methanol in water [buffered with 0.025 M aqueous ammonium bicarbonate, adjusted to pH 7 with $CO_2$ (s)]) to give the title compound (14.6 mg, 0.035 mmol, 60.9% yield). $^1$H NMR (500 MHz, DMSO-d$_6$) δ ppm 9.12 (s, 1H), 6.44 (s, 1H), 3.93 (s, 2H), 3.46 (s, 2H), 3.01 (t, J=5.1 Hz, 4H), 2.70 (t, J=5.8 Hz, 2H), 2.61 (dt, J=14.5, 8.3 Hz, 9H), 2.57 (s, 1H); MS (APCI$^+$) m/z 414 [M+H]$^+$.

Example 149: 5-(8-fluoro-6-hydroxy-2-{[rac-(1R,2R)-2-(pyridin-4-yl)cyclopropyl]methyl}-1,2,3,4-tetrahydroisoquinolin-7-yl)-1$\lambda^6$,2,5-thiadiazolidine-1,1,3-trione (Compound 248)

Example 149A: 5-[6-(benzyloxy)-8-fluoro-2-{[rac-(1R,2R)-2-(pyridin-4-yl)cyclopropyl]methyl}-1,2,3,4-tetrahydroisoquinolin-7-yl]-1$\lambda^6$,2,5-thiadiazolidine-1,1,3-trione, Ammonia Salt Sodium triacetoxyborohydride (64 mg, 0.30 mmol, 1.2 equivalents) was added to a suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.25 mmol, 1 equivalent, Example 54A), triethylamine (0.11 mL, 0.80 mmol, 3.2 equivalents), and rac-(1R,2R)-2-(pyridin-4-yl)cyclopropane-1-carbaldehyde (44 mg, 0.30 mmol, 1.2 equivalents) in acetonitrile (1.2 mL) at 23° C. The reaction mixture was stirred for 18 hours at 23° C. A solution of rac-(1R,2R)-2-(pyridin-4-yl)cyclopropane-1-carbaldehyde (150 mg, 1.02 mmol, 4.1 equivalents) in acetonitrile (0.5 mL) was added at 23° C. The reaction mixture was stirred for 5 hours at 23° C. The reaction mixture was diluted sequentially with saturated aqueous ammonium chloride solution (0.5 mL) and dimethyl sulfoxide (3.0 mL). The diluted mixture was purified by reversed-phase flash column chromatography (100 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (84 mg, 0.16 mmol, 64% yield). MS (APCI$^+$) m/z 523 [M+H]$^+$.

Example 149B: 5-(8-fluoro-6-hydroxy-2-{[rac-(1R,2R)-2-(pyridin-4-yl)cyclopropyl]methyl}-1,2,3,4-tetrahydroisoquinolin-7-yl)-1$\lambda^6$,2,5-thiadiazolidine-1,1,3-trione, Ammonia Salt A mixture of palladium-on-carbon (10 weight %, 34 mg, 0.03 mmol, 20 mol %), ammonium formate (51 mg, 0.80 mmol, 5.0 equivalents), and 5-[6-(benzyloxy)-8-fluoro-2-{[rac-(1S,2S)-2-(pyridin-4-yl)cyclopropyl]methyl}-1,2,3,4-tetrahydroisoquinolin-7-yl]-1$\lambda^6$,2,5-thiadiazolidine-1,1,3-trione, ammonia salt (84 mg, 0.16 mmol, 1 equivalent) in ethanol (1.6 mL) was stirred for 20 hours at 23° C. The reaction mixture was then filtered through a plug of diatomaceous earth (1.0 cm×0.5 cm). The filter cake was washed with methanol (3×1.0 mL). The filtrates were combined, and the combined filtrates were concentrated. The residue obtained was purified by reversed-phase flash-column chromatography (50 g RediSep Rf (Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=40 mL/minute) to furnish the title compound (35 mg, 0.078 mmol, 48% yield). $^1$H NMR (400 MHz, DMSO-d$_6$) δ ppm 9.60 (bs, 1H), 8.38 (d, J=5.2 Hz, 2H), 7.15-7.12 (m, 2H), 6.52 (s, 1H), 4.25-4.02 (m, 2H), ~3.22-3.15 (m, 2H)*, 3.90 (s, 2H), 2.93 (bs, 2H), 2.00 (dt, J=8.9, 4.9 Hz, 1H), 1.63-1.56 (m, 1H), 1.20 (dt, J=8.5, 5.1 Hz, 1H), 1.15 (dt, J=8.7, 5.3 Hz, 1H); *resonance obscured by solvent. MS (APCI$^+$) m/z 433 [M+H]$^+$.

Example 150: 5-[2-(2-cyclopentyl-2-methoxyethyl)-8-fluoro-6-hydroxy-1,2,3,4-tetrahydroisoquinolin-7-yl]-1$\lambda^6$,2,5-thiadiazolidine-1,1,3-trione (Compound 249)

Example 150A: 5-[6-(benzyloxy)-2-(2-cyclopentyl-2-methoxyethyl)-8-fluoro-1,2,3,4-tetrahydroisoquinolin-7-yl]-1$\lambda^6$,2,5-thiadiazolidine-1,1,3-trione, Ammonia Salt Sodium triacetoxyborohydride (79 mg, 0.38 mmol, 1.5 equivalents) was added to a suspension of 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.25 mmol, 1 equivalent, Example 54A), triethylamine (0.14 mL, 1.00 mmol, 4.0 equivalents), and 2-cyclopentyl-2-methoxyacetaldehyde (54 mg, 0.38 mmol, 1.5 equivalents) in acetonitrile (1.2 mL) at 23° C. The reaction mixture was stirred for 3 hours at 23° C. The reaction mixture was diluted sequentially with saturated aqueous ammonium chloride solution (0.5 mL) and dimethyl sulfoxide (3.0 mL). The diluted mixture was purified by reversed-phase flash column chromatography (100 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute) to furnish the title compound (101 mg, 0.19 mmol, 78% yield). MS (APCI$^+$) m/z 518 [M+H]$^+$.

Example 150B: 5-[2-(2-cyclopentyl-2-methoxyethyl)-8-fluoro-6-hydroxy-1,2,3,4-tetrahydroisoquinolin-7-yl]-1$\lambda^6$,2,5-thiadiazolidine-1,1,3-trione, Ammonia Salt A solution of boron trichloride in dichloromethane (1.0 M, 2.0 mL, 2.00 mmol, 10.3 equivalents) was added to a suspension of the product of Example 150A (101 mg, 0.195 mmol, 1 equivalent) and pentamethylbenzene (38 mg, 0.256 mmol, 1.3 equivalents) in dichloromethane (1.0 mL) at −78° C. The reaction vessel was immediately transferred to a cooling bath at 0° C. The reaction mixture was stirred for 1 hour at 0° C. The reaction vessel was then transferred to a cooling bath at −78° C. and cooled over 15 minutes to −78° C. A solution of boron tribromide in dichloromethane (0.2 mL, 0.20 mmol, 1.0 equivalent) was added at −78° C. The reaction vessel was immediately transferred to a cooling bath at 0° C. The reaction mixture was stirred for 1 hour at 0° C. The reaction vessel was then transferred to a cooling bath at −78° C. and cooled over 15 minutes to −78° C. The reaction mixture was diluted slowly ethanol (1.0 mL) at −78° C. The diluted mixture was warmed over 15 minutes to 23° C. The warmed mixture was concentrated. The residue obtained was purified by reversed-phase flash column chromatography (50 g RediSep Rf Gold® C18 column, eluted with a gradient of 10-100% [v/v]methanol-0.025 M aqueous ammonium bicarbonate solution [acidified with solid carbon dioxide] over 10 column volumes, then isocratically eluted with 100% methanol for 3 column volumes, flow rate=40 mL/minute). The fractions containing product were collected and concentrated. The residue obtained was repurified by reversed-phase flash column chromatography (5.5 g RediSep Rf Gold® C18 column, eluted with a gradient of 10-100% [v/v]methanol-0.025 M aqueous ammonium bicarbonate solution [acidified with solid carbon dioxide] over 10 column volumes, then isocratically eluted with 100% methanol for 3 column volumes, flow rate=13 mL/minute) to furnish the title compound (9 mg, 0.020 mmol, 10% yield). $^1$H NMR (400 MHz, DMSO-$d_6$) δ ppm 9.62 (bs, 1H), 7.26-6.93 (m, 1H), 6.54 (s, 1H), 3.94 (s, 2H), 3.37 (s, 3H), 3.09-2.75 (m, 2H), 2.19-2.03 (m, 1H), 1.79-1.17 (m, 8H); MS (APCI$^+$) m/z 428 [M+H]$^+$.

Example 151: 5-{2-[(2R)-2-amino-4-cyclohexylbutanoyl]-8-fluoro-6-hydroxy-1,2,3,4-tetrahydroisoquinolin-7-yl}-1$\lambda^6$,2,5-thiadiazolidine-1,1,3-trione (Compound 250)

Example 151A: (9H-fluoren-9-yl)methyl {(2R)-1-[6-(benzyloxy)-8-fluoro-7-(1,1,4-trioxo-1$\lambda^6$,2,5-thiadiazolidin-2-yl)-3,4-dihydroisoquinolin-2(1H)-yl]-4-cyclohexyl-1-oxobutan-2-yl}carbamate, Ammonia Salt N,N-Diisopropylethylamine (0.30 mL, 1.73 mmol, 6.9 equivalents) was added to a suspension of 2-(1H-benzotriazole-1-yl)-1,1,3,3-tetramethylaminium tetrafluoroborate (TBTU, 88 mg, 0.28 mmol, 1.1 equivalents), (R)-α-[[(9H-fluoren-9-ylmethoxy)carbonyl]amino]cyclohexanebutanoic acid (153 mg, 0.38 mmol, 1.5 equivalents), and 5-[6-(benzyloxy)-8-fluoro-1,2,3,4-tetrahydroisoquinolin-7-yl]-1$\lambda^6$,2,5-thiadiazolidine-1,1,3-trione, trifluoroacetate (nominally 0.25 mmol, 1 equivalent, Example 54A) in acetonitrile (1.2 mL) at 23° C. The reaction mixture was stirred for 18 hours at 23° C. The reaction mixture was diluted water (0.5 mL) and dimethyl sulfoxide (1.0 mL). The diluted mixture was purified by reversed-phase flash column chromatography (100 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=60 mL/minute). The fractions containing product were collected and concentrated. The title compound obtained was used without further purification in the following step. MS (APCI$^+$) m/z 781 [M+H]$^+$.

Example 151B: 5-{2-[(2R)-2-amino-4-cyclohexylbutanoyl]-8-fluoro-6-hydroxy-1,2,3,4-tetrahydroisoquinolin-7-yl}-1$\lambda^6$,2,5-thiadiazolidine-1,1,3-trione, Ammonia Salt A mixture of palladium-on-carbon (10 weight %, 53 mg, 0.05 mmol, 10 mol %), ammonium formate (79 mg, 1.25 mmol, 5.0 equivalents), and the product of Example 151A (nominally 0.25 mmol, 1 equivalent) in ethanol (1.3 mL) was stirred for 1.5 hours at 50° C. The reaction mixture was then cooled to 23° C. The cooled mixture was filtered through a plug of diatomaceous earth (1.0 cm×0.5 cm). The filter cake was rinsed with methanol (3×1.0 mL). The filtrates were combined, and the combined filtrates were concentrated. The residue obtained was purified by reversed-phase flash column chromatography (50 g RediSep Rf Gold® C18 column, eluted with a gradient of 10-100% [v/v] methanol-0.025 M aqueous ammonium bicarbonate solution [acidified with solid carbon dioxide] over 10 column volumes, then isocratically eluted with 100% methanol for 3 column volumes, flow rate=40 mL/minute) to furnish the title compound (35 mg, 0.072 mmol, 30% over three steps). $^1$H NMR (400 MHz, DMSO-$d_6$) δ ppm 6.58 (s, 1H), 4.73-4.26 (m, 1H), 3.96 (s, 2H), 3.81-3.63 (m, 2H), 1.83-1.53 (m, 7H), 1.36-1.08 (m, 6H), 0.97-0.80 (m, 2H); MS (APCI$^+$) m/z 469 [M+H]$^+$.

Example 152: 5-(8-fluoro-6-hydroxy-2-{3-[(propan-2-yl)oxy]propyl}-1,2,3,4-tetrahydroisoquinolin-7-yl)-1$\lambda^6$,2,5-thiadiazolidine-1,1,3-trione (Compound 251)

The product of Example 145A (50.4 mg, 0.103 mmol) in tetrahydrofuran (4 mL) was added to 5% Pd/C, wet (50 mg, 0.219 mmol) in a 20 mL Barnstead STEM RS10 reactor, and the mixture was stirred at 25° C. under an atmosphere of 57-65 psi of hydrogen for 21.5 hours. The reaction mixture was filtered, and the filtrate was concentrated under reduced pressure. The product was purified by reversed-phase column chromatography (60 g Biotage® Sfär C18 Duo 100 Å 30 µm column, 10 to 100% methanol in water [buffered with 0.025 M aqueous ammonium bicarbonate, adjusted to pH 7 with $CO_2$ (s)]) to give the title compound (32.3 mg, 0.080 mmol, 78% yield). $^1$H NMR (600 MHz, DMSO-$d_6$) δ ppm 9.64 (s, 1H), 6.57 (s, 1H), 4.14 (s, 1H), 3.94 (s, 2H), 3.55 (p, J=6.1 Hz, 1H), 3.44 (t, J=5.9 Hz, 2H), 3.23 (s, 5H), 2.98 (s, 2H), 1.93 (s, 2H), 1.09 (d, J=6.1 Hz, 6H); MS (APCI$^+$) m/z 402 [M+H]$^+$.

Example 153: 5-{8-fluoro-6-hydroxy-2-[2-(1-methyl-1H-pyrazol-4-yl)ethyl]-1,2,3,4-tetrahydroisoquinolin-7-yl}-1$\lambda^6$,2,5-thiadiazolidine-1,1,3-trione (Compound 252)

Example 153A: 5-{6-(benzyloxy)-8-fluoro-2-[2-(1-methyl-1H-pyrazol-4-yl pyrazol-4-yl)ethyl]-1,2,3,4-tetrahydroisoquinolin-7-yl}-1$\lambda^6$,2,5-thiadiazolidine-1,1,3-trione To a vial containing 5-[6-(benzyloxy)-8-fluoro-1,2,3,4-tetrahydroisoquinolin-7-yl]-1$\lambda^6$,2,5-thiadiazolidine-1,1,3-trione 2,2,2-trifluoroacetate (Example 93A, theoretically 0.15 mmol) were added 1,2-dichloroethane (0.77 mL) and triethylamine (0.043 mL, 0.31 mmol). The mixture was stirred for 5 minutes, then 2-(1-methyl-1H-pyrazol-4-yl)acetaldehyde (0.028 g, 0.23 mmol) was added. After 30 minutes, sodium triacetoxyhydroborate (0.081 g, 0.38 mmol) was added. After 14 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.065 g, 0.13 mmol, 85% yield over two steps). $^1$H NMR (400 MHz, DMSO-$d_6$-$D_2O$) δ ppm 7.58 (s, 1H), 7.47 (d, J=7.4 Hz, 2H), 7.38-7.32 (m, 3H), 7.32-7.25 (m, 1H), 6.88 (s, 1H), 5.14 (s, 2H), 4.33 (br s, 2H), 3.99 (s, 2H), 3.77 (s, 3H), 3.48 (br s, 2H), 3.45-3.31 (m, 2H), 3.13-3.00 (m, 2H), 2.90 (t, J=8.2 Hz, 2H); MS (APCI$^+$) m/z 500.3 [M+H]$^+$.

Example 153B: 5-{8-fluoro-6-hydroxy-2-[2-(1-methyl-1H-pyrazol-4-yl)ethyl]-1,2,3,4-tetrahydroisoquinolin-7-yl}-1λ$^6$,2,5-thiadiazolidine-1,1,3-trione A vial containing a suspension of 5-{6-(benzyloxy)-8-fluoro-2-[2-(1-methyl-1H-pyrazol-4-yl)ethyl]-1,2,3,4-tetrahydroisoquinolin-7-yl}-1λ$^6$,2,5-thiadiazolidine-1,1,3-trione (0.063 g, 0.13 mmol) and 1,2,3,4,5-pentamethylbenzene (0.056 g, 0.38 mmol) in dichloromethane (1.3 mL) was cooled to −78° C. with stirring under an atmosphere of nitrogen. Next, trichloroborane (1.0 M in dichloromethane) (1.0 mL, 1.0 mmol) was added slowly. The resulting brownish mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.046 g, 0.11 mmol, 89% yield). $^1$H NMR (500 MHz, DMSO-$d_6$-$D_2O$) δ ppm 7.54 (s, 1H), 7.34 (s, 1H), 6.57 (s, 1H), 4.15 (br s, 2H), 3.98 (s, 2H), 3.75 (s, 3H), 3.26 (br s, 4H), 2.95 (s, 2H), 2.85 (t, J=8.1 Hz, 2H); MS (ESI$^+$) m/z 410.1 [M+H]$^+$.

Example 153C:
2-(1-methyl-1H-pyrazol-4-yl)acetaldehyde

To a flask were added 2-(1-methyl-1H-pyrazol-4-yl)ethan-1-ol (0.200 g, 1.59 mmol) and dichloromethane (7.9 mL). The suspension was stirred at ambient temperature and Dess-Martin periodinane (1.01 g, 2.38 mmol) was added in portions. After 30 minutes, the solid materials were removed by filtration over diatomaceous earth with the aid of tert-butyl methyl ether/ethyl acetate (1:1 v/v). The filtrate was concentrated under reduced pressure. The residue was treated with tert-butyl methyl ether/ethyl acetate (1:1 v/v) (50 mL) and stirred with 0.1 M sodium thiosulfate/saturated aqueous sodium bicarbonate (1:1 v/v) (50 mL) for 15 minutes. The layers were then separated, and the aqueous phase was extracted with tert-butyl methyl ether/ethyl acetate (1:1 v/v) (3×20 mL). The organic phases were combined, washed with brine, dried over magnesium sulfate/sodium sulfate (1:1 w/w), and concentrated under reduced pressure. The residue was filtered over a thin pad of silica gel using heptanes/ethyl acetate (1:1 v/v) to give the title compound (0.077 g, 0.62 mmol, 39% yield). $^1$H NMR (500 MHz, CDCl$_3$) δ ppm 9.71 (t, J=2.0 Hz, 1H), 7.39 (s, 1H), 7.33 (s, 1H), 3.90 (s, 3H), 3.57 (dt, J=1.9, 0.6 Hz, 2H).

Example 154: 5-(2-{2-[1-(2,2-difluoroethyl)-3,5-dimethyl-1H-pyrazol-4-yl]ethyl}-8-fluoro-6-hydroxy-1,2,3,4-tetrahydroisoquinolin-7-yl)-1λ$^6$,2,5-thiadiazolidine-1,1,3-trione (Compound 253)

Example 154A: 5-[6-(benzyloxy)-2-{2-[1-(2,2-difluoroethyl)-3,5-dimethyl-1H-pyrazol-4-yl]ethyl}-8-fluoro-], 2,3,4-tetrahydroisoquinolin-7-yl)-1λ$^6$,2,5-thiadiazolidine-1,1,3-trione To a vial containing 5-[6-(benzyloxy)-8-fluoro-1,2,3,4-tetrahydroisoquinolin-7-yl]-1λ$^6$,2,5-thiadiazolidine-1,1,3-trione 2,2,2-trifluoroacetate (Example 93A, theoretically 0.15 mmol) were added 1,2-dichloroethane (0.77 mL) and triethylamine (0.043 mL, 0.31 mmol). The mixture was stirred for 5 minutes, then 2-(1-(2,2-difluoroethyl)-3,5-dimethyl-1H-pyrazol-4-yl)acetaldehyde (0.046 g, 0.23 mmol) was added. After 30 minutes, sodium triacetoxyhydroborate (0.081 g, 0.38 mmol) was added. After 14 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.076 g, 0.13 mmol, 86% yield over two steps). $^1$H NMR (400 MHz, DMSO-$d_6$-$D_2O$) δ ppm 7.51-7.44 (m, 2H), 7.38-7.32 (m, 2H), 7.32-7.24 (m, 1H), 6.89 (s, 1H), 6.22 (tt, J=55.0, 3.8 Hz, 1H), 5.14 (s, 2H), 4.41 (td, J=15.1, 3.8 Hz, 2H), 4.28 (br s, 2H), 3.99 (s, 2H), 3.35 (br s, 2H), 3.24-3.14 (m, 2H), 3.13-3.01 (m, 2H), 2.86-2.71 (m, 2H), 2.19 (s, 3H), 2.11 (s, 3H); MS (APCI$^+$) m/z 578.3 [M+H]$^+$.

Example 154B: 5-(2-(2-(1-(2,2-difluoroethyl)-3,5-dimethyl-1H-pyrazol-4-yl)ethyl)-8-fluoro-6-hydroxy-1,2,3,4-tetrahydroisoquinolin-7-yl)-1,2,5-thiadiazolidin-3-one 1,1-dioxide A vial containing a suspension of 5-[6-(benzyloxy)-2-{2-[1-(2,2-difluoroethyl)-3,5-dimethyl-1H-pyrazol-4-yl]ethyl}-8-fluoro-1,2,3,4-tetrahydroisoquinolin-7-yl]-1λ$^6$,2,5-thiadiazolidine-1,1,3-trione (0.074 g, 0.13 mmol) and 1,2,3,4,5-pentamethylbenzene (0.057 g, 0.38 mmol) in dichloromethane (1.3 mL) was cooled to −78° C. with stirring under an atmosphere of nitrogen. Next, trichloroborane (1.0 M in dichloromethane) (1.0 mL, 1.0 mmol) was added slowly. The resulting brownish mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 tpm column, 10-100% gradient of methanol in water (buffered with 0.025 M aqueous ammonium bicarbonate, adjusted to pH 7 with dry ice)] to give the title compound (0.053 g, 0.11 mmol, 86% yield). $^1$H NMR (600 MHz, DMSO-d$_6$) δ ppm 9.84 (br s, 1H), 9.72 (s, 1H), 6.60 (s, 1H), 6.27 (tt, J=55.1, 3.9 Hz, 1H), 4.57 (br s, 1H), 4.44 (td, J=15.0, 3.9 Hz, 2H), 4.19 (br s, 1H), 3.96 (s, 2H), 3.81 (br s, 1H), 3.27 (br s, 1H), 3.17 (br s, 2H), 3.04 (s, 2H), 2.80 (t, J=8.6 Hz, 2H), 2.21 (s, 3H), 2.13 (s, 3H); MS (ESI$^+$) m/z 487.6 [M+H]$^+$.

Example 154C: 1-(2,2-difluoroethyl)-3,5-dimethyl-1H-pyrazole-4-carbaldehyde

To a vial were added 3,5-dimethyl-1H-pyrazole-4-carbaldehyde (0.050 g, 0.40 mmol), potassium carbonate (0.111 g, 0.806 mmol), 2,2-difluoroethyl trifluoromethanesulfonate (0.129 g, 0.604 mmol), and acetonitrile (1.0 mL). The vial was capped, and the mixture was heated to 60° C. After 18 hours, the reaction mixture was cooled to ambient temperature and filtered over a thin pad of diatomaceous earth with the aid of dichloromethane. The filtrate was concentrated under reduced pressure and purified using silica gel chromatography [4 g column, 0-100% gradient of ethyl acetate in heptanes] to give the title compound (0.057 g, 0.31 mmol, 76% yield). $^1$H NMR (600 MHz, CDCl$_3$) δ ppm 9.93 (s, 1H), 6.11 (tt, J=55.4, 4.4 Hz, 1H), 4.34 (td, J=13.2, 4.4 Hz, 2H), 2.54 (s, 3H), 2.44 (s, 3H); MS (APCI$^+$) m/z 230.6 [M+CH$_3$CN+H]$^+$.

Example 154D: 1-(2,2-difluoroethyl)-4-(2-methoxyvinyl)-3,5-dimethyl-1H-pyrazole

To a flask were added (methoxymethyl)triphenylphosphonium chloride (1.05 g, 3.07 mmol) and tetrahydrofuran (5.9 mL). The flask was cooled to 0° C., then potassium 2-methylpropan-2-olate (1.0 M in tetrahydrofuran) (2.8 mL, 2.8 mmol) was added. The white suspension immediately gave way to a dark red suspension, which was stirred for 15 minutes. Next, a solution of 1-(2,2-difluoroethyl)-3,5-dimethyl-1H-pyrazole-4-carbaldehyde (0.445 g, 2.37 mmol) in tetrahydrofuran (5.9 mL) was added. The resulting mixture was stirred at 0° C. for 2 hours and then at ambient temperature for 5 hours. The mixture was then poured into saturated aqueous ammonium chloride (80 mL) and extracted with ethyl acetate (4×25 mL). The organic phases were combined, washed with brine, dried over sodium sulfate, and concentrated under reduced pressure. The residue was purified using silica gel chromatography [24 g column, 0-100% gradient of ethyl acetate in heptanes] to give 1-(2,2-difluoroethyl)-4-(2-methoxyvinyl)-3,5-dimethyl-1H-pyrazole as a mixture of olefin isomers [69:31 (E) to (Z)] (0.205 g, 0.948 mmol, 40% yield). Data for (E)-isomer: $^1$H NMR (500 MHz, CDCl$_3$) δ ppm 6.57 (d, J=13.0 Hz, 1H), 6.04 (tt, J=55.9, 4.5 Hz, 1H), 5.48 (d, J=13.1 Hz, 1H), 4.30 (td, J=13.3, 4.6 Hz, 2H), 3.66 (s, 3H), 2.22 (s, 3H), 2.21 (s, 3H). Data for (Z)-isomer: $^1$H NMR (500 MHz, CDCl$_3$) δ ppm 6.06 (tt, J=55.6, 4.6 Hz, 1H), 6.02 (d, J=6.7 Hz, 1H), 4.98 (d, J=6.7 Hz, 1H), 4.30 (td, J=13.3, 4.6 Hz, 2H), 3.67 (s, 3H), 2.20 (s, 3H), 2.16 (s, 3H); MS (APCI$^+$) m/z 217.6 [M+H]$^+$.

Example 154E: 2-(1-(2,2-difluoroethyl)-3,5-dimethyl-1H-pyrazol-4-yl)acetaldehyde To a vial were added 1-(2,2-difluoroethyl)-4-(2-methoxyvinyl)-3,5-dimethyl-1H-pyrazole (0.170 g, 0.786 mmol) and tetrahydrofuran (2.6 mL). The vial was cooled to 0° C. The solution was treated with 6.0 M hydrochloric acid (2.6 mL, 16 mmol) and the ice bath was subsequently removed. The reaction mixture was allowed to warm to ambient temperature and then heated to 50° C. After 16 hours, the vial was cooled to ambient temperature and the solution was transferred to a beaker containing saturated aqueous sodium bicarbonate (60 mL). The resulting mixture was stirred for 15 minutes and then extracted with ethyl acetate (3×30 mL). The organic phases were combined, washed with brine, dried over sodium sulfate, and concentrated under reduced pressure. The residue was purified using silica gel chromatography [4 g column, 0-100% gradient of ethyl acetate in heptanes] to give the title compound (0.135 g, 0.668 mmol, 85% yield). $^1$H NMR (600 MHz, CDCl$_3$) δ ppm 9.59 (t, J=2.3 Hz, 1H), 6.06 (tt, J=55.7, 4.4 Hz, 1H), 4.32 (td, J=13.4, 4.4 Hz, 2H), 3.42 (d, J=2.3 Hz, 2H), 2.19 (s, 3H), 2.16 (s, 3H); MS (ESI$^+$) m/z 203.4 [M+H]$^+$.

Example 155: 5-[7-amino-1-fluoro-3-hydroxy-7-(4-methylpentyl)-5,6,7,8-tetrahydronaphthalen-2-yl]-1λ$^6$,2,5-thiadiazolidine-1,1,3-trione (Compound 254)

Example 155A: N'-[6-(benzyloxy)-8-fluoro-2-[(2E)-4-methylpenta-2,4-dien-1-yl]-7-(1,1,4-trioxo-1λ$^6$,2,5-thiadiazolidin-2-yl)-1,2,3,4-tetrahydronaphthalen-2-yl]benzohydrazide To a solution of the product of Example 141B (0.5208 g, 0.895 mmol) and [(di(1-adamantyl)-butylphosphine)-2-(2'-amino-1,1'-biphenyl)]palladium(II) methanesulfonate, (cataCXium® A Pd G3, 0.033 g, 0.045 mmol) in N,N-dimethylacetamide (5.2 mL), was added N,N-diisoproplylethylamine (0.469 mL, 2.69 mmol), followed by 2-bromopropene (0.118 mL, 1.343 mmol). The resulting mixture was degassed by 5 vacuum/nitrogen backfills, and then heated to 100° C. After 24 hours, the reaction mixture was cooled to ambient temperature and diluted with acetonitrile (20 mL). Celite® (10 g) was added and the mixture was concentrated to give a powder which was dry loaded onto a Teledyne ISCO 275 g reversed-phase C18 column and eluted with a gradient of 10-100% methanol in pH7 buffer to give the title compound as the ammonium salt (0.2766 g, 0.445 mmol, 49.7% yield) as a mixture of E and Z isomers. MS (APCI$^+$) m/z 605 [M+H]$^+$.

Example 155B: N'-[8-fluoro-6-hydroxy-2-(4-methylpentyl)-7-(1,1,4-trioxo-1λ$^6$,2,5-thiadiazolidin-2-yl)-1,2,3,4-tetrahydronaphthalen-2-yl]benzohydrazide A suspension of the product of Example 155A (0.425 g, 0.684 mmol) and 10% palladium (II) hydroxide on carbon (0.230 g, 50 weight % in water, 0.820 mmol) in a mixture of methanol (8.54 mL) and tetrahydrofuran (2.85 mL) was stirred for 16 hours under 60 psi of hydrogen. Filtration and concentration of the filtrate gave the title compound (0.2794 g, 0.539 mmol, 79% yield) which was used for the next reaction without purification. MS (APCI$^+$) m/z 519 [M+H]$^+$.

Example 155C: 5-[7-amino-1-fluoro-3-hydroxy-7-(4-methylpentyl)-5,6,7,8-tetrahydronaphthalen-2-yl]-1λ$^6$,2,5-thiadiazolidine-1,1,3-trione To a thoroughly degassed solution (5× vacuum/nitrogen backfills) of the product of Example 155B (0.2990 g, 0.577 mmol) in methanol (6 mL) was added a solution of samarium(II) iodide (17.3 mL, 0.1 M in tetrahydrofuran, 1.73 mmol) slowly. After 5 minutes, the reaction mixture was quenched with water (1.5 mL) and diluted with acetonitrile (15 mL). Celite® (3 g) was added, and the resulting mixture was concentrated to give a powder, which was dry loaded onto a Teledyne ISCO 100 g reversed-phase C18 column and eluted with a gradient of 10-100% methanol in buffer (0.025 M ammonium bicarbonate in water acidified to pH 7 by adding dry ice) to give the title compound (0.097 g, 0.243 mmol, 42.1% yield). $^1$H NMR (500 MHz, DMSO-d$_6$) δ ppm 9.29 (s, 1H), 8.17-7.57 (m, 3H), 6.51 (s, 1H), 4.00-3.90 (m, 2H), 2.81-2.72 (m, 3H), 2.68 (d, J=16.5 Hz, 1H), 1.86 (t, J=6.9 Hz, 2H), 1.60-1.49 (m, 3H), 1.43-1.32 (m, 2H), 1.16 (q, J=7.2 Hz, 2H), 0.88 (dd, J=6.6, 1.3 Hz, 6H); MS (APCI$^+$) m/z 400 [M+H]$^+$.

Example 156: 5-(7-amino-1-fluoro-3-hydroxy-7-propyl-5,6,7,8-tetrahydronaphthalen-2-yl)-1λ$^6$,2,5-thiadiazolidine-1,1,3-trione (Compound 255)

To a thoroughly degassed solution (5× vacuum/nitrogen backfills) of the product of Example 142 (0.0456 g, 0.096 mmol) in methanol (1 mL) was added a solution of samarium(II) iodide (2.87 mL, 0.1 M in tetrahydrofuran, 0.287 mmol) slowly. After 10 minutes, the reaction mixture was quenched with water (0.25 mL) and diluted with acetonitrile (3 mL). Celite® (1 g) was added, and the resulting mixture was concentrated to give a powder which was dry loaded onto a Teledyne ISCO 50 g reversed-phase C18 column and eluted with a gradient of 10-100% methanol in buffer (0.025 M ammonium bicarbonate in water acidified to pH 7 by adding dry ice) to give the title compound (0.0118 g, 0.033 mmol, 34.5% yield). $^1$H NMR (500 MHz, DMSO-d$_6$) δ ppm 6.49 (s, 1H), 3.98-3.88 (m, 2H), 2.77-2.70 (m, 3H), 2.63 (d, J=16.7 Hz, 1H), 1.82 (t, J=6.8 Hz, 2H), 1.58-1.51 (m, 2H), 1.43-1.31 (m, 2H), 0.89 (t, J=7.2 Hz, 3H); MS (APCI$^+$) m/z 358 [M+H]$^+$.

Example 157: 5-{2-[2-(1,3-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione (Compound 256)

Example 157A: 5-{6-(benzyloxy)-2-[2-(1,3-dimethyl-1H-pyrazol-4-yl)ethyl]-8-fluoro-1,2,3,4-tetrahydroisoquinolin-7-yl}-1λ$^6$,2,5-thiadiazolidine-1,1,3-trione To a vial containing 5-[6-(benzyloxy)-8-fluoro-1,2,3,4-tetrahydroisoquinolin-7-yl]-1λ$^6$,2,5-thiadiazolidine-1,1,3-trione, trifluoroacetic acid salt (theoretically 0.15 mmol, Example 93A) were added 1,2-dichloroethane (0.77 mL) and triethylamine (0.043 mL, 0.31 mmol). The mixture was stirred for 5 minutes, then 2-(1,3-dimethyl-1H-pyrazol-4-yl) acetaldehyde (0.032 g, 0.23 mmol, Example 157D) was added. After 30 minutes, sodium triacetoxyhydroborate (0.081 g, 0.38 mmol) was added. After 14 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.070 g, 0.14 mmol, 89% yield over two steps). $^1$H NMR (500 MHz, DMSO-d$_6$-D$_2$O) δ ppm 7.49-7.46 (m, 2H), 7.46 (s, 1H), 7.37-7.32 (m, 2H), 7.32-7.26 (m, 1H), 6.89 (s, 1H), 5.14 (s, 2H), 4.32 (br s, 2H), 3.99 (s, 2H), 3.68 (s, 3H), 3.33 (t, J=8.6 Hz, 2H), 3.06 (t, J=6.3 Hz, 2H), 2.83 (dd, J=9.1, 7.9 Hz, 2H), 2.11 (s, 3H); MS (ESI$^+$) m/z 513.9 [M+H]$^+$.

Example 157B: 5-{2-[2-(1,3-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione A flask containing a suspension of 5-{6-(benzyloxy)-2-[2-(1,3-dimethyl-1H-pyrazol-4-yl)ethyl]-8-fluoro-1,2,3,4-tetrahydroisoquinolin-7-yl}-1λ$^6$,2,5-thiadiazolidine-1,1,3-trione (0.066 g, 0.13 mmol) and 1,2,3,4,5-pentamethylbenzene (0.057 g, 0.39 mmol) in dichloromethane (1.3 mL) was cooled to −78° C. with stirring under an atmosphere of nitrogen. Next, trichloroborane (1.0 M in dichloromethane) (1.0 mL, 1.0 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.043 g, 0.10 mmol, 79% yield). $^1$H NMR (500 MHz, DMSO-d$_6$-D$_2$O) δ ppm 7.45 (s, 1H), 6.59 (s, 1H), 4.30 (br s, 2H), 3.98 (s, 2H), 3.68 (s, 3H), 3.53 (br s, 2H), 3.30 (t, J=8.3 Hz, 2H), 3.07-2.96 (m, 2H), 2.82 (dd, J=9.6, 7.1 Hz, 2H), 2.10 (s, 3H); MS (ESI$^+$) m/z 423.8 [M+H]$^+$.

Example 157C: 4-(2-methoxyvinyl)-1,3-dimethyl-1H-pyrazole

To a flask were added (methoxymethyl)triphenylphosphonium chloride (1.62 g, 4.71 mmol) and tetrahydrofuran (6.0 mL). The flask was cooled to 0° C., then potassium 2-methylpropan-2-olate (1.0 M in tetrahydrofuran, 4.4 mL, 4.4 mmol) was added. Fifteen minutes later, a solution of 1,3-dimethyl-1H-pyrazole-4-carbaldehyde (0.450 g, 3.62 mmol) in tetrahydrofuran (6.0 mL) was added. The resulting mixture was stirred at 0° C. for 2 hours and then at ambient temperature for 46 hours. The mixture was then poured into saturated aqueous ammonium chloride (80 mL) and extracted with ethyl acetate (4×25 mL). The organic phases were combined, washed with brine, dried over sodium sulfate, and concentrated under reduced pressure. The residue was purified using silica gel chromatography [24 g column, 0-100% gradient of ethyl acetate in heptanes] to give the title compound as a mixture of olefin isomers [60:40 (E) to (Z)] (0.387 g, 2.54 mmol, 70% yield). Data for (E)-isomer: $^1$H NMR (400 MHz, CDCl$_3$) δ ppm 7.16 (s, 1H), 6.69 (d, J=13.0 Hz, 1H), 5.54 (d, J=13.1 Hz, 1H), 3.78 (s, 3H), 3.63 (s, 3H), 2.23 (s, 3H). Data for (Z)-isomer: $^1$H NMR (400 MHz, CDCl$_3$) δ ppm 7.65 (s, 1H), 6.01 (d, J=6.4

Hz, 1H), 5.12 (d, J=6.5 Hz, 1H), 3.80 (s, 3H), 3.75 (s, 3H), 2.22 (s, 3H); MS (ESI⁺) m/z 153.3 [M+H]⁺.

Example 157D:
2-(1,3-dimethyl-1H-pyrazol-4-yl)acetaldehyde

To a vial were added 4-(2-methoxyvinyl)-1,3-dimethyl-1H-pyrazole (0.200 g, 1.31 mmol) and tetrahydrofuran (6.6 mL). The vial was cooled to 0° C. The solution was treated with 6.0 M hydrochloric acid (6.6 mL, 39 mmol) and the ice bath was subsequently removed. The vial was allowed to warm to ambient temperature and then heated to 50° C. After 16 hours, the vial was cooled to ambient temperature and the solution was transferred to a beaker containing saturated aqueous sodium bicarbonate (60 mL). The resulting mixture was stirred for 15 minutes and then extracted with ethyl acetate (3×30 mL). The organic phases were combined, washed with brine, dried over sodium sulfate, and concentrated under reduced pressure. The residue was purified using silica gel chromatography [24 g column, 0-100% gradient of ethyl acetate in heptanes] to give 2-(1,3-dimethyl-1H-pyrazol-4-yl)acetaldehyde (0.037 g, 0.27 mmol, 20% yield). ¹H NMR (600 MHz, CDCl₃) δ ppm 9.67 (t, J=2.1 Hz, 1H), 7.25 (s, 1H), 3.82 (s, 3H), 3.49 (dd, J=2.1, 0.6 Hz, 2H), 2.18 (s, 3H).

Example 158: 5-{2-[2-(1,5-dimethyl-1H-pyrazol-4-yl)ethyl]-8-fluoro-6-hydroxy-1,2,3,4-tetrahydroisoquinolin-7-yl}-1λ⁶,2,5-thiadiazolidine-1,1,3-trione (Compound 257)

Example 158A: 5-{6-(benzyloxy)-2-[2-(1,5-dimethyl-1H-pyrazol-4-yl)ethyl]-8-fluoro-1,2,3,4-tetrahydroisoquinolin-7-yl}-1λ⁶,2,5-thiadiazolidine-1,1,3-trione To a vial containing 5-[6-(benzyloxy)-8-fluoro-1,2,3,4-tetrahydroisoquinolin-7-yl]-1λ⁶,2,5-thiadiazolidine-1,1,3-trione, trifluoroacetic acid salt (theoretically 0.15 mmol, Example 93A) were added 1,2-dichloroethane (0.77 mL) and triethylamine (0.043 mL, 0.31 mmol). The mixture was stirred for 5 minutes, then 2-(1,5-dimethyl-1H-pyrazol-4-yl)acetaldehyde (0.032 g, 0.23 mmol, Example 158D) was added. After 30 minutes, sodium triacetoxyhydroborate (0.081 g, 0.38 mmol) was added. After 14 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.068 g, 0.13 mmol, 86% yield over two steps). ¹H NMR (400 MHz, DMSO-d₆-D₂O) δ ppm 7.50-7.44 (m, 2H), 7.37-7.32 (m, 2H), 7.32-7.28 (m, 1H), 7.27 (s, 1H), 6.88 (s, 1H), 5.14 (s, 2H), 4.35 (br s, 2H), 4.00 (s, 2H), 3.66 (s, 3H), 3.49 (br s, 2H), 3.32 (dd, J=10.4, 6.4 Hz, 2H), 3.05 (t, J=5.3 Hz, 2H), 2.83 (dd, J=9.7, 7.0 Hz, 2H), 2.18 (s, 3H); MS (ESI⁺) m/z 513.9 [M+H]⁺.

Example 158B: 5-{2-[2-(1,5-dimethyl-1H-pyrazol-4-yl)ethyl]-8-fluoro-6-hydroxy-1, 2, 3,4-tetrahydroisoquinolin-7-yl}-1λ⁶,2,5-thiadiazolidine-1,1,3-trione A flask containing a suspension of 5-{6-(benzyloxy)-2-[2-(1,5-dimethyl-1H-pyrazol-4-yl)ethyl]-8-fluoro-1,2,3,4-tetrahydroisoquinolin-7-yl}-1λ⁶,2,5-thiadiazolidine-1,1,3-trione (0.064 g, 0.12 mmol) and 1,2,3,4,5-pentamethylbenzene (0.055 g, 0.37 mmol) in dichloromethane (1.2 mL) was cooled to −78° C. with stirring under an atmosphere of nitrogen. Next, trichloroborane (1.0 M in dichloromethane) (0.99 mL, 0.99 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.041 g, 0.097 mmol, 78% yield). ¹H NMR (400 MHz, DMSO-d₆-D₂O) δ ppm 7.27 (s, 1H), 6.59 (s, 1H), 4.29 (br s, 2H), 4.00 (s, 2H), 3.65 (s, 3H), 3.47 (br s, 2H), 3.29 (t, J=8.5 Hz, 2H), 3.01 (t, J=6.2 Hz, 2H), 2.81 (dd, J=9.6, 7.7 Hz, 2H), 2.16 (s, 3H); MS (ESI⁺) m/z 423.8 [M+H]⁺.

Example 158C:
4-(2-methoxyvinyl)-1,5-dimethyl-1H-pyrazole

To a flask were added (methoxymethyl)triphenylphosphonium chloride (1.62 g, 4.71 mmol) and tetrahydrofuran (6.0 mL). The flask was cooled to 0° C., then potassium 2-methylpropan-2-olate (1.0 M in tetrahydrofuran) (4.4 mL, 4.4 mmol) was added. Fifteen minutes later, a solution of 1,5-dimethyl-1H-pyrazole-4-carbaldehyde (0.450 g, 3.62 mmol) in tetrahydrofuran (6.0 mL) was added. The resulting mixture was stirred at 0° C. for 2 hours and then at ambient temperature for 46 hours. The mixture was then poured into saturated aqueous ammonium chloride (80 mL) and extracted with ethyl acetate (4×25 mL). The organic phases were combined, washed with brine, dried over sodium sulfate, and concentrated under reduced pressure. The residue was purified using silica gel chromatography [12 g column, 0-100% gradient of ethyl acetate in heptanes] to give the title compound as a mixture of olefin isomers [50:50 (E) to (Z)] (0.408 g, 2.68 mmol, 74% yield). Data for mixture of isomers: ¹H NMR (600 MHz, CDCl₃) δ ppm 7.78 (s, 1H), 7.35 (s, 1H), 6.73 (d, J=12.9 Hz, 1H), 6.01 (d, J=6.5 Hz, 1H), 5.52 (d, J=12.9 Hz, 1H), 5.04 (dd, J=6.5, 0.5 Hz, 1H), 3.75 (s, 3H), 3.75 (s, 3H), 3.74 (s, 3H), 3.64 (s, 3H), 2.21 (s, 3H), 2.20 (s, 3H); MS (ESI⁺) m/z 153.3 [M+H]⁺.

Example 158D:
2-(1,5-dimethyl-1H-pyrazol-4-yl)acetaldehyde

To a vial were added 4-(2-methoxyvinyl)-1,5-dimethyl-1H-pyrazole (0.200 g, 1.31 mmol) and tetrahydrofuran (6.6 mL). The vial was cooled to 0° C. The solution was treated with 6.0 M hydrochloric acid (6.6 mL, 39 mmol) and the ice bath was subsequently removed. The vial was allowed to warm to ambient temperature and then heated to 50° C. After 16 hours, the vial was cooled to ambient temperature and the solution was transferred to a beaker containing saturated aqueous sodium bicarbonate (60 mL). The resulting mixture was stirred for 15 minutes and then extracted with ethyl acetate (3×30 mL). The organic phases were combined, washed with brine, dried over sodium sulfate, and concentrated under reduced pressure. The residue was purified using silica gel chromatography [12 g column, 0-100% gradient of ethyl acetate in heptanes] to give the title compound (0.035 g, 0.25 mmol, 19% yield). $^1$H NMR (600 MHz, CDCl$_3$) δ ppm 9.63 (t, J=2.3 Hz, 1H), 7.33 (s, 1H), 3.79 (s, 3H), 3.46 (d, J=2.3 Hz, 2H), 2.18 (s, 3H).

Example 159: N-(cyclopropylmethyl)-8-fluoro-6-hydroxy-7-(1,1,4-trioxo-1λ$^6$,2,5-thiadiazolidin-2-yl)-3,4-dihydroisoquinoline-2(1H)-carboxamide (Compound 258)

Example 159A: 6-(benzyloxy)-N-(cyclopropylmethyl)-8-fluoro-7-(1,1,4-trioxo-1λ$^6$,2,5-thiadiazolidin-2-yl)-3,4-dihydroisoquinoline-2(1H)-carboxamide The product of Example 54A (39.1 mg, 0.1 mmol) was dissolved in acetonitrile (1 mL). N,N-Diisopropylethylamine (87 μL, 0.5 mmol) and triphosgene (10.4 mg, 0.035 mmol) in acetonitrile (1 mL) were added successively and the mixture was stirred at room temperature for 20 minutes. Cyclopropylmethanamine (0.29 M in 5:2 N,N-dimethylformamide/acetonitrile, 700 L) was then added and the mixture was stirred for 1 hour at room temperature. The reaction mixture was directly purified by reversed-phase preparative HPLC on a Phenomenex® Luna® C8(2) 5 μm 100 Å AXIA™ column (50 mm×30 mm). A gradient of acetonitrile (A) and 0.1% trifluoroacetic acid in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound. MS (APCI$^+$) m/z 489.1 [M+H]$^+$.

Example 159B: N-(cyclopropylmethyl)-8-fluoro-6-hydroxy-7-(1,1,4-trioxo-1λ$^6$,2,5-thiadiazolidin-2-yl)-3,4-dihydroisoquinoline-2(1H)-carboxamide A mixture of the above product from Example 159A and 5% Pd/C (5 mg) in methanol (5 mL) was stirred under hydrogen (45 psi) at room temperature for overnight. The crude reaction mixture was filtered through a pad of diatomaceous earth and concentrated. The residue was reconstituted in methanol (2 mL) and purified by reversed-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (13.5 mg, 0.034 mmol, 34% yield for two steps). $^1$H NMR (500 MHz, DMSO-d$_6$) δ ppm 7.38-6.86 (m, 2H), 6.74 (t, J=5.5 Hz, 1H), 6.51 (s, 1H), 4.38 (s, 2H), 3.95 (s, 2H), 3.52 (t, J=5.8 Hz, 2H), 2.93 (dd, J=6.7, 5.5 Hz, 2H), 2.67 (t, J=5.5 Hz, 2H), 1.04-0.88 (m, 1H), 0.44-0.32 (m, 2H), 0.19-0.12 (m, 2H); MS (APCI$^+$) m/z 399.2 [M+H]$^+$.

Example 160: 5-{(7S)-7-[(3,3-difluoropropyl)amino]-1-fluoro-3-hydroxy-5,6,7,8-tetrahydronaphthalen-2-yl}-1λ$^6$,2,5-thiadiazolidine-1,1,3-trione (Compound 259)

The product of Example 124B (150 mg, 0.381 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide(70:30) at a concentration of 5 mg/mL. The sample was loaded into the modifier stream in 2 mL (10 mg) injections. The mobile phase was held isocratically at 40% cosolvent:CO$_2$. Fraction collection was time triggered. The instrument was fitted with a CHIRALPAK® IC column with dimensions 21 mm i.d.×250 mm length with 5 μm particles. The earlier eluting enantiomer peak gave the title compound (61.5 mg, 0.156 mmol, 82% recovery). $^1$H NMR and MS data were identical to those from Example 124B. Absolute stereochemistry was tentatively assigned in analogy to the chromatography elution order to the product of Example 18

Example 161: 5-{(7R)-7-[(3,3-difluoropropyl)amino]-1-fluoro-3-hydroxy-5,6,7,8-tetrahydronaphthalen-2-yl}-1λ$^6$,2,5-thiadiazolidine-1,1,3-trione (Compound 260)

The product of Example 124B (150 mg, 0.381 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide(70:30) at a concentration of 5 mg/mL. The sample was loaded into the modifier stream in 2 mL (10 mg) injections. The mobile phase was held isocratically at 40% cosolvent:CO$_2$. Fraction collection was time triggered. The instrument was fitted with a CHIRALPAK® IC column with dimensions 21 mm i.d.×250 mm length with 5 m particles. The later eluting enantiomer peak gave the title compound (55.0 mg, 0.140 mmol, 73.3% recovery). $^1$H NMR and MS data were identical to those from Example 124B. Absolute stereochemistry was tentatively assigned in analogy to the chromatography elution order to the product of Example 19.

Example 162: 8-fluoro-6-hydroxy-N-[(oxan-4-yl)methyl]-7-(1,1,4-trioxo-1λ$^6$,2,5-thiadiazolidin-2-yl)-3,4-dihydroisoquinoline-2(1H)-carboxamide (Compound 261)

Example 162A: 6-(benzyloxy)-8-fluoro-N-[(oxan-4-yl)methyl]-7-(1,1,4-trioxo-1λ$^6$,2,5-thiadiazolidin-2-yl)-3,4-dihydroisoquinoline-2(1H)-carboxamide The title compound was prepared from (tetrahydro-2H-pyran-4-yl)methanamine using the procedures described for Example 159A. MS (APCI$^+$) m/z 533.2 [M+H]$^+$.

Example 162B: 8-fluoro-6-hydroxy-N-[(oxan-4-yl)methyl]-7-(1,1,4-trioxo-1λ⁶,2,5-thiadiazolidin-2-yl)-3,4-dihydroisoquinoline-2(1H)-carboxamide The title compound was prepared from the above Example 162A using the procedures described for Example 159B in 37% yield (for 2 steps). $^1$H NMR (500 MHz, DMSO-d$_6$) δ ppm 6.68 (t, J=5.6 Hz, 1H), 6.49 (s, 1H), 4.36 (s, 2H), 3.94 (s, 2H), 3.82 (ddd, J=11.1, 4.1, 1.8 Hz, 2H), 3.50 (t, J=5.8 Hz, 2H), 3.27-3.18 (m, 2H), 2.93 (dd, J=6.9, 5.6 Hz, 2H), 2.65 (t, J=5.7 Hz, 2H), 1.72-1.61 (m, 1H), 1.57-1.50 (m, 2H), 1.16-1.04 (m, 2H); MS (APCI$^+$) m/z 433.3 [M+H]$^+$.

Example 163: N-[(3,3-difluorocyclobutyl)methyl]-8-fluoro-6-hydroxy-7-(1,1,4-trioxo-1λ⁶,2,5-thiadiazolidin-2-yl)-3,4-dihydroisoquinoline-2(1H)-carboxamide (Compound 262)

Example 163A: 6-(benzyloxy)-N-[(3,3-difluorocyclobutyl)methyl]-8-fluoro-7-(1,1,4-trioxo-1λ⁶,2,5-thiadiazolidin-2-yl)-3,4-dihydroisoquinoline-2(1H)-carboxamide The title compound was prepared from (3,3-difluorocyclobutyl)methanamine using the procedures described for Example 159A. MS (APCI$^+$) m/z 539.1 [M+H]$^+$.

Example 163B: N-[(3,3-difluorocyclobutyl)methyl]-8-fluoro-6-hydroxy-7-(1,1,4-trioxo-1λ⁶,2,5-thiadiazolidin-2-yl)-3,4-dihydroisoquinoline-2(1H)-carboxamide The title compound was prepared from the above Example 163A using the procedures described for Example 159B in 46% yield (for 2 steps). $^1$H NMR (600 MHz, DMSO-d$_6$) δ ppm 6.82 (t, J=5.6 Hz, 1H), 6.49 (s, 1H), 4.36 (s, 2H), 3.94 (s, 2H), 3.50 (t, J=5.8 Hz, 2H), 3.16 (t, J=5.8 Hz, 2H), 2.65 (t, J=5.8 Hz, 2H), 2.56 (ddd, J=14.3, 8.8, 5.5 Hz, 2H), 2.31-2.24 (m, 3H); MS (APCI$^+$) m/z 449.2 [M+H]$^+$.

Example 164: 8-fluoro-6-hydroxy-N-[(oxolan-2-yl)methyl]-7-(1,1,4-trioxo-1λ⁶,2,5-thiadiazolidin-2-yl)-3,4-dihydroisoquinoline-2(1H)-carboxamide (Compound 263)

Example 164A: 6-(benzyloxy)-8-fluoro-N-[(oxolan-2-yl)methyl]-7-(1,1,4-trioxo-1λ⁶,2,5-thiadiazolidin-2-yl)-3,4-dihydroisoquinoline-2(1H)-carboxamide The title compound was prepared from (tetrahydrofuran-2-yl)methanamine using the procedures described for Example 159A. MS (APCI$^+$) m/z 519.2 [M+H]$^+$.

Example 164B: 8-fluoro-6-hydroxy-N-[(oxolan-2-yl)methyl]-7-(1,1,4-trioxo-1λ⁶,2,5-thiadiazolidin-2-yl)-3,4-dihydroisoquinoline-2(1H)-carboxamide The title compound was prepared from the above Example 164A using the procedures described for Example 159B in 31% yield (for 2 steps). $^1$H NMR (500 MHz, DMSO-d$_6$) δ ppm 6.71 (t, J=5.7 Hz, 1H), 6.51-6.47 (m, 1H), 4.36 (s, 2H), 3.94 (s, 2H), 3.85 (p, J=6.3 Hz, 1H), 3.77-3.69 (m, 1H), 3.65-3.54 (m, 1H), 3.50 (t, J=5.8 Hz, 2H), 3.15-3.01 (m, 2H), 2.68-2.62 (m, 2H), 1.88-1.71 (m, 3H), 1.58-1.47 (m, 1H); MS (APCI$^+$) m/z 429.2 [M+H]$^+$.

Example 165: N-(2-cyclopropylethyl)-8-fluoro-6-hydroxy-7-(1,1,4-trioxo-1λ⁶,2,5-thiadiazolidin-2-yl)-3,4-dihydroisoquinoline-2(1H)-carboxamide (Compound 264)

Example 165A: 6-(benzyloxy)-N-(2-cyclopropylethyl)-8-fluoro-7-(1,1,4-trioxo-1λ⁶,2,5-thiadiazolidin-2-yl)-3,4-dihydroisoquinoline-2(1H)-carboxamide The title compound was prepared from 2-cyclopropylethan-1-amine using the procedures described for Example 159A. MS (APCI$^+$) m/z 503.1 [M+H]$^+$.

Example 165B: N-(2-cyclopropylethyl)-8-fluoro-6-hydroxy-7-(1,1,4-trioxo-1λ⁶,2,5-thiadiazolidin-2-yl)-3,4-dihydroisoquinoline-2(1H)-carboxamide The title compound was prepared from the above Example 165A using the procedures described for Example 159B in 28% yield (for 2 steps). $^1$H NMR (500 MHz, DMSO-d$_6$) δ ppm 6.63 (t, J=5.5 Hz, 1H), 6.48 (s, 1H), 4.35 (s, 2H), 3.93 (s, 2H), 3.49 (t, J=5.8 Hz, 2H), 3.15-3.06 (m, 2H), 2.68-2.60 (m, 2H), 1.32 (q, J=7.1 Hz, 2H), 0.76-0.55 (m, 1H), 0.37 (dd, J=8.1, 1.7 Hz, 2H), 0.12--0.07 (m, 2H); MS (APCI$^+$) m/z 413.2 [M+H]$^+$.

Example 166: N-[(1,3-dimethyl-1H-pyrazol-5-yl)methyl]-8-fluoro-6-hydroxy-7-(1,1,4-trioxo-1λ⁶,2,5-thiadiazolidin-2-yl)-3,4-dihydroisoquinoline-2(1H)-carboxamide (Compound 265)

Example 166A: 6-(benzyloxy)-N-[(1,3-dimethyl-1H-pyrazol-5-yl)methyl]-8-fluoro-7-(1,1,4-trioxo-1λ⁶,2,5-thiadiazolidin-2-yl)-3,4-dihydroisoquinoline-2(1H)-carboxamide The title compound was prepared from (1,3-dimethyl-1H-pyrazol-5-yl)methanamine using the procedures described for Example 159A. MS (APCI$^+$) m/z 543.1 [M+H]$^+$.

Example 166B: N-[(1,3-dimethyl-1H-pyrazol-5-yl)ethyl)methyl]-8-fluoro-6-hydroxy-7-(1,1,4-trioxo-1λ⁶,2,5-thiadiazolidin-2-yl)-3,4-dihydroisoquinoline-2(1H)-carboxamide The title compound was prepared from the above Example 166A using the procedures described for Example 159B in 5% yield (for 2 steps). $^1$H NMR (500 MHz, DMSO-d$_6$) δ ppm 7.12 (t, J=5.5 Hz, 1H), 6.49 (s, 1H), 5.86 (s, 1H), 4.38 (s, 2H), 4.21 (d, J=5.5 Hz, 2H), 3.93 (s, 2H), 3.67 (s, 3H), 3.52 (t, J=5.8 Hz, 2H), 2.69-2.63 (m, 2H), 2.06 (s, 3H); MS (APCI$^+$) m/z 453.3 [M+H]$^+$.

Example 167: 5-{2-[2-(1-tert-butyl-3,5-dimethyl-1H-pyrazol-4-yl)ethyl]-8-fluoro-6-hydroxy-1,2,3,4-tetrahydroisoquinolin-7-yl}-1λ⁶,2,5-thiadiazolidine-1,1,3-trione (Compound 266)

Example 167A: 5-(6-(benzyloxy)-2-(2-(1-(tert-butyl)-3,5-dimethyl-1H-pyrazol-4-yl)ethyl)-8-fluoro-1,2,3,4-tetrahydroisoquinolin-7-yl)-1,2,5-thiadiazolidin-3-one 1,1-dioxide To a vial containing 5-[6-(benzyloxy)-8-fluoro-1,2,3,4-tetrahydroisoquinolin-7-yl]-1λ⁶,2,5-thiadiazolidine-1,1,3- trione, trifluoroacetic acid salt (theoretically 0.15 mmol, Example 93A) were added 1,2-dichloroethane (0.77 mL) and triethylamine (0.043 mL, 0.31 mmol). The mixture was stirred for 5 minutes, then 2-(1-(tert-butyl)-3,5-dimethyl-1H-pyrazol-4-yl)acetaldehyde (0.045 g, 0.23 mmol, Example 167D) was added. After 30 minutes, sodium triacetoxyhydroborate (0.081 g, 0.38 mmol) was added. After 36 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.074 g, 0.13 mmol, 85% yield over two steps). $^1$H NMR (600 MHz, DMSO-$d_6$) δ ppm 9.83 (br s, 1H), 7.50 (d, J=7.4 Hz, 2H), 7.36 (t, J=7.4 Hz, 2H), 7.30 (t, J=7.2 Hz, 1H), 6.90 (s, 1H), 5.17 (s, 2H), 4.62 (br s, 1H), 4.23 (br s, 1H), 3.97 (s, 2H), 3.81 (br s, 1H), 3.16 (br s, 2H), 3.06 (s, 2H), 2.76 (s, 2H), 2.34 (s, 3H), 2.09 (s, 3H), 1.52 (s, 9H); MS (APCI$^+$) m/z 570.4 [M+H]$^+$.

Example 167B: 5-{2-[2-(1-tert-butyl-3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione A flask containing a suspension of 5-(6-(benzyloxy)-2-(2-(1-(tert-butyl)-3,5-dimethyl-1H-pyrazol-4-yl)ethyl)-8-fluoro-1,2,3,4-tetrahydroisoquinolin-7-yl)-1,2,5-thiadiazolidin-3-one 1,1-dioxide (0.071 g, 0.13 mmol) and 1,2,3,4,5-pentamethylbenzene (0.056 g, 0.38 mmol) in dichloromethane (1.3 mL) was cooled to −78° C. with stirring under an atmosphere of nitrogen. Next, trichloroborane (1.0 M in dichloromethane) (1.0 mL, 1.0 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.057 g, 0.12 mmol, 94% yield). $^1$H NMR (400 MHz, DMSO-$d_6$-$D_2$O) δ ppm 6.60 (s, 1H), 4.30 (br s, 2H), 4.02 (s, 2H), 3.47 (br s, 2H), 3.12 (dd, J=11.4, 6.2 Hz, 2H), 3.02 (t, J=5.7 Hz, 2H), 2.73 (dd, J=9.3, 6.0 Hz, 2H), 2.28 (s, 3H), 2.05 (s, 3H), 1.47 (s, 9H); MS (APCI$^+$) m/z 480.3 [M+H]$^+$.

Example 167C: 1-(tert-butyl)-4-(2-methoxyvinyl)-3,5-dimethyl-1H-pyrazole

To a flask were added (methoxymethyl)triphenylphosphonium chloride (1.11 g, 3.25 mmol) and tetrahydrofuran (4.2 mL). The flask was cooled to 0° C., then potassium 2-methylpropan-2-olate (1.0 M in tetrahydrofuran) (3.0 mL, 3.0 mmol) was added. Fifteen minutes later, a solution of 1-(tert-butyl)-3,5-dimethyl-1H-pyrazole-4-carbaldehyde (0.450 g, 2.50 mmol) in tetrahydrofuran (4.2 mL) was added. The resulting mixture was stirred at 0° C. for 1 hour and then at ambient temperature for 17 hours. The mixture was then poured into saturated aqueous ammonium chloride (80 mL) and extracted with ethyl acetate (4×25 mL). The organic phases were combined, washed with brine, dried over sodium sulfate, and concentrated under reduced pressure. The residue was purified using silica gel chromatography [40 g column, 0-100% gradient of ethyl acetate in heptanes] to give the title compound as a mixture of olefin isomers [73:27 (E) to (Z)] (0.444 g, 2.13 mmol, 85% yield). Data for (E)-isomer: $^1$H NMR (500 MHz, CDCl$_3$) δ ppm 6.52 (d, J=13.0 Hz, 1H), 5.50 (d, J=13.0 Hz, 1H), 3.65 (s, 3H), 2.36 (s, 3H), 2.22 (s, 3H), 1.61 (s, 9H). Data for (Z)-isomer: $^1$H NMR (500 MHz, CDCl$_3$) δ ppm 6.01 (d, J=6.7 Hz, 1H), 4.99 (d, J=6.7 Hz, 1H), 3.65 (s, 3H), 2.31 (s, 3H), 2.17 (s, 3H), 1.61 (s, 9H); MS (APCI$^+$) m/z 209.7 [M+H]$^+$.

Example 167D: 2-(1-(tert-butyl)-3,5-dimethyl-1H-pyrazol-4-yl)acetaldehyde

To a vial were added 1-(tert-butyl)-4-(2-methoxyvinyl)-3,5-dimethyl-1H-pyrazole (0.200 g, 0.960 mmol) and tetrahydrofuran (4.8 mL). The vial was cooled to 0° C. The solution was treated with 6.0 M hydrochloric acid (4.8 mL, 29 mmol) and the ice bath was subsequently removed. The vial was allowed to warm to ambient temperature and then heated to 50° C. After 3 hours, the vial was cooled to ambient temperature and the solution was transferred to a beaker containing saturated aqueous sodium bicarbonate (60 mL). The resulting mixture was stirred for 15 minutes and then extracted with ethyl acetate (3×30 mL). The organic phases were combined, washed with brine, dried over sodium sulfate, and concentrated under reduced pressure. The residue was purified using silica gel chromatography [4 g column, 0-100% gradient of ethyl acetate in heptanes] to give the title compound (0.169 g, 0.870 mmol, 91% yield). $^1$H NMR (400 MHz, CDCl$_3$) δ ppm 9.53 (t, J=2.6 Hz, 1H), 3.37 (d, J=2.6 Hz, 2H), 2.31 (s, 3H), 2.17 (s, 3H), 1.62 (s, 9H); MS (ESI$^+$) m/z 195.5 [M+H]$^+$.

Example 168: 5-[2-(aminomethyl)-4-fluoro-6-hydroxy-2,3-dihydro-1H-inden-5-yl]-1λ$^6$,2,5-thiadiazolidine-1,1,3-trione (Compound 267)

Example 168A: 5-(benzyloxy)-7-fluoro-2,3-dihydro-1H-inden-1-one

To a mixture of 5-bromo-7-fluoro-2,3-dihydro-1H-inden-1-one (59 g, 232 mmol), water (20.88 mL, 1159 mmol) and cesium carbonate (177 g, 543 mmol) in N,N-dimethylformamide (600 mL) was added RockPhos Pd G3 precatalyst (1.944 g, 2.318 mmol) under N2 at 25° C. The mixture was heated to 60° C. and stirred for 12 hours at 60° C. under N2. Then the mixture was cooled to 25° C. Benzyl bromide (33.0 mL, 278 mmol) was added to the mixture, and the mixture was stirred for 2 hours at 25° C. One additional vial on a 59 g scale (with respect to 5-bromo-7-fluoro-2,3-dihydro-1H-inden-1-one) was set up in parallel as described above. These two reaction mixtures were combined and diluted with water (2 L) and ethyl acetate (800 mL). Then the resulting mixture was filtered through diatomaceous earth. The two phases of the filtrate were cut, and the aqueous phase was extracted with ethyl acetate (2×800 mL). The combined organic phases were washed with brine (3×500 mL), dried over Na$_2$SO$_4$, and concentrated under reduced pressure. The residue was purified by column chromatography on silica gel eluted with ethyl acetate/petroleum ether (0-10%) to give the title compound (76 g, 267 mmol, 57.6% yield). $^1$H NMR (400 MHz, CDCl$_3$) δ ppm 7.46-7.35 (m, 5H), 6.81-6.76 (m, 1H), 6.61 (dd, J=10.88, 1.88 Hz, 1H), 5.13 (s, 2H), 3.12-3.06 (m, 2H), 2.73-2.67 (m, 2H).

Example 168B: 5-(benzyloxy)-2-bromo-7-fluoro-2,3-dihydro-1H-inden-1-one

To a solution of the product from Example 168A (25 g, 88 mmol) in chloroform (125 mL) and ethyl acetate (125 mL) was added copper(II) bromide (23.53 g, 105 mmol) at 25° C. Then the mixture was stirred for 2 hours at 80° C. Then copper(II) bromide (23.53 g, 105 mmol) was added to the reaction mixture at 25° C. and the mixture was stirred for 2 hours at 80° C. One additional vial on a 20 g scale and one additional vial on 25 g scale were set up in parallel as described above. These three reaction mixtures were combined and filtered. The filtrate was concentrated under reduced pressure. The residue was triturated with 5:1 petroleum ether/ethyl acetate and filtered. The filter cake was the title compound. The filtrate was purified by flash column chromatography (10:1 petroleum ether/ethyl acetate) and combined with the filter cake to give the title compound (67.5 g, 181 mmol, 73.7% yield). $^1$H NMR (400 MHz, CDCl$_3$) δ ppm 7.47-7.35 (m, 5H), 6.78-6.74 (m, 1H), 6.67 (dd, J=10.63, 1.88 Hz, 1H), 5.19-5.12 (m, 2H), 4.62 (dd, J=7.50, 3.13 Hz, 1H), 3.78 (dd, J=18.39, 7.50 Hz, 1H), 3.37 (dd, J=18.39, 3.13 Hz, 1H).

Example 168C: 5-(benzyloxy)-7-fluoro-1-oxo-2,3-dihydro-1H-indene-2-carbonitrile

To a solution of sodium cyanide (18.6 g, 380 mmol) in N,N-dimethylformamide (280 mL) and water (40 mL) was added a solution of the product from Example 168B (42.5 g, 114 mmol) in N,N-dimethylformamide (120 mL) dropwise at 0° C. Then the mixture was stirred for 30 minutes at 25° C. One additional vial on a 1 g scale, one additional vial on a 2.8 g scale, one additional vial on a 7.6 g scale, and one additional vial on a 25 g scale were set up in parallel as described above. Then the mixture was diluted with water (4 L) and purified by reversed-phase column chromatography (Agela Claricep™ Flash AQ C18 Column, 20-35 μm, 100 Å, 800 g, flow rate 100 mL/minute, 0-100% gradient of acetonitrile in water, wavelength: 220 & 254 nm). The eluent was concentrated under reduced pressure to give crude product. The crude product was purified by column chromatography on silica gel eluted with tetrahydrofuran/petroleum ether (0-30%) to give the title compound (45.2 g, 145 mmol, 69.3% yield). $^1$H NMR (400 MHz, DMSO-d$_6$) δ ppm 7.52-7.31 (m, 6H), 7.09 (s, 1H), 7.01 (br d, J=11.51 Hz, 1H), 5.27 (s, 2H).

Example 168D: 5-(benzyloxy)-7-fluoro-1-hydroxy-2,3-dihydro-1H-indene-2-carbonitrile To a solution of the product from Example 168C (30 g, 96 mmol) in methanol (300 mL) and tetrahydrofuran (300 mL) was added sodium borohydride (5.45 g, 144 mmol) in portions at 0° C. Then the mixture was stirred for 2 hours at 25° C. Three additional vials on a 500 mg scale, one additional vial on a 5.7 g scale, and one additional vial on an 8 g scale were set up in parallel as described above. These six reactions were combined and quenched with water (1500 mL) and extracted with ethyl acetate (3×500 mL). The combined organic layers were washed with brine (300 mL), dried over Na$_2$SO$_4$, and concentrated under reduced pressure to give the crude product. The crude product was purified by column chromatography on silica gel eluted with petroleum ether/tetrahydrofuran (10:1 to 5:1, 10:1 byproduct, 5:1 product) to give the title compound (35 g, 111 mmol, 77% yield). $^1$H NMR (400 MHz, CDCl$_3$) δ ppm 7.41 (d, J=4.38 Hz, 5H), 6.67 (br d, J=5.38 Hz, 1H), 6.62 (dt, J=10.76, 2.44 Hz, 1H), 5.67 (t, J=4.63 Hz, 1H), 5.48 (t, J=5.38 Hz, 1H), 5.06 (s, 2H), 3.54-3.33 (m, 2H), 3.30-3.08 (m, 1H), 2.52 (d, J=4.88 Hz, 1H), 2.38 (d, J=5.38 Hz, 1H).

Example 168E: 2-(aminomethyl)-7-fluoro-2,3-dihydro-1H-inden-5-ol hydrochloride

To a mixture of Pd—C(5 g, 4.70 mmol) in methanol (500 mL) and HCl (50 mL, 600 mmol) was added the product from Example 168D (10 g, 31.8 mmol) at 25° C. Then the mixture was stirred for 48 hours at 25° C. under H2 (15 psi). One additional vial on a 10 g scale was set up in parallel as described above. These two reaction mixtures were combined and filtered through diatomaceous earth washed with methanol (1000 mL). The filtrate was evaporated under reduced pressure to give the title compound (13.7 g, 56.6 mmol, 89% yield), which was used directly for the next step. $^1$H NMR (400 MHz, DMSO-d$_6$) δ ppm 10.11-9.26 (m, 1H), 8.14 (br s, 3H), 6.49 (s, 1H), 6.36 (dd, J=10.88, 1.50 Hz, 1H), 2.83-3.02 (m, 4H), 2.77-2.55 (m, 3H).

Example 168F: tert-butyl [(4-fluoro-6-hydroxy-2,3-dihydro-1H-inden-2-yl)methyl]carbamate To a solution of the product from Example 168E (15.2 g, 62.8 mmol) in tetrahydrofuran (150 mL) and water (150 mL) was added sodium bicarbonate (26.4 g, 314 mmol) and then di-tert-butyl dicarbonate (21.89 mL, 94 mmol) was added dropwise at 0° C. Then the mixture was stirred for 12 hours at 25° C. One additional vial on a 500 mg scale and one additional vial on a 6 g scale were set up in parallel as described above. These three reactions were combined. The resulting mixture was diluted with water (500 mL) and extracted with ethyl acetate (3×200 mL). The combined organic phases were washed with brine (200 mL), dried over Na$_2$SO$_4$, and concentrated under reduced pressure. The crude product was purified by column chromatography on silica gel eluted with petroleum ether/ethyl acetate (20:1-5:1) to give the title compound (21.4 g, 72.3 mmol, 80% yield). $^1$H NMR (400 MHz, CDCl$_3$) δ ppm 6.48 (s, 1H), 6.38 (br d, J=10.13 Hz, 1H), 4.71 (br s, 1H), 3.29-3.14 (m, 1H), 3.29-3.14 (m, 1H), 3.05-2.91 (m, 2H), 2.75-2.50 (m, 3H), 1.46 (d, J=1.50 Hz, 10H).

Example 168G: tert-butyl ({4-fluoro-6-[(2-methoxyethoxy)methoxy]-2,3-dihydro-1H-inden-2-yl}methyl)carbamate To a solution of the product from Example 168F (5.6 g, 17.92 mmol) in anhydrous tetrahydrofuran (150 mL) was added cesium carbonate (8.76 g, 26.9 mmol) at 25° C. and then 2-methoxyethoxymethyl chloride (2.435 mL, 21.50 mmol) was added dropwise at 0° C. Then the mixture was stirred for 1 hour at 0° C. Thin layer chromatography (phosphomolybdic acid, petroleum ether:ethyl acetate=3:1) showed 50% of starting material remained. Then cesium carbonate (5.84 g, 17.92 mmol) and 2-methoxyethoxymethyl chloride (2.029 mL, 17.92 mmol) were added to the mixture and stirred for 1 hour at 0° C. Thin layer chromatography (phosphomolybdic acid, petroleum ether:ethyl acetate=3:1) showed 50% of starting material still remained. One additional vial on a 1.3 g scale and one additional vial on a 5.6 g scale were set up in parallel as described above. These three reactions were combined. The combined reaction mixtures were diluted with water (600 mL) and extracted with ethyl acetate (3×200 mL). The combined organic phases were washed with brine (200 mL), dried over $Na_2SO_4$, and concentrated under reduced pressure to give the crude product. Two additional vials on a 2 g scale were set up as described above. The crude products were combined and purified by column chromatography on silica gel eluted with ethyl acetate/petroleum ether (10-12%) to give a mixture of the products of Examples 168F and 168G (18 g), which was used directly. To a solution of the products of Examples 168F and 168G (1 g, 3.55 mmol) in acetone (10 mL) was added cesium carbonate (1.737 g, 5.33 mmol) at 25° C. and then 2-methoxyethoxymethyl chloride (0.483 mL, 4.27 mmol) was added dropwise at 0° C. Then the mixture was stirred for 1 hour at 0° C. Seventeen additional vials on a 1 g scale were set up in parallel as described above. These reactions were combined. The resulting mixture was diluted with water (600 mL) and extracted with ethyl acetate (3×200 mL). The combined organic phases were washed with brine (200 mL), dried over $Na_2SO_4$, and concentrated under reduced pressure to give the crude product. The crude product was purified by column chromatography on silica gel eluted with ethyl acetate/petroleum ether (10-12%) to give the title compound (17 g, 41.4 mmol, 64.7% yield). $^1$H NMR (400 MHz, $CDCl_3$) δ ppm 6.71 (s, 1H), 6.61-6.54 (m, 1H), 5.22 (s, 2H), 4.66 (br s, 1H), 3.81 (dd, J=5.50, 3.88 Hz, 2H), 3.57 (dd, J=5.44, 3.81 Hz, 3H), 3.39 (s, 3H), 3.20 (br d, J=5.50 Hz, 2H), 3.03 (br dd, J=15.51, 7.50 Hz, 2H), 1.46 (s, 9H), 2.55-2.75 (m, 3H).

Example 168H: tert-butyl ({4-fluoro-5-iodo-6-[(2-methoxyethoxy)methoxy]-2,3-dihydro-1H-inden-2-yl}methyl)carbamate To a solution from the product of Example 168G (5.9 g, 14.37 mmol) in anhydrous tetrahydrofuran (150 mL) was added n-butyllithium (34.5 mL, 86 mmol) dropwise at −70° C. under $N_2$. The mixture was stirred for 60 minutes at −70° C. under N2. Then a solution of I2 (23.71 g, 93 mmol) in tetrahydrofuran (30 mL) was added at −70° C. under N2. The mixture was stirred for 60 minutes at −70° C. under N2. Then the mixture was quenched with saturated $NH_4Cl$ aqueous solution and saturated $Na_2S_2O_3$ aqueous solution (1:1, 500 mL) dropwise. The resulting solution was extracted with ethyl acetate (3×200 mL). The combined organic phases were washed with brine (200 mL), dried over $Na_2SO_4$, and concentrated under reduced pressure to give crude product. One additional vial on a 5 g scale and one additional vial on a 5.9 g scale were set up in parallel as described above. These crude products were combined and purified by column chromatography on silica gel eluted with ethyl acetate:petroleum ether=15-20% to give the title compound (14.5 g, 26.3 mmol, 64.3% yield). $^1$H NMR (400 MHz, $CDCl_3$) δ ppm 6.80 (s, 1H), 5.31 (s, 2H), 4.66 (br s, 1H), 3.93-3.82 (m, 2H), 3.63-3.54 (m, 2H), 3.39 (s, 3H), 3.26-3.13 (m, 2H), 3.12-2.99 (m, 2H), 2.75-2.61 (m, 3H), 1.46 (s, 9H).

Example 168I: tert-butyl [(2-{[(tert-butoxycarbonyl)amino]methyl}-4-fluoro-6-[(2-methoxyethoxy)methoxy]-2,3-dihydro-1H-inden-5-yl)amino]acetate To a solution of the product of Example 168H (2 g, 3.63 mmol) in dioxane (20 mL) was added cesium carbonate (3.55 g, 10.90 mmol) followed by tert-butyl 2-aminoacetate (1.430 g, 10.90 mmol) at 25° C. Then BrettPhos Pd G3 precatalyst (0.725 g, 0.799 mmol) was added under N2. Then the mixture was stirred for 4 hours at 95° C. under N2. One additional vial on a 735 mg scale and six additional vials on a 2 g scale were set up in parallel as described above. The resulting mixture was diluted with water (500 mL) and extracted with ethyl acetate (3×200 mL). The combined organic phases were washed with brine (200 mL), dried over $Na_2SO_4$, and concentrated under reduced pressure to give the crude product. The crude product was purified by column chromatography on silica gel eluted with ethyl acetate/petroleum ether=11-18%) to give the title compound (10 g, 19.05 mmol, 70.9% yield). $^1$H NMR: (400 MHz, $CDCl_3$) δ ppm 6.77 (s, 1H), 5.26 (s, 2H), 4.64 (br s, 1H), 4.41 (br s, 1H), 3.95 (br s, 2H), 3.89-3.81 (m, 2H), 3.61-3.55 (m, 2H), 3.43-3.35 (m, 3H), 3.19 (br s, 2H), 3.07-2.87 (m, 2H), 2.73-2.50 (m, 3H), 1.46 (s, 18H).

Example 168J: tert-butyl [(2-{[(tert-butoxycarbonyl)amino]methyl}-4-fluoro-6-[(2-methoxyethoxy)methoxy]-2,3-dihydro-1H-inden-5-yl) ({[(prop-2-en-1-yl)oxy]carbonyl}sulfamoyl)amino]acetate To a solution of chlorosulfonyl isocyanate (1.985 mL, 22.86 mmol) in dichloromethane (3 mL) was added allyl alcohol (1.555 mL, 22.86 mmol) dropwise at 0° C. The mixture was stirred for 30 minutes at 0° C. under N2. Then the mixture was added to a mixture of the product of Example 168I (6 g, 11.43 mmol) and triethylamine (4.78 mL, 34.3 mmol) in dichloromethane (60 mL) dropwise at 0° C. The resulting mixture was stirred for 2 hours at 0° C. under N2. Then the mixture was diluted with water (30 mL) and the organic phase was dried over $Na_2SO_4$ and concentrated under reduced pressure to give the title compound (8.5 g, 12.84 mmol, 112% yield), which was used directly for the next step. MS (ESI$^+$) m/z 661 [M+23, M+46]$^+$.

Example 168K: tert-butyl ({4-fluoro-6-[(2-methoxyethoxy)methoxy]-5-(1,1,4-trioxo-1λ$^6$,2,5-thiadiazolidin-2-yl)-2,3-dihydro-1H-inden-2-yl}methyl)carbamate To a solution of the product of Example 168J (2.2 g, 3.32 mmol) in anhydrous methanol (22 mL) was added 4 Å molecular sieves (2.2 g). The resulting mixture was stirred for 10 minutes at 25° C. Then tetrakis(triphenylphosphine)palladium(0) (150 mg, 0.130 mmol) and sodium methoxide (4.31 g, 19.95 mmol) were added at 25° C. under N2. The mixture was stirred for 2 hours at 60° C. under N2. One additional vial on a 200 mg scale and one additional vial on a 2 g scale were set up in parallel as described above. These three reactions were combined. The combined mixture was filtered, and the filter cake was washed with water (100 mL) and methanol (20 mL). The filtrate was adjusted to pH=4 with aqueous HCl (1 mol/L) and extracted with ethyl acetate (3×50 mL). The combined organic phases were washed with a mixture of brine and aqueous HCl (1 mol/L) (4:1) (50 mL), dried over $Na_2SO_4$, and concentrated under reduced pressure to give the crude product. The crude product was purified by preparative HPLC [Shimadzu LC-8A preparative HPLC; Agela DuraShell C18 column, 250×70 mm×10 μm, flow rate 130 mL/minute, 20-40% in 20 minutes gradient of acetonitrile in water (10 mM $NH_4HCO_3$)]. To the product-containing eluent solution was added 1 M HCl (aqueous solution) to pH=4 and extracted with ethyl acetate (3×200 mL). The combined organic phases were washed with brine (200 mL), dried over $Na_2SO_4$ and concentrated under reduced pressure to give the title compound (1.5 g, 2.83 mmol, 42.6% yield). $^1H$ NMR (400 MHz, DMSO-$d_6$) δ ppm 7.06-6.99 (m, 1H), 6.92 (s, 1H), 5.25 (s, 2H), 4.40 (s, 3H), 3.76-3.69 (m, 2H), 3.45 (dd, J=5.38, 4.00 Hz, 2H), 3.22 (s, 3H), 3.04-2.86 (m, 4H), 2.68-2.56 (m, 3H), 1.38 (s, 9H).

Example 168L: 5-[2-(aminomethyl)-4-fluoro-6-hydroxy-2,3-dihydro-1H-inden-5-yl]-1$\lambda^6$,2,5-thiadiazolidine-1,1,3-trione 2,2,2-trifluoroacetate To a solution of the product of Example 168K (1.3 g, 2.453 mmol) in dichloromethane (18 mL) was added trifluoroacetic acid (6 mL, 78 mmol) dropwise at 0° C. The mixture was stirred for 2 hours at 25° C. One additional vial on a 100 mg scale was set up in parallel as described above. These two reactions were combined. The combined mixtures were evaporated under reduced pressure. The residue was triturated with methanol/water (3:1) to give the title compound (430 mg, 0.989 mmol, 31.5% yield) as a trifluoroacetate salt. $^1H$ NMR (400 MHz, DMSO-$d_6$) δ ppm 9.13 (br s, 1H), 7.78 (br s, 3H), 6.57 (s, 1H), 3.96 (s, 2H), 3.05-2.86 (m, 4H), 2.77-2.58 (m, 3H); MS (ESP) m/z 314 [M−H]$^-$.

Example 169: 5-(4-fluoro-6-hydroxy-2-{[(3-methylbutyl)amino]methyl}-2,3-dihydro-1H-inden-5-yl)-1$\lambda^6$,2,5-thiadiazolidine-1,1,3-trione (Compound 268)

To a suspension of the product of Example 168L (25 mg, 0.058 mmol) in dichloromethane (0.75 mL) and ethanol (0.5 mL) was added triethylamine (0.011 ml, 0.082 mmol). The resulting suspension was stirred at ambient temperature for 5 minutes. Then 3-methylbutanal (8.31 μL, 0.076 mmol) was added and stirred further for 21 hours. Thereafter, sodium tetrahydroborate (5.5 mg, 0.146 mmol) was added and stirred further for 3 hours. The reaction mixture was diluted with methanol (5 mL) and concentrated under reduced pressure. The residue was purified by reversed-phase column chromatography (60 g Biotage® Sfär C18 Duo 100 Å 30 μm column, flow rate 50 mL/minute, 10 to 100% $CH_3OH$ in water [buffered with 0.025 M aqueous ammonium bicarbonate, adjusted to pH 7 with $CO_2$ (s)]) to afford the title compound (11.3 mg, 0.029 mmol, 50.3% yield). $^1H$ NMR (400 MHz, DMSO-$d_6$) δ ppm 8.99 (s, 1H), 8.13 (s, 2H), 6.55 (s, 1H), 3.89 (s, 2H), 3.03-3.92 (m, 4H), 2.89 (dd, J=9.9, 6.4 Hz, 2H), 2.72 (p, J=7.2 Hz, 1H), 2.66-2.57 (m, 2H), 1.66-1.51 (m, 1H), 1.50-1.40 (m, 2H), 0.86 (d, J=6.6 Hz, 6H); MS (APCI$^+$) m/z 386 [M+H]$^+$.

Example 170: 5-(2-{[bis(3-methylbutyl)amino]methyl}-4-fluoro-6-hydroxy-2,3-dihydro-1H-inden-5-yl)-1$\lambda^6$,2,5-thiadiazolidine-1,1,3-trione (Compound 269)

To a suspension of the product of Example 168L (30 mg, 0.070 mmol) in dichloromethane (1.0 mL) was added triethylamine (0.019 mL, 0.140 mmol). The resulting suspension was stirred at ambient temperature for 5 minutes. Then 3-methylbutanal (9.20 μL, 0.084 mmol) dissolved in dichloromethane (1.0 mL) was added and the reaction mixture was stirred further for 10 minutes. Thereafter, sodium triacetoxyhydroborate (37.0 mg, 0.175 mmol) was added and the reaction was stirred at ambient temperature. After 14 hours, the reaction mixture was diluted with saturated aqueous sodium bicarbonate (20 mL) and stirred at ambient temperature for 20 minutes. Then the mixture was extracted with dichloromethane. The combined organic layers were dried over sodium sulfate, filtered, and concentrated under reduced pressure. The product was purified by reversed-phase column chromatography (60 g Biotage® Sfär C18 Duo 100 Å 30 μm column, flow rate 50 mL/minute, 10 to 100% $CH_3OH$ in water [buffered with 0.025 M aqueous ammonium bicarbonate, adjusted to pH 7 with $CO_2(s)$]) to afford the title compound (18.4 mg, 0.040 mmol, 57.8% yield). $^1H$ NMR (600 MHz, DMSO-$d_6$) δ ppm 9.07 (s, 1H), 8.86 (s, 1H), 6.58 (s, 1H), 3.92 (s, 2H), 3.27 (s, 2H), 3.16-3.05 (m, 6H), 2.86 (s, 1H), 2.70-2.60 (m, 2H), 1.65-1.58 (m, 2H), 1.54 (s, 4H), 0.92 (d, J=6.5 Hz, 12H); MS (APCI$^+$) m/z 456 [M+H]$^+$.

Example 171: 8-fluoro-6-hydroxy-N-[(oxolan-3-yl)methyl]-7-(1,1,4-trioxo-1$\lambda^6$,2,5-thiadiazolidin-2-yl)-3,4-dihydroisoquinoline-2(1H)-carboxamide (Compound 270)

Example 171A: 6-(benzyloxy)-8-fluoro-N-[(oxolan-3-yl)methyl]-7-(1,1,4-trioxo-1$\lambda^6$,2,5-thiadiazolidin-2-yl)-3,4-dihydroisoquinoline-2(1H)-carboxamide The title compound was prepared from (tetrahydrofuran-3-yl)methanamine using the procedures described for Example 159A. MS (APCI$^+$) m/z 531.2 [M+H]$^+$.

Example 171B: 8-fluoro-6-hydroxy-N-[(oxolan-3-yl)methyl]-7-(1,1,4-trioxo-1$\lambda^6$,2,5-thiadiazolidin-2-yl)-3,4-dihydroisoquinoline-2(1H)-carboxamide The title compound was prepared from the above Example 171A using the procedures described for Example 159B in 29% yield (for 2 steps). $^1H$ NMR (600 MHz, DMSO-$d_6$) δ ppm 6.78 (t, J=5.6 Hz, 1H), 6.49 (s, 1H), 4.36 (s, 2H), 3.94 (s, 2H), 3.69 (td, J=8.0, 5.7 Hz, 1H), 3.65-3.55 (m, 2H), 3.50 (t, J=5.8 Hz, 2H), 3.42 (dd, J=8.5, 5.2 Hz, 1H), 3.08-2.96 (m, 2H), 2.65 (t, J=5.8 Hz, 2H), 2.41-2.32 (m, 1H), 1.87 (dtd, J=12.2, 8.0, 5.7 Hz, 1H), 1.58-1.49 (m, 1H); MS (APCI$^+$) m/z 429.2 [M+H]$^+$.

Example 172: N-[(1,5-dimethyl-1H-pyrazol-4-yl)methyl]-8-fluoro-6-hydroxy-7-(1,1,4-trioxo-1$\lambda^6$,2,5-thiadiazolidin-2-yl)-3,4-dihydroisoquinoline-2(1H)-carboxamide (Compound 271)

Example 172A: 6-(benzyloxy)-N-[(1,5-dimethyl-1H-pyrazol-4-yl)methyl]-8-fluoro-7-(1,1,4-trioxo-1$\lambda^6$,2,5-thiadiazolidin-2-yl)-3,4-dihydroisoquinoline-2(1H)-carboxamide The title compound was prepared from (1,5-dimethyl-1H-pyrazol-4-yl)methanamine using the procedures described for Example 159A. MS (APCI$^+$) m/z 543.2 [M+H]$^+$.

Example 172B: N-[(1,5-dimethyl-1H-pyrazol-4-yl)methyl]-8-fluoro-6-hydroxy-7-(1,1,4-trioxo-1$\lambda^6$,2,5-thiadiazolidin-2-yl)-3,4-dihydroisoquinoline-2(1H)-carboxamide The title compound was prepared from the above Example 172A using the procedures described for Example 159B in 19% yield (for 2 steps). ¹H NMR (500 MHz, DMSO-d₆) δ ppm 7.00 (t, J=5.7 Hz, 1H), 6.49 (s, 1H), 5.86 (s, 1H), 4.37 (s, 2H), 4.10 (d, J=5.7 Hz, 2H), 3.93 (s, 2H), 3.62 (s, 3H), 3.51 (t, J=5.8 Hz, 2H), 2.65 (t, J=5.5 Hz, 2H), 2.17 (d, J=0.7 Hz, 3H); MS (APCI⁺) m/z 453.3 [M+H]⁺.

Example 173: 8-fluoro-6-hydroxy-N-[(1-methyl-1H-pyrazol-5-yl)methyl]-7-(1,1,4-trioxo-1$\lambda^6$,2,5-thiadiazolidin-2-yl)-3,4-dihydroisoquinoline-2(1H)-carboxamide (Compound 272)

Example 173A: 6-(benzyloxy)-8-fluoro-N-[(1-methyl-1H-pyrazol-5-yl)methyl]-7-(1,1,4-trioxo-1$\lambda^6$,2,5-thiadiazolidin-2-yl)-3,4-dihydroisoquinoline-2(1H)-carboxamide The title compound was prepared from (1-methyl-1H-pyrazol-5-yl)methanamine using the procedures described for Example 159A. MS (APCI⁺) m/z 529.1 [M+H]⁺.

Example 173B: 8-fluoro-6-hydroxy-N-[(1-methyl-1H-pyrazol-5-yl)methyl]-7-(1,1,4-trioxo-1$\lambda^6$ 2,5-thiadiazolidin-2-yl)-3,4-dihydroisoquinoline-2(1H)-carboxamide The title compound was prepared from the above Example 172A using the procedures described for Example 159B in 18% yield (for 2 steps). ¹H NMR (600 MHz, DMSO-d₆) δ ppm 7.25 (d, J=1.8 Hz, 1H), 7.16 (t, J=5.5 Hz, 1H), 6.55-6.46 (m, 1H), 6.09 (d, J=1.8 Hz, 1H), 4.39 (s, 2H), 4.28 (d, J=5.5 Hz, 2H), 3.93 (s, 2H), 3.77 (s, 3H), 3.53 (t, J=5.8 Hz, 2H), 2.66 (t, J=5.8 Hz, 2H); MS (APCI⁺) m/z 439.3 [M+H]⁺.

Example 174: 5-(2-{2-[3,5-dimethyl-1-(propan-2-yl)-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione (Compound 273)

Example 174A: 5-[6-(benzyloxy)-2-{2-[3,5-dimethyl-]-(propan-2-yl)-1H-pyrazol-4-yl]ethyl}-8-fluoro-1,2,3,4-tetrahydroisoquinolin-7-yl]-1$\lambda^6$,2,5-thiadiazolidine-1,1,3-trione To a vial containing 5-[6-(benzyloxy)-8-fluoro-1,2,3,4-tetrahydroisoquinolin-7-yl]-1$\lambda^6$,2,5-thiadiazolidine-1,1,3-trione, trifluoroacetic acid salt (theoretically 0.15 mmol, Example 93A) were added 1,2-dichloroethane (0.77 mL) and triethylamine (0.043 mL, 0.31 mmol). The mixture was stirred for 5 minutes, then 2-(1-isopropyl-3,5-dimethyl-1H-pyrazol-4-yl)acetaldehyde (0.041 g, 0.23 mmol, Example 174D) was added. After 30 minutes, sodium triacetoxyhydroborate (0.081 g, 0.38 mmol) was added. After 13 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.077 g, 0.14 mmol, 90% yield over two steps). ¹H NMR (600 MHz, DMSO-d₆) δ ppm 9.88 (br s, 1H), 7.54-7.47 (m, 2H), 7.38-7.33 (m, 2H), 7.32-7.28 (m, 1H), 6.91 (s, 1H), 5.17 (s, 2H), 4.62 (br s, 1H), 4.39 (hept, J=6.6 Hz, 1H), 4.24 (br s, 1H), 3.97 (s, 2H), 3.81 (br s, 1H), 3.20 (br s, 3H), 3.07 (br s, 2H), 2.78 (t, J=8.6 Hz, 2H), 2.19 (s, 3H), 2.12 (s, 3H), 1.30 (d, J=6.5 Hz, 6H); MS (APCI⁺) m/z 556.4 [M+H]⁺.

Example 174B: 5-(2-{2-[3,5-dimethyl-1-(propan-2-yl)-1H-pyrazol-4-yl]ethyl}-8-fluoro-6-hydroxy-1,2,3,4-tetrahydroisoquinolin-7-yl)-1$\lambda^6$,2,5-thiadiazolidine-1,1,3-trione A flask containing a suspension of 5-[6-(benzyloxy)-2-{2-[3,5-dimethyl-1-(propan-2-yl)-1H-pyrazol-4-yl]ethyl}-8-fluoro-1,2,3,4-tetrahydroisoquinolin-7-yl]-1$\lambda^6$,2,5-thiadiazolidine-1,1,3-trione (0.074 g, 0.13 mmol) and 1,2,3,4,5-pentamethylbenzene (0.059 g, 0.40 mmol) in dichloromethane (1.3 mL) was cooled to −78° C. with stirring under an atmosphere of nitrogen. Next, trichloroborane (1.0 M in dichloromethane) (1.1 mL, 1.1 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.048 g, 0.10 mmol, 78% yield). ¹H NMR (600 MHz, DMSO-d₆) δ ppm 9.89 (br s, 1H), 9.74 (s, 1H), 6.60 (s, 1H), 4.56 (br s, 1H), 4.39 (hept, J=6.6 Hz, 1H), 4.20 (br s, 1H), 3.96 (s, 2H), 3.79 (br s, 1H), 3.36 (br s, 1H), 3.19 (br s, 2H), 3.04 (br s, 2H), 2.78 (t, J=8.6 Hz, 2H), 2.19 (s, 3H), 2.12 (s, 3H), 1.30 (d, J=6.6 Hz, 6H); MS (ESI⁺) m/z 466.0 [M+H]⁺.

Example 174C: 1-isopropyl-4-(2-methoxyvinyl)-3,5-dimethyl-1H-pyrazole

To a flask were added (methoxymethyl)triphenylphosphonium chloride (1.21 g, 3.52 mmol) and tetrahydrofuran (4.5 mL). The flask was cooled to 0° C., then potassium 2-methylpropan-2-olate (1.0 M in tetrahydrofuran) (3.3 mL, 3.3 mmol) was added. Fifteen minutes later, a solution of 1-isopropyl-3,5-dimethyl-1H-pyrazole-4-carbaldehyde (0.450 g, 2.71 mmol) in tetrahydrofuran (4.5 mL) was added. The resulting mixture was stirred at 0° C. for 1 hour and then at ambient temperature for 23 hours. The mixture was then poured into saturated aqueous ammonium chloride (80 mL) and extracted with ethyl acetate (4×25 mL). The organic phases were combined, washed with brine, dried over sodium sulfate, and concentrated under reduced pressure. The residue was purified using silica gel chromatography [40 g column, 0-100% gradient of ethyl acetate in heptanes] to give the title compound as a mixture of olefin isomers [71:29 (E) to (Z)] (0.415 g, 2.14 mmol, 79% yield). Data for (E)-isomer: ¹H NMR (400 MHz, CDCl₃) δ ppm 6.55 (d, J=13.0 Hz, 1H), 5.53 (d, J=13.0 Hz, 1H), 4.46-4.22 (m, 1H), 3.65 (s, 3H), 2.24 (s, 3H), 2.20 (s, 3H), 1.44 (d, J=6.6 Hz, 6H). Data for (Z)-isomer: ¹H NMR (400 MHz, CDCl₃) δ ppm 5.98 (d, J=6.8 Hz, 1H), 5.00 (d, J=6.7 Hz, 1H), 4.46-4.22 (m, 1H), 3.66 (s, 3H), 2.19 (s, 3H), 2.18 (s, 3H), 1.44 (d, J=6.6 Hz, 6H); MS (ESI$^+$) m/z 195.5 [M+H]$^+$.

Example 174D: 2-(1-isopropyl-3,5-dimethyl-1H-pyrazol-4-yl)acetaldehyde

To a vial were added 1-isopropyl-4-(2-methoxyvinyl)-3,5-dimethyl-1H-pyrazole (0.206 g, 1.06 mmol) and tetrahydrofuran (5.3 mL). The vial was cooled to 0° C. The solution was treated with 6.0 M hydrochloric acid (5.3 mL, 32 mmol) and the ice bath was subsequently removed. The vial was allowed to warm to ambient temperature and then heated to 50° C. After 1 hour, the vial was cooled to ambient temperature and the solution was transferred to a beaker containing saturated aqueous sodium bicarbonate (60 mL). The resulting mixture was stirred for 15 minutes and then extracted with ethyl acetate (3×30 mL). The organic phases were combined, washed with brine, dried over sodium sulfate, and concentrated under reduced pressure. The residue was purified using silica gel chromatography [12 g column, 0-100% gradient of ethyl acetate in heptanes] to give the title compound (0.074 g, 0.41 mmol, 39% yield). $^1$H NMR (500 MHz, CDCl$_3$) δ ppm 9.55 (t, J=2.6 Hz, 1H), 4.42-4.30 (m, 1H), 3.38 (d, J=2.6 Hz, 2H), 2.18 (s, 3H), 2.15 (s, 3H), 1.45 (d, J=6.6 Hz, 6H); MS (ESI$^+$) m/z 213.5 [M+CH$_3$OH+H]$^+$.

Example 175: 5-(2-{[(3-cyclopropylpropyl)amino]methyl}-4-fluoro-6-hydroxy-2,3-dihydro-1H-inden-5-yl)-1λ$^6$,2,5-thiadiazolidine-1,1,3-trione (Compound 274)

To a suspension of the product of Example 168L (50 mg, 0.116 mmol) in dichloromethane (1.5 mL) and ethanol (1 mL) was added triethylamine (0.023 mL, 0.163 mmol). The reaction mixture was stirred at ambient temperature for 5 minutes. Then 3-cyclopropylpropanal (0.019 mL, 0.151 mmol) was added and the reaction was stirred at ambient temperature for 22 hours. Thereafter, sodium tetrahydroborate (11.01 mg, 0.291 mmol) was added and the resultant mixture was stirred further for 2 hours at ambient temperature. The reaction mixture was diluted with methanol (10 mL) and concentrated with diatomaceous earth for dry loading. The residue was purified by reversed-phase column chromatography (60 g Biotage® Sfär C18 Duo 100 Å 30 μm column, flow rate 50 mL/minute, 10 to 100% CH$_3$OH in water [buffered with 0.025 M aqueous ammonium bicarbonate, adjusted to pH 7 with CO$_2$ (s)]) to afford the title compound (13.9 mg, 0.035 mmol, 30.0% yield). $^1$H NMR (400 MHz, DMSO-d$_6$) δ ppm 6.54 (s, 1H), 3.90 (s, 2H), 3.01-2.86 (m, 4H), 2.86-2.78 (m, 2H), 2.74-2.55 (m, 3H), 1.62 (p, J=7.6 Hz, 2H), 1.20 (q, J=7.3 Hz, 2H), 0.70-0.59 (m, 1H), 0.42-0.33 (m, 2H), 0.02--0.06 (m, 2H); MS (APCI$^+$) m/z 398 [M+H]$^+$.

Example 176: 5-(4-fluoro-6-hydroxy-2-{[(2-methylpropyl)amino]methyl}-2,3-dihydro-1H-inden-5-yl)-1λ$^6$,2,5-thiadiazolidine-1,1,3-trione (Compound 275)

To a suspension of the product of Example 168L (25 mg, 0.058 mmol) in dichloromethane (0.750 ml) and ethanol (0.5 ml) was added triethylamine (0.011 ml, 0.082 mmol). The reaction mixture was stirred at ambient temperature for 5 minutes, then freshly distilled isobutyraldehyde (6.95 μL, 0.076 mmol) was added and the resultant mixture was stirred further for 17.5 hours. Thereafter, sodium tetrahydroborate (5.51 mg, 0.146 mmol) was added and the mixture was stirred for 2 hours. The reaction mixture was diluted with methanol (10 mL) and concentrated under reduced pressure. The residue was purified by reversed-phase column chromatography (60 g Biotage® Sfär C18 Duo 100 Å 30 μm column, flow rate 50 mL/minute, 10 to 100% CH$_3$OH in water [buffered with 0.025 M aqueous ammonium bicarbonate, adjusted to pH 7 with CO$_2$ (s)]) to give the title compound (8.1 mg, 0.022 mmol, 37.5% yield). $^1$H NMR (600 MHz, DMSO-d$_6$) δ ppm 9.04 (s, 1H), 6.58 (s, 1H), 3.93 (s, 2H), 3.05-2.97 (m, 3H), 2.97 (s, 1H), 2.82-2.75 (m, 1H), 2.75-2.72 (m, 2H), 2.69-2.62 (m, 2H), 1.97-1.89 (m, 1H), 0.96-0.92 (m, 6H); MS (APCI$^+$) m/z 372 [M+H]$^+$.

Example 177: 5-{2-[2-(1-ethyl-3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione (Compound 276)

Example 177A: 5-{6-(benzyloxy)-2-[2-(1-ethyl-3,5-dimethyl-1H-pyrazol-4-yl)ethyl]-8-fluoro-1,2,3,4-tetrahydroisoquinolin-7-yl}-1λ$^6$,2,5-thiadiazolidine-1,1,3-trione To a vial containing 5-[6-(benzyloxy)-8-fluoro-1,2,3,4-tetrahydroisoquinolin-7-yl]-1λ$^6$,2,5-thiadiazolidine-1,1,3-trione, trifluoroacetic acid salt (theoretically 0.15 mmol, Example 93A) were added 1,2-dichloroethane (0.77 mL) and triethylamine (0.043 mL, 0.31 mmol). The mixture was stirred for 5 minutes, then 2-(1-ethyl-3,5-dimethyl-1H-pyrazol-4-yl)acetaldehyde (0.038 g, 0.23 mmol, Example 177D) was added. After 30 minutes, sodium triacetoxyhydroborate (0.081 g, 0.38 mmol) was added. After 13 hours, the reaction mixture was poured into saturated aqueous sodium bicarbonate (50 mL) with the aid of dichloromethane. The resulting biphasic mixture was stirred for 20 minutes. The layers were then separated, and the aqueous phase was extracted with dichloromethane (4×25 mL). The organic phases were combined, washed with brine, dried over sodium sulfate, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.074 g, 0.14 mmol, 89% yield over two steps). $^1$H NMR (500 MHz, DMSO-d$_6$-D$_2$O) δ ppm 7.45 (d, J=7.1 Hz, 2H), 7.33 (t, J=7.4 Hz, 2H), 7.28 (dd, J=8.4, 6.1 Hz, 1H), 6.88 (s, 1H), 5.12 (s, 2H), 4.34 (br s, 2H), 4.02 (s, 2H), 3.90 (q, J=7.2 Hz, 2H), 3.49 (br s, 2H), 3.16 (t, J=8.2 Hz, 2H), 3.06 (t, J=6.2 Hz, 2H), 2.84-2.68 (m, 2H), 2.14 (s, 3H), 2.07 (s, 3H), 1.19 (t, J=7.2 Hz, 3H); MS (APCI$^+$) m/z 542.3 [M+H]$^+$.

Example 177B: 5-{2-[2-(1-ethyl-3,5-dimethyl-1H-pyrazol-4-yl)ethyl]-8-fluoro-6-hydroxy-1,2,3,4-tetrahydroisoquinolin-7-yl}-1λ$^6$,2,5-thiadiazolidine-1,1,3-trione A flask containing a suspension of 5-{6-(benzyloxy)-2-[2-(1-ethyl-3,5-dimethyl-1H-pyrazol-4-yl)ethyl]-8-fluoro-1,2,3,4-tetrahydroisoquinolin-7-yl}-1λ$^6$,2,5-thiadiazolidine-1,1,3-trione (0.070 g, 0.13 mmol) and 1,2,3,4,5-pentamethylbenzene (0.058 g, 0.39 mmol) in dichloromethane (1.3 mL) was cooled to −78° C. with stirring under an atmosphere of nitrogen. Next, trichloroborane (1.0 M in dichloromethane) (1.0 mL, 1.0 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.054 g, 0.12 mmol, 92% yield). $^1$H NMR (500 MHz, DMSO-$d_6$) δ ppm 9.86 (br s, 1H), 9.74 (s, 1H), 6.60 (s, 1H), 4.57 (br s, 1H), 4.20 (br s, 1H), 3.96 (s, 2H), 3.93 (q, J=7.2 Hz, 2H), 3.80 (br s, 1H), 3.36 (br s, 1H), 3.18 (br s, 2H), 3.04 (br s, 2H), 2.87-2.71 (m, 2H), 2.19 (s, 3H), 2.10 (s, 3H), 1.23 (t, J=7.2 Hz, 3H); MS (ESI$^+$) m/z 452.0 [M+H]$^+$.

Example 177C: 1-ethyl-4-(2-methoxyvinyl)-3,5-dimethyl-1H-pyrazole

To a flask were added (methoxymethyl)triphenylphosphonium chloride (1.32 g, 3.84 mmol) and tetrahydrofuran (4.9 mL). The flask was cooled to 0° C., then potassium 2-methylpropan-2-olate (1.0 M in tetrahydrofuran) (3.6 mL, 3.6 mmol) was added. Fifteen minutes later, a solution of 1-ethyl-3,5-dimethyl-1H-pyrazole-4-carbaldehyde (0.450 g, 2.96 mmol) in tetrahydrofuran (4.9 mL) was added. The resulting mixture was stirred at 0° C. for 1 hour and then at ambient temperature for 17 hours. The mixture was then poured into saturated aqueous ammonium chloride (80 mL) and extracted with ethyl acetate (4×25 mL). The organic phases were combined, washed with brine, dried over sodium sulfate, and concentrated under reduced pressure. The residue was purified using silica gel chromatography [40 g column, 0-100% gradient of ethyl acetate in heptanes] to give the title compound [62:38 (E) to (Z)] (0.342 g, 1.90 mmol, 64% yield). Data for (E)-isomer: $^1$H NMR (400 MHz, CDCl$_3$) δ ppm 6.56 (d, J=13.1 Hz, 1H), 5.52 (d, J=13.0 Hz, 1H), 4.08-3.96 (m, 2H), 3.65 (s, 3H), 2.22 (s, 3H), 2.20 (s, 3H), 1.36 (t, J=7.3 Hz, 3H). Data for (Z)-isomer: $^1$H NMR (400 MHz, CDCl$_3$) δ ppm 5.99 (d, J=6.7 Hz, 1H), 5.00 (d, J=6.7 Hz, 1H), 4.08-3.96 (m, 2H), 3.66 (s, 3H), 2.18 (2 overlapped singlets, 6H), 1.36 (t, J=7.3 Hz, 3H); MS (ESI$^+$) m/z 181.6 [M+H]$^+$.

Example 177D: 2-(1-ethyl-3,5-dimethyl-1H-pyrazol-4-yl)acetaldehyde

To a vial were added 1-ethyl-4-(2-methoxyvinyl)-3,5-dimethyl-1H-pyrazole (0.200 g, 1.11 mmol) and tetrahydrofuran (5.6 mL). The vial was cooled to 0° C. The solution was treated with 6.0 M hydrochloric acid (5.6 mL, 33 mmol) and the ice bath was subsequently removed. The vial was allowed to warm to ambient temperature and then heated to 50° C. After 1 hour, the vial was cooled to ambient temperature and the solution was transferred to a beaker containing saturated aqueous sodium bicarbonate (60 mL). The resulting mixture was stirred for 15 minutes and then extracted with ethyl acetate (3×30 mL). The organic phases were combined, washed with brine, dried over sodium sulfate, and concentrated under reduced pressure. The residue was purified using silica gel chromatography [12 g column, 0-100% gradient of ethyl acetate in heptanes] to give the title compound (0.114 g, 0.686 mmol, 62% yield). $^1$H NMR (400 MHz, CDCl$_3$) δ ppm 9.56 (t, J=2.5 Hz, 1H), 4.03 (q, J=7.3 Hz, 2H), 3.39 (d, J=2.5 Hz, 2H), 2.17 (s, 3H), 2.15 (s, 3H), 1.38 (t, J=7.3 Hz, 3H); MS (ESI$^+$) m/z 167.2 [M+H]$^+$.

Example 178: N-(2,2-dimethylpropyl)-8-fluoro-6-hydroxy-7-(1,1,4-trioxo-1λ$^6$,2,5-thiadiazolidin-2-yl)-3,4-dihydroisoquinoline-2(1H)-carboxamide (Compound 277)

Example 178A: 6-(benzyloxy)-N-(2,2-dimethylpropyl)-8-fluoro-7-(1,1,4-trioxo-1λ$^6$,2,5-thiadiazolidin-2-yl)-3,4-dihydroisoquinoline-2(1H)-carboxamide The title compound was prepared from 2,2-dimethylpropan-1-amine using the procedures described for Example 159A. MS (APCI$^+$) m/z 505.2 [M+H]$^+$.

Example 178B: N-(2,2-dimethylpropyl)-8-fluoro-6-hydroxy-7-(1,1,4-trioxo-1λ$^6$,2,5-thiadiazolidin-2-yl)-3,4-dihydroisoquinoline-2(1H)-carboxamide The title compound was prepared from the above Example 178A using the procedures described for Example 159B in 14% yield (for 2 steps). $^1$H NMR (400 MHz, DMSO-$d_6$) δ ppm 7.10 (s, 1H), 6.56-6.47 (m, 2H), 4.39 (s, 2H), 3.94 (s, 2H), 3.53 (t, J=5.8 Hz, 2H), 2.90 (d, J=6.1 Hz, 2H), 2.66 (t, J=5.7 Hz, 2H), 0.81 (s, 9H); MS (APCI$^+$) m/z 415.2 [M+H]$^+$.

Example 179: 8-fluoro-6-hydroxy-N-(3-methoxypropyl)-7-(1,1,4-trioxo-1λ$^6$,2,5-thiadiazolidin-2-yl)-3,4-dihydroisoquinoline-2(1H)-carboxamide (Compound 278)

Example 179A: 6-(benzyloxy)-8-fluoro-N-(3-methoxypropyl)-7-(1,1,4-trioxo-1λ$^6$,2,5-thiadiazolidin-2-yl)-3,4-dihydroisoquinoline-2(1H)-carboxamide The title compound was prepared from 3-methoxypropan-1-amine using the procedures described for Example 159A. MS (APCI$^+$) m/z 507.2 [M+H]$^+$.

Example 179B: 8-fluoro-6-hydroxy-N-(3-methoxypropyl)-7-(1,1,4-trioxo-1λ$^6$,2,5-thiadiazolidin-2-yl)-3,4-dihydroisoquinoline-2(1H)-carboxamide The title compound was prepared from the above Example 179A using the procedures described for Example 159B in 13% yield (for 2 steps). $^1$H NMR (400 MHz, DMSO-$d_6$) δ ppm 6.62 (t, J=5.4 Hz, 1H), 6.49 (s, 1H), 4.35 (s, 2H), 3.94 (s, 2H), 3.49 (t, J=5.8 Hz, 2H), 3.31 (q, J=6.4 Hz, 2H), 3.21 (s, 3H), 3.08 (q, J=6.6 Hz, 2H), 2.65 (t, J=5.8 Hz, 2H), 1.65 (p, J=6.6 Hz, 2H); MS (APCI$^+$) m/z 417.2 [M+H]$^+$.

Example 180: 8-fluoro-6-hydroxy-N-(3-methoxy-2,2-dimethylpropyl)-7-(1,1,4-trioxo-1λ⁶,2,5-thiadiazolidin-2-yl)-3,4-dihydroisoquinoline-2(1H)-carboxamide (Compound 279)

Example 180A: 6-(benzyloxy)-8-fluoro-N-(3-methoxy-2,2-dimethylpropyl)-7-(1,1,4-trioxo-1λ⁶,2,5-thiadiazolidin-2-yl)-3,4-dihydroisoquinoline-2(1H)-carboxamide The title compound was prepared from 3-methoxy-2,2-dimethylpropan-1-amine using the procedures described for Example 159A. MS (APCI⁺) m/z 535.2 [M+H]⁺.

Example 180B: 8-fluoro-6-hydroxy-N-(3-methoxy-2,2-dimethylpropyl)-7-(1,1,4-trioxo-1λ⁶,2,5-thiadiazolidin-2-yl)-3,4-dihydroisoquinoline-2(1H)-carboxamide The title compound was prepared from the above Example 180A using the procedures described for Example 159B in 7% yield (for 2 steps). $^1$H NMR (400 MHz, DMSO-d$_6$) δ ppm 6.49 (s, 1H), 6.42 (t, J=6.1 Hz, 1H), 4.38 (s, 2H), 3.94 (s, 2H), 3.51 (t, J=5.7 Hz, 2H), 3.23 (s, 3H), 3.03 (s, 2H), 2.98 (d, J=6.0 Hz, 2H), 2.66 (t, J=5.7 Hz, 2H), 0.79 (s, 6H); MS (APCI⁺) m/z 445.3 [M+H]⁺.

Example 181: N-[2-(dimethylamino)ethyl]-8-fluoro-6-hydroxy-7-(1,1,4-trioxo-1λ⁶,2,5-thiadiazolidin-2-yl)-3,4-dihydroisoquinoline-2(1H)-carboxamide (Compound 280)

Example 181A: 6-(benzyloxy)-N-[2-(dimethylamino)ethyl]-8-fluoro-7-(1,1,4-trioxo-1λ⁶,2,5-thiadiazolidin-2-yl)-3,4-dihydroisoquinoline-2(1H)-carboxamide The title compound was prepared from N,N-dimethylethane-1,2-diamine using the procedures described for Example 159A. MS (APCI⁺) m/z 506.2 [M+H]⁺.

Example 181B: N-[2-(dimethylamino)ethyl]-8-fluoro-6-hydroxy-7-(1,1,4-trioxo-1λ⁶,2,5-thiadiazolidin-2-yl)-3,4-dihydroisoquinoline-2(1H)-carboxamide The title compound was prepared from the above Example 181A using the procedures described for Example 159B in 8% yield (for 2 steps). $^1$H NMR (400 MHz, DMSO-d$_6$) δ ppm 9.27 (s, 1H), 9.10 (s, 1H), 6.88 (m, 1H), 6.52 (s, 1H), 4.40 (s, 2H), 3.94 (s, 2H), 3.53 (t, J=5.7 Hz, 2H), 3.39-3.34 (m, 2H), 3.08 (s, 2H), 2.76 (s, 6H), 2.69 (t, J=5.9 Hz, 2H); MS (APCI⁺) m/z 416.3 [M+H]⁺.

Example 182: 8-fluoro-6-hydroxy-N-[2-(1-methylcyclopropyl)ethyl]-7-(1,1,4-trioxo-1λ⁶,2,5-thiadiazolidin-2-yl)-3,4-dihydroisoquinoline-2(1H)-carboxamide (Compound 281)

Example 182A: 6-(benzyloxy)-8-fluoro-N-[2-(1-methylcyclopropyl)ethyl]-7-(1,1,4-trioxo-1λ⁶,2,5-thiadiazolidin-2-yl)-3,4-dihydroisoquinoline-2(1H)-carboxamide The title compound was prepared from 2-(1-methylcyclopropyl)ethan-1-amine using the procedures described for Example 159A. MS (APCI⁺) m/z 517.2 [M+H]⁺.

Example 182B: 8-fluoro-6-hydroxy-N-[2-(1-methylcyclopropyl)ethyl]-7-(1,1,4-trioxo-1λ⁶,2,5-thiadiazolidin-2-yl)-3,4-dihydroisoquinoline-2(1H)-carboxamide The title compound was prepared from the above Example 182A using the procedures described for Example 159B in 6% yield (for 2 steps). $^1$H NMR (400 MHz, DMSO-d$_6$) δ ppm 6.56 (t, J=5.5 Hz, 1H), 6.48 (s, 1H), 4.34 (s, 2H), 3.93 (s, 2H), 3.48 (t, J=5.8 Hz, 2H), 3.14-3.07 (m, 2H), 2.64 (t, J=5.7 Hz, 2H), 1.40-1.32 (m, 2H), 1.01 (s, 3H), 0.32-0.15 (m, 4H); MS (APCI⁺) m/z 427.3 [M+H]⁺.

Example 183: 8-fluoro-6-hydroxy-N-(2-methoxyethyl)-7-(1,1,4-trioxo-1λ⁶,2,5-thiadiazolidin-2-yl)-3,4-dihydroisoquinoline-2(1H)-carboxamide (Compound 282)

Example 183A: 6-(benzyloxy)-8-fluoro-N-(2-methoxyethyl)-7-(1,1,4-trioxo-1λ⁶,2,5-thiadiazolidin-2-yl)-3,4-dihydroisoquinoline-2(1H)-carboxamide The title compound was prepared from 2-methoxyethan-1-amine using the procedures described for Example 159A. MS (APCI⁺) m/z 493.1 [M+H]⁺.

Example 183B: 8-fluoro-6-hydroxy-N-(2-methoxyethyl)-7-(1,1,4-trioxo-1λ⁶,2,5-thiadiazolidin-2-yl)-3,4-dihydroisoquinoline-2(1H)-carboxamide The title compound was prepared from the above Example 183A using the procedures described for Example 159B in 12% yield (for 2 steps). $^1$H NMR (400 MHz, DMSO-d$_6$) δ ppm 6.69 (t, J=5.5 Hz, 1H), 6.49 (s, 1H), 4.35 (s, 2H), 3.94 (s, 2H), 3.50 (t, J=5.8 Hz, 2H), 3.33 (s, 2H), 3.23 (s, 3H), 3.22-3.14 (m, 2H), 2.65 (t, J=5.8 Hz, 2H); MS (APCI⁺) m/z 403.2 [M+H]⁺.

Example 184: 8-fluoro-6-hydroxy-N-[(oxetan-3-yl)methyl]-7-(1,1,4-trioxo-1λ⁶,2,5-thiadiazolidin-2-yl)-3,4-dihydroisoquinoline-2(1H)-carboxamide (Compound 283)

Example 184A: 6-(benzyloxy)-8-fluoro-N-[(oxetan-3-yl)methyl]-7-(1,1,4-trioxo-1λ⁶,2,5-thiadiazolidin-2-yl)-3,4-dihydroisoquinoline-2(1H)-carboxamide The title compound was prepared from oxetan-3-ylmethanamine using the procedures described for Example 159A. MS (APCI⁺) m/z 505.1 [M+H]⁺.

Example 184B: 8-fluoro-6-hydroxy-N-[(oxetan-3-yl)methyl]-7-(1,1,4-trioxo-1λ⁶,2,5-thiadiazolidin-2-yl)-3,4-dihydroisoquinoline-2(1H)-carboxamide The title compound was prepared from the above Example 184A using the procedures described for Example 159B in 4% yield (for 2 steps). $^1$H NMR (400 MHz, DMSO-d$_6$) δ ppm 9.54-9.31 (m, 2H), 4.93 (t, J=5.3 Hz, 1H), 4.67-4.58 (m, 1H), 4.49 (s, 2H), 4.42-4.30 (m, 1H), 3.94 (s, 2H), 3.69-3.57 (m, 2H), 3.47 (d, J=4.5 Hz, 2H), 3.21 (dd, J=12.6, 7.9 Hz, 1H), 2.91-2.77 (m, 2H), 2.31-2.18 (m, 1H); MS (APCI⁺) m/z 415.2 [M+H]⁺.

Example 185: 8-fluoro-6-hydroxy-N-(2-phenylethyl)-7-(1,1,4-trioxo-1λ⁶,2,5-thiadiazolidin-2-yl)-3,4-dihydroisoquinoline-2(1H)-carboxamide (Compound 284)

Example 185A: 6-(benzyloxy)-8-fluoro-N-(2-phenylethyl)-7-(1,1,4-trioxo-1λ⁶,2,5-thiadiazolidin-2-yl)-3,4-dihydroisoquinoline-2(1H)-carboxamide The title compound was prepared from 2-phenylethan-1-amine using the procedures described for Example 159A. MS (APCI⁺) m/z 539.2 [M+H]⁺.

Example 185B: 8-fluoro-6-hydroxy-N-(2-phenylethyl)-7-(1,1,4-trioxo-1λ⁶,2,5-thiadiazolidin-2-yl)-3,4-dihydroisoquinoline-2(1H)-carboxamide The title compound was prepared from the above Example 185A using the procedures described for Example 159B in 14% yield (for 2 steps). ¹H NMR (400 MHz, DMSO-d₆) δ ppm 7.31-7.22 (m, 2H), 7.22-7.13 (m, 3H), 6.76 (t, J=5.4 Hz, 1H), 6.49 (s, 1H), 4.35 (s, 2H), 3.95 (s, 2H), 3.49 (t, J=5.8 Hz, 2H), 3.24 (dd, J=8.4, 6.3 Hz, 2H), 2.73 (dd, J=8.7, 6.4 Hz, 2H), 2.64 (t, J=5.8 Hz, 2H); MS (APCI⁺) m/z 449.3 [M+H]⁺.

Example 186: N-[3-(dimethylamino)propyl]-8-fluoro-6-hydroxy-7-(1,1,4-trioxo-1λ⁶,2,5-thiadiazolidin-2-yl)-3,4-dihydroisoquinoline-2(1H)-carboxamide (Compound 285)

Example 186A: 6-(benzyloxy)-N-[3-(dimethylamino)propyl]-8-fluoro-7-(1,1,4-trioxo-1λ⁶,2,5-thiadiazolidin-2-yl)-3,4-dihydroisoquinoline-2(1H)-carboxamide The title compound was prepared from N,N-dimethylpropane-1,3-diamine using the procedures described for Example 159A. MS (APCI⁺) m/z 520.1 [M+H]⁺.

Example 186B: N-[3-(dimethylamino)propyl]-8-fluoro-6-hydroxy-7-(1,1,4-trioxo-1λ⁶,2,5-thiadiazolidin-2-yl)-3,4-dihydroisoquinoline-2(1H)-carboxamide The title compound was prepared from the above Example 186A using the procedures described for Example 159B in 4% yield (for 2 steps). ¹H NMR (400 MHz, DMSO-d₆) δ ppm 6.55-6.43 (m, 1H), 4.20 (s, 2H), 3.94 (s, 2H), 3.39-3.35 (m, 2H), 3.22-3.14 (m, 2H), 2.86-2.78 (m, 8H), 2.75 (t, J=6.0 Hz, 2H), 1.88-1.75 (m, 2H); MS (APCI⁺) m/z 430.3 [M+H]⁺.

Example 187: 5-[2-(3-cyclohexylpropyl)-8-fluoro-6-hydroxy-1,2,3,4-tetrahydroisoquinolin-7-yl]-1λ⁶,2,5-thiadiazolidine-1,1,3-trione (Compound 286)

Example 187A: 5-[6-(benzyloxy)-2-(3-cyclohexylpropyl)-8-fluoro-1,2,3,4-tetrahydroisoquinolin-7-yl]-1λ⁶,2,5-thiadiazolidine-1,1,3-trione, Ammonia Salt Sodium triacetoxyborohydride (77.0 mg, 0.36 mmol, 1.2 equivalents) was added in one portion to a suspension of 3-cyclohexylpropionaldehyde (100 mg, 0.69 mmol, 2.3 equivalents), the product of Example 54A (nominally 0.30 mmol, 1 equivalent), and triethylamine (0.13 mL, 0.93 mmol, 3.1 equivalents) in acetonitrile (0.86 mL, 0.35 M) at 23° C. The reaction mixture was stirred for 18 hours at 23° C. The product mixture was diluted sequentially with saturated aqueous ammonium chloride solution (0.5 mL), water (0.5 mL), and dimethyl sulfoxide (1.0 mL). The diluted mixture was purified by reversed-phase flash column chromatography (50 g RediSep Rf Gold® C18 column, elution with a gradient of 10-100% [v/v] methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (134 mg, 0.25 mmol, 84% yield). MS (APCI⁺) m, z 516 [M+H]⁺.

Example 187B: 5-[2-(3-cyclohexylpropyl)-8-fluoro-6-hydroxy-1,2,3,4-tetrahydroisoquinolin-7-yl]-1λ⁶,2,5-thiadiazolidine-1,1,3-trione, Ammonia Salt A suspension of palladium-on-carbon (10 weight %, 27 mg, 0.025 mmol, 10 mol %), ammonium formate (79 mg, 1.26 mmol, 5 equivalents), and the product of Example 187A (134 mg, 0.25 mmol, 1 equivalent) in ethanol (2.5 mL, 0.1 M) was stirred for 18 hours at 23° C. The product mixture was filtered through a plug of diatomaceous earth (1.0 cm×0.5 cm). The filter cake was rinsed with methanol (3×1.0 mL). The filtrates were combined, and the combined filtrates were concentrated. The residue obtained was purified by reversed-phase flash column chromatography (50 g RediSep Rf Gold® C18 column, elution with a gradient of 10-100% [v/v]methanol-0.025 M aqueous ammonium bicarbonate solution [acidified with solid carbon dioxide] over 10 column volumes, then isocratic elution with 100% methanol for 3 column volumes, flow rate=60 mL/minute) to furnish the title compound (75 mg, 0.17 mmol, 67% yield). 1H NMR (400 MHz, DMSO-d₆) δ ppm 9.67 (s, 1H), 6.58 (s, 1H), 4.54-4.06 (m, 2H), 3.94 (s, 2H), 3.82-3.48 (m, 1H), 3.25-2.91 (m, 5H), 1.87-1.56 (m, 7H), 1.32-1.04 (m, 6H), 0.95-0.82 (m, 2H); MS (APCI⁺) m/z 467 [M+H+CH₃CN]⁺.

Example 188: 5-(7-{[(3,5-dimethyl-1,2-oxazol-4-yl)methyl]amino}-1-fluoro-3-hydroxy-5,6,7,8-tetrahydronaphthalen-2-yl)-1λ⁶,2,5-thiadiazolidine-1,1,3-trione (Compound 287)

Example 188A: 5-[3-(benzyloxy)-7-{[(3,5-dimethyl-1,2-oxazol-4-yl)methyl]amino}-1-fluoro-5,6,7,8-tetrahydronaphthalen-2-yl]-1λ⁶,2,5-thiadiazolidine-1,1,3-trione, Ammonium Salt To a vial containing the product of Example 67F (0.080 g, 0.20 mmol) were added 1,2-dichloroethane (0.99 mL) and (3,5-dimethylisoxazol-4-yl)methanamine (0.037 g, 0.30 mmol). The resulting mixture was stirred at ambient temperature. After 30 minutes, sodium triacetoxyhydroborate (0.105 g, 0.495 mmol) was added. Fourteen hours later, the reaction mixture was diluted with acetonitrile (3 mL), saturated aqueous ammonium chloride (3 mL), and water (3 mL). The resulting mixture was concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound as the ammonium salt (0.082 g, 0.16 mmol, 78% yield). ¹H NMR (600 MHz, DMSO-d₆-D₂O) (ppm 7.47 (d, J=7.1 Hz, 2H), 7.36-7.31 (m, 2H), 7.30-7.26 (m, 1H), 6.76 (s, 1H), 5.10 (s, 2H), 4.10 (s, 2H), 3.98 (dd, J=15.8, 13.8 Hz, 2H), 3.54 (tdd, J=10.6, 8.6, 5.5, 3.0 Hz, 1H), 3.25 (dd, J=16.1, 5.5

Hz, 1H), 2.88 (ddd, J=17.5, 5.2, 3.4 Hz, 1H), 2.80 (ddd, J=17.2, 11.5, 5.4 Hz, 1H), 2.69 (dd, J=16.0, 10.4 Hz, 1H), 2.45 (s, 3H), 2.35-2.31 (m, 1H), 2.29 (s, 3H), 1.80 (qd, J=12.0, 5.3 Hz, 1H); MS (ESI$^+$) m/z 515.0 [M+H]$^+$.

Example 188B: 5-(7-{[(3,5-dimethyl-1,2-oxazol-4-yl)methyl]amino}-1-fluoro-3-hydroxy-5,6,7,8-tetra-hydronaphthalen-2-yl)-1$\lambda^6$,2,5-thiadiazolidine-1,1,3-trione A flask containing a suspension of 5-[3-(benzyloxy)-7-{[(3,5-dimethyl-1,2-oxazol-4-yl)methyl]amino}-1-fluoro-5,6,7,8-tetrahydronaphthalen-2-yl]-1$\lambda^6$,2,5-thiadiazolidine-1,1,3-trione ammonium salt (0.079 g, 0.15 mmol) and 1,2,3,4,5-pentamethylbenzene (0.066 g, 0.44 mmol) in dichloromethane (1.5 mL) was cooled to −78° C. with stirring under an atmosphere of nitrogen. Next, trichloroborane (1.0 M in dichloromethane) (1.2 mL, 1.2 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 µm column, 10-100% gradient of methanol in water (buffered with 0.025 M aqueous ammonium bicarbonate, adjusted to pH 7 with dry ice)] to give the title compound (0.046 g, 0.11 mmol, 73% yield). $^1$H NMR (500 MHz, DMSO-d$_6$-D$_2$O) δ ppm 6.49 (s, 1H), 4.08 (s, 2H), 3.99 (dd, J=15.9, 13.8 Hz, 2H), 3.51 (ddt, J=14.3, 10.5, 4.4 Hz, 1H), 3.19 (dd, J=15.9, 5.5 Hz, 1H), 2.87-2.70 (m, 2H), 2.56 (dd, J=15.9, 10.3 Hz, 1H), 2.41 (s, 3H), 2.28 (br s, 1H), 2.27 (s, 3H), 1.72 (qd, J=11.8, 5.5 Hz, 1H); MS (ESI$^+$) m/z 424.8 [M+H]$^+$.

Example 189: 5-{2-[3-(2,2-dimethylcyclopropyl)propyl]-8-fluoro-6-hydroxy-1,2,3,4-tetrahydroisoquinolin-7-yl}-1$\lambda^6$,2,5-thiadiazolidine-1,1,3-trione (Compound 288)

Example 189A: tert-butyl 8-fluoro-6-hydroxy-7-(1,1,4-trioxo-1$\lambda^6$,2,5-thiadiazolidin-2-yl)-3,4-dihydroisoquinoline-2(1H)-carboxylate A suspension of the product of Example 44H (150 mg, 0.31 mmol, 1 equivalent), palladium on carbon (33 mg, 0.03 mmol, 10 mol %) and ammonium formate (58 mg, 0.92 mmol, 3.0 equivalents) in ethanol (1.5 mL, 0.2 M) was sealed in a 20 mL pressure-release scintillation vial outfitted with a septum-equipped screw cap. The sealed reaction vessel was placed in a heating block that had been preheated to 50° C. The reaction mixture was stirred for 1 hour at 50° C. The product mixture was cooled to 23° C. The cooled mixture was filtered through a plug of diatomaceous earth (1.0 cm×0.5 cm). The filter cake was rinsed with methanol (3×3.0 mL). The filtrates were combined, and the combined filtrates were concentrated. The residue obtained was used without further purification in the following step. MS (APCI$^+$) m/z 419 [M+NH$_4$]$^+$.

Example 189B: 5-(8-fluoro-6-hydroxy-1,2,3,4-tetrahydroisoquinolin-7-yl)-1$\lambda^6$,2,5-thiadiazolidine-1,1,3-trione Trifluoroacetate Trifluoroacetic acid (0.35 mL, 4.58 mmol, 15.0 equivalents) was added to a suspension of the product of Example 189A (nominally 0.31 mmol, 1 equivalent) in dichloromethane (1.5 mL, 0.2 M) at 23° C. The reaction mixture was stirred for 1 hour at 23° C. The product mixture was diluted with ether (5.0 mL) and acetonitrile (2.0 mL). The mixture was concentrated. The residue obtained was reconcentrated from 20% acetonitrile-ether (v/v, 5.0 mL). The residue of the title compound obtained was dried under vacuum for 18 hours at 23° C. (137 mg) and was used without further purification in the following step. 1H NMR (500 MHz, DMSO-d$_6$) δ ppm 9.26 (s, 2H), 6.59 (s, 1H), 4.15 (s, 2H), 4.09 (s, 2H), 3.33 (bs, 2H), 2.92 (t, J=6.21 Hz, 2H).

Example 189C: 5-{2-[3-(2,2-dimethylcyclopropyl)propyl]-8-fluoro-6-hydroxy-1,2,3,4-tetrahydroisoquinolin-7-yl}-1$\lambda^6$,2,5-thiadiazolidine-1,1,3-trione, Ammonia Salt Dess-Martin periodinane (331.0 mg, 0.78 mmol, 2.6 equivalents) was added to a solution of 3-(2,2-dimethylcyclopropyl)propanol (100.0 mg, 0.78 mmol, 2.6 equivalents) in dichloromethane (3.90 mL) at 23° C. The reaction mixture was stirred for 20 minutes at 23° C. The product mixture was then diluted with ether (10 mL). The diluted mixture was filtered through a diatomaceous earth plug (2.0 cm×1.0 cm). The filter cake was rinsed with ether (3×2 mL). The filtrates were combined, and the combined filtrates were concentrated to a viscous suspension (~1 mL). Pentane (5 mL) was added to the mixture. The resulting suspension was filtered through a diatomaceous earth plug (1.0 cm×0.5 cm). The filter cake was rinsed with pentane (3×1 mL). The filtrates were combined, and the combined filtrates were concentrated. The residue obtained, 3-(2,2-dimethylcyclopropyl)propanal, was added to a suspension of the product of Example 189B (nominally 0.31 mmol, 1 equivalent) and triethylamine (0.13 mL, 0.92 mmol, 3.0 equivalents) in acetonitrile (3.0 mL, 0.1 M) at 23° C. The reaction mixture was stirred for 2 minutes at 23° C. Sodium triacetoxyborohydride (78 mg, 0.37 mmol, 1.2 equivalents) was added in one portion at 23° C. The reaction mixture was stirred for 30 minutes at 23° C. The product mixture was diluted with water (0.5 mL). The diluted product mixture was concentrated to ~1 mL volume. The concentrated mixture was diluted with dimethyl sulfoxide (2 mL). The diluted mixture was purified by reversed-phase flash column chromatography (30 g RediSep Rf Gold® C18 column, elution with a gradient of 10-100% [v/v]methanol-0.025 M aqueous ammonium bicarbonate solution [acidified with solid carbon dioxide] over 10 column volumes, then isocratic elution with 100% methanol for 3 column volumes, flow rate=40 mL/minute) to furnish the title compound (98 mg, 0.24 mmol, 75% over three steps). $^1$H NMR (500 MHz, DMSO-d$_6$) δ ppm 9.69 (s, 1H), 9.63 (bs, 1H), 6.58 (s, 1H), 4.57-4.04 (m, 1H), 3.94 (s, 2H), 3.67 (bs, 1H), 3.23 (bs, 2H), 3.00 (bs, 2H), 1.80 (h, J=7.6 Hz, 1H), 1.40 (dq, J=14.4, 7.2 Hz, 1H), 1.29 (dq, J=14.6, 7.5 Hz, 1H), 1.04 (s, 3H), 1.03 (s, 3H), 0.52 (dtd, J=8.6, 7.2, 5.2 Hz, 1H), 0.39 (dd, J=8.5, 4.0 Hz, 1H), −0.05 (dd, J=5.3, 3.9 Hz, 1H); MS (APCI$^+$) m/z 412 [M+H]$^+$.

Example 190: 5-[(3S)-5-fluoro-7-hydroxy-3-methyl-1,2,3,4-tetrahydroisoquinolin-6-yl]-1$\lambda^6$,2,5-thiadiazolidine-1,1,3-trione (Compound 289)

Example 190A: tert-butyl {(2S)-1-[4-(benzyloxy)-6-bromo-2-fluoro-3-(2,2,2-trifluoroacetamido)phenyl]propan-2-yl}carbamate A solution of n-butyllithium in hexanes (2.44 M, 6.90 mL, 16.83 mmol, 2.2 equivalents) was added to a solution of diisopropylamine (2.62 mL, 18.36 mmol, 2.4 equivalents) in tetrahydrofuran (40 mL) at −76° C. (internal temperature). A slight exotherm was registered. The reaction mixture was stirred for 20 minutes until an internal temperature of −76° C. was reestablished. A solution of the product of Example 12C (3.00 g, 7.65 mmol, 1 equivalent) in tetrahydrofuran (15.0 mL) was added dropwise over 45 minutes such that the maximum internal temperature observed was <−72° C. (internal temperature). After completion of the addition the reaction mixture was stirred for 30 minutes at <−72° C. (internal temperature). A solution of (S)-tert-butyl 4-methyl-1,2,3-oxathiazolidine-3-carboxylate 2,2-dioxide (2.36 g, 9.95 mmol, 1.3 equivalents) in tetrahydrofuran (15.0 mL) was then added dropwise over 45 minutes such that the maximum internal temperature observed during the course of the addition was <−72° C. After completion of the addition the reaction mixture was stirred for 30 minutes at <−72° C. (internal temperature). Aqueous hydrogen chloride solution (1.0 M, 10.0 mL, 1.3 equivalents) was then added at −76° C. (internal temperature). The reaction vessel was immediately removed from its cooling bath and allowed to warm over 30 minutes to −23° C. Additional aqueous hydrogen chloride solution (1.0 M, 25.0 mL, 3.27 equivalents) was added at 23° C. The reaction mixture was stirred for 25 minutes at 23° C. The product mixture was then partitioned between ethyl acetate (200 mL) and water (20 mL). The aqueous layer was extracted with ethyl acetate (100 mL). The organic layers were combined, and the combined organic layers were washed sequentially with saturated aqueous ammonium bisulfate solution (50 mL) and saturated aqueous sodium chloride solution (20 mL). The washed organic layer was dried over sodium sulfate. The dried solution was filtered, and the filtrate was concentrated. The residue obtained was dissolved in 10% acetone-20% ethyl acetate-ether mixture (v/v/v, 30 mL). Diatomaceous earth (5 g) was added to the solution and the mixture was concentrated. The residue obtained was purified by flash column chromatography (40 g RediSep Rf Gold® silica column, elution with a gradient from 0-100% [v/v]ethyl acetate-heptanes). The fractions containing product were collected and the combined fractions were concentrated. The title compound thus obtained was used without further purification in the following step. MS (APCI$^+$) m/z 449 [M−C(O)OC(CH$_3$)$_3$+H]$^+$.

Example 190B: Methyl {[6-(benzyloxy)-4-bromo-3-{(2S)-2-[(tert-butoxycarbonyl)amino]propyl}-2-fluorophenyl](trifluoroacetyl)amino}acetate Methyl bromoacetate (0.78 mL, 8.42 mmol, 1.1 equivalents) was added to a suspension of the product of Example 190A (nominally 7.65 mmol, 1 equivalent), cesium carbonate (2.12 g, 15.30 mmol, 2.0 equivalents), and potassium iodide (1.27 g, 7.65 mmol, 1.0 equivalent) in acetone (40 mL, 0.2 M) at 23° C. The reaction mixture was stirred for 23 hours at 23° C. The reaction vessel was sealed with a reflux condenser and the sealed reaction vessel was placed in a heating block that had been preheated to 60° C. The reaction mixture was stirred for 3 hours at 60° C. The product mixture was then concentrated under a stream of nitrogen to a viscous suspension (~10 mL). The suspension was partitioned between ethyl acetate (75 mL) and saturated aqueous ammonium chloride solution (30 mL). The aqueous layer was extracted with ethyl acetate (25 mL). The organic layers were combined, and the combined organic layers were washed with saturated aqueous sodium chloride solution (20 mL). The washed organic layer was dried over sodium sulfate. The dried solution was filtered. Diatomaceous earth (~10 g) was added to the filtrate and the mixture was concentrated. The residue obtained was purified by flash column chromatography (80 g RediSep Rf Gold® silica column, elution with a gradient from 0-100% [v/v]ethyl acetate-heptanes) to furnish the title compound (2.68 g, 4.31 mmol, 56% yield). MS (APCI$^+$) m/z 621 [M+H]$^+$.

Example 190C: Methyl {[6-(benzyloxy)-3-{(2S)-2-[(tert-butoxycarbonyl)amino]propyl}-4-ethenyl-2-fluorophenyl](trifluoroacetyl)amino}acetate A suspension of cesium carbonate (2.12 g, 6.50 mmol, 2.0 equivalents), potassium vinyltrifluoroborate (871 mg, 6.50 mmol, 2.0 equivalents), bis(triphenylphosphine)palladium (II) dichloride (114 mg, 0.16 mmol, 5.0 mol %), and the product of Example 190B (nominally 2.02 g, 3.25 mmol, 1 equivalent) in 20% water-dioxane (v/v, 32.5 mL, 0.1 M) in a 100 mL round-bottom flask was outfitted with a reflux condenser and sealed with a rubber septum. The sealed reaction mixture was deoxygenated by iterative subjections to vacuum (~5 seconds) and subsequent backfilling with nitrogen (×2). The reaction vessel was placed in a heating block that had been preheated to 80° C. The reaction mixture was stirred for 1 hour at 80° C. The product mixture was then cooled to 23° C. The cooled product mixture was filtered through a plug of diatomaceous earth (3.0 cm×1.0 cm). The filter cake was washed with ethyl acetate (3×15 mL). The filtrates were combined, and the combined filtrates were concentrated. The residue obtained was partitioned between ethyl acetate (50 mL) and water (10 mL). The organic layer was washed with saturated aqueous sodium chloride solution (10 mL). The washed organic layer was dried over sodium sulfate. The dried solution was filtered. Diatomaceous earth (~5 g) was added to the solution and the mixture was concentrated. The residue obtained was purified by flash column chromatography (80 g RediSep Rf Gold® silica column, elution with a gradient from 0-100% [v/v] ethyl acetate-heptanes). The fractions containing the title compound were collected and concentrated. The title compound obtained (1.62 g, <88% yield) was used without further purification in the following step. MS (APCI$^+$) m/z 469 [M−C(O)OC(CH$_3$)$_3$+H]$^+$.

Example 190D: Methyl {[6-(benzyloxy)-3-{(2S)-2-[(tert-butoxycarbonyl)amino]propyl}-2-fluoro-4-formylphenyl](trifluoroacetyl)amino}acetate A solution of N-methylmorpholine N-oxide in water (50% w/v, 2.00 mL, 8.55 mmol, 3.0 equivalents) was added to a suspension of potassium osmate dihydrate (42 mg, 0.14 mmol, 4.0 mol %) and the product of Example 190C (nominally 1.62 g, 2.85 mmol, 1 equivalent) in 25% water-tetrahydrofuran mixture (v/v, 28 mL, 0.1 M) at 23° C. The reaction mixture was stirred for 18 hours at 23° C. Sodium metaperiodate (1.83 g, 8.55 mmol, 3.0 equivalents) was added in one portion at 23° C. The reaction mixture was stirred for 3 hours at 23° C. The product mixture was diluted sequentially with saturated aqueous sodium thiosulfate solution (15 mL), water (10 mL), and ethyl acetate (75 mL). The diluted mixture was stirred for 20 minutes at 23° C. The resulting biphasic mixture was then transferred to a separatory funnel and the layers that formed were separated. The aqueous layer was extracted with ethyl acetate (25 mL). The organic layers were combined, and the combined organic layers were washed with saturated aqueous sodium chloride solution (15 mL). The washed organic layer was dried over sodium sulfate. The dried solution was filtered. Diatomaceous earth (~10 g) was added to the filtrate and the mixture was concentrated. The residue obtained was purified by flash column chromatography (120 g RediSep Rf Gold® silica column, elution with a gradient from 0-100% [v/v]ethyl acetate-heptanes) to furnish the title compound (410 mg, 0.71 mmol, 25% yield). MS (APCI$^+$) m/z 471 [M-C(O)OC(CH$_3$)$_3$+H]$^+$.

Example 190E: tert-butyl (3S)-7-(benzyloxy)-5-fluoro-6-[(2-methoxy-2-oxoethyl) (trifluoroacetyl) amino]-3-methyl-3,4-dihydroisoquinoline-2(1H)-carboxylate Triethylsilane (0.38 mL, 2.36 mmol, 3.5 equivalents) and boron trifluoride diethyl etherate (0.26 mL, 2.02 mmol, 3.0 equivalents) were added dropwise in sequence to a solution of the product of Example 190D (385.0 mg, 0.68 mmol, 1 equivalent) in dichloromethane (7.0 mL) at a rate such that the internal temperature did not exceed −77° C. The reaction mixture was stirred for 1 hour at an internal temperature <−75° C. Additional triethylsilane (0.10 mL, 0.63 mmol, 0.92 equivalents) was added at rate such that the internal temperature did not exceed −75° C. The reaction mixture was stirred for 20 minutes at an internal temperature <−75° C. Additional boron trifluoride diethyl etherate (0.26 mL, 2.02 mmol, 0.75 equivalent) was added such that the internal temperature did not exceed −75° C. The reaction mixture was stirred for 20 minutes at an internal temperature <−75° C. Additional triethylsilane (0.10 mL, 0.63 mmol, 0.92 equivalents) and boron trifluoride diethyl etherate (0.26 mL, 2.02 mmol, 0.75 equivalent) were added sequentially such that the internal temperature did not exceed −75° C. The reaction mixture was stirred for 20 minutes at an internal temperature <−75° C. The product mixture was then diluted sequentially with saturated aqueous sodium bicarbonate solution (2 mL), water (1 mL), and ethyl acetate (25 mL) and the diluted mixture was allowed to warm over 16 hours to 23° C. The warmed mixture was partitioned between water (2 mL) and ethyl acetate (15 mL). The organic layer was washed with saturated aqueous sodium chloride solution (2 mL). The washed organic layer was dried over sodium sulfate. The dried solution was filtered, and the filtrate was concentrated. The residue obtained was dissolved in ~10% toluene-heptanes (v/v, 8 mL) and the solution was purified by flash column chromatography (40 g RediSep Rf Gold® silica column, elution with a gradient from 0-100% [v/v] ethyl acetate-heptanes) to furnish the title compound (307 mg, 0.543 mmol, 82% yield). MS (APCI$^+$) m/z 612 [M+CH$_3$N+H]$^+$.

190F: tert-butyl (3S)-7-(benzyloxy)-5-fluoro-6-[(2-methoxy-2-oxoethyl)amino]-3-methyl-3,4-dihydroisoquinoline-2(1H)-carboxylate A solution of sodium methoxide in methanol (0.5 M, 2.77 mL, 1.38 mmol, 2.5 equivalents) was added to a solution of the product of Example 190E (307 mg, 0.55 mmol, 1 equivalent) in anhydrous methanol (2.8 mL, 0.2 M) in a sealed reaction vial under nitrogen at 23° C. The reaction vessel was placed in a heating block that had been preheated to 50° C. The reaction mixture was stirred for 30 minutes at 50° C. The reaction mixture was cooled to 23° C. The cooled mixture was diluted with saturated aqueous ammonium chloride solution (3 mL). The diluted mixture was concentrated under a stream of nitrogen. The residue obtained was partitioned between ethyl acetate (25 mL) and water (5 mL). The aqueous layer was extracted with ethyl acetate (2×10 mL). The organic layers were combined, and the combined organic layers were washed sequentially with saturated aqueous sodium bicarbonate solution (10 mL) and saturated aqueous sodium chloride solution (5 mL). The washed organic layer was dried over sodium sulfate. The dried solution was filtered, and the filtrate was concentrated. The title compound obtained was used without further purification in the following step. MS (APCI$^+$) m/z 459 [M+H]$^+$.

Example 190G: tert-butyl (3S)-7-(benzyloxy)-5-fluoro-6-[(2-methoxy-2-oxoethyl) ({[(prop-2-en-1-yl)oxy]carbonyl}sulfamoyl)amino]-3-methyl-3,4-dihydroisoquinoline-2(1H)-carboxylate Allyl alcohol (0.04 mL, 0.61 mmol, 1.1 equivalents) was added to a solution of chlorosulfonyl isocyanate (0.05 mL, 0.61 mmol, 1.1 equivalents) in dichloromethane (2.8 mL) at 0° C. The reaction mixture was stirred for 30 minutes at 0° C. A solution of the product of Example 190F (nominally 0.55 mmol, 1 equivalent) and N,N-diisopropylethylamine (0.19 mL, 1.11 mmol, 2.0 equivalents) in dichloromethane (2.8 mL, 0.1 M overall) was added dropwise over 3 minutes at 0° C. The reaction mixture was stirred for 1 hour at 0° C. The product mixture was diluted with water (5 mL). The resulting biphasic mixture was stirred for 30 minutes. The mixture was then transferred to a separatory funnel and the layers that formed were separated. The aqueous layer was extracted with dichloromethane (2×10 mL). The organic layers were combined, and the combined organic layers were washed with saturated aqueous sodium chloride solution (5 mL). The washed organic layer was dried over sodium sulfate. The dried solution was filtered, and the filtrate was concentrated. The title compound obtained was used without further purification in the following step. MS (APCI$^+$) m/z 639 [M+NH$_4$]$^+$.

Example 190H: tert-butyl (3S)-7-(benzyloxy)-5-fluoro-3-methyl-6-(1,1,4-trioxo-1$\lambda^6$,2,5-thiadiazolidin-2-yl)-3,4-dihydroisoquinoline-2(1H)-carboxylate A solution of sodium methoxide in methanol (0.5 M, 3.32 mL, 1.66 mmol, 3.0 equivalents) was added to a suspension of the product of Example 190G (nominally 0.554 mmol, 1 equivalent) and tetrakis(triphenylphosphine)palladium(0) (32 mg, 0.03 mmol, 0.05 equivalents) in methanol (3.0 mL, 0.19 M) under nitrogen at 23° C. The reaction vessel was placed in a heating block that had been preheated to 60° C. The reaction mixture was stirred for 10 minutes at 60° C. The product mixture was then cooled to 23° C. The cooled mixture was diluted with saturated aqueous ammonium chloride solution (3.0 mL). The diluted mixture was partially concentrated. The residue obtained was suspended in dimethyl sulfoxide (10 mL) and water (3 mL). The diluted mixture was purified by reversed-phase flash column chromatography (100 g RediSep Rf Gold® C18 column, elution with a gradient of 10-100% [v/v]methanol-0.025 M aqueous ammonium bicarbonate solution [acidified with solid carbon dioxide] over 10 column volumes, then isocratic elution with 100% methanol for 3 column volumes, flow rate=80 mL/minute) to furnish the title compound (65 mg, 0.13 mmol, 23% over three steps). MS (APCI$^+$) m/z 523 [M+NH$_4$]$^+$.

Example 190I: tert-butyl (3S)-5-fluoro-7-hydroxy-3-methyl-6-(1,1,4-trioxo-1$\lambda^6$,2,5-thiadiazolidin-2-yl)-3,4-dihydroisoquinoline-2(1H)-carboxylate, Ammonia Salt A suspension of the product of Example 190H (65 mg, 0.13 mmol, 1 equivalent), palladium on carbon (14 mg, 0.01 mmol, 0.1 equivalent) and ammonium formate (20 mg, 0.32 mmol, 2.5 equivalents) in ethanol (1.3 mL, 0.1 M) was sealed in a 20 mL pressure-release scintillation vial outfitted with a septum-equipped screw cap. The sealed reaction vessel was placed in a heating block that had been preheated to 50° C. The reaction mixture was stirred for 30 minutes at 50° C. The product mixture was cooled to 23° C. The cooled mixture was filtered through a plug of diatomaceous earth (1.0 cm×0.5 cm). The filter cake was rinsed with methanol (3×1.0 mL). The filtrates were combined, and the combined filtrates were concentrated. The residue obtained was dissolved in 50% water-dimethyl sulfoxide (v/v, 6 mL). The solution was purified by reversed-phase flash column chromatography (30 g RediSep Rf Gold® C18 column, elution with a gradient of 5-100% [v/v] methanol-0.025 M aqueous ammonium bicarbonate solution [acidified with solid carbon dioxide] over 10 column volumes, then isocratic elution with 100% methanol for 3 column volumes, flow rate=35 mL/minute) to furnish the title compound (22.5 mg, 0.050 mmol, 41% yield). MS (APCI$^+$) m/z 433 [M+NH$_4$]$^+$.

Example 190J: 5-[(3S)-5-fluoro-7-hydroxy-3-methyl-1,2,3,4-tetrahydroisoquinolin-6-yl]-1λ$^6$,2,5-thiadiazolidine-1,1,3-trione, Hydrochloride Salt A solution of hydrogen chloride in dioxane (4.0 M, 0.14 mL, 0.56 mmol, 10.8 equivalents) was added to the product of Example 190J (22.5 mg, 0.05 mmol, 1 equivalent) at 23° C. The reaction mixture was stirred for 30 minutes at 23° C. The product mixture was concentrated under a stream of nitrogen to furnish the title compound (hydrochloride salt) with one equivalent of ammonium chloride as an excipient (16.9 mg, 0.046 mmol, 88% yield). $^1$H NMR (400 MHz, DMSO-d$_6$) 3 ppm 10.49 (bs, 1H), 9.78 (bs, 1H), 9.47 (bs, 1H), 7.27 (apparent triplet, 3×NH, 3H), 6.67 (s, 1H), 4.34 (s, 2H), 4.30-4.17 (m, 2H), 3.52-3.39 (m, 2H), 2.96 (dd, J=16.8, 4.6 Hz, 1H), 2.57 (dd, J=17.1, 10.8 Hz, 1H), 1.40 (d, J=6.4 Hz, 3H); MS (APCI$^+$) m/z 316 [M+H]$^+$.=

Example 191: 5-(7-{[2-(3,5-dimethyl-1,2-oxazol-4-yl)ethyl]amino}-1-fluoro-3-hydroxy-5,6,7,8-tetrahydronaphthalen-2-yl)-1λ$^6$,2,5-thiadiazolidine-1,1,3-trione (Compound 290)

Example 191A: 5-[3-(benzyloxy)-7-{[2-(3,5-dimethyl-1,2-oxazol-4-yl)ethyl]amino}-1-fluoro-5,6,7,8-tetrahydronaphthalen-2-yl]-1λ$^6$,2,5-thiadiazolidine-1,1,3-trione To a vial containing the product of Example 67F (0.080 g, 0.20 mmol) were added 1,2-dichloroethane (0.99 mL) and 2-(3,5-dimethylisoxazol-4-yl)ethan-1-amine (0.042 g, 0.30 mmol). The resulting mixture was stirred at ambient temperature. After 30 minutes, sodium triacetoxyhydroborate (0.105 g, 0.495 mmol) was added. Fourteen hours later, the reaction mixture was diluted with acetonitrile (3 mL), saturated aqueous ammonium chloride (3 mL), and water (3 mL). The resulting mixture was concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.077 g, 0.15 mmol, 74% yield). $^1$H NMR (500 MHz, DMSO-d$_6$) δ ppm 8.70 (br s, 2H), 7.49 (d, J=7.4 Hz, 2H), 7.34 (t, J=7.4 Hz, 2H), 7.31-7.25 (m, 1H), 6.75 (s, 1H), 5.11 (s, 2H), 3.97 (dd, J=17.4, 13.4 Hz, 2H), 3.51 (br s, 1H), 3.20-3.07 (m, 3H), 2.91-2.72 (m, 2H), 2.68 (dd, J=8.4, 6.9 Hz, 2H), 2.62 (dd, J=16.3, 9.6 Hz, 1H), 2.35 (s, 3H), 2.21 (s, 3H), 2.19 (br s, 1H), 1.74 (qd, J=11.4, 5.3 Hz, 1H); MS (ESI$^+$) m/z 529.0 [M+H]$^+$.

Example 191B: 5-(7-{[2-(3,5-dimethyl-1,2-oxazol-4-yl)ethyl]amino}-1-fluoro-3-hydroxy-5,6,7,8-tetrahydronaphthalen-2-yl)-1λ$^6$,2,5-thiadiazolidine-1,1,3-trione A flask containing a suspension of 5-[3-(benzyloxy)-7-{[2-(3,5-dimethyl-1,2-oxazol-4-yl)ethyl]amino}-1-fluoro-5,6,7,8-tetrahydronaphthalen-2-yl]-1λ$^6$,2,5-thiadiazolidine-1,1,3-trione (0.072 g, 0.14 mmol) and 1,2,3,4,5-pentamethylbenzene (0.060 g, 0.41 mmol) in dichloromethane (1.4 mL) was cooled to −78° C. with stirring under an atmosphere of nitrogen. Next, trichloroborane (1.0 M in dichloromethane) (1.1 mL, 1.1 mmol) was added. The resulting mixture was stirred at −78° C. for 10 minutes, and then the dry ice-acetone bath was replaced with an ice-water bath. After 60 minutes, the mixture was recooled to −78° C., diluted with dichloromethane (3 mL), and quenched via the successive addition of ethyl acetate (3 mL) and ethanol (3 mL). The mixture was then allowed to warm to ambient temperature and stirred for 15 minutes. The mixture was concentrated under reduced pressure and then co-evaporated with ethanol (2×5 mL). The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound (0.049 g, 0.11 mmol, 83% yield). $^1$H NMR (500 MHz, DMSO-d$_6$) δ ppm 9.29 (br s, 1H), 8.65 (br s, 2H), 6.48 (s, 1H), 3.95 (dd, J=15.9, 13.4 Hz, 2H), 3.53-3.44 (m, 1H), 3.15-3.07 (m, 3H), 2.82 (dt, J=17.3, 4.8 Hz, 1H), 2.74 (td, J=11.7, 11.2, 4.9 Hz, 1H), 2.67 (dd, J=9.6, 6.6 Hz, 2H), 2.56 (dd, J=16.1, 9.8 Hz, 1H), 2.35 (s, 3H), 2.21 (s, 3H), 2.19-2.15 (m, 1H), 1.78-1.65 (m, 1H); MS (ESI$^+$) m/z 439.1 [M+H]$^+$.

Example 192: 5-[(2R)-4-fluoro-6-hydroxy-2-{[(3-methylbutyl)amino]methyl}-2,3-dihydro-1H-inden-5-yl]-1λ$^6$,2,5-thiadiazolidine-1,1,3-trione (Compound 291)

The product of Example 169 was separated by preparative chiral SFC. Preparative SFC was performed on a Waters SFC80Q system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% trifluoroacetic acid:triethylamine) at a flow rate of 70 g/minute. The column was at ambient temperature and the back pressure regulator was set to maintain 120 bar. The sample was dissolved in methanol: dichloromethane 1:4 at concentration of 4 mg/mL. The sample was loaded into the modifier stream in 2 mL injections. The mobile phase was held isocratically at 40% cosolvent:CO$_2$. The instrument was fitted with a CHIRAL-PAK® IC column with dimensions 30 mm i.d.×250 mm length with 5 μm particles. The earlier eluting enantiomer peak gave the title compound (14 mg, 0.036 mmol, 38.4% yield). $^1$H NMR (600 MHz, DMSO-d$_6$) δ ppm 6.57 (s, 1H), 3.92 (s, 2H), 3.02-2.92 (m, 4H), 2.89-2.84 (m, 2H), 2.76-

2.79 (m, 1H), 2.68-2.61 (m, 2H), 1.62 (hept, J=6.7 Hz, 1H), 1.49-1.43 (m, 2H), 0.89 (d, J=6.7 Hz, 6H); MS (APCI$^+$) m/z 386 [M+H]$^+$.

Example 193: 5-[(2S)-4-fluoro-6-hydroxy-2-{[(3-methylbutyl)amino]methyl}-2,3-dihydro-1H-inden-5-yl]-1$\lambda^6$,2,5-thiadiazolidine-1,1,3-trione (Compound 292)

The product of Example 169 was separated by preparative chiral SFC. Preparative SFC was performed on a Waters SFC80Q system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% trifluoroacetic acid:triethylamine) at a flow rate of 70 g/minute. The column was at ambient temperature and the back pressure regulator was set to maintain 120 bar. The sample was dissolved in methanol:dichloromethane 1:4 at concentration of 4 mg/mL. The sample was loaded into the modifier stream in 2 mL injections. The mobile phase was held isocratically at 40% cosolvent:CO$_2$. The instrument was fitted with a CHIRAL-PAK® IC column with dimensions 30 mm i.d.×250 mm length with 5 μm particles. The later eluting enantiomer peak gave the title compound (9.5 mg, 0.025 mmol, 26% yield). $^1$H NMR (600 MHz, DMSO-d$_6$) δ ppm 6.58 (s, 1H), 3.93 (s, 2H), 3.04-2.96 (m, 4H), 2.93-2.87 (m, 2H), 2.78-2.70 (m, 1H), 2.68-2.62 (m, 2H), 1.62 (hept, J=6.6 Hz, 1H), 1.51-1.44 (m, 2H), 0.89 (d, J=6.6 Hz, 6H); MS (APCI$^+$) m/z 386 [M+H]$^+$.

Example 194: 5-[8-fluoro-6-hydroxy-2-(4-methoxybutyl)-1,2,3,4-tetrahydroisoquinolin-7-yl]-1$\lambda^6$,2,5-thiadiazolidine-1,1,3-trione (Compound 293)

Example 194A: 5-(8-fluoro-6-hydroxy-1,2,3,4-tetrahydroisoquinolin-7-yl)-1$\lambda^6$,2,5-thiadiazolidine-1,1,3-trione hydrochloride (Alternative Preparation of Example 441)

A solution of hydrogen chloride in dioxane (4.0 M, 1.25 mL, 4.98 mmol, 4.8 equivalents) was added to a suspension of the product of Example 189A (nominally 1.04 mmol, 1 equivalent) in dioxane (4.15 mL, 0.25 M) at 23° C. The reaction mixture was stirred for 2 hours at 23° C. The mixture was diluted with ether (3.0 mL) and the diluted mixture was concentrated. The residue obtained was dried for 18 hours in a vacuum oven at 50° C. Additional hydrogen chloride solution in dioxane (4.0 M, 3.0 mL, 12.00 mmol, 11.5 equivalents) was added to the residue obtained at 23° C. The reaction mixture was stirred for 18 hours at 23° C. The reaction mixture was diluted with ether (3.0 mL) and the diluted mixture was concentrated. The residue obtained was dried for 6 hours in a vacuum oven at 50° C. to furnish the title compound. $^1$H NMR (500 MHz, DMSO-d$_6$) δ ppm 10.28 (bs, 1H), 9.40 (bs, 1H), 6.62 (s, 1H), 4.22 (s, 2H), 4.13 (s, 2H), 3.34-3.28 (m, 2), 2.93 (t, J=6.2 Hz, 2H); MS (APCI$^+$) m/z 316 [M+H]$^+$.

Example 194B: 5-[8-fluoro-6-hydroxy-2-(4-methoxybutyl)-1,2,3,4-tetrahydroisoquinolin-7-yl]-1$\lambda^6$,2,5-thiadiazolidine-1,1,3-trione The product of Example 194A (20 mg, 0.056 mmol, 1.0 equivalent) was dissolved in sodium acetate/acetic acid buffer (pH 4-5, 1.0 mL). 4-methoxybutanal (0.6 M in methanol, 246 μL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was concentrated, and the residue was purified by reversed-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (6.8 mg, 0.018 mmol, 30% yield). $^1$H NMR (400 MHz, DMSO-d$_6$) δ ppm 6.44 (s, 1H), 3.93 (s, 2H), 3.41 (s, 2H), 3.25-3.19 (m, 5H), 2.71 (t, J===5.7 Hz, 2H), 2.60 (t, J=58 Hz, 2H), 2.50-2.45 (m, 2H), 1.57-1.47 (m, 4H); MS (APCI$^+$) m/z 388 [M+H]$^+$.

Example 195: 5-(8-fluoro-6-hydroxy-2-{3-[3-(trifluoromethyl)phenyl]propyl}-1,2,3,4-tetrahydroisoquinolin-7-yl)-1$\lambda^6$,2,5-thiadiazolidine-1,1,3-trione (Compound 294)

The product of Example 194A (20 mg, 0.056 mmol, 1.0 equivalents) was dissolved in sodium acetate/acetic acid buffer (pH 4-5, 1.0 mL). 3-(3-(Trifluoromethyl)phenyl)propanal (0.6 M in methanol, 246 μL, 0.15 mmol, 2.5 equivalents) was added to at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was concentrated, and the residue was purified by reversed-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (9.3 mg, 0.019 mmol, 32% yield). $^1$H NMR (400 MHz, DMSO-d$_6$) δ ppm 7.61-7.47 (m, 3H), 6.45 (s, 1H), 3.93 (s, 21H), 3.41 (s, 31H), 2.77-2.68 (m, 4-1), 2.59 (t, J=5.8 Hz, 2H), 2.47 (t, J=7.0 Hz, 2H), 1.84 (p, J=7.2 Hz, 2H); MS (APCI$^+$) m/z 488 [M+H]$^+$.

Example 196: 5-(8-fluoro-6-hydroxy-2-{2-methyl-3-[4-(propan-2-yl)phenyl]propyl}-1,2,3,4-tetrahydroisoquinolin-7-yl)-1$\lambda^6$,2,5-thiadiazolidine-1,1,3-trione (Compound 295)

The product of Example 194A (20 mg, 0.056 mmol, 1.0 equivalent) was dissolved in sodium acetate/acetic acid buffer (pH 4-5, 1.0 mL). 3-(4-Isopropylphenyl)-2-methylpropanal (0.6 M in methanol, 246 μL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 μm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15%

A) to afford the title compound (2 mg, 0.0042 mmol, 7% yield). $^1$H NMR (400 MHz, DMSO-d$_6$) δ ppm 7.14 (d, J=: 8.0 Hz, 2H), 7.08 (d, J=7.9 Hz, 2H), 6.44 (s, 1H), 3.93 (s, 2H), 3.40 (s, 3H), 2.84 (p, J=6.9 Hz, 1H), 2.74-2.68 (m, 2H), 2.62-2.57 (m, 2H), 2.39-2.22 (m, 3H), 2.10-1.94 (m, 1H), 1.18 (d, J=6.9 Hz, 6H), 0.80 (d, J=6.5 Hz, 3H); MS (APCI$^+$) m/z 476 [M+H]$^+$.

Example 197: 5-{2-[4-(5,5-dimethyl-1,3-dioxan-2-yl)butyl]-8-fluoro-6-hydroxy-1,2,3,4-tetrahydroisoquinolin-7-yl}-1λ$^6$,2,5-thiadiazolidine-1,1,3-trione (Compound 296)

The product of Example 194A (20 mg, 0.056 mmol, 1.0 equivalent) was dissolved in sodium acetate/acetic acid buffer (pH 4-5, 1.0 mL). 4-(5,5-Dimethyl-1,3-dioxan-2-yl) butanal (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (9.4 mg, 0.020 mmol, 34% yield). $^1$H NMR (400 MHz, DMSO-d$_6$) δ ppm 9.24 (s, 1H), 7.13 (s, 1H), 6.49 (s, 1H), 4.42 (t, J=4.9 Hz, 1H), 3.93 (s, 2H), 3.54-3.47 (m, 4H), 3.41-3.34 (m, 4H), 2.94-2.63 (m, 4H), 1.66-1.51 (m, 4H), 1.44-1.32 (m, 2H), 1.07 (s, 3H), 0.67 (s, 31H); MS (APCI$^+$) m/z 472 [M+H]$^+$.

Example 198: 5-{8-fluoro-6-hydroxy-2-[2-(2,6,6-trimethylcyclohex-1-en-1-yl)ethyl]-1,2,3,4-tetrahydroisoquinolin-7-yl}-1λ$^6$,2,5-thiadiazolidine-1,1,3-trione (Compound 297)

The product of Example 194A (20 mg, 0.056 mmol, 1.0 equivalent) was dissolved in sodium acetate/acetic acid buffer (pH 4-5, 1.0 mL). 2-(2,6,6-Trimethylcyclohex-1-en-1-yl)acetaldehyde (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (8.2 mg, 0.018 mmol, 31% yield). $^1$H NMR (400 MHz, DMSO-d$_6$) δ ppm 6.45 (s, 1H), 3.93 (s, 2H), 3.52-3.48 (m, 2H), 3.32-3.28 (m, 2H), 2.84-2.61 (m, 4-1), 2.29-2.20 (m, 2H), 1.96-1.85 (m, 2H), 1.61 (s, 3H), 1.57-1.48 (nm, 2H), 1.43-1.35 (m, 2H), 0.99 (s, 6H); MS (APCI$^+$) m/z 452 [M+H]$^+$.

Example 199: 5-(8-fluoro-6-hydroxy-2-pentyl-1,2,3,4-tetrahydroisoquinolin-7-yl)-1λ$^6$,2,5-thiadiazolidine-1,1,3-trione (Compound 298)

The product of Example 194A (20 mg, 0.056 mmol, 1.0 equivalent) was dissolved in sodium acetate/acetic acid buffer (pH 4-5, 1.0 mL). Pentanal (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 5% A, 0.5-8.0 minutes linear gradient 5-100% A, 8.0-9.0 minutes 100% A, 9.0-9.1 minutes linear gradient 100-5% A, 9.1-10.0 minutes 5% A) to afford the title compound (6 mg, 0.016 mmol, 27% yield). $^1$H NMR (400 MHz, DMSO-d$_6$) δ ppm 9.36 (s, 1H), 7.10 (s, 1H), 6.51 (s, 1H), 3.96-3.54 (m, 4H), 3.17-2.62 (m, 6H), 1.71-1.53 (nm, 21), 1.38-1.23 (m, 4H), 0.89 (t, J=6.9 Hz, 3H); MS (APCI$^+$) m/z 372 [M+H]$^+$.

Example 200: 5-{8-fluoro-2-[3-(4-fluorophenyl) propyl]-6-hydroxy-1,2,3,4-tetrahydroisoquinolin-7-yl}-1λ$^6$,2,5-thiadiazolidine-1,1,3-trione (Compound 299)

The product of Example 194A (20 mg, 0.056 mmol, 1.0 equivalent) was dissolved in sodium acetate/acetic acid buffer (pH 4-5, 1.0 mL). 3-(4-Fluorophenyl)propanal (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (8.9 mg, 0.020 mmol, 34% yield). 1H NMR (400 MHz, DMSO-d$_6$) δ ppm 7.29-7.21 (m, 2H), 7.14-7.03 (m, 2H), 6.44 (s, 1H), 3.93 (s, 2H), 3.41 (s, 2H), 2.71 (t, J=5.8 Hz, 2H), 2.65-2.56 (m, 4H), 2.46 (t, J=7.1 Hz, 2H), 1.79 (p, J=7.4 Hz, 2H); MS (APCI$^+$) m/z 438 [M+H]$^+$.

Example 201: tert-butyl [(1r,4r)-4-{2-[8-fluoro-6-hydroxy-7-(1,1,4-trioxo-1λ$^6$,2,5-thiadiazolidin-2-yl)-3,4-dihydroisoquinolin-2(1H)-yl]ethyl}cyclohexyl] carbamate (Compound 300)

The product of Example 194A (20 mg, 0.056 mmol, 1.0 equivalent) was dissolved in sodium acetate/acetic acid buffer (pH 4-5, 1.0 mL). tert-Butyl [(1r,4r)-4-(2-oxoethyl) cyclohexyl]carbamate (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-

10.0 minutes 15% A) to afford the title compound (12.5 mg, 0.024 mmol, 40% yield). $^1$H NR (400 MHz, DMSO-d$_6$) δ ppm 9.23 (s, 1H), 7.12 (s, 1H), 6.65 (d, =8.1 Hz, 1-H), 6.48 (s, 1-H), 3.93 (s, 2-), 3.83-3.47 (m, 2H), 3.22-3.05 (m, 2H), 2.79 (s, 4H), 1.80-1.66 (m, 5H), 1.46 (s, 2H), 1.39-1.34 (m, 10H), 1.18-1.05 (m, 2H), 0.95 (td, J=14.1, 13.4, 7.3 Hz, 2H); MS (APCI$^+$) min 527 [M+H]$^+$.

Example 202: 5-{2-[3-(4-tert-butylphenyl)propyl]-8-fluoro-6-hydroxy-1,2,3,4-tetrahydroisoquinolin-7-yl}-1λ$^6$,2,5-thiadiazolidine-1,1,3-trione (Compound 301)

The product of Example 194A (20 mg, 0.056 mmol, 1.0 equivalent) was dissolved in sodium acetate/acetic acid buffer (pH 4-5, 1.0 mL). 3-(4-(tert-Butyl)phenyl)propanal (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (8 mg, 0.017 mmol, 28% yield). $^1$H NMR (400 MHz, DMSO-d$_6$) δ ppm 7.32-7.25 (m, 2H), 7.17-7.10 (m, 2H), 6.44 (s, 1H), 3.93 (s, 2H), 3.41 (s, 2H), 2.71 (t, J=5.7 Hz, 2H), 2.63-2.52 (m, 4H), 2.47 (d, J=7.2 Hz, 2H), 1.85-1.73 (m, 2H), 1.26 (s, 9H); MS (APCI$^+$) m=476 [M+H]$^+$.

Example 203: 5-[8-fluoro-6-hydroxy-2-(3,5,5-trimethylhexyl)-1,2,3,4-tetrahydroisoquinolin-7-yl]-1λ$^6$,2,5-thiadiazolidine-1,1,3-trione (Compound 302)

The product of Example 194A (20 mg, 0.056 mmol, 1.0 equivalent) was dissolved in sodium acetate/acetic acid buffer (pH 4-5, 1.0 mL). 3,5,5-Trimethylhexanal (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (7.8 mg, 0.018 mmol, 31% yield). $^1$H NMR (400 MHz, DMSO-d$_6$) δ ppm 9.21 (s, 1H), 7.10 (s, 1H), 6.48 (s, 1H), 3.93 (s, 2H), 3.85-3.42 (m, 2H), 3.05-2.54 (m, 6H), 1.59-1.49 (m, 2H), 1.49-1.34 (m, 1H), 1.25 (dd, J=13.9, 3.1 Hz, 111H), 1.05 (dd, J=14.0, 5.6 Hz, 11-), 0.93 (d, J=6.3 Hz, 3H), 0.89 (s, 9H); MS (APCI$^+$) m/z 428 [M+H]$^+$.

Example 204: 5-{8-fluoro-2-[3-(2-fluorophenyl)propyl]-6-hydroxy-1,2,3,4-tetrahydroisoquinolin-7-yl}-1λ$^6$,2,5-thiadiazolidine-1,1,3-trione (Compound 303)

The product of Example 194A (20 mg, 0.056 mmol, 1.0 equivalent) was dissolved in sodium acetate/acetic acid buffer (pH 4-5, 1.0 mL). 3-(2-Fluorophenyl)propanal (0.6 M in methanol, 246 µL, 0.15 mmol, 2.5 equivalents) was added at room temperature. Sodium cyanoborohydride resin (Biotage® MP-Cyanoborohydride, 2.28 mmol/g, 63 mg, 0.14 mmol, 2.5 equivalents) was added and the reaction was stirred overnight at room temperature. The reaction mixture was filtered and concentrated, and the residue was purified by reversed-phase preparative HPLC on a Waters XBridge™ C8 5 µm column (75 mm×30 mm). A gradient of methanol (A) and 25 mM ammonium bicarbonate buffer (pH 10) in water (B) was used, at a flow rate of 40 mL/minute (0-0.5 minutes 15% A, 0.5-8.0 minutes linear gradient 15-100% A, 8.0-9.0 minutes 100% A, 9.0-9.1 minutes linear gradient 100-15% A, 9.1-10.0 minutes 15% A) to afford the title compound (0.1 mg, 0.0002 mmol, 1% yield). $^1$H NMR (400 MHz, DMSO-d$_6$) δ ppm 7.36-7.28 (m, 1H), 7.28-7.18 (m, 1H), 7.17-7.08 (m, 2H), 6.44 (s, 1H), 3.93 (s, 2H), 3.41 (s, 3H), 2.75-2.62 (m, 4H), 2.59 (t, J=5.8 Hz, 2H), 2.55-2.51 (m, 1H), 1.79 (p, J=7.3 Hz, 2H); MS (APCI$^+$) m/z 438 [M+H]$^+$.

Example 205: 3-hydroxybutyl 4,4,8-trifluoro-6-hydroxy-7-(1,1,4-trioxo-1λ$^6$,2,5-thiadiazolidin-2-yl)-3,4-dihydroisoquinoline-2(1H)-carboxylate (Compound 304)

Example 205A: 4-nitrophenyl 6-(benzyloxy)-4,4,8-trifluoro-7-(1,1,4-trioxo-1λ$^6$,2,5-thiadiazolidin-2-yl)-3,4-dihydroisoquinoline-2(1H)-carboxylate To a solution of the product of Example 127P (100 mg, 0.211 mmol) in tetrahydrofuran (1 mL) was added triethylamine (0.035 mL, 0.253 mmol) followed by 4-nitrophenyl carbonochloridate (63.7 mg, 0.316 mmol) at 0° C. The mixture was stirred for 2 hours at 20° C. The mixture was then diluted with water (10 mL) and extracted with ethyl acetate (3×10 mL). The combined organic layers were washed with brine (10 mL), dried over Na$_2$SO$_4$, filtered and concentrated under reduced pressure. The residue was purified by preparative thin-layer chromatography (ethyl acetate:methanol=5:1) to give the title compound (80 mg, 0.135 mmol, 57.7% yield). $^1$H NMR (400 MHz, DMSO-d$_6$) δ ppm 3.90-4.08 (m, 2H), 4.09-4.28 (m, 1H), 4.30-4.51 (m, 1H), 4.70 (br s, 1H), 4.89 (br s, 1H), 5.26 (s, 2H), 7.25 (s, 1H), 7.27-7.40 (m, 3H), 7.43-7.61 (m, 4H), 8.29 (d, J=9.01 Hz, 2H).

Example 205B: 3-hydroxybutyl 6-(benzyloxy)-4,4,8-trifluoro-7-(1,1,4-trioxo-1λ$^6$,2,5-thiadiazolidin-2-yl)-3,4-dihydroisoquinoline-2(1H)-carboxylate To a solution of the product of Example 205A (80 mg, 0.122 mmol) in tetrahydrofuran (1 mL) was added butane-1,3-diol (32.9 mg, 0.365 mmol) followed by potassium tert-butoxide (40.9 mg, 0.365 mmol) at 0° C. The mixture was stirred for 1 hour at 20° C. The mixture was diluted with water (10 mL), extracted with ethyl acetate (3×10 mL). The combined organic layers were washed with brine (10 mL), dried over Na$_2$SO$_4$, filtered and concentrated under reduced pressure to give the title compound (40 mg, 0.074 mmol, 54.5% yield) which was used for next step without further purification. MS (ESI$^-$) m/z 542 [M–H]$^-$.

Example 205C: 3-hydroxybutyl 4,4,8-trifluoro-6-hydroxy-7-(1,1,4-trioxo-1λ$^6$,2,5-thiadiazolidin-2-yl)-3,4-dihydroisoquinoline-2(1H)-carboxylate A mixture of wet Pd(OH)$_2$/C (9.30 mg, 50%) and the product of Example 205B (40 mg, 0.066 mmol) in tetrahydrofuran (2 mL) was stirred under H2 (15 psi) at 20° C. for 12 hours. The mixture was filtered, and the filtrate was concentrated under reduced pressure. The residue was purified by preparative HPLC on a Phenomenex® C18 Gemini-NX 3 μm 150×30 mm column eluted with a gradient of acetonitrile (A) and 10 mM $NH_4HCO_3$ in water (B) at a flow rate of 60 mL/minute (0-8 minutes linear gradient 1-25% A, 8-10 minutes 100% A) to give the title compound (12 mg, 0.026 mmol, 38.3% yield) after lyophilization. $^1$H NMR (400 MHz, DMSO-$d_6$) δ ppm 1.06 (d, J=6.11 Hz, 3H), 1.48-1.77 (m, 2H), 3.64-3.79 (m, 1H), 4.01 (s, 2H), 4.03-4.10 (m, 2H), 4.10-4.19 (m, 2H), 4.55 (br s, 2H), 6.96 (s, 1H); MS (ESI$^-$) m/z 452 [M−H]$^-$.

Example 206: 5-(2-{[(2-cyclobutylethyl)amino]methyl}-4-fluoro-6-hydroxy-2,3-dihydro-1H-inden-5-yl)-1λ$^6$,2,5-thiadiazolidine-1,1,3-trione (Compound 305)

To a suspension of the product of Example 168L (150 mg, 0.349 mmol) in dichloromethane (1.75 mL) and ethanol (1.5 mL). was added triethylamine (0.068 mL, 0.489 mmol). The reaction mixture was stirred at ambient temperature for 5 minutes. Then 2-cyclobutylacetaldehyde (44.6 mg, 0.454 mmol) in dichloromethane (0.5 mL) was added and the reaction mixture was stirred further for 18 hours at ambient temperature. Thereafter, sodium tetrahydroborate (33.0 mg, 0.873 mmol) was then added and the resultant mixture was stirred further for 4 hours. The reaction mixture was diluted with methanol and concentrated with diatomaceous earth for dry loading. The product was purified by reversed-phase column chromatography (120 g Agela Technologies Claricep™ Flash C18 100 Å 40-60 μm column, flow rate 50 mL/minute, 10 to 100% $CH_3OH$ in water [buffered with 0.025 M aqueous ammonium bicarbonate, adjusted to pH 7 with $CO_2$ (s)]) to give the title compound (12.2 mg, 0.031 mmol, 8.79% yield). $^1$H NMR (600 MHz, DMSO-$d_6$) δ ppm 7.26 (s, 1H), 6.66 (s, 1H), 6.48 (m, 1H), 3.95-3.92 (m, 2H), 3.16-3.11 (m, 1H), 3.06-2.98 (m, 1H), 2.92-2.80 (m, 1H), 2.80-2.74 (m, 1H), 2.71-2.63 (m, 1H), 2.59-2.52 (m, 1H), 2.44-2.38 (m, 2H), 2.66-2.34 (m, 1H), 2.21-2.13 (m, 1H), 2.09-2.08 (m, 1H), 2.03-1.96 (m, 2H), 1.86-1.76 (m, 1H), 1.62-1.55 (m, 2H), 1.55-1.47 (m, 2H); MS (APCI$^+$) m/z 398 [M+H]$^+$.

Example 207: 5-{2-[2-(3,5-dimethyl-1,2-oxazol-4-yl)ethyl]-4,4,8-trifluoro-6-hydroxy-1,2,3,4-tetrahydroisoquinolin-7-yl}-1λ$^6$,2,5-thiadiazolidine-1,1,3-trione (Compound 306)

Example 207A: ethyl 2-(3,5-dimethylisoxazol-4-yl)acetate

To a solution of the product of Example 127A (6 g, 32.2 mmol) in ethanol (60 mL) was added $K_2CO_3$ (8.91 g, 64.4 mmol) followed by hydroxylamine hydrochloride (3.36 g, 48.3 mmol) at 20° C. The mixture was heated at 80° C. for 3 hours. The mixture was diluted with water (150 mL) and extracted with ethyl acetate (3×80 mL). The combined organic layers were washed with brine (200 mL), dried over $Na_2SO_4$, filtered and concentrated under reduced pressure to give the title compound (4.4 g, 24.0 mmol, 74.5% yield) which was used for the next step without purification. MS (ESI$^+$) m/z 184 [M+H]$^+$.

Example 207B: 2-(3,5-dimethylisoxazol-4-yl)ethanol

To a solution of the product of Example 207A (4.5 g, 24.56 mmol) in tetrahydrofuran (2 mL) was added $LiAlH_4$ (1.865 g, 49.1 mmol) in portions at 0° C. The mixture was stirred at 20° C. for 2 hours before it was quenched at 20° C. by adding water (0.1 mL), an aqueous solution of NaOH (0.1 mL, 15% in water) and water (0.3 mL) successively. The mixture was then filtered, and the filtrate was concentrated under reduced pressure to give the title compound (2 g, 14.2 mmol, 51.9% yield) which was used for the next step without further purification. MS (ESI$^+$) m/z 142 [M+H]$^+$.

Example 207C: 2-(3,5-dimethylisoxazol-4-yl)acetaldehyde

To a solution of the product of Example 207B (700 mg, 4.46 mmol) in dichloromethane (2 mL) was added Dess-Martin periodinane (1,1,1-tris(acetyloxy)-1,1-dihydro-1,2-benzodioxol-3-(1H)-one) (2839 mg, 6.69 mmol) at 20° C. The mixture was stirred at 20° C. for 2 hours. The mixture was concentrated under reduced pressure. The residue was purified by flash column chromatography (petroleum ether:ethyl acetate=10:1) to give the title compound (460 mg, 3.30 mmol, 66.7% yield). $^1$H NMR (400 MHz, CDCl$_3$) δ ppm 2.11-2.24 (m, 3H), 2.30-2.43 (m, 3H), 3.43 (d, J=1.47 Hz, 2H), 9.67 (t, J=1.71 Hz, 1H).

Example 207D: 5-{6-(benzyloxy)-2-[2-(3,5-dimethyl-1,2-oxazol-4-yl)ethyl]-4,4,8-trifluoro-1,2,3,4-tetrahydroisoquinolin-7-yl}-1λ$^6$,2,5-thiadiazolidine-1,1,3-trione The title compound was prepared using the procedures described for Example 127Q from 207C in 43.1% yield. MS (ESI$^-$) m/z 549 [M−H]$^-$.

Example 207E: 5-{2-[2-(3,5-dimethyl-1, 2-oxazol-4-yl)ethyl]-4,4,8-trifluoro-6-hydroxy-1,2,3,4-tetrahydroisoquinolin-7-yl}-1λ$^6$,2,5-thiadiazolidine-1,1,3-trione The title compound was prepared using the procedures described for Example 127R from 207D in 48.3% yield. $^1$H NMR (400 MHz, DMSO-$d_6$) δ ppm 2.17 (s, 3H), 2.30 (s, 3H), 2.56 (br d, J=7.50 Hz, 3H), 2.67 (br s, 2H), 3.17 (br t, J=11.44 Hz, 2H), 3.65 (br s, 2H), 4.03 (s, 2H), 6.91 (s, 1H), 6.95 (s, 1H), 6.95 (s, 1H), 7.08 (s, 1H), 7.20 (s, 1H), 10.07 (br s, 1H); MS (ESI$^-$) m/z 459 [M−H]$^-$.

Example 208: 5-[(7R)-1-fluoro-3-hydroxy-7-{[(3R)-3-hydroxybutyl]amino}-5,6,7,8-tetrahydronaphthalen-2-yl]-1λ$^6$,2,5-thiadiazolidine-1,1,3-trione (Compound 307)

Example 208A: 5-[3-(benzyloxy)-1-fluoro-7-{[(3R)-3-hydroxybutyl]amino}-5,6,7,8-tetrahydronaphthalen-2-yl]-1λ$^6$,2,5-thiadiazolidine-1,1,3-trione To a solution of the product of Example 67F (0.537 g, 1.327 mmol) in ethanol (11 mL) was added (2R)-4-aminobutan-2-ol hydrochloride (0.250 g, 1.99 mmol) and triethylamine (0.555 mL, 3.98 mmol). After 30 minutes sodium cyanoborohydride (0.100 g, 1.592 mmol) was added as a solid. After 16 hours, the reaction mixture was quenched with ammonium hydroxide (0.151 mL, 7.96 mmol), then diluted with acetonitrile (10 mL) and water (2 mL). Celite® (5 g) was added and the mixture was concentrated in vacuo. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give the title compound (0.4591 g, 0.961 mmol, 72.4% yield). MS (APCI$^+$) m/z 478 [M+H]$^+$.

Example 208B: 5-(1-fluoro-3-hydroxy-7-{[(3R)-3-hydroxybutyl]amino}-5,6,7,8-tetrahydronaphthalen-2-yl)-1λ$^6$,2,5-thiadiazolidine-1,1,3-trione To a suspension of the product of Example 208A (0.4591 g, 0.961 mmol) and pentamethylbenzene (0.275 g, 1.857 mmol) in dichloromethane (9 mL) at −78° C. was added a solution of boron trichloride (13.9 mL, 1 M in dichloromethane, 13.9 mmol) slowly along the side of the flask. The resulting mixture was stirred for 5 minutes, then warmed to an internal temperature of 0° C., then cooled to −78° C. and quenched with ethyl acetate (4.6 mL), followed by ethanol (4.6 mL). The reaction mixture was warmed to ambient temperature and concentrated in vacuo. The crude solid was triturated with heptanes (3×9 mL), 1:1 ethyl acetate/heptanes (2×5 mL), dichloromethane (2×5 mL) and acetonitrile (2×4.6 mL) to give a gummy solid. The crude product was dissolved in methanol (15 mL) and Celite® (5 g) was added and the resulting mixture concentrated under reduced pressure to give a powder, which was dry loaded onto a Teledyne ISCO 100 g reversed-phase C18 column and purified by a gradient of 10-100% methanol in buffer (0.025 M ammonium carbonate in water, modified to pH 7 with dry ice), monitoring at 206 nm to give the title compound (0.2464 g, 0.636 mmol, 66.2% yield). $^1$H NMR (400 MHz, DMSO-d$_6$) δ ppm 9.23 (s, 1H), 8.44 (s, 2H), 6.47 (d, J=1.4 Hz, 1H), 4.83 (s, 1H), 3.94 (s, 2H), 3.74 (dddd, J=8.3, 6.4, 4.0, 2.3 Hz, 1H), 3.45 (s, 1H), 3.11 (ddd, J=21.0, 17.4, 5.3 Hz, 3H), 2.77 (tp, J=17.2, 5.2 Hz, 2H), 2.59-2.50 (m, 1H), 2.15 (d, J=12.2 Hz, 1H), 1.80-1.54 (m, 3H), 1.11 (d, J=6.1 Hz, 3H); MS (APCI$^+$) m/z 388 [M+H]$^+$.

Example 208C: 5-[(7R)-1-fluoro-3-hydroxy-7-{[(3R)-3-hydroxybutyl]amino}-5,6,7,8-tetrahydronaphthalen-2-yl]-1λ$^6$,2,5-thiadiazolidine-1,1,3-trione The product of Example 208B (0.2464 g, 0.636 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide(70:30) at a concentration of 5 mg/mL. The sample was loaded into the modifier stream in 2 mL (10 mg) injections. The mobile phase was held isocratically at 40% cosolvent:CO$_2$. Fraction collection was time triggered. The instrument was fitted with a CHIRALPAK® IC column with dimensions 21 mm i.d.×250 mm length with 5 m particles. The later eluting enantiomer peak gave the title compound (0.0569 g, 0.147 mmol, 46.2% recovery). $^1$H NMR and MS data were identical to those from Example 208B. Absolute stereochemistry was tentatively assigned in analogy to the chromatography elution order to the product of Example 19.

Example 209: 5-{(7R)-1-fluoro-3-hydroxy-7-[(4-hydroxy-3,3-dimethylbutyl)amino]-5,6,7,8-tetrahydronaphthalen-2-yl}-1λ$^6$,2,5-thiadiazolidine-1,1,3-trione (Compound 308)

Example 209A: 5-{3-(benzyloxy)-1-fluoro-7-[(4-hydroxy-3, 3-dimethylbutyl)amino]-5,6,7,8-tetrahydronaphthalen-2-yl}-1λ$^6$,2,5-thiadiazolidine-1,1,3-trione To a solution of the product of Example 67F (0.439 g, 1.085 mmol) in ethanol (8.8 mL) was added 4-amino-2,2-dimethylbutan-1-ol hydrochloride (0.250 g, 1.627 mmol) and triethylamine (0.454 mL, 3.25 mmol). After 30 minutes sodium cyanoborohydride (0.082 g, 1.302 mmol) was added as a solid. After 16 hours, the reaction mixture was quenched with ammonium hydroxide (0.123 mL, 6.51 mmol), then diluted with acetonitrile (10 mL) and water (2 mL). Celite® (4 g) was added and the mixture was concentrated in vacuo to give a powder. The resultant mixture was dry loaded onto a Teledyne ISCO 275 g reversed-phase C18 column and eluted with a gradient of 10-100% methanol in buffer (0.025 M ammonium bicarbonate in water acidified to pH 7 by adding dry ice) to give the title compound (0.4332 g, 0.857 mmol, 79% yield). MS (APCI$^+$) m/z 506 [M+H]$^+$.

Example 209B: 5-{1-fluoro-3-hydroxy-7-[(4-hydroxy-3, 3-dimethylbutyl)amino]-5,6,7,8-tetrahydronaphthalen-2-yl}-1λ$^6$,2,5-thiadiazolidine-1,1,3-trione, Hydrochloride Salt To a suspension of the product of example 209A (0.4332 g, 0.857 mmol) and pentamethylbenzene (0.246 g, 1.658 mmol) in dichloromethane (8.6 mL) at −78° C. was added a solution of boron trichloride (12.4 mL, 1 M in dichloromethane, 12.4 mmol) slowly along the side of the flask. The resulting mixture was stirred for 5 minutes, then warmed to an internal temperature of 0° C., then cooled to −78° C. and quenched with ethyl acetate (4.3 mL), followed by ethanol (4.3 mL). The reaction mixture was warmed to ambient temperature and concentrated in vacuo. The crude solid was triturated with heptanes (3×9 mL), 1:1 ethyl acetate/heptanes (2×5 mL), dichloromethane (2×5 mL) and acetonitrile (2×2.5 mL) to give the title compound as the hydrochloride salt (0.2511 g, 0.556 mmol, 67.0% yield). $^1$H NMR (400 MHz, DMSO-d$_6$) δ ppm 10.05 (s, 1H), 8.84 (dt, J=23.9, 5.9 Hz, 1H), 6.53 (d, J=1.3 Hz, 1H), 4.28 (s, 2H), 3.44 (q, J=7.0 Hz, 2H), 3.16-3.08 (m, 3H), 3.01 (dq, J=11.9, 6.3 Hz, 2H), 2.82 (dt, J=17.3, 4.5 Hz, 1H), 2.74 (ddd, J=17.3, 11.5, 5.5 Hz, 1H), 2.59 (dd, J=16.1, 10.1 Hz, 1H), 2.24-2.18 (m, 1H), 1.72 (qd, J=11.8, 5.5 Hz, 1H), 1.62-1.55 (m, 2H), 0.85 (s, 6H); MS (APCI$^+$) m/z 416 [M+H]$^+$.

Example 209C: 5-{(7R)-1-fluoro-3-hydroxy-7-[(4-hydroxy-3, 3-dimethylbutyl)amino]-5,6,7,8-tetrahydronaphthalen-2-yl}-1λ$^6$,2,5-thiadiazolidine-1,1,3-trione The product of Example 209B (0.2511 g, 0.556 mmol) was separated by preparative chiral SFC. Preparative SFC was performed on a THAR/Waters SFC80 system running under SuperChrom™ software control. The preparative SFC system was equipped with an 8-way preparative column switcher, CO$_2$ pump, modifier pump, automated back pressure regulator (ABPR), UV detector, and 6-position fraction collector. The mobile phase comprised of supercritical CO$_2$ supplied by a Dewar of bone-dry non-certified CO$_2$ pressurized to 350 psi with a modifier of methanol (0.1% triethylamine) at a flow rate of 70 g/minute. The column was at ambient temperature and the back pressure regulator was set to maintain 100 bar. The sample was dissolved in methanol:dimethyl sulfoxide (70:30) at a concentration of 5 mg/mL. The sample was loaded into the modifier stream in 2 mL (10 mg) injections. The mobile phase was held isocratically at 40% cosolvent:$CO_2$. Fraction collection was time triggered. The instrument was fitted with a CHIRAL-PAK® IC column with dimensions 21 mm i.d.×250 mm length with 5 m particles. The later eluting enantiomer peak gave the title compound (0.0624 g, 0.150 mmol, 54.1% recovery). $^1$H NMR and MS data were identical to those from Example 209B. Absolute stereochemistry was tentatively assigned in analogy to the chromatography elution order to the product of Example 19.

Example 210: 5-[1-fluoro-3-hydroxy-6-(3-hydroxy-3-methylbutoxy)-5,6,7,8-tetrahydronaphthalen-2-yl]-1$\lambda^6$,2,5-thiadiazolidine-1,1,3-trione (Compound 309)

Example 210A: 3-(benzyloxy)-1,6-dibromonaphthalen-2-amine

To a solution of 3-(benzyloxy)naphthalen-2-amine (International Patent Publication WO2008148744; 4.34 g, 13.9 mmol) in $CHCl_3$ (100 mL) was added $Br_2$ (1.58 mL, 30.6 mmol) in $CHCl_3$ (20 mL) dropwise at room temperature and stirring was continued for 12 hours. The mixture was poured into saturated $NaHCO_3$ solution (100 mL) and the layers were separated. The aqueous phase was extracted with ethyl acetate (3×100 mL) and all the organic layers were combined, dried over $MgSO_4$, filtered and concentrated to give the title compound (8.10 g, 11.9 mmol, 86% yield, 60% purity). $^1$H NMR (400 MHz, DMSO-$d_6$) δ ppm 5.30 (s, 2H), 5.51 (s, 2H), 7.40-7.47 (m, 5H), 7.57 (d, J=7.5 Hz, 2H), 7.72 (d, J=8.8 Hz, 1H), 7.92 (d, J=2.2 Hz, 1H).

Example 210B: 3-(benzyloxy)-6-bromonaphthalen-2-amine

To a solution of Example 210A (16.0 g, 39.3 mmol) in ethanol (640 mL) at room temperature was added tin (5.60 g, 47.2 mmol) in one portion followed by concentrated HCl (160 mL) and the mixture was heated at 90° C. for one hour. The reaction mixture was cooled to room temperature and was poured into a saturated $NaHCO_3$ solution (300 mL) and extracted with ethyl acetate (3×300 mL). The combined organic phases were washed with brine (200 mL), dried with $Na_2SO_4$, filtered and concentrated under reduced to give the title compound (10 g, 21.3 mmol, 54% yield). $^1$H NMR (400 MHz, DMSO-$d_6$) δ ppm 5.24 (s, 2H), 5.30 (s, 2H), 6.92 (s, 1H), 7.22-7.29 (m, 2H), 7.31-7.37 (m, 2H), 7.37-7.47 (m, 3H), 7.55 (d, J=7.0 Hz, 2H), 7.79 (d, J=2.0 Hz, 1H).

Example 210C: 3-(benzyloxy)-6-bromo-1-fluoronaphthalen-2-amine

To a solution of Example 210B (15 g, 32.0 mmol) in tetrahydrofuran (200 mL) was added N-fluoro-N-(phenylsulfonyl)benzenesulfonamide (10.6 g, 33.6 mmol) at room temperature and stirring was continued for 12 hours. The mixture was quenched with aqueous sodium thiosulfate (20 mL) and extracted with ethyl acetate (3×200 mL). The combined organic fractions were washed with brine (20 mL), filtered and concentrated under reduced pressure. The residue was purified by silica gel chromatography eluted with petroleum ether:ethyl acetate=100:1 to 50:1 to give the title compound (7.3 g, 19 mmol, 59% yield). $^1$H NMR (400 MHz, DMSO-$d_6$) δ ppm 5.21-5.33 (m, 4H), 7.25 (s, 1H), 7.32-7.38 (m, 1H), 7.40-7.46 (m, 3H), 7.55-7.60 (m, 2H), 7.63-7.68 (m, 1H), 7.93 (t, J=1.7 Hz, 1H).

Example 210D: Methyl {[3-(benzyloxy)-6-bromo-1-fluoronaphthalen-2-yl]amino}acetate To a solution of Example 210C (7.3 g, 19.0 mmol) in N,N-dimethylformamide (30 mL) was added N,N-diisopropylethylamine (13 mL, 76 mmol) and methyl 2-bromoacetate (17.4 g, 114 mmol) at ambient temperature, and the mixture was warmed to 65° C. and stirred for 12 hours. The reaction mixture was cooled to room temperature and extracted with ethyl acetate (3×80 mL). The combined organic fractions were washed with brine (50 mL), dried with $Na_2SO_4$, filtered and concentrated under reduced pressure. The residue was triturated with petroleum ether:ethyl acetate=5:1 (30 mL) then filtered to give the title compound (5.6 g, 10.7 mmol, 56% yield). $^1$H NMR (400 MHz, DMSO-$d_6$) δ ppm 3.62 (s, 3H), 4.21 (dd, J=6.7, 3.9 Hz, 2H), 5.28 (s, 2H), 5.59 (td, J=6.7, 2.4 Hz, 1H), 7.27 (s, 1H), 7.33-7.38 (m, 1H), 7.39-7.45 (m, 3H), 7.55 (d, J=7.1 Hz, 2H), 7.62 (d, J=8.8 Hz, 1H), 7.93 (s, 1H).

Example 210E: Methyl {[3-(benzyloxy)-6-bromo-1-fluoronaphthalen-2-yl][(tert-butoxycarbonyl) sulfamoyl]amino}acetate To a solution of sulfurisocyanatidic chloride (2.87 g, 20.3 mmol) in $CH_2Cl_2$ (4 mL) was added dropwise a solution of 2-methylpropan-2-ol (1.9 mL, 20 mmol) in $CH_2Cl_2$ (2.00 mL) at 0° C. The mixture was stirred at room temperature for 1 hour. To this mixture was added a solution of Example 210D (5.3 g, 10 mmol) and triethylamine (5.65 mL, 40.5 mmol) in $CH_2Cl_2$ (7 mL) at 0° C. The reaction was allowed to warm to ambient temperature and stirred for 2 hours. The mixture was concentrated under reduced pressure to give the title compound (6 g, 9.7 mmol, 96% yield). The title compound was used for the next step without purification. $^1$H NMR (400 MHz, DMSO-$d_6$) δ ppm 1.30 (s, 9H), 3.53 (s, 3H), 4.45 (d, J=18.0 Hz, 1H), 4.76 (d, J=18.0 Hz, 1H), 5.17-5.35 (m, 2H), 7.31-7.37 (m, 2H), 7.38-7.44 (m, 2H), 7.52-7.62 (m, 3H), 7.92 (d, J=8.8 Hz, 1H), 8.12 (s, 1H).

Example 210F: Methyl {[3-(benzyloxy)-6-bromo-1-fluoronaphthalen-2-yl](sulfamoyl)amino}acetate To a solution of Example 210E (7 g, 11 mmol) in $CH_2Cl_2$ (100 mL) was added trifluoroacetic acid (20 mL, 260 mmol) dropwise at 0° C. The mixture was stirred at room temperature for 1 hour. The reaction mixture was concentrated under reduced pressure. The pH was adjusted to approximately 8 by progressively adding aqueous sodium bicarbonate solution. The aqueous phase was extracted with ethyl acetate (3×100 mL). The combined organic layers were washed with brine (100 mL), dried with $Na_2SO_4$, filtered and concentrated under reduced pressure to give the title compound (4.6 g, 8.4 mmol, 74% yield. $^1$H NMR (400 MHz, DMSO-$d_6$) δ ppm 3.51-3.60 (m, 3H), 4.25-4.37 (m, 1H), 4.42-4.54 (m, 1H), 5.18-5.36 (m, 2H), 7.10 (s, 2H), 7.31-7.47 (m, 4H), 7.55-7.62 (m, 3H), 7.92 (d, J=8.9 Hz, 1H), 8.15 (s, 1H).

Example 210G: 5-[3-(benzyloxy)-6-bromo-1-fluoronaphthalen-2-yl]-1λ⁶,2,5-thiadiazolidine-1,1,3-trione To a solution of Example 210F (4.6 g, 8.42 mmol) in tetrahydrofuran (50 mL) at room temperature was added 4 g of activated 4 Å molecular sieves and sodium methanolate in methanol (3.62 g, 12.63 mmol). The mixture was stirred at room temperature for 15 minutes. The reaction was quenched by addition of 60 mL of 1 N HCl and extracted with ethyl acetate (3×100 mL). The combined organic fractions were washed with brine (100 mL), dried with $Na_2SO_4$, filtered and concentrated under reduced pressure to give the title compound (3.7 g, 6.9 mmol, 82% yield). $^1$H NMR (400 MHz, DMSO-$d_6$) δ ppm 4.38 (s, 2H), 5.26 (s, 2H), 7.31-7.41 (m, 3H), 7.44 (s, 1H), 7.53 (d, J=7.0 Hz, 2H), 7.60 (dd, J=8.9, 1.8 Hz, 1H), 7.92 (d, J=8.9 Hz, 1H), 8.16 (s, 1H).

Example 210H: 5-[3-(benzyloxy)-1-fluoro-6-(3-hydroxy-3-methylbutoxy)naphthalen-2-yl]-1λ⁶,2,5-thiadiazolidine-1,1,3-trione To a vial were added 5-[3-(benzyloxy)-6-bromo-1-fluoronaphthalen-2-yl]-1λ⁶,2,5-thiadiazolidine-1,1,3-trione (Example 210G, 0.150 g, 0.322 mmol), methanesulfonato(2-(di-tert-butylphosphino)-3-methoxy-6-methyl-2',4',6'-triisopropyl-1,1'-biphenyl)(2'-amino-1,1'-biphenyl-2-yl)palladium(II) (0.005 g, 0.006 mmol), and cesium carbonate (0.315 g, 0.967 mmol). The vial was sealed, evacuated, and refilled with nitrogen. The evacuation/refill cycle was repeated three additional times. Degassed N,N-dimethylformamide (1.1 mL) was added, followed by a solution of 3-methylbutane-1,3-diol (0.168 g, 1.61 mmol) in degassed N,N-dimethylformamide (0.54 mL). The vial was heated to 80° C. After 2 hours, the vial was cooled to ambient temperature, whereupon 3-hydroxy-3-methylbutyl 4-methylbenzenesulfonate (0.050 g, 0.19 mmol) was added to convert the 5-[3-(benzyloxy)-1-fluoro-6-hydroxynaphthalen-2-yl]-1λ⁶,2,5-thiadiazolidine-1,1,3-trione side product to desired product. The mixture was stirred at ambient temperature for 60 hours, and then the reaction mixture was partitioned between 1 M hydrochloric acid (40 mL) and ethyl acetate (30 mL). The layers were separated, and the aqueous phase was extracted with ethyl acetate (2×30 mL). The organic layers were combined, washed with brine, dried over sodium sulfate, filtered, and concentrated under reduced pressure. The residue was purified using reversed-phase chromatography [120 g Biotage® Sfär C18 Duo 100 Å 30 μm column, 10-100% gradient of acetonitrile in water (buffered with 0.1% trifluoroacetic acid)] to give the title compound (0.086 g, 0.18 mmol, 54% yield). $^1$H NMR (500 MHz, DMSO-$d_6$) δ ppm 7.88 (d, J=9.1 Hz, 1H), 7.54-7.49 (m, 2H), 7.42-7.36 (m, 2H), 7.36-7.31 (m, 3H), 7.11 (dd, J=9.1, 2.4 Hz, 1H), 5.25 (s, 2H), 4.50 (s, 2H), 4.21 (t, J=7.2 Hz, 2H), 1.91 (t, J=7.1 Hz, 2H), 1.19 (s, 6H); MS (APCI$^+$) m/z 488.2 [M+H]$^+$.

Example 210I. 5-[1-fluoro-3-hydroxy-6-(3-hydroxy-3-methylbutoxy)naphthalen-2-yl]-1λ⁶,2,5-thiadiazolidine-1,1,3-trione A vial was charged with the product of Example 210H (0.079 g, 0.16 mmol), ammonium formate (0.061 g, 0.97 mmol), and ethanol (0.80 mL). The vial was purged with nitrogen, then 10% palladium on carbon (0.017 g, 0.016 mmol) was added. The vial was capped, purged with nitrogen, and heated to 60° C. After 2 hours, the vial was cooled to ambient temperature and the reaction mixture was filtered over diatomaceous earth with the aid of methanol. The filtrate was concentrated under reduced pressure. The residue was purified using reversed-phase chromatography [120 g Biotage® Sfär C18 Duo 100 Å 30 Lm column, 10-100% gradient of acetonitrile in water (buffered with 0.1% trifluoroacetic acid)] to give the title compound (0.032 g, 0.081 mmol, 50% yield). $^1$H NMR (600 MHz, DMSO-$d_6$) δ ppm 10.53 (br s, 1H), 7.80 (d, J=9.1 Hz, 1H), 7.21 (s, 1H), 7.03-6.99 (m, 2H), 4.46 (s, 2H), 4.18 (t, J=7.2 Hz, 2H), 1.89 (t, J=7.2 Hz, 2H), 1.19 (s, 6H); MS (ESI$^+$) m/z 381.0 [M−H$_2$O+H]$^+$.

Example 210J: 5-[1-fluoro-3-hydroxy-6-(3-hydroxy-3-methylbutoxy)-5,6,7,8-tetrahydronaphthalen-2-yl]-1λ⁶,2,5-thiadiazolidine-1,1,3-trione In a Parr shaker, 10% palladium on carbon (0.039 g, 0.0555 mmol, 50 weight % in water) was added to a solution of the product from Example 210I (0.0393 g, 0.099 mmol) in trifluoroethanol (4 mL). The reactor was purged with nitrogen and then was stirred under hydrogen (120 psi) at 25° C. until hydrogen uptake was complete (5 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (2.2 mg, 5.2 μmol, 5.3% yield). $^1$H NMR (500 MHz, DMSO-$d_6$) δ ppm 8.94 (br s, 1H), 7.07 (br s, 4H), 6.41 (s, 1H), 4.15 (s, 1H), 3.92 (s, 2H), 3.70-3.64 (m, 1H), 3.62-3.50 (m, 2H), 2.89 (dd, J=16.8, 4.5 Hz, 1H), 2.68-2.51 (m, 3H), 1.93-1.87 (m, 1H), 1.72 (dt, J=13.1, 6.6 Hz, 1H), 1.67 (s, 1H), 1.08 (s, 6H); MS (ESI$^-$) m/z 401 [M−H]$^-$.

Example 211: 5-[6-(cyclopropylmethoxy)-1-fluoro-3-hydroxy-5,6,7,8-tetrahydronaphthalen-2-yl]-1λ⁶,2,5-thiadiazolidine-1,1,3-trione (Compound 310)

Example 211A: 5-[3-(benzyloxy)-1-fluoro-6-hydroxynaphthalen-2-yl]-1λ⁶,2,5-thiadiazolidine-1,1,3-trione To a vial was added 5-[3-(benzyloxy)-6-bromo-1-fluoronaphthalen-2-yl]-1λ⁶,2,5-thiadiazolidine-1,1,3-trione (Example 210G, 0.250 g, 0.537 mmol), methanesulfonato(2-(di-tert-butylphosphino)-3-methoxy-6-methyl-2',4',6'-triisopropyl-1,1'-biphenyl)(2'-amino-1,1'-biphenyl-2-yl)palladium(II) (0.005 g, 0.005 mmol), 2-(di-tert-butylphosphino)-3-methoxy-6-methyl-2',4',6'-triisopropyl-1,1'-biphenyl (0.003 g, 0.005 mmol), and cesium carbonate (0.525 g, 1.61 mmol). The vial was sealed, evacuated, and refilled with nitrogen. The evacuation/refill cycle was repeated three additional times. Next, a degassed mixture of water (0.058 mL, 3.2 mmol) and N,N-dimethylacetamide (2.7 mL) was added. The vial was heated to 80° C. After 4 hours, the vial was cooled to ambient temperature, and the reaction mixture was partitioned between 1 M hydrochloric acid (50 mL) and ethyl acetate (30 mL). The layers were separated, and the aqueous phase was extracted with ethyl acetate (2×30 mL). The organic layers were combined and washed with saturated aqueous ammonium chloride (4×30 mL). The ammonium chloride washes were combined and back extracted with ethyl acetate (30 mL). The organic phases were combined, washed with brine/1 M hydrochloric acid (4:1 v/v) (30 mL), dried over sodium sulfate, filtered, and concentrated under reduced pressure. The residue was purified using reversed-phase chromatography [120 g Biotage® Sfär C18 Duo 100 Å 30 µm column, 10-100% gradient of acetonitrile in water (buffered with 0.1% trifluoroacetic acid)] to give the title compound (0.159 g, 0.395 mmol, 74% yield). $^1$H NMR (400 MHz, DMSO-$d_6$) δ ppm 10.15 (br s, 1H), 7.84 (d, J=8.9 Hz, 1H), 7.55-7.46 (m, 2H), 7.41-7.35 (m, 2H), 7.35-7.30 (m, 1H), 7.22 (s, 1H), 7.10 (t, J=2.0 Hz, 1H), 7.04 (dd, J=9.0, 2.3 Hz, 1H), 5.23 (s, 2H), 4.48 (s, 2H); MS (APCI$^+$) m/z 403.3 [M+H]$^+$.

Example 211B: 5-[3-(benzyloxy)-6-(cyclopropylmethoxy)-1-fluoronaphthalen-2-yl]-1λ$^6$,2,5-thiadiazolidine-1,1,3-trione To a vial were added the product of Example 211A (0.100 g, 0.249 mmol), (bromomethyl)cyclopropane (0.067 g, 0.50 mmol), cesium carbonate (0.243 g, 0.746 mmol), and N,N-dimethylformamide (0.99 mL). The resulting mixture was stirred at ambient temperature. After 14 hours, the reaction mixture was partitioned between 1 M hydrochloric acid (25 mL) and ethyl acetate (15 mL). The layers were separated, and the aqueous phase was extracted with ethyl acetate (2×10 mL). The organic layers were combined and washed with saturated aqueous ammonium chloride (3×15 mL). The ammonium chloride washes were combined and back extracted with ethyl acetate (15 mL). The organic layers were combined, washed with brine/1 M hydrochloric acid (4:1 v/v) (15 mL), dried over sodium sulfate, filtered, and concentrated under reduced pressure. The residue was purified using reversed-phase chromatography [120 g Agela Claricep™ spherical C18 100 Å 40-60 µm column, 10-100% gradient of acetonitrile in water (buffered with 0.1% trifluoroacetic acid)] to give the title compound (0.084 g, 0.18 mmol, 74% yield). $^1$H NMR (600 MHz, DMSO-$d_6$) δ ppm 7.88 (d, J=9.1 Hz, 1H), 7.52-7.50 (m, 2H), 7.40-7.36 (m, 2H), 7.35-7.32 (m, 1H), 7.31 (s, 1H), 7.27 (t, J=1.8 Hz, 1H), 7.14 (dd, J=9.1, 2.4 Hz, 1H), 5.25 (s, 2H), 4.51 (s, 2H), 3.95 (d, J=7.0 Hz, 2H), 1.34-1.24 (m, 1H), 0.65-0.55 (m, 2H), 0.41-0.31 (m, 2H); MS (APCI$^+$) m/z 456.2 [M+H]$^+$.

Example 211C: 5-[6-(cyclopropylmethoxy)-1-fluoro-3-hydroxynaphthalen-2-yl]-1λ$^6$,2,5-thiadiazolidine-1,1,3-trione A vial was charged with the product of Example 211B (0.074 g, 0.16 mmol), ammonium formate (0.061 g, 0.97 mmol), and ethanol (0.81 mL). The vial was purged with nitrogen, then 10% palladium on carbon (0.017 g, 0.016 mmol) was added. The vial was capped, purged with nitrogen, and heated to 50° C. After 1.5 hours, the vial was cooled to ambient temperature and the reaction mixture was filtered over diatomaceous earth with the aid of methanol. The filtrate was concentrated under reduced pressure. The residue was purified using reversed-phase chromatography [120 g Agela Claricep™ spherical C18 100 Å 40-60 µm column, 10-100% gradient of methanol in water (buffered with 0.1% trifluoroacetic acid)] to give the title compound (0.050 g, 0.14 mmol, 84% yield). $^1$H NMR (500 MHz, DMSO-$d_6$) δ ppm 10.57 (br s, 1H), 7.80 (d, J=9.1 Hz, 1H), 7.16 (t, J=1.9 Hz, 1H), 7.04 (dd, J=9.1, 2.4 Hz, 1H), 6.99 (s, 1H), 4.49 (s, 2H), 3.93 (d, J=7.0 Hz, 2H), 1.34-1.22 (m, 1H), 0.62-0.57 (m, 2H), 0.39-0.33 (m, 2H); MS (APCI$^+$) m/z 367.3 [M+H]$^+$.

Example 211D: 5-[6-(cyclopropylmethoxy)-1-fluoro-3-hydroxy-5,6,7,8-tetrahydronaphthalen-2-yl]-1λ$^6$,2,5-thiadiazolidine-1,1,3-trione In a Parr shaker, 10% palladium on carbon (0.044 g, 0.0627 mmol, 50 weight % in water) was added to a solution of the product from Example 211C (0.0443 g, 0.121 mmol) in trifluoroethanol (4.8 mL). The reactor was purged with nitrogen and then was stirred under hydrogen (120 psi) at 25° C. until hydrogen uptake was complete (4 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (4.5 mg, 0.012 mmol, 7.3% yield). $^1$H NMR (600 MHz, DMSO-$d_6$) δ ppm 8.96 (br s, 1H), 7.08 (br s, 4H), 6.41 (s, 1H), 3.92 (s, 2H), 3.70 (dddd, J=9.2, 7.1, 4.4, 2.5 Hz, 1H), 3.30 (d, J=6.7 Hz, 2H), 2.89 (dd, J=16.6, 4.6 Hz, 1H), 2.67-2.56 (m, 2H), 2.53-2.48 (m, 1H), 1.92-1.85 (m, 1H), 1.71 (dtd, J=13.5, 7.9, 5.8 Hz, 1H), 0.98 (ttt, J=8.0, 6.8, 4.9 Hz, 1H), 0.48-0.40 (m, 2H), 0.18-0.12 (m, 2H); MS (ESI$^-$) m/z 369 [M−H]$^-$.

Example 212: 5-{6-[(4,4-difluorobutyl)amino]-1-fluoro-3-hydroxy-5,6,7,8-tetrahydronaphthalen-2-yl}-1λ$^6$,2,5-thiadiazolidine-1,1,3-trione (Compound 311)

Example 212A: 5-{3-(benzyloxy)-6-[(4, 4-difluorobutyl)amino]-1-fluoronaphthalen-2-yl}-1λ$^6$,2,5-thiadiazolidine-1,1,3-trione, Trifluoroacetic Acid Salt To a vial were added 5-[3-(benzyloxy)-6-bromo-1-fluoronaphthalen-2-yl]-1λ$^6$,2,5-thiadiazolidine-1,1,3-trione (Example 210G, 0.150 g, 0.322 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (0.015 g, 0.016 mmol), 2-(dicyclohexylphosphino)3,6-dimethoxy-2',4',6'-triisopropyl-1,1'-biphenyl (0.009 g, 0.016 mmol), 4,4-difluorobutan-1-amine hydrochloride (0.094 g, 0.65 mmol), and cesium carbonate (0.420 g, 1.29 mmol). The vial was sealed, evacuated, and refilled with nitrogen. The evacuation/refill cycle was repeated three additional times. Degassed N,N-dimethylformamide (1.6 mL) was added and the vial was heated to 80° C. After 22 hours, the vial was cooled to ambient temperature and the reaction mixture was partitioned between 1 M hydrochloric acid (40 mL) and ethyl acetate (30 mL). The layers were separated, and the aqueous phase was extracted with ethyl acetate (2×30 mL). The organic layers were combined, washed with brine, dried over sodium sulfate, filtered, and concentrated under reduced pressure. The residue was purified using reversed-phase chromatography [120 g Biotage® Sfär C18 Duo 100 Å 30 µm column, 10-100% gradient of acetonitrile in water (buffered with 0.1% trifluoroacetic acid)] to give the title compound (0.088 g, 0.18 mmol, 55% yield). $^1$H NMR (400 MHz, DMSO-$d_6$) δ ppm 7.67 (d, J=9.0 Hz, 1H), 7.52-7.48 (m, 2H), 7.40-7.35 (m, 2H), 7.35-7.30 (m, 1H), 7.06 (s, 1H), 6.92 (dd, J=8.9, 2.0 Hz, 1H), 6.67 (t, J=2.0 Hz, 1H), 6.14 (tt, J=56.8, 4.4 Hz, 1H), 5.21 (s, 2H), 4.46 (s, 2H), 3.17 (t, J=7.0 Hz, 2H), 2.03-1.86 (m, 2H), 1.72 (dq, J=10.6, 7.2 Hz, 2H); MS (APCI$^+$) m/z 494.2 [M+H]$^+$.

Example 212B: 5-{6-[(4, 4-difluorobutyl)amino]-1-fluoro-3-hydroxynaphthalen-2-yl}-1$\lambda^6$,2,5-thiadiazolidine-1,1,3-trione, Trifluoroacetic Acid Salt A flask containing a suspension of the product of Example 212A (0.085 g, 0.17 mmol) and 1,2,3,4,5-pentamethylbenzene (0.076 g, 0.51 mmol) in dichloromethane (1.7 mL) was cooled to −78° C. with stirring under an atmosphere of nitrogen. Next, trichloroborane (1.0 M in dichloromethane) (1.4 mL, 1.4 mmol) was added. The resulting mixture was stirred at −78° C. for 10 minutes, and then the dry ice-acetone bath was replaced with an ice-water bath. One hour later, the flask was recooled to −78° C. The reaction mixture was diluted with dichloromethane (3 mL) and quenched via the successive addition of ethyl acetate (3 mL) and ethanol (3 mL). The mixture was allowed to warm to ambient temperature and stirred for 15 minutes before being concentrated under reduced pressure. The residue was co-evaporated with ethanol (2×5 mL) and purified using reversed-phase chromatography [120 g Biotage® Sfär C18 Duo 100 Å 30 µm column, 10-100% gradient of methanol in water (buffered with 0.1% trifluoroacetic acid)] to give the title compound (0.050 g, 0.12 mmol, 72% yield). $^1$H NMR (400 MHz, DMSO-d$_6$) δ ppm 10.23 (br s, 1H), 7.61 (d, J=9.0 Hz, 1H), 6.84 (dd, J=9.1, 2.1 Hz, 1H), 6.76 (s, 1H), 6.54 (s, 1H), 6.13 (tt, J=56.9, 4.4 Hz, 1H), 4.44 (s, 2H), 3.16 (t, J=7.0 Hz, 2H), 2.02-1.86 (m, 2H), 1.77-1.64 (m, 2H); MS (APCI$^+$) m/z 404.3 [M+H]$^+$.

Example 212C: 5-{6-[(4, 4-difluorobutyl)amino]-1-fluoro-3-hydroxy-5,6,7,8-tetrahydronaphthalen-2-yl}-1$\lambda^6$,2,5-thiadiazolidine-1,1,3-trione In a Parr shaker, 10% palladium on carbon (0.0416 g, 0.0592 mmol, 50 weight % in water) was added to a solution of the product from Example 212B (0.0416 g, 0.103 mmol) in trifluoroethanol (4 mL). The reactor was purged with nitrogen and then was stirred under hydrogen (120 psi) at 25° C. until hydrogen uptake was complete (5 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (7.5 mg, 0.018 mol, 18% yield). $^1$H NMR (600 MHz, DMSO-d$_6$) δ ppm 9.18 (br s, 1H), 8.42 (br s, 2H), 6.48 (s, 1H), 6.15 (tt, J=56.6, 4.2 Hz, 1H), 3.93 (s, 2H), 3.42 (s, 1H), 3.13-3.04 (m, 3H), 2.79 (dt, J=16.9, 4.9 Hz, 1H), 2.71 (dd, J=16.4, 9.8 Hz, 1H), 2.57 (ddd, J=16.7, 10.7, 6.0 Hz, 1H), 2.21-2.15 (m, 1H), 2.00-1.87 (m, 1H), 1.78-1.64 (m, 3H); MS (ESI$^+$) m/z 408 [M+H]$^+$.

Example 213: 5-[6-(4,4-difluorobutoxy)-1-fluoro-3-hydroxy-5,6,7,8-tetrahydronaphthalen-2-yl]-1$\lambda^6$,2,5-thiadiazolidine-1,1,3-trione (Compound 312)

Example 213A: 5-[3-(benzyloxy)-6-(4, 4-difluorobutoxy)-1-fluoronaphthalen-2-yl]-1$\lambda^6$,2,5-thiadiazolidine-1,1,3-trione To a vial were added the product of Example 211A (0.100 g, 0.249 mmol), 4-bromo-1,1-difluorobutane (0.086 g, 0.50 mmol), cesium carbonate (0.243 g, 0.746 mmol), and N,N-dimethylformamide (0.99 mL). The resulting mixture was stirred at ambient temperature. After 14 hours, the reaction mixture was partitioned between 1 M hydrochloric acid (25 mL) and ethyl acetate (15 mL). The layers were separated, and the aqueous phase was extracted with ethyl acetate (2×10 mL). The organic layers were combined and washed with saturated aqueous ammonium chloride (3×15 mL). The ammonium chloride washes were combined and back extracted with ethyl acetate (15 mL). The organic layers were combined, washed with brine/1 M hydrochloric acid (4:1 v/v) (15 mL), dried over sodium sulfate, filtered, and concentrated under reduced pressure. The residue was purified using reversed-phase chromatography [120 g Agela Claricep™ spherical C18 100 Å 40-60 µm column, 10-100% gradient of acetonitrile in water (buffered with 0.1% trifluoroacetic acid)] to give the title compound (0.077 g, 0.16 mmol, 63% yield). $^1$H NMR (500 MHz, DMSO-d$_6$) δ ppm 7.89 (d, J=9.1 Hz, 1H), 7.55-7.48 (m, 2H), 7.42-7.36 (m, 2H), 7.36-7.31 (m, 2H), 7.31 (t, J=1.9 Hz, 1H), 7.15 (dd, J=9.1, 2.4 Hz, 1H), 6.19 (tt, J=56.7, 4.3 Hz, 1H), 5.26 (s, 2H), 4.51 (s, 2H), 4.15 (t, J=6.3 Hz, 2H), 2.09-1.95 (m, 2H), 1.95-1.85 (m, 2H); MS (APCI$^+$) m/z 495.3 [M+H]$^+$.

Example 213B: 5-[6-(4, 4-difluorobutoxy)-1-fluoro-3-hydroxynaphthalen-2-yl]-1$\lambda^6$,2,5-thiadiazolidine-1,1,3-trione A vial was charged with the product of Example 213A (0.056 g, 0.11 mmol), ammonium formate (0.043 g, 0.68 mmol), and ethanol (0.57 mL). The vial was purged with nitrogen, then 10% palladium on carbon (0.012 g, 0.011 mmol) was added. The vial was capped, purged with nitrogen, and heated to 50° C. After 1.5 hours, the vial was cooled to ambient temperature and the reaction mixture was filtered over diatomaceous earth with the aid of methanol. The filtrate was concentrated under reduced pressure. The residue was purified using reversed-phase chromatography [120 g Agela Claricep™ spherical C18 100 Å 40-60 µm column, 10-100% gradient of methanol in water (buffered with 0.1% trifluoroacetic acid)] to give the title compound (0.039 g, 0.095 mmol, 84% yield). $^1$H NMR (500 MHz, DMSO-d$_6$) δ ppm 10.57 (br s, 1H), 7.82 (d, J=9.1 Hz, 1H), 7.20 (t, J=1.9 Hz, 1H), 7.04 (dd, J=9.1, 2.4 Hz, 1H), 7.01 (s, 1H), 6.18 (tt, J=56.8, 4.4 Hz, 1H), 4.48 (s, 2H), 4.14 (t, J=6.3 Hz, 2H), 2.09-1.95 (m, 2H), 1.94-1.84 (m, 2H); MS (APCI$^+$) m/z 405.3 [M+H]$^+$.

Example 213C: 5-[6-(4, 4-difluorobutoxy)-1-fluoro-3-hydroxy-5,6,7,8-tetrahydronaphthalen-2-yl]-1$\lambda^6$,2,5-thiadiazolidine-1,1,3-trione In a Parr shaker, 10% palladium on carbon (0.074 g, 0.105 mmol, 50 weight % in water) as a solid was added to a solution of the product from Example 213B (0.0742 g, 0.150 mmol) in trifluoroethanol (6 mL). The reactor was purged with nitrogen and then was stirred under hydrogen (120 psi) at 25° C. until hydrogen uptake was complete (5 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (15.0 mg, 0.350 mol, 23.5% yield).

¹H NMR (600 MHz, DMSO-d₆) δ ppm 8.96 (br s, 1H), 7.07 (br s, 3H), 6.41 (s, 1H), 6.07 (tt, J=57.0, 4.5 Hz, 1H), 3.92 (s, 2H), 3.68 (s, 1H), 3.55-3.43 (m, 2H), 2.90 (dd, J=16.6, 4.5 Hz, 1H), 2.68-2.60 (m, 2H), 2.60-2.51 (m, 1H), 1.98-1.77 (m, 3H), 1.75-1.68 (m, 1H), 1.60 (p, J=6.6 Hz, 2H); MS (ESI⁻) m/z 424 [M−H]⁻.

Example 214: 5-{1-fluoro-3-hydroxy-6-[(3-methylbutyl)amino]-5,6,7,8-tetrahydronaphthalen-2-yl}-1λ⁶,2,5-thiadiazolidine-1,1,3-trione (Compound 313)

Example 214A: 5-{3-(benzyloxy)-1-fluoro-6-[(3-methylbutyl)amino]naphthalen-2-yl}-1λ⁶,2,5-thiadiazolidine-1,1,3-trione To a vial were added 5-[3-(benzyloxy)-6-bromo-1-fluoronaphthalen-2-yl]-1λ⁶,2,5-thiadiazolidine-1,1,3-trione (Example 210G, 0.150 g, 0.322 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (0.015 g, 0.016 mmol), 2-(dicyclohexylphosphino)3,6-dimethoxy-2',4',6'-triisopropyl-1,1'-biphenyl (0.009 g, 0.02 mmol), and cesium carbonate (0.315 g, 0.967 mmol). A solution of 3-methylbutan-1-amine (0.056 g, 0.65 mmol) in degassed N,N-dimethylformamide (1.6 mL) was added and the vial was heated to 80° C. After 2 hours, the vial was cooled to ambient temperature and the reaction mixture was partitioned between 1 M hydrochloric acid (40 mL) and ethyl acetate (30 mL). The layers were separated, and the aqueous phase was extracted with ethyl acetate (2×30 mL). The organic layers were combined, washed with brine, dried over sodium sulfate, filtered, and concentrated under reduced pressure. The residue was purified using reversed-phase chromatography [120 g Biotage® Sfär C18 Duo 100 Å 30 μm column, 10-100% gradient of acetonitrile in water (buffered with 0.1% trifluoroacetic acid)] to give the title compound as the corresponding trifluoroacetic acid salt (0.137 g, 0.234 mmol, 73% yield). ¹H NMR (400 MHz, DMSO-d₆) δ ppm 7.67 (d, J=9.0 Hz, 1H), 7.50 (d, J=7.0 Hz, 2H), 7.42-7.35 (m, 2H), 7.35-7.29 (m, 1H), 7.08 (s, 1H), 6.94 (dd, J=9.1, 2.1 Hz, 1H), 6.67 (s, 1H), 5.21 (s, 2H), 4.48 (s, 2H), 3.11 (t, J=7.4 Hz, 2H), 1.72 (dq, J=13.3, 6.7 Hz, 1H), 1.51 (q, J=7.0 Hz, 2H), 0.94 (d, J=6.7 Hz, 6H); MS (ESI⁺) m/z 472.0 [M+H]⁺.

Example 214B: 5-{1-fluoro-3-hydroxy-6-[(3-methylbutyl)amino]naphthalen-2-yl}-1λ⁶,2,5-thiadiazolidine-1,1,3-trione, Trifluoroacetic Acid Salt A flask containing a suspension of the product of Example 214A (0.129 g, 0.220 mmol) and 1,2,3,4,5-pentamethylbenzene (0.098 g, 0.66 mmol) in dichloromethane (2.2 mL) was cooled to −78° C. with stirring under an atmosphere of nitrogen. Next, trichloroborane (1.0 M in dichloromethane) (1.8 mL, 1.8 mmol) was added. The resulting mixture was stirred at −78° C. for 10 minutes, and then the dry ice-acetone bath was replaced with an ice-water bath. One hour later, the flask was recooled to −78° C. The reaction mixture was diluted with dichloromethane (3 mL) and quenched via the successive addition of ethyl acetate (3 mL) and ethanol (3 mL). The mixture was allowed to warm to ambient temperature and stirred for 15 minutes before being concentrated under reduced pressure. The residue was co-evaporated with ethanol (2×5 mL) and purified using reversed-phase chromatography [120 g Biotage® Sfär C18 Duo 100 Å 30 μm column, 10-100% gradient of methanol in water (buffered with 0.1% trifluoroacetic acid)] to give the title compound (0.080 g, 0.21 mmol, 95% yield). ¹H NMR (400 MHz, DMSO-d₆) δ ppm 10.19 (br s, 1H), 7.60 (d, J=9.0 Hz, 1H), 6.85 (dd, J=9.1, 2.1 Hz, 1H), 6.76 (s, 1H), 6.54 (t, J=1.9 Hz, 1H), 4.43 (s, 2H), 3.09 (t, J=7.3 Hz, 2H), 1.73 (dp, J=13.3, 6.6 Hz, 1H), 1.50 (q, J=7.0 Hz, 2H), 0.93 (d, J=6.6 Hz, 6H); MS (APCI⁺) m/z 382.3 [M+H]⁺.

Example 214C: 5-{1-fluoro-3-hydroxy-6-[(3-methylbutyl)amino]-5,6,7,8-tetrahydronaphthalen-2-yl}-1λ⁶,2,5-thiadiazolidine-1,1,3-trione In a Parr shaker, 10% palladium on carbon (0.0674 g, 0.0960 mmol, 50 weight % in water) was added to a solution of the product from Example 214B (0.0674 g, 0.177 mmol) in trifluoroethanol (7 mL). The reactor was purged with nitrogen and then was stirred under hydrogen (120 psi) at 25° C. until hydrogen uptake was complete (5 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (15.3 mg, 0.0400 mol, 22.5% yield). ¹H NMR (600 MHz, DMSO-d₆) δ ppm 9.18 (br s, 1H), 8.41 (br s, 2H), 6.49 (d, J=1.3 Hz, 1H), 3.93 (s, 2H), 3.47-3.42 (m, 1H), 3.11 (dd, J=16.3, 4.5 Hz, 1H), 3.02 (t, J=8.2 Hz, 2H), 2.80 (dt, J=16.7, 4.3 Hz, 1H), 2.73 (dd, J=16.3, 9.9 Hz, 1H), 2.57 (ddd, J=16.8, 10.9, 5.9 Hz, 1H), 2.23-2.17 (m, 1H), 1.75-1.60 (m, 2H), 1.50 (ddt, J=10.1, 8.1, 4.0 Hz, 2H), 0.92 (d, J=6.6 Hz, 6H); MS (ESI⁺) m/z 386 [M+H]⁺.

Example 215: 5-[1-fluoro-3-hydroxy-6-(3-methylbutoxy)-5,6,7,8-tetrahydronaphthalen-2-yl]-1λ⁶,2,5-thiadiazolidine-1,1,3-trione (Compound 314)

Example 215A: 5-[3-(benzyloxy)-1-fluoro-6-(3-methylbutoxy)naphthalen-2-yl]-1λ⁶,2,5-thiadiazolidine-1,1,3-trione To a vial were added the product of Example 211A (0.100 g, 0.249 mmol), 1-bromo-3-methylbutane (0.075 g, 0.50 mmol), cesium carbonate (0.243 g, 0.746 mmol), and N,N-dimethylformamide (0.99 mL). The resulting mixture was stirred at ambient temperature. After 14 hours, the reaction mixture was partitioned between 1 M hydrochloric acid (25 mL) and ethyl acetate (15 mL). The layers were separated, and the aqueous phase was extracted with ethyl acetate (2×10 mL). The organic layers were combined and washed with saturated aqueous ammonium chloride (3×15 mL). The ammonium chloride washes were combined and back extracted with ethyl acetate (15 mL). The organic layers were combined, washed with brine/1 M hydrochloric acid (4:1 v/v) (15 mL), dried over sodium sulfate, filtered, and concentrated under reduced pressure. The residue was purified using reversed-phase chromatography [120 g Agela Claricep™ spherical C18 100 Å 40-60 μm column, 10-100% gradient of acetonitrile in water (buffered with 0.1% trifluoroacetic acid)] to give the title compound (0.092 g, 0.20 mmol, 79% yield). ¹H NMR (500 MHz, DMSO-d₆) δ ppm 7.88 (d, J=9.1 Hz, 1H), 7.53-7.49 (m, 2H), 7.41-7.37 (m, 2H), 7.36-7.30 (m, 3H), 7.12 (dd, J=9.1, 2.4 Hz, 1H), 5.25 (s, 2H), 4.51 (s, 2H), 4.12 (t, J=6.7 Hz, 2H), 1.82 (dp, J=13.4, 6.7 Hz, 1H), 1.68 (q, J=6.7 Hz, 2H), 0.96 (d, J=6.6 Hz, 6H); MS (APCI$^+$) m/z 473.3 [M+H]$^+$.

Example 215B: 5-[1-fluoro-3-hydroxy-6-(3-methylbutoxy)naphthalen-2-yl]-1λ$^6$,2,5-thiadiazolidine-1,1,3-trione A vial was charged with the product of Example 215A (0.090 g, 0.19 mmol), ammonium formate (0.072 g, 1.1 mmol), and ethanol (0.96 mL). The vial was purged with nitrogen, then 10% palladium on carbon (0.020 g, 0.019 mmol) was added. The vial was capped, purged with nitrogen, and heated to 50° C. After 1.5 hours, the vial was cooled to ambient temperature and the reaction mixture was filtered over diatomaceous earth with the aid of methanol. The filtrate was concentrated under reduced pressure. The residue was purified using reversed-phase chromatography [120 g Agela Claricep™ spherical C18 100 Å 40-60 μm column, 10-100% gradient of methanol in water (buffered with 0.1% trifluoroacetic acid)] to give the title compound (0.054 g, 0.14 mmol, 73% yield). $^1$H NMR (500 MHz, DMSO-d$_6$) δ ppm 10.52 (br s, 1H), 7.80 (d, J=9.1 Hz, 1H), 7.21 (t, J=1.9 Hz, 1H), 7.02 (dd, J=9.2, 2.3 Hz, 1H), 7.00 (s, 1H), 4.46 (s, 2H), 4.10 (t, J=6.7 Hz, 2H), 1.81 (dp, J=13.3, 6.7 Hz, 1H), 1.67 (q, J=6.7 Hz, 2H), 0.95 (d, J=6.7 Hz, 6H); MS (APCI$^+$) m/z 383.2 [M+H]$^+$.

Example 215C: 5-[1-fluoro-3-hydroxy-6-(3-methylbutoxy)-5,6,7,8-tetrahydronaphthalen-2-yl]-1λ$^6$,2,5-thiadiazolidine-1,1,3-trione In a Parr shaker, 10% palladium on carbon (0.0912 g, 0.130 mmol, 50 weight % in water) was added to a solution of the product from Example 215B (0.0912 g, 0.238 mmol) in trifluoroethanol (9.5 mL). The reactor was purged with nitrogen and then was stirred under hydrogen (120 psi) at 25° C. until hydrogen uptake was complete (4 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (16.7 mg, 0.0410 mmol, 17.4% yield). $^1$H NMR (600 MHz, DMSO-d$_6$) δ ppm 9.55 (br s, 1H), 6.44 (d, J=1.3 Hz, 1H), 4.17 (s, 2H), 3.71-3.63 (m, 1H), 3.50 (dt, J=9.4, 6.7 Hz, 1H), 3.45 (dt, J=9.4, 6.7 Hz, 1H), 2.90 (dd, J=16.9, 4.5 Hz, 1H), 2.68-2.49 (m, 3H), 1.89 (dtd, J=13.5, 7.6, 6.9, 3.8 Hz, 1H), 1.77-1.66 (m, 1H), 1.63 (dq, J=13.4, 6.7 Hz, 1H), 1.38 (q, J=7.0 Hz, 2H), 0.86 (dd, J=6.6, 2.1 Hz, 6H); MS (ESI$^-$) m/z 385 [M–H]$^-$.

Example 216: 5-{1-fluoro-3-hydroxy-6-[(3-hydroxy-3-methylbutyl)amino]-5,6,7,8-tetrahydronaphthalen-2-yl}-1λ$^6$,2,5-thiadiazolidine-1,1,3-trione (Compound 315)

Example 216A: 5-{3-(benzyloxy)-1-fluoro-6-[(3-hydroxy-3-methylbutyl)amino]naphthalen-2-yl}-1λ$^6$,2,5-thiadiazolidine-1,1,3-trione, trifluoroacetic Acid Salt To a vial were added 5-[3-(benzyloxy)-6-bromo-1-fluoronaphthalen-2-yl]-1λ$^6$,2,5-thiadiazolidine-1,1,3-trione (Example 210G, 0.150 g, 0.322 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (0.015 g, 0.016 mmol), 2-(dicyclohexylphosphino)3,6-dimethoxy-2',4',6'-triisopropyl-1,1'-biphenyl (0.009 g, 0.02 mmol), and cesium carbonate (0.315 g, 0.967 mmol). The vial was sealed, evacuated, and refilled with nitrogen. The evacuation/refill cycle was repeated three additional times. A solution of 4-amino-2-methylbutan-2-ol (0.067 g, 0.65 mmol) in degassed N,N-dimethylformamide (1.6 mL) was added and the vial was heated to 80° C. After 2 hours, the vial was cooled to ambient temperature and the reaction mixture was partitioned between 1 M hydrochloric acid (40 mL) and ethyl acetate (30 mL). The layers were separated, and the aqueous phase was extracted with ethyl acetate (2×30 mL). The organic layers were combined, washed with brine, dried over sodium sulfate, filtered, and concentrated under reduced pressure. The residue was purified using reversed-phase chromatography [120 g Biotage® Sfär C18 Duo 100 Å 30 μm column, 10-100% gradient of acetonitrile in water (buffered with 0.1% trifluoroacetic acid)] to give the title compound (0.098 g, 0.20 mmol, 62% yield). $^1$H NMR (400 MHz, DMSO-d$_6$) δ ppm 7.67 (d, J=9.0 Hz, 1H), 7.50 (d, J=7.0 Hz, 2H), 7.41-7.35 (m, 2H), 7.35-7.30 (m, 1H), 7.09 (s, 1H), 6.92 (dd, J=9.0, 2.1 Hz, 1H), 6.67 (s, 1H), 5.21 (s, 2H), 4.47 (s, 2H), 3.17 (dd, J=9.8, 6.0 Hz, 2H), 1.73 (dd, J=9.8, 6.0 Hz, 2H), 1.18 (s, 6H); MS (ESI$^+$) m/z 487.6 [M+H]$^+$.

Example 216B: 5-{1-fluoro-3-hydroxy-6-[(3-hydroxy-3-methylbutyl)amino]naphthalen-2-yl}-1λ$^6$,2,5-thiadiazolidine-1,1,3-trione A vial was charged with the product of Example 216A (0.092 g, 0.19 mmol), ammonium formate (0.072 g, 1.1 mmol), and ethanol (0.95 mL). The vial was purged with nitrogen, then 10% palladium on carbon (0.020 g, 0.019 mmol) was added. The vial was capped, purged with nitrogen, and heated to 50° C. After 2 hours, the vial was cooled to ambient temperature and the reaction mixture was filtered over diatomaceous earth with the aid of methanol. The filtrate was concentrated under reduced pressure. The residue was purified using reversed-phase chromatography [120 g Biotage® Sfär C18 Duo 100 Å 30 μm column, 10-100% gradient of methanol in water (buffered with 0.1% trifluoroacetic acid)] to give the title compound as the corresponding trifluoroacetic acid salt (0.072 g, 0.14 mmol, 74% yield). $^1$H NMR (600 MHz, DMSO-d$_6$) δ ppm 10.27 (br s, 1H), 7.61 (d, J=9.0 Hz, 1H), 6.85 (dd, J=9.1, 2.2 Hz, 1H), 6.78 (s, 1H), 6.57 (s, 1H), 4.46 (s, 2H), 3.22-3.08 (m, 2H), 1.76-1.67 (m, 2H), 1.17 (s, 6H); MS (APCI$^+$) m/z 398.3 [M+H]$^+$.

Example 216C: 5-{1-fluoro-3-hydroxy-6-[(3-hydroxy-3-methylbutyl)amino]-5,6,7,8-tetrahydronaphthalen-2-yl}-1λ$^6$,2,5-thiadiazolidine-1,1,3-trione In a Parr shaker, 10% palladium on carbon (0.0624 g, 0.0889 mmol, 50 weight % in water) was added to a solution of the product from Example 216B (0.0624 g, 0.122 mmol) in trifluoroethanol (4.9 mL). The reactor was purged with nitrogen and then was stirred under hydrogen (120 psi) at 25° C. until hydrogen uptake was complete (5 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (19.2 mg, 0.0480 mol, 39.2% yield). $^1$H NMR (500 MHz, DMSO-$d_6$) δ ppm 9.17 (br s, 1H), 8.31 (br s, 2H), 6.49 (d, J=1.3 Hz, 1H), 4.58 (br s, 1H), 3.93 (s, 2H), 3.47-3.42 (m, 1H), 3.19-3.04 (m, 3H), 2.84-2.68 (m, 2H), 2.57 (ddd, J=16.8, 10.8, 5.9 Hz, 1H), 2.22-2.16 (m, 1H), 1.76-1.64 (m, 3H), 1.16 (s, 6H); MS (ESI$^+$) m/z 402 [M+H]$^+$.

Example 217: tert-butyl (2-{[5-fluoro-7-hydroxy-6-(1,1,4-trioxo-1$\lambda^6$,2,5-thiadiazolidin-2-yl)-1,2,3,4-tetrahydronaphthalen-2-yl]oxy}ethyl)carbamate (Compound 316)

Example 217A: tert-butyl (2-{[7-(benzyloxy)-5-fluoro-6-(1,1,4-trioxo-1$\lambda^6$,2,5-thiadiazolidin-2-yl)naphthalen-2-yl]oxy}ethyl)carbamate To a vial were added the product of Example 211A (0.100 g, 0.249 mmol), tert-butyl (2-chloroethyl)carbamate (0.223 g, 1.24 mmol), tetrabutylammonium bromide (0.040 g, 0.12 mmol), potassium phosphate tribasic (0.264 g, 1.24 mmol), and N,N-dimethylacetamide (0.99 mL). The vial was heated to 50° C. After 5 hours, the vial was cooled to ambient temperature and the reaction mixture was partitioned between 0.5 M hydrochloric acid (40 mL) and ethyl acetate (20 mL). The layers were separated, and the aqueous phase was extracted with ethyl acetate (2×20 mL). The organic layers were combined and washed with saturated aqueous ammonium chloride (3×15 mL). The ammonium chloride washes were combined and back extracted with ethyl acetate (15 mL). The organic layers were combined, washed with brine/1 M hydrochloric acid (4:1 v/v) (15 mL), dried over sodium sulfate, filtered, and concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound as the corresponding ammonium salt (0.111 g, 0.197 mmol, 79% yield). $^1$H NMR (400 MHz, DMSO-$d_6$-$D_2O$) δ ppm 7.83 (d, J=9.1 Hz, 1H), 7.51-7.46 (m, 2H), 7.34 (t, J=7.3 Hz, 2H), 7.28 (t, J=7.2 Hz, 1H), 7.21-7.13 (m, 2H), 7.05 (dd, J=9.1, 2.3 Hz, 1H), 5.18 (s, 2H), 4.12 (s, 2H), 4.06-4.01 (m, 2H), 3.33 (t, J=5.4 Hz, 2H), 1.32 (s, 9H); MS (APCI$^+$) m/z 446.3 [M-C(O)OC(CH$_3$)$_3$+H]$^+$.

Example 217B: tert-butyl (2-{[5-fluoro-7-hydroxy-6-(1,1,4-trioxo-1$\lambda^6$,2,5-thiadiazolidin-2-yl)naphthalen-2-yl]oxy}ethyl)carbamate A vial was charged with the product of Example 217A (0.108 g, 0.192 mmol), ammonium formate (0.073 g, 1.2 mmol), and ethanol (0.96 mL). The vial was purged with nitrogen, then 10% palladium on carbon (0.020 g, 0.019 mmol) was added. The vial was capped, purged with nitrogen, and heated to 50° C. After 1 hour, the vial was cooled to ambient temperature and the reaction mixture was filtered over diatomaceous earth with the aid of methanol. The filtrate was concentrated under reduced pressure. The residue was purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound as the corresponding ammonium salt (0.081 g, 0.17 mmol, 90% yield). $^1$H NMR (400 MHz, DMSO-$d_6$-$D_2O$) δ ppm 7.78 (d, J=9.0 Hz, 1H), 7.08 (t, J=1.9 Hz, 1H), 6.98 (dd, J=9.2, 2.4 Hz, 1H), 6.95 (s, 1H), 4.10 (s, 2H), 4.02 (t, J=5.6 Hz, 2H), 3.33 (t, J=5.5 Hz, 2H), 1.34 (s, 9H); MS (APCI$^+$) m/z 397.3 [M-C(O)OC(CH$_3$)$_3$+CH$_3$CN+H]$^+$.

Example 217C: tert-butyl (2-{[5-fluoro-7-hydroxy-6-(1,1,4-trioxo-1$\lambda^6$,2,5-thiadiazolidin-2-yl)-1,2,3,4-tetrahydronaphthalen-2-yl]oxy}ethyl)carbamate, Ammonium Salt In a Parr shaker, 10% palladium on carbon (0.16 g, 0.057 mmol, 50 weight % in water) was added to a solution of the product from Example 217B (0.0772 g, 0.169 mmol) in trifluoroethanol (2 mL). The reactor was purged with nitrogen and then was stirred under hydrogen (120 psi) at 25° C. until hydrogen uptake was complete (4 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (34.8 mg, 0.073 mmol, 43.1% yield). $^1$H NMR (600 MHz, DMSO-$d_6$) δ ppm 9.31 (br s, 1H), 6.75 (t, J=5.6 Hz, 1H), 6.42 (s, 1H), 4.07 (s, 2H), 3.76-3.67 (m, 1H), 3.47 (dt, J=9.7, 6.2 Hz, 1H), 3.42 (dt, J=9.7, 6.0 Hz, 1H), 3.05 (q, J=6.0 Hz, 2H), 2.89 (dd, J=16.9, 4.5 Hz, 1H), 2.62 (td, J=18.3, 17.2, 6.5 Hz, 2H), 2.56-2.47 (m, 1H), 1.87 (s, 1H), 1.73 (dq, J=13.3, 7.1 Hz, 1H), 1.37 (s, 9H); MS (ESI$^-$) m/z 458 [M–H]$^-$.

Example 218: 5-(1-fluoro-3-hydroxy-6-methoxy-5,6,7,8-tetrahydronaphthalen-2-yl)-1$\lambda^6$,2,5-thiadiazolidine-1,1,3-trione (Compound 317)

Example 218A: 5-[3-(benzyloxy)-1-fluoro-6-methoxynaphthalen-2-yl]-1$\lambda^6$,2,5-thiadiazolidine-1,1,3-trione To a vial were added 5-[3-(benzyloxy)-6-bromo-1-fluoronaphthalen-2-yl]-1$\lambda^6$,2,5-thiadiazolidine-1,1,3-trione (Example 210G, 0.075 g, 0.16 mmol), tris(dibenzylideneacetone)dipalladium(0) (0.007 g, 0.008 mmol), di-tert-butyl (2',4',6'-triisopropyl-3,6-dimethoxy-[1,1'-biphenyl]-2-yl)phosphine (0.009 g, 0.02 mmol), and cesium carbonate (0.110 g, 0.338 mmol). The vial was sealed, evacuated, and refilled with nitrogen. The evacuation/refill cycle was repeated three additional times. Next, a solution of methanol (0.039 mL, 0.97 mmol) in degassed dimethylacetamide (0.40 mL) was added. The vial was heated to 60° C. After 14 hours, the vial was cooled to ambient temperature and the reaction mixture was partitioned between 1 M hydrochloric acid (25 mL) and ethyl acetate (25 mL). The layers were separated, and the aqueous phase was extracted with ethyl acetate (2×20 mL). The organic layers were combined, washed with brine, dried over sodium sulfate, filtered, and concentrated under reduced pressure. The residue was purified using reversed-phase chromatography [60 g Biotage® Sfär C18 Duo 100 Å 30 μm column, 10-100% gradient of methanol in water (buffered with 0.025 M aqueous ammonium bicarbonate, adjusted to pH 7 with dry ice)] to give the title compound as the corresponding ammonium salt (0.046 g, 0.11 mmol, 66% yield). $^1$H NMR (500 MHz, DMSO-$d_6$) δ ppm 7.84 (d, J=9.1 Hz, 1H), 7.59-7.52 (m, 2H), 7.40-7.34

(m, 2H), 7.33-7.28 (m, 1H), 7.26-7.22 (m, 2H), 7.11 (br s, 3H), 7.09 (dd, J=9.1, 2.4 Hz, 1H), 5.25 (s, 2H), 4.07 (s, 2H), 3.87 (s, 3H); MS (APCI$^+$) m/z 417.0 [M+H]$^+$.

Example 218B: 5-(1-fluoro-3-hydroxy-6-methoxynaphthalen-2-yl)-1$\lambda^6$,2,5-thiadiazolidine-1,1,3-trione A flask containing a suspension of the product of Example 218A (0.083 g, 0.19 mmol) and 1,2,3,4,5-pentamethylbenzene (0.085 g, 0.57 mmol) in dichloromethane (1.9 mL) was cooled to −78° C. with stirring under an atmosphere of nitrogen. Next, trichloroborane (1.0 M in dichloromethane) (1.5 mL, 1.5 mmol) was added. The resulting mixture was stirred at −78° C. for 10 minutes, and then the dry ice-acetone bath was replaced with an ice-water bath. One hour later, the flask was recooled to −78° C. The reaction mixture was diluted with dichloromethane (3 mL) and quenched via the successive addition of ethyl acetate (3 mL) and ethanol (3 mL). The mixture was allowed to warm to ambient temperature and stirred for 15 minutes before being concentrated under reduced pressure. The residue was co-evaporated with ethanol (2×5 mL) and purified using reversed-phase chromatography [120 g Agela Claricep™ spherical C18 100 Å 40-60 μm column, 10-100% gradient of methanol in water (buffered with 0.025 M aqueous ammonium bicarbonate, adjusted to pH 7 with dry ice)] to give the title compound as the corresponding ammonium salt (0.052 g, 0.15 mmol, 79% yield). $^1$H NMR (600 MHz, DMSO-d$_6$) δ ppm 7.77 (d, J=9.1 Hz, 1H), 7.58 (br s, 3H), 7.13 (t, J=1.8 Hz, 1H), 6.99 (dd, J=9.1, 2.5 Hz, 1H), 6.97 (s, 1H), 4.07 (s, 2H), 3.84 (s, 3H); MS (ESI$^-$) m/z 325.0 (M−H)$^-$.

Example 218C: 5-(1-fluoro-3-hydroxy-6-methoxy-5,6,7,8-tetrahydronaphthalen-2-yl)-1$\lambda^6$,2,5-thiadiazolidine-1,1,3-trione In a Parr shaker, 10% palladium on carbon (0.0582 g, 0.0829 mmol, 50 weight % in water) was added to a solution of the product from Example 218B (0.0582 g, 0.178 mmol) in trifluoroethanol (7.1 mL). The reactor was purged with nitrogen and then was stirred under hydrogen (120 psi) at 25° C. until hydrogen uptake was complete (4 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound as the corresponding ammonium salt (24.3 mg, 0.070 mmol, 39.2% yield). $^1$H NMR (600 MHz, DMSO-d$_6$) δ ppm 8.96 (br s, 1H), 7.13 (br s, 4H), 6.41 (d, J=1.4 Hz, 1H), 3.93 (s, 2H), 3.63-3.55 (m, 1H), 3.28 (s, 3H), 2.88 (dd, J=16.7, 4.4 Hz, 1H), 2.67-2.55 (m, 2H), 2.56-2.46 (m, 1H), 1.95-1.85 (m, 1H), 1.73 (dq, J=13.6, 7.1 Hz, 1H); MS (ESI$^-$) m/z 329 [M−H]$^-$.

Example 219: 5-{6-[(cyclopropylmethyl)amino]-1-fluoro-3-hydroxy-5,6,7,8-tetrahydronaphthalen-2-yl}-1$\lambda^6$,2,5-thiadiazolidine-1,1,3-trione (Compound 318)

Example 219A: 5-{3-(benzyloxy)-6-[(cyclopropylmethyl)amino]-1-fluoronaphthalen-2-yl}-1$\lambda^6$,2,5-thiadiazolidine-1,1,3-trione To a vial were added 5-[3-(benzyloxy)-6-bromo-1-fluoronaphthalen-2-yl]-1$\lambda^6$,2,5-thiadiazolidine-1,1,3-trione (Example 210G, 0.150 g, 0.322 mmol), [(2-di-cyclohexylphosphino-3,6-dimethoxy-2',4',6'-triisopropyl-1,1'-biphenyl)-2-(2'-amino-1,1'-biphenyl)]palladium(II) methanesulfonate (0.015 g, 0.016 mmol), 2-(dicyclohexylphosphino)3,6-dimethoxy-2',4',6'-triisopropyl-1,1'-biphenyl (0.009 g, 0.02 mmol), and cesium carbonate (0.315 g, 0.967 mmol). A solution of cyclopropylmethanamine (0.046 g, 0.65 mmol) in degassed N,N-dimethylformamide (1.6 mL) was added and the vial was heated to 80° C. After 2 hours, the vial was cooled to ambient temperature and the reaction mixture was partitioned between 1 M hydrochloric acid (40 mL) and ethyl acetate (30 mL). The layers were separated, and the aqueous phase was extracted with ethyl acetate (2×30 mL). The organic layers were combined, washed with brine, dried over sodium sulfate, filtered, and concentrated under reduced pressure. The residue was purified using reversed-phase chromatography [120 g Biotage® Sfär C18 Duo 100 Å 30 μm column, 10-100% gradient of acetonitrile in water (buffered with 0.1% trifluoroacetic acid)] to give the title compound as the corresponding trifluoroacetic acid salt (0.149 g, 0.261 mmol, 81% yield). $^1$H NMR (400 MHz, DMSO-d$_6$) δ ppm 7.69 (d, J=9.0 Hz, 1H), 7.53-7.46 (m, 2H), 7.42-7.35 (m, 2H), 7.35-7.29 (m, 1H), 7.09 (s, 1H), 7.00 (dd, J=9.0, 2.1 Hz, 1H), 6.72 (s, 1H), 5.21 (s, 2H), 4.50 (s, 2H), 3.01 (d, J=6.7 Hz, 2H), 1.21-1.00 (m, 1H), 0.58-0.45 (m, 2H), 0.33-0.20 (m, 2H); MS (ESI$^+$) m/z 455.7 [M+H]$^+$.

Example 219B: 5-{6-[(cyclopropylmethyl)amino]-1-fluoro-3-hydroxynaphthalen-2-yl}-1$\lambda^6$,2,5-thiadiazolidine-1,1,3-trione A flask containing a suspension of the product of Example 219A (0.142 g, 0.249 mmol) and 1,2,3,4,5-pentamethylbenzene (0.111 g, 0.748 mmol) in dichloromethane (2.5 mL) was cooled to −78° C. with stirring under an atmosphere of nitrogen. Next, trichloroborane (1.0 M in dichloromethane) (2.0 mL, 2.0 mmol) was added. The resulting mixture was stirred at −78° C. for 10 minutes, and then the dry ice-acetone bath was replaced with an ice-water bath. One hour later, the flask was recooled to −78° C. The reaction mixture was diluted with dichloromethane (3 mL) and quenched via the successive addition of ethyl acetate (3 mL) and ethanol (3 mL). The mixture was allowed to warm to ambient temperature and stirred for 15 minutes before being concentrated under reduced pressure. The residue was co-evaporated with ethanol (2×5 mL) and purified using reversed-phase chromatography [120 g Biotage® Sfär C18 Duo 100 Å 30 μm column, 10-100% gradient of methanol in water (buffered with 0.1% trifluoroacetic acid)] to give the title compound as the corresponding trifluoroacetic acid salt (0.093 g, 0.19 mmol, 78% yield). $^1$H NMR (400 MHz, DMSO-d$_6$) δ ppm 10.28 (br s, 1H), 7.62 (d, J=9.1 Hz, 1H), 6.92 (dd, J=9.1, 2.1 Hz, 1H), 6.77 (s, 1H), 6.59 (s, 1H), 4.45 (s, 2H), 2.99 (d, J=6.7 Hz, 2H), 1.16-1.03 (m, 1H), 0.53-0.47 (m, 2H), 0.28-0.23 (m, 2H); MS (APCI$^+$) m/z 366.3 [M+H]$^+$.

Example 219C: 5-{6-[(cyclopropylmethyl)amino]-1-fluoro-3-hydroxy-5,6,7,8-tetrahydronaphthalen-2-yl}-1$\lambda^6$,2,5-thiadiazolidine-1,1,3-trione In a Parr shaker, 10% palladium on carbon (0.0674 g, 0.0960 mmol, 50 weight % in water) was added to a solution of the product from Example 219B (0.0674 g, 0.140 mmol) in trifluoroethanol (5.6 mL). The reactor was purged with nitrogen and then was stirred under hydrogen (120 psi) at 25° C. until hydrogen uptake was complete (5 days). The reactor was purged with nitrogen, and the crude reaction mixture was filtered, washing the solid with methanol. Celite® (1 g) was added to the filtrate, and the resulting mixture was then concentrated in vacuo to give a solid which was dry loaded onto a Teledyne ISCO 50 g reversed-phase C18 column and eluted with a gradient of 10 to 100% methanol in buffer (0.025 M aqueous ammonium bicarbonate, adjusted to pH 7 with dry ice) observing at 206 nM, to give the title compound (24.8 mg, 0.067 mol, 47.8% yield). $^1$H NMR (500 MHz, DMSO-$d_6$) δ ppm 9.16 (br s, 1H), 8.47 (br s, 2H), 6.47 (s, 1H), 3.93 (s, 2H), 3.07 (dd, J=16.4, 5.0 Hz, 1H), 2.97-2.85 (m, 2H), 2.83-2.76 (m, 1H), 2.71 (dd, J=16.4, 10.0 Hz, 1H), 2.56 (td, J=10.9, 5.3 Hz, 1H), 2.20 (d, J=10.0 Hz, 1H), 1.68 (qd, J=11.3, 5.6 Hz, 1H), 1.04 (tt, J=7.6, 4.6 Hz, 1H), 0.63-0.56 (m, 2H), 0.39-0.32 (m, 2H); MS (ESI$^+$) m/z 370 [M+H]$^+$.

Example 220: 5-[6-(2-aminoethoxy)-1-fluoro-3-hydroxy-5,6,7,8-tetrahydronaphthalen-2-yl]-1λ$^6$,2,5-thiadiazolidine-1,1,3-trione (Compound 319)

To a suspension of the product of Example 217 (11.6 mg, 0.0240 mmol) in 1,2-dichloroethane (0.45 mL) was added trifluoroacetic acid (0.090 mL, 1.168 mmol). After 1 hour the reaction mixture was sonicated for 2 minutes and then stirring continued. After 2 hours, the reaction mixture was sonicated for 2 minutes and then diluted with methanol (0.5 mL) and acetonitrile (0.5 mL). The resulting solution was concentrated, and the residue was dissolved in 1:1 methanol/acetonitrile (1 mL), Celite® (1 g) was added and the resulting mixture was concentrated under reduced pressure to give a powder. The solid was dry loaded onto a 50 g Teledyne ISCO reversed-phase C18 column and eluted with a gradient of 10 to 100% methanol in buffer (0.025 M ammonium bicarbonate in water, adjusted to pH 7 with dry ice) to give the title compound (5.9 mg, 0.016 mmol, 67.3% yield). $^1$H NMR (500 MHz, DMSO-$d_6$) δ ppm 7.73 (br s, 4H), 6.43 (s, 1H), 3.95 (d, J=13.1 Hz, 1H), 3.91 (d, J=13.1 Hz, 1H), 3.83-3.75 (m, 1H), 3.66 (dt, J=10.4, 5.2 Hz, 1H), 3.60 (dt, J=10.5, 5.2 Hz, 1H), 3.00-2.89 (m, 3H), 2.68 (dq, J=19.8, 7.0, 6.5 Hz, 2H), 2.59-2.50 (m, 1H), 1.92-1.80 (m, 2H); MS (APCI$^+$) m/z 360 [M+H]$^+$.

Example 221: 5-{2-[2-(3,5-dimethyl-1H-pyrazol-4-yl)ethyl]-4,4,8-trifluoro-6-hydroxy-1,2,3,4-tetrahydroisoquinolin-7-yl}-1λ$^6$,2,5-thiadiazolidine-1,1,3-trione (Compound 320)

Example 221A: ethyl 2-(3,5-dimethyl-1-((2-(trimethylsilyl)ethoxy)methyl)-1H-pyrazol-4-yl)acetate To a solution of the product of Example 127B (450 mg, 2.470 mmol) and Cs$_2$CO$_3$ (1609 mg, 4.94 mmol) in acetonitrile (5 mL) was added 2-(trimethylsilyl)ethoxymethyl chloride (SEM-Cl, 0.657 mL, 3.70 mmol) dropwise at 0° C. The mixture was stirred at 20° C. under N2 for 12 hours. The reaction mixture was diluted with water (20 mL) and extracted with ethyl acetate (3×5 mL). The combined organic layers were washed with brine (3×5 mL), dried over Na$_2$SO$_4$ and concentrated under reduced pressure. The residue was purified by flash column chromatography (petroleum ether:ethyl acetate=20:1) to give the title compound (630 mg, 2.02 mmol, 82% yield). MS (ESI$^+$) m/z 313 [M+H]$^+$.

Example 221B: 2-(3,5-dimethyl-1-((2-(trimethylsilyl)ethoxy)methyl)-1H-pyrazol-4-yl)ethanol The title compound was prepared from the product of Example 221A using the procedures described for Example 127D in 98% yield. MS (ESI$^+$) m/z 271 [M+H]$^+$.

Example 221C: 2-(3,5-dimethyl-1-((2-(trimethylsilyl)ethoxy)methyl)-1H-pyrazol-4-yl)acetaldehyde The title compound was prepared from the product of Example 221B using the procedures described for Example 127E in 55% yield. $^1$H NMR (400 MHz, CDCl$_3$) δ ppm −0.10-0.02 (m, 9H), 0.80-0.95 (m, 2H), 2.18 (s, 3H), 2.21-2.31 (m, 3H), 3.42 (d, J=2.38 Hz, 2H), 3.49-3.62 (m, 2H), 5.19-5.44 (m, 2H), 9.58 (t, J=2.31 Hz, 1H).

Example 221D: 5-{6-(benzyloxy)-2-[2-(3,5-dimethyl-1-{[2-(trimethylsilyl)ethoxy]methyl}-1H-pyrazol-4-yl)ethyl]-4,4,8-trifluoro-1,2,3,4-tetrahydroisoquinolin-7-yl}-1λ$^6$,2,5-thiadiazolidine-1,1,3-trione The title compound was prepared using the procedures described for Example 127Q from the product of Example 221C in 53.2% yield. $^1$H NMR (400 MHz, CDCl$_3$) δ ppm −0.05 (s, 9H), 0.73-0.92 (m, 3H), 1.01 (br s, 3H), 1.16-1.39 (m, 3H), 1.96 (br s, 3H), 2.50 (br s, 4H), 2.77-3.06 (m, 2H), 3.50-3.57 (m, 2H), 4.22 (br s, 2H), 4.96 (br s, 2H), 5.25 (br s, 2H), 6.73-7.26 (m, 6H).

Example 221E: 5-{2-[2-(3,5-dimethyl-1H-pyrazol-4-yl)ethyl]-4,4,8-trifluoro-6-hydroxy-1,2,3,4-tetrahydroisoquinolin-7-yl}-1λ$^6$,2,5-thiadiazolidine-1,1,3-trione The title compound was prepared using the procedures described for Example 127R from the product of Example 221D in 25.4% yield. $^1$H NMR (400 MHz, methanol-$d_4$) δ ppm 2.20 (s, 6H), 2.49-2.79 (m, 4H), 3.15 (br t, J=11.82 Hz, 2H), 3.72 (s, 2H), 4.30 (s, 2H), 6.89-7.09 (m, 1H), 7.00 (s, 1H); MS (ESI$^−$) m/z 458 [M−H]$^−$.

Example 222: N-(cyclohexylmethyl)-8-fluoro-6-hydroxy-7-(1,1,4-trioxo-1λ$^6$,2,5-thiadiazolidin-2-yl)-3,4-dihydroisoquinoline-2(1H)-carboxamide (Compound 321)

Example 222A: 6-(benzyloxy)-N-(cyclohexylmethyl)-8-fluoro-7-(1,1,4-trioxo-1λ$^6$,2,5-thiadiazolidin-2-yl)-3,4-dihydroisoquinoline-2(1H)-carboxamide The title compound was prepared from cyclohexylmethanamine using the procedures described for Example 159A. MS (APCI$^+$) m/z 531.2 [M+H]$^+$.

Example 222B: N-(cyclohexylmethyl)-8-fluoro-6-hydroxy-7-(1,1,4-trioxo-1λ$^6$,2,5-thiadiazolidin-2-yl)-3,4-dihydroisoquinoline-2(1H)-carboxamide The title compound was prepared from the above Example 222A using the procedures described for Example 159B in 33% yield (for 2 steps). $^1$H NMR (600 MHz, DMSO-$d_6$) δ ppm 7.06 (s, 3H), 6.60 (t, J=5.6 Hz, 1H), 6.49 (d, J=1.2 Hz, 1H), 4.35 (s, 2H), 3.94 (s, 2H), 3.50 (t, J=5.8 Hz, 2H), 2.88 (t, J=7.0 Hz, 2H), 2.65 (t, J=5.8 Hz, 2H), 1.68-1.56 (m, 6H), 1.41 (m, 1H), 1.13 (m, 2H), 0.82 (m, 2H); MS (APCI$^+$) m/z 441.2 [M+H]$^+$.

Example 223: N-[8-fluoro-6-hydroxy-7-(1,1,4-trioxo-1λ$^6$,2,5-thiadiazolidin-2-yl)-1,2,3,4-tetrahydronaphthalen-2-yl]acetamide (Compound 322)

Example 223A: 5-[7-amino-3-(benzyloxy)-1-fluoro-5,6,7,8-tetrahydronaphthalen-2-yl]-1λ$^6$,2,5-thiadiazolidine-1,1,3-trione To a solution of 5-[3-(benzyloxy)-1-fluoro-7-oxo-5,6,7,8-tetrahydronaphthalen-2-yl]-1λ$^6$,2,5-thiadiazolidine-1,1,3-trione (0.2 g, 0.495 mmol, Example 67F) in methanol (5 mL) was added ammonium acetate (1.8 g, 23.35 mmol) at room temperature. After 1 hour, NaBH$_3$CN (0.047 g, 0.742 mmol) was added to the suspension. The mixture was stirred at room temperature for 18 hours before it was diluted with N,N-dimethylformamide, purified by preparative HPLC on a Phenomenex® Luna® 10 m C18 column (30 mm×250 mm) eluted with a gradient of acetonitrile (A) and 0.1% trifluoroacetic acid in water (B) at a flow rate of 50 mL/minute (0-1 minute 10% A, 1-20 minutes linear gradient 10-90%) to give the title compound as a trifluoroacetic acid salt (85 mg, 0.164 mmol, 33.1% yield). $^1$H NMR (500 MHz, DMSO-d$_6$) δ ppm 7.99 (d, J=5.3 Hz, 3H), 7.51-7.45 (m, 2H), 7.39-7.32 (m, 2H), 7.34-7.27 (m, 1H), 6.79 (s, 1H), 5.13 (s, 2H), 4.09 (s, 2H), 3.46 (m, 1H), 3.05 (dd, J=16.3, 5.5 Hz, 1H), 2.84 (m, 2H), 2.55 (d, J=9.6 Hz, 1H), 2.07 (m, 1H), 1.72 (m, 1H); MS (APCI$^+$) m/z 406.1 [M+H]$^+$.

Example 223B: N-[6-(benzyloxy)-8-fluoro-7-(1,1,4-trioxo-1λ$^6$,2,5-thiadiazolidin-2-yl)-1,2,3,4-tetrahydronaphthalen-2-yl]acetamide To a suspension of the product from Example 223A (43 mg, 0.106 mmol) and triethylamine (53.7 mg, 0.530 mmol) in tetrahydrofuran-dichloromethane (2:1 ratio, 1 mL) at 23° C. was added acetic anhydride (21.65 mg, 0.212 mmol) at 23° C. to give a solution. The mixture was stirred at 23° C. for 0.5 hour. The reaction mixture was concentrated in vacuo. The residue was purified by chromatography on silica gel eluted with 1-10% methanol in dichloromethane to give the title compound as a triethylamine salt (46 mg, 0.084 mmol, 79% yield). $^1$H NMR (400 MHz, methanol-d$_4$) δ ppm 7.53-7.47 (m, 2H), 7.38-7.30 (m, 2H), 7.30-7.22 (m, 1H), 6.69 (d, J=1.6 Hz, 1H), 5.13 (s, 2H), 4.56 (s, 2H), 4.28 (d, J=14.0 Hz, 1H), 4.22 (d, J=14.0 Hz, 1H), 4.07 (m, 1H), 3.19 (q, J=7.3 Hz, 6H), 3.01 (dd, J=16.6, 5.6 Hz, 1H), 2.86 (dd, J=7.5, 5.4 Hz, 2H), 2.49 (dd, J=16.6, 8.8 Hz, 1H), 1.99 (m, 1H), 1.95 (s, 3H), 1.72 (m, 1H), 1.30 (t, J=7.3 Hz, 9H).

Example 223C: N-[8-fluoro-6-hydroxy-7-(1,1,4-trioxo-1λ$^6$,2,5-thiadiazolidin-2-yl)-1,2,3,4-tetrahydronaphthalen-2-yl]acetamide A mixture of the above product from Example 223B, N-[6-(benzyloxy)-8-fluoro-7-(1,1,4-trioxo-1λ$^6$,2,5-thiadiazolidin-2-yl)-1,2,3,4-tetrahydronaphthalen-2-yl]acetamide, triethylamine (73 mg, 0.133 mmol) and 5% Pd/C (72 mg) in tetrahydrofuran (4 mL) was stirred under hydrogen (80 psi) at room temperature for 2.5 hours. The crude reaction mixture was filtered through a pad of diatomaceous earth and concentrated. The residue was purified by chromatography on silica gel eluted with 1-10% methanol in dichloromethane to give the title compound (50 mg, 0.11 mmol, 82% yield) as a triethylamine salt. $^1$H NMR (600 MHz, DMSO-d$_6$) δ ppm 9.02 (s, 1H), 8.86 (s, 1H), 7.92 (d, J=7.2 Hz, 1H), 6.43 (d, J=1.3 Hz, 1H), 3.96-3.86 (m, 3H), 3.09 (q, J=7.3 Hz, 6H), 2.85-2.79 (m, 1H), 2.78-2.64 (m, 2H), 2.34 (dd, J=16.4, 8.8 Hz, 1H), 1.89-1.83 (m, 1H), 1.82 (s, 3H), 1.57 (m, 1H), 1.17 (t, J=7.3 Hz, 9H); MS (APCI$^+$) m/z 358.5 [M+H]$^+$.

An aliquot (25 mg) of the triethylamine salt product obtained above was purified by preparative HPLC on Phenomenex® Luna® 10 m C18 columns (30 mm×250 mm) eluted with a gradient of acetonitrile (A) and 0.1% trifluoroacetic acid in water (B) at a flow rate of 50 mL/minute (0-1 minute 5% A, 1-20 minutes linear gradient 10-50%) to give the title compound as a free base (15 mg). $^1$H NMR (500 MHz, DMSO-d$_6$) δ ppm 9.97 (s, 1H), 7.93 (d, J=7.2 Hz, 1H), 6.48 (s, 1H), 4.31 (s, 2H), 3.93-3.86 (m, 1H), 2.84 (dd, J=16.4, 5.6 Hz, 1H), 2.81-2.66 (m, 2H), 2.35 (dd, J=16.3, 8.8 Hz, 1H), 1.89-1.83 (m, 1H), 1.82 (s, 3H), 1.64-1.53 (m, 1H); MS (APCI$^-$) m/z 356.4 [M−H]$^-$.

Example 224: 5-[1-fluoro-3-hydroxy-7-(4-methylpentyl)-5,6,7,8-tetrahydronaphthalen-2-yl]-1λ$^6$,2,5-thiadiazolidine-1,1,3-trione (Compound 323)

Example 224A: 5-[3-(benzyloxy)-1-fluoro-7-(4-methylpent-1-yn-1-yl)naphthalen-2-yl]-1λ$^6$,2,5-thiadiazolidine-1,1,3-trione, Ammonium Salt To a 20 mL pressure release vial were added the product of Example 1G (0.500 g, 1.08 mmol), [1,1'-bis(di-tert-butylphosphino)ferrocene]dichloropalladium(II) (0.021 g, 0.032 mmol), and copper(I) iodide (0.020 g, 0.11 mmol). The vial was capped, evacuated, and refilled with nitrogen. Thereafter, N,N-dimethylformamide (5 mL), triethylamine (1.50 mL, 10.8 mmol), and 4-methyl-1-pentyne (0.253 mL, 2.15 mmol) were added. The vial was evacuated and refilled with nitrogen five times and then heated to 60° C. After 26 hours, the vial was cooled to ambient temperature. Additional [1,1'-bis(di-tert-butylphosphino)ferrocene]dichloropalladium(II) (0.021 g, 0.032 mmol) and copper(I) iodide (0.020 g, 0.11 mmol) were added. The vial was evacuated and refilled with nitrogen three times, then more 4-methyl-1-pentyne (0.253 mL, 2.15 mmol) was added. The vial was again heated to 60° C. Forty-one hours later, the vial was cooled to ambient temperature and the reaction was quenched with 1 M sodium hydrogen sulfate (15 mL). The resulting mixture was extracted with ethyl acetate (3×10 mL). The organic layers were combined, washed with brine/1 M hydrochloric acid (4:1 v/v) (5 mL), dried over sodium sulfate, and filtered. The filtrate was loaded onto diatomaceous earth (2 g), concentrated under reduced pressure, and purified using reversed-phase chromatography [100 g Isco RediSep Rf Gold® C18 column, 10-100% gradient of methanol in water (buffered with 0.025 M aqueous ammonium bicarbonate, adjusted to pH 7 with dry ice)] to give the title compound (0.223 g, 0.462 mmol, 43% yield). MS (ESI$^-$) m/z 465.0 [M−H]$^-$.

Example 224B: 5-(1-fluoro-3-hydroxy-7-(4-methylpentyl)-5,6,7,8-tetrahydronaphthalen-2-yl)-1,2,5-thiadiazolidin-3-one 1,1-dioxide, Ammonium Salt To a 20 mL Barnstead Hast C reactor containing 10% palladium hydroxide on carbon (0.44 g, 1.6 mmol) were added 5-[3-(benzyloxy)-1-fluoro-7-(4-methylpent-1-yn-1-yl)naphthalen-2-yl]-1λ$^6$,2,5-thiadiazolidine-1,1,3-trione, ammonium salt (0.223 g, 0.462 mmol) and 2,2,2-trifluoroethanol (10 mL). The resulting mixture was stirred at 35°

C. for 20 hours under an atmosphere of hydrogen at 56 psi. The catalyst was then removed by filtration and washed with methanol. The filtrate was loaded onto diatomaceous earth (2 g), concentrated under reduced pressure, and purified using reversed-phase chromatography [100 g Isco RediSep Rf Gold® C18 column, 10-100% gradient of methanol in water (buffered with 0.025 M aqueous ammonium bicarbonate, adjusted to pH 7 with dry ice)] to give the title compound (0.0987 g, 0.246 mmol, 53% yield). $^1$H NMR (600 MHz, DMSO-$d_6$) δ ppm 8.92 (br s, 1H), 7.09 (br s, 4H), 6.41 (d, J=1.3 Hz, 1H), 3.93 (d, J=1.0 Hz, 2H), 2.75-2.58 (m, 3H), 2.04 (dd, J=16.5, 10.4 Hz, 1H), 1.85-1.79 (m, 1H), 1.61-1.50 (m, 2H), 1.40-1.29 (m, 4H), 1.25 (dtd, J=12.7, 11.0, 5.6 Hz, 1H), 1.20-1.13 (m, 2H), 0.87 (d, J=6.6 Hz, 6H); MS (APCI$^+$) m/z 402.4 [M+NH$_4$]$^+$.

Example 225: 5-(8-fluoro-6-hydroxy-2-{[(2S)-5-oxopyrrolidin-2-yl]methyl}-1,2,3,4-tetrahydroisoquinolin-7-yl)-1λ$^6$,2,5-thiadiazolidine-1,1,3-trione (Compound 324)

Example 225A: 5-[6-(benzyloxy)-8-fluoro-2-{[(2S)-5-oxopyrrolidin-2-yl]methyl}-1,2,3,4-tetrahydroisoquinolin-7-yl]-1λ$^6$,2,5-thiadiazolidine-1,1,3-trione A suspension of the product of Example 54A (nominally 0.315 mmol, 1 equivalent), potassium carbonate (218 mg, 1.58 mmol, 5.0 equivalents), and (S)-5-(bromomethyl)pyrrolidin-2-one (79 mg, 0.44 mmol, 1.4 equivalents) in acetonitrile (1.00 mL, ~0.3 M) was sealed in a 1 dram vial. The sealed reaction vessel was placed in a heating block that had been preheated to 70° C. The reaction mixture was stirred for 20 hours at 70° C. The product mixture was cooled to 23° C. The cooled product mixture was carefully poured into a stirred mixture of aqueous hydrochloric acid solution (3 M, 5 mL), water (10 mL), and ethyl acetate (15 mL). The mixture was stirred for 10 minutes at 23° C. The mixture was then transferred to a separatory funnel and the layers that formed were separated. The aqueous layer was extracted with ethyl acetate (2×10 mL). The aqueous layer was concentrated. The solid residue obtained was triturated with methanol (5×6 mL). The supernatants were combined and filtered through a plug of diatomaceous earth (0.5 cm×1.0 cm). The filter cake was rinsed with methanol (3×3 mL). The filtrates were combined, and the combined filtrates were concentrated. The residue obtained was used without further purification in the following step. MS (APCI$^-$) m/z 487 [M-H]$^-$.

Example 225B: 5-(8-fluoro-6-hydroxy-2-{[(2S)-5-oxopyrrolidin-2-yl]methyl}-1,2,3,4-tetrahydroisoquinolin-7-yl)-1λ$^6$,2,5-thiadiazolidine-1,1,3-trione A suspension of palladium on carbon (10% weight, 17 mg, 0.02 mmol, 5 mol %), the product of Example 225A (nominally 0.315 mmol, 1 equivalent), and ammonium formate (60 mg, 0.95 mmol, 3.0 equivalents) in ethanol (4.0 mL) was stirred for 3 hours at 23° C. The reaction vessel was placed in a heating block that had been preheated to 50° C. The reaction mixture was stirred for 2 hours at 50° C. The reaction mixture was cooled to 23° C. Additional palladium on carbon (10% weight, 17 mg, 0.02 mmol, 5 mol %) and ammonium formate (72 mg, 1.14 mmol, 3.6 equivalents) was added. The reaction vessel was placed in a heating block that had been preheated to 60° C. The reaction mixture was stirred for 2 hours at 60° C. The product mixture was then cooled to 23° C. The cooled mixture was filtered through a plug of diatomaceous earth (0.5 cm×1.0 cm). The filter cake was washed with methanol (3×3 mL). The filtrates were combined, and the combined filtrates were concentrated. The residue obtained was purified by reversed-phase flash column chromatography (30 g RediSep Rf Gold® C18 column, eluted with a gradient of 5-100% methanol-0.025 M aqueous ammonium bicarbonate solution [acidified with solid carbon dioxide]) to furnish the title compound (55 mg, 0.14 mmol, 42% yield, three steps). $^1$H NMR (500 MHz, DMSO-$d_6$) δ ppm 10.97 (bs, 1H), 9.74 bs, 1H), 8.00 (bs, 1H), 6.58 (s, 1H), 4.27-4.05 (m, 2H), 3.96 (s, 2H), 3.01-2.86 (m, 1H), 2.28-2.09 (m, 3H), 1.76-1.68 (m, 1H); MS (APCI$^+$) m/z 399 [M+H]$^+$.

Example 226: 5-[(3S)-5-fluoro-7-hydroxy-3-(4-methylpentyl)-1,2,3,4-tetrahydroisoquinolin-6-yl]-1λ$^6$,2,5-thiadiazolidine-1,1,3-trione (Compound 325)

Example 226A: methyl (S)-2-((tert-butoxycarbonyl)amino)pent-4-enoate

Iodomethane (14.5 mL, 232 mmol, 2.0 equivalents) was added to a suspension of potassium carbonate (32.1 g, 232 mmol, 2.0 equivalents) and (S)-2-((tert-butoxycarbonyl)amino)pent-4-enoic acid (25.0 g, 116 mmol, 1 equivalent) in acetone (465 mL, 0.25 M) at 23° C. The reaction mixture was stirred for 24 hours at 23° C. Additional iodomethane (14.5 mL, 232 mmol, 2.0 equivalents) was added at 23° C. The reaction mixture was stirred for 3 days at 23° C. The product mixture was partially concentrated. The residue obtained was partitioned between water (150 mL) and ethyl acetate (400 mL). The aqueous layer was extracted with ethyl acetate (150 mL). The organic layers were combined, and the combined organic layers were washed with saturated aqueous sodium chloride solution (50 mL). The washed organic layer was dried over magnesium sulfate. The dried solution was filtered, and the filtrate was concentrated. The title compound obtained was used without further purification in the following step. TLC R$_f$=0.37 (1% acetic acid-20% ethyl acetate-heptanes, ninhydrin). $^1$H NMR (600 MHz, CDCl$_3$) δ ppm 5.73-5.65 (m, 1H), 5.15-5.10 (m, 2H), 5.02 (bs, 1H), 4.40-4.36 (m, 1H), 3.73 (s, 3H), 2.58-2.42 (m, 2H), 1.43 (s, 9H).

Example 226B: methyl (S)-2-((tert-butoxycarbonyl)amino)-6-methylhept-4-enoate

A solution of (1,3-bis-(2,4,6-trimethylphenyl)-2-imidazolidinylidene)dichloro(o-isopropoxyphenylmethylene)ruthenium (282 mg, 0.45 mmol, 4.5 mol %) and the product of Example 226A (2.29 g, 10.00 mmol, 1 equivalent) in dichloromethane (100 mL) in a 500 mL round-bottom flask outfitted with a septum-capped reflux condenser was deoxygenated by iterative subjections to vacuum (~5 seconds) and subsequent backfilling with nitrogen (×2). The reaction vessel was briefly unsealed and liquid 3-methyl-1-butene (~15.0 mL, 135 mmol, 13.5 equivalents) was added. The reaction vessel was sealed with the reflux condenser (under nitrogen) and the sealed vessel was placed in a heating block that had been preheated to 50° C. The reaction mixture was stirred for 20 hours at 50° C. The product mixture was then cooled to 23° C. The cooled product mixture was concentrated. The residue obtained was purified by flash column chromatography (elution initially with heptanes, grading to 10% [v/v]ethyl acetate-heptanes, one step) to furnish the title compound (<1.98 g, <73% yield). TLC R$_f$=0.20 (10% ethyl acetate-heptanes, para-anisaldehyde).). 1H NMR (500 MHz, CDCl$_3$) δ ppm 5.48 (dd, J=15.3, 6.7 Hz, 1H), 5.26-5.20 (m, 1H), 5.00 (bs, 1H), 4.38-4.30 (m, 1H), 3.72 (s, 3H), 2.51-2.35 (m, 3H), 1.44 (s, 9H), 0.96 (d, J=2.8 Hz, 3H), 0.95 (d, J=2.8 Hz, 3H).

Example 226C: methyl (S)-2-((tert-butoxycarbonyl)amino)-6-methylheptanoate

A suspension of the product of Example 226B (nominally 1.91 g, 7.04 mmol, 1 equivalent) and palladium on carbon (10% weight, 533.0 mg, 0.50 mmol, 7.1 mol %) in tetrahydrofuran (14.0 mL) was stirred vigorously for 20 hours under an atmosphere of hydrogen (1 atm) in a sealed 100 mL round-bottom flask at 23° C. The product mixture was diluted with methanol (15 mL) and filtered through a plug of diatomaceous earth (2.0 cm×4.0 cm). The filter cake was rinsed with methanol (3×5 mL). The filtrates were combined, and the combined filtrates were concentrated. The title compound obtained was used without further purification in the following step. TLC R$_f$=0.24 (10% ethyl acetate-heptanes, para-anisaldehyde). $^1$H NMR (500 MHz, CDCl$_3$) δ ppm 5.02-4.94 (m, 1H), 4.31-4.25 (m, 1H), 3.73 (s, 3H), 1.81-1.71 (m, 1H), 1.64-1.58 (m, 1H), 1.44 (s, 9H), 1.39-1.27 (m, 3H), 1.22-1.13 (m, 2H), 0.86 (d, J=6.1 Hz, 6H).

Example 226D: tert-butyl (S)-(1-hydroxy-6-methylheptan-2-yl)carbamate

A solution of lithium borohydride in tetrahydrofuran (2.0 M, 7.04 mL, 14.08 mmol, 2.0 equivalents) was added to a solution of the product of Example 226C (nominally 7.04 mmol, 1 equivalent) in tetrahydrofuran (50 mL, 0.14 M) at 0° C. The reaction mixture was warmed over 20 hours to 23° C. The product mixture was then diluted sequentially with saturated aqueous ammonium chloride (5 mL), water (15 mL), and ethyl acetate (60 mL) at 23° C. The resulting biphasic mixture was stirred for 30 minutes. The mixture was then transferred to a separatory funnel and the layers that formed were separated. The aqueous layer was extracted with ethyl acetate (35 mL). The organic layers were combined, and the combined organic layers were washed with saturated aqueous sodium chloride solution (10 mL). The washed organic layer was dried over sodium sulfate. The dried solution was filtered, and the filtrate was concentrated. The residue obtained was purified by flash column chromatography (elution with 33% ethyl acetate-heptanes) to furnish the title compound (983 mg, 4.01 mmol, 57% yield, four steps). $^1$H NMR (600 MHz, CDCl$_3$) δ ppm 4.62 (bs, 1H), 3.69-3.49 (m, 3H), 2.54 (bs, 1H), 1.44 (s, 9H), 1.41-1.13 (m, 6H), 0.88 (dd, J=6.6, 3.5 Hz, 1H), 0.86 (d, J=6.6 Hz).

Example 226E: tert-butyl (4S)-4-(4-methylpentyl)-2-oxo-1,2λ$^4$,3-oxathiazolidine-3-carboxylate A solution of thionyl chloride in dichloromethane (2.0 M, 2.00 mL, 4.00 mmol, 1.1 equivalents) was added dropwise to a solution of imidazole (989.3 mg, 14.53 mmol, 4.0 equivalents) and triethylamine (1.19 mL, 8.53 mmol, 2.4 equivalents) in dichloromethane (30.0 mL) at −40° C. The reaction mixture was stirred for 10 minutes at −40° C. A solution of the product of Example 226D (891 mg, 3.63 mmol, 1 equivalent) in dichloromethane (6.0 mL, 0.1 M overall) was added dropwise via syringe pump over 30 minutes at −40° C. The reaction mixture was allowed to warm over 2 days to 23° C. The product mixture was diluted with saturated aqueous sodium chloride solution (8 mL). The aqueous layer was extracted with dichloromethane (15 mL). The organic layers were combined, and the combined organic layers were dried over sodium sulfate. The dried solution was filtered, and the filtrate was concentrated. The residue obtained was purified by flash column chromatography (elution with 10% ethyl acetate-heptanes) to furnish the title compound (599 mg, 2.05 mmol, 57% yield). TLC R$_f$=0.68 (25% ethyl acetate-heptanes, cerium ammonium molybdate). $^1$H NMR (500 MHz, CDCl$_3$) δ ppm 4.81-4.70 (m, 2H), 4.04-3.95 (m, 1H), 2.14-2.04 (m, 1H), 1.75-1.63 (m, 1H), 1.53 (s, 9H), 1.35-1.15 (m, 4H), 0.92-0.85 (m, 1H), 0.87 (dd, J=6.6, 3.0 Hz, 6H); MS (APCI$^+$) m/z 309 [M+NH$_4$]$^+$.

Example 226F: tert-butyl (S)-4-(4-methylpentyl)-1,2,3-oxathiazolidine-3-carboxylate 2,2-dioxide Ruthenium(III) chloride hydrate (4.6 mg, 0.02 mmol, 1.0 mol %) and sodium periodate (659.0 mg, 3.08 mmol, 1.5 equivalents) were added in succession to a solution of the product of Example 226E (599.0 mg, 2.06 mmol, 1 equivalent) in 20% water-acetonitrile mixture (v/v, 7 mL, 0.29 M) at 23° C. The reaction mixture was stirred for 10 minutes at 23° C. The product mixture was then diluted with ethyl acetate (15 mL). The diluted mixture was filtered through a plug of diatomaceous earth (5.0 cm×3.0 cm). The filter cake was rinsed with ethyl acetate (3×15 mL). The filtrates were combined. The combined filtrates were transferred to a separatory funnel and washed with saturated aqueous sodium thiosulfate solution (15 mL). The aqueous layer was extracted with ethyl acetate (15 mL). The organic layers were combined, and the combined organic layers were washed successively with saturated aqueous sodium thiosulfate solution (10 mL) and saturated aqueous sodium chloride solution (20 mL). The washed organic layer was dried over magnesium sulfate. The dried solution was filtered through a plug of diatomaceous earth (5.0 cm×3.0 cm). The filter cake was washed with ethyl acetate (3×15 mL). The filtrates were combined, and the combined filtrates were concentrated. The residue obtained was dissolved in ether (3 mL) and filtered through a plug of silica gel (0.5 cm×3.0 cm). The filter cake was washed with ether (3×2 mL). The filtrates were combined, and the combined filtrates were concentrated to furnish the title compound (584 mg, 1.90 mmol, 92% yield). TLC R$_f$=0.43 (20% ethyl acetate-heptanes, cerium ammonium molybdate). 1H NMR (600 MHz, CDCl$_3$) δ ppm 4.63 (ddd, J=9.2, 5.9, 0.8 Hz, 1H), 4.32-4.22 (m, 2H), 1.94-1.84 (m, 1H), 1.83-1.72 (m, 1H), 1.55 (s, 9H), 1.39-1.26 (m, 2H), 1.26-1.17 (m, 2H), 0.91 (d, J=6.6 Hz, 1H), 0.87 (dd, J=6.6, 3.7 Hz, 6H); MS (APCI$^+$) m/z 325 [M+NH$_4$]$^+$.

Example 226G: tert-butyl {(2S)-1-[4-(benzyloxy)-6-bromo-2-fluoro-3-(2,2,2-trifluoroacetamido)phenyl]-6-methylheptan-2-yl}carbamate A solution of n-butyllithium in hexanes (1.91 M, 2.08 mL, 3.96 mmol, 2.1 equivalents) was added to a solution of diisopropylamine (0.59 mL, 4.15 mmol, 2.2 equivalents) in tetrahydrofuran (8.0 mL) at −78° C. The reaction mixture was stirred for 10 minutes at −78° C. A solution of the product of Example 12C (777.0 mg, 1.98 mmol, 1.05 equivalents) in tetrahydrofuran (3.0 mL) was added dropwise via syringe pump over 20 minutes at −78° C. The reaction mixture was stirred for 30 minutes at −78° C. A solution of the product of Example 226F (580.0 mg, 1.89 mmol, 1 equivalent) in tetrahydrofuran (3.0 mL; 0.14 M overall) was added dropwise over 20 minutes at −78° C. The reaction mixture was stirred for 30 minutes at −78° C. Aqueous hydrochloric acid solution (3 M, 3.14 mL, 9.43 mmol, 5.0 equivalents) was added at −78° C. The resulting mixture was warmed over 30 minutes to 23° C. The product mixture was diluted with ethyl acetate (30 mL). The resulting biphasic mixture was then transferred to a separatory funnel and the layers that formed were separated. The organic layer was washed with saturated aqueous sodium chloride solution (5 mL). The washed organic layer was dried over sodium sulfate. The dried solution was filtered, and the filtrate was concentrated. The title compound obtained was used without further purification in the following step. MS (APCI$^+$) m/z 619 [M+H]$^+$.

Example 226H: Methyl {[6-(benzyloxy)-4-bromo-3-{(2S)-2-[(tert-butoxycarbonyl)amino]-6-methylheptyl}-2-fluorophenyl](trifluoroacetyl)amino}acetate Methyl bromoacetate (0.18 mL, 1.98 mmol, 1.1 equivalents) was added to a suspension of the product of Example 226G (nominally 1.89 mmol, 1 equivalent), potassium carbonate (782 mg, 5.66 mmol, 3.0 equivalents), and potassium iodide (157 mg, 0.94 mmol, 0.5 equivalent) in acetone (9.5 mL, 0.2 M) at 23° C. The reaction mixture was stirred for 65 hours at 23° C. The product mixture was concentrated under a stream of nitrogen. The residue obtained was partitioned between ethyl acetate (20 mL), water (3 mL), and saturated aqueous ammonium chloride solution (5 mL). The organic layer was washed with saturated aqueous sodium chloride solution (3 mL). The washed organic layer was dried over sodium sulfate. The dried solution was filtered. Diatomaceous earth (~5 g) was added to the solution and the mixture was concentrated. The residue obtained was purified by flash column chromatography (40 g RediSep Rf Gold® silica column, elution with a gradient from 0-60% ethyl acetate-heptanes) to furnish the title compound (945 mg, 1.37 mmol, 72% yield, two steps). MS (APCI$^+$) m/z 591 [M+H—C(O)OC(CH$_3$)$_3$]$^+$.

Example 226I: methyl {[6-(benzyloxy)-3-{(2S)-2-[(tert-butoxycarbonyl)amino]-6-methylheptyl}-4-ethenyl-2-fluorophenyl](trifluoroacetyl)amino}acetate A suspension of cesium carbonate (890 mg, 2.73 mmol, 2.0 equivalents), potassium vinyltrifluoroborate (366 mg, 2.73 mmol, 2.0 equivalents), bis(triphenylphosphine)palladium(II) dichloride (48.0 mg, 0.07 mmol, 5.0 mol %), and the product of Example 226H (945 mg, 1.37 mmol, 1 equivalent) in 20% water-dioxane (v/v, 11.0 mL, 0.15 M) in a 20 mL scintillation vial outfitted with a septum-sealed screw cap. The sealed reaction mixture was deoxygenated by iterative subjections to vacuum (~5 seconds) and subsequent backfilling with nitrogen (×3). The reaction vessel was placed in a heating block that had been preheated to 80° C. The reaction mixture was stirred for 1.5 hours at 80° C. The reaction mixture was then heated to 100° C. The reaction mixture was stirred for 3 hours at 100° C. The product mixture was then cooled to 23° C. The cooled product mixture was filtered through a plug of diatomaceous earth (3.0 cm×1.0 cm). The filter cake was washed with ethyl acetate (3×15 mL). The filtrates were combined, and the combined filtrates were concentrated. The residue obtained was partitioned between ethyl acetate (50 mL) and water (10 mL). The organic layer was washed with saturated aqueous sodium chloride solution (10 mL). The washed organic layer was dried over sodium sulfate. The dried solution was filtered. Diatomaceous earth (~5 g) was added to the solution and the mixture was concentrated. The residue obtained was purified by flash column chromatography (40 g RediSep Rf Gold® silica column, elution with a gradient from 0-60% [v/v]ethyl acetate-heptanes). The title compound obtained (623 mg, <71% yield) was used without further purification in the following step. MS (APCI$^+$) m/z 538 [M-C(O)OC(CH$_3$)$_3$+H]$^+$.

Example 226J: Methyl {[6-(benzyloxy)-3-{(2S)-2-[(tert-butoxycarbonyl)amino]-6-methylheptyl}-2-fluoro-4-formylphenyl](trifluoroacetyl)amino}acetate A solution of N-methylmorpholine N-oxide in water (50% w/v, 0.69 mL, 2.93 mmol, 3.0 equivalents) was added to a suspension of potassium osmate dihydrate (14.0 mg, 0.04 mmol, 4.0 mol %) and the product of Example 226I (623 mg, 0.98 mmol, 1 equivalent) in 25% water-tetrahydrofuran mixture (v/v, 10 mL, ~0.1 M) at 23° C. The reaction mixture was stirred for 18 hours at 23° C. Sodium metaperiodate (209 mg, 0.975 mmol, 1.0 equivalent) was added in one portion at 23° C. The reaction mixture was stirred for 6 hours at 23° C. Additional sodium metaperiodate (187 mg, 0.86 mmol, 0.89 equivalent) was added in one portion at 23° C. The reaction mixture was stirred for 30 minutes at 23° C. The product mixture was then diluted sequentially with saturated aqueous sodium thiosulfate solution (10 mL), water (5 mL), and ethyl acetate (50 mL). The diluted mixture was stirred for 15 minutes at 23° C. The resulting biphasic mixture was then transferred to a separatory funnel and the layers that formed were separated. The aqueous layer was extracted with ethyl acetate (2×25 mL). The organic layers were combined, and the combined organic layers were washed sequentially with saturated aqueous sodium thiosulfate solution (10 mL) and saturated aqueous sodium chloride solution (15 mL). The washed organic layer was dried over sodium sulfate. The dried solution was filtered, and the filtrate was concentrated. The title compound obtained was used in the following step without further purification. MS (APCI$^+$) m/z 541 [M-C(O)OC(CH$_3$)$_3$+H]$^+$.

Example 226K: tert-butyl (3S)-7-(benzyloxy)-5-fluoro-6-[(2-methoxy-2-oxoethyl) (trifluoroacetyl)amino]-3-(4-methylpentyl)-3,4-dihydroisoquinoline-2(1H)-carboxylate Triethylsilane (0.86 mL, 5.36 mmol, 5.5 equivalents) and boron trifluoride diethyl etherate (0.62 mL, 4.8 mmol, 5.0 equivalents) were added dropwise in sequence to a solution of the product of Example 226J (nominally 0.98 mmol, 1 equivalent) in dichloromethane (10.0 mL) at −78° C. The reaction mixture was stirred for 45 minutes at −78° C. The product mixture was then diluted sequentially with saturated aqueous sodium bicarbonate solution (4 mL) and water (1 mL). The diluted mixture was warmed over 1 hour to 23° C., with stirring. The resulting biphasic mixture was then transferred to a separatory funnel and the layers that formed were separated. The aqueous layer was extracted with dichloromethane (15 mL). The organic layers were combined, and the combined organic layers were washed with saturated aqueous sodium chloride solution (5 mL). The washed organic layer was dried over sodium sulfate. The dried solution was filtered. Diatomaceous earth (~5 g) was added to the solution and the mixture was concentrated. The residue obtained was purified by flash column chromatography (40 g RediSep Rf Gold® silica column, elution with a gradient from 0-25% [v/v]ethyl acetate-heptanes). The fractions containing product were collected and concentrated. The title compound obtained (<400 mg, <66% over two steps) was used without further purification in the following step. MS (APCI$^+$) m/z 525 [M+H—C(O)OC(CH$_3$)$_3$]$^+$.

Example 226L: tert-butyl (3S)-7-(benzyloxy)-5-fluoro-6-[(2-methoxy-2-oxoethyl)amino]-3-(4-methylpentyl)-3,4-dihydroisoquinoline-2(1H)-carboxylate A solution of sodium methoxide in methanol (25% w/v, 0.35 mL, 1.60 mmol, 2.5 equivalents) was added to a solution of the product of Example 226K (~400 mg, ~0.64 mmol, 1 equivalent) in anhydrous methanol (3.2 mL, 0.2 M) in a 20 mL scintillation vial equipped with a pressure-relief septum screw-cap under nitrogen at 23° C. The sealed reaction mixture was subjected to vacuum (~5 seconds) and subsequent backfilling with nitrogen (×3). The sealed reaction mixture was placed in a heating block that had been preheated to 60° C. The reaction mixture was stirred for 10 minutes at 60° C. The reaction mixture was then cooled to 23° C. A solution of hydrogen chloride in dioxane (4 M, 0.80 mL, 3.20 mmol, 5 equivalents) was added to the cooled reaction mixture at 23° C. The reaction mixture was stirred for 10 minutes at 23° C. The product mixture was diluted sequentially with ethyl acetate (30 mL), water (3 mL), and saturated aqueous sodium chloride solution (5 mL). The resulting biphasic mixture was then transferred to a separatory funnel and the layers that formed were separated. The aqueous layer was extracted with ethyl acetate (3×15 mL). The organic layers were combined, and the combined organic layers were washed with saturated aqueous sodium chloride solution (7 mL). The washed organic layer was dried over sodium sulfate. The dried solution was filtered, and the filtrate was concentrated. The title compound obtained was used without further purification in the following step. MS (APCI$^+$) m/z 529 [M+H]$^+$.

Example 226M: tert-butyl (3S)-7-(benzyloxy)-5-fluoro-6-[(2-methoxy-2-oxoethyl)({[(prop-2-en-1-yl)oxy]carbonyl}sulfamoyl)amino]-3-(4-methylpentyl)-3,4-dihydroisoquinoline-2(1H)-carboxylate Allyl alcohol (0.05 mL, 0.74 mmol, 1.2 equivalents) was added to a solution of chlorosulfonyl isocyanate (0.06 mL, 0.69 mmol, 1.1 equivalents) in dichloromethane (3.20 mL) at 0° C. The reaction mixture was stirred for 1 hour at 0° C. A solution of the product of Example 226L (nominally 0.64 mmol, 1 equivalent) and triethylamine (0.27 mL, 1.92 mmol, 3.0 equivalents) in dichloromethane (3.20 mL, 0.1 M overall) was added dropwise at 0° C. The reaction mixture was stirred for 2 hours at 0° C. The product mixture was diluted with saturated aqueous sodium chloride solution (3 mL). The resulting biphasic mixture was then transferred to a separatory funnel and the layers that formed were separated. The aqueous layer was extracted with dichloromethane (2×5 mL). The organic layers were combined, and the combined organic layers were dried over sodium sulfate. The dried solution was filtered, and the filtrate was concentrated. The title compound obtained was used without further purification in the following step. MS (APCI$^+$) m/z 709 [M+NH$_4$]$^+$.

Example 226N: tert-butyl (3S)-7-(benzyloxy)-5-fluoro-3-(4-methylpentyl)-6-(1,1,4-trioxo-1λ$^6$,2,5-thiadiazolidin-2-yl)-3,4-dihydroisoquinoline-2(1H)-carboxylate A solution of sodium methoxide in methanol (0.5 M, 3.84 mL, 1.92 mmol, 3.0 equivalents) was added to a suspension of the product of Example 226M (nominally 0.64 mmol, 1 equivalent) and tetrakis(triphenylphosphine)palladium(0) (37 mg, 0.03 mmol, 0.05 equivalents) in anhydrous methanol (2.0 mL, 0.32 M) under nitrogen at 23° C. The reaction vessel (20 mL pressure-relief vial with a septum-equipped screw cap) was sealed. The sealed reaction mixture was deoxygenated by iterative subjections to vacuum (~5 seconds) and subsequent backfilling with nitrogen (×3). The reaction vessel was placed in a heating block that had been preheated to 60° C. The reaction mixture was stirred for 10 minutes at 60° C., and then the reaction mixture was cooled to 23° C. The cooled mixture was partitioned between aqueous hydrochloric acid solution (3.0 M, 2.5 mL) and ethyl acetate (15 mL). The aqueous layer was extracted with ethyl acetate (10 mL). The organic layers were combined, and the combined organic layers were dried over sodium sulfate. The dried solution was filtered. Diatomaceous earth (~7 g) was added to the filtrate and the mixture was concentrated. The residue obtained was purified by flash column chromatography (12 g RediSep Rf Gold® silica column, elution with a gradient from 0-100% acetonitrile-ethyl acetate) to furnish the title compound (284 mg, 0.493 mmol, 77% yield). MS (APCI$^+$) m/z 593 [M+NH$_4$]$^+$.

Example 226O: 5-[(3S)-7-(benzyloxy)-5-fluoro-3-(4-methylpentyl)-1,2,3,4-tetrahydroisoquinolin-6-yl]-1λ$^6$,2,5-thiadiazolidine-1,1,3-trione A solution of boron trichloride in dichloromethane (1.0 M, 7.00 mL, 7.00 mmol, 14.2 equivalents) was added slowly to a solution of the product of Example 226N (nominally 0.493 mmol, 1 equivalent) and pentamethylbenzene (80 mg, 0.54 mmol, 1.1 equivalents) in dichloromethane at −78° C. The cooling bath was immediately removed and replaced with a separate cooling bath at 0° C. The reaction mixture was warmed over 1 hour to 0° C. The reaction mixture was cooled to −78° C. Additional boron trichloride in dichloromethane (1.0 M, 5.00 mL, 5.00 mmol, 10.1 equivalents) was added slowly at −78° C. The cooling bath was immediately removed and replaced with a separate cooling bath at 0° C. The reaction mixture was warmed over 30 minutes to 0° C. The product mixture was cooled to −78° C. The mixture was slowly diluted with ethanol (5.0 mL) at −78° C. The diluted mixture was concentrated. The title compound obtained was used without further purification in the following step. MS (APCI$^+$) m/z 476 [M+H]$^+$.

Example 226P: 5-[(3S)-5-fluoro-7-hydroxy-3-(4-methylpentyl)-1,2,3,4-tetrahydroisoquinolin-6-yl]-1λ$^6$,2,5-thiadiazolidine-1,1,3-trione, Ammonia Salt A suspension of the product of Example 226O (nominally 0.493 mmol, 1 equivalent), palladium on carbon(10% weight, 52 mg, 0.05 mmol, 0.1 equivalents), and ammonium formate (155 mg, 2.47 mmol, 5.0 equivalents) in ethanol (5.00 mL, ~0.1 M) was sealed in a 20 mL pressure-relief vial with a septum equipped screw-cap. The sealed reaction vessel was placed in a heating block that had been preheated to 60° C. The reaction mixture was stirred for 4 hours at 60° C. The product mixture was cooled to 23° C. The cooled product mixture was filtered through a plug of diatomaceous earth (0.5 cm×1.0 cm). The filter cake was rinsed with methanol (3×3 mL). The filtrates were combined, and the combined filtrates were concentrated. The residue obtained was purified by reversed-phase flash column chromatography (100 g RediSep Rf Gold® C18 column, elution with a gradient of 5-100% methanol-0.025 M aqueous ammonium bicarbonate solution [acidified with solid carbon dioxide]) to furnish recovered starting material (18.5 mg, 8%) and the title compound (5.5 mg, 0.014 mmol, 3% yield, 2 steps). $^1$H NMR (600 MHz, DMSO-$d_6$) δ ppm 6.55 (s, 1H), 4.19 (s, 2H), 3.95 (s, 2H), 2.93 (dd, J=16.7, 4.7 Hz, 1H), 2.46 (dd, J=16.8, 11.1 Hz, 1H), 1.71-1.65 (m, 1H), 1.61-1.52 (m, 2H), 1.46-1.39 (m, 2H), 1.23-1.17 (m, 2H), 0.91-0.86 (m, 7H); MS (APCI$^+$) m/z 386 [M+H]$^+$.

Biological Assays

Abbreviations

BSA for bovine serum albumin; DMEM for Dulbecco's modified Eagle's medium; DMSO for dimethyl sulfoxide; DTT for dithiothreitol; EDTA for ethylenediaminetetraacetic acid; EGTA for ethylene glycol-bis(2-aminoethylether)-N,N,N',N'-tetraacetic acid; FBS for fetal bovine serum; HEPES for 4-(2-hydroxyethyl)piperazine-1-ethanesulfonic acid; IFNγ for interferon gamma; PBS for phosphate-buffered saline; PE labeled for phydoerythrin labeled; RPMI 1640 for Roswell Park Memorial Institute 1640 medium; S-MEM for minimum essential medium Eagle, Spinner modification; TNFα for tumor necrosis factor alpha; and Tween® 20 for polyethylene glycol sorbitan monolaurate.

Example 227: Mobility Shift Assay Used to Determine Potency of PTPN2 Inhibitors

Compound activity was determined using in house His tagged PTPN2 (TC45) protein (SEQ ID NO: 1) in an in vitro enzymatic reaction. The enzymatic assay used to determine activity was a mobility shift assay using a LabChip EZ Reader by Caliper Life Sciences. The enzymatic reaction was carried out in assay buffer (50 mM HEPES pH 7.5, 1 mM EGTA, 10 mM EDTA, 0.01% Tween® 20, and 2 mM DTT). The compounds were dispensed on a white 384 well ProxiPlate™ (PerkinElmer Catalog #6008289) plate using the Labcyte Echo at varying concentrations (12 point, 1:3 dilution). The enzyme (at 0.5 nM) was incubated with compound for 10 minutes at room temperature. Then the substrate (phosphorylated insulin receptor probe sequence: ((OG488)-(NH—$CH_2$—$CH_2$—O—$CH_2$—$CH_2$—O—$CH_2$—CO)-T-R-D-I-(PY)-E-T-D-Y-Y-R-K-K-$NH_2$) (SEQ ID NO: 2) was added at 2 μM to the plates and incubated for another 10 minutes at room temperature. Finally, a quench solution (water and 4-bromo-3-(2-oxo-2-propoxyethoxy)-5-(3-{[1-(phenylmethanesulfonyl)piperidin-4-yl]amino}phenyl)thiophene-2-carboxylic acid) was added to the plates, which were then run on the EZ Reader (excitation 488 nm, emission 530 nm) to measure % conversion (the amount of phosphorylated substrate which was de-phosphorylated by PTPN2). Each plate had a 100% control (inhibitor: 4-bromo-3-(2-oxo-2-propoxyethoxy)-5-(3-{[1-(phenylmethanesulfonyl)piperidin-4-yl]amino}phenyl)thiophene-2-carboxylic acid) and 0% control (DMSO), which were used to calculate % inhibition. The % inhibition was then used to calculate the $IC_{50}$ values.

Example 228: Mobility Shift Assay (MSA) Used to Determine Potency of PTPN1 Inhibitors Compound activity was determined using in house His tagged full-length PTPN1 protein (SEQ ID NO: 3) in an in vitro enzymatic reaction. The enzymatic assay used to determine activity is a mobility shift assay using a LabChip EZ Reader by Caliper Life Sciences. The enzymatic reaction was carried out in assay buffer (50 mM HEPES pH 7.5, 1 mM EGTA, 10 mM EDTA, 0.01% Tween® 20, and 2 mM DTT). The compounds were dispensed on a white 384 well ProxiPlate™ (PerkinElmer Cat$^\#$ 6008289) plate using a Labcyte Echo® liquid handler at varying concentrations (12 point, 1:3 dilution). The enzyme (at 0.5 nM) was incubated with compound for 10 minutes at room temperature. Then the substrate (phosphorylated insulin receptor probe sequence: ((OG488)-(NH—$CH_2$—$CH_2$—O—$CH_2$—$CH_2$—O—$CH_2$—CO)-T-R-D-I-(PY)-E-T-D-Y-Y-R-K-K-$NH_2$) (SEQ ID NO: 2) was added at 2 μM to the plates and incubated for another 10 minutes at room temperature. Finally, a quench solution (water and 4-bromo-3-(2-oxo-2-propoxyethoxy)-5-(3-{[1-(phenylmethanesulfonyl)piperidin-4-yl]amino}phenyl)thiophene-2-carboxylic acid) was added to the plates, which were then run on the EZ Reader (excitation 488 nm, emission 530 nm) to measure % conversion (the amount of phosphorylated substrate which was de-phosphorylated by PTPN1). Each plate had a 100% control (inhibitor: 4-bromo-3-(2-oxo-2-propoxyethoxy)-5-(3-{[1-(phenylmethanesulfonyl)piperidin-4-yl]amino}phenyl)thiophene-2-carboxylic acid) and 0% control (DMSO), which were used to calculate % inhibition. The % inhibition was then used to calculate the $IC_{50}$ values.

Table 2 below summarizes the $IC_{50}$ data obtained using the PTPN2 MSA assay and the PTPN1 MSA assay for exemplary compounds of the disclosure. In this table, "A" represents an $IC_{50}$ of less than 1 nM; "B" an $IC_{50}$ of between 1 nM and 10 nM; "C" an $IC_{50}$ of greater than 10 nM to 100 nM; and "D" an $IC_{50}$ of greater than 100 nM.

TABLE 2

$IC_{50}$ values of exemplary compounds of the disclosure in the PTPN2 and PTPN1 Mobility Shift Assays (MSA).

| Compound No. | PTPN2 MSA $IC_{50}$ (nM) | PTPN1 MSA $IC_{50}$ (nM) | Compound No. | PTPN2 MSA $IC_{50}$ (nM) | PTPN1 MSA $IC_{50}$ (nM) |
|---|---|---|---|---|---|
| 100 | C | B | 101 | B | B |
| 102 | A | B | 103 | C | |
| 104 | C | C | 105 | B | B |
| 106 | C | C | 107 | C | C |
| 108 | C | C | 109 | C | C |
| 110 | C | C | 111 | C | C |
| 112 | D | D | 113 | D | D |
| 114 | C | C | 115 | C | C |
| 116 | C | C | 117 | C | C |
| 118 | B | B | 119 | B | B |
| 120 | B | B | 121 | B | C |
| 122 | B | C | 123 | B | B |
| 124 | B | B | 125 | B | C |
| 126 | B | B | 127 | B | B |
| 128 | B | B | 129 | B | B |
| 130 | B | B | 131 | B | B |
| 132 | C | C | 133 | B | B |
| 134 | C | C | 135 | C | C |
| 136 | C | C | 137 | A | B |
| 138 | C | C | 139 | B | C |
| 140 | C | C | 141 | B | C |
| 142 | B | C | 143 | C | D |
| 144 | B | C | 145 | C | C |
| 146 | B | | 147 | C | C |

TABLE 2-continued

IC$_{50}$ values of exemplary compounds of the disclosure in the PTPN2 and PTPN1 Mobility Shift Assays (MSA).

| Compound No. | PTPN2 MSA IC$_{50}$ (nM) | PTPN1 MSA IC$_{50}$ (nM) | Compound No. | PTPN2 MSA IC$_{50}$ (nM) | PTPN1 MSA IC$_{50}$ (nM) |
|---|---|---|---|---|---|
| 148 | A | A | 149 | B | C |
| 150 | B | B | 151 | B | C |
| 152 | B |   | 153 | C | C |
| 154 | B | C | 155 | C | C |
| 156 | B | B | 157 | B | C |
| 158 | C | D | 159 | C | C |
| 160 | C | C | 161 | B | C |
| 162 | B | C | 163 | C | D |
| 164 | C | D | 165 | C | C |
| 166 | A | B | 167 | B | C |
| 168 | C | C | 169 | C |   |
| 170 | C | D | 171 | B | B |
| 172 | C | C | 173 | B | B |
| 174 | B | B | 175 | B | C |
| 176 | C | C | 177 | A | B |
| 178 | A | B | 179 | C | C |
| 180 | C | D | 181 | B | B |
| 182 | C | C | 183 | D | D |
| 184 | D | D | 185 | B | B |
| 186 | C | C | 187 | B | B |
| 188 | C | C | 189 | B | D |
| 190 | B | C | 191 | C | C |
| 192 | C | C | 193 | D | C |
| 194 | B | B | 195 | C | C |
| 196 | C | C | 197 | C | C |
| 198 | C | D | 199 | A | A |
| 200 | A | A | 201 | A | A |
| 202 | A | B | 203 | A | B |
| 204 | A | B | 205 | B | C |
| 206 | C | C | 207 | C | C |
| 208 | C | C | 209 | B | B |
| 210 | D | C | 211 | B | B |
| 212 | D | D | 213 | D | D |
| 214 | C | C | 215 | D | D |
| 216 | D | D | 217 | D | D |
| 218 | D | C | 219 | C | C |
| 220 | C | C | 221 | C | B |
| 222 | C | C | 223 | C | B |
| 224 | D | C | 225 | B | C |
| 226 | C | C | 227 | D | D |
| 228 | D | C | 229 | C | C |
| 230 | D | C | 231 | C | B |
| 232 | D | C | 233 | D | C |
| 234 | C | B | 235 | C | C |
| 236 | D | C | 237 | D | D |
| 238 | B | B | 239 | B | B |
| 240 | C | D | 241 | C | C |
| 242 | C | C | 243 | B | B |
| 244 | C | C | 245 | C | C |
| 246 | C | C | 247 | C | C |
| 248 | C | C | 249 | C | C |
| 250 | C | C | 251 | C | C |
| 252 | D | D | 253 | B | B |
| 254 | C | C | 255 | D | C |
| 256 | B | B | 257 | B | B |
| 258 | B | B | 259 | C | C |
| 260 | B | B | 261 | C | C |
| 262 | C | B | 263 | C |   |
| 264 | C | C | 265 | C |   |
| 266 | B | B | 267 | C |   |
| 268 | C | C | 269 | B | B |
| 270 | C | C | 271 | C | C |
| 272 | C | C | 273 | B | B |
| 274 | B | B | 275 | C | C |
| 276 | A | B | 277 | B | C |
| 278 | C | C | 279 | C | C |
| 280 | D | D | 281 | C | C |
| 282 | C | C | 283 | C | D |
| 284 | C | C | 285 | C |   |
| 286 | B | B | 287 | C | D |
| 288 | C | B | 289 | C | D |
| 290 | B | B | 291 | B | B |
| 292 | C | C | 293 | C | C |
| 294 | C | C | 295 | C | D |
| 296 | C | D | 297 | A | B |
| 298 | C | C | 299 | B | C |
| 300 | B | B | 301 | C | D |
| 302 | B | C | 303 | B |   |
| 304 | D | D | 305 | C | C |
| 306 | D | D | 307 | B | B |
| 308 | B | B | 309 | C | C |
| 310 | C | C | 311 | B | B |
| 312 | C | C | 313 | B | C |
| 314 | C | D | 315 | B | C |
| 316 | C | D | 317 | C | D |
| 318 | B | C | 319 | C | D |
| 320 | D | D | 321 | B | B |
| 322 | C |   | 323 | B |   |
| 324 | B |   | 325 | B |   |

Example 229: B16F10 IFNγ-Induced Cellular Growth Inhibition Assay

B16F10 mouse melanoma cells (ATCC Cat$^\#$ CRL-6475, Manassas, Va.) were seeded at a density of 500 cells per well in a 384-well clear bottom plate (Corning Cat$^\#$3765, Corning, N.Y.) in 25 μL total volume of DMEM+10% FBS (Sigma Cat$^\#$ D6429 and Sigma Cat$^\#$ F4135, St. Louis, Mo.). Cells were allowed to adhere overnight at 37° C.+5% CO$_2$. On the following day, 12.5 μL of mouse IFNγ (RD systems Cat$^\#$485-MI/CF, Minneapolis, Minn.) was added to half of the plate (columns 13-24) at a concentration of 2 ng/mL for a final assay concentration of 0.5 ng/mL of IFNγ. Media only (12.5 μL of DMEM+10% FBS) was added to the remainder of the plate (columns 1-12). Next, compounds resuspended in DMSO (Sigma Cat$^\#$ D2650) at 100 mM were diluted in semi-log dilutions in DMSO ranging from 100 mM to 0.001 mM and DMSO only controls were included. The compound/DMSO dilutions were further diluted 1:250 in DMEM+10% FBS, and 12.5 μL of these dilutions were added in triplicates to cells of both treatment arms (with and without IFNγ). Final compound concentrations ranged from 100 μM to 0.001 μM with a final DMSO concentration of 0.1%. Compounds were only dosed in the inner 240 wells, avoiding the outer 2-well perimeter of the plate to minim/ze edge effects. Finally, the plate was loaded into an IncuCyte® S3 Live Cell Analysis System (Essen Bioscience-Sartorius, Ann Arbor, Mich.) maintained in a 37° C.+5% CO$_2$ incubator, allowed to equilibrate for 2 hours, and imaged every 6 hours for 5 days. Confluence over time for compound dilutions in the presence and absence of IFNγ was measured. Growth inhibition values were obtained when the "DMSO/no IFNγ" control reached confluence >95%. At these time points, for each compound the percent growth inhibition at every compound dose level was calculated relative to the "DMSO/with IFNγ" control and used to determine the IC$_{50}$.

Finding novel strategies to inhibit tumor growth is an active field of research in oncology drug discovery. The growth of certain cancer types, among them melanoma, can be suppressed by IFNγ, a cytokine produced by cells of the immune system like T cells or NK cells. Ablation of IFNγ signaling promotes tumor growth. In contrast, enhancing IFNγ signaling amplifies tumor growth inhibition. Because PTPN2 and PTPN1 are negative regulators of cytokine signaling including IFNγ signaling through the dephosphorylation of JAK and STAT proteins, a potent compound should promote tumor growth arrest in the presence of IFNγ.

Compounds of the present disclosure amplify B16F10 melanoma growth inhibition in the presence of IFNγ. Importantly, no tumor growth inhibition is observed in the absence of IFNγ indicating an on target mechanism of the compounds.

Table 3 below summarizes the B16F10 IFNγ-induced cellular growth inhibition $IC_{50}$ values for exemplary compounds of the disclosure. In this table, "A" represents an $IC_{50}$ of less than 1 μM; "B" an $IC_{50}$ of between 1 μM and 10 μM; "C" an $IC_{50}$ of greater than 10 μM to 100 μM; and "D" an $IC_{50}$ of greater than 100 μM.

TABLE 3

$IC_{50}$ values of exemplary compounds of the disclosure in the B16F10 IFNγ-induced cellular growth inhibition (GI) assay.

| Compound No. | B16F10 GI IC50 (μM) | Compound No. | B16F10 GI IC50 (μM) |
|---|---|---|---|
| 102 | A | 103 | B |
| 104 | C | 106 | C |
| 107 | C | 108 | C |
| 109 | C | 111 | C |
| 112 | C | 116 | B |
| 117 | B | 118 | A |
| 119 | B | 120 | A |
| 122 | B | 123 | B |
| 124 | A | 125 | C |
| 126 | B | 127 | A |
| 128 | B | 129 | A |
| 130 | B | 131 | A |
| 133 | A | 134 | B |
| 135 | B | 136 | D |
| 137 | C | 139 | C |
| 142 | C | 143 | B |
| 145 | B | 146 | A |
| 148 | A | 150 | B |
| 151 | B | 153 | D |
| 155 | C | 156 | A |
| 157 | B | 161 | C |
| 166 | A | 169 | C |
| 172 | B | 173 | A |
| 174 | A | 175 | A |
| 177 | A | 178 | A |
| 179 | B | 180 | B |
| 184 | C | 185 | A |
| 187 | A | 188 | A |
| 189 | B | 190 | B |
| 194 | B | 196 | B |
| 197 | B | 199 | A |
| 200 | A | 202 | A |
| 203 | A | 205 | B |
| 206 | B | 208 | C |
| 209 | B | 211 | A |
| 214 | B | 217 | B |
| 218 | C | 221 | B |
| 223 | A | 225 | B |
| 229 | B | 231 | B |
| 234 | B | 235 | B |
| 238 | B | 241 | C |
| 243 | B | 245 | B |
| 247 | C | 250 | D |
| 251 | B | 252 | C |
| 253 | B | 254 | B |
| 255 | B | 257 | B |
| 258 | B | 259 | B |
| 260 | A | 262 | C |
| 268 | B | 269 | C |
| 276 | B | 286 | B |
| 288 | B | 291 | A |
| 292 | B | 293 | B |
| 306 | D | 307 | A |
| 308 | A | | |

Example 230: Human Whole Blood pSTAT1 Proximal Pharmacodynamic (PD) Assay

Human blood samples were acquired through internal AbbVie Inc's blood donation program in accordance with AbbVie's Occupational Safety and Health Administration protocols. Blood was collected by venipuncture into sodium heparin coated vacutainer tubes and kept at room temperature for no longer than 1 hour prior to the experiment initiation. Human blood samples (90 μL) were added to the individual wells of 96-well plates containing 10 μL of 10× working stock solutions of increasing concentrations of compounds to achieve final concentrations ranging from 0.025 μM to 500 μM and incubated for 3 hours at 37° C. To induce STAT1 phosphorylation the samples were then treated with recombinant human IFNγ (R&D Systems, Catalog#285-IF, Minneapolis, Minn.; 100 nM final concentration) for 20 minutes, and 3 μL/well BV421 labeled anti-CD14 surface antibody (Biolegend, San Diego, Calif., Catalog#301830) was added for 45 minutes before fixation and red blood cell lysis was performed with BD Phosflow Lyse/Fix buffer (BD Biosciences, San Jose, Calif., Catalog#558049). Cells were subsequently permeabilized on ice by the addition of BD Perm III buffer (BD Biosciences, San Jose, Calif., Catalog#558050) and stored at −80° C. until use. Before staining, the cells were washed with PBS containing 0.1% BSA. Optim/zed concentrations of BUV395 labeled anti-CD45 (BD Biosciences, San Jose, Calif., Catalog#563792) and PE labeled anti-phospho-STAT1 (pY701; Invitrogen, Carlsbad, Calif., Catalog#12-9008-42) antibodies were added to the cell suspensions and incubated for 2 hours. The cells were washed with PBS containing 0.1% BSA and analyzed on a BD LSRFortessa™ X20 flow cytometer (BD Biosciences, San Jose, Calif.) using BD FACSDiva™ software. The data was analyzed using FlowJo V10 analysis software (Flow Jo LLC, Ashland, Oreg.). The amount of STAT phosphorylation was measured by the mean fluorescence intensity (MFI) of pSTAT1 in CD14+monocytes. Compound dose-response curves were determined using a four-parameter logistic-nonlinear regression model from which half maximal effective concentrations ($EC_{50}$) were calculated. All statistical analyses utilized GraphPad software (San Diego, Calif.).

Protein tyrosine phosphatases PTPN2 and PTPN1 are negative regulators of several cellular pathways among them JAK/STAT mediated cytokine signaling (e.g. IFNγ, IFNα, IL2). Inhibition of PTPN2/N1 is expected to elevate STAT phosphorylation by delaying the dephosphorylation of STAT proteins. The impact of compounds on IFNγ signaling was evaluated via measuring the phosphorylation of the direct PTPN2/N1 target, STAT1, as proximal translational pharmacodynamic markers in human whole blood. The cells contained in whole blood provide a close physiologically relevant setting as well as facilitate assessment of small molecule protein binding characteristics and the amount of free drug available for action on its target. In human whole blood spiked with active compounds, a dose dependent enhancement of STAT1 phosphorylation after stimulation with IFNγ was observed. Compounds of the present disclosure amplify the IFNγ-induced phosphorylation of STAT1. Table 4 below summarizes the pSTAT $EC_{50}$ values for exemplary compounds of the disclosure.

Protein tyrosine phosphatases PTPN2 and PTPN1 are negative regulators of several cellular pathways among them JAK/STAT mediated cytokine signaling (e.g. IFNγ, IFNα, IL2). Inhibition of PTPN2/N1 is expected to elevate STAT phosphorylation by delaying the dephosphorylation of STAT proteins. The impact of compounds on IFNγ signaling was evaluated via measuring the phosphorylation of the direct PTPN2/N1 target, STAT1, as proximal translational pharmacodynamic markers in human whole blood. The cells contained in whole blood provide a close physiologically relevant setting as well as facilitate assessment of small molecule protein binding characteristics and the amount of free drug available for action on its target. In human whole blood spiked with active compounds, a dose dependent enhancement of STAT1 phosphorylation after stimulation with IFNγ was observed. Compounds of the present disclosure amplify the IFNγ-induced phosphorylation of STAT1. Table 4 below summarizes the pSTAT $EC_{50}$ values for exemplary compounds of the disclosure.

TABLE 4

Comparison of $IC_{50}$ values of select compounds in the B16F10 growth inhibition assay and $EC_{50}$ values in human whole blood IFNγ-induced STAT1 phosphorylation.

| Compound | B16F10 Growth Inhibition $IC_{50}$ (μM) | Human Whole Blood IFNγ induced pSTAT1 $EC_{50}$ (μM) |
|---|---|---|
| Compound V | 3.2 | |
| Compound W | 4.1 | |
| Compound X | 4.1 | |
| Compound Y | 5.8 | 38 |
| Compound Z | 17.8 | >500 |
| 118 | 0.11 | 0.58 |
| 133 | 0.22 | 1.6 |
| 146 | <0.05 | 0.4 |
| 177 | 0.14 | 2 |
| 199 | <0.05 | 0.83 |
| 200 | <0.05 | 2.4 |
| 259 | 1.5 | 14.2 |
| 260 | 0.18 | 4.4 |

Example 231: T Cell Function Assays

Pan T cells were isolated from C57BL6 splenocytes using a MACS Pan T cell isolation kit II (Miltenyi Biotec, Auburn, Calif.) according to the manufacturer's instructions. Isolated T cells (200,000 cells/well in a 96 well flat-bottom plate) were cultured in RPMI 1640 supplemented with 10% FBS, 50 nM 2-mercaptoethanol, 100 U/mL penicillin, and 100 µg/mL streptomycin, and incubated with 0.3 µM compound or DMSO in duplicates. After 1 hour, mouse T cell activator CD3/CD28 Dynabeads (ThermoFisher Scientific, Waltham, Mass.) were added at a 1:5 beads to cells ratio to stimulate the T cells for 3 days. T cells with or without compound were incubated in the absence of T cell activator beads to evaluate if compounds nonspecifically stimulate the T cells. After 3 days of stimulation, supernatants were collected and IFNγ and TNFα in supernatants were assessed using an MSD V-plex assay (Meso Scale Discovery, Rockville, Md.).

The increase of T cell activation and most importantly T cell function is a main strategy for novel immune oncology approaches to promote tumor immunity. In vitro assays using primary T cells are commonly used to assess the impact of compound on T cell activation and function.

A read out for T cell function important for tumor immunity is the production of pro-inflammatory, anti-tumorigenic cytokines like IFNγ and TNFα. This can be assessed through the detection of cytokines in the supernatants of in vitro stimulated T cells. An immune stimulatory compound is expected to increase the production of IFNγ and TNFα. Compounds of the present disclosure promote IFNγ and TNFα production of stimulated T cells. Importantly, compounds did not nonspecifically increase IFNγ and TNFα production in the absence of TCR stimulation. Table 5 below summarizes the amount of IFNγ and TNFα produced from T cells either stimulated through the TCR (anti-CD3/CD28) or left unstimulated (no stimulation) for 3 days for exemplary compounds of the disclosure.

Compound Y

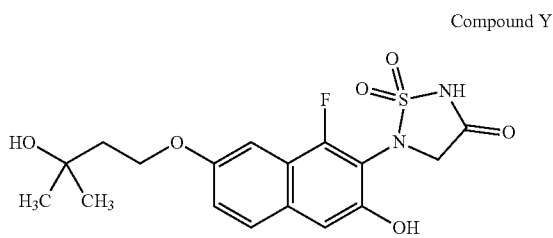 [SMILES: CC(C)(O)CCOc1ccc2cc(O)c(N3CC(=O)NS3(=O)=O)c(F)c2c1]

TABLE 5

Cytokine data from the T cell function assays.

| Compound No. | IFNγ [pg/mL] no stimulation | IFNγ [pg/mL] anti-CD3/ CD28 | TNFα [pg/mL] no stimulation | TNFα [pg/mL] anti-CD3/ CD28 |
|---|---|---|---|---|
| DMSO | 1.1 | 49 | 1.1 | 73.7 |
| 118 | 1.8 | 261.3 | 1.1 | 159.1 |
| 133 | 1.0 | 204.1 | 0.8 | 142.0 |
| 148 | 1.0 | 168.4 | 0.8 | 123.4 |
| 177 | 1.0 | 168.2 | 0.7 | 113.7 |
| 199 | 1.8 | 212.9 | 1.1 | 147.8 |
| 204 | 1.8 | 148.8 | 1.1 | 105.4 |
| 254 | 0.7 | 97.0 | 1.1 | 91.2 |
| 260 | 0.8 | 139.6 | 1.1 | 100.0 |
| 291 | 0.7 | 83.3 | 1.1 | 91.2 |
| 307 | 1.2 | 66.7 | 1.1 | 89.5 |
| Compound Y | 1.2 | 67.2 | 1.0 | 32.5 |

Example 232. In Vivo Efficacy of PTPN2 Inhibitors in MC38 Mouse Tumor Model and Impact on Pharmacodynamic Markers Mice.

All experiments were conducted in compliance with AbbVie's Institutional Animal Care and Use Committee and the National Institutes of Health Guide for Care and Use of Laboratory Animals guidelines in a facility accredited by the Association for the Assessment and Accreditation of Laboratory Animal Care. C57Bl/6 female mice were obtained from Charles River (Wilmington, Mass.). The mice were group-housed 10 per cage. Food and water were available ad libitum. Animals were acclimated to the animal facilities for a period of at least one week prior to commencement of experiments. Animals were tested in the light phase of a 12-hour light: 12-hour dark schedule (lights on 0600 hours).

Tumor Cell Inoculation and Treatments.

Cells were grown to passage 3 in vitro. A total of $1 \times 10^5$ viable MC-38 cells were inoculated subcutaneously into the right flank of female C57Bl/6 mice (7-12 weeks old) on Day 0. The injection volume was 0.1 mL and was composed of a 1:1 mixture of S-MEM and Matrigel® (Corning, N.Y., USA). Tumors were size matched on Day 14 and the mice had a mean body weight of ~21 g. The mean tumor volume (TV) at size match was approximately 196±64 $mm^3$. Following size match, treatments were initiated on the same day. Dosing of mice was conducted orally, twice a day (BID) at 7 a.m. and 5 p.m. for 21 days. Mice were dosed (10 mg/kg/dose) with either Compound 118 or vehicle controls (n=15 mice/group). Compound 118 was formulated in 10% ethanol, 30% PEG-400 and 60% Phosal-50PG and was dosed at 10 mL/kg. Tumor volume was calculated three times weekly. Measurements of the length (L) and width (W) of the tumor were taken via electronic caliper and the volume was calculated according to the following equation: $V = L \times W^2 / 2$ using Study Director Version 3.1.399.22 (Studylog Systems, Inc, CA, USA). Mice were euthanized when tumor volume was <3000 $mm^3$ or skin ulcerations occurred. Tumor growth inhibition (TGI) was calculated as TGI=1−(Mean $TV_{Timepoint(Treatment)}$/Mean $TV_{Timepoint\ (Vehicle)}$) for each timepoint that tumor volumes were measured. Reported $TGI_{Max}$ is the largest TGI value for any timepoint that tumors volumes were collected for that treatment group.

pSTAT5 Flow Cytometry Assay in Mouse Whole Blood.

Whole blood was drawn into EDTA powder coated tubes by cardiac puncture from mice on day 8 of dosing with Compound 118 (2 hours after the $16^{th}$ dose). 90 µL of whole blood were stimulated with 10 µL of murine IL-2 to achieve a final concentration of 100 ng IL-2/mL (R&D Systems, Minneapolis, Minn., cat #402-ML) for 20 minutes at 37° C., 5% $CO_2$. After stimulation, 1.8 mL of prewarmed BD Phosflow Lyse/Fix Buffer (BD Biosciences, San Jose, Calif.) was added for 20 minutes at 37° C. Cells were washed twice in FACS buffer (Dulbecco's PBS with 0.2% BSA) and incubated for 30 minutes on ice in cold Perm Buffer III (BD Biosciences, San Jose, Calif.). Cells were washed with FACS buffer and resuspended in 50 µL of FACS buffer with antibodies and stained for 3 hours at room temperature with gentle shaking. The antibodies added were a combination of the following: anti-CD3-AF647, clone 145-2C11 (Biolegend, Cat #564279); anti-CD4-FITC, clone GK1.5 (Biolegend, San Diego, Calif., Cat #100406); anti-pSTAT5 (pY694)-PE, clone 47 (BD Biosciences, San Jose, Calif., Cat #562077); anti-CD45-BUV395, clone 30-F11 (BD Biosciences, San Jose, Calif., cat #564279). After staining, cells were washed twice with FACS buffer, and the samples were acquired on a BD LSRFortessa™ X20 flow cytometers (BD Biosciences, San Jose, Calif.) and analyzed with FLowJo V10 software (FlowJo, Ashland, Oreg.). The mean fluorescence intensity (MFI) of pSTAT5 as a measure of the amount of phosphorylated STAT5 in the CD3+ T cell population from vehicle or Compound 118 treated animals was reported.

Granzyme B Staining of CD8 T Cells Flow Cytometry Assay in Mouse Spleen.

Mice were sacrificed on day 8 of dosing with Compound 118 (2 hours after the $16^{th}$ dose) and spleens were excised. Spleens were dissociated with a gentleMACS dissociator (Miltenyi Biotec, Bergisch Gladbach, Germany), red blood cells lysed, and single cell suspensions were prepared. Splenocytes were stained with Zombie UV™ Fixable Viability kit (Biolegend, San Diego, Calif.) diluted in Dulbecco's PBS for 10 minutes at room temperature to exclude dead cells followed by staining for surface markers for 45 minutes on ice using the following flow cytometry antibodies diluted in autoMACS Running Buffer (Miltenyi Biotec, Bergisch Gladbach, Germany): Brilliant Violet 510-labeled anti-CD45, Brilliant Ultraviolet 395-labeled anti-CD3, Brilliant Violet 786-labeled anti-CD4, APC/Cy7-labeled anti-CD8. Cells were washed twice with autoMACS Running Buffer, permeabilized with Fixation/Permeabilization buffer (FoxP3/Transcription Factor Staining Buffer Set; eBioscience) and stained intracellularly with PE-labeled anti-Granzyme B antibody diluted in Permeabilization buffer (FoxP3/Transcription Factor Staining Buffer Set; eBioscience, San Diego, Calif.) for 1 hour on ice. After staining, cells were washed twice with autoMACS Running Buffer, and the samples were acquired on a BD LSRFortessa™ X20 flow cytometers (BD Biosciences, San Jose, Calif.) and analyzed with FLowJo V10 software (FlowJo, Ashland, Oreg.). The frequency of Granzyme B+ cells within the CD8+ T cell population in vehicle or Compound 118 treated animals was reported.

Cytokine Measurement in Mouse Plasma.

Whole blood was drawn into EDTA powder coated tubes by cardiac puncture from mice on day 8 of dosing with Compound 118 (2 hours after the $16^{th}$ dose) and plasma was prepared by centrifugation. Cytokines in plasma were measured using the Th1/Th2 Cytokine & Chemokine 20-Plex Mouse ProcartaPlex™ Panel 1 (Invitrogen, Carlsbad, Calif.). IP10 levels (pg/mL) in vehicle or Compound 118 treated animals were reported.

Results

Expression within tumor cells of the phosphatases PTPN2 and its highly homologous counterpart, PTPN1, were recently described to be negative regulators of tumor-directed immune responses. The functional activity of PTPN2 to inhibit signaling cascades of extrinsic factors within tumor cells, particularly de-phosphorylation of STAT molecules downstream of the IFNγ receptor was defined as a significant contributor to the ability of tumor cells to evade or suppress anti-tumor immune responses. To confirm these claims, specific inhibitors of PTPN2/N1 were created and tested for their ability to inhibit tumor growth and elicit anti-tumor inflammation in an in vivo syngeneic mouse tumor model. Mice were inoculated on their hind flank with the murine colon adenocarcinoma, MC-38. Following two weeks of tumor cell growth, mice began oral BID treatment for 21 days with either the vehicle or the formulated Compound 118. Compound 118 was well tolerated, without obvious adverse health events. However, within 7-10 days of treatment, apparent tumor stasis and shrinkage was observed in animals dosed with Compound 118. Eventually, 70% of mice treated with Compound 118 achieved complete cures, and an overall $TGI_{Max}$ of 94% (Table 6). Significant tumor efficacy observed with Compound 118 was followed by further examination of direct target engagement of the compounds in vivo as well as their effects on anti-tumor immune responses.

IL2 signaling in T cells promotes T cell homeostasis and proliferation. STAT5 is a signaling molecule in the IL2 pathway and a direct target of PTPN2 and PTPN1 which serve as negative regulators of IL2 signaling. A PTPN2/N1 inhibitor is expected to increase the phosphorylation of STAT5 upon stimulation with IL2. To demonstrate in vivo target engagement, we measured pSTAT5 levels in T cells from whole blood of PTPN2/N1 inhibitor dosed animals after ex vivo stimulation of whole blood with IL2. In mice treated with Compound 118, pSTAT5 levels in whole blood T cells were 1.6-fold higher (MFI=1261±97) than in vehicle control treated animals (MFI=802±52) (Table 6).

One desirable effect of immunotherapy is the induction of functional cytotoxic T cells which can improve tumor immunity. In Compound 118 treated mice, the frequency of functional, granzyme B (GzB) producing cells within the cytotoxic CD8+T population in the spleen was 3.9-fold higher (4.3±0.9%) than in vehicle control treated animals (1.1±0.1%) (Table 6).

Because a PTPN2/N1 inhibitor promotes IFNγ signaling by increasing the phosphorylation of JAK and STAT signaling molecules and IP10 is an IFNγ induced protein, a PTPN2/N1 inhibitor is expected to increase the production of IP10. IP10 levels in plasma of Compound 118 treated mice were 1.7-fold higher (256±30 pg/mL) than in vehicle control treated animals (153±15 pg/mL) (Table 6).

TABLE 6

Impact of oral BID dosing with indicated treatment on tumor growth and PD marker movement in the MC-38 syngeneic tumor model. $TGI_{Max}$ was determined over the entirety of the study. PD markers were evaluated on day 8 of dosing (2 hours post $16^{th}$ dose). Data are represented as value ± SEM.

| Compound | Tumor Growth Inhibition (Max) compared to vehicle [%] | % GzB+ cells within splenic CD8+ T cells | pSTAT5 level [MFI] in CD3+ T cells from IL2 stimulated whole blood | IP10 in plasma [pg/mL] |
|---|---|---|---|---|
| Vehicle | – | 1.1 ± 0.1 | 802 ± 52 | 153 ± 15 |
| 118 | 94 | 4.3 ± 0.9 | 1261 ± 97 | 256 ± 30 |

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound represented by:

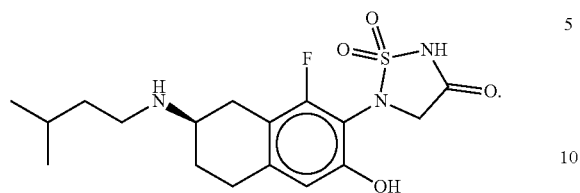

2. A compound, wherein the compound is 5-{(7R)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione, or a pharmaceutically acceptable salt thereof.

3. The compound of claim 2, wherein the compound is the pharmaceutically acceptable salt of 5-{(7R)-1-fluoro-3-hydroxy-7-[(3-methylbutyl)amino]-5,6,7,8-tetrahydronaphthalen-2-yl}-1$\lambda^6$,2,5-thiadiazolidine-1,1,3-trione.

* * * * *